(12) United States Patent
Facciotti et al.

(10) Patent No.: US 6,566,583 B1
(45) Date of Patent: May 20, 2003

(54) SCHIZOCHYTRIUM PKS GENES

(76) Inventors: Daniel Facciotti, 2636 Lafayette Dr., Davis, CA (US) 95616; James George Metz, 2830 Belhaven Pl., Davis, CA (US) 95616; Michael Lassner, 721 Falcon Ave., Davis, CA (US) 95616

( * ) Notice: Subject to any disclaimer, the term of this patent is extended or adjusted under 35 U.S.C. 154(b) by 0 days.

(21) Appl. No.: 09/231,899

(22) Filed: Jan. 14, 1999

Related U.S. Application Data

(63) Continuation-in-part of application No. 09/090,793, filed on Jun. 4, 1998.
(60) Provisional application No. 60/048,650, filed on Jun. 4, 1997.

(51) Int. Cl.[7] .......................... C12N 15/82; C12N 1/20; C07H 21/04
(52) U.S. Cl. ...................... 800/281; 536/23.2; 435/419; 435/252.3; 435/320.1
(58) Field of Search ........................ 536/23.2; 435/419, 435/252.3, 320.1; 800/281

(56) References Cited

U.S. PATENT DOCUMENTS

| | | | |
|---|---|---|---|
| 5,246,841 A | 9/1993 | Kondo | |
| 5,639,790 A | 6/1997 | Davies | |
| 5,672,491 A | 9/1997 | Kao | |
| 5,683,898 A | 11/1997 | Kondo | |

FOREIGN PATENT DOCUMENTS

| | | |
|---|---|---|
| WO | WO93/23545 | 11/1993 |
| WO | WO96/21735 | 7/1996 |
| WO | WO 98/55625 | 12/1998 |

OTHER PUBLICATIONS

Van de Loo, "An oleate 12–hydroxylase from Ricinus communis L. is a fatty acyl desaturase homolog", 1995, Pro. Natl. Acad. Sci. vol. 92, pp. 6743–6747.*
Broun et al, "Catalytic Plasticity of Fatty Acid Modification Enzymes Underlying Chemical Diversity of Plant Lipids", 1998, Science vol. 282, pp. 1315–1317.*
Doerks, "Protein annotation: detective work for function prediction", 1998, TIG vol. 14 No. 6, pp. 248–250.*
Smith et al, The challenges of genome sequence annotation or "The devil is in the details", 1997, Nature Biotechnology vol. 15, pp 1222–1223.*
Brenner, "Errors in genome annotation" 1999, TIG, vol. 15 No. 4, pp 132–133.*
Bork, Go hunting in sequence databases but watch out for the traps, 1996, TIG, vol. 12 No. 10, pp. 425–427.*
Delong & Yayanos, (1986) *Appl. Environ. Microbiol.* 51(4): 730–737.
Facciotti et al., (1998) *Clon. and Charac. of PUFA Genes from Marine Bac.* 14.
Hopwood & Sherman, (1990) *Annu. Rev. Genet.* 24:37–66.
Hutchinson, (1995) *Annu. Rev. Microbiol.* 49: 201–238.
Jostensen & Landfald, (1997) *High Prev. of PUFA Produc. Bac. in Arctic Invert.* 95–101.
Katz & Donadio, (1993) *Annu. Rev. Microbiol.* 47: 875–912.
Kyle et al., (1990) *HortScience.* 25: 1523–26.
Nakahara, (1995) *Yukagaku* 44(10) : 821–7.
Nasu et al., (1997) *J. Ferment. Bioeng.* 122: 467–473.
Nogi et al., (1998) *Photobac.Profundum sp. nov., A New Mod. Barophilic Bac.* 2: 1–7.
Somerville, (1993) Am. J. Clin. Nutr.58. 2. (*supplement*): 270–S–275–S.
Watanabe et al., (1997) *J. Biochem.* 122: 467–473.
Yazawa, (1996) *Lipids 31 (supplement)*: S–297–S–300.

\* cited by examiner

Primary Examiner—Elizabeth F. McElwain

(57) ABSTRACT

The present invention relates to compositions and methods for preparing poly-unsaturated long chain fatty acids in plants, plant parts and plant cells, such as leaves, roots, fruits and seeds. Nucleic acid sequences and constructs encoding PKS-like genes required for the poly-unsaturated long chain fatty acid production, including the genes responsible for eicosapentenoic acid production of *Shewanella putrefaciens* and novel genes associated with the production of docosahexenoic acid in *Vibrio marinus* are used to generate transgenic plants, plant parts and cells which contain and express one or more transgenes encoding one or more of the PKS-like genes associated with such long chain polyunsaturated fatty acid production. Expression of the PKS-like genes in the plant system permits the large scale production of poly-unsaturated long chain fatty acids such as eicosapentenoic acid and docosahexenoic acid for modification of the fatty acid profile of plants, plant parts and tissues. Manipulation of the fatty acid profiles allows for the production of commercial quantities of novel plant oils and products.

36 Claims, 134 Drawing Sheets

Orf6    8.3 KB - 293 kD
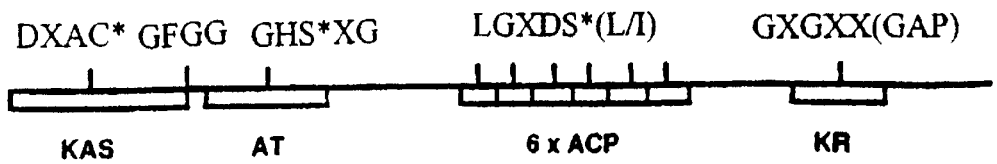
Acetate-like    FIG. 2A
Orf7    2.3 KB - 84 kD
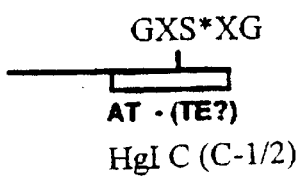
HgI C (C-1/2)
FIG. 2B
Orf3    0.8 KB - 30 kD
☐ Het I- pantetheine transferase
FIG. 2E
Orf8    6.0 KB - 217 kD
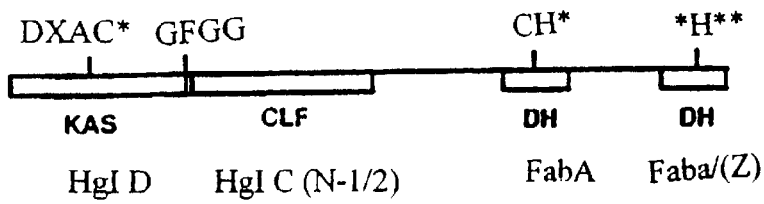
HgI D    HgI C (N-1/2)    FabA    Faba/(Z)
FIG. 2C
Orf9    1.6 KB - 59 kD
☐
Anabeana - Orf552 homolog
FIG. 2D

```
GATCTCTTAC AAAGAAACTA TCTCAATGTG AATTTAACCT TAATTCCGTT TAATTACGGC    60
CTGATAGAGC ATCACCCAAT CAGCCATAAA ACTGTAAAGT GGGTACTCAA AGGTGGCTGG   120
GCGATTCTTC TCAAATACAA AGTGCCCAAC CCAAGCAAAT CCATATCCGA TAACAGGTAA   180
AAGTAGCAAT AAACCCCAGC GCTGAGTTAG TAATACATAA GCGAATAATA GGATCACTAA   240
ACTACTGCCG AAATAGTGTA ATATTCGACA GTTTCTATGC TGATGTTGAG ATAAATAAAA   300
AGGGTAAAAT TCAGCAAAAG AACGATAGCG CTTACTCATT ACTCACACCT CGGTAAAAAA   360
GCAACTCGCC ATTAACTTGG CCAATCGTCA GTGTTCTAT CGTCTCAAAG TTATGCCGAC    420
TAAATAACTC TATATGTGCA CAAAAACTCC GATACCATCA AGATGAAGTT              480
GTTCATCACA CCAACTCAAA ACTGCGTCGA TAAGCTTACT GCCATAGCCC TTGCCTTGCT   540
CCACATTTGC GATAGCAATA AACTGTAAAA TGCCACATTG GCCACTTGGT AAGCTCTCTA   600
TAATCTGATT TTCTTTGTTA ATAAGTGCCT GAGTTGAATA CCAACCAGTA CTTAACAACA   660
TCTTTAAACG CCAATGCCAA AAACGCGCTT CACCTAAGGG AACCTGCTGA GTCACTATGC   720
AGGCTACGCC TATCAATCTA TCCCCAACGA ACATACCAAT AAGTGCTTGC TCCTGTTGCC   780
AGAGCTCATT GAGTTCTTCT CGCGAAGCTT CGCCAAGCCC TTGCTCATAC TGCGCTTGAT   840
CACCACTAAA AAGTGTTTCG ATAAAAAAGG GATCATCATG ATAGGCGTTA TAGAGAATAG   900
AGGCTGCTAT GCGTAAATCT TCTGCCGTGA GATAAACTGC ACGACACTCT TCCATGGCTT   960
GATCTTCCAT TGTTATTGTC CTTGACCTTG ATCACACAAC ACCAATGTAA CAAGACTGTA  1020
```

FIG. 4A-1

```
TAGAAGTGCA ATTAATAATC AATTCGTGCA TTAAGCAGGT CAGCATTTCT TTGCTAAACA 1080
AGCTTTATTG GCTTTGACAA AACTTTGCCT AGACTTTAAC GATAGAAATC ATAATGAAAG 1140
AGAAAAGCTA CAACCTAGAG GGGAATAATC AAACAACTGC TAAGATCTAG ATAATGTAAT 1200
AAACACCGAG TTTATCGACC ATACTTAGAT AGAGTCATAG CAACGAGAAT AGTTATGGAT 1260
ACAACGCCGC AAGATCTATC ACACCTGTTT TTACAGCTAG GATTAGCAAA TGATCAACCC 1320
GCAATTGAAC AGTTATCAA TGACCATCAA TTAGCGGACA ATATATTGCT ACATCAAGCA 1380
AGCTTTTGGA GCCCATCGCA AAAGCACTTC TTAATTGAGT CATTTAATGA AGATGCCCAG 1440
TGGACCGAAG TCATCGACCA CTTAGACACC TTTATTAAGAA AAAACTAACC ATTACAACAG 1500
CAACTTTAAA TTTTGCCGTA AGCCATCTCC CCCCACCCCA CAACAGCGTT GTTGCTTATG 1560
ACCACTGGAG TACATTCGTC TTTAGTCGTT TTACCATCAC CATGGGTACG TTGAGTGCGA 1620
TAAAAAAGCA CATAAACTTC TTTATCGGCC TGAATATAGG CTTCGTTAAA ATCAGCTGTT 1680
CCCATTAAAG TAACCACTTG CTCTTTACTC ATGCCTAGAG ATATCTTTGT CAAATTGTCA 1740
CGGTTTTTAT CTTGAGTTTT CTCCCAAGCA CCGTGATTAT CCCAGTCAGA TTCCCCATCA 1800
CCAACATTGA CCACACAGCC CGTTAGCCCT AAGCTTGCAA TCCCAAAACA TGCTAAACCT 1860
AATAATTTAT TTTTCATTTT AACTTCCTGT TATGACATTA TTTTTGCTTA GAAGAAAAGC 1920
AACTTACATG CCAAAACACA AGCTGTTGTT TTAAATGACT TTATTATTA TTAGCCTTTT 1980
AGGATATGCC TAGAGCAATA ATAATTACCA ATGTTTAAGG AATTTGACTA ACTATGAGTC 2040
```

FIG. 4A-2

```
CGATTGAGCA AGTGCTAACA GCTGCTAAAA AAATCAATGA ACAAGGTAGA GAACCAACAT 2100
TAGCATTGAT TAAAACCAAA CTTGGTAATA GCATCCCAAT GCGCGAGTTA ATCCAAGGTT 2160
TGCAACAGTT TAAGTCTATG AGTGCAGAAG AAAGACAAGC AATACCTAGC AGCTTAGCAA 2220
CAGCAAAAGA AACTCAATAT GGTCAATCAA GCTTATCTCA ATCTGAACAA GCTGATAGGA 2280
TCCTCCAGCT AGAAAACGCC CTCAATGAAT TAAGAAACGA ATTTAATGGG CTAAAAAGTC 2340
AATTTGATAA CTTACAACAA AACCTGATGA ATAAAGAGCC TGACACCAAA TGCATGTAAT 2400
TGAACTACGA TTTGAATGTT TTGATAAACAC CACGATTACT GCAGCAGAAA AAGCCATTAA 2460
TGGTTTGCTT GAAGCTTATC GAGCCAATGG CCAGGTTCTA GGTCGTGAAT TTGCCGTTGC 2520
ATTTAACGAT GGTGAGTTTA AAGCACGCAT GTTAACCCCA GAAAAAAGCA GCTTATCTAA 2580
ACGCTTTAAT AGTCCTTGGG TAAATAGTGC ACTCGAAGAG CTAACCGAAG CCAAATTGCT 2640
TGCGCCACGT GAAAAGTATA TTGGCCAAGA TATTAATTCT GAAGCATCTA GCCAAGACAC 2700
ACCAAGTTGG CAGCTACTTT ACACAAGTTA TGTGCACATG TGCTCACCAC TAAGAAATGG 2760
CGACACCCTG CAGCCTATTC CACTGTATCA AATTCCAGCA ACTGCCAACG GCGATCATAA 2820
ACGAATGATC CGTTGGCAAA CAGAATGGCA AGCTTGTGAT GAATTGCAAA TGGCCGCAGC 2880
TACTAAAGCT GAATTTGCCG CACTTGAAGA GCTAACCAGT CATCAGAGTG ATCTATTTAG 2940
GCGTGGTTGG GACTTACGTG GCAGAGTCGA ATACTTGACG AAAATTCCGA CCTATTACTA 3000
TTTATACCGT GTTGGGCGGTG AAAGCTTAGC AGTAGAAAAG CAGCGCTCTT GTCCTAAGTG 3060
```

FIG. 4A-3

```
TGGCAGTCAA GAATGGCTGC TCGATAAACC ATTATTGGAT ATGTTCCATT TTCGCTGTGA 3120
CACCTGCCGC ATCGTATCTA ATATCTCTTG GGACCATTTA TAACTCTTCC GAGTCTTATC 3180
ACACTAGAGT TTAGTCAGCA TAAAAATGGC GCTTATATTT CAATTAAAAG AAATATAAGC 3240
GCCATTTCA TCGATACTAT ATATCAGCAG ACTATTTTCC GCGTAAATTA GCCCACATTA 3300
ATTTCATTCT TTGCCAGATC CCTGGATGAT CTAGTTGTGG CATCGACTCT TCAATAGGTT 3360
TAACCGCAGG TGTAACCCTT GGAGTCAATT CGTTTATAAA CTCGTTTAAA CTGTCACTTA 3420
ATTTAACGCT TTGTACTTCA CCTGGAATTT CAATCCATAC GCTGCCATCA CTATTATTAA 3480
CCGTCAACAT TTTATCTTCA TCATCAAGAA TACCAATAAA CCAAGTCGGC TCTTGCTTAA 3540
GCTTTCTCTT CATCATTAAA TGACCAATGA TGTTTTGTTG TAAGTATTCA AAATCAGTTT 3600
GATCCCACAC TTGGATTAGC TCACCTTGGC CCCATTGTGA GTCAAAAAAT AGCGGGTGCAG 3660
AAAAATGACT GCCAAAAAAT GGATTAATTT CTGCAGATAA TGTCATTTCA AGTGCTGTTT 3720
CAACATTAGC AAATTCACCA GGTTGTTGAC GTACAACCGA TTGCCAAAAC ACTGCGCCAT 3780
CGGAGCCCGC TTCGGCGACA ACACACTCAG ACTTTTGTCC TTGCGCATAA TATCTTGGCT 3840
GTTCACCAAG CTTATCCATG TAGGCTTGTT GATATTTAGA TAAAAAAGA TCTAAAGCAG 3900
GTAAAGAAGA CACTTAAGCC AGTTCCAAAA TCAGTTATAA TAGGGGTCTA TTTTGACATG 3960
GAAACCGTAT TGATGACACA ACATCATGAT CCCTACAGTA ACGCCCCCGA ACTTTCTGAA 4020
TTAACTTTAG GAAAGTCGAC CGGTTATCAA GAGCAGTATG ATGCATCTTT ACTACAAGCG 4080
```

| | | | | | |
|---|---|---|---|---|---|
| TGCCGCGTAA | ATTAAACCGT | GATGCTATCG | GTCTAACCAA | TGAGCTACCT | TTTCATGGCT 4140 |
| GTGATATTTG | GACTGGCTAC | GAACTGTCTT | GGCTAAATGC | TAAAGGCAAG | CCAATGATTG 4200 |
| CTATTGCAGA | CTTTAACCTA | AGTTTGATA | GTAAAAATCT | GATGCGAGTCT | AAGTCGTTTA 4260 |
| AGCTGTATTT | AAACAGCTAT | AACCAAACAC | GATTTGATAG | CGTTCAAGCG | GTTCAAGAAC 4320 |
| GTTTAACTGA | AGACTTAAGC | GCCTGTGCCC | AAGGCACAGT | TACGGTAAAA | GTGATTGAAC 4380 |
| CTAAGCAATT | TAACCACCTG | AGAGTGGTTG | ATATGCCAGG | TACCTGCATT | GACGATTTAG 4440 |
| ATATTGAAGT | TGATGACTAT | AGCTTTAACT | CTGACTATCT | CACCGACAGT | GTTGATGACA 4500 |
| AAGTCATGGT | TGCTGAAACG | CTAACGTCAA | ACTTATTGAA | ATCAAACTGC | CTAATCACTT 4560 |
| CTCAGCCTGA | CTGGGTACA | GTGATGATCC | GTTATCAAGG | GCCTAAGATA | GACCGTGAAA 4620 |
| AGCTACTTAG | ATATCTGATT | TCATTTAGAC | AGCACAATGA | ATTTCATGAG | CAGTGTGTTG 4680 |
| AGCGTATATT | TGTTGATTTA | AAGCACTATT | GCCAATGTGC | CAAACTTACT | GTCTATGCAC 4740 |
| GTTATACCCG | CCGTGGTGGT | TTAGATATCA | ACCCATATCG | TAGCGACTTT | GAAAACCCTG 4800 |
| CAGAAAATCA | GCGCCTAGCG | AGACAGTAAT | TGATTGCAGT | ACCTACAAAA | AACAATGCCT 4860 |
| ATAAGCCAAG | CTTATGGGCA | TTTTTATATT | ATCAACTTGT | CATCAAACCT | CAGCCGCCAA 4920 |
| GCCTTTTAGT | TTTATCGCTA | AATTAAGCCG | CTCTCTCAGC | CAAATATTTG | CAGGATTTTG 4980 |
| CTGTAATTTA | TGGCTCCACA | CCATGAAATA | CTCTATCGGC | TCTACCGCAA | AAGGTAAGTC 5040 |
| AAATACCTGT | AAGCCAAACA | GCTTGGCATA | TTCGTCAGTG | TGGGCTTTTG | ACGCGATAGC 5100 |

FIG. 4A-5

```
TAACGCATCA CTTTTTGAGG CAACCGACAT GATACTTAAT ATTGATGATT GCTCGCTGTG 5160
CATTGCCTT  GCCGGTAACA CCTGTTTAGT CAGCAAGTCG GCAACACTTA AATTGTAGCG 5220
GCGCATCTTA AAAATAATAT GCTTTTCATT AAAGTATTGC TCTTGCGTCA ACCCACCTTG 5280
GATCCTTGGG TGAGCATTTC GTGCCACACA AACTAATTTA TCCTGCATTA CTTTTTGACT 5340
CTTAAATGCC GCAGATTCTG GCAGCCAAAT ATCTAAGGCT AAATCCACCT TTTCTAGTTG 5400
TAGGTCCATC TGCAACTCTT CTTCAATGAG CGGCGGCTCA CGAAATACAA TATTAATTGC 5460
AGTGCCCTGT AACACTTGCT CAATTTGATC TTGCAAGAGT TGTATTGCCG ACTCGCTGGC 5520
ATACACATAA AAAGTTCGCT CACTTGAAGT GGGGTCAAAT GCTTCAAAGC TAGTCGCAAC 5580
TTGCTCAATT GTTGACATAG CGCCCGCGAG CTGTTGATAA AGCGTCATCG CACTTGCGGT 5640
AGGTTTAACT CCCCTACCCA CTCGAGTAAA CAACTCTTCT CCAACAATAC TTTTTAGCCT 5700
CGAAATCGCA TTACTAACCG ACGACTGAGT CAAATCCAGC TCTTCTGCCG CCCGGCTAAA 5760
AGATGAGGTG CGATACACCG CAGTAAAAAC GCGAAATAAA TTAAGATCAA AAGCTTTTTG 5820
CTGCGACATA AATCAGCTAT CTCCTTATCC TTATCCTTAT CCTTATAAAA AGTTAGCTCC 5880
AGAGCACTCT AGCTCAAAAA CAACTCAGCG TATTAAGCCA ATATTTTGGG AACTCAATTA 5940
ATATTCATAA TAAAAGTATT CATAATATAA ATACCAAGTC ATAATTTAGC CCTAATTATT 6000
AATCAATTCA AGTTACCTAT ACTGGCCTCA ATTAAGCAAA TGTCTCATCA GTCTCCCTGC 6060
AACTAAATGC AATATTGAGA CATAAAGCTT TGAACTGATT CAATCTTACG AGGGTAACTT 6120
```

FIG. 4A-6

| | | | | |
|---|---|---|---|---|
|ATGAAACAGA|CTCTAATGGC|TATCTCAATC|ATGTCGCTTT|TTTCATTCAA|TGCGCTAGCA 6180|
|GCGCAACATG|AACATGACCA|CATCACTGTT|GATTACGAAG|GGAAAGCCGC|AACAGAACAC 6240|
|ACCATAGCTC|ACAACCAAGC|TGTAGCTAAA|ACACTTAACT|TTGCCGACAC|GCGTGCATTT 6300|
|GAGCAATCGT|CTAAAAATCT|AGTCGCCAAG|TTTGATAAAG|CAACTGCCGA|TATATTACGT 6360|
|GCCGAATTTG|CTTTTATTAG|CGATGAAATC|CCTGACTCGG|TTAACCCGTC|TCTCTACCGT 6420|
|CAGGCTCAGC|TTAATATGGT|GCCTAATGGT|CTGTATAAAG|TGAGCGATGG|CATTTACCAG 6480|
|GTCCGCGGTA|CCGACTTATC|TAACCTTACA|CTTATCCGCA|GTGATAACGG|TTGGATAGCA 6540|
|TACGATGTTT|TGTTAACCAA|AGAAGCAGCA|AAAGCCTCAC|TACAATTTGC|GTTAAAGAAT 6600|
|CTACCTAAAG|ATGGCGATTT|ACCCGTGTT|GCGATGATTT|ACTCCCATAG|CCATGCGGAC 6660|
|CACTTTGGCG|GAGCTCGCGG|TGTTCAAGAG|ATGTTCCCTG|ATGTCAAAGT|CTACGGCTCA 6720|
|GATAACATCA|CTAAAGAAAT|TGTCGATGAG|AACGTACTTG|CCGGTAACGC|CATGAGCCGC 6780|
|CGCGCAGCTT|ATCAATACG|CGCAACACTG|GGCAAACATG|ACCACGGTAT|TGTTGATGCT 6840|
|GCGCTAGGTA|AAGGTCTATC|AAAAGGTGAA|ATCACTTACG|TCGCCCCAGA|CTACACCTTA 6900|
|AACAGTGAAG|GCAAATGGGA|AACGCTGACG|ATTGATGGTC|TAGAGATGGT|GTTTATGGAT 6960|
|GCCTCGGGCA|CCGAAGCTGA|GTCAGAAATG|ATCACTTATA|TTCCCTCTAA|AAAAGCGCTC 7020|
|TGGACGGCGG|AGCTTACCTA|TCAAGGTATG|CACAACATTT|ATACGCTGCG|CGGCGCTAAA 7080|
|GTACGTGATG|CGCTCAAGTG|GTCAAAAGAT|ATCAACGAAA|TGATCAATGC|CTTTGGTCAA 7140|

FIG. 4A-7

```
GATGTCGAAG TGCTGTTTGC CTCGCACTCT GCGCCAGTGT GGGGTAACCA AGCGGATCAAC 7200
GATTTCTTAC GCCTACAGCG TGATAACTAC GGCCTAGTGC ACAATCAAAC CTTGAGACTT 7260
GCCAACGATG GTGTCGGTAT ACAAGATATT GGCGATGCGA TTCAAGACAC GATTCCAGAG 7320
TCTATCTACA AGACGTGGCA TACCAATGGT TACCACGGCA CTTATAGCCA TAACGCTAAA 7380
GCGGTTTATA ACAAGTATCT AGGCTACTTC GATATGAACC CAGCCAACCT TAATCCGCTG 7440
CCAACCAAGC AAGAATCTGC CAAGTTTGTC GAATACATGG GCGGCGCAGA TGCCGCAATT 7500
AAGCGCGCTA AAGATGATTA CGCTCAAGGT GAATACCGCT TTGTTGCAAC GGCATTAAAT 7560
AAGGTGGTGA TGGCCGAGCC AGAAAATGAC TCCGCTCGTC AATTGCTAGC CGATACCTAT 7620
GAGCAACTTG GTTATCAAGC AGAAGGGGCT GGCTGGAGAA ACATTACTT AACTGGCGCA 7680
CAAGAGCTAC GAGTAGGTAT TCAAGCTGAT GCGCCTAAAA CCGCATCGGC AGATGTCATC 7740
AGTGAAATGG ACATGCCGAC TTCCTCGCGG TGAAGATTGA TAGTCAACAG 7800
GCGGCTAAGC ACGGCTTAGT TAAGATGAAT GTTATCACCC CTGATACTAA AGATATTCTC 7860
TATATTGAGC TAAGCAACGG TAACTTAAGC AACGCAGTGG TCGACAAAGA GCAAGCAGCT 7920
GACGCAAACC TTATGGTTAA TAAAGCTGAC GTTAACCGCA TCTTACTTGG CCAAGTAACC 7980
CTAAAAGCGT TATTAGCCAG CGGCGATGCC AAGCTCACTG GTGATAAAAC GGCATTAGT 8040
AAAATAGCCG ATAGCATGGT CGAGTTTACA CCTGACTTCG AAATCGTACC AACGCCTGTT 8100
AAATGAGGCA TTAATCTCAA CAAGTGCAAG CTAGACATAA AAATGGGGCG ATTAGACGCC 8160
```

FIG. 4A-8

```
CCATTTTTTA TGCAATTTTG AACTAGCTAG TCTTAGCTGA AGCTCGAACA ACAGCTTTAA 8220
AATTCACTTC TTCTGCTGCA ATACTTATTT GCTGACACTG ACCAATACTC AGTGCAAAAC 8280
GATAACTATC ATCAAGATGG CCCAGTAAAC AATGCCAATT ATCAGCAGCG TTCATTTGCT 8340
GTTCTTTAGC CTCAATCAAA CCTAAAACCAG ACTTTTGTGG CTCAGCGTTA GGCTTATTAG 8400
AACTCGACTC TAGTAAAGCA AGACCAATAT CTTGTTTTAA CAAAACCTGT CGCTGATTAA 8460
GTTGATGCTC AACCTTGTGA TCCGCAATAG CATCGGAAAT ATCAACACAA TGGCTCAAGC 8520
TTTTAGGTGC ATTAACTCCA AGAAAAGTTT CGCTCAGTGC AGAGAAGTCA AACGCAAAAG 8580
ATTTTAGCGA TAATGCCAGC CCAAGTCCTT TCGCTTTAAT GTAAGACTCC TTGAGCGCCC 8640
ACAAATCAAA AAAGCGGTCT CGCTGCAAGG CCTCTGGTAA CGCTAACAAG GCTCGCTTTT 8700
CTGATTCAGA GAAATAATGA CTAAGAATAG AGTGGATATT GGTGCTGTTA CGGCAACGCT 8760
CAATGTCGAC GCCAAACTCA ATACTAGCAG AGTCAGTTTC CTCCTTGCTT GCCTGACTGG 8820
CGCCTTTATT ATCAGCAGTG CAAATGCCTA CTAATAGCCA ATCTCCACTA TGACTCACAT 8880
TAAAGTGGAC CCCGGTTTGA GCAAATTGCG CATCACTCAA TCTAGGCTTA CCTTTGTCGC 8940
CATATTCAAA GCGCCATTCA TTGGGGCGTA TTTCACTATG TTGTGACAAT AAAGCGCGCA 9000
AATAGCCTCT TACCATTAAA CCTTGAGTTT TAGCTTCTTG TTTAATGTAG CGATTAACCT 9060
TAATTAACTC ATCTTCAGGC AGCCATGACT TAACCAACTC TGTAGTCTGG TTATCGCACT 9120
CTTGTATTGT TAACGGACAG AAGTATAAGG AAATCAATCG AGAAGTTAGC AATTTTTCAG 9180
```

FIG. 4A-9

```
GACACTCTTT AAAGCAACAA ACATAACCCC TATTTTTACC AATTTAAGAT CAAAACTAAA 9240
GCCAAAACTA ATTGAGAATA GTGTCAAACT AGCTTTAAAG GAAAAAAATA TAAAAGAAC 9300
ATTATACTTG TATAAATTAT TTTACACACC AAAGCCATGA TCTTCACAAA ATTAGCTCCC 9360
TCTCCCTAAA ACAAGATTGA ATAAAAAAAT AAACCCTTAAC TTTCATATAG ATAAAACAAA 9420
CCAATGGGAT AAAGTATATT GAATTCATTT TTAAGGAAAA ATTCAAATTG AATTCAAGCT 9480
CTTCAGTAAA AGCATATTTT GCCGTTAGTG TGAAAAAAAA CAAATTTAAA AACCAACATA 9540
GAACAAATAA GCAGACAATA AAACCAAGGC GCAACACAAA CAACGCGCTT ACAATTTTCA 9600
CAAAAAAGCA ACAAGAGTAA CGTTTAGTAT TTGGATATGG TTATTGTAAT TGAGAATTTT 9660
ATAACAATTA TATTAAGGGA ATGAGTATGT TTTTAAATTC AAAACTTTCG CGCTCAGTCA 9720
AACTTGCCAT ATCCGCAGGC TTAACAGCCT CGCTAGCTAT GCCTGTTTTT GCAGAAGAAA 9780
CTGCTGCTGA AGAACAAATA GAAAGAGTCG CAGTGACCGG ATCGCGAATC GCTAAAGCAG 9840
AGCTAACTCA ACCAGCTCCA GTCGTCAGCC TTTCAGCCGA AGAACTGACA AAATTTGGTA 9900
ATCAAGATTT AGGTAGCGTA CTAGCAGAAT TACCTGCTAT TGGTGCAACC AACACTATTA 9960
TTGGTAATAA CAATAGCAAC TCAAGGCGCAG GTGTTAGCTC AGCAGACTTG CGTCGTCTAG 10020
GTGCTAACAG AACCTTAGTA TTAGTCAACG GTAAGCGCTA CGTTGCCGGC CAACCGGGCT 10080
CAGCTGAGGT AGATTTGTCA ACTATACCAA CTAGCATGAT CTCGCGAGTT GAGATTGTAA 10140
CCGGCGGTGC TTCAGCAATT TATGGTTCGG ACGCTGTATC AGGTGTTATC AACGTTATCC 10200
```

FIG. 4A-10

```
TTAAAGAAGA  CTTTGAAGGC  TTTGAGTTTA  ACGCACGTAC  TAGCGGGTTCT  ACTGAAAGTG  10260
TAGGCACTCA  AGAGCACTCT  TTTGACATTT  TGGGTGGTGC  AAACGTTGCA  GATGGACGTG  10320
GTAATGTAAC  CTTCTACGCA  GGTTATGAAC  GTACAAAAGA  AGTCATGGCT  ACCGACATTC  10380
GCCAATTCGA  TGCTTGGGGA  ACAATTAAAA  ACGAAGCCGA  TGGTGGTGAA  GATGATGGTA  10440
TTCCAGACAG  ACTACGTGTA  CCACGAGTTT  ATTCTGAAAT  GATTAATGCT  ACCGGTGTTA  10500
TCAATGCATT  TGGTGGTGGA  ATTGGTCGCT  CAACCTTTGA  CAGTAACGGC  AATCCTATTG  10560
CACAACAAGA  ACGTGATGGG  ACTAACAGCT  TTGCATTTGG  TTCATTCCCT  AATGGCTGTG  10620
ACACATGTTT  CAACACTGAA  GCATACGAAA  ACTATATTCC  AGGGGTAGAA  AGAATAAACG  10680
TTGGCTCATC  ATTCAACTTT  GATTTACCG   ATAACATTCA  ATTTTACACT  GACTTCAGAT  10740
ATGTAAAGTC  AGATATATCAG  CAACAATTTC  AGCCTTCATT  CCGTTTTGGT  AACATTAATA  10800
TCAATGTTGA  AGATAAACGC  TTTTGAATG   ACGACTTGCG  TCAGCAAATG  CTCGATGCGG  10860
GTCAAACCAA  TGCTAGTTTT  GCCAAGTTTT  TTGATGAATT  AGGAAATCGC  TCAGCAGAAA  10920
ATAAACGCGA  ACTTTTCCGT  TACGTAGGTG  GCTTTAAAGG  TGGCTTTGAT  ATTAGCGAAA  10980
CCATATTTGA  TTACGACCTT  TACTATGTTT  ATGGCGAGAC  TAATAACCGT  CGTAAAACCC  11040
TTAATGACCT  AATTCCTGAT  AACTTTGTCG  CAGCTGTCGA  CTCTGTTATT  GATCCTGATA  11100
GTCAAACCAA  AGCGGTGTCGC  TCACAAGTAG  CAAGCGCTCA  AGGCGATGAC  TATACAGATC  11160
CCGCGTCTGT  GACTGTGTTG  CTTATAACCC  ATTTGGCATG  GGTCAAGCTT  11220
```

FIG. 4A-11

| | | | | |
|---|---|---|---|---|
| CAGCAGAAGC | CCGCGACTGG | GTTTCTGCTG | ATGTGACTCG | TGAAGACAAA ATAACTCAAC 11280 |
| AAGTGATTGG | TGGTACTCTC | GGTACCGATT | CTGAAGAACT | ATTTGAGCTT CAAGGTGGTG 11340 |
| CAATCGCTAT | GGTTGTTGGT | TTTGAATACC | GTGAAGAAAC | GTCTGGTTCA ACAACCGATG 11400 |
| AATTTACTAA | AGCAGGTTTC | TTGACAAGCG | CTGCAACGCC | AGATTCTTAT GGCGAATACG 11460 |
| ACGTGACTGA | GTATTTTGTT | GAGGTGAACA | TCCCAGTACT | AAAAGAATTA CCTTTTGCAC 11520 |
| ATGAGTTGAG | CTTTGACGGT | GCATACCGTA | ATGCTGATTA | CTCACATGCC GGTAAGACTG 11580 |
| AAGCATGGAA | AGCTGGTATG | TTCTACTCAC | CATTAGAGCA | ACTTGCATTA CGTGGTACGG 11640 |
| TAGGTGAAGC | AGTACGAGCA | CCAAACATTG | CAGAAGCCTT | TAGTCCACGC TCTCCTGGTT 11700 |
| TTGGCCGCGT | TTCAGATCCA | TGTGATGCAG | ATAACATTAA | TGACGATCCG GATCGCGTGT 11760 |
| CAAACTGTGC | AGCATTGGGG | ATCCCTCCAG | GATTCCAAGC | TAATGATAAC GTCAGTGTAG 11820 |
| ATACCTTATC | TGGTGGTAAC | CCAGATCTAA | AACCTGAAAC | ATCAACATCC TTTACAGGTG 11880 |
| GTCTTGTTTG | GACACCAACG | TTTGCTGACA | TTGTCAGTAG | CCACCCAGAC TGTGGCTGAT TATTATGATA 11940 |
| TTCAAATTGA | GGATGCTATT | TTGTCAGTAG | CCACCCAGAC | TGTGGCTGAT AACTGTGTTG 12000 |
| ACTCAACTGG | CGGACCTGAC | ACCGACTTCT | GTAGTCAAGT | TGATCGTAAT CCAACGACCT 12060 |
| ATGATATTGA | ACTTGTTCGC | TCTGGTTATC | TAAATGCCGC | GGCATTGAAT ACCAAAGGTA 12120 |
| TTGAATTTCA | AGCTGCATAC | TCATTAGATC | TAGAGTCTTT | CAACGCGCCT GGTGAACTAC 12180 |
| GCTTCAACCT | ATTGGGGAAC | CAATTACTTG | AACTAGAACG | TCTTGAATTC CAAAATCGTC 12240 |

FIG. 4A-12

```
CTGATGAGAT TAATGATGAA AAAGGCGAAG TAGGTGATCC AGAGCTGCAG TTCCGCCTAG 12300
GCATCGATTA CCGTCTAGAT GATCTAAGTG TTAGCTGGAA CACGCGTTAT ATTGATAGCG 12360
TAGTAACTTA TGATGTCTCT GAAAATGGTG GCTCTCCTGA AGATTATAT  CCAGGCCACA 12420
TAGGCTCAAT GACAACTCAT GACTTGAGCG CTACATACTA CATCAATGAG AACTTCATGA 12480
TTAACGGTGG TGTACGTAAC CTATTTGACG CACTTCCACC TGGATACACT AACGATGCGC 12540
TATATGATCT AGTTGGTCGC CGTGCATTCC TAGGTATTAA GGTAATGATG TAATTAATTA 12600
TTACGCCTCT AACTAATAAA AATGCAATCT CTTCGTAGAG ATTGCATTTT TTTATGAAAT 12660
CCAATCTTAA ACTGGTTCTC CGAGCATCTT ACGCCTTAAA AACCCCGCCC CTCAATGTAA 12720
CGCCAAAGTT AATTGCTTAC ACGCACTTAC ACAAACGAAC AATTTCATTA ACACGAGACA 12780
CAGCTCACGC TTTTTATTTT ACCCTTGATT TTACTACATA AAATTGCGTT TTAGCGCACA 12840
AGTGTTCTCC CAAGCTGGTC GTATCTGTAA TTATTCAGTC CCAGGTGATT GTATTGACCC 12900
ATAAGCTCAG GTAGTCTGCT CTGCCATTAG CTAAACAATA TTGACAAAAT GGCGATAAAA 12960
TGTGGCTTAG CGCTAAGTTC ACCGTAAGTT TTATCGGCAT TAAGTCCCAA CAGATTATTA 13020
ACGGAAACCC GCTAAACTGA TGGCAAAAAT AAATAGTGAA CACTTGGATG AAGCTACTAT 13080
TACTTCGAAT AAGTGTACGC AAACAGAGAC TGAGGCTCGG CATAGAAATG CCACTACAAC 13140
ACCTGAGATG CGCCGATTCA TACAAGAGTC GGATCTCAGT GTTAGCCAAC TGTCTAAAAT 13200
ATTAAATATC AGTGAAGCTA CCGTACGTAA GTGGCGCAAG CGTGACTCTG TCGAAAACTG 13260
```

FIG. 4A-13

```
TCCTAATACC CCGCACCATC TCAATACCAC GCTAACCCCT TTGCAAGAAT ATGTGGTTGT 13320
GGGCCTGCGT TATCAATTGA AAATGCCATT AGACAGATTG CTCAAAGCAA CCCAAGAGTT 13380
TATCAATCCA AACGTGTCGC GCTCAGGTTT AGCAAGATGT TTGAAGCGTT ATGGCGTTTC 13440
ACGGGTGAGT GATATCCAAA GCCCACACGT ACCAATGCGC TACTTTAATC AAATTCCAGT 13500
CACTCAAGGC AGCGATGTGC AAACCTACAC CCTGCACTAT GAAACGCTGG CAAAAACCTT 13560
AGCCTTACCT AGTACCGATG GTGACAATGT GGTGCAAGTG GTGTCTCTCA CCATTCCACC 13620
AAAGTTAACC GAAGAAGCAC CCAGTTCAAT TTTGCTCGGC ATTGATCCTC ATAGCGACTG 13680
GATCTATCTC GACATATACC AAGATGGCAA TACACAAGCC ACGAATAGAT ATATGGCTTA 13740
TGTGCTAAAA CACGGGCCAT TCCATTTACG AAAGTTACTC GTGCGTAACT ATCACACCTT 13800
TTTACAGCGC TTTCCTGGAG CGACGCAAAA TCGCCGCCCC TCTAAAGATA TGCCTGAAAC 13860
AATCAACAAG ACGCCTGAAA CACAGGCACC CAGTGGAGAC TCATAATGAG CCAGACCTCT 13920
AAACCTACAA ACTCAGCAAC TGAGCAAGCA CAAGACTCAC AAGCTGACTC TCGTTTAAAT 13980
AAACGACTAA AAGATATGCC AATTGCTATT GTTGGCATGG CGAGTATTTT TGCAAACTCT 14040
CGCTATTTGA ATAAGTTTTG GGACTTAATC AGCGAAAAAA TTGATGCGAT TACTGAATTA 14100
CCATCAACTC ACTGGCAGCC TGAAGAATAT TACGACGCAG ATAAAACCGC AGCAGACAAA 14160
AGCTACTGTA AACGTGGTGG CTTTTTGCCA GATGTAGACT TCAACCCAAT GGAGTTTGGC 14220
CTGCCGCCAA ACATTTTGGA ACTGACCGAT TCATCGCAAC TATTATCACT CATCGTTGCT 14280
```

FIG. 4A-14

```
AAAGAAGTGT TGGCTGATGC TAACTTACCT GAGAATTACG ACCGCGATAA AATTGGTATC 14340
ACCTTAGGTG TCGGCGGTGG TCAAAAAATT AGCCACAGCC TAACAGCGCG TCTGCAATAC 14400
CCAGTATTGA AGAAAGTATT CGCCAATAGC GGCATTAGTG ACACCGACAG CGAAATGCTT 14460
ATCAAGAAAT TCCAAGACCA ATATGTACAC TGGGAAGAAA ACTCGTTCCC AGGTTCACTT 14520
GGTAACGTTA TTGCGGGCCG TATCGCCAAC CGCTTCGATT TTGGCGGGCAT GAACTGTGTG 14580
GTTGATGCTG CCTGTGCTGG ATCACTTGCT GCTATGCGTA TGGCGCTAAC AGAGCTAACT 14640
GAAGGTCGCT CTGAAATGAT GATCACCGGT GGTGTGTGTA CTGATAACTC ACCCTCTATG 14700
TATATGAGCT TTTCAAAAAC GCCCGCCTTT ACCACTAACG AAACCATTCA GCCATTTGAT 14760
ATCGACTCAA AAGGCATGAT GATTGGTGAA GGTATTGGCA TGGTGGCGCT AAAGCGTCTT 14820
GAAGATGCAG AGCGCGATGG CGACCGCATT TACTCTGTAA TGGTGCATCA 14880
TCTGACGGTA AGTTTAAATC AATCTATGCC CCTCGCCCAT CAGGCCAAGC TAAAGCACTT 14940
AACCGTGCCT ATGATGACGC AGGTTTTGCG CCGCATACCT TAGGTCTAAT TGAAGCTCAC 15000
GGAACAGGTA CTGCAGCAGG TGACGCGGCA GAGTTTGCCG GCCTTTGCTC AGTATTGCT 15060
GAAGGCAACG ATACCAAGCA ACACATTGCG CTAGGTTCAG TTAAATCACA AATTGGTCAT 15120
ACTAAATCAA CTGCAGGTAC AGCAGGTTTA ATTAAAGCTG CTCTTGCTTT GCATCACAAG 15180
GTACTGCCGC CGACCATTAA CGTTAGTCAG CCAAGCCCTA AACTTGATAT CGAAAACTCA 15240
CCGTTTTATC TAAACACTGA GACTCGTCCA TGGTTACCAC GTGTTGATGG TACGCCCGCG 15300
```

FIG. 4A-15

```
CGCGCGGGTA TTAGCTCATT TGGTTTTGGT GGCACTAACT TCCATTTTGT ACTAGAAGAG 15360
TACAACCAAG AACACAGCCG TACTGATAGC GAAAAAGCTA AGTATCGTCA ACGCCAAGTG 15420
GCGCAAAGCT TCCTTGTTAG CGCAAGCGAT AAAGCATCGC TAATTAACGA GTTAAACGTA 15480
CTAGCAGCAT CTGCAAGCCA AGCTGAGTTT ATCCCTCAAAG ATGCAGCAGC AAACTATGGC 15540
GTACGTGAGC TTGATAAAAA TGCACCACGG ATCGGTTTAG TTGCAAACAC AGCTGAAGAG 15600
TTAGCAGGCC TAATTAAGCA AGCACTTGCC AAACTAGCAG CTAGCGATGA TAACGCATGG 15660
CAGCTACCTG GTGGCACTAG CTACCGCGCC AAGGTAAAGT TGCCGCACTG TTATTACCCA 15720
TTTGCTGGCC AAGGTTCACA ATATCTCAAT ACCTTACTTG TTATTACCCA 15780
GAGATGCGTC AGCAATTTGT AACTGCAGAT AAAGTATTTG CCGCAAATGA TAAAACGCCG 15840
TTATCGCAAA CTCTGTATCC AAAGCCTGTA TTTAATAAAG ATGAATTAAA GGCTCAAGAA 15900
GCCATTTTGA CCAATACCGC CAATGCCCAA AGCGCAATTG GTGCGATTTC AATGGGTCAA 15960
TACGATTTGT TTACTGCGGC TGGCTTTAAT GCCGACATGG TTGCAGGCCA TAGCTTTGGT 16020
GAGCTAAGTG CACTGTGTGC TGCAGGTGTT ATTTCAGCTG ATGACTACTA CAAGCTGGCT 16080
TTTGCTCGTG GTGAGGCTAT GGCAACAAAA GCACCGGCTA AAGACGGCGT TGAAGCC 16140
GCAGGAGCAA TGTTTGCAAT CATAACCAAG AGTGCTGCAG ACCTTGAAAC CGTTGAAGCC 16200
ACCATCGCTA AATTTGATGG GGTGAAAGTC GCTAACTATA ACGCGCCAAC GCAATCAGTA 16260
ATTGCAGGCC CAACAGCAAC TACCGCTGAT GCGGCTAAAG CGCTAACTGA GCTTGGTTAC 16320
```

FIG. 4A-16

```
AAAGCGATTA ACCTGCCAGT ATCAGGTGCA TTCCACACTG AACTTGTTGG TCACGCTCAA  16380
GCGCCATTTG CTAAAGCGAT TGACGCAGCC AAATTTACTA AAACAAGCCG AGCACTTTAC  16440
TCAAATGCAA CTGGCGGACT TTATGAAAGC ACTGCTGCAA AGATTAAAGC CTCGTTTAAG  16500
AAACATATGC TTCAATCAGT GCGCTTTACT AGCCAGCTAG AAGCCATGTA CAACGACGGC  16560
GCCCGTGTAT TTGTTGAATT TGGTCCAAAG AACATCTTAC AAAAATTAGT TCAAGGCACG  16620
CTTGTCAACA CTGAAAAATGA AGTTTGCACT ATCTCTATCA ACCCTAATCC TAAAGTTGAT  16680
AGTGATCTGC AGCTTAAGCA AGCAGCAATG CAGCTAGCGG TTACTGGTGT GGTACTCAGT  16740
GAAATTGACC CATACCAAGC CGATATATGCC GCACCAGCGA AAAAGTCGCC AATGAGCATT  16800
TCGCTTAATG CTGCTAACCA TATCAGCAAA GCAACTCGCG CTAAGATGGC CAAGTCTTTA  16860
GAGACAGGTA TCGTCACCTC GCAAATAGAA CATGTTATTG AAGAAAAAAT CGTTGAAGTT  16920
GAGAAACTGG TTGAAGTCGA AAAGATCGTC GAAAAAGTGG TTGAAGTAGA GAAAGTTGTT  16980
GAGGTTGAAG CTCCTGTTAA TTCAGTGCAA GCCAATGCAA TTCAAACCCG TTCAGTTGTC  17040
GCTCCAGTAA TAGAGAACCA AAAAACAGTA AGCCAGCAGT CCAGAGCATT  17100
AGTGGTGATG CACTCAGCAA CTTTTTTGCT GCACAGCAGC AAACCGCACA GTTGCATCAG  17160
CAGTTCTTAG CTATTCCGCA GCAATATGGT GAGACGTTCA CTACGCTGAT GACCGAGCAA  17220
GCTAAACTGG CAAGTTCTGG TGTTGCAATT CCAGAGAGTC TGCAACGCTC AATGGAGCAA  17280
TTCCACCAAC TACAAGCGCA AACACTACAA AGCCACACCC AGTTCCTTGA GATGCAAGCG  17340
```

FIG. 4A-17

| | | | | |
|---|---|---|---|---|
| GGTAGCAACA | TTGCAGCGTT | AAACCTACTC | AATAGCAGCC | AAGCAACTTA | CGCTCCAGCC | 17400 |
| ATTCACAATG | AAGCGATTCA | AAGCCAAGTG | GTTCAAAGCC | AAACTGCAGT | CCAGCCAGTA | 17460 |
| ATTTCAACAC | AAGTTAACCA | TGTGTCAGAG | CAGCCAACTC | AAGCTCCAGC | TCCAAAAGCG | 17520 |
| CAGCCAGCAC | CTGTGACAAC | TGCAGTTCAA | ACTGCTCCGG | CACAAGTTGT | TCGTCAAGCC | 17580 |
| GCACCAGTTC | AAGCCGCTAT | TGAACCGATT | AATACAAGTG | TTGCGACTAC | AACGCCTTCA | 17640 |
| GCCTTCAGCG | CCGAAACAGC | CCTGAGCGCA | ACAAAAGTCC | AAGCCACTAT | GCTTGAAGTG | 17700 |
| GTTGCTGAGA | AAACCGGTTA | CCCAACTGAA | ATGCTAGAGC | TTGAAATGGA | TATGGAAGCC | 17760 |
| GATTTAGGCA | TCGATTCTAT | CAAGCGTGTA | GAAATTCTTG | GCACAGTACA | AGATGAGCTA | 17820 |
| CCGGGTCTAC | CTGAGCTTAG | CCCTGAAGAT | CTAGCTGAGT | GTCGAACGCT | AGGCGAAATC | 17880 |
| GTTGACTATA | TGGGCAGTAA | ACTGCCGGCT | GAAGGCTCTA | TGAATTCTCA | GCTGTCTACA | 17940 |
| GGTTCCGCAG | CTGCGACTCC | TGCAGCGAAT | GGTCTTTTCTG | CGGAGAAAGT | TCAAGCGACT | 18000 |
| ATGATGTCTG | TGGTTGCCGA | AAAGACTGGC | TACCCAACTG | AAATGCTAGA | GCTTGAAATG | 18060 |
| GATATGGAAG | CCGATTTAGG | CATAGATTCT | ATCAAGCGCG | TTGAAATTCT | TGGCACAGTA | 18120 |
| CAAGATGAGC | TACCGGGTCT | ACCTGAGCTT | AGCCCTGAAG | ATCTAGCTGA | GTGTCGTACT | 18180 |
| CTAGGCGAAA | TCGTTGACTA | TATGAACTCT | AAACTCGCTG | ACGGCTCTAA | GCTGCCGGCT | 18240 |
| GAAGGCTCTA | TGAATTCTCA | GCTGTCTACA | AGTGCCGCAG | CTGCGACTCC | TGCAGCGAAT | 18300 |
| GGTCTCTCTG | CGGAGAAAGT | TCAAGCGACT | ATGATGTCTG | TGGTTGCCGA | AAAGACTGGC | 18360 |

FIG. 4A-18

```
TACCCAACTG AAATGCTAGA ACTTGAAATG GATATGGAAG CTGACCTTGG CATCGATTCA 18420
ATCAAGCGCG TTGAAATTCT TGGCACAGTA CAAGATGAGC TACCGGGTTT ACCTGAGCTA 18480
AATCCAGAAG ATTTGGCAGA GTGTCGTACT CTTGGCGAAA TCGTGACTTA TATGAACTCT 18540
AAACTCGCTG ACGGCTCTAA GCTGCCAGCT GAAGGCTCTA TGCACTATCA GCTGTCTACA 18600
AGTACCGCTG CTGCGACTCC TGTAGCGAAT GGTCTCTCTG CAGAAAAAGT TCAAGCGACC 18660
ATGATGTCTG TAGTTGCAGA TAAAAACTGG TACCCAACTG AAATGCTTGA ACTTGAAATG 18720
GATATGGAAG CCGATTTAGG TATCGATTCT ATCAAGCGCG TTGAAATTCT TGGCACAGTA 18780
CAAGATGAGC TACCGGGTTT ACCTGAGCTA AATCCAGAAG ATCTAGCAGA GTGTCGCACC 18840
CTAGGCGAAA TCGTTGACTA TATGGGCAGT AAACTGCCGG CTGAAGGCTC TGCTAATACA 18900
AGTGCCGCTG CGTCTCTTAA TGTTAGTGCC GTTGCGGCGC CTCAAGCTGC TGCGACTCCT 18960
GTATCGAACG GTCTCTCTGC AGAGAAAGTG CAAAGCACTA TGATGTCAGT AGTTGCAGAA 19020
AAGACCGGCT ACCCAACTGA AATGCTAGAA CTTGGCATGG ATATGGAAGC CGATTTAGGT 19080
ATCGACTCAA TTAAACGCGT TGAGATTCTT GGCACAGTAC AAGATGAGCT ACCGGGTCTA 19140
CCAGAGCTTA ATCCTGAAGA TTTAGCTGAG TGCCGTACGC TGGGCGAAAT CGTTGACTAT 19200
ATGAACTCTA AGCTGGCTGA CGGCTCTAAG CTTCCAGCTG AAGGCTCTGC TAATACAAGT 19260
GCCACTGCTG CGACTCCTGC AGTGAATGGT CTTTCTGCTG ACAAGGTACA GGGCGACTATG 19320
ATGTCTGTAG TTGCTGAAAA GACCGGCTAC CCAACTGAAA TGCTAGAACT TGGCATGGAT 19380
```

FIG. 4A-19

```
ATGGAAGCAG ACCTTGGTAT TGATTCTATT AAGCGCGTTG AAATTCTTGG CACAGTACAA 19440
GATGAGCTCC CAGGTTTACC TGAGCTTAAT CCTGAAGATC TCGCTGAGTG CCGCACGCTT 19500
GGCGAAATCG TTAGCTATAT GAACTCTCAA CTGGCTGATG GCTCTAAACT TTCTACAAGT 19560
GCGGCTGAAG GCTCTGCTGA TACAAGTGCT GCAAATGCTG CAAAGCCGGC AGCAATTTCG 19620
GCAGAACCAA GTGTTGAGCT TCCTCCTCAT AGCGAGGTAG CGCTAAAAAA GCTTAATGCG 19680
GCGAACAAGC TAGAAAATTG TTTCGCCGCA GACGCAAGTG TTGTGATTAA CGATGATGGT 19740
CACAACGCAG GCGTTTTAGC TGAGAAACTT ATTAAACAAG GCCTAAAAGT AGCCGTTGTG 19800
CGTTTACCGA AAGGTCAGCC TCAATCGCCA CTTTCAAGCG ATGTTGCTAG CTTTGAGCTT 19860
GCCTCAAGCC AAGAATCTGA GCTTGAAGCC CAGTTATCGC CAGAAGCGAA GCAGATTGAA 19920
ACTCAGGTTG GCGCTATTGG TGGCTTTATT CACTTGCAAC CAGAAGCGAA TACAGAAGAG 19980
CAAACGGCAG TAAACCTAGA TGCGCAAAGT TTTACTCACG TTAGCAATGC GTTCTTGTGG 20040
GCCAAATTAT TGCAACCAAA GCTCGTTGCT GGAGCAGATG CGCGTCGCTG TTTTGTAACA 20100
GTAAGCCGTA TCGACGGTGG CTTTGGTTAC CTAAATACTG ACGCCCTAAA AGATGCTGAG 20160
CTAAACCAAG CAGCATTAGC TGGTTTAACT AAAACCTTAA GCCATGAATG GCCACAAGTG 20220
TTCTGTCGCG CGCTAGATAT TGCAACAGAT GTTGATGCAA CCCATCTTGC TGATGCAATC 20280
ACCAGTGAAC TATTTGATAG CCAAGCTCAG CTACCTGAAG TGGGCTTAAG CTTAATTGAT 20340
GGCAAAGTTA ACCGCGTAAC TCTAGTTGCT GCTGAAGCTG CAGATAAAAC AGCAAAAGCA 20400
```

FIG. 4A-20

```
GAGCTTAACA GCACAGATAA AATCTTAGTG ACTGGTGGGG CAAAAGGGGT GACATTTGAA 20460
TGTGCACTGG CATTAGCATC TCGCAGCCAG TCTCACTTTA TCTTAGCTGG GCGCAGTGAA 20520
TTACAAGCTT TACCAAGCTG GGCTGAGGGT AAGCAAACTA GCGAGCTAAA ATCAGCTGCA 20580
ATCGCACATA TTATTTCTAC TGGTCAAAAG CCAACGCCTA AGCAAGTTGA AGCCGCTGTG 20640
TGGCCAGTGC AAAGCAGCAT TGAAATTAAT GCCGCCCTAG CCGCCTTTAA CAAAGTTGGC 20700
GCCTCAGCTG AATACGTCAG ACCGATAGCG CCGCAATCAC AGCAGCACTT 20760
AATGGTCGCT CAAATGAGAT CACCGGTCTT ATTCATGGCG CAGGTGTACT AGCCGACAAG 20820
CATATTCAAG ACAAGACTCT TGCTGAACTT GCTAAAGTTT ATGGCACTAA AGTCAACGGC 20880
CTAAAAGCGC TGCTCGCGGC ACTTGAGCCA AGCAAAAATTA AATTACTTGC TATGTTCTCA 20940
TCTGCAGCAG GTTTTTACGG TAATATCGGC CAAAGCGATT ACGCGATGTC GAACGATATT 21000
CTTAACAAGG CAGCGCTGCA GTTCACCGCT CGCAACCCAC AAGCTAAAGT CATGAGCTTT 21060
AACTGGGGTC CTTGGGATGG CGGCATGGTT AACCCAGCGC TTAAAAAGAT GTTTACCGAG 21120
CGTGGTGTGT ACGTTATTCC ACTAAAAGCA GGTGCAGAGC TATTTGCCAC TCAGCTATTG 21180
GCTGAAACTG GCGTGCAGTT GCTCATTGGT ACGTCAATGC AAGGTGGCAG CGACACTAAA 21240
GCAACTGAGA CTGCTTCTGT AAAAAAGCTT AATGCGGGTG AGGTGCTAAG TGCATCGCAT 21300
CCGCGTGCTG GTGCACAAAA AACACCACTA CAAGCTGTCA CTGCAACGCG TCTGTTAACC 21360
CCAAGTGCCA TGGTCTTCAT TGAAGATCAC CGCATTGGCG GTAACAGTGT GTTGCCAACG 21420
```

FIG. 4A-21

```
GTATGCGCCA TCGACTGGAT GCGTGAAGCG GCAAGCGACA TGCTTGGCGC TCAAGTTAAG 21480
GTACTTGATT ACAAGCTATT AAAAGGCATT GTATTTGAGA CTGATGAGCC GCAAGAGTTA 21540
ACACTTGAGC TAACGCCAGA CGATTCAGAC GAAGCTACGC TACAAGCATT AATCAGCTGT 21600
AATGGGCGTC CGCAATACAA GGCGACGCTT ATCAGTGATA ATGCCGATAT TAAGCAACTT 21660
AACAAGCAGT TTGATTTAAG CGCTAAGGCG ATTACCACAG CAAAAGAGCT TTATAGCAAC 21720
GGCACCTTGT TCCACGGTCC GGCTCTACAA GGGATCCAAT CTGTAGTGCA GTTCGATGAT 21780
CAAGGCTTAA TTGCTAAAGT CGCTCTGCCT AAGGTTGAAC TTAGCGATTG TGGTGAGTTC 21840
TTGCCGCAAA CCCACATGGG TGGCAGTCAA CCTTTTGCTG AGGACTTGCT ATTACAAGCT 21900
ATGCTGGTTT GGGCTCGCCT TAAAAACTGGC TCGGCAAGTT TGCCATCAAG CATTGGTGAG 21960
TTTACCTCAT ACCAACCAAT GGCCTTTGGT GAAACTGGTA CCATAGAGCT TGAAGTGATT 22020
AAGCACAACA AACGCTCACT TGAAGCGAAT GTTGCGCTAT ATCGTGACAA CGGCGAGTTA 22080
AGTGCCATGT TTAAGTCAGC TTAAGTCAGC TAAAATCACC ATTAGCAAAA GCTTAAATTC AGCATTTTTA 22140
CCTGCTGTCT TAGCAAACGA CAGTGAGGCG AATTAGTGGA ACAAACGCCT AAAGCTAGTG 22200
CGATGCCGCT GCGCATCGCA CTTATCTTAC TGCCAACACC GCAGTTTGAA GTTAACTCTG 22260
TCGACCAGTC AGTATTAGCC AGCTATCAAA CACTGCAGCC TGAGCTAAAT GCCCTGCTTA 22320
ATAGTGCGCC GACACCTGAA ATGCTCAGCA TCACTATCTC AGATGATAGC GATGCAAACA 22380
GCTTTGAGTC GCAGCTAAAT GCTGCGACCA ACGCAATTAA CAATGGCTAT ATCGTCAAGC 22440
```

FIG. 4A-22

```
TTGCTACGGC AACTCACGCT TTGTTAATGC TGCCTGCATT AAAAGCGGCG CAAATGCGGA 22500
TCCATCCTCA TGCGCAGCTT GCCGCTATGC AGCAAGCTAA ATCGACGCCA ATGAGTCAAG 22560
TATCTGGTGA GCTAAAGCTT GGCGCTAATG CGCTAAGCCT AGCTCAGACT AATGCGCTGT 22620
CTCATGCTTT AAGCCAAGCC AAGCGTAACT TAACTGATGT CAGGCGTGAAT GAGTGTTTTG 22680
AGAACCTCAA AAGTGAACAG CAGTTCACAG AGGTTTATTC GCTTATTCAG CAACTTGCTA 22740
GCCGCACCCA TGTGAGAAAA GAGGTTAATC AAGGTGTGGA ACTTGGCCCT AAACAAGCCA 22800
AAAGCCACTA TTGGTTTAGC GAATTTCACC TGCTGCCATC AACTTTATTA 22860
ATGGCCAACA AGCAACCAGC TATGTGCTTA CTCAAGGTTC AGGATTGTTA GCTGCGAAAT 22920
CAATGCTAAA CCAGCAAAGA TTAATGTTTA TCTTGCCGGG TAACAGTCAG CAACAAATAA 22980
CCGCATCAAT AACTCAGTTA ATGCAGCAAT TAGAGCGTTT GCAGGTAACT GAGGTTAATG 23040
AGCTTTCTCT AGAATGCCAA CTAGAGCTGC TCAGCATAAT GTATGACAAC TTAGTCAACG 23100
CAGACAAACT CACTACTCGC GATAGTAAGC CCGCTTATCA GGCTGTGATT CAAGCAAGCT 23160
CTGTTAGCGC TGCAAAGCAA GAGTTAAGCG CGCTTAACGA TGCACTCACA GCGCTGTTTG 23220
CTGAGCAAAC AAACGCCACA TCAACGAATA AAGGCTTAAT CCAATACAAA ACACCGGCGG 23280
GCAGTTACTT AACCCTAACA CCGCTTGGCA GCAACAATGA CAACGCCCAA GCGGGTCTTG 23340
CTTTGTCTA TCCGGGTGTG ACGCCGATAT GCTTAATGAG CTGCATCAGT 23400
ACTTCCCTGC GCTTTACGCC AAACTTGAGC GTGAAGGCGA TTTAAAGGCG ATGCTACAAG 23460
```

FIG. 4A-23

```
CAGAAGATAT CTATCATCTT GACCCTAAAC ATGCTGCCCA AATGAGCTTA GGTGACTTAG 23520
CCATTGCTGG CGTGGGGAGC AGCTACCTGT TAACTCAGCT GCTCACCGAT GAGTTTAATA 23580
TTAAGCCTAA TTTTGCATTA GGTTACTCAA TGGGTGAAGC ATCAATGTGG GCAAGCTTAG 23640
GCGTATGGCA AAACCCGCAT GCGCTGATCA GCAAAACCCA AACCGACCCG CTATTTACTT 23700
CTGCTATTTC CGGCAAATTG ACCGGGTTA GCAAGCTTG GCAGCTTGAT GATACCGCAG 23760
CGGAAATCCA GTGGAATAGC TTTGTGGTTA GAAGTGAAGC AGCGCCGATT GAAGCCTTGC 23820
TAAAAGATTA CCCACACGCT TACCTCGCGA TTATTCAAGG GGATACCTGC GTAATCGCTG 23880
GCTGTGAAAT CCAATGTAAA GCGCTACTTG CAGCACTGGG TAAACGCGGT ATTGCAGCTA 23940
ATCGTGTAAC GGCGATGCAT ACGCAGCCTG CGATGCAAGA GCATCAAAAT GTGATGGATT 24000
TTTATCTGCA ACCGTTAAAA GCAGAGCTTC CTAGTGAAAT AAGCTTTATC AGCGCCGCTG 24060
ATTAACTGC CAAGCAAACG GTGAGTGAGC AAGCACTTAG CAGCCAAGTC GTTGCTCAGT 24120
CTATTGCCGA CACCTTCTGC CAAACCCTTGG ACTTTACCGC GCTAGTACAT CACGCCCAAC 24180
ATCAAGGCGC TAAGCTGTTT GTTGAAATTG GCGCGGATAG ACAAAACTGC ACCTTGATAG 24240
ACAAGATTGT TAAACAAGAT GGTGCCAGCA GTGTACAACA TCAACCTTGT TGCACAGTGC 24300
CTATGAACGC AAAAGGTAGC CAAGATATTA CCAGCCGTGAT TAAAGCGCTT GGCCAATTAA 24360
TTAGCCATCA GGTGCCATTA TCGGTGCAAC CATTTATTGA TGGACTCAAG CGCGAGCTAA 24420
CACTTTGCCA ATTGACCAGC CAACAGCTGG CAGCACATGC AAATGTTGAC AGCAAGTTTG 24480
```

FIG. 4A-24

```
AGTCTAACCA AGACCATTTA CTTCAAGGGG AAGTCTAATG TCATTACCAG ACAATGCTTC 24540
TAACCACCTT TCTGCCAACC AGAAAGGCGC ATCTCAGGCA AGTAAAACCA GTAAGCAAAG 24600
CAAAATCGCC ATTGTCGGTT TAGCCACTCT GTATCCAGAC GCTAAAACCC CGCAAGAATT 24660
TTGGCAGAAT TTGCTGGATA AACGCGACTC TCGCAGCACC TTAACTAACG AAAAACTCGG 24720
CGCTAACAGC CAAGATTATC AAGGTGTGCA AGGCCAATCT GACCGTTTTT ATTGTAATAA 24780
AGGCGGCTAC ATTGAGAACT TCAGCTTTAA TGCTGCAGGC TACAAATTGC CGGAGCAAAG 24840
CTTAAATGGC TTGGACGACA GCTTCCTTTG GGCGCTCGAT ACTAGCCGTA ACGCACTAAT 24900
TGATGCTGGT ATTGATATCA ACGGCGCTGA TTTAAGCCGC GCAGGTGTAG TCATGGGCGC 24960
GCTGTCGTTC CCAACTACCC GCTCAAACGA TCTGTTTTTG CCAATTTATC ACAGCGCCGT 25020
TGAAAAAGCC CTGCAAGATA AACTAGGCGT AAAGGCATTT AAGCTAAGCC CAACTAATGC 25080
TCATACCGCT CGCGCGGCAA ATGAGAGCAG CCTAAAATGCA GCCAATGGTG CCATTGCCCA 25140
TAACAGCTCA AAAGTGGTGG CCGATGCACT TGGCCTTGGC GGCGCACAAC TAAGCCTAGA 25200
TGCTGCCTGT GCTAGTTCGG TTTACTCATT AAAGCTTGCC TGCGATTACC TAAGCACTGG 25260
CAAAGCCGAT ATCATGCTAG CAGGCGCAGT ATCTGGCGCG CCATGGTATC TCAGTACCGT 25320
GGGATTCTCA ATCTTCCACG CCTACCCAGA CCATGGTATC TCAGTACCGT TTATTAATAT 25380
```

```
AGTCTAACCA AGACCATTTA CTTCAAGGGG AAGTCTAATG TCATTACCAG ACAATGCTTC 24540
TAACCACCTT TCTGCCAACC AGAAAGGCGC ATCTCAGGCA AGTAAAACCA GTAAGCAAAG 24600
CAAAATCGCC ATTGTCGGTT TAGCCACTCT GTATCCAGAC GCTAAAACCC CGCAAGAATT 24660
TTGGCAGAAT TTGCTGGATA AACGCGACTC TCGCAGCACC TTAACTAACG AAAAACTCGG 24720
CGCTAACAGC CAAGATTATC AAGGTGTGCA AGGCCAATCT GACCGTTTTT ATTGTAATAA 24780
AGGCGGCTAC ATTGAGAACT TCAGCTTTAA TGCTGCAGGC TACAAATTGC CGGAGCAAAG 24840
CTTAAATGGC TTGGACGACA GCTTCCTTTG GGCGCTCGAT ACTAGCCGTA ACGCACTAAT 24900
TGATGCTGGT ATTGATATCA ACGGCGCTGA TTTAAGCCGC GCAGGTGTAG TCATGGGCGC 24960
GCTGTCGTTC CCAACTACCC GCTCAAACGA TCTGTTTTTG CCAATTTATC ACAGCGCCGT 25020
TGAAAAAGCC CTGCAAGATA AACTAGGCGT AAAGGCATTT AAGCTAAGCC CAACTAATGC 25080
TCATACCGCT CGCGCGGCAA ATGAGAGCAG CCTAAAATGCA GCCAATGGTG CCATTGCCCA 25140
TAACAGCTCA AAAGTGGTGG CCGATGCACT TGGCCTTGGC GGCGCACAAC TAAGCCTAGA 25200
TGCTGCCTGT GCTAGTTCGG TTTACTCATT AAAGCTTGCC TGCGATTACC TAAGCACTGG 25260
CAAAGCCGAT ATCATGCTAG CAGGCGCAGT ATCTGGCGCG CCATGGTATC GATCCTTTCT 25320
GGGATTCTCA ATCTTCCACG CCTACCCAGA CCATGGTATC TCAGTACCGT TTATTAATAT 25380
CAGTAAAGGT TTGTTTGCTG GCGAAGGCGC TGGCGTATTA TGGCGTAGGTC TTGATGCCAG 25440
TGCCGAGCGC GACAATGACA AAATCTATGC GGTTGTTAGC GGCGTAGGTC GTCTTGAAGA 25500
```

FIG. 4A-25

```
CGGTAAAGGC CAGTTTGTAT TAAGCCCTAA TCCAAAAGGT CAGGTGAAGG CCTTTGAACG 25560
TGCTTATGCT GCCAGTGACA TTGAGCCAAA AGACATTGAA GTGATTGAGT GCCACGCAAC 25620
AGGCACACCG CTTGGCGATA AAATTGAGCT CACTTCAATG GAAACCTTCT TTGAAGACAA 25680
GCTGCAAGGC ACCGATGCAC CGTTAATTGG CTCAGCTAAG TCTAACTTAG GCCACCTATT 25740
AACTGCAGCG CATGCGGGGA TCATGAAGAT GATCTTCGCC ATGAAAGAAG GTTACCTGCC 25800
GCCAAGTATC AATATTAGTG ATGCTATCGC TTCGCCGAAA AAACTCTTCG GTAAACCAAC 25860
CCTGCCTAGC ATGGTTCAAG GCTGGCCAGA TAAGCCATCG AATAATCATT TTGGTGTAAG 25920
AACCCGTCAC GCAGGGCGTAT CGGTATTTGG CTTTGGTGGC TGTAACGCCC ATCTGTTGCT 25980
TGAGTCATAC AACGGCAAAG GAACAGTAAA GGCAGAAGCC ACTCAAGTAC CGCGTCAAGC 26040
TGAGCCGCTA AAAGTGGTTG GCCTTGCCTC GCACTTTGGG CCTCTTAGCA GCATTAATGC 26100
ACTCAACAAT GCTGTGACCC AAGATGGGAA TGGCTTTATC GAACTGCCGA AAAAGCGCTG 26160
GAAAGGCCTT GAAAAGCACA GTGAACTGTT AGCTGAATTT GGCTTAGCAT CTGCGCCAAA 26220
AGGTGCTTAT GTTGATAACT TCGAGCTGGA CTTTTTACGC TTTAAACTGC CGCCAAACGA 26280
AGATGACCGT TTGATCTCAC AGCAGCTAAT GCTAATGCGA GTAACAGACG AAGCCATTCG 26340
TGATGCCAAG CTTGAGCCGG GGCAAAAAGT AGCTGTATTA GTGGCAATGG AAACTGAGCT 26400
TGAACTGCAT CAGTTCCGCG GCCGGGTTAA CTTGCATACT CAATTAGCGC AAAGTCTTGC 26460
CGCCATGGGC GTGAGTTTAT CAACGGATGA ATACCAAGCG CTTGAAGCCA TCGCCATGGA 26520
```

FIG. 4A-26

```
CAGCCGTGCTT GATGCTGCCA AGCTCAATCA GTACACCAGC TTTATTGGTA ATATTATGGC 26580
GTCACGCCGTG GCGTCACTAT GGGACTTTAA TGGCCCAGCC TTCACTATTT CAGCAGCAGA 26640
GCAATCTGTG AGCCGCTGTA TCGATGTGGC GCAAAACCTC ATCATGGAGG ATAACCTAGA 26700
TGCGGGTGGTG ATTGCAGCGG TCGATCTCTC TGGTAGCTTT GAGCAAGTCA TTCTTAAAAA 26760
TGCCATTGCA CCTGTAGCCA TTGAGCCAAA CCTCGAAGCA AGCCTTAATC CAACATCAGC 26820
AAGCTGGAAT GTCGGTGAAG GTGCTGGCGC GGTCGTGCTT GTTAAAAATG AAGCTACATC 26880
GGGCTGCTCA TACGGCCAAA TTGATGCACT TGGCTTTGCT AAAAACTGCCG AAACAGCGTT 26940
GGCTACCGAC AAGCTACTGA CACAGACTGC CACAGACTTT AATAAGGTTA AAGTGATTGA 27000
AACTATGGCA GCGCCTGCTA GCCAAATTCA ATTAGCGCCA ATAGTTAGCT CTCAAGTGAC 27060
TCACACTGCT GCAGAGCAGC GTGTTGGTCA CTGCTTTGCT GCAGCGGGTA TGGCAAGCCT 27120
ATTACACGGC TTACTTAACT TAAATACTGT AGCCCAAACC AATAAAGCCA ATTGCGCGCT 27180
TATCAACAAT ATCAGTGAAA ACCAATTATC ACAGCTGTTG ATTAGCCAAA CAGCGAGCGA 27240
ACAACAAGCA TTAACCGCGC GTTTAAGCAA TGAGCTTAAA TCCGATGCTA AACACCAACT 27300
GGTTAAGCAA GTCACCTTAG GTGGCCGTGA TATCTACCAG CATATTGTTG ATACACCGCT 27360
TGCAAGCCTT GAAAGCATTA CTCAGAAAATT GGCGCAAGCG ACAGCATCGA CAGTGGTCAA 27420
CCAAGTTAAA CCTATTAAGG CCGCTGGCTC AGTCGAAATG GCTAACTCAT TCGAAACGGA 27480
AAGCTCAGCA GAGCCACAAA TAACAATTGC AGCACAACAG ACTGCAAACA TTGGGGTCAC 27540
```

FIG. 4A-27

```
CGCTCAGGCA ACCAAACGTG AATTAGGTAC CCCACCAATG ACAACAAATA CCATTGCTAA 27600
TACAGCAAAT AATTTAGACA AGACTCTTGA GACTGTTGCT GGCAATACTG TTGCTAGCAA 27660
GGTTGGCTCT GGCGACATAG TCAATTTTCA ACAGAACCAA CAATTGGCTC AACAAGCTCA 27720
CCTCGCCTTT CTTGAAAGCC GCAGTGCGGG TATGAAGGTG GCTGATGCTT TATTGAAGCA 27780
ACAGCTAGCT CAAGTAACAG GCCAAAACTAT CGATAATCAG GCCCTCGATA CTCAAGCCGT 27840
CGATACTCAA ACAAGCGAGA ATGTAGCGAT TGCCGCAGAA TCACCAGTTC AAGTTACAAC 27900
ACCTGTTCAA GTTACAACAC CTGTTCAAAT CAGTGTTGTG GAGTTAAAAC CAGATCACGC 27960
TAATGTGCCA CCATACACGC CGCCAGTGCC TGCATTAAAG CCGTGTATCT GGAACTATGC 28020
CGATTTAGTT GAGTACGCAG AAGGCGATAT CGCCAAGGTA TTTGGCAGTG ATTATGCCAT 28080
TATCGACAGC TACTCGCGCC GCGTACGTCT ACCGACCACT GACTACCTGT TGGTATCGCG 28140
CGTGACCAAA CTTGATGCGA CCATCAATCA ATTTAAGCCA TGCTCAATGA CCACTGAGTA 28200
CGACATCCCT GTTGATGCGC CGTACTTAGT AGACGGACAA ATCCCCTTGGG CGGTAGCAGT 28260
AGAATCAGGC CAATGTGACT TGATGCTTAT TAGCTATCTC GGTATCGACT TTGAGAACAA 28320
AGGCGAGCGG GTTTATCGAC TACTCGATTG TACCCTCACC TTCCTAGGCG ACTTGCCACG 28380
TGGCGGAGAT ACCCTACGTT ACGACATTAA GATCAATAAC TATGCTCGCA ACGGCGACAC 28440
CCTGCTGTTC TTCTTCTCGT ATGAGTGTTT TGTTGGCGAC AAGATGATCC TCAAGATGGA 28500
TGGCGGCTGC GCTGGCTTCT TCACTGATGA AGAGCTTGCC GACGGTAAAG GCGTGATTCG 28560
```

FIG. 4A-28

```
CACAGAAGAA GAGATTAAAG CTCGCAGCCT AGTGCAAAAG CAACGCTTTA ATCCGTTACT 28620
AGATTGTCCT AAAACCCAAT TTAGTTATGG TGATATTCAT AAGCTATTAA CTGCTGATAT 28680
TGAGGGTTGT TTTGGCCCAA GCCACAGTGG CGTCCACCAG CCGTCACTTT GTTTCGCATC 28740
TGAAAAATTC TTGATGATTG AACAAGTCAG CAAGGTTGAT CGCACTGGCG GTACTTGGGG 28800
ACTTGGCTTA ATTGAGGGTC ATAAGCAGCT TGAAGCAGAC CACTGGTACT TCCCATGTCA 28860
TTTCAAGGGC GACCAAGTGA TGGCTGGCTC GCTAATGGCT GAAGGTTGTG GCCAGTTATT 28920
GCAGTTCTAT ATGCTGCACC TTGGTATGCA TACCCAAACT AAAAATGGTC GTTTCCAACC 28980
TCTTGAAAAC GCCTCACAGC AAGTACGCTG TCGCGGTCAA GTGCTGCCAC AATCAGGCGT 29040
GCTAACTTAC CGTATGGAAG TGACTGAAAT CGGTTTCAGT CCACGCCCAT ATGCTAAAGC 29100
TAACATCGAT ATCTTGCTTA ATGGCAAAGC GGTAGTGGAT TTCCAAAACC TAGGGGTGAT 29160
GATAAAAGAG GAAGATGAGT GTACTCGTTA TCCACTTTTG ACTGAATCAA CAACGGCTAG 29220
CACTGCACAA GTAAACGCTC AAACAAGTGC GAAAAAGGTA TACAAGCCAG CATCAGTCAA 29280
TGCGCCATTA ATGGCACAAA TTCCTGATCT GACTAAAGAG CCAAACAAGG GCGTTATTCC 29340
GATTTCCCAT GTTGAAGCAC CAATTACGCC AGACTACCCG AACCGTGTAC CTGATACAGT 29400
GCCATTCACG CCGTATCACA TGTTTGAGTT TGCTACAGGC AATATCGAAA ACTGTTTCGG 29460
GCCAGAGTTC TCAATCTATC GCGGCATGAT CCCACCACGT ACACCATGCG GTGACTTACA 29520
AGTGACCACA CGTGTGATTG AAGTTAACGG TAAGCGTGGC GACTTTAAAA AGCCATCATC 29580
```

FIG. 4A-29

```
GTGTATCGCT GAATATGAAG TGCCTGCAGA TGCGTGGTAT TTCGATAAAA ACAGCCACGG 29640
CGCAGTGATG CCATATTCAA TTTTAATGGA GATCTCACTG CAACCTAACG GCTTTATCTC 29700
AGGTTACATG GGCACAACCC TAGGCTTCCC TGGCCTTGAG CTGTTCTTCC GTAACTTAGA 29760
CGGTAGCGGT GAGTTACTAC GTGAAGTAGA TTTACGTGGT AAAACCATCC GTAACGACTC 29820
ACGTTTATTA TCAACAGTGA TGGCCCGGCAC TAACATCATC CAAAGCTTTA GCTTCGAGCT 29880
AAGCACTGAC GGTGAGCCTT TCTATCGCGG CACTGCGGTA TTTGGCTATT TTAAAGGTGA 29940
CGCACTTAAA GATCAGCTAG GCCTAGATAA CGGTAAAGTC ACTCAGCCAT GGCATGTAGC 30000
TAACGGCGTT GCTGCAAGCA CTAAGGTGAA CCTGCTTGAT AAGAGCTGCC GTCACTTTAA 30060
TGCGCCAGCT AACCAGCCAC ACTATCGTCT AGCCGGTGGT CAGCTGAACT TTATCGACAG 30120
TGTTGAAATT GTTGATAATG GCGGCACCCA AGGTTTAGGT TACTTGTATG CCGAGCGCAC 30180
CATTGACCCA AGTGATTGGT TCTTCCAGTT CCACTTCCAC CAAGATCCGG TTATGCCAGG 30240
CTCCTTAGGT GTTGAAGCAA TTATTGAAAC CATGCAAGCT TACGCTATTA GTAAAGACTT 30300
GGGCGCAGAT TTCAAAAATC CTAAGTTTGG TCAGATTTTA TCGAACATCA AGTGGAAGTA 30360
TCGCGGTCAA ATCAATCCGC TGAACAAGCA GATGTCTATG GATGTCAGCA TTACTTCAAT 30420
CAAAGATGAA GACGGTAAGA AAGTCATCAC AGGTAATGCC AGCTTGAGTA AAGATGGTCT 30480
GCGCATATAC GAGGTCTTCG ATATAGCTAT CAGCATCGAA GAATCTGTAT AAATCGGAGT 30540
GACTGTCTGG CTATTTTACT CAATTTCTGT GTCAAAAGTG CTCACCTATA TTCATAGGCT 30600
```

FIG. 4A-30

```
GCGGCGCTTTT  TTCTGGAAAT  TGAGCAAAAG  TATCTGCGTC  CTAACTCGAT  TTATAAGAAT  30660
GGTTTAATTG   AAAAGAACAA  CAGCTAAGAG  CCGCAAGCTC  AATATAAATA  ATTAAGGGTC  30720
TTACAAATAA   TGAATCCTAC  AGCAACTAAC  GAAATGCTTT  CTCCGTGGCC  ATGGGCTGTG  30780
ACAGAGTCAA   ATATCAGTTT  TGACGTGCAA  GTGATGGAAC  AACAACTTAA  AGATTTTAGC  30840
CGGGCATGTT   ACGTGGTCAA  TCATGCCGAC  CACGGCTTTG  GTATTGCGCA  AACTGCCGAT  30900
ATCGTGACTG   AACAAGCGGC  AAACAGCACA  GATTTACCTG  TTAGTGCTTT  TACTCCTGCA  30960
TTAGGTACCG   AAAGCCTAGG  CGACAATAAT  TTCCGCCGCG  TTCACGGCGT  TAAATACGCT  31020
TATTACGCAG   GCGCTATGGC  AAACGGTATT  TCATCTGAAG  AGCTAGTGAT  TGCCCTAGGT  31080
CAAGCTGGCA   TTTTGTGTGG  TTCGTTTGGA  GCAGCCGGTC  TTATTCCAAG  TCGCGTTGAA  31140
GCGGCAATTA   ACCGTATTCA  AGCAGCGCTG  CCAAATGGCC  CTTATATGTT  TAACCTTATC  31200
CATAGTCCTA   GCGAGCCAGC  ATTAGAGCGT  GGCAGCGTAG  AGCTATTTTT  AAAGCATAAG  31260
GTACGCACCG   TTGAAGCATC  AGCTTTCTTA  GGTCTAACAC  CACAAATCGT  CTATTACCGT  31320
GCAGCAGGAT   TGAGCCGAGA  CGCACAAGGT  AAAGTTGTGG  TTGGTAACAA  GGTTATCGCT  31380
AAAGTAAGTC   GCACCGAAGT  GGCTGAAAAG  TTTATGATGC  CAGCGCCCGC  AAAAATGCTA  31440
CAAAAACTAG   TTGATGACGG  TTCAATTACC  GCTGAGCAAA  TGGAGCTGGC  GCAACTTGTA  31500
CCTATGGCTG   ACGACATCAC  TGCAGAGGCC  GATTCAGGTG  GCCATACTGA  TAACCGTCCA  31560
TTAGTAACAT   TGCTGCCAAC  CATTTTAGCG  CTGAAAGAAG  AAATTCAAGC  TAAATACCAA  31620
```

FIG. 4A-31

| | | | | | |
|---|---|---|---|---|---|
| TACGACACTC | CTATTCGTGT | CGGTTGTGTGGT | GGCGGTGTGG | GTACGCCTGA | TGCAGCGCTG | 31680
| GCAACGTTTA | ACATGGGCGC | GGCGTATATT | GTTACCGGCT | CTATCAACCA | AGCTTGTGTT | 31740
| GAAGCGGGCG | CAAGTGATCA | CACTCGTAAA | TTACTTGCCA | CCACTGAAAT | GGCCGATGTG | 31800
| ACTATGCAC | CAGCTGCAGA | TATGTTCGAG | ATGGGCGTAA | AACTGCAGGT | GGTTAAGCGC | 31860
| GGCACGCTAT | TCCCAATGCG | CGCTAACAAG | CTATATGAGA | TCTACACCCG | TTACGATTCA | 31920
| ATCGAAGCGA | TCCCATTAGA | CGAGCGTGAA | AAGCTTGAGA | AACAAGTATT | CCGCTCAAGC | 31980
| CTAGATGAAA | TATGGGCAGG | TACAGTGGCG | CACTTTAACG | AGCGCGACCC | TAAGCAAATC | 32040
| GAACGCGCAG | AGGGTAACCC | TAAGCGTAAA | ATGGCATTGA | TTTTCCGTTG | GTACTTAGGT | 32100
| CTTTCTAGTC | GCTGGTCAAA | CTCAGGCGAA | GTGGGTCGTG | AAATGGATTA | TCAAATTTGG | 32160
| GCTGGCCCTG | CTCTCGGTGC | ATTTAACCAA | TGGGCAAAAG | GCAGTTACTT | AGATAACTAT | 32220
| CAAGACCGAA | ATGCCGTCGA | TTTGGCAAAG | CACTTAATGT | ACGGCGCGGC | TTACTTAAAT | 32280
| CGTATTAACT | CGCTAACGGC | TCAAGGCGTT | AAAGTGCCAG | CACAGTTACT | TCGCTGGAAG | 32340
| CCAAACCAAA | GAATGGCCTA | ATACACTTAC | AAAGCACCAG | TCTAAAAAGC | CACTAATCTT | 32400
| GATTAGTGGC | TTTTTTTATT | GTGGTCAATA | TGAGGCTATT | TAGCCTGTAA | GCCTGAAAAT | 32460
| ATCAGCACTC | TGACTTTACA | AGCAAATTAT | AATTAAGGCA | GGGCTCTACT | CATTTATACT | 32520
| GCTAGCAAAC | AAGCAAGTTG | CCCAGTAAAA | CAACAAGGTA | CCTGATTTAT | ATCGTCATAA | 32580
| AAGTTGGCTA | GAGATTCGTT | ATTGATCTTT | ACTGATTAGA | GTCGCTCTGT | TTGGAAAAAG | 32640

FIG. 4A-32

```
GTTTCTCGTT ATCATCAAAA TACACTCTCA AACCTTTAAT CAATTACAAC TTAGGCTTTC 32700
TGCGGGCATT TTTATCTTAT TTGCCACAGC TAGTTAAATT ATCTGAGCAA GAGCTCACCT TTTAGGTTTT GGGTGCAACT 32760
ACCATTAATT GAGGCCTCAT TAGTTAAATT ATCTGAGCAA GAGCTCACCT CTTTAAATTA 32820
CGCTTTTCAG CAAATGAGAA AGCCACTACA AACCATTAAT TACGACTATG CGGTGTGGGA 32880
CAGAACCTAC AGCTATATGA AATCAAACTC AGCGAGCGCT AAAAGGTACT ATGAAAAACA 32940
TGAGTACCCA GATGATACGT TCAAGAGTTT AAAAGTCGAC GGAGTATTTA TATTCAACCG 33000
TACAAATCAG CCAGTTTTTA GTAAAGGTTT TAATCATAGA AATGATATAC CGCTGGTCTT 33060
TGAATTAACT GACTTTAAAC AACATCCACA AAACATCGCA TTATCTCCAC AAACCAAACA 33120
GGCACACCCA CCGGCAAGTA AGCCGTTAGA CTCCCCTGAT GATGTGCCTT CTACCCATGG 33180
GGTTATCGCC ACACGATACG GTCCAGCAAT TTATAGCTCT TAAATTGATG AATGGTTCAT 33240
TCGTAGCGGC TCCCAACTTG GTTATTTAGT CTTCATTAGG GCTATGGCTG ATGCCGCAGA 33300
CGCTGAGCTA TCGCAATACA CTGCCGCAGG TGTTGAAATC AAAGTAACCG CTACATCCGA 33360
CGCACAATTA GCGAGATTAG GCGCAAACAC TAAGCTTAAT AAAGTAACCG CTACATCCGA 33420
ACGGTTAATA ACTAAATGTCG ATGGTAAGCC TCTGTTGAAG TTAGTGCTTT ACCATACCAA 33480
TAACCAACCG CCGCCGATGC TAGATTACAG TATAATAATT CTATTAGTTG AGATGTCATT 33540
TTTACTGATC CTCGCTTATT TCCTTTACTC CTACTTCTTA GTCAGGCCAG TTAGAAAGCT 33600
GGCTTCAGAT ATTAAAAAAA TGGATAAAAG TCGTGAAATT AAAAAGCTAA GGTATCACTA 33660
```

FIG. 4A-33

```
CCCTATTACT GAGCTAGTCA AAGTTGCGAC TCACTTCAAC GCCCTAATGG GGACGATTCA 33720
GGAACAAACT AAACAGCTTA ATGAACAAGT TTTTATTGAT AAATTAACCA ATATTCCCAA 33780
TCGTCGCGCT TTTGAGCAGC GACTTGAAAC CTATTGCCAA CTGCTAGCCC GGCAACAAAT 33840
TGGCTTTACT CTCATCATTG CCGATGTGGA TCATTTTAAA GAGTACAACG ATACTCTTGG 33900
GCACCCTGCT GGGGATGAAG CATTAATAAA AGTGGCACAA ACACTATCGC AACAGTTTTA 33960
CCGTGCAGAA GATATTGTG CCCGTTTTGG TGGTGAAGAA TTTATTATGT TATTTCGAGA 34020
CATACCTGAT GAGCCCTTGC AGAGAAAGCT CGATGCGATG CTGCACTCTT TTGCAGAGCT 34080
CAACCTACCT CATCCAAACT CATCAACCGC TAATTACGTT ACTGTGAGCC TTGGGGTTTG 34140
CACAGTTGTT GCTGTTGATG ATTTTGAATT TAAAAGTGAG TCGCATATTA TTGGCAGTCA 34200
GGCTGCATTA ATCGCAGATA AGGCGCTTTA TCATGCTAAA GCCTGTGGTC GTAACCAGTT 34260
GTCAAAAACT ACTATTACTG TTGATGAGAT TGAGCAATTA GAAGCAAATA AAATCGGTCA 34320
TCAAGCCTAA ACTCGTTCGA GTACTTTCCC CTAAGTCAGA GCATCAATAG ACTTCAAGAT 34380
GTGGCTACAA GGCTTACTCT TTCAAAACCT TAATGACAGC TAATGGTCGC AATACAATAA 34440
TTTAAGTCAA TTTAGCCTAT TAAACAGAGT TAATGACAGC TCATGGTCGC AACTTATTAG 34500
CTATTTCTAG CAATATAAAA ACTTATCCAT TAGTAGTAAC CAATAAAAAA ACTAATATAT 34560
AAAACTATTT AATCATTATT TTACAGATGA TTAGCTACCA CCCACCTTAA GCTGGCTATA 34620
TTCGCACTAG TAAAAATAAA CATTAGATCG GGTTCAGATC AATTTACGAG TCTCGTATAA 34680
```

FIG. 4A-34

```
AATGTACAAT AATTCACTTA ATTTAATACT GCATATTTTT ACAAGTAGAG AGCGGTGATG   34740
AAACAAAATA CGAAAGGCTT TACATTAATT GAATTAGTCA TCGTGATTAT TATTCTCGGT   34800
ATACTTGCTG CTGTGGCACT GCCGAAATTC ATCAATGTTC AAGATGACGC TAGGATCTCT   34860
GCGATGAGCG GTCAGTTTTC ATCATTTGAA AGTGCCGTAA AACTATACCA TAGCGGTTGG   34920
TTAGCCAAAG GCTACAACAC TGCGGTTGAA AAGCTCTCAG GCTTTGGCCA AGGTAATGTT   34980
GCATCAAGTG ACACAGTTT TCCGTACTCA ACATCAGGCA CGAGTACTGA TGTGCATAAA   35040
GCTTGTGGTG AACTATGGCA TGGCATTACC GATACAGACT TCACAATTGG TGCGGTTAGT   35100
GATGGCGATC TAATGACTGC AGATGTCGAT ATTGCTTACA CCTATCGTGG TGATATGTGT   35160
ATCTATCGCG ATCTGTATTT TATTCAGCGC TCATTACCTA CTAAGGTGAT GAACTACAAA   35220
TTTAAAACTG GTGAAATAGA AATTATTGAT GCTTTCTACA ACCCTGACGG CTCAACTGGT   35280
CAATTACCAT AAATTTGGCG CTTATCTAAG TTGTACTTGC TCTGACCGAC ACAAATAATG   35340
TCGTTCTCA GCATATATCA AAATACACAG CAAAAATTTG GGGTTAGCTA TATAGCTAAC   35400
CCCAAATCAT ATCTAACTTT ACACTGCCATC TAATTCCAAA CAGTATCCAG CCAAAAGCCT   35460
AAACTATTGT TGACTCAGCG CGATGCAACA AACAAGTCTT GGATGCGCAAT   35520
ACCTGAGCTA TCAAAAATGG TCACCTCATC AGCACTTTGA CGTCCTGTTG CGGACTCGTT   35580
TATCACCTGA CCAATCTCAA TTATCGGCGT ATTTCTGCTA TGTTGAAACT CACCAATAAC   35640
AATAGATTGA GAAGCAAAGT CGCAAAACAA GCGAGCATGA CTATATAGGT CAGTTGGCAA   35700
```

```
CTCTTGCTTA CCCACTTTAT CAGCGCCCAT TGCAGAAATA TGCGTTCCTG CTTGTACCCA 35760
CTGCGCTTCA AATAAAGGCG CTTGAGCTGT GGTTGCTGTG ATAATAATAT CTGCTTGTTC 35820
ACAAGCAGCT TGTGCATCAC AAGCTTCGGC ATTAATGCCT TTTTCTAATA AACGCTTAAC 35880
CAAGTTTTCA GTTTTGCTAG CACTACGGCC AACTACCAAT ACCTTAGTTA ATGAACGAAC 35940
CTTGCTCACT GCTAGCACTT CATATTCAGC CTGATGACCG GTACCAAAAA CAGTTAATAC 36000
CGTAGCATCT TCTCTCGCGA GGTAACTCAC TGCTACTGCA TCGGCAGCAC CAGTGCGGTA 36060
AGCATTAACG GTAGTGGCAG CAATCACCGN CTGCAACATA CCGGTTAATG GATCGAGTAA 36120
AAATACGTTA GTGCCGTGGC ATGGTAAACC ATGTTTATGG TTATCAGGCC AATAGCTGCC 36180
TGTTTTCCAG CCGACAAGGT TTGGCGTTGA AGCCGACTTT AATGAGAACA TTTCATTAAG 36240
GTTCGCGCCC TGTGCATTAA CTACCGGGAA CAAGGTTGCT TTATCATCTA CGGCAGCGAC 36300
AAACGCTTCT TTAACAGCGA TATAAGCCAG CTCATGGGAG ATGAGCTTTG ATGTTTGCGC 36360
TTCAGTTAAA TAGATCATAT TACCACCCCT GCACTCGATT CCAGATCTCA TAGCCACCAT 36420
TATCACCATC AGTATCAAAT ACATGGTACT GAGCGTGCAT TGAAGCTGTT GCACAGGCGT 36480
GGTTCGGCAA AATATGTAGA CGACTACCTA CCGGGAACTG CGCTAAATCA ATAACGCCGC 36540
CATCAACTGC TTCAATAATG CCGTGCTCTT GATTAACAGT TATAACCTGT AGACCTGATA 36600
ACACGTGACC GCTGTCGTCA CACACTAAAC CATAACCACA ATCTTTTGGC TGCTCTGCAG 36660
TACCTCTATC ACCCGAAAGA GCCATCCAAC CCGCATCAAT GAAAATCCAG TTTTTATCAG 36720
```

FIG. 4A-36

```
GATTATGACC AATAACACTG GTCACTACCG TTGCGGGCAAT ATCAGTTAAC TGACACACGT 36780
TTAGCCCTGC CATGACTAAA TCGAAGAAGG TGTACACACC CGCTCTAACC TCGGTGATCC 36840
CATCAAGGTT TTGATAGCTT TGCGCTGTTG GTGTTGAACC AATACTAACG ATGTCACATT 36900
GCATACCCGC TGGCGCGAATG CGTCAGCAGC TTGTACAGCC GCTGCAACTT CATTTGCGC 36960
CGCATCAATT AATTGCTGTT TTTCAAAACA TTGATATGAC TCACCAGCGT GAGTNAGTAC 37020
GCCGTGAAAA CTCGCTGCGC CAGACGTTAG TATCTGAGCA ATTTCAATCA ACTTATCGGC 37080
TTCCGGTGGA ATACCACCAC GATGGCCATC ACAATCAATT TCAATTAATG CTGGTATTTG 37140
GCAGTCATAA GAACCACAGA AATGATTTAG CTGATGCGCT TGCTCAACAC TATCAAGTAA 37200
AACTCTTGCA TTAATACCTT GGTCCAACAT TTTAGCAATA CGGGCAACT TACCATCGGC 37260
AATACCTACT GCATAAATAA TGTCTGTGTA ACCTTTAGAT GCTAAGGCCT CGGCCTCTTT 37320
TACCGTTGAT ACAGTGACTG GTGAGTTTTT AGTGGGTAAT AAAAACTCGG CTGCTTCAAG 37380
TGATCTTAAC GTTTTAAAAT GCGGTCTTAG GTTTGCACCT AATCCTTCAA TTTTTGGCG 37440
TAGTTGACTG AGGTTATTAA TAAATACTGG CTTATTTACA TATAAAAACG GTGTATCAAT 37500
TGCTTGATAC TGACTTTGCT GAGTCGTGGA AAGTATTTGA GTAGATGGCA TCTTTAATAT 37560
CCTAGTTCAT CAATCAATCT ATGCCTAGCC ACAGTGGCTT GTATTCATGA 37620
TGCTTTGGAA AATGCTTATA TTCAAAGTAT TTGAAAGACA TCAAACTTCT TGTTTAATGC 37680
TCAGTATCCA CCAGCACGCA TTTATTTTAT ATTAACTATT ATCAAGATAT AGATTAGGTT 37740
```

FIG. 4A-37

```
CAAACCAAAT GATTAGTACT GAAGATCTAC GTTTTATCAG CGTAATCGCC AGTCATCGCA  37800
CCTTAGCTGA TGCCGCTAGA ACACTAAATA TCACGCCACC ATCAGTGACA TTAAGGTTGC  37860
AGCATATTGA AAAGAAACTA TCGATTAGCC TGATC                             37895
```

| | | | |
|---|---|---|---|
| MKQTLMAISI | MSLFSFNALA | AQHEHDHITV | DYEGKAATEH |
| TIAHNQAVAK | TLNFADTRAF | EQSSKNLVAK | FDKATADILR |
| AEFAFISDEI | PDSVNPSLYR | QAQLNMVPNG | YKVSDGIYQV |
| RGTDLSNLTL | IRSDNGWIAY | DVLLTKEAAK | ASLQFALKNL |
| PKDGDPVVAM | IYSHSHADHF | GGARGVQEMF | PDVKVYGSDN |
| ITKEIVDENV | LAGNAMSRRA | AYQYGATLGK | HDHGIVDAAL |
| GKGLSKGEIT | YVAPDYTLNS | EGKWETLTID | GLEMVFMDAS |
| GTEAESEMIT | YIPSKKALWT | AELTYQGMHN | IYTLRGAKVR |
| DALKWSKDIN | EMINAFGQDV | EVLFASHSAP | VWGNQAINDF |
| LRLQRDNYGL | VHNQTLRLAN | DGVGIQDIGD | AIQDTIPESI |
| YKTWHTNGYH | GTYSHNAKAV | YNKYLGYFD | MNPANLNPLP |
| TKQESAKFVE | YMGGADAAIK | RAKDDYAQGE | YRFVATALNK |
| VVMAEPENDS | ARQLLADTYE | QLGYQAEGAG | WRNIYLTGAQ |
| ELRVGIQAGA | PKTASADVIS | EMDMPTLFDF | LAVKIDSQQA |
| AKHGLVKMNV | ITPDTKDILY | IELSNGNLSN | AVVDKEQAAD |
| ANLMVNKADV | NRILLGQVTL | KALLASGDAK | LTGDKTAFSK |
| IADSMVEFTP | DFEIVPTPVK | | |

8186
STKASARVVA KFNVEEAAIS IQQCQGISLA FRYSDDLHGL

LCHWNDAANM QQEKAEILGL GSKQPEANPK NSSSELLALG

IDQKLLVQRQ NLQHEVKHDA IADSIDVCHS LSKPANVGLF

TESLASFDFA FSKLSLALGL GKAKIYSEKL AWLDFFRDRQ

LAEPLALLAR KESESFYHSL ISHINTSNRC REIDVGFEIS

ASDTEEKSAQ SAGKNDATCI GVLLWDGSHS VNFHVGTQAF

QADSLRPKGK DGYEFRWENP RIESHQSLLA RLYGRVM
9016

GCTAGTCTTA GCTGASRTHR YSAASRAGCT CGAACAACAG CTTTAAAATT
CACTTCTTCT GCTGCAATAC TTATTTGCTG ACACTGACCA ATACTCAGTG
CAAAACGATA ACTATCATCA AGATGGAAAR GVAVAAAYSH ASNVAGGAAA
ASRGNGNCYS GNGYSRAAHA RGTYRSRASA SHSCCCAGTA AACAATGCCA
ATTATCAGCA GCGTTCATTT GCTGTTCTTT AGCCTCAATC AAACCTAAAC
CAGACTTTTG TGGCTCAGCG TTAGGCTTAT TAGGYCYSHS TRASNASAAA
AASNMTGNGN GYSAAGGYGY SRYSGNRGAA ASNRYSASNS RAACTCGACT
CTAGTAAAGC AAGACCAATA TCTTGTTTTA ACAAACCTG TCGCTGATTA
AGTTGATGCT CAACCTTGTG ATCCGCAATA GCATCGGAAA TSRSRGAAGY
ASGNYSVAGN ARGGNASNGN HSGVAYSHSA SAAAAASSRA TCAACACAAT
GGCTCAAGCT TTTAGGTGCA TTAACTCCAA GAAAAGTTTC GCTCAGTGCA
GAGAAGTCAA ACGCAAAAGA TTTTAGCGAT AATGCCAGCA SVACYSHSSR
SRYSRAAASN VAGYHTHRGS RAASRHASHA AHSRYSSRAA CCAAGTCCTT
TCGCTTTAAT GTAAGACTCC TTGAGCGCCC ACAAATCAAA AAAGCGGTCT
CGCTGCAAGG CCTCTGGTAA CGCTAACAAG GCTCGCTTTT GYGYYSAAYS
TYRSRGYSAA TRASHHARGA SARGGNAAGR AAAAARGYSG CTGATTCAGA
GAAATAATGA CTAAGAATAG AGTGGATATT GGTGCTGTTA CGGCAACGCT
CAATGTCGAC GCCAAACTCA ATACTAGCAG AGTCAGTTTC SRGSRHTYRH
SSRSRHSASN THRSRASNAR GCYSARGGAS VAGYHGSRAA SRASTHRGCT
CCTTGCTTGC CTGACTGGCG CCTTTATTAT CAGCAGTGCA AATGCCTACT
AATAGCCAAT CTCCACTATG ACTCACATTA AAGTGGACCC CGGTTTGAGY
SSRAAGNSRA AGYYSASNAS AATHRCYSGY VATRASGYSR HSSRVAASNH
HSVAGYTHRG NGCAAATTGC GCATCACTCA ATCTAGGCTT ACCTTTGTCG

FIG. 4D-1

```
CCATATTCAA AGCGCCATTC ATTGGGGCGT ATTTCACTAT GTTGTGACAA
TAAAGCGCGC AAAHGNAAAS SRARGRYSGY YSASGYTYRG HARGTRGASN
RARGGSRHSG NSRAAARGAA TAGCCTCTTA CCATTAAACC TTGAGTTTTA
GCTTCTTGTT TAATGTAGCG ATTAACCTTA ATTAACTCAT CTTCAGGCAG
CCATGACTTA ACCAACTCTY RGYARGVAMT GYGNTHRYSA AGGNYSTYRA
RGASNVAYSG ASGRTRSRYS VAGTGTAGTC TGGTTATCGC ACTCTTGTAT
TGTTAACGGA CAGAAGTATA AGGAAATCAA
                                *
                               9157
```

FIG. 4D-2

9681
MSMFLNSKLS RSVKLAISAG LTASLAMPVF AEETAAEEQI ERVAVTGSRI
AKAELTQPAP VVSLSAEELT KFGNQDLGSV LAELPAIGAT NTIIGNNNSN
SSAGVSSADL RRLGANRTLV LVNGKRYVAG QPGSAEVDLS TIPTSMISRV
EIVTGGASAI YGSDAVSGVI NVILKEDFEG FEFNARTSGS TESVGTQEHS
FDILGGANVA DGRGNVTFYA GYERTKEVMA TDIRQFDAWG TIKNEADGGE
DDGIPDRLRV PRVYSEMINA TGVINAFGGG IGRSTFDSNG NPIAQQERDG
TNSFAFGSFP NGCDTCFNTE AYENYIPGVE RINVGSSFNF DFTDNIQFYT
DFRYVKSDIQ QQFQPSFRFG NININVEDNA FLNDDLRQQM LDAGQTNASF
AKFFDELGNR SAENKRELFR YVGGFKGGFD ISETIFDYDL YVVYGETNNR
RKTLNDLIPD NFVAAVDSVI DPDTGLAACR SQVASAQGDD YTDPASVNGS
DCVAYNPFGM GQASAEARDW VSADVTREDK ITQQVIGGTL GTDSEELFEL
QGGAIAMVVG FEYREETSGS TTDEFTKAGF LTSAATPDSY GEYDVTEYFV
EVNIPVLKEL PFAHELSFDG AYRNADYSHA GKTEAWKAGM FYSPLEQLAL
RGTVGEAVRA PNIAEAFSPR SPGFGRVSDP CDADNINDDP DRVSNCAALG
IPPGFQANDN VSVDTLSGGN PDLKPETSTS FTGGLVWTPT FADNLSFTVD
YYDIQIEDAI LSVATQTVAD NCVDSTGGPD TDFCSQVDRN PTTYDIELVR
SGYLNAAALN TKGIEFQAAY SLDLESFNAP GELRFNLLGN QLLELERLEF
QNRPDEINDE KGEVGDPELQ FRLGIDYRLD DLSVSWNTRY IDSVVTYDVS
ENGGSPEDLY PGHIGSMTTH DLSATYYINE NFMINGGVRN LFDALPPGYT
NDALYDLVGR RAFLGIKVMM
12590

MAKINSEHLD EATITSNKCT QTETEARHRN ATTTPEMRRF IQESDLSVSQ
LSKILNISEA TVRKWRKRDS VENCPNTPHH LNTTLTPLQE YVVVGLRYQL
KMPLDRLLKA TQEFINPNVS RSGLARCLKR YGVSRVSDIQ SPHVPMRYFN
QIPVTQGSDV QTYTLHYETL AKTLALPSTD GDNVQVVSL TIPPKLTEEA
PSSILLGIDP HSDWIYLDIY QDGNTQATNR YMAYVLKHGP FHLRKLLVRN
YHTFLQRFPG ATQNRRPSKD MPETINKTPE TQAPSGDS

MSQTSKPTNS ATEQAQDSQA DSRLNKRLKD MPIAIVGMAS IFANSRYLNK
FWDLISEKID AITELPSTHW QPEEYYDADK TAADKSYCKR GGFLPDVDFN
PMEFGLPPNI LELTDSSQLL SLIVAKEVLA DANLPENYDR DKIGITLGVG
GGQKISHSLT ARLQYPVLKK VFANSGISDT DSEMLIKKFQ DQYVHWEENS
FPGSLGNVIA GRIANRFDFG GMNCVVDAAC AGSLAAMRMA LTELTEGRSE
MMITGGVCTD NSPSMYMSFS KTPAFTTNET IQPFDIDSKG MMIGEGIGMV
ALKRLEDAER DGDRIYSVIK GVGASSDGKF KSIYAPRPSG QAKALNRAYD
DAGFAPHTLG LIEAHGTGTA AGDAAEFAGL CSVFAEGNDT KQHIALGSVK
SQIGHTKSTA GTAGLIKAAL ALHHKVLPPT INVSQPSPKL DIENSPFYLN
TETRPWLPRV DGTPRRAGIS SFGFGGTNFH FVLEEYNQEH SRTDSEKAKY
RQRQVAQSFL VSASDKASLI NELNVLAASA SQAEFILKDA AANYGVRELD
KNAPRIGLVA NTAEELAGLI KQALAKLAAS DDNAWQLPGG TSYRAAAVEG
KVAALFAGQG SQYLNMGRDL TCYYPEMRQQ FVTADKVFAA NDKTPLSQTL
YPKPVFNKDE LKAQEAILTN TANAQSAIGA ISMGQYDLFT AAGFNADMVA
GHSFGELSAL CAAGVISADD YYKLAFARGE AMATKAPAKD GVEADAGAMF
AIITKSAADL ETVEATIAKF DGVKVANYNA PTQSVIAGPT ATTADAAKAL
TELGYKAINL PVSGAFHTEL VGHAQAPFAK AIDAAKFTKT SRALYSNATG
GLYESTAAKI KASFKKHMLQ SVRFTSQLEA MYNDGARVFV EFGPKNILQK
LVQGTLVNTE NEVCTISINP NPKVDSDLQL KQAAMQLAVT GVVLSEIDPY
QADIAAPAKK SPMSISLNAA NHISKATRAK MAKSLETGIV TSQIEHVIEE
KIVEVEKLVE VEKIVEKVVE VEKVVEVEAP VNSVQANAIQ TRSVVAPVIE
NQVVSKNSKP AVQSISGDAL SNFFAAQQQT AQLHQQFLAI PQQYGETFTT
LMTEQAKLAS SGVAIPESLQ RSMEQFHQLQ AQTLQSHTQF LEMQAGSNIA
ALNLLNSSQA TYAPAIHNEA IQSQVVQSQT AVQPVISTQV NHVSEQPTQA
PAPKAQPAPV TTAVQTAPAQ VVRQAAPVQA AIEPINTSVA TTTPSAFSAE

FIG. 4G-1

TALSATKVQA TMLEVVAEKT GYPTEMLELE MDMEADLGID SIKRVEILGT
VQDELPGLPE LSPEDLAECR TLGEIVDYMG SKLPAEGSMN SQLSTGSAAA
TPAANGLSAE KVQATMMSVV AEKTGYPTEM LELEMDMEAD LGIDSIKRVE
ILGTVQDELP GLPELSPEDL AECRTLGEIV DYMNSKLADG SKLPAEGSMN
SQLSTSAAAA TPAANGLSAE KVQATMMSVV AEKTGYPTEM LELEMDMEAD
LGIDSIKRVE ILGTVQDELP GLPELNPEDL AECRTLGEIV TYMNSKLADG
SKLPAEGSMH YQLSTSTAAA TPVANGLSAE KVQATMMSVV ADKTGYPTEM
LELEMDMEAD LGIDSIKRVE ILGTVQDELP GLPELNPEDL AECRTLGEIV
DYMGSKLPAE GSANTSAAAS LNVSAVAAPQ AAATPVSNGL SAEKVQSTMM
SVVAEKTGYP TEMLELGMDM EADLGIDSIK RVEILGTVQD ELPGLPELNP
EDLAECRTLG EIVDYMNSKL ADGSKLPAEG SANTSATAAT PAVNGLSADK
VQATMMSVVA EKTGYPTEML ELGMDMEADL GIDSIKRVEI LGTVQDELPG
LPELNPEDLA ECRTLGEIVS YMNSQLADGS KLSTSAAEGS ADTSAANAAK
PAAISAEPSV ELPPHSEVAL KKLNAANKLE NCFAADASVV INDDGHNAGV
LAEKLIKQGL KVAVVRLPKG QPQSPLSSDV ASFELASSQE SELEASITAV
IAQIETQVGA IGGFIHLQPE ANTEEQTAVN LDAQSFTHVS NAFLWAKLLQ
PKLVAGADAR RCFVTVSRID GGFGYLNTDA LKDAELNQAA LAGLTKTLSH
EWPQVFCRAL DIATDVDATH LADAITSELF DSQAQLPEVG LSLIDGKVNR
VTLVAAEAAD KTAKAELNST DKILVTGGAK GVTFECALAL ASRSQSHFIL
AGRSELQALP SWAEGKQTSE LKSAAIAHII STGQKPTPKQ VEAAVWPVQS
SIEINAALAA FNKVGASAEY VSMDVTDSAA ITAALNGRSN EITGLIHGAG
VLADKHIQDK TLAELAKVYG TKVNGLKALL AALEPSKIKL LAMFSSAAGF
YGNIGQSDYA MSNDILNKAA LQFTARNPQA KVMSFNWGPW DGGMVNPALK

FIG. 4G-2

```
KMFTERGVYV IPLKAGAELF ATQLLAETGV QLLIGTSMQG GSDTKATETA
SVKKLNAGEV LSASHPRAGA QKTPLQAVTA TRLLTPSAMV FIEDHRIGGN
SVLPTVCAID WMREAASDML GAQVKVLDYK LLKGIVFETD EPQELTLELT
PDDSDEATLQ ALISCNGRPQ YKATLISDNA DIKQLNKQFD LSAKAITTAK
ELYSNGTLFH GPRLQGIQSV VQFDDQGLIA KVALPKVELS DCGEFLPQTH
MGGSQPFAED LLLQAMLVWA RLKTGSASLP SSIGEFTSYQ PMAFGETGTI
ELEVIKHNKR SLEANVALYR DNGELSAMFK SAKITISKSL NSAFLPAVLA
NDSEAN
    *
 22173
```

```
MPLRIALILL PTPQFEVNSV DQSVLASYQT LQPELNALLN SAPTPEMLSI
TISDDSDANS FESQLNAATN AINNGYIVKL ATATHALLML PALKAAQMRI
HPHAQLAAMQ QAKSTPMSQV SGELKLGANA LSLAQTNALS HALSQAKRNL
TDVSVNECFE NLKSEQQFTE VYSLIQQLAS RTHVRKEVNQ GVELGPKQAK
SHYWFSEFHQ NRVAAINFIN GQQATSYVLT QGSGLLAAKS MLNQQRLMFI
LPGNSQQQIT ASITQLMQQL ERLQVTEVNE LSLECQLELL SIMYDNLVNA
DKLTTRDSKP AYQAVIQASS VSAAKQELSA LNDALTALFA EQTNATSTNK
GLIQYKTPAG SYLTLTPLGS NNDNAQAGLA FVYPGVGTVY ADMLNELHQY
FPALYAKLER EGDLKAMLQA EDIYHLDPKH AAQMSLGDLA IAGVGSSYLL
TQLLTDEFNI KPNFALGYSM GEASMWASLG VWQNPHALIS KTQTDPLFTS
AISGKLTAVR QAWQLDDTAA EIQWNSFVVR SEAAPIEALL KDYPHAYLAI
IQGDTCVIAG CEIQCKALLA ALGKRGIAAN RVTAMHTQPA MQEHQNVMDF
YLQPLKAELP SEISFISAAD LTAKQTVSEQ ALSSQVVAQS IADTFCQTLD
FTALVHHAQH QGAKLFVEIG ADRQNCTLID KIVKQDGASS VQHQPCCTVP
MNAKGSQDIT SVIKALGQLI SHQVPLSVQP FIDGLKRELT LCQLTSQQLA
AHANVDSKFE SNQDHLLQGE V
```
24515

MSLPDNASNH LSANQKGASQ ASKTSKQSKI AIVGLATLYP DAKTPQEFWQ
NLLDKRDSRS TLTNEKLGAN SQDYQGVQGQ SDRFYCNKGG YIENFSFNAA
GYKLPEQSLN GLDDSFLWAL DTSRNALIDA GIDINGADLS RAGVVMGALS
FPTTRSNDLF LPIYHSAVEK ALQDKLGVKA FKLSPTNAHT ARAANESSLN
AANGAIAHNS SKVVADALGL GGAQLSLDAA CASSVYSLKL ACDYLSTGKA
DIMLAGAVSG ADPFFINMGF SIFHAYPDHG ISVPFDASSK GLFAGEGAGV
LVLKRLEDAE RDNDKIYAVV SGVGLSNDGK GQFVLSPNPK GQVKAFERAY
AASDIEPKDI EVIECHATGT PLGDKIELTS METFFEDKLQ GTDAPLIGSA
KSNLGHLLTA AHAGIMKMIF AMKEGYLPPS INISDAIASP KKLFGKPTLP
SMVQGWPDKP SNNHFGVRTR HAGVSVFGFG GCNAHLLLES YNGKGTVKAE
ATQVPRQAEP LKVVGLASHF GPLSSINALN NAVTQDGNGF IELPKKRWKG
LEKHSELLAE FGLASAPKGA YVDNFELDFL RFKLPPNEDD RLISQQLMLM
RVTDEAIRDA KLEPGQKVAV LVAMETELEL HQFRGRVNLH TQLAQSLAAM
GVSLSTDEYQ ALEAIAMDSV LDAAKLNQYT SFIGNIMASR VASLWDFNGP
AFTISAAEQS VSRCIDVAQN LIMEDNLDAV VIAAVDLSGS FEQVILKNAI
APVAIEPNLE ASLNPTSASW NVGEGAGAVV LVKNEATSGC SYGQIDALGF
AKTAETALAT DKLLSQTATD FNKVKVIETM AAPASQIQLA PIVSSQVTHT
AAEQRVGHCF AAAGMASLLH GLLNLNTVAQ TNKANCALIN NISENQLSQL
LISQTASEQQ ALTARLSNEL KSDAKHQLVK QVTLGGRDIY QHIVDTPLAS
LESITQKLAQ ATASTVVNQV KPIKAAGSVE MANSFETESS AEPQITIAAQ
QTANIGVTAQ ATKRELGTPP MTTNTIANTA NNLDKTLETV AGNTVASKVG
SGDIVNFQQN QQLAQQAHLA FLESRSAGMK VADALLKQQL AQVTGQTIDN
QALDTQAVDT QTSENVAIAA ESPVQVTTPV QVTTPVQISV VELKPDHANV
PPYTPPVPAL KPCIWNYADL VEYAEGDIAK VFGSDYAIID SYSRRVRLPT
TDYLLVSRVT KLDATINQFK PCSMTTEYDI PVDAPYLVDG QIPWAVAVES
GQCDLMLISY LGIDFENKGE RVYRLLDCTL TFLGDLPRGG DTLRYDIKIN
NYARNGDTLL FFFSYECFVG DKMILKMDGG CAGFFTDEEL ADGKGVIRTE

FIG. 4I-1

```
EEIKARSLVQ  KQRFNPLLDC  PKTQFSYGDI  HKLLTADIEG  CFGPSHSGVH
QPSLCFASEK  FLMIEQVSKV  DRTGGTWGLG  LIEGHKQLEA  DHWYFPCHFK
GDQVMAGSLM  AEGCGQLLQF  YMLHLGMHTQ  TKNGRFQPLE  NASQQVRCRG
QVLPQSGVLT  YRMEVTEIGF  SPRPYAKANI  DILLNGKAVV  DFQNLGVMIK
EEDECTRYPL  LTESTTASTA  QVNAQTSAKK  VYKPASVNAP  LMAQIPDLTK
EPNKGVIPIS  HVEAPITPDY  PNRVPDTVPF  TPYHMFEFAT  GNIENCFGPE
FSIYRGMIPP  RTPCGDLQVT  TRVIEVNGKR  GDFKKPSSCI  AEYEVPADAW
YFDKNSHGAV  MPYSILMEIS  LQPNGFISGY  MGTTLGFPGL  ELFFRNLDGS
GELLREVDLR  GKTIRNDSRL  LSTVMAGTNI  IQSFSFELST  DGEPFYRGTA
VFGYFKGDAL  KDQLGLDNGK  VTQPWHVANG  VAASTKVNLL  DKSCRHFNAP
ANQPHYRLAG  GQLNFIDSVE  IVDNGGTEGL  GYLYAERTID  PSDWFFQFHF
HQDPVMPGSL  GVEAIIETMQ  AYAISKDLGA  DFKNPKFGQI  LSNIKWKYRG
QINPLNKQMS  MDVSITSIKD  EDGKKVITGN  ASLSKDGLRI  YEVFDIAISI
EESV
  *
30529
```

FIG. 4I-2

30730
*
MNPTATNEML SPWPWAVTES NISFDVQVME QQLKDFSRAC
YVVNHADHGF GIAQTADIVT EQAANSTDLP VSAFTPALGT
ESLGDNNFRR VHGVKYAYYA GAMANGISSE ELVIALGQAG
ILCGSFGAAG LIPSRVEAAI NRIQAALPNG PYMFNLIHSP
SEPALERGSV ELFLKHKVRT VEASAFLGLT PQIVYYRAAG
LSRDAQGKVV VGNKVIAKVS RTEVAEKFMM PAPAKMLQKL
VDDGSITAEQ MELAQLVPMA DDITAEADSG GHTDNRPLVT
LLPTILALKE EIQAKYQYDT PIRVGCGGGV GTPDAALATF
NMGAAYIVTG SINQACVEAG ASDHTRKLLA TTEMADVTMA
PAADMFEMGV KLQVVKRGTL FPMRANKLYE IYTRYDSIEA
IPLDEREKLE KQVFRSSLDE IWAGTVAHFN ERDPKQIERA
EGNPKRKMAL IFRWYLGLSS RWSNSGEVGR EMDYQIWAGP
ALGAFNQWAK GSYLDNYQDR NAVDLAKHLM YGAAYLNRIN
SLTAQGVKVP AQLLRWKPNQ RMA
                        *
                     32358

MRKPLQTINY DYAVWDRTYS YMKSNSASAK RYYEKHEYPD
DTFKSLKVDG VFIFNRTNQP VFSKGFNHRN DIPLVFELTD
FKQHPQNIAL SPQTKQAHPP ASKPLDSPDD VPSTHGVIAT
RYGPAIYYSS TSILKSDRSG SQLGYLVFIR LIDEWFIAEL
SQYTAAGVEI AMADAADAQL ARLGANTKLN KVTATSERLI
TNVDGKPLLK LVLYHTNNQP PPMLDYSIII LLVEMSFLLI
LAYFLYSYFL VRPVRKLASD IKKMDKSREI KKLRYHYPIT
ELVKVATHFN ALMGTIQEQT KQLNEQVFID KLTNIPNRRA
FEQRLETYCQ LLARQQIGFT LIIADVDHFK EYNDTLGHLA
GDEALIKVAQ TLSQQFYRAE DICARFGGEE FIMLFRDIPD
EPLQRKLDAM LHSFAELNLP HPNSSTANYV TVSLGVCTVV
AVDDFEFKSE SHIIGSQAAL IADKALYHAK ACGRNQALSK
TTITVDEIEQ LEANKIGHQ

```
AATAGATCGACTCGCAAAAGTTGCTTAAGATAGTGTCAATATAGCTTCTTATTTGTA
AATATTGTTTTTTATGTGTAAACATGTTTAGTGTGTGTAAATGCTGTTAATTATCCT
TTTGGGATTGTAATAGCTGATGTTGCTGGCTAATGAGTACTTTTAGTTCGGCAATAT
CTTGCTTTAAATCGCTAACTTCAGTTTTTAATTCACCCACACTTGTTGTATTTTTAA
GGCTCTCTTCCCCACCATCGACAAACCAGGATGATATGAAACCGGTAAACGTACCAA
AGAGACCGACACCTGCAGTCATGAGTAATGCCGCAATGATACGTCCGCCAGTGGTGA
CGGGGTAGTAGTCACCGTAACCAACAGTCGTTATTGTCACAAATGACCACCAAAGTG
CGTCGATGCCGTTATTGATGTTACTGCCTACTTGATCCTGTTCTAACAATAAAATAC
CGATAGCACCAAAGGTGACAAGGATGAAGGATATCGCAGATACCAGCGAAAAGGTGG
CTTTAAACCGATGTTCAAAAATCATTTTTAAGATAATTTTTGATGAGCGTATATTCT
GAATAGATCTTAATACTCTAGCGATACGAATTATGCGAATAAACTGCAGTTGCTCGA
CCATCGGAATACTCGACAGTAGGTCAATCCAACCCCATTTCATAAACTGAAATTTAT
TCTCAGCTTGGTGAAAGCGAATTACAAAGTCAGTGAAAAGAATAAGCAAATCGTAT
TATCTACGCTCGTTAATATTTCAGTGACGTTACTTGAAAAGGTAAAAATAAGTTGCA
GTAGTGATGATACGACCACATGAAGTGATAAAATAAGCATGAAAATCTGAAATGGAT
TTACATCACTGTTGTTTTGGTGCCACTTTTAAGGTTCGTTTTCACAATCTGCTGCC
TCGGTTCATTGATTTGTTAATATAAACCTTAGTCAGTAGCAAGACAAAATATATTT
ACATCAATGTCATCGTATTATTCAACCGCGCGTCGTGTATTCAGACCAAGATCGTTG
TATATGTTAGTCATGTAGCGATGAGATTATCATGCGACAGGAGAGAATTATGTTTGT
TATTATTTTTTACGTACCTAAAGTTAATGTTGAAGAAGTAAAACAGGCGTTATTTAA
CGTCGGAGCTGGCACCATCGGTGATTATGATAGTTGTGCTTGGCAATGTTTGGGGAC
TGGGCAGTTCCAACCTTTACTTGGTAGCCAGCCACATATTGGTAAGCTAAATGAGGT
TGAATTCGTTGATGAGTTTAGAGTAGAAATGGTTTGTCGAGCAGAAAATGTAAGGGC
AGCAATAAATGCACTTATTGCTGCGCACCCTTATGAAGAACCTGCTTATCATATTCT
GCAAACATTGAATCTTGATGAGTTACCTTAAGTTAGATGCACTGCACTTAATTGGTT
CGCTGTGCTAGGTTAGCAATTAGCAATTTTGACCATGTTAGCGATAGTTTTGGCACA
```

FIG. 5-1

```
AGTGATCGATATTAAACTATCCGATTCAGATCCCATTTTTACTGCTGAATTAGGTTT
CATTACACTTGTTCTAGTGGTTTTTCCCGACAGGTGTAACTCTGTTACTTGCGTAAG
GTTGATAATCTCTACCGCATTGGCAGGAGTTACACCTGCACCAGGCATAATACTAAT
TCTACCATCTGCTTGGTTAACTAACGTTTGGATTAAGGCGCAGCCTTCTAGCGCTTG
AGCTTGTTGACCAGAGGTTAAAATACGCTCACAACCAGCAGTGATCAAGGTCTCCAA
GGCTTGTTGTGGATCATTACACAAGTCGAAAGCGCGGTGGAAGGTTACGCCGAGATC
ACGTGATGCCACCATTAAGCGTTTTAAAGCTGGCTCGTCAATATTACCATCTGCTGT
TAACGCGCCAATAACGACCCCTTGGACACCGAGTAACTTCATGAATTTGATGTCGGA
AACCATAATATCAACTTCTTGTTCGCTATATACAAAATCACCGGCGCGAGGGCGAAT
AATGGCATAAATGGGGATCGTTGCTAGATCAATAGACTTTTGTACAAAACCTGCGTT
GGCGGTCAAGCCACCTAATGCTAATGCCGAGCACAACTCAATACGATCGGCGCCAGA
TGCTTGAGCCGTCAGCAGTGATTCTATATTATCGACACATACTTCTATTGTCATTGT
CATATACTTCTCTTTAAAAGTTTATTAAAAATAATAAAGCCAGCATAAGTCGTTTT
ATACAATATGAAAGGGGAAAAGGCGACTTAGCTCGCCTAGATCAATTATTATGGCAG
AATACTGCCGTATTGTGATTAGAAAGACAGTTTTTTAAGCTCAATAGCCGTTATCGC
GTTGTTATCTACCATCGTGTAACTTTTCTGGCCTGGGTGCTTTATTAACACTGTTTC
AGTGGCTGGATTAGGGTGAAATGATTCTTTTTTCAAATCTGTTTTTTTGTATTTGAA
CGTACCTGTAATGTCTTGCTGCTCACGAAGACGTACAAATATTGGTTGCGCATAGCT
TGGTAGTGCCGCATTGACATGTTGATAGAATTCAGACGCTGAAAATTCATGAATAGG
GCAATTCAAAGTCAGCGCGACCATGCCTGCTCGGCCATCGTGATGTGGGAGCTTGAC
ACCATAAGCCACACTTTGCTCAATTTGCACAAAATCGTTAACTTGAGCTTCTACTTG
CGTCGTGGCGACATTTTCACCTTTCCAGCGGAATGTATCACCTAATCTATCCACAAA
GGAAATATGGCGATAACCTTGGTAATGAACGAGATCGCCGGTATTAAAATAACAGTC
ACCGTCTTTTAATACTGACTTAAATAGCTTTTTATTACTTTCGTTGTCATCGGTATA
ACCATCAAATGGTGAACGTTTAGTTATCTTTGTTAGCAGTAGCCCTGTTTCTCCCGT
```

FIG. 5-2

```
TTTTACTTTGGTCATTTTCCCTTTCGCATTATACACAGGTTTGTCATTGTCAATATC
ATATTGTATGACGGTAAAAGCAAGTGGAGTAACCCCGCTGTATGCGGTAAGTTCAG
CGCATTGGAGAACACAAGATTACACTCACTGGCGCCATAGAATTCATTAATATGCTC
GATCCCAAAACGTTGTTGGAAATGATCCCAAATTTCGGGGCGTAATCCATTACCTAT
GATTTTCTTTATATTATGCTGTTTGTCTTTATTGCTAGGCGGTACATTTAATAAATA
ACGGCAGAGCTCGCCGATGTAAGTAAACGCAGTGGCATTATGAGCACGAACTTCATC
CCAAAAGCGACTTGAACTGAATTTTTCAGAAAGTGCGAGGGTTGCTGCGCTACCAAA
CACGGCGCTTAATGACACTGTCAGTGCATTGTTATGGTATAGGGGAGTGATAAATA
CAATACATCATCAGCTGTTAAGCGTAATGATGCCATCCCCATGCCTGCCATGGATTT
AAACCAACGGTGATGGCTCATTCTTGCTGCTTTTGGCAGTCCAGTTTTTCCCGAGGT
AAAGATATAAAACGCGCAATGCTTAAGCTGTATTTGTGCTGTTGATTCAGGGTTCAA
TACTGAATATCCTGCGACTAGTGTAGATATGTTTTTATAACCATCACTCATGTCTGG
CGTTTCTAAAGCGGGTACGTAAAAGACATTCTGTTGTAATGTCGATGACAAATTGGT
TTCAATATTATTAATGGCGGATGTGTATAGTTCATCTGCGATGAGTAATTTGGTATC
GACCACGCTAAGACTATGTTCGAGGATTGAATCCCGTTGTGTCGTATTTATCATACA
AGCAATCGCGCCAAGCTTGACAACTGCGAGGGCAATAATGATGGTTTCAGGCCTGTT
ATCGAGCATGATGGCGACTTTATCATTTTTACCAATGCCGTATTCATGAAGGAAATG
GGCATATTGATTTGCTTGCTTATTCAATGAATCGTAACTATAACGCTGGTCTTTAAA
TTGTATTGCGATCAAGTCAGAGTTATTGACAGCTTGCTGCTCTAGTAATAAACCAAT
AGACATAAAACGTTCGGGCTTTGCTTGTTGTAAGTGCCATAAGCCTTTGATGATTGG
CTTTGGGGTTTTTAATAGATTGATGGTACTTTTCAGGAATTGTTTGCCGGTTATAAC
AGTCATAAGCTAATTCTTTTATCAAGAAGAGGGGTTATGACACCAAATAAATGGGT
CACGCGTTGGTTTAATTTGGTTAGACTAAATGTGTTGTTTTGCTGTGATAATGCGAC
GTTCAAACAAACTTGAGAAGGTAAAAAATAGCATTTTTAAATTGAACATCAATACT
AATGTGTTGAATATCAATCAAGTTTTCTAACTGTGCGAGCACGCGTGCTTTAGCAAA
```

FIG. 5-3

```
CATGCCATGTGCTATTGCTGTTTTAAACCCATTAGTTTCGCTGGGATAAAATGTAA
ATGGATTGGATTTGTGTCTTTGGAGATATAAGCATATTTATATACGTCAAAAGGACT
AAATTTAAACAATGAAATCGGCTCGTAAGCATAATTCGCTGGCGTATTTACTATTTT
CTCACCGCTGGAACGTTGAGATCGTTGGCACGTTTTCGCTGTTTCGTTTTCTGTAA
GAATGTCGATGTACACTCCCACGCAAATTGTCCATCTACAAACACATCAATATGAGT
ATCAATGAAACGTCCTGTATCCGTTATGTACTCCTTAATTACACGACATGTGCTCGT
CAATATCGCGTTTAATGCTATCGGTTGATGTTGTGTTATGCGATTTCGATAATGGAC
TAGTCCTAATATAGATATCGGAAATTGTGTTGATGTCATGAGTTTCATCAATAATGG
AAAGATCATCACAAATGGATAAGTAACCGGTACATAGTTTGTGTTATTAAACCCACA
GCATTTAATATATTGCTTTAAATTTCGCTGATCTATTTTTTGTCCACTGATACTAAA
TTGCTCAGTACACACTTGTGTCGACCAAGTGTTCATCAGTGTTTTAACAATTGTATT
GACCACTGCTTTCACATATAAAAGCGAGATAATCGGTTGCTTTGTTAACAGTGTGAT
CTGGTTAGCGTGCATTGAAATAATTCATATAAGAGTATGTAGCATTTATGTTAATAT
TTTGTTTTGGAAGTTGAATTGGCGAATCCGTAATCGGTTTATGGCAGTTCGGTCAAA
TACTTCAGGTAAACTCGTTACTCATACCATTGATAGTGTTAAAGTGATTGACTGAAT
AAAGAATAGAGCTAAAAGTGGAAAAATTATGCAAGATGCGGGTATGTTATTACGCAT
TGCTTATGAGGCAATGAAAGAGTTAGAGGTTGATGTCATTGAAGTACTTTCTCGTTG
TAACATAAGTGAAGAAGTACTGAATGATAAGGATCTTCGCACACCTAATCATGCACA
AACACATTTTTGGCAAGTATTAGAAGACATATCACAAGATCCTAACATCGGCATTTC
ACTTGGTGAGAGAATGCCAGTGTTCACGGGGCAGGTATTACAGTATCTTTTTCTCAG
TAGTCCTACATTTGGTACTGGCTGGGAACGCGCAACAAATACTTTCGATTAATCAG
TGATGCGGCGAGTGTTTCTATCAAGATGGAAGGCTGTGAAGCGCGATTATCTGTGAA
CTTAGATGGTTTAGCGGAAGATGCGAATCGTCATTTGAATGATTGCCTAGTGATCGG
TGCATTTAAATTTTGTTTATATGTGACAGAAGGCGAATTTAAAGTAAGCAAAATAGC
CTTTGCTCATGCTCGCCCGAAAGATATTACTGCCTATACCAATGTATTTACATGTCC
```

FIG. 5-4

```
GATTGAGTTTGCTGCCGAAGATAATTATATTTATTTCGATGCTGATTTACTCGAACG
TCCTTCTTCGCATGCGGAGCCTGAGCTATTCGCCTTACACGATCAGCTTGCAAGCCG
TAAAATAGCCAAGTTAGAACTGCAAGATTTAGTGGATAAAGTACGTAAGGTTATTGC
ACAACAACTTGAGTCTGGTGTGGTGACTTTAGAAAGTATCGCCACTGAACTTGACAT
GAAACCACGTATGCTAAGAGCGAAGTTAGCTGACATTGATTATAACTTTAATCAAAT
ACTCGCTGATTTTCGTTGCGAGTTATCAAAAAACTGTTGGCGAATACGGACGAGTC
TATTGATCAGATTGTCTATCTCACTGGTTTTTCTGAACCAAGTACTTTTTATCGTGC
CTTTAAGCGCTGGGTTAAAATGACGCCAATTGAATATCGCCGTAGCAAACTCGCGGT
TAGGCATGCTAATCAACACGAGTCCTAAAAATTCGCTGCTTAGTGCATAGTGCATAG
TGCATAGTGCTAGTAAGCCAAGTACAAAGCGTTAAAGTTAAGTACTTGAGCGAACCA
TCAGACACCACTTACTAGATTAAGCACCTATTAATGATTGACCACAAATTCTGATCG
TATTGCCTGTGATCCCTGCAGCTTGAGGTTGCGCAAAAAAGCTATCGCTTCAGCAA
CATCAACTGGCTTACCACCTTGTTTTAATGAATTCATACGACGACCAGCTTCACGAA
CTGTAAATGGAATCGCTGCTGTCATTTTTGTTTCAATAAAGCCTGGTGCAACAGCAT
TAATGGTGATGTATTTGTCTGCAAGCGGAGTTTGCATTGCATCAACATAACCAATGA
CTGCGGCCTTAGACGTTGCATAATTAGTCTGACCAAAGTTACCCGCAATCCCACTCA
TCGAAGACACACAAACAATGCGGCCATAGTCGTTGAGCAGATCATCATTTAGCAGTC
GCTCATTGATTCTTTCCATTGCCGACAAGTTAATATCCATCAGTACATCCCAATGGT
TATCCGGCATACGTGCTAGCGTTTTGTCTTTTGTTACCCCGGCATTATGGACGATGA
TATCAAGCGACTGTTCTCGCACAAAGTCAGCAATGATATTTGGGGCGTCAGCAGCGG
TAATATCAGCAACAATGCTGCTACCTTTCAAGCAATGAGCTACTTTTTCAAGGTCCT
GTTTTAATGCCGGAATGTCTAAGCAAATAACATGTGCGCCATCACGGGCGAGTGTTT
CAGCAATAGCAGCCCCGATGCCACGTGATGCACCAGTGACAAGTGCTGTCTTTCCTT
GTAATGGTTTTGCCGTGTTACTTGTTTCGTTAATAACTTCGTTAATAACTTCGTTAA
```

FIG. 5-5

```
TAACTTCGTTAATAGCCCCATTAATCGAACCGGGTTTTACGTTAATAACCTGTGCTG
AGATATAGGCTGATTTTGCTGAGGTTAAGAAACGTAGCGGGGCCTCTAATAATTGCT
CACTACCAGGTTGTACATAGATAAGTTGACAGGTACTACCATTCTTGCCTATTTCTT
TGGCGACACTGCGACAAAACCCTTCTAAAGATCTTTGTACAGTCGCGTAGCTTACAT
CGTCAAGATGTTCACTCGGATGACCTAACACGATCACTCTGCTGCATGGCGAGAGCT
GCTTAATTACAGGTTGAAAAAACGATGTAATGCACTTAATTGCTTGCTGTTCTTAA
TGCCTGAGGCGTCGAAGATAATACCGTTGAAGCGATCTGTTTTAGCGATAGCATTAA
GGCTAATAGGTGTCGCGACTAAAGACGTTTGATTAAATTCAATATTAAGATCGGCTA
ACGCTGACGTGTTATTAGGATAAGAAATCGTGACTTCAGCATCTTTAAATGTGTTAA
GAATGGGTTTAATTAATTTGCTGTTGCTGGCTGCGCCGATGAGTAAGTTGCCAGAGA
TGAGATCGGTTCCCTGATCGTAGCGTGTTAACGTAACCGGTCGTGGCAGATTAAGCG
CTTTAAATAAACCTGATGTCCACTTGCCATTAGCGAGTTTTGCGTATGTATCCGTCA
TTTTCTAATCCTTGTTATAGTGAACAGTTTGAATCTCGAAGATGTACATGTGTTAAA
AATTATCTGATAGCTATGACTTATCTGCCACTACGTAATAATAAATAGACCAGTTCA
TTACATCGTTAATCGATATAGTATAACTAAATACTAAGTAAATTATAATGATAAGAC
TGTTATCGTACTCGGATCAAACTCTGATCAGCAAATAATCAAATTAGAGTTTTTATT
TTAAACTTGTATCAACAATGTTACATTAATGTATCTTACGTCTAATGTGCTACGGGC
ATATTTAAGTCACTAAATTAAAGGAATAAACCATGACAGGTCAAACAATAAGAAGAG
TAGCAATTATCGGCGGTAACCGTATCCCGTTTGCACGTTCAAATACAGCGTATTCAA
AACTAAGTAACCAAGATATGCTGACGGAAACTATCCGTGGCTTGGTGGTTAAATATA
ACCTACGTGGTGAACAACTGGGGGAAGTTGTTGCTGGTGCGGTAATTAAGCATTCTC
GTGATTTTAACTTAACACGTGAAGCCGTGCTAAGTGCAGGTCTTGCACCTGAAACGC
CTTGTTATGACATTCAACAAGCTTGTGGTACTGGTCTAGCTGCAGCTATCCAAGTAG
CAAACAAAATTGCGCTTGGTCAAATAGAAGCGGGTATTGCTGGTGGTTCTGATACGA
```

FIG. 5-6

```
CATCAGATGCACCGATTGCAGTCAGTGAAGGCATGCGTAGTGTATTACTTGAGCTTA
ATCGAGCTAAAACGGGTAAGCAACGTTTGAAAGCACTATCTCGTCTACGTCTAAAAC
ACTTTGCGCCACTAACGCCTGCAAATAAAGAGCCGCGTACCAAAATGGCGATGGGCG
ATCATTGTCAAGTAACAGCGAAGAGTGGAATATCTCACGTGAAGCACAAGATGCAT
TGGCCTGCGCAAGTCATCAAAATTAGCTGCAGCATATGAAGAAGGTTTCTTTGATA
CGTTAGTTTCACCTATGGCCGGCTTAACGAAAGATAACGTATTACGCGCAGATACAA
CAGTTGAGAAACTGGCTAAATTGAAACCTTGTTTTGATAAAGTAAACGGCACTATGA
CGGCGGGTAACAGTACTAACCTTACCGATGGAGCATCAGCTGTATTACTTGCAAGTG
AAGAATGGGCAGCGGCACATAACTTACCAGTACAAGCTTATCTAACATTTGGTGAAA
CGGCCGCTATCGACTTCGTTGATAAGAAGAAGGTCTGTTAATGGCGCCTGCATACG
CAGTGCCAAAAATGTTGAAGCGTGCTGGCCTTACATTACAAGACTTCGATTACTATG
AAATACATGAAGCATTTGCTGCGCAGTTATTAGCAACGCTAGCAGCTTGGGAAGACG
AAAAATTCTGTAAAGAAAACTGGGTCTAGATGCTGCGCTTGGTTCAATTGATATGA
CCAAGTTAAACGTGAAAGGGAGTAGCTTAGCCACGGGTCACCCATTTGCCGCAACTG
GTGGTCGTGTTGTCGCTACGCTAGCGCAATTACTTGATCAGAAGGTTCAGGTCGTG
GTTTGATCTCGATTTGTGCTGCTGGTGGTCAAGGTATCACGGCAATTTTAGAGAAAT
AAACGCACTGTTTATTATCTATTGATTAAGCTGTCCTGAGATACTGGATATTTTAA
ATAAAACGCCAATACTGCAGAGTATTGGCGTTTTTTTGTAATACCAATTCCTATATA
ACGGTGCATTTTAAACACTTAATTTCCGGCATTGGTATCATAAAAAGCAGCACCGA
AGTGCTGCTTGATTGTAGATTAACCTATTAAAATAGAGAGGCTAGAATTAGTCTTCG
TATGCTTCATTATGTACGCCAGCTGCACGACCCGATGGATCAGCATTGTTTTGGAAA
CTTTCATCCCAAGCTAATGCTTCTACAGTTGAACAAGCAACGGATTTACCAAACGGT
ACGCATTTCGCTGCTGAATCACCTGGGAAGTGATCTTCAAAGATGGCACGATAGTAG
TAACCTTCTTTCGTATCTGGTGTGTTAATTGGGAACTTAAATGCTGCACTTGCTAAC
ATTTGATCAGTTACCGCTTCTTCAACGTGTACTTTAAGTTGGTCAATCCAAGAATAA
```

FIG. 5-7

```
CCAACACCATCAGAGAATTGTTCTTTTGACGCCATACAATTTCTTCAGGTAGTAAA
TCTTCAAATGCTTCTCGAATGATGTTTTTCTCAATGCGGTCGCCCGTGATCATTTTT
AGTTCAGGGTTTAGACGCATTGACGCATCAACAAATTCTTTATCTAAGAAAGGAACA
CGTGCTTCGATGCCCCAAGCTGCCATAGATTTGTTTGCACGTAAGCAATCAAACATA
TGTAATTTATTTACTTTACGTACCGTCTCTTCATGGAATTCTTTCGCATTTGGCGCT
TTGTGGAAGTACAAGTAACCACCGAACAGTTCATCAGCACCTTCACCAGAAAGCACC
ATCTTAATCCCCATGGCTTTAATTTTACGTGCCATTAGGTACATAGGGGTTGATGCA
CGAATTGTTGTTACATCGTAGGTTTCAATGTGGTAAATCACGTCGCGTAAAGCGTCG
ATACCTTCTTGCACAGTAAATTCAATTGATGATGGATAGTACCTAAGTGATCTGCC
ACTTTTTGTGCAGCGGCTAAATCTGGAGAACCATTTAGGCCTACAGAGAAAGAGTGT
AGTTGTGGCCACCATGCTTCGGTTTTACCACCGTCTTCAATACGACGTTTTGCATAC
TGTTGGGTGATTGCTGAAATAACAGATGAATCTAACCCGCCTGATAATAATACGCCG
TAAGGTACATCACACATTAATTGACGTTTAACTGCATCTTCCAAACCTTGCTTAACA
ACGCTTTTATCACCACCATTTTGTGCAACGTTATCAAAATCTTTCCAATCACGTTGA
TAATAAGGCGTGACTACACCATCCTTACTCCACAGGTAATGACCTGCTGGGAATTCT
TCAATTTGAGTACAAATTGGCACTAGTGCTTTCATTTCAGAGGCAACATAAAGTTA
CCGTGTTCATCATAGCCCGTATAAGAGGGATGATACCGATATGGTCACGGCCAATC
AGGTAAGCGTCCTCTGTTTCGTCATATAAAGCGAAAGCAAAATACCATTTAGATCA
TCTAAAAATTGTGTGCCTTTTTCTTTATATAGCGCAAGTATCACTTCGCAATCTGAT
TCTGTTTGGAATTCAAAGTCTACGTTCAGCGTTTTCTTTAAATCTTTGTGGTTATAA
ATTTCACCATTAACAGCAAGTACGTGTGTCTTTTCTTCATTATATAGCGGCTGTGCA
CCATTATTTACATCGACAATAGCAAGACGTTCATGAACTAAAATAGCATTGTCACTT
GTATAGATACCTGACCAATCTGGGCCGCGGTGACGTAGTAACTTTGATAGTTCTAGT
GCTTGTTCGCGAAGAGGTTTAATGTCTGATTTGATGTCTAGAATTCCGAATATTGAG
```

FIG. 5-8

```
CACATAACTAATTCCTTCTGGGGCTGCGTCTGCAGCTAACTTTCTAAATAGTGTGTC
TAATTTGCCACATTGTAGATTTAATGCAAACATTAATGATAAAACATTTATAAAAA
TGTAATTCAATGTGGAATCGATAATTTAATGGCTTAAAAGTGAAGATCCATTAATTG
TGATGGCGAGGTGATAGACCAATGTAGACCTTAATGAATAAAGCAGGCACGATTGAA
TCCATTCAACGCAAAGTGGTACTAACTATTGTTTTAAACGTTATAAATAGTGTTTTA
AAGGTTATAAGTAAATAATTTAAAAACAATAATAATCCACATGCATTAAATTTATCA
TGATAAACCGCTATATCTCAATGGCAATTTGGGATAAGTGTAAAATATATGTAAAAT
GAATGAGTTGACTTGCTTTTTTTACACTAAGTGATGAAATTAAAGCTAGATGTCGTT
GTTAGCATTGATTAATAACGTACTAAAATACGACATCTAGTATAGAAATTTAAAAAA
CAGTTGGTTTTGATAGCATAACTGCATAAACTAATCAGCTTATTGTCTGTAATATTT
TTGTAATTTAAATAGGTTTAATAAAATTATATGTCTGATAAATATAAACCGTACGAC
CTTTCCTTTAAAAAGACGTTTTGCTGCCTAAGTTTTGGCCTGTGTGGTTCGGGGTG
TTTGCAATATACTTATTAGCTTTTATGCCAGTAAAGCCGCGTGATAAATTTGCTCGA
TTCATAGCGAAGAAATTGTTTAGTCTAAAAATGATGGCAAAGCGTAAAAGGTAGCA
AAGATCAATTTATCTATGTGCTTCCCTGAAATGGATGATACGGAACAAGACCGTATA
ATCATGGTCAATCTAGTTACTTTTGTCAAACTATCTTAAGTTATGCAGAGCCAAGT
GCGCGTAGTCGTGCTTATAACCGTGACCGTATGATAGTGCATGGTGGCGAGAATTTA
TTTCCGCTACTTGAACAAGGTAAGGCTTGTATCTTATTAGTGCCGCATAGCTTCGCT
ATTGATTTGCAGGTTTACACATTGCTTCTTATGGCGCGCCATTTTGTACTATGTTT
AACAATTCTGAGAATGAGTTGTTCGATTGGCTGATGACACGTCAACGCGCTATGTTT
GGAGGCACTGTTTATCACCGCAAGGCAGGGCTAGGGGCTCTAGTTAAATCACTTAAG
AGCGGTGAAAGCTGTTATTACTTACCTGATGAAGACCATGGACCTAAGCGTAGTGTA
TTTGCGCCTTTATTTGCGACTCAAAAGCAACTTTACCTGTAATGGGCAAGCTAGCA
GAAAAACAAATGCACTCGTTGTTCCTGTTTATGCGGCATATAATGAATCACTAGGT
AAATTTGAAACCTTTATTCGACCAGCAATGCAAAACTTTCCATCAGAAAGCCCAGAA
CAAGATGCAGTGATGATGAATAAAGAGATTGAAGCCTTGATTGAATGTGGTGTTGAT
```

FIG. 5-9

```
CAATATATGTGGACACTTAGATTATTGAGAACACGTCCGGACGGTAAAAAATCTAC
TAATAAAGTTTAATAAACACCATAATCTTCGTTGAATATGGTGTTTACCCCCTGAA
TACCCTCTAAATTAATAACAAAAAAGCCATTTACGTAACATCTAATGATGATTTAG
CCTGCACTTGCTTTGTTTTAGTCTTAAGAGCCTAATAAACTTGATCTAGGTATAGA
TTCTGTCTTTCTTTACGTAACGCGATCTATTTTTTTAACCGATAGTTGTTATAATT
AGTTTCATATGAAAGAGATATCGTTTCAGTAAAAGCTATTTCGTTTCAATAGATAAT
TTATTTATAGTCATATTTTCTGTAATGACAATCATTTTCTCATCTAGACTATAGATA
AGAATACGAATTAAGTAAGAACATTAATTTTACAAGAATATAAAATATCCCATCGGA
GCTATAAGAATGAAAAGACTAAAATTGTTTGTACAATTGGTCCAAAAACTGAATCA
GTAGAGAAACTAACAGAGCTTGTTAATGCAGGCATGAACGTTATGCGTTTAAATTTC
TCTCATGGTAACTTTGCTGAACATTCAGTGCGTATTCAAAATATCCGTCAAGTAAGT
GAAAACCTGAATAAGAAAATTGCTGTTTTACTGGATACTAAAGGTCCAGAAATCCGT
ACGATTAAACTAGAAAACGGTGACGATGTAATGTTGACCGCTGGTCAGTCATTCACG
TTTACAACAGACATTAACGTGGTAGGTAATAAAGACTGTGTTGCTGTAACATATGCT
GGTTTTGCTAAAGACCTTAATCCTGGTGCAATCATCCTTGTTGATGATGGTTTAATT
GAAATGGAAGTTGTTGCAACAACTGACACTGAAGTTAAATGTACAGTATTAAATACT
GGTGCACTTGGTGAAAATAAAGGCGTTAACTTACCTAACATCAGTGTAGGTCTACCT
GCATTGTCAGAAAAGATAAAGCTGATTTAGCGTTTGGTTGTGAGCAAGAAGTTGAT
TTTGTTGCTGCATCATTTATTCGTAAGGCTGATGATGTAAGAGAAATTCGTGAAATC
CTATTTAATAATGGTGGCGAAAACATTCAGATTATCTCGAAAATTGAAAACCAAGAA
GGTGTAGACAATTTCGATGAAATCTTAGCTGAATCAGACGGTATCATGGTTGCTCGT
GGCGATCTCGGTGTTGAGATCCCAGTTGAAGAAGTGATCATGGCACAGAAGATGATG
ATCAAAAAATGTAATAAAGCAGGTAAAGTTGTAATTACTGCAACACAAATGCTTGAT
TCAATGATCAGTAACCCACGTCCAACACGTGCAGAAGCGGGCGATGTTGCCAATGCT
GTGCTTGACGGTACCGACGCGGTAATGCTTTCTGGTGAAACTGCGAAAGGTAAATAC
```

FIG. 5-10

```
CCAGTTGAAGCTGTGTCTATCATGGCAAACATCTGTGAACGTACTGATAACTCAATG
TCTTCGGATTTAGGTGCGAACATTGTTGCTAAAAGCATGCGCATTACAGAAGCTGTG
TGTAAAGGTGCGGTAGAAACAACAGAAAATTGTGTGCTCCACTTATTGTTGTTGCA
ACTCGTGGCGGTAAATCAGCAAATCTGTTCGTAAATACTTCCCGAAAGCAAATATT
CTTGCTATCACAACAAATGAAAAGCAGCGCAACAGTTATGCCTAACTAAAGGCGTA
AGCAGCTGCATCGTTGAGCAGATTGATAGCACTGATGAGTTCTACCGTAAAGGTAAA
GAGCTTGCATTAGCAACTGGTTTAGCTAAAGAAGGCGATATCGTTGTTATGGTATCA
GGTGCGTTAGTACCATCAGGTACAACGAATACGGCATCTGTTCACCAACTTTAAGTT
GCCATATTGATATTATAAAAAGAGAGCGTATGCTCTCTTTTTTTATATCTGTAGTT
TATATGTCTGTACAAAAAATGATAAGAGTACATAAACTATTAATATAGCGTAATA
TATAATGATTAACGGTGATGAAAGGGTTAAATAAATGGATAGTGCTAAACATAAAAT
TGGCTTAGTCCTTTCTGGCGGTGGTGCGAAAGGTATTGCTCATCTTGGTGTATTAAA
ATACCTGTTAGAGCAAGATATAAGACCGAATGTAATTGCGGGTACAAGTGCTGGCTC
TATGGTTGGTGCACTTTATTGCTCAGGACTTGAGATTGATGACATTTTACAATTCTT
CATCGATGTAAAACCTTTTTCTTGGAAGTTTACCCGTGCCCGTGCTGGCTTTATAGA
CCCGGCAAAATTATATCCTGAAGTGCTAAAATATATCCCCGAGGATAGCTTTGAGTA
CCTTCAACCTGAATTGCGCATTGTTGCCACCAACATGTTACTCGGTAAAGAGCATAT
ATTTAAAGATGGCTCCGTGATTAATGCCTTATTAGCATCAGCCAGCTACCCTTTAGT
TTTTTCTCCGATGATCATTGACGATCAAGTGTATTCAGATGGCGGTATTGTTAATCA
TTTCCCCGTGAGTGTCATTGAAGATGATTGCGATAAAATAATCGGCGTATACGTGTC
GCCCATTCGTCAGGTCGAAGCTGACGAACTCGAGTATAAAAGACGTGGTATTACG
TGCGTTCACGCTGCAGGGTAGTGGTGCTGAATTAGATAAACTATCGCAATGTGATGT
GCAAATTTATCCAGAAGCGCTATTGAATTACAATACGTTTGCAACCGATGAAAAATC
ATTACGGGAGATCTACCAGATTGGTTATGATGCTGCAAAAGATCAACATGACAACCT
TATGGCATTGAAAGAAAGTATCACCACCAGCGAGGTTAAAAAGAACGTCTTTAGCAA
```

FIG. 5-11

```
ATGGTTTGGTGATAAACTTGCTAGCAACAGCGGCAAATAGCGGCCCACACGGATTTA
TACACTAGGATAATGGGCGTTAATAGCCTCACTGTCGTTGTGTGGTCTCTAATTTTA
GCTAAATCTTGTGTTATACTGACTTCCTATTAATCATAAACGATTTATCACGGTAAA
CATGACTCAAATAAATAACCCGCTTCACGGCATGACACTCGAAAAGTAATTAACAG
TCTCGTTGAACAATATGGCTGGGATGGTCTTGGATACTACATCAACATTCGTTGCTT
TACTGAAAATCCAAGTGTTAAGTCTAGTCTTAAATTTTACGTAAAACCCCTTGGGC
ACGTGATAAGTAGAAGCGCTATATATCAAAATGGTGACTGAAGGCTAACTGTCTCC
ACGCTAGCGAACCGCTGTTTATAGTTAATATAAGTACTATAAGCAGGGCTCGTTAAT
TCAGTATGTAATTAATCCTGAATACCTCCGCTTATTTCAACATTGTACTCTCTAGAT
AACACTCTCAACATTACACCTTCAACATCACAGCCTCCACATAACATCCGATGACAT
AGCCCTGTTATTTTCACATTATCTATATGCTATATATTTAGCCATTTGATCAAT
TGAGTTAATTTCTGCAATGACAAAGATATACCATCATCCAGTACAAATTTATTATGA
AGATACCGACCATTCTGGTGTTGTTTACCACCCTAACTTTTTAAAATACTTTGAACG
TGCACGTGAGCATGTGATAAATAGTGACTTACTAGCAACATTGTGGAATGAACGCGG
TTTAGGTTTTGCGGTGTATAAAGCCAATATGACTTTTCAGGATGGGGTCGAATTTGC
TGAAGTGTGTGATATTCGCACTTCTTTTGTCCTAGACGGTAAGTACAAAACGATCTG
GCGCCAAGAAGTATGGCGTCCGAATGCGACTAGGGCTGCCGTTATCGGTGATATTGA
AATGGTGTGCTTAGACAAACAAAACGTTTACAGCCCATCCCTGATGATGTTAGC
TGCAATGGTTAGTGAATAAATGGTTCATGCATAAATAGTTAATACATGATTCTGGCC
CGTCACGTTTACAGATAAGAGGCATCCGATGCCTCCTTCCTATTACCAATACTACTG
CTTATCCCTTTCTAACTATCTTTAGCGTCCATAACACACTGAGCATTTATTCTATTA
ATCAGTGATTGTGATTTAATTATCTTCTATATATGTAATTTAATGTAATTTTCAATT
TATTTTTAGCTACATTAAGGCTTACGAATGTACGCTAAAATGAGATGTCAGACTAAT
TTTAGCTTATTAATCTGTTAGCCGTTTATATTTTATAAAGATGGGATTTAACTTAAA
```

FIG. 5-12

```
TGCAATTAATTATGGCGTAAATAGAGTGAAAACATGGCTAATATTCACTAAGTCCTG
AATTTTATATAAGTTTAATCTGTTATTTTAGCGTTTACCTGGTCTTATCAGTGAGG
TTTATAGCCATTATTAGTGGGATTGAAGTGATTTTTAAAGCTATGTATATTATTGCA
AATATAAATTGTAACAATTAAGACTTTGGACACTTGAGTTCAATTTCGAATTGATTG
GCATAAATTTAAAACAGCTAAATCTACCTCAATCATTTTAGCAAATGTATGCAGGT
AGATTTTTTCGCCATTTAAGAGTACACTTGTACGCTAGGTTTTGTTTAGTGTGCA
AATGAACGTTTTGATGAGCATTGTTTTAGAGCACAAATAGATCCTTACAGGAGCA
ATAACGCAATGGCTAAAAGAACACCACATCGATTAAGCACGCCAAGGATGTGTTAA
GTAGTGATGATCAACAGTTAAATTCTCGCTTGCAAGAATGTCCGATTGCCATCATTG
GTATGGCATCGGTTTTTGCAGATGCTAAAAACTTGGATCAATTCTGGGATAACATCG
TTGACTCTGTGGACGCTATTATTGATGTGCCTAGCGATCGCTGGAACATTGACGACC
ATTACTCGGCTGATAAAAAGCAGCTGACAAGACATACTGCAAACGCGGTGGTTTCA
TTCCAGAGCTTGATTTTGATCCGATGGAGTTTGGTTTACCGCCAAATATCCTCGAGT
TAACTGACATCGCTCAATTGTTGTCATTAATTGTTGCTCGTGATGTATTAAGTGATG
CTGGCATTGGTAGTGATTATGACCATGATAAAATTGGTATCACGCTGGGTGTCGGTG
GTGGTCAGAAACAAATTTCGCCATTAACGTCGCGCCTACAAGGCCCGGTATTAGAAA
AAGTATTAAAAGCCTCAGGCATTGATGAAGATGATCGCGCTATGATCATCGACAAAT
TTAAAAAAGCCTACATCGGCTGGGAAGAGAACTCATTCCCAGGCATGCTAGGTAACG
TTATTGCTGGTCGTATCGCCAATCGTTTTGATTTTGGTGGTACTAACTGTGTGGTTG
ATGCGGCATGCGCTGGCTCCCTTGCAGCTGTTAAAATGGCGATCTCAGACTTACTTG
AATATCGTTCAGAAGTCATGATATCGGGTGGTGTATGTTGTGATAACTCGCCATTCA
TGTATATGTCATTCTCGAAAACACCAGCATTTACCACCAATGATGATATCCGTCCGT
TTGATGACGATTCAAAAGGCATGCTGGTTGGTGAAGGTATTGGCATGATGGCGTTTA
AACGTCTTGAAGATGCTGAACGTGACGGCGACAAAATTTATTCTGTACTGAAAGGTA
TCGGTACATCTTCAGATGGTCGTTTCAAATCTATTTACGCTCCACGCCCAGATGGCC
AAGCAAAAGCGCTAAAACGTGCTTATGAAGATGCCGGTTTTGCCCCTGAAACATGTG
```

FIG. 5-13

```
GTCTAATTGAAGGCCATGGTACGGGTACCAAAGCGGGTGATGCCGCAGAATTTGCTG
GCTTGACCAAACACTTTGGCGCCGCCAGTGATGAAAGCAATATATCGCCTTAGGCT
CAGTTAAATCGCAAATTGGTCATACTAAATCTGCGGCTGGCTCTGCGGGTATGATTA
AGGCGGCATTAGCGCTGCATCATAAAATCTTACCTGCAACGATCCATATCGATAAAC
CAAGTGAAGCCTTGGATATCAAAAACAGCCCGTTATACCTAAACAGCGAAACGCGTC
CTTGGATGCCACGTGAAGATGGTATTCCACGTCGTGCAGGTATCAGCTCATTTGGTT
TTGGCGGCACCAACTTCCATATTATTTTAGAAGAGTATCGCCCAGGTCACGATAGCG
CATATCGCTTAAACTCAGTGAGCCAAACTGTGTTGATCTCGGCAAACGACCAACAAG
GTATTGTTGCTGAGTTAAATAACTGGCGTACTAAACTGGCTGTCGATGCTGATCATC
AAGGGTTTGTATTTAATGAGTTAGTGACAACGTGGCCATTAAAAACCCCATCCGTTA
ACCAAGCTCGTTTAGGTTTTGTTGCGCGTAATGCAAATGAAGCGATCGCGATGATTG
ATACGGCATTGAAACAATTCAATGCGAACGCAGATAAAATGACATGGTCAGTACCTA
CCGGGGTTTACTATCGTCAAGCCGGTATTGATGCAACAGGTAAAGTGGTTGCGCTAT
TCTCAGGGCAAGGTTCGCAATACGTGAACATGGGTCGTGAATTAACCTGTAACTTCC
CAAGCATGATGCACAGTGCTGCGGCGATGGATAAAGAGTTCAGTGCCGCTGGTTTAG
GCCAGTTATCTGCAGTTACTTTCCCTATCCCTGTTTATACGGATGCCGAGCGTAAGC
TACAAGAAGAGCAATTACGTTTAACGCAACATGCGCAACCAGCGATTGGTAGTTTGA
GTGTTGGTCTGTTCAAAACGTTTAAGCAAGCAGGTTTTAAAGCTGATTTTGCTGCCG
GTCATAGTTTCGGTGAGTTAACCGCATTATGGGCTGCCGATGTATTGAGCGAAAGCG
ATTACATGATGTTAGCGCGTAGTCGTGGTCAAGCAATGGCTGCGCCAGAGCAACAAG
ATTTTGATGCAGGTAAGATGGCCGCTGTTGTTGGTGATCCAAAGCAAGTCGCTGTGA
TCATTGATACCCTTGATGATGTCTCTATTGCTAACTTCAACTCGAATAACCAAGTTG
TTATTGCTGGTACTACGGAGCAGGTTGCTGTAGCGGTTACAACCTTAGGTAATGCTG
GTTTCAAAGTTGTGCCACTGCCGGTATCTGCTGCGTTCCATACACCTTTAGTTCGTC
ACGCGCAAAAACCATTTGCTAAAGCGGTTGATAGCGCTAAATTTAAAGCGCCAAGCA
TTCCAGTGTTTGCTAATGGCACAGGCTTGGTGCATTCAAGCAAACCGAATGACATTA
```

FIG. 5-14

```
AGAAAAACCTGAAAAACCACATGCTGGAATCTGTTCATTTCAATCAAGAAATTGACA
ACATCTATGCTGATGGTGGCCGCGTATTTATCGAATTTGGTCCAAAGAATGTATTAA
CTAAATTGGTTGAAAACATTCTCACTGAAAAATCTGATGTGACTGCTATCGCGGTTA
ATGCTAATCCTAAACAACCTGCGGACGTACAAATGCGCCAAGCTGCGCTGCAAATGG
CAGTGCTTGGTGTCGCATTAGACAATATTGACCCGTACGACGCCGTTAAGCGTCCAC
TTGTTGCGCCGAAAGCATCACCAATGTTGATGAAGTTATCTGCAGCGTCTTATGTTA
GTCCGAAAACGAAGAAGCGTTTGCTGATGCATTGACTGATGGCTGGACTGTTAAGC
AAGCGAAAGCTGTACCTGCTGTTGTGTCACAACCACAAGTGATTGAAAAGATCGTTG
AAGTTGAAAGATAGTTAACGCATTGTCGAAGTAGAGCGTATTGTCGAAGTAGAAA
AAATCGTCTACGTTAATGCTGACGGTTCGCTTATATCGCAAAATAATCAAGACGTTA
ACAGCGCTGTTGTTAGCAACGTGACTAATAGCTCAGTGACTCATAGCAGTGATGCTG
ACCTTGTTGCCTCTATTGAACGCAGTGTTGGTCAATTTGTTGCACACCAACAGCAAT
TATTAAATGTACATGAACAGTTTATGCAAGGTCCACAAGACTACGCGAAAACAGTGC
AGAACGTACTTGCTGCGCAGACGAGCAATGAATTACCGGAAAGTTTAGACCGTACAT
TGTCTATGTATAACGAGTTCCAATCAGAAACGCTACGTGTACATGAAACGTACCTGA
ACAATCAGACGAGCAACATGAACACCATGCTTACTGGTGCTGAAGCTGATGTGCTAG
CAACCCCAATAACTCAGGTAGTGAATACAGCCGTTGCCACTAGTCACAAGGTAGTTG
CTCCAGTTATTGCTAATACAGTGACGAATGTTGTATCTAGTGTCAGTAATAACGCGG
CGGTTGCAGTGCAAACTGTGGCATTAGCGCCTACGCAAGAAATCGCTCCAACAGTCG
CTACTACGCCAGCACCGCATTGGTTGCTATCGTGGCTGAACCTGTGATTGTTGCGC
ATGTTGCTACAGAAGTTGCACCAATTACACCATCAGTTACACCAGTTGTCGCAACTC
AAGCGGCTATCGATGTAGCAACTATTAACAAAGTAATGTTAGAAGTTGTTGCTGATA
AAACCGGTTATCCAACGGATATGCTGGAACTGAGCATGGACATGGAAGCTGACTTAG
GTATCGACTCAATCAAACGTGTTGAGATATTAGGCGCAGTACAGGAATTGATCCCTG
ACTTACCTGAACTTAATCCTGAAGATCTTGCTGAGCTACGCACGCTTGGTGAGATTG
TCGATTACATGAATTCAAAAGCCCAGGCTGTAGCTCCTACAACAGTACCTGTAACAA
```

FIG. 5-15

```
GTGCACCTGTTTCGCCTGCATCTGCTGGTATTGATTTAGCCCACATCCAAAACGTAA
TGTTAGAAGTGGTTGCAGACAAAACCGGTTACCCAACAGACATGCTAGAACTGAGCA
TGGATATGGAAGCTGACTTAGGTATTGATTCAATCAAGCGTGTGGAAATCTTAGGTG
CAGTACAGGAGATCATAACTGATTTACCTGAGCTAAACCCTGAAGATCTTGCTGAAT
TACGCACCCTAGGTGAAATCGTTAGTTACATGCAAAGCAAAGCGCCAGTCGCTGAAA
GTGCGCCAGTGGCGACGGCTCCTGTAGCAACAAGCTCAGCACCGTCTATCGATTTGA
ACCACATTCAAACAGTGATGATGGATGTAGTTGCAGATAAGACTGGTTATCCAACTG
ACATGCTAGAACTTGGCATGGACATGGAAGCTGATTTAGGTATCGATTCAATCAAAC
GTGTGGAAATATTAGGCGCAGTGCAGGAGATCATCACTGATTTACCTGAGCTAAACC
CAGAAGACCTCGCTGAATTACGCACGCTAGGTGAAATCGTTAGTTACATGCAAAGCA
AAGCGCCAGTCGCTGAGAGTGCGCCAGTAGCGACGGCTTCTGTAGCAACAAGCTCTG
CACCGTCTATCGATTTAAACCATATCCAAACAGTGATGATGGAAGTGGTTGCAGACA
AAACCGGTTATCCAGTAGACATGTTAGAACTTGCTATGGACATGGAAGCTGACCTAG
GTATCGATTCAATCAAGCGTGTAGAAATTTTAGGTGCGGTACAGGAAATCATTACTG
ACTTACCTGAGCTTAACCCTGAAGATCTTGCTGAACTACGTACATTAGGTGAAATCG
TTAGTTACATGCAAAGCAAAGCGCCCGTAGCTGAAGCGCCTGCAGTACCTGTTGCAG
TAGAAAGTGCACCTACTAGTGTAACAAGCTCAGCACCGTCTATCGATTTAGACCACA
TCCAAAATGTAATGATGGATGTTGTTGCTGATAAGACTGGTTATCCTGCCAATATGC
TTGAATTAGCAATGGACATGGAAGCCGACCTTGGTATTGATTCAATCAAGCGTGTTG
AAATTCTAGGCGCGGTACAGGAGATCATTACTGATTTACCTGAACTAAACCCAGAAG
ACTTAGCTGAACTACGTACGTTAGAAGAAATTGTAACCTACATGCAAAGCAAGGCGA
GTGGTGTTACTGTAAATGTAGTGGCTAGCCCTGAAAATAATGCTGTATCAGATGCAT
TTATGCAAAGCAATGTGGCGACTATCACAGCGGCCGCAGAACATAAGGCGGAATTTA
AACCGGCGCCGAGCGCAACCGTTGCTATCTCTCGTCTAAGCTCTATCAGTAAAATAA
GCCAAGATTGTAAAGGTGCTAACGCCTTAATCGTAGCTGATGGCACTGATAATGCTG
```

FIG. 5-16

```
TGTTACTTGCAGACCACCTATTGCAAACTGGCTGGAATGTAACTGCATTGCAACCAA
CTTGGGTAGCTGTAACAACGACGAAAGCATTTAATAAGTCAGTGAACCTGGTGACTT
TAAATGGCGTTGATGAAACTGAAATCAACAACATTATTACTGCTAACGCACAATTGG
ATGCAGTTATCTATCTGCACGCAAGTAGCGAAATTAATGCTATCGAATACCCACAAG
CATCTAAGCAAGGCCTGATGTTAGCCTTCTTATTAGCGAAATTGAGTAAAGTAACTC
AAGCCGCTAAAGTGCGTGGCGCCTTTATGATTGTTACTCAGCAGGGTGGTTCATTAG
GTTTTGATGATATCGATTCTGCTACAAGTCATGATGTGAAAACAGACCTAGTACAAA
GCGGCTTAAACGGTTTAGTTAAGACACTGTCTCACGAGTGGGATAACGTATTCTGTC
GTGCGGTTGATATTGCTTCGTCATTAACGGCTGAACAAGTTGCAAGCCTTGTTAGTG
ATGAACTACTTGATGCTAACACTGTATTAACAGAAGTGGGTTATCAACAAGCTGGTA
AAGGCCTTGAACGTATCACGTTAACTGGTGTGGCTACTGACAGCTATGCATTAACAG
CTGGCAATAACATCGATGCTAACTCGGTATTTTAGTGAGTGGTGGCGCAAAAGGTG
TAACTGCACATTGTGTTGCTCGTATAGCTAAAGAATATCAGTCTAAGTTCATCTTAT
TGGGACGTTCAACGTTCTCAAGTGACGAACCGAGCTGGGCAAGTGGTATTACTGATG
AAGCGGCGTTAAAGAAAGCAGCGATGCAGTCTTTGATTACAGCAGGTGATAAACCAA
CACCCGTTAAGATCGTACAGCTAATCAAACCAATCCAAGCTAATCGTGAAATTGCGC
AAACCTTGTCTGCAATTACCGCTGCTGGTGGCCAAGCTGAATATGTTTCTGCAGATG
TAACTAATGCAGCAAGCGTACAAATGGCAGTCGCTCCAGCTATCGCTAAGTTCGGTG
CAATCACTGGCATCATTCATGGCGCGGGTGTGTTAGCTGACCAATTCATTGAGCAAA
AAACACTGAGTGATTTTGAGTCTGTTTACAGCACTAAAATTGACGGTTTGTTATCGC
TACTATCAGTCACTGAAGCAAGCAACATCAAGCAATTGGTATTGTTCTCGTCAGCGG
CTGGTTTCTACGGTAACCCCGGCCAGTCTGATTACTCGATTGCCAATGAGATCTTAA
ATAAAACCGCATACCGCTTTAAATCATTGCACCCACAAGCTCAAGTATTGAGCTTTA
ACTGGGGTCCTTGGGACGGTGGCATGGTAACGCCTGAGCTTAAACGTATGTTTGACC
AACGTGGTGTTTACATTATTCCACTTGATGCAGGTGCACAGTTATTGCTGAATGAAC
```

FIG. 5-17

```
TAGCCGCTAATGATAACCGTTGTCCACAAATCCTCGTGGGTAATGACTTATCTAAAG
ATGCTAGCTCTGATCAAAAGTCTGATGAAAAGAGTACTGCTGTAAAAAGCCACAAG
TTAGTCGTTTATCAGATGCTTTAGTAACTAAAAGTATCAAAGCGACTAACAGTAGCT
CTTTATCAAACAAGACTAGTGCTTTATCAGACAGTAGTGCTTTTCAGGTTAACGAAA
ACCACTTTTTAGCTGACCACATGATCAAAGGCAATCAGGTATTACCAACGGTATGCG
CGATTGCTTGGATGAGTGATGCAGCAAAAGCGACTTATAGTAACCGAGACTGTGCAT
TGAAGTATGTCGGTTTCGAAGACTATAAATTGTTTAAAGGTGTGGTTTTTGATGGCA
ATGAGGCGGCGGATTACCAAATCCAATTGTCGCCTGTGACAAGGGCGTCAGAACAGG
ATTCTGAAGTCCGTATTGCCGCAAAGATCTTTAGCCTGAAAAGTGACGGTAAACCTG
TGTTTCATTATGCAGCGACAATATTGTTAGCAACTCAGCCACTTAATGCTGTGAAGG
TAGAACTTCCGACATTGACAGAAAGTGTTGATAGCAACAATAAAGTAACTGATGAAG
CACAAGCGTTATACAGCAATGGCACCTTGTTCCACGGTGAAAGTCTGCAGGGCATTA
AGCAGATATTAAGTTGTGACGACAAGGGCCTGCTATTGGCTTGTCAGATAACCGATG
TTGCAACAGCTAAGCAGGGATCCTTCCCGTTAGCTGACAACAATATCTTTGCCAATG
ATTTGGTTTATCAGGCTATGTTGGTCTGGGTGCGCAAACAATTTGGTTTAGGTAGCT
TACCTTCGGTGACAACGGCTTGGACTGTGTATCGTGAAGTGGTTGTAGATGAAGTAT
TTTATCTGCAACTTAATGTTGTTGAGCATGATCTATTGGGTTCACGCGGCAGTAAAG
CCCGTTGTGATATTCAATTGATTGCTGCTGATATGCAATTACTTGCCGAAGTGAAAT
CAGCGCAAGTCAGTGTCAGTGACATTTTGAACGATATGTCATGATCGAGTAAATAAT
AACGATAGGCGTCATGGTGAGCATGGCGTCTGCTTTCTTCATTTTTTAACATTAACA
ATATTAATAGCTAAACGCGGTTGCTTTAAACCAAGTAAACAAGTGCTTTTAGCTATT
ACTATTCCAAACAGGATATTAAAGAGAATATGACGGAATTAGCTGTTATTGGTATGG
ATGCTAAATTTAGCGGACAAGACAATATTGACCGTGTGGAACGCGCTTTCTATGAAG
GTGCTTATGTAGGTAATGTTAGCCGCGTTAGTACCGAATCTAATGTTATTAGCAATG
GCGAAGAACAAGTTATTACTGCCATGACAGTTCTTAACTCTGTCAGTCTACTAGCGC
```

FIG. 5-18

```
AAACGAATCAGTTAAATATAGCTGATATCGCGGTGTTGCTGATTGCTGATGTAAAAA
GTGCTGATGATCAGCTTGTAGTCCAATTGCATCAGCAATTGAAAACAGTGTGCGA
GTTGTGTTGTTATTGCTGATTTAGGCCAAGCATTAAATCAAGTAGCTGATTTAGTTA
ATAACCAAGACTGTCCTGTGGCTGTAATTGGCATGAATAACTCGGTTAATTTATCTC
GTCATGATCTTGAATCTGTAACTGCAACAATCAGCTTTGATGAAACCTTCAATGGTT
ATAACAATGTAGCTGGGTTCGCGAGTTTACTTATCGCTTCAACTGCGTTTGCCAATG
CTAAGCAATGTTATATACGCCAACATTAAGGGCTTCGCTCAATCGGGCGTAAATG
CTCAATTTAACGTTGGAAACATTAGCGATACTGCAAAGACCGCATTGCAGCAAGCTA
GCATAACTGCAGAGCAGGTTGGTTTGTTAGAAGTGTCAGCAGTCGCTGATTCGGCAA
TCGCATTGTCTGAAAGCCAAGGTTTAATGTCTGCTTATCATCATACGCAAACTTTGC
ATACTGCATTAAGCAGTGCCCGTAGTGTGACTGGTGAAGGCGGGTGTTTTTCACAGG
TCGCAGGTTTATTGAAATGTGTAATTGGTTTACATCAACGTTATATTCCGGCGATTA
AAGATTGGCAACAACCGAGTGACAATCAAATGTCACGGTGGCGGAATTCACCATTCT
ATATGCCTGTAGATGCTCGACCTTGGTTCCCACATGCTGATGGCTCTGCACACATTG
CCGCTTATAGTTGTGTGACTGCTGACAGCTATTGTCATATTCTTTTACAAGAAAACG
TCTTACAAGAACTTGTTTTGAAAGAAACAGTCTTGCAAGATAATGACTTAACTGAAA
GCAAGCTTCAGACTCTTGAACAAAACAATCCAGTAGCTGATCTGCGCACTAATGGTT
ACTTTGCATCGAGCGAGTTAGCATTAATCATAGTACAAGGTAATGACGAAGCACAAT
TACGCTGTGAATTAGAAACTATTACAGGGCAGTTAAGTACTACTGGCATAAGTACTA
TCAGTATTAAACAGATCGCAGCAGACTGTTATGCCCGTAATGATACTAACAAAGCCT
ATAGCGCAGTGCTTATTGCCGAGACTGCTGAAGAGTTAAGCAAAGAAATAACCTTGG
CGTTTGCTGGTATCGCTAGCGTGTTTAATGAAGATGCTAAAGAATGGAAAACCCCGA
AGGGCAGTTATTTTACCGCGCAGCCTGCAAATAAACAGGCTGCTAACAGCACACAGA
ATGGTGTCACCTTCATGTACCCAGGTATTGGTGCTACATATGTTGGTTTAGGGCGTG
ATCTATTTCATCTATTCCCACAGATTTATCAGCCTGTAGCGGCTTTAGCCGATGACA
```

FIG. 5-19

```
TTGGCGAAAGTCTAAAAGATACTTTACTTAATCCACGCAGTATTAGTCGTCATAGCT
TTAAAGAACTCAAGCAGTTGGATCTGGACCTGCGCGGTAACTTAGCCAATATCGCTG
AAGCCGGTGTGGGTTTTGCTTGTGTGTTTACCAAGGTATTTGAAGAAGTCTTTGCCG
TTAAAGCTGACTTTGCTACAGGTTATAGCATGGGTGAAGTAAGCATGTATGCAGCAC
TAGGCTGCTGGCAGCAACCGGGATTGATGAGTGCTCGCCTTGCACAATCGAATACCT
TTAATCATCAACTTTGCGGCGAGTTAAGAACACTACGTCAGCATTGGGGCATGGATG
ATGTAGCTAACGGTACGTTCGAGCAGATCTGGGAAACCTATACCATTAAGGCAACGA
TTGAACAGGTCGAAATTGCCTCTGCAGATGAAGATCGTGTGTATTGCACCATTATCA
ATACACCTGATAGCTTGTTGTTAGCCGGTTATCCAGAAGCCTGTCAGCGAGTCATTA
AGAATTTAGGTGTGCGTGCAATGGCATTGAATATGGCGAACGCAATTCACAGCGCGC
CAGCTTATGCCGAATACGATCATATGGTTGAGCTATACCATATGGATGTTACTCCAC
GTATTAATACCAAGATGTATTCAAGCTCATGTTATTTACCGATTCCACAACGCAGCA
AAGCGATTTCCCACAGTATTGCTAAATGTTTGTGTGATGTGGTGGATTTCCCACGTT
TGGTTAATACCTTACATGACAAAGGTGCGCGGGTATTCATTGAAATGGGTCCAGGTC
GTTCGTTATGTAGCTGGGTAGATAAGATCTTAGTTAATGGCGATGGCGATAATAAAA
AGCAAAGCCAACATGTATCTGTTCCTGTGAATGCCAAAGGCACCAGTGATGAACTTA
CTTATATTCGTGCGATTGCTAAGTTAATTAGTCATGGCGTGAATTTGAATTTAGATA
GCTTGTTTAACGGGTCAATCCTGGTTAAAGCAGGCCATATAGCAAACACGAACAAAT
AGTCAACATCGATATCTAGCGCTGGTGAGTTATACCTCATTAGTTGAAATATGGATT
TAAAGAGAGTAATTATGGAAAATATTGCAGTAGTAGGTATTGCTAATTTGTTCCCGG
GCTCACAAGCACCGGATCAATTTTGGCAGCAATTGCTTGAACAACAAGATTGCCGCA
GTAAGGCGACCGCTGTTCAAATGGGCGTTGATCCTGCTAAATATACCGCCAACAAAG
GTGACACAGATAAATTTTACTGTGTGCACGGCGGTTACATCAGTGATTTCAATTTTG
ATGCTTCAGGTTATCAACTCGATAATGATTATTTAGCCGGTTTAGATGACCTTAATC
AATGGGGGCTTTATGTTACGAAACAAGCCCTTACCGATGCGGGTTATTGGGGCAGTA
```

FIG. 5-20

```
CTGCACTAGAAAACTGTGGTGTGATTTTAGGTAATTTGTCATTCCCAACTAAATCAT
CTAATCAGCTGTTTATGCCTTTGTATCATCAAGTTGTTGATAATGCCTTAAAGGCGG
TATTACATCCTGATTTTCAATTAACGCATTACACAGCACCGAAAAAACACATGCTG
ACAATGCATTAGTAGCAGGTTATCCAGCTGCATTGATCGCGCAAGCGGCGGGTCTTG
GTGGTTCACATTTTGCACTGGATGCGGCTTGTGCTTCATCTTGTTATAGCGTTAAGT
TAGCGTGTGATTACCTGCATACGGGTAAAGCCAACATGATGCTTGCTGGTGCGGTAT
CTGCAGCAGATCCTATGTTCGTAAATATGGGTTTCTCGATATTCCAAGCTTACCCAG
CTAACAATGTACATGCCCCGTTTGACCAAAATTCACAAGGTCTATTTGCCGGTGAAG
GCGCGGGCATGATGGTATTGAAACGTCAAAGTGATGCAGTACGTGATGGTGATCATA
TTTACGCCATTATTAAAGGCGGCGCATTATCGAATGACGGTAAAGGCGAGTTTGTAT
TAAGCCCGAACACCAAGGGCCAAGTATTAGTATATGAACGTGCTTATGCCGATGCAG
ATGTTGACCCGAGTACAGTTGACTATATTGAATGTCATGCAACGGGCACACCTAAGG
GTGACAATGTTGAATTGCGTTCGATGGAAACCTTTTTCAGTCGCGTAAATAACAAAC
CATTACTGGGCTCGGTTAAATCTAACCTTGGTCATTTGTTAACTGCCGCTGGTATGC
CTGGCATGACCAAAGCTATGTTAGCGCTAGGTAAAGGTCTTATTCCTGCAACGATTA
ACTTAAAGCAACCACTGCAATCTAAAAACGGTTACTTTACTGGCGAGCAAATGCCAA
CGACGACTGTGTCTTGGCCAACAACTCCGGGTGCCAAGGCAGATAAACCGCGTACCG
CAGGTGTGAGCGTATTTGGTTTTGGTGGCAGCAACGCCCATTTGGTATTACAACAGC
CAACGCAAACACTCGAGACTAATTTTAGTGTTGCTAAACCACGTGAGCCTTTGGCTA
TTATTGGTATGGACAGCCATTTTGGTAGTGCCAGTAATTTAGCGCAGTTCAAAACCT
TATTAAATAATAATCAAAATACCTTCCGTGAATTACCAGAACAACGCTGGAAAGGCA
TGGAAAGTAACGCTAACGTCATGCAGTCGTTACAATTACGCAAAGCGCCTAAAGGCA
GTTACGTTGAACAGCTAGATATTGATTTCTTGCGTTTTAAAGTACCGCCTAATGAAA
AAGATTGCTTGATCCCGCAACAGTTAATGATGATGCAAGTGGCAGACAATGCTGCGA
AAGACGGAGGTCTAGTTGAAGGTCGTAATGTTGCGGTATTAGTAGCGATGGGCATGG
```

FIG. 5-21

```
AACTGGAATTACATCAGTATCGTGGTCGCGTTAATCTAACCACCCAAATTGAAGACA
GCTTATTACAGCAAGGTATTAACCTGACTGTTGAGCAACGTGAAGAACTGACCAATA
TTGCTAAAGACGGTGTTGCCTCGGCTGCACAGCTAAATCAGTATACGAGTTTCATTG
GTAATATTATGGCGTCACGTATTTCGGCGTTATGGATTTTTCTGGTCCTGCTATTA
CCGTATCGGCTGAAGAAACTCTGTTTATCGTTGTGTTGAATTAGCTGAAATCTAT
TTCAAACCAGTGATGTTGAAGCCGTTATTATTGCTGCTGTTGATTTGTCTGGTTCAA
TTGAAAACATTACTTTACGTCAGCACTACGGTCCAGTTAATGAAAGGGATCTGTAA
GTGAATGTGGTCCGGTTAATGAAAGCAGTTCAGTAACCAACAATATTCTTGATCAGC
AACAATGGCTGGTGGGTGAAGGCGCAGCGGCTATTGTCGTTAAACCGTCATCGCAAG
TCACTGCTGAGCAAGTTTATGCGCGTATTGATGCGGTGAGTTTTGCCCCTGGTAGCA
ATGCGAAAGCAATTACGATTGCAGCGGATAAAGCATTAACACTTGCTGGTATCAGTG
CTGCTGATGTAGCTAGTGTTGAAGCACATGCAAGTGGTTTTAGTGCCGAAAATAATG
CTGAAAAACCGCGTTACCGACTTTATACCCAAGCGCAAGTATCAGTTCGGTGAAAG
CCAATATTGGTCATACGTTTAATGCCTCGGGTATGGCGAGTATTATTAAAACGGCGC
TGCTGTTAGATCAGAATACGAGTCAAGATCAGAAAAGCAAACATATTGCTATTAACG
GTCTAGGTCGTGATAACAGCTGCGCGCATCTTATCTTATCGAGTTCAGCGCAAGCGC
ATCAAGTTGCACCAGCGCCTGTATCTGGTATGGCCAAGCAACGCCCACAGTTAGTTA
AAACCATCAAACTCGGTGGTCAGTTAATTAGCAACGCGATTGTTAACAGTGCGAGTT
CATCTTTACACGCTATTAAAGCGCAGTTTGCCGGTAAGCACTTAAACAAAGTTAACC
AGCCAGTGATGATGGATAACCTGAAGCCCCAAGGTATTAGCGCTCATGCAACCAATG
AGTATGTGGTGACTGGAGCTGCTAACACTCAAGCTTCTAACATTCAAGCATCTCATG
TTCAAGCGTCAAGTCATGCACAAGAGATAGCACCAAACCAAGTTCAAAATATGCAAG
CTACAGCAGCCGCTGTAAGTTCACCCCTTTCTCAACATCAACACACAGCGCAGCCCG
TAGCGGCACCGAGCGTTGTTGGAGTGACTGTGAAACATAAAGCAAGTAACCAAATTC
ATCAGCAAGCGTCTACGCATAAAGCATTTTAGAAAGTCGTTTAGCTGCACAGAAAA
```

FIG. 5-22

```
ACCTATCGCAACTTGTTGAATTGCAAACCAAGCTGTCAATCCAAACTGGTAGTGACA
ATACATCTAACAATACTGCGTCAACAAGCAATACAGTGCTAACAAATCCTGTATCAG
CAACGCCATTAACACTTGTGTCTAATGCGCCTGTAGTAGCGACAAACCTAACCAGTA
CAGAAGCAAAAGCGCAAGCAGCTGCTACACAAGCTGGTTTTCAGATAAAAGGACCTG
TTGGTTACAACTATCCACCGCTGCAGTTAATTGAACGTTATAATAAACCAGAAAACG
TGATTTACGATCAAGCTGATTTGGTTGAATTCGCTGAAGGTGATATTGGTAAGGTAT
TTGGTGCTGAATACAATATTATTGATGGCTATTCGCGTCGTGTACGTCTGCCAACCT
CAGATTACTTGTTAGTAACACGTGTTACTGAACTTGATGCCAAGGTGCATGAATACA
AGAAATCATACATGTGTACTGAATATGATGTGCCTGTTGATGCACCGTTCTTAATTG
ATGGTCAGATCCCTTGGTCTGTTGCCGTCGAATCAGGCCAGTGTGATTTGATGTTGA
TTTCATATATCGGTATTGATTTCCAAGCGAAAGGCGAACGTGTTTACCGTTTACTTG
ATTGTGAATTAACTTTCCTTGAAGAGATGGCTTTTGGTGGCGATACTTTACGTTACG
AGATCCACATTGATTCGTATGCACGTAACGGCGAGCAATTATTATTCTTCTTCCATT
ACGATTGTTACGTAGGGGATAAGAAGGTACTTATCATGCGTAATGGTTGTGCTGGTT
TCTTTACTGACGAAGAACTTTCTGATGGTAAAGGCGTTATTCATAACGACAAAGACA
AAGCTGAGTTTAGCAATGCTGTTAAATCATCATTCACGCCGTTATTACAACATAACC
GTGGTCAATACGATTATAACGACATGATGAAGTTGGTTAATGGTGATGTTGCCAGTT
GTTTTGGTCCGCAATATGATCAAGGTGGCCGTAATCCATCATTGAAATTCTCGTCTG
AGAAGTTCTTGATGATTGAACGTATTACCAAGATAGACCCAACCGGTGGTCATTGGG
GACTAGGCCTGTTAGAAGGTCAGAAAGATTTAGACCCTGAGCATTGGTATTTCCCTT
GTCACTTTAAAGGTGATCAAGTAATGGCTGGTTCGTTGATGTCGGAAGGTTGTGGCC
AAATGGCGATGTTCTTCATGCTGTCTCTTGGTATGCATACCAATGTGAACAACGCTC
GTTTCCAACCACTACCAGGTGAATCACAAACGGTACGTTGTCGTGGGCAAGTACTGC
CACAGCGCAATACCTTAACTTACCGTATGGAAGTTACTGCGATGGGTATGCATCCAC
AGCCATTCATGAAAGCTAATATTGATATTTTGCTTGACGGTAAAGTGGTTGTTGATT
```

FIG. 5-23

```
TCAAAAACTTGAGCGTGATGATCAGCGAACAAGATGAGCATTCAGATTACCCTGTAA
CACTGCCGAGTAATGTGGCGCTTAAAGCGATTACTGCACCTGTTGCGTCAGTAGCAC
CAGCATCTTCACCCGCTAACAGCGCGGATCTAGACGAACGTGGTGTTGAACCGTTTA
AGTTTCCTGAACGTCCGTTAATGCGTGTTGAGTCAGACTTGTCTGCACCGAAAAGCA
AAGGTGTGACACCGATTAAGCATTTGAAGCGCCTGCTGTTGCTGGTCATCATAGAG
TGCCTAACCAAGCACCGTTTACACCTTGGCATATGTTTGAGTTTGCGACGGGTAATA
TTTCTAACTGTTTCGGTCCTGATTTTGATGTTTATGAAGGTCGTATTCCACCTCGTA
CACCTTGTGGCGATTTACAAGTTGTTACTCAGGTTGTAGAAGTGCAGGGCGAACGTC
TTGATCTTAAAAATCCATCAAGCTGTGTAGCTGAATACTATGTACCGGAAGACGCTT
GGTACTTTACTAAAAACAGCCATGAAACTGGATGCCTTATTCATTAATCATGGAAA
TTGCATTGCAACCAAATGGCTTTATTTCTGGTTACATGGGCACGACGCTTAAATACC
CTGAAAAGATCTGTTCTTCCGTAACCTTGATGGTAGCGGCACGTTATTAAAGCAGA
TTGATTTACGCGGCAAGACCATTGTGAATAAATCAGTCTTGGTTAGTACGGCTATTG
CTGGTGGCGCGATTATTCAAAGTTTCACGTTTGATATGTCTGTAGATGGCGAGCTAT
TTTATACTGGTAAAGCTGTATTTGGTTACTTTAGTGGTGAATCACTGACTAACCAAC
TGGGCATTGATAACGGTAAAACGACTAATGCGTGGTTTGTTGATAACAATACCCCCG
CAGCGAATATTGATGTGTTTGATTTAACTAATCAGTCATTGGCTCTGTATAAAGCGC
CTGTGGATAAACCGCATTATAAATTGGCTGGTGGTCAGATGAACTTTATCGATACAG
TGTCAGTGGTTGAAGGCGGTGGTAAAGCGGGCGTGGCTTATGTTTATGGCGAACGTA
CGATTGATGCTGATGATTGGTTCTTCCGTTATCACTTCCACCAAGATCCGGTGATGC
CAGGTTCATTAGGTGTTGAAGCTATTATTGAGTTGATGCAGACCTATGCGCTTAAAA
ATGATTTGGGTGGCAAGTTTGCTAACCCACGTTTCATTGCGCCGATGACGCAAGTTG
ATTGGAAATACCGTGGGCAAATTACGCCGCTGAATAAACAGATGTCACTGGACGTGC
ATATCACTGAGATCGTGAATGACGCTGGTGAAGTGCGAATCGTTGGTGATGCGAATC
TGTCTAAAGATGGTCTGCGTATTTATGAAGTTAAAAACATCGTTTTAAGTATTGTTG
```

FIG. 5-24

```
AAGCGTAAAGGGTCAAGTGTAACGTGCTTAAGCGCCGCATTGGTTAAAGACGCTTTG
CACGCCGTGAATCCGTCCATGGAGGCTTGGGGTTGGCATCCATGCCAACAACAGCAA
GCTTACTTTAATCAATACGGCTTGGTGTCCATTTAGACGCCTCGAACTTAGTAGTTA
ATAGACAAAATAATTTAGCTGTGGAATGAATATAGTAAGTAATCATTCGGCAGCTAC
AAAAAAGGAATTAAGAATGTCGAGTTTAGGTTTTAACAATAACAACGCAATTAACTG
GGCTTGGAAAGTAGATCCAGCGTCAGTTCATACACAAGATGCAGAAATTAAAGCAGC
TTTAATGGATCTAACTAAACCTCTCTATGTGGCGAATAATTCAGGCGTAACTGGTAT
AGCTAATCATACGTCAGTAGCAGGTGCGATCAGCAATAACATCGATGTTGATGTATT
GGCGTTTGCGCAAAGTTAAACCCAGAAGATCTGGGTGATGATGCTTACAAGAAACA
GCACGGCGTTAAATATGCTTATCATGGCGGTGCGATGGCAAATGGTATTGCCTCGGT
TGAATTGGTTGTTGCGTTAGGTAAAGCAGGGCTGTTATGTTCATTTGGTGCTGCAGG
TCTAGTGCCTGATGCGGTTGAAGATGCAATTCGTCGTATTCAAGCTGAATTACCAAA
TGGCCCTTATGCGGTTAACTTGATCCATGCACCAGCAGAAGAAGCATTAGAGCGTGG
CGCGGTTGAACGTTTCCTAAAACTTGGCGTCAAGACGGTAGAGGCTTCAGCTTACCT
TGGTTTAACTGAACACATTGTTTGGTATCGTGCTGCTGGTCTAACTAAAAACGCAGA
TGGCAGTGTTAATATCGGTAACAAGGTTATCGCTAAAGTATCGCGTACCGAAGTTGG
TCGCCGCTTTATGGAACCTGCACCGCAAAAATTACTGGATAAGTTATTAGAACAAAA
TAAGATCACCCCTGAACAAGCTGCTTTAGCGTTGCTTGTACCTATGGCTGATGATAT
TACTGGGGAAGCGGATTCTGGTGGTCATACAGATAACCGTCCGTTTTTAACATTATT
ACCGACGATTATTGGTCTGCGTGATGAAGTGCAAGCGAAGTATAACTTCTCTCCTGC
ATTACGTGTTGGTGCTGGTGGTGGTATCGGAACGCCTGAAGCAGCACTCGCTGCATT
TAACATGGGCGCGGCTTATATCGTTCTGGGTTCTGTGAATCAGGCGTGTGTTGAAGC
GGGTGCATCTGAATATACTCGTAAACTGTTATCGACAGTTGAAATGGCTGATGTGAC
TATGGCACCTGCTGCAGATATGTTTGAAATGGGTGTGAAGCTGCAAGTATTAAAACG
CGGTTCTATGTTCGCGATGCGTGCGAAGAAACTGTATGACTTGTATGTGGCTTATGA
```

FIG. 5-25

```
CTCGATTGAAGATATCCCAGCTGCTGAACGTGAGAAGATTGAAAAACAAATCTTCCG
TGCAAACCTAGACGAGATTTGGGATGGCACTATCGCTTTCTTTACTGAACGCGATCC
AGAAATGCTAGCCCGTGCAACGAGTAGTCCTAAACGTAAATGGCACTTATCTTCCG
TTGGTATCTTGGCCTTTCTTCACGCTGGTCAAACACAGGCGAGAAGGGACGTGAAAT
GGATTATCAGATTTGGGCAGGCCCAAGTTAGGTGCATTCAACAGCTGGGTGAAAGG
TTCTTACCTTGAAGACTATACCCGCCGTGGCGCTGTAGATGTTGCTTTGCATATGCT
TAAAGGTGCTGCGTATTTACAACGTGTAAACCAGTTGAAATTGCAAGGTGTTAGCTT
AAGTACAGAATTGGCAAGTTATCGTACGAGTGATTAATGTTACTTGATGATATGTGA
ATTAATTAAAGCGCCTGAGGGCGCTTTTTTGGTTTTAACTCAGGTGTTGTAACTC
GAATTGCCCCTTTCAAGTTAGATCGATTACTCACTCACAATATGTTGATATCGCAC
TTGCCATATACTTGCTCATCCAAAGCCCTATATTGATAATGGTGTTAATAGTCTTTA
ATATCCGAGTCTTTCTTCAGCATAATACTAATATAGAGACTCGACCAATGTTAAACA
CAACAAAGAATATATTCTTGTGTACTGCCTTATTATTAACGAGTGCGAGTACGACAG
CTACTACGCTAAACAATTCGATATCAGCAATTGAACAACGTATTTCTGGTCGTATCG
GTGTGGCTGTTTTAGATACGCAAATAAACAAACGTGGGCTTACAATGGTGATGCAC
ATTTTCCGATGATGAGTACATTCAAAACCCTCGCTTGCGCGAAATGCTAAGTGAAT
CGACAAATGGTAATCTGGATCCCAGTACTAGCTCATTGATAAAGGCTGAAGAATTAA
TCCCTTGGTCACCAGTCACTAAAACGTTTGTGAATAACACTATTACAGTGGCGAAAG
CGTGTGAAGCAACAATGCTGACCAGTGATAATACCGCGGCTAATATTGTTTTACAGT
ATATCGGAGGCCCTCAAGGCGTTACTGCATTCTTGCGAGAAATTGGTGATGAAGAGA
GTCAGTTAGATCGTATAGAACCTGAATTGATGAAGCTAAGGTCGGAGACTTGCGTG
ATACCACGACACCGAAAGCCATAGTTACCACGCTCAACAAACTACTACTTGGTGATG
TTCTACTTGATTTGGATAAAAACCAACTTAAAACATGGATGCAAATAATAAAGTGT
CAGATCCTTTACTGCGTTCTATATTACCGCAAGGCTGGTTTATTGCCGACCGCTCAG
GTGCGGGTGGTAATGGTTCTCGAGGTATAACTGCTATGCTTTGGCACTCCGAGCGTC
```

FIG. 5-26

```
AACCGCTAATCATCAGTATTTATTTAACCGAAACTGAGTTAGCAATGGCAATGCGCA
ATGAGATTATTGTTGAGATCGGTAAGCTGATATTCAAAGAATACGCGGTGAAATAAT
AAGTTATTTTTTGATAATACTTTAACGAGCGTAGCTATCGAAGTGAGGGCGTCAATT
AGACACCTTTGCTTCCCCTACAAAATCTAATGTGTATTACCTCGGCTAGTACAATTG
CCCTAAGTTATTTCTGTCCAGCTTTGGCTTAGTGCAATTGCGTTAGCCAATGTGAAC
ACCAAGGGACTTTGTCGTACCATAACTACCAAGCGACTTTGTCGTTTTATCTTTTC
TTAGACAAACAGAGGTTAAATGAGTGACGCCTTCCAAATCACAGGAATGAATCCGCA
TTTCAATAAATCTAACCCGTACCAACTCCGTACAAGTTGATCTTTAGTTGTTTAAA
ATCTATAATAAATTCAATTACGGAATTAATCCGTACAACTGGAGGTTTTATGGCTAC
TGCAAGACTTGATATCCGTTTGGATGAAGAAATCAAAGCTAAGGCTGAGAAAGCATC
AGCTTTACTCGGCTTAAAAAGTTTAACCGAATACGTTGTTCGCTTAATGGACGAAGA
TTCAACTAAAGTAGTTTCTGAGCATGAGAGTATTACCGTTGAAGCGAATGTATTCGA
CCAATTTATGGCTGCTTGTGATGAAGCGAAAGCCCCAAATAAAGCATTACTTGAAGC
CGCTGTATTTACTCAGAATGGTGAGTTTAAGTGAGTTATTCCAAACGTTTCAAAGAA
CTGGATAAATCAAAACATGACAGAGCATCATTTGACTGTGGCGAAAAGAGCTAAAT
GATTTTATCCAAACTCAAGCAGCCAAACATATGCAAGCAGGTATTAGCCGCACTCTG
GTTTTACCTGCTTCTGCGCCGTTACCAAACAAAAATATCCAATTTGCTCATTTTAT
AGTATCGCGCCAAGCTCAATTAGCCGCGATACGTTACCACAAGCAATGGCTAAAAAG
TTACCACGTTATCCTATCCCTGTTTTTCTTTTGGCTCAACTTGCCGTCCATAAAGAG
TTTCATGGGAGTGGGTTAGGCAAAGTTAGCTTAATTAAAGCGTTAGAGTACCTTTGG
GAAATTAACTCTCACATGAGAGCTTACGCCATCGTTGTTGATTGTTTAACTGAACAA
GCTGAGTCATTCTACGCTAAATATGGTTTCGACGTTCTCTGCGAAATAAATGGTCGA
GTAAGAATGTTCATATCAATGAAACAGTCAATCAGTTATTCACTTAACAGTAAGAG
TTAGTATAACAGTTGTATGAATTAAATTTATTATATTCGGTAATCTCATTGCGATCA
CGCTAGAAGTGCGAGCGGGTCAGACCGAGGCCACAATAGCAGCCGTTACGTTTAGGG
```

FIG. 5-27

```
GATGACTTAAAAAGATAACTACTACGTCAGTGGCGATCCTAGAGGATTAAAGGTTTA
TGATTCACAACATTTATTTATTGTGCTTAATTTTTTCTATCCAATATGCGCAAGCTG
TAAATATCACTGAAGTAGACTTTTATGTCAGTGATGATATCCCTAAAGATGTTGCCA
AATTAAAGATAGGTGAATCCATAACGAACTCCAGCCTTATTCTAAGTAACTCATCTA
TTCCACTCTCGCGGGAGACGGGTAACATATATTACTCTTCATCAATTGCTAACTTGA
ACTATGACTCGATAGAATTTGTTATGGCTCAATTGATGGCCGAAGATTCCAGCCTTT
ACAAGATGCTGGTAAATAGCGATAGGTTGTCCGTGCTAGTAATGACATCTTCCCAGT
CCACAGATCTCTATGGCTCGACTTACTCGGCTTATTTCCTAATGTTGCGGTCATCG
ATTTGAATTGTGACTCGCTAACTTTAGAACATGAGCTCGGCCATCTATACGGAGCTG
AACATGAAGAAATATATGACGACTATGTCTTCTATGCTGCGATATGTGGAGACTATA
CGACTATCATGAACTCTATGCAGCCTGAAATGAAAGAAAAACAAATGATAAAGGCAT
ATTCATTCCCTGAATTAAAAGTGGATGGCTTGCAGTGCGGAAATGAAAATACGAATA
ACAAAAAGGTTATTTTAGACAATATTGGTCGGTTTAGATAGGATTGGGATATTATTC
TCATTCGGCTCTACTTAGTGCTGTTATTATGAGTGCCAGTGCTTCTATCTACGATAT
TGGTCTTAACAAGTATTTATCTATAGACGCTAAGGTGTTATGTATTTAAGGGATGTT
CAAGATGAAACTAGGTGTAAACGATGTATAGTTGTATAACATTTTTTCAACGGTTGG
AACGTTCGATTCTATCGGGTAACAAGACCGCGACGATCCGCGATAAGTCCGATAGTC
ATTACTTAGTTGGTCAGATGTTAGATGCTTGTACTCACGAAGATAATCGGAAAATGT
GTCAAATAGAAATACTGAGCATTGAATATGTGACGTTTAGTGAATTAAACCGTGCGC
ACGCCAATGCTGAAGGTTTACCGTTTTTGTTTATGCTTAAGTGGATAGTTCGAAAGA
TTTATCCGACTTCAAATGATTTATTTTTCATAAGTTTCAGAGTTGTAACTATCGATA
TCTTATAAGTCTTAGTGCACAAACAGAACTATTTATAGCGCTCAAGAAGGCGATAA
TTTGATAATGAATTATCGCCTTGTTACTATTAAGAGACTTTAAATGACTGAGATATA
AGATATGACACGGAAGAACATATTGATCACAGGCGCAAGTTCAGGGTTGGGCCGAGG
TATGGCCATCGAATTTGCAAAATCAGGTCATAACTTAGCACTTTGTGCACGTAGACT
```

FIG. 5-28

TGATAATTTAGTTGCACTGAAAGCAGAACTCTTAGCCCTCAATCCTCACATCCAAAT
CGAAATAAAACCTCTTGATGTCAATGAACATGAACAAGTCTTCACTGTTTTCCATGA
ATTCAAAGCTGAATTTGGTACGCTTGATCGTATTATTGTTAATGCTGGATTAGGCAA
GGGTGGATCC
         *
       40138

FIG. 5-29

1
AAATGCAATTAATTATGGCGTAAATAGAGTGAAAACATGGCTAATATTCACTAAGTC
CTGAATTTTATATAAAGTTTAATCTGTTATTTTAGCGTTTACCTGGTCTTATCAGTG
AGGTTTATAGCCATTATTAGTGGGATTGAAGTGATTTTTAAAGCTATGTATATTATT
GCAAATATAAATTGTAACAATTAAGACTTTGGACACTTGAGTTCAATTTCGAATTGA
TTGGCATAAAATTTAAAACAGCTAAATCTACCTCAATCATTTTAGCAAATGTATGCA
GGTAGATTTTTTTCGCCATTTAAGAGTACACTTGTACGCTAGGTTTTTGTTTAGTGT
GCAAATGAACGTTTTGATGAGCATTGTTTTAGAGCACAAAATAGATCCTTACAGGA
GCAATAACGCAATGGCTAAAAGAACACCACATCGATTAAGCACGCCAAGGATGTGT
TAAGTAGTGATGATCAACAGTTAAATTCTCGCTTGCAAGAATGTCCGATTGCCATCA
TTGGTATGGCATCGGTTTTTGCAGATGCTAAAAACTTGGATCAATTCTGGGATAACA
TCGTTGACTCTGTGGACGCTATTATTGATGTGCCTAGCGATCGCTGGAACATTGACG
ACCATTACTCGGCTGATAAAAAGCAGCTGACAAGACATACTGCAAACGCGGTGGTT
TCATTCCAGAGCTTGATTTTGATCCGATGGAGTTTGGTTTACCGCCAAATATCCTCG
AGTTAACTGACATCGCTCAATTGTTGTCATTAATTGTTGCTCGTGATGTATTAAGTG
ATGCTGGCATTGGTAGTGATTATGACCATGATAAAATTGGTATCACGCTGGGTGTCG
GTGGTGGTCAGAAACAAATTTCGCCATTAACGTCGCGCCTACAAGGCCCGGTATTAG
AAAAAGTATTAAAAGCCTCAGGCATTGATGAAGATGATCGCGCTATGATCATCGACA
AATTTAAAAAGCCTACATCGGCTGGGAAGAGAACTCATTCCCAGGCATGCTAGGTA
ACGTTATTGCTGGTCGTATCGCCAATCGTTTTGATTTTGGTGGTACTAACTGTGTGG
TTGATGCGGCATGCGCTGGCTCCCTTGCAGCTGTTAAAATGGCGATCTCAGACTTAC
TTGAATATCGTTCAGAAGTCATGATATCGGGTGGTGTATGTTGTGATAACTCGCCAT
TCATGTATATGTCATTCTCGAAAACACCAGCATTTACCACCAATGATGATATCCGTC
CGTTTGATGACGATTCAAAAGGCATGCTGGTTGGTGAAGGTATTGGCATGATGGCGT
TTAAACGTCTTGAAGATGCTGAACGTGACGGCGACAAAATTTATTCTGTACTGAAAG
GTATCGGTACATCTTCAGATGGTCGTTTCAAATCTATTTACGCTCCACGCCCAGATG
GCCAAGCAAAAGCGCTAAAACGTGCTTATGAAGATGCCGGTTTTGCCCCTGAAACAT
GTGGTCTAATTGAAGGCCATGGTACGGGTACCAAAGCGGGTGATGCCGCAGAATTTG

FIG. 6-1

```
CTGGCTTGACCAAACACTTTGGCGCCGCCAGTGATGAAAAGCAATATATCGCCTTAG
GCTCAGTTAAATCGCAATTGGTCATACTAAATCTGCGGCTGGCTCTGCGGGTATGA
TTAAGGCGGCATTAGCGCTGCATCATAAATCTTACCTGCAACGATCCATATCGATA
AACCAAGTGAAGCCTTGGATATCAAAACAGCCCGTTATACCTAAACAGCGAAACGC
GTCCTTGGATGCCACGTGAAGATGGTATTCCACGTCGTGCAGGTATCAGCTCATTTG
GTTTTGGCGGCACCAACTTCCATATTATTTTAGAAGAGTATCGCCCAGGTCACGATA
GCGCATATCGCTTAAACTCAGTGAGCCAAACTGTGTTGATCTCGGCAAACGACCAAC
AAGGTATTGTTGCTGAGTTAAATAACTGGCGTACTAAACTGGCTGTCGATGCTGATC
ATCAAGGGTTTGTATTTAATGAGTTAGTGACAACGTGGCCATTAAAAACCCCATCCG
TTAACCAAGCTCGTTTAGGTTTTGTTGCGCGTAATGCAAATGAAGCGATCGCGATGA
TTGATACGGCATTGAAACAATTCAATGCAACGCAGATAAAATGACATGGTCAGTAC
CTACCGGGGTTTACTATCGTCAAGCCGGTATTGATGCAACAGGTAAAGTGGTTGCGC
TATTCTCAGGGCAAGGTTCGCAATACGTGAACATGGGTCGTGAATTAACCTGTAACT
TCCCAAGCATGATGCACAGTGCTGCGGCGATGGATAAAGAGTTCAGTGCCGCTGGTT
TAGGCCAGTTATCTGCAGTTACTTTCCCTATCCCTGTTTATACGGATGCCGAGCGTA
AGCTACAAGAAGAGCAATTACGTTTAACGCAACATGCGCAACCAGCGATTGGTAGTT
TGAGTGTTGGTCTGTTCAAAACGTTTAAGCAAGCAGGTTTTAAAGCTGATTTTGCTG
CCGGTCATAGTTTCGGTGAGTTAACCGCATTATGGGCTGCCGATGTATTGAGCGAAA
GCGATTACATGATGTTAGCGCGTAGTCGTGGTCAAGCAATGGCTGCGCCAGAGCAAC
AAGATTTTGATGCAGGTAAGATGGCCGCTGTTGTTGGTGATCCAAAGCAAGTCGCTG
TGATCATTGATACCCTTGATGATGTCTCTATTGCTAACTTCAACTCGAATAACCAAG
TTGTTATTGCTGGTACTACGGAGCAGGTTGCTGTAGCGGTTACAACCTTAGGTAATG
CTGGTTTCAAAGTTGTGCCACTGCCGGTATCTGCTGCGTTCCATACACCTTTAGTTC
GTCACGCGCAAAACCATTTGCTAAAGCGGTTGATAGCGCTAAATTTAAAGCGCCAA
GCATTCCAGTGTTTGCTAATGGCACAGGCTTGGTGCATTCAAGCAAACCGAATGACA
TTAAGAAAAACCTGAAAACCACATGCTGGAATCTGTTCATTTCAATCAAGAAATTG
```

FIG. 6-2

```
ACAACATCTATGCTGATGGTGGCCGCGTATTTATCGAATTTGGTCCAAAGAATGTAT
TAACTAAATTGGTTGAAAACATTCTCACTGAAAAATCTGATGTGACTGCTATCGCGG
TTAATGCTAATCCTAAACAACCTGCGGACGTACAAATGCGCCAAGCTGCGCTGCAAA
TGGCAGTGCTTGGTGTCGCATTAGACAATATTGACCCGTACGACGCCGTTAAGCGTC
CACTTGTTGCGCCGAAAGCATCACCAATGTTGATGAAGTTATCTGCAGCGTCTTATG
TTAGTCCGAAAACGAAGAAGCGTTTGCTGATGCATTGACTGATGGCTGGACTGTTA
AGCAAGCGAAAGCTGTACCTGCTGTTGTGTCACAACCACAAGTGATTGAAAAGATCG
TTGAAGTTGAAAAGATAGTTAACGCATTGTCGAAGTAGAGCGTATTGTCGAAGTAG
AAAAAATCGTCTACGTTAATGCTGACGGTTCGCTTATATCGCAAAATAATCAAGACG
TTAACAGCGCTGTTGTTAGCAACGTGACTAATAGCTCAGTGACTCATAGCAGTGATG
CTGACCTTGTTGCCTCTATTGAACGCAGTGTTGGTCAATTTGTTGCACACCAACAGC
AATTATTAAATGTACATGAACAGTTTATGCAAGGTCCACAAGACTACGCGAAAACAG
TGCAGAACGTACTTGCTGCGCAGACGAGCAATGAATTACCGGAAAGTTTAGACCGTA
CATTGTCTATGTATAACGAGTTCCAATCAGAAACGCTACGTGTACATGAAACGTACC
TGAACAATCAGACGAGCAACATGAACACCATGCTTACTGGTGCTGAAGCTGATGTGC
TAGCAACCCCAATAACTCAGGTAGTGAATACAGCCGTTGCCACTAGTCACAAGGTAG
TTGCTCCAGTTATTGCTAATACAGTGACGAATGTTGTATCTAGTGTCAGTAATAACG
CGGCGGTTGCAGTGCAAACTGTGGCATTAGCGCCTACGCAAGAAATCGCTCCAACAG
TCGCTACTACGCCAGCACCCGCATTGGTTGCTATCGTGGCTGAACCTGTGATTGTTG
CGCATGTTGCTACAGAAGTTGCACCAATTACACCATCAGTTACACCAGTTGTCGCAA
CTCAAGCGGCTATCGATGTAGCAACTATTAACAAAGTAATGTTAGAAGTTGTTGCTG
ATAAAACCGGTTATCCAACGGATATGCTGGAACTGAGCATGGACATGGAAGCTGACT
TAGGTATCGACTCAATCAAACGTGTTGAGATATTAGGCGCAGTACAGGAATTGATCC
CTGACTTACCTGAACTTAATCCTGAAGATCTTGCTGAGCTACGCACGCTTGGTGAGA
TTGTCGATTACATGAATTCAAAAGCCCAGGCTGTAGCTCCTACAACAGTACCTGTAA
```

FIG. 6-3

```
CAAGTGCACCTGTTTCGCCTGCATCTGCTGGTATTGATTTAGCCCACATCCAAACG
TAATGTTAGAAGTGGTTGCAGACAAAACCGGTTACCCAACAGACATGCTAGAACTGA
GCATGGATATGGAAGCTGACTTAGGTATTGATTCAATCAAGCGTGTGGAAATCTTAG
GTGCAGTACAGGAGATCATAACTGATTTACCTGAGCTAAACCCTGAAGATCTTGCTG
AATTACGCACCCTAGGTGAAATCGTTAGTTACATGCAAAGCAAAGCGCCAGTCGCTG
AAAGTGCGCCAGTGGCGACGGCTCCTGTAGCAACAAGCTCAGCACCGTCTATCGATT
TGAACCACATTCAAACAGTGATGATGGATGTAGTTGCAGATAAGACTGGTTATCCAA
CTGACATGCTAGAACTTGGCATGGACATGGAAGCTGATTTAGGTATCGATTCAATCA
ACGTGTGGAAATATTAGGCGCAGTGCAGGAGATCATCACTGATTTACCTGAGCTAA
ACCCAGAAGACCTCGCTGAATTACGCACGCTAGGTGAAATCGTTAGTTACATGCAAA
GCAAAGCGCCAGTCGCTGAGAGTGCGCCAGTAGCGACGGCTTCTGTAGCAACAAGCT
CTGCACCGTCTATCGATTTAAACCATATCCAAACAGTGATGATGGAAGTGGTTGCAG
ACAAAACCGGTTATCCAGTAGACATGTTAGAACTTGCTATGGACATGGAAGCTGACC
TAGGTATCGATTCAATCAAGCGTGTAGAAATTTTAGGTGCGGTACAGGAAATCATTA
CTGACTTACCTGAGCTTAACCCTGAAGATCTTGCTGAACTACGTACATTAGGTGAAA
TCGTTAGTTACATGCAAAGCAAAGCGCCCGTAGCTGAAGCGCCTGCAGTACCTGTTG
CAGTAGAAAGTGCACCTACTAGTGTAACAAGCTCAGCACCGTCTATCGATTTAGACC
ACATCCAAAATGTAATGATGGATGTTGTTGCTGATAAGACTGGTTATCCTGCCAATA
TGCTTGAATTAGCAATGGACATGGAAGCCGACCTTGGTATTGATTCAATCAAGCGTG
TTGAAATTCTAGGCGCGGTACAGGAGATCATTACTGATTTACCTGAACTAAACCCAG
AAGACTTAGCTGAACTACGTACGTTAGAAGAAATTGTAACCTACATGCAAAGCAAGG
CGAGTGGTGTTACTGTAAATGTAGTGGCTAGCCCTGAAAATAATGCTGTATCAGATG
CATTTATGCAAAGCAATGTGGCGACTATCACAGCGGCCGCAGAACATAAGGCGGAAT
TTAAACCGGCGCCGAGCGCAACCGTTGCTATCTCTCGTCTAAGCTCTATCAGTAAAA
TAAGCCAAGATTGTAAAGGTGCTAACGCCTTAATCGTAGCTGATGGCACTGATAATG
CTGTGTTACTTGCAGACCACCTATTGCAAACTGGCTGGAATGTAACTGCATTGCAAC
CAACTTGGGTAGCTGTAACAACGACGAAGCATTTAATAAGTCAGTGAACCTGGTGA
```

FIG. 6-4

```
CTTTAAATGGCGTTGATGAAACTGAAATCAACAACATTATTACTGCTAACGCACAAT
TGGATGCAGTTATCTATCTGCACGCAAGTAGCGAAATTAATGCTATCGAATACCCAC
AAGCATCTAAGCAAGGCCTGATGTTAGCCTTCTTATTAGCGAAATTGAGTAAAGTAA
CTCAAGCCGCTAAAGTGCGTGGCGCCTTTATGATTGTTACTCAGCAGGGTGGTTCAT
TAGGTTTTGATGATATCGATTCTGCTACAAGTCATGATGTGAAAACAGACCTAGTAC
AAAGCGGCTTAAACGGTTTAGTTAAGACACTGTCTCACGAGTGGGATAACGTATTCT
GTCGTGCGGTTGATATTGCTTCGTCATTAACGGCTGAACAAGTTGCAAGCCTTGTTA
GTGATGAACTACTTGATGCTAACACTGTATTAACAGAAGTGGGTTATCAACAAGCTG
GTAAAGGCCTTGAACGTATCACGTTAACTGGTGTGGCTACTGACAGCTATGCATTAA
CAGCTGGCAATAACATCGATGCTAACTCGGTATTTTAGTGAGTGGTGGCGCAAAAG
GTGTAACTGCACATTGTGTTGCTCGTATAGCTAAAGAATATCAGTCTAAGTTCATCT
TATTGGGACGTTCAACGTTCTCAAGTGACGAACCGAGCTGGGCAAGTGGTATTACTG
ATGAAGCGGCGTTAAAGAAAGCAGCGATGCAGTCTTTGATTACAGCAGGTGATAAAC
CAACACCCGTTAAGATCGTACAGCTAATCAAACCAATCCAAGCTAATCGTGAAATTG
CGCAAACCTTGTCTGCAATTACCGCTGCTGGTGGCCAAGCTGAATATGTTTCTGCAG
ATGTAACTAATGCAGCAAGCGTACAAATGGCAGTCGCTCCAGCTATCGCTAAGTTCG
GTGCAATCACTGGCATCATTCATGGCGCGGGTGTGTTAGCTGACCAATTCATTGAGC
AAAAAACACTGAGTGATTTTGAGTCTGTTTACAGCACTAAAATTGACGGTTTGTTAT
CGCTACTATCAGTCACTGAAGCAAGCAACATCAAGCAATTGGTATTGTTCTCGTCAG
CGGCTGGTTTCTACGGTAACCCCGGCCAGTCTGATTACTCGATTGCCAATGAGATCT
TAAATAAAACCGCATACCGCTTTAAATCATTGCACCCACAAGCTCAAGTATTGAGCT
TTAACTGGGGTCCTTGGGACGGTGGCATGGTAACGCCTGAGCTTAAACGTATGTTTG
ACCAACGTGGTGTTTACATTATTCCACTTGATGCAGGTGCACAGTTATTGCTGAATG
AACTAGCCGCTAATGATAACCGTTGTCCACAAATCCTCGTGGGTAATGACTTATCTA
AAGATGCTAGCTCTGATCAAAAGTCTGATGAAAGAGTACTGCTGTAAAAAAGCCAC
AAGTTAGTCGTTTATCAGATGCTTTAGTAACTAAAAGTATCAAAGCGACTAACAGTA
```

FIG. 6-5

```
GCTCTTTATCAAACAAGACTAGTGCTTTATCAGACAGTAGTGCTTTTCAGGTTAACG
AAAACCACTTTTTAGCTGACCACATGATCAAAGGCAATCAGGTATTACCAACGGTAT
GCGCGATTGCTTGGATGAGTGATGCAGCAAAGCGACTTATAGTAACCGAGACTGTG
CATTGAAGTATGTCGGTTTCGAAGACTATAAATTGTTTAAAGGTGTGGTTTTTGATG
GCAATGAGGCGGCGGATTACCAAATCCAATTGTCGCCTGTGACAAGGGCGTCAGAAC
AGGATTCTGAAGTCCGTATTGCCGCAAAGATCTTTAGCCTGAAAAGTGACGGTAAAC
CTGTGTTTCATTATGCAGCGACAATATTGTTAGCAACTCAGCCACTTAATGCTGTGA
AGGTAGAACTTCCGACATTGACAGAAGTGTTGATAGCAACAATAAAGTAACTGATG
AAGCACAAGCGTTATACAGCAATGGCACCTTGTTCCACGGTGAAAGTCTGCAGGGCA
TTAAGCAGATATTAAGTTGTGACGACAAGGGCCTGCTATTGGCTTGTCAGATAACCG
ATGTTGCAACAGCTAAGCAGGATCCTTCCCGTTAGCTGACAACAATATCTTTGCCA
ATGATTTGGTTTATCAGGCTATGTTGGTCTGGGTGCGCAAACAATTTGGTTTAGGTA
GCTTACCTTCGGTGACAACGGCTTGGACTGTGTATCGTGAAGTGGTTGTAGATGAAG
TATTTATCTGCAACTTAATGTTGTTGAGCATGATCTATTGGGTTCACGCGGCAGTA
AAGCCCGTTGTGATATTCAATTGATTGCTGCTGATATGCAATTACTTGCCGAAGTGA
AATCAGCGCAAGTCAGTGTCAGTGACATTTTGAACGATATGTCATGATCGAGTAAAT
AATAACGATAGGCGTCATGGTGAGCATGGCGTCTGCTTTCTTCATTTTTTAACATTA
ACAATATTAATAGCTAAACGCGGTTGCTTTAAACCAAGTAAACAAGTGCTTTTAGCT
ATTACTATTCCAAACAGGATATTAAAGAGAATATGACGGAATTAGCTGTTATTGGTA
TGGATGCTAAATTTAGCGGACAAGACAATATTGACCGTGTGGAACGCGCTTTCTATG
AAGGTGCTTATGTAGGTAATGTTAGCCGCGTTAGTACCGAATCTAATGTTATTAGCA
ATGGCGAAGAACAAGTTATTACTGCCATGACAGTTCTTAACTCTGTCAGTCTACTAG
CGCAAACGAATCAGTTAAATATAGCTGATATCGCGGTGTTGCTGATTGCTGATGTAA
AAAGTGCTGATGATCAGCTTGTAGTCCAATTGCATCAGCAATTGAAAACAGTGTG
CGAGTTGTGTTGTTATTGCTGATTTAGGCCAAGCATTAAATCAAGTAGCTGATTTAG
```

FIG. 6-6

```
TTAATAACCAAGACTGTCCTGTGGCTGTAATTGGCATGAATAACTCGGTTAATTTAT
CTCGTCATGATCTTGAATCTGTAACTGCAACAATCAGCTTTGATGAAACCTTCAATG
GTTATAACAATGTAGCTGGGTTCGCGAGTTTACTTATCGCTTCAACTGCGTTTGCCA
ATGCTAAGCAATGTTATATATACGCCAACATTAAGGGCTTCGCTCAATCGGGCGTAA
ATGCTCAATTTAACGTTGGAAACATTAGCGATACTGCAAAGACCGCATTGCAGCAAG
CTAGCATAACTGCAGAGCAGGTTGGTTTGTTAGAAGTGTCAGCAGTCGCTGATTCGG
CAATCGCATTGTCTGAAAGCCAAGGTTTAATGTCTGCTTATCATCATACGCAAACTT
TGCATACTGCATTAAGCAGTGCCCGTAGTGTGACTGGTGAAGGCGGGTGTTTTTCAC
AGGTCGCAGGTTTATTGAAATGTGTAATTGGTTTACATCAACGTTATATTCCGGCGA
TTAAAGATTGGCAACAACCGAGTGACAATCAAATGTCACGGTGGCGGAATTCACCAT
TCTATATGCCTGTAGATGCTCGACCTTGGTTCCCACATGCTGATGGCTCTGCACACA
TTGCCGCTTATAGTTGTGTGACTGCTGACAGCTATTGTCATATTCTTTTACAAGAAA
ACGTCTTACAAGAACTTGTTTTGAAAGAAACAGTCTTGCAAGATAATGACTTAACTG
AAAGCAAGCTTCAGACTCTTGAACAAACAATCCAGTAGCTGATCTGCGCACTAATG
GTTACTTTGCATCGAGCGAGTTAGCATTAATCATAGTACAAGGTAATGACGAAGCAC
AATTACGCTGTGAATTAGAAACTATTACAGGGCAGTTAAGTACTACTGGCATAAGTA
CTATCAGTATTAAACAGATCGCAGCAGACTGTTATGCCCGTAATGATACTAACAAAG
CCTATAGCGCAGTGCTTATTGCCGAGACTGCTGAAGAGTTAAGCAAAGAAATAACCT
TGGCGTTTGCTGGTATCGCTAGCGTGTTTAATGAAGATGCTAAAGAATGGAAAACCC
CGAAGGGCAGTTATTTTACCGCGCAGCCTGCAAATAAACAGGCTGCTAACAGCACAC
AGAATGGTGTCACCTTCATGTACCCAGGTATTGGTGCTACATATGTTGGTTTAGGGC
GTGATCTATTTCATCTATTCCCACAGATTTATCAGCCTGTAGCGGCTTTAGCCGATG
ACATTGGCGAAAGTCTAAAAGATACTTTACTTAATCCACGCAGTATTAGTCGTCATA
GCTTTAAAGAACTCAAGCAGTTGGATCTGGACCTGCGCGGTAACTTAGCCAATATCG
CTGAAGCCGGTGTGGGTTTTGCTTGTGTGTTTACCAAGGTATTTGAAGAAGTCTTTG
CCGTTAAAGCTGACTTTGCTACAGGTTATAGCATGGGTGAAGTAAGCATGTATGCAG
CACTAGGCTGCTGGCAGCAACCGGGATTGATGAGTGCTCGCCTTGCACAATCGAATA
```

FIG. 6-7

```
CCTTTAATCATCAACTTTGCGGCGAGTTAAGAACACTACGTCAGCATTGGGGCATGG
ATGATGTAGCTAACGGTACGTTCGAGCAGATCTGGGAAACCTATACCATTAAGGCAA
CGATTGAACAGGTCGAAATTGCCTCTGCAGATGAAGATCGTGTGTATTGCACCATTA
TCAATACACCTGATAGCTTGTTGTTAGCCGGTTATCCAGAAGCCTGTCAGCGAGTCA
TTAAGAATTTAGGTGTGCGTGCAATGGCATTGAATATGGCGAACGCAATTCACAGCG
CGCCAGCTTATGCCGAATACGATCATATGGTTGAGCTATACCATATGGATGTTACTC
CACGTATTAATACCAAGATGTATTCAAGCTCATGTTATTTACCGATTCCACAACGCA
GCAAAGCGATTTCCCACAGTATTGCTAAATGTTTGTGTGATGTGGTGGATTTCCCAC
GTTTGGTTAATACCTTACATGACAAAGGTGCGCGGGTATTCATTGAAATGGGTCCAG
GTCGTTCGTTATGTAGCTGGGTAGATAAGATCTTAGTTAATGGCGATGGCGATAATA
AAAAGCAAAGCCAACATGTATCTGTTCCTGTGAATGCCAAAGGCACCAGTGATGAAC
TTACTTATATTCGTGCGATTGCTAAGTTAATTAGTCATGGCGTGAATTTGAATTTAG
ATAGCTTGTTTAACGGGTCAATCCTGGTTAAAGCAGGCCATATAGCAAACACGAACA
AATAGTCAACATCGATATCTAGCGCTGGTGAGTTATACCTCATTAGTTGAAATATGG
ATTTAAAGAGAGTAATTATGGAAAATATTGCAGTAGTAGGTATTGCTAATTTGTTCC
CGGGCTCACAAGCACCGGATCAATTTTGGCAGCAATTGCTTGAACAACAAGATTGCC
GCAGTAAGGCGACCGCTGTTCAAATGGGCGTTGATCCTGCTAAATATACCGCCAACA
AAGGTGACACAGATAAATTTTACTGTGTGCACGGCGGTTACATCAGTGATTTCAATT
TTGATGCTTCAGGTTATCAACTCGATAATGATTATTTAGCCGGTTTAGATGACCTTA
ATCAATGGGGCTTTATGTTACGAAACAAGCCCTTACCGATGCGGGTTATTGGGGCA
GTACTGCACTAGAAACTGTGGTGTGATTTTAGGTAATTTGTCATTCCCAACTAAAT
CATCTAATCAGCTGTTTATGCCTTTGTATCATCAAGTTGTTGATAATGCCTTAAAGG
CGGTATTACATCCTGATTTTCAATTAACGCATTACACAGCACCGAAAAAAACACATG
CTGACAATGCATTAGTAGCAGGTTATCCAGCTGCATTGATCGCGCAAGCGGCGGGTC
TTGGTGGTTCACATTTTGCACTGGATGCGGCTTGTGCTTCATCTTGTTATAGCGTTA
AGTTAGCGTGTGATTACCTGCATACGGGTAAGCCAACATGATGCTTGCTGGTGCGG
```

FIG. 6-8

```
TATCTGCAGCAGATCCTATGTTCGTAAATATGGGTTTCTCGATATTCCAAGCTTACC
CAGCTAACAATGTACATGCCCCGTTTGACCAAAATTCACAAGGTCTATTTGCCGGTG
AAGGCGCGGGCATGATGGTATTGAAACGTCAAAGTGATGCAGTACGTGATGGTGATC
ATATTTACGCCATTATTAAAGGCGGCGCATTATCGAATGACGGTAAAGGCGAGTTTG
TATTAAGCCCGAACACCAAGGGCCAAGTATTAGTATATGAACGTGCTTATGCCGATG
CAGATGTTGACCCGAGTACAGTTGACTATATTGAATGTCATGCAACGGGCACACCTA
AGGGTGACAATGTTGAATTGCGTTCGATGGAAACCTTTTTCAGTCGCGTAAATAACA
AACCATTACTGGGCTCGGTTAAATCTAACCTTGGTCATTTGTTAACTGCCGCTGGTA
TGCCTGGCATGACCAAAGCTATGTTAGCGCTAGGTAAAGGTCTTATTCCTGCAACGA
TTAACTTAAAGCAACCACTGCAATCTAAAAACGGTTACTTTACTGGCGAGCAAATGC
CAACGACGACTGTGTCTTGGCCAACAACTCCGGGTGCCAAGGCAGATAAACCGCGTA
CCGCAGGTGTGAGCGTATTTGGTTTTGGTGGCAGCAACGCCCATTTGGTATTACAAC
AGCCAACGCAAACACTCGAGACTAATTTTAGTGTTGCTAAACCACGTGAGCCTTTGG
CTATTATTGGTATGGACAGCCATTTTGGTAGTGCCAGTAATTTAGCGCAGTTCAAAA
CCTTATTAAATAATAATCAAAATACCTTCGTGAATTACCAGAACAACGCTGGAAAG
GCATGGAAAGTAACGCTAACGTCATGCAGTCGTTACAATTACGCAAAGCGCCTAAAG
GCAGTTACGTTGAACAGCTAGATATTGATTTCTTGCGTTTTAAAGTACCGCCTAATG
AAAAAGATTGCTTGATCCCGCAACAGTTAATGATGATGCAAGTGGCAGACAATGCTG
CGAAAGACGGAGGTCTAGTTGAAGGTCGTAATGTTGCGGTATTAGTAGCGATGGGCA
TGGAACTGGAATTACATCAGTATCGTGGTCGCGTTAATCTAACCACCCAAATTGAAG
ACAGCTTATTACAGCAAGGTATTAACCTGACTGTTGAGCAACGTGAAGAACTGACCA
ATATTGCTAAAGACGGTGTTGCCTCGGCTGCACAGCTAAATCAGTATACGAGTTTCA
TTGGTAATATTATGGCGTCACGTATTTCGGCGTTATGGGATTTTCTGGTCCTGCTA
TTACCGTATCGGCTGAAGAAACTCTGTTTATCGTTGTGTTGAATTAGCTGAAAATC
TATTTCAAACCAGTGATGTTGAAGCCGTTATTATTGCTGCTGTTGATTTGTCTGGTT
CAATTGAAAACATTACTTTACGTCAGCACTACGGTCCAGTTAATGAAAAGGGATCTG
```

FIG. 6-9

```
TAAGTGAATGTGGTCCGGTTAATGAAAGCAGTTCAGTAACCAACAATATTCTTGATC
AGCAACAATGGCTGGTGGGTGAAGGCGCAGCGGCTATTGTCGTTAAACCGTCATCGC
AAGTCACTGCTGAGCAAGTTTATGCGCGTATTGATGCGGTGAGTTTTGCCCCTGGTA
GCAATGCGAAAGCAATTACGATTGCAGCGGATAAAGCATTAACACTTGCTGGTATCA
GTGCTGCTGATGTAGCTAGTGTTGAAGCACATGCAAGTGGTTTTAGTGCCGAAAATA
ATGCTGAAAAACCGCGTTACCGACTTTATACCCAAGCGCAAGTATCAGTTCGGTGA
AGCCAATATTGGTCATACGTTTAATGCCTCGGGTATGGCGAGTATTATTAAAACGG
CGCTGCTGTTAGATCAGAATACGAGTCAAGATCAGAAAAGCAAACATATTGCTATTA
ACGGTCTAGGTCGTGATAACAGCTGCGCGCATCTTATCTTATCGAGTTCAGCGCAAG
CGCATCAAGTTGCACCAGCGCCTGTATCTGGTATGGCCAAGCAACGCCCACAGTTAG
TTAAAACCATCAAACTCGGTGGTCAGTTAATTAGCAACGCGATTGTTAACAGTGCGA
GTTCATCTTTACACGCTATTAAAGCGCAGTTTGCCGGTAAGCACTTAAACAAAGTTA
ACCAGCCAGTGATGATGGATAACCTGAAGCCCCAAGGTATTAGCGCTCATGCAACCA
ATGAGTATGTGGTGACTGGAGCTGCTAACACTCAAGCTTCTAACATTCAAGCATCTC
ATGTTCAAGCGTCAAGTCATGCACAAGAGATAGCACCAAACCAAGTTCAAAATATGC
AAGCTACAGCAGCCGCTGTAAGTTCACCCCTTTCTCAACATCAACACACAGCGCAGC
CCGTAGCGGCACCGAGCGTTGTTGGAGTGACTGTGAAACATAAAGCAAGTAACCAAA
TTCATCAGCAAGCGTCTACGCATAAAGCATTTTTAGAAAGTCGTTTAGCTGCACAGA
AAAACCTATCGCAACTTGTTGAATTGCAAACCAAGCTGTCAATCCAAACTGGTAGTG
ACAATACATCTAACAATACTGCGTCAACAAGCAATACAGTGCTAACAAATCCTGTAT
CAGCAACGCCATTAACACTTGTGTCTAATGCGCCTGTAGTAGCGACAAACCTAACCA
GTACAGAAGCAAAAGCGCAAGCAGCTGCTACACAAGCTGGTTTTCAGATAAAAGGAC
CTGTTGGTTACAACTATCCACCGCTGCAGTTAATTGAACGTTATAATAAACCAGAAA
ACGTGATTTACGATCAAGCTGATTTGGTTGAATTCGCTGAAGGTGATATTGGTAAGG
TATTTGGTGCTGAATACAATATTATTGATGGCTATTCGCGTCGTGTACGTCTGCCAA
CCTCAGATTACTTGTTAGTAACACGTGTTACTGAACTTGATGCCAAGGTGCATGAAT
```

FIG. 6-10

```
ACAAGAAATCATACATGTGTACTGAATATGATGTGCCTGTTGATGCACCGTTCTTAA
TTGATGGTCAGATCCCTTGGTCTGTTGCCGTCGAATCAGGCCAGTGTGATTTGATGT
TGATTTCATATATCGGTATTGATTTCCAAGCGAAAGGCGAACGTGTTTACCGTTTAC
TTGATTGTGAATTAACTTTCCTTGAAGAGATGGCTTTTGGTGGCGATACTTTACGTT
ACGAGATCCACATTGATTCGTATGCACGTAACGGCGAGCAATTATTATTCTTCTTCC
ATTACGATTGTTACGTAGGGGATAAGAAGGTACTTATCATGCGTAATGGTTGTGCTG
GTTTCTTTACTGACGAAGAACTTTCTGATGGTAAAGGCGTTATTCATAACGACAAAG
ACAAAGCTGAGTTTAGCAATGCTGTTAAATCATCATTCACGCCGTTATTACAACATA
ACCGTGGTCAATACGATTATAACGACATGATGAAGTTGGTTAATGGTGATGTTGCCA
GTTGTTTTGGTCCGCAATATGATCAAGGTGGCCGTAATCCATCATTGAAATTCTCGT
CTGAGAAGTTCTTGATGATTGAACGTATTACCAAGATAGACCCAACCGGTGGTCATT
GGGGACTAGGCCTGTTAGAAGGTCAGAAAGATTTAGACCCTGAGCATTGGTATTTCC
CTTGTCACTTTAAAGGTGATCAAGTAATGGCTGGTTCGTTGATGTCGGAAGGTTGTG
GCCAAATGGCGATGTTCTTCATGCTGTCTCTTGGTATGCATACCAATGTGAACAACG
CTCGTTTCCAACCACTACCAGGTGAATCACAAACGGTACGTTGTCGTGGGCAAGTAC
TGCCACAGCGCAATACCTTAACTTACCGTATGGAAGTTACTGCGATGGGTATGCATC
CACAGCCATTCATGAAAGCTAATATTGATATTTTGCTTGACGGTAAAGTGGTTGTTG
ATTTCAAAAACTTGAGCGTGATGATCAGCGAACAAGATGAGCATTCAGATTACCCTG
TAACACTGCCGAGTAATGTGGCGCTTAAAGCGATTACTGCACCTGTTGCGTCAGTAG
CACCAGCATCTTCACCCGCTAACAGCGCGGATCTAGACGAACGTGGTGTTGAACCGT
TTAAGTTTCCTGAACGTCCGTTAATGCGTGTTGAGTCAGACTTGTCTGCACCGAAAA
GCAAAGGTGTGACACCGATTAAGCATTTTGAAGCGCCTGCTGTTGCTGGTCATCATA
GAGTGCCTAACCAAGCACCGTTTACACCTTGGCATATGTTTGAGTTTGCGACGGGTA
ATATTTCTAACTGTTTCGGTCCTGATTTTGATGTTTATGAAGGTCGTATTCCACCTC
GTACACCTTGTGGCGATTTACAAGTTGTTACTCAGGTTGTAGAAGTGCAGGGCGAAC
GTCTTGATCTTAAAAATCCATCAAGCTGTGTAGCTGAATACTATGTACCGGAAGACG
```

FIG. 6-11

```
CTTGGTACTTTACTAAAAACAGCCATGAAAACTGGATGCCTTATTCATTAATCATGG
AAATTGCATTGCAACCAAATGGCTTTATTTCTGGTTACATGGGCACGACGCTTAAAT
ACCCTGAAAAAGATCTGTTCTTCCGTAACCTTGATGGTAGCGGCACGTTATTAAAGC
AGATTGATTTACGCGGCAAGACCATTGTGAATAAATCAGTCTTGGTTAGTACGGCTA
TTGCTGGTGGCGCGATTATTCAAAGTTTCACGTTTGATATGTCTGTAGATGGCGAGC
TATTTTATACTGGTAAAGCTGTATTTGGTTACTTTAGTGGTGAATCACTGACTAACC
AACTGGGCATTGATAACGGTAAAACGACTAATGCGTGGTTTGTTGATAACAATACCC
CCGCAGCGAATATTGATGTGTTTGATTTAACTAATCAGTCATTGGCTCTGTATAAAG
CGCCTGTGGATAAACCGCATTATAAATTGGCTGGTGGTCAGATGAACTTTATCGATA
CAGTGTCAGTGGTTGAAGGCGGTGGTAAAGCGGGCGTGGCTTATGTTTATGGCGAAC
GTACGATTGATGCTGATGATTGGTTCTTCCGTTATCACTTCCACCAAGATCCGGTGA
TGCCAGGTTCATTAGGTGTTGAAGCTATTATTGAGTTGATGCAGACCTATGCGCTTA
AAAATGATTTGGGTGGCAAGTTTGCTAACCCACGTTTCATTGCGCCGATGACGCAAG
TTGATTGGAAATACCGTGGGCAAATTACGCCGCTGAATAAACAGATGTCACTGGACG
TGCATATCACTGAGATCGTGAATGACGCTGGTGAAGTGCGAATCGTTGGTGATGCGA
ATCTGTCTAAAGATGGTCTGCGTATTTATGAAGTTAAAAACATCGTTTTAAGTATTG
TTGAAGCGTAAAGGGTCAAGTGTAACGTGCTTAAGCGCCGCATTGGTTAAAGACGCT
TTGCACGCCGTGAATCCGTCCATGGAGGCTTGGGGTTGGCATCCATGCCAACAACAG
CAAGCTTACTTTAATCAATACGGCTTGGTGTCCATTTAGACGCCTCGAACTTAGTAG
TTAATAGACAAAATAATTTAGCTGTGGAATGAATATAGTAAGTAATCATTCGGCAGC
TACAAAAAAGGAATTAAGAATGTCGAGTTTAGGTTTTAACAATAACAACGCAATTAA
CTGGGCTTGGAAAGTAGATCCAGCGTCAGTTCATACACAAGATGCAGAAATTAAAGC
AGCTTTAATGGATCTAACTAAACCTCTCTATGTGGCGAATAATTCAGGCGTAACTGG
TATAGCTAATCATACGTCAGTAGCAGGTGCGATCAGCAATAACATCGATGTTGATGT
ATTGGCGTTTGCGCAAAAGTTAAACCCAGAAGATCTGGGTGATGATGCTTACAAGAA
ACAGCACGGCGTTAAATATGCTTATCATGGCGGTGCGATGGCAAATGGTATTGCCTC
```

FIG. 6-12

```
GGTTGAATTGGTTGTTGCGTTAGGTAAAGCAGGGCTGTTATGTTCATTTGGTGCTGC
AGGTCTAGTGCCTGATGCGGTTGAAGATGCAATTCGTCGTATTCAAGCTGAATTACC
AAATGGCCCTTATGCGGTTAACTTGATCCATGCACCAGCAGAAGAAGCATTAGAGCG
TGGCGCGGTTGAACGTTTCCTAAAACTTGGCGTCAAGACGGTAGAGGCTTCAGCTTA
CCTTGGTTTAACTGAACACATTGTTTGGTATCGTGCTGCTGGTCTAACTAAAAACGC
AGATGGCAGTGTTAATATCGGTAACAAGGTTATCGCTAAAGTATCGCGTACCGAAGT
TGGTCGCCGCTTTATGGAACCTGCACCGCAAAAATTACTGGATAAGTTATTAGAACA
AAATAAGATCACCCCTGAACAAGCTGCTTTAGCGTTGCTTGTACCTATGGCTGATGA
TATTACTGGGGAAGCGGATTCTGGTGGTCATACAGATAACCGTCCGTTTTTAACATT
ATTACCGACGATTATTGGTCTGCGTGATGAAGTGCAAGCGAAGTATAACTTCTCTCC
TGCATTACGTGTTGGTGCTGGTGGTGGTATCGGAACGCCTGAAGCAGCACTCGCTGC
ATTTAACATGGGCGCGGCTTATATCGTTCTGGGTTCTGTGAATCAGGCGTGTGTTGA
AGCGGGTGCATCTGAATATACTCGTAAACTGTTATCGACAGTTGAAATGGCTGATGT
GACTATGGCACCTGCTGCAGATATGTTTGAAATGGGTGTGAAGCTGCAAGTATTAAA
ACGCGGTTCTATGTTCGCGATGCGTGCGAAGAAACTGTATGACTTGTATGTGGCTTA
TGACTCGATTGAAGATATCCCAGCTGCTGAACGTGAGAAGATTGAAAAACAAATCTT
CCGTGCAAACCTAGACGAGATTTGGGATGGCACTATCGCTTTCTTTACTGAACGCGA
TCCAGAAATGCTAGCCCGTGCAACGAGTAGTCCTAAACGTAAATGGCACTTATCTT
CCGTTGGTATCTTGGCCTTTCTTCACGCTGGTCAAACACAGGCGAGAAGGGACGTGA
AATGGATTATCAGATTTGGGCAGGCCCAAGTTTAGGTGCATTCAACAGCTGGGTGAA
AGGTTCTTACCTTGAAGACTATACCCGCCGTGGCGCTGTAGATGTTGCTTTGCATAT
GCTTAAAGGTGCTGCGTATTTACAACGTGTAAACCAGTTGAAATTGCAAGGTGTTAG
CTTAAGTACAGAATTGGCAAGTTATCGTACGAGTGATTAATGTTACTTGATGATATG
TGAATTAATTAAAGCGCCTGAGGGCGCTTTTTTTGGTTTTTAACTCAGGTGTTGTAA
CTCGAAATTGCCCCTTTC
                    *
                  19227
```

FIG. 6-13 pro vm orf7

| EPA (%Fatty acids) | DHA (%Fatty acids) | 20 deg C |
|---|---|---|
| 0.00 | 0.06 | pEPAD8 |
| 0.60 | 0.70 | 4 |
| 0.64 | 0.66 | 5 |
| 0.33 | 0.22 | 6s |
| 0.45 | 0.59 | 6l |
|  |  | *23 deg C* |
| 0.02 | 0.06 | pEPAD8 |
| 0.32 | 0.62 | 4 |
| 0.27 | 0.22 | 6s |
| 0.18 | 0.65 | 6l |

FIGURE 16

```
ATT GGT AAA AAT AGG GGT TAT GTT TGT TGC TTT AAA GAG TGT CCT GAA
 I   G   K   N   R   G   Y   V   C   C   F   K   E   C   P   E

9157
AAA TTG CTA ACT TCT CGA TTG ATT TCC TTA TAC TTC TGT CCG TTA ACA
 K   L   L   T   S   R   L   I   S   L   Y   F   C   P   L   T

ATA CAA GAG TGC GAT AAC CAG ACT ACA GAG TTG GTT AAG TCA TGG CTG
 I   Q   E   C   D   N   Q   T   T   E   L   V   K   S   W   L

CCT GAA GAT GAG TTA ATT AAG GTT AAT CGC TAC ATT AAA CAA GAA GCT
 P   E   D   E   L   I   K   V   N   R   Y   I   K   Q   E   A

9016
AAA ACT CAA GGT TTA ATG GTA AGA G
 K   T   Q   G   L   M   V   R
```

FIG. 24

```
AGCGAAATGC TTATCAAGAA ATTCCAAGAT CAATACATCA CTGGGAAGAA AATTCATTCC    60
CTGGTTCACT GGGTAACGTT ATTTCCGGCC GTATTGCTAA CCGCTTCGAC CTTGGTGGCA   120
TGAACTGTGT CGTTGATGCA GCATGTGCAG GCCCTCTTGC TGCATTGCGT ATGGCATTAA   180
GCGAGCTTGT TGAAGGCCGC AGCGAAATGA TGATTACAGG TGGTGTGTGT ACCGATAACT   240
CACCAACCAT GTACATGAGC TTCTCTAAAA CACCGGCATT CACGACAAAC GAAACAATTC   300
AACCATTCGA TATTGACTCG AAAGGTATGA TGATTGGTGA AGGTATCGGT ATGATTGCGC   360
TTAAACGTCT TGAAGACGCA GAGCGTGATG GCGACCGTAT CTATTCCGTG ATTAAAGGTG   420
TTGGGTGCAT CTTCAGACGG TAATTTATTA AGAGTANTTA TGCGCNTCGT CCTGAAGGTC   480
AGGCTAAGGC ACTTAAACGT GCTTACGACG ATGCAGGTTT CGCACCGCAC ACACTTGGCT   540
TACTTGAAGC CCACGGCACA GGCACAGCAG CAGGTGATGT GGCAGAATTC AGTGGTCTTA   600
ACTCTGTATT CAGTGAAGGC AATGACGAAA AGCAACACAT CGGCATTAGGT TCAGTGAAAT   660
CACAGATTGG TCACACTAAA TCAACAGCGG GTACTGCGGG TCTAATCAAA GCGTCTTTAG   720
CACTGCACCA TAAAGTACTG CCGCCAACAA TCAATGTAAC CAGCCCTAAC CCTAAACTGA   780
ATATTGAAGA CTCGCCTTTC TACCTCAATA CACAGACGCG TCCATGGATG CAACGTGTCG   840
ATGGTACACC GCGTCGTGCT GGTATTAGCT CATTTGGTTT TGGTG                   885
```

FIG. 25

```
                                    20                    40                     60
                                     *                     *                      *
3-2(-VECTO      CCAAGCTAAA GCACTTAACC GTGCTTATGA AGATGCCGGT TTTGCCCCTG AAACATGTGG
                |||||||||| |||||||||| |||||||||| |  ||||||| |||||||||| ||||||||||
jmpl str +      CCAAGCTAAA GCACTTAACC GTGCCTATGA TGATGCCGGT TTTGCCCCTG AAACATGTGG
                |||||||||| |||||||||| ||||  ||||  |||||||||| |||||||||| ||||||||||
3-2(-VECTO      CCAAGCTAAA GCACTTAACC GTGCTTATGA AGATGCCGGT TTTGCCCCTG AAACATGTGG 80                   100                    120
                                     *                     *                      *
3-2(-VECTO      TCTAATTGAA GGCCATGGTA CGGGTACCAA AGCGGGTGAT GCCGCAGAAT TGCTGGCTT
                |||||||||| |||||||||| |   ||   |  |||||||| |||||||||| |  ||||||
jmpl str +      TCTAATTGAA GGCCATGGTA C
                |||||||||| |||||||||| |
3-2(-VECTO      TCTAATTGAA GGCCATGGTA C AGA ACGCAAAGTT GCCGCACTGT TTGGTCGCCA
                 |   |  |||||| |||||||||| ||||||||||
                CAA AGCGGGTGAT GCCGCACTGT TTGGTCGCTT
```

FIG. 26-1

```
                            140                160                180
                             *                  *                  *
3-2(-VECTO  GACCAAACAC TTTGGCGCCG CCAGTGATGA AAAGCAATAT ATCGCCTTAG GCTCAGTTAA jmpl str +                                                C ATTGCGCTAG GTTCAGTTAA
                                                          | ||  ||||    ||||||||
3-2(-VECTO                                                T ATCGCCTTAG GCTCAGTTAA jmpl str +  AGGTTCACAA
            |||    |||
3-2(-VECTO  GACCTAACAC 200                220                240
                             *                  *                  *
3-2(-VECTO  ATCGCAAATT GGTCATACTA AATCTGCGGC TGGCTCTGCG GGTATGATTA AGGCGGCATT jmpl str +                                                CG GCTTCGATTT TGGCGGCATG
                                                          || |  ||  ||  |||| ||||
3-2(-VECTO                                                CG CGTATGATTA AGGCGGCATT jmpl str +  ATCACAAATT GGTCATACTA AATCAACTGC AGGT
            |||  ||||| ||||||||||  ||| |  ||   ||
3-2(-VECTO  ATCGCAAATT GGTCATACTA AATCTGCGGC TGGC
```

FIG. 26-2

```
jmpl st +                                              GCACTGCT GCAAGCATGA ACGCGTCGTT
                                                       || |||   |    ||||  ||||||||
3-2 (-VECTO                                            GCTCTGCG GCTATCATTA ACGCGGCATT
                                                                                   300
                    *         *         *         *         *         *         *
3-2 (-VECTO  AGCGCTGCAT CATAAAATCT TACCTGCAAC GATCCATATC GATAAACCAA GTGAAGCCTT jmpl st +    AACGGTG
             ||   ||
3-2 (-VECTO  AGCGCTG jmpl st +      T
               |
3-2 (-VECTO    A jmpl st +                                              TCCCTGGTGC TAACCATATC AGCAAACCA
                                                       |   |||    |||||||   |||  ||
3-2 (-VECTO                                            TACCTGCAAC GATCCATATC GATAAACCA
                                                                                   360
                    *         *         *         *         *         *         *
3-2 (-VECTO  GGATATCAAA AACAGCCCGT TATACCTAAA CAGCGAAACG CGTCCTTGGA TGCCACGTGA
```

FIG. 26-3

```
jmpl str +      CTCACCTT TGTATCTAAA CACTGAGACT TCGTCCATGG TTACCACGTGT
                 - - | || ||||||  || || ||   |||||| |||  - |||||||||
3-2(-VECTO      CAGCCCCGT TATACCTAAA CAGCGAAACG GCGTCCTTGG ATGCCACGTGA
                                         380                    400
                                          *                      *
3-2(-VECTO      AGATGGTATT CCACGTCGTG CAGGTATTAG CTCATTTGGT TTTGGTGGC jmpl str +      TGATGGTACG CCGCGCCGCG CGGGTATTAG CTCATTTGGT TTTGGTGGC>
                ||||||||   ||  || ||  | |||||||| |||||||||| |||||||||
3-2(-VECTO      AGATGGTATT CCACGTCGTG CAGGTATTAG CTCATTTGGT TTTGGTGGC
```

FIG. 26-4

```
CGCTGCCGCCGCGTCTCGCCGCGCCGCGCCGCGCCGCCGCCGCTCGCGCGCACGCC
CGCGCGTCTCGCCGCGCCTGCTGTCTCGAACGAGCTTCTCGAGAAGGCCGAGACCGTCG
TCATGGAGGTCCTCGCCGCCAAGACTGGCTACGAGACTGACATGATCGAGTCCGACATG
GAGCTCGAGACTGAGCTCGGCATTGACTCCATCAAGCGTGTCGAGATCCTCTCCGAGGT
TCAGGCCATGCTCAACGTCGAGGCCAAGGACGTCGACGCTCTCAGCCGCACTCGCACTG
TGGGTGAGGTCGTCAACGCCATGAAGGCTGAGATCGCTGGTGGCTCTGCCCCGGCGCCT
GCCGCCGCTGCCCCAGGTCCGGCTGCTGCCGCCCCTGCGCCTGCTGTCTCGAGCGAGCT
TCTCGAGAAGGCCGAGACTGTCGTCATGGAGGTCCTCGCCGCCAAGACTGGCTACGAGA
CTGACATGATTGAGTCCGACATGGAGCTCGAGACCGAGCTCGGCATTGACTCCATCAAG
CGTGTCGAGATTCTCTCCGAGGTTCAGGCCATGCTCAACGTCGAGGCCAAGGACGTCGA
CGCTCTCAGCCGCACTCGCACTGTTGGTGAGGTCGTCGATGCCATGAAGGCTGAGATCG
CTGGCAGCTCCGCCTCGGCGCCTGCCGCCGCTGCTCCTGCTCCGGCTGCTGCCGCTCCT
GCGCCCGCTGCCGCCGCCCTGCTGTCTCGAACGAGCTTCTCGAGAAAGCCGAGACTGT
CGTCATGGAGGTCCTCGCCGCCAAGACTGGCTACGAGACTGACATGATCGAGTCCGACA
TGGAGCTCGAGACTGAGCTCGGCATTGACTCCATCAAGCGTGTCGAGATCCTCTCCGAG
GTTCAGGCCATGCTCAACGTCGAGGCCAAGGACGTCGATGCCCTCAGCCGCACCCGCAC
TGTTGGCGAGGTTGTCGATGCCATGAAGGCCGAGATCGCTGGTGGCTCTGCCCCGGCGC
CTGCCGCCGCTGCCCCTGCTCCGGCTGCCGCCGCCCTGCTGTCTCGAACGAGCTTCTT
GAGAAGGCCGAGACTGTCGTCATGGAGGTCCTCGCCGCCAAGACTGGCTACGAGACCGA
CATGATCGAGTCCGACATGGAGCTCGAGACCGAGCTCGGCATTGACTCCATCAAGCGTG
TCGAGATTCTCTCCGAGGTTCAGGCCATGCTCAACGTCGAGGCCAAGGACGTCGATGCT
CTCAGCCGCACTCGCACTGTTGGCGAGGTCGTCGATGCCATGAAGGCTGAGATCGCCGG
CAGCTCCGCCCCGGCGCCTGCCGCCGCTGCTCCTGCTCCGGCTGCTGCCGCTCCTGCGC
CCGCTGCCGCTGCCCCTGCTGTCTCGAGCGAGCTTCTCGAGAAGGCCGAGACCGTCGTC
ATGGAGGTCCTCGCCGCCAAGACTGGCTACGAGACTGACATGATTGAGTCCGACATGGA
GCTCGAGACTGAGCTCGGCATTGACTCCATCAAGCGTGTCGAGATCCTCTCCGAGGTTC
AGGCCATGCTCAACGTCGAGGCCAAGGACGTCGATGCCCTCAGCCGCACCCGCACTGTT
GGCGAGGTTGTCGATGCCATGAAGGCCGAGATCGCTGGTGGCTCTGCCCCGGCGCCTGC
CGCCGCTGCCCCTGCTCCGGCTGCCGCCGCCCTGCTGTCTCGAACGAGCTTCTTGAGA
AGGCCGAGACCGTCGTCATGGAGGTCCTCGCCGCCAAGACTGGCTACGAGACCGACATG
ATCGAGTCCGACATGGAGCTCGAGACCGAGCTCGGCATTGACTCCATCAAGCGTGTCGA
GATTCTCTCCGAGGTTCAGGCCATGCTCAACGTCGAGGCCAAGGACGTCGACGCTCTCA
GCCGCACTCGCACTGTTGGCGAGGTCGTCGATGCCATGAAGGCTGAGATCGCTGGTGGC
TCTGCCCCGGCGCCTGCCGCCGCTGCTCCTGCCTCGGCTGGCGCCGCGCCTGCGGTCAA
GATTGACTCGGTCCACGGCGCTGACTGTGATGATCTTTCCCTGATGCACGCCAAGGTGG
TTGACATCCGCCGCCCGGACGAGCTCATCCTGGAGCGCCCCGAGAACCGCCCCGTTCTC
GTTGTCGATGACGGCAGCGAGCTCACCCTCGCCCTGGTCCGCGTCCTCGGCGCCTGCGC
CGTTGTCCTGACCTTTGAGGGTCTCCAGCTCGCTCAGCGCGCTGGTGCCGCTGCCATCC
GCCACGTGCTCGCCAAGGATCTTTCCGCGGAGAGCGCCGAGAAGGCCATCAAGGAGGCC
GAGCAGCGCTTTGGCGCTCTCGGCGGCTTCATCTCGCAGCAGGCGGAGCGCTTCGAGCC
CGCCGAAATCCTCGGCTTCACGCTCATGTGCGCCAAGTTCGCCAAGGCTTCCCTCTGCA
CGGCTGTGGCTGGCGGCCGCCCGGCCTTTATCGGTGTGGCGCGCCTTGACGGCCGCCTC
```

FIG. 27A-1

```
GGATTCACTTCGCAGGGCACTTCTGACGCGCTCAAGCGTGCCCAGCGTGGTGCCATCTT
TGGCCTCTGCAAGACCATCGGCCTCGAGTGGTCCGAGTCTGACGTCTTTTCCCGCGGCG
TGGACATTGCTCAGGGCATGCACCCCGAGGATGCCGCCGTGGCGATTGTGCGCGAGATG
GCGTGCGCTGACATTCGCATTCGCGAGGTCGGCATTGGCGCAAACCAGCAGCGCTGCAC
GATCCGTGCCGCCAAGCTCGAGACCGGCAACCCGCAGCGCCAGATCGCCAAGGACGACG
TGCTGCTCGTTTCTGGCGGCGCTCGCGGCATCACGCCTCTTTGCATCCGGGAGATCACG
CGCCAGATCGCGGGCGGCAAGTACATTCTGCTTGGCCGCAGCAAGGTCTCTGCGAGCGA
ACCGGCATGGTGCGCTGGCATCACTGACGAGAAGGCTGTGCAAAAGGCTGCTACCCAGG
AGCTCAAGCGCGCCTTTAGCGCTGGCGAGGGCCCCAAGCCCACGCCCCGCGCTGTCACT
AAGCTTGTGGGCTCTGTTCTTGGCGCTCGCGAGGTGCGCAGCTCTATTGCTGCGATTGA
AGCGCTCGGCGGCAAGGCCATCTACTCGTCGTGCGACGTGAACTCTGCCGCCGACGTGG
CCAAGGCCGTGCGCGATGCCGAGTCCCAGCTCGGTGCCCGCGTCTCGGGCATCGTTCAT
GCCTCGGGCGTGCTCCGCGACCGTCTCATCGAGAAGAAGCTCCCCGACGAGTTCGACGC
CGTCTTTGGCACCAAGGTCACCGGTCTCGAGAACCTCCTCGCCGCCGTCGACCGCGCCA
ACCTCAAGCACATGGTCCTCTTCAGCTCGCTCGCCGGCTTCCACGGCAACGTCGGCCAG
TCTGACTACGCCATGGCCAACGAGGCCCTTAACAAGATGGGCCTCGAGCTCGCCAAGGA
CGTCTCGGTCAAGTCGATCTGCTTCGGTCCCTGGGACGGTGGCATGGTGACGCCGCAGC
TCAAGAAGCAGTTCCAGGAGATGGGCGTGCAGATCATCCCCGCGAGGGCGGCGCTGAT
ACCGTGGCGCGCATCGTGCTCGGCTCCTCGCCGGCTGAGATCCTTGTCGGCAACTGGCG
CACCCCGTCCAAGAAGGTCGGCTCGGACACCATCACCCTGCACCGCAAGATTTCCGCCA
AGTCCAACCCCTTCCTCGAGGACCACGTCATCCAGGGCCGCCGCGTGCTGCCCATGACG
CTGGCCATTGGCTCGCTCGCGGAGACCTGCCTCGGCCTCTTCCCCGGCTACTCGCTCTG
GGCCATTGACGACGCCCAGCTCTTCAAGGGTGTCACTGTCGACGGCGACGTCAACTGCG
AGGTGACCCTCACCCCGTCGACGGCGCCCTCGGGCCGCGTCAACGTCCAGGCCACGCTC
AAGACCTTTTCCAGCGGCAAGCTGGTCCCGGCCTACCGCGCCGTCATCGTGCTCTCCAA
CCAGGGCGCGCCCCGGCCAACGCCACCATGCAGCCGCCCTCGCTCGATGCCGATCCGG
CGCTCCAGGGCTCCGTCTACGACGGCAAGACCCTCTTCCACGGCCCGGCCTTCCGCGGC
ATCGATGACGTGCTCTCGTGCACCAAGAGCCAGCTTGTGGCCAAGTGCAGCGCTGTCCC
CGGCTCCGACGCCGCTCGCGGCGAGTTTGCCACGGACACTGACGCCCATGACCCCTTCG
TGAACGACCTGGCCTTTCAGGCCATGCTCGTCTGGGTGCGCCGCACGCTCGGCCAGGCT
GCGCTCCCCAACTCGATCCAGCGCATCGTCCAGCACCGCCCGGTCCCGCAGGACAAGCC
CTTCTACATTACCCTCCGCTCCAACCAGTCGGGCGGTCACTCCCAGCACAAGCACGCCC
TTCAGTTCCACAACGAGCAGGGCGATCTCTTCATTGATGTCCAGGCTTCGGTCATCGCC
ACGGACAGCCTTGCCTTCTAA
```

FIG. 27A-2

```
TGCCGTCTTTGAGGAGCATGACCCCTCCAACGCCGCCTGCACGGGCCACGACTCCATTT
CTGCGCTCTCGGCCCGCTGCGGCGGTGAAAGCAACATGCGCATCGCCATCACTGGTATG
GACGCCACCTTTGGCGCTCTCAAGGGACTCGACGCCTTCGAGCGCGCCATTTACACCGG
CGCTCACGGTGCCATCCCACTCCCAGAAAAGCGCTGGCGCTTTCTCGGCAAGGACAAGG
ACTTTCTTGACCTCTGCGGCGTCAAGGCCACCCCGCACGGCTGCTACATTGAAGATGTT
GAGGTCGACTTCCAGCGCCTCCGCACGCCCATGACCCCTGAAGACATGCTCCTCCCTCA
GCAGCTTCTGGCCGTCACCACCATTGACCGCGCCATCCTCGACTCGGGAATGAAAAAGG
GTGGCAATGTCGCCGTCTTTGTCGGCCTCGGCACCGACCTCGAGCTCTACCGTCACCGT
GCTCGCGTCGCTCTCAAGGAGCGCGTCCGCCCTGAAGCCTCCAAGAAGCTCAATGACAT
GATGCAGTACATTAACGACTGCGGCACATCCACATCGTACACCTCGTACATTGGCAACC
TCGTCGCCACGCGCGTCTCGTCGCAGTGGGGCTTCACGGGCCCCTCCTTTACGATCACC
GAGGGCAACAACTCCGTCTACCGCTGCGCCGAGCTCGGCAAGTACCTCCTCGAGACCGG
CGAGGTCGATGGCGTCGTCGTTGCGGGTGTCGATCTCTGCGGCAGTGCCGAAAACCTTT
ACGTCAAGTCTCGCCGCTTCAAGGTGTCCACCTCCGATACCCGCGCGCCAGCTTTGAC
GCCGCCGCCGATGGCTACTTTGTCGGCGAGGGCTGCGGTGCCTTTGTGCTCAAGCGTGA
GACTAGCTGCACCAAGGACGACCGTATCTACGCTTGCATGGATGCCATCGTCCCTGGCA
ACGTCCCTAGCGCCTGCTTGCGCGAGGCCCTCGACCAGGCGCGCGTCAAGCCGGGCGAT
ATCGAGATGCTCGAGCTCAGCGCCGACTCCGCCCGCCACCTCAAGGACCCGTCCGTCCT
GCCCAAGGAGCTCACTGCCGAGGAGGAAATCGGCGGCCTTCAGACGATCCTTCGTGACG
ATGACAAGCTCCCGCGCAACGTCGCAACGGGCAGTGTCAAGGCCACCGTCGGTGACACC
GGTTATGCCTCTGGTGCTGCCAGCCTCATCAAGGCTGCGCTTTGCATCTACAACCGCTA
CCTGCCAGCAACGGCGACGACTGGGATGAACCCGCCCCTGAGGCGCCCTGGGACAGCA
CCCTCTTTGCGTGCCAGACCTCGCGCGCTTGGCTCAAGAACCCTGGCGAGCGTCGCTAT
GCGGCCGTCTCGGGCGTCTCCGAGACGCGCTCGTGCTATTCCGTGCTCCTCTCCGAAGC
CGAGGGCCACTACGAGCGCGAGAACCGCATCTCGCTCGACGAGGAGGCGCCCAAGCTCA
TTGTGCTTCGCGCCGACTCCCACGAGGAGATCCTTGGTCGCCTCGACAAGATCCGCGAG
CGCTTCTTGCAGCCCACGGGCGCCGCCCGCGCGAGTCCGAGCTCAAGGCGCAGGCCCG
CCGCATCTTCCTCGAGCTCCTCGGCGAGACCCTTGCCCAGGATGCCGCTTCTTCAGGCT
CGCAAAAGCCCCTCGCTCTCAGCCTCGTCTCCACGCCCTCCAAGCTCCAGCGCGAGGTC
GAGCTCGCGGCCAAGGGTATCCCGCGCTGCCTCAAGATGCGCCGCGATTGGAGCTCCCC
TGCTGGCAGCCGCTACGCGCCTGAGCCGCTCGCCAGCGACCGCGTCGCCTTCATGTACG
GCGAAGGTCGCAGCCCTTACTACGGCATCACCCAAGACATTCACCGCATTTGGCCCGAA
CTCCACGAGGTCATCAACGAAAGACGAACCGTCTCTGGGCCGAAGGCGACCGCTGGGT
CATGCCGCGCGCCAGCTTCAAGTCGGAGCTCGAGAGCCAGCAGCAAGAGTTTGATCGCA
ACATGATTGAAATGTTCCGTCTTGGAATCCTCACCTCAATTGCCTTCACCAATCTGGCG
CGCGACGTTCTCAACATCACGCCCAAGGCCGCCTTTGGCCTCAGTCTTGGCGAGATTTC
CATGATTTTTGCCTTTTCCAAGAAGAACGGTCTCATCTCCGACCAGCTCACCAAGGATC
TTCGCGAGTCCGACGTGTGGAACAAGGCTCTGGCCGTTGAATTAATGCGCTGCGCGAG
GCCTGGGGCATTCCACAGAGTGTCCCCAAGGACGAGTTCTGGCAAGGCTACATTGTGCG
CGGCACCAAGCAGGATATCGAGGCGGCCATCGCCCGGACAGCAAGTACGTGCGCCTCA
CCATCATCAATGATGCCAACACCGCCCTCATTAGCGGCAAGCCCGACGCCTGCAAGGCT
GCGATCGCGCGTCTCGGTGGCAACATTCCTGCGCTTCCCGTGACCCAGGGCATGTGCGG
CCACTGCCCCGAGGTGGGACCTTATACCAAGGATATCGCCAAGATCCATGCCAACCTTG
```

FIG. 27B-1

```
AGTTCCCCGTTGTCGACGGCCTTGACCTCTGGACCACAATCAACCAGAAGCGCCTCGTG
CCACGCGCCACGGGCGCCAAGGACGAATGGGCCCCTTCTTCCTTTGGCGAGTACGCCGG
CCAGCTCTACGAGAAGCAGGCTAACTTCCCCCAAATCGTCGAGACCATTTACAAGCAAA
ACTACGACGTCTTTGTCGAGGTTGGGCCCAACAACCACCGTAGCACCGCAGTGCGCACC
ACGCTTGGTCCCCAGCGCAACCACCTTGCTGGCGCCATCGACAAGCAGAACGAGGATGC
TTGGACGACCATCGTCAAGCTTGTGGCTTCGCTCAAGGCCCACCTTGTTCCTGGCGTCA
CGATCTCGCCGCTGTACCACTCCAAGCTTGTGGCGGAGGCTCAGGCTTGCTACGCTGCG
CTCTGCAAGGGTGAAAAGCCCAAGAAGAACAAGTTTGTGCGCAAGATTCAGCTCAACGG
TCGCTTCAACAGCAAGGCGGACCCCATCTCCTCGGCCGATCTTGCCAGCTTTCCGCCTG
CGGACCCTGCCATTGAAGCCGCCATCTCGAGCCGCATCATGAAGCCTGTCGCTCCCAAG
TTCTACGCGCGTCTCAACATTGACGAGCAGGACGAGACCCGAGATCCGATCCTCAACAA
GGACAACGCGCCGTCTTCTTCTTCTTCTTCTTCTTCTTCTTCTTCTTCTTCTTCTTCTC
CGTCGCCTGCTCCTTCGGCCCCGTGCAAAGAAGGCTGCTCCCGCCGCGGAGACCAAG
GCTGTTGCTTCGGCTGACGCACTTCGCAGTGCCCTGCTCGATCTCGACAGTATGCTTGC
GCTGAGCTCTGCCAGTGCCTCCGGCAACCTTGTTGAGACTGCGCCTAGCGACGCCTCGG
TCATTGTGCCGCCCTGCAACATTGCGGATCTCGGCAGCCGCGCCTTCATGAAAACGTAC
GGTGTTTCGGCGCCTCTGTACACGGGCGCCATGGCCAAGGGCATTGCCTCTGCGGACCT
CGTCATTGCCGCCGGCCGCCAGGGCATCCTTGCGTCCTTTGGCGCCGGCGGACTTCCCA
TGCAGGTTGTGCGTGAGTCCATCGAAAGATTCAGGCCGCCCTGCCCAATGGCCCGTAC
GCTGTCAACCTTATCCATTCTCCCTTTGACAGCAACCTCGAAAAGGGCAATGTCGATCT
CTTCCTCGAGAAGGGTGTCACCTTTGTCGAGGCCTCGGCCTTTATGACGCTCACCCCGC
AGGTCGTGCGGTACCGCGCGGCTGGCCTCACGCGCAACGCCGACGGCTCGGTCAACATC
CGCAACCGTATCATTGGCAAGGTCTCGCGCACCGAGCTCGCCGAGATGTTCATGCGTCC
TGCGCCGAGCACCTTCTTCAGAAGCTCATTGCTTCCGGCGAGATCAACCAGGAGCAGG
CCGAGCTCGCCCGCCGTGTTCCCGTCGCTGACGACATCGCGGTCGAAGCTGACTCGGGT
GGCCACACCGACAACCGCCCCATCCACGTCATTCTGCCCCTCATCATCAACCTTCGCGA
CCGCCTTCACCGCGAGTGCGGCTACCCGGCCAACCTTCGCGTCCGTGTGGGCGCCGGCG
GTGGCATTGGGTGCCCCCAGGCGGCGCTGGCCACCTTCAACATGGGTGCCTCCTTTATT
GTCACCGGCACCGTGAACCAGGTCGCCAAGCAGTCGGGCACGTGCGACAATGTGCGCAA
GCAGCTCGCGAAGGCCACTTACTCGGACGTATGCATGGCCCCGGCTGCCGACATGTTCG
AGGAAGGCGTCAAGCTTCAGGTCCTCAAGAAGGGAACCATGTTTCCCTCGCGCGCCAAC
AAGCTCTACGAGCTCTTTTGCAAGTACGACTCGTTCGAGTCCATGCCCCCGCAGAGCT
TGCGCGCGTCGAGAAGCGCATCTTCAGCCGCGCGCTCGAAGAGGTCTGGGACGAGACCA
AAAACTTTTACATTAACCGTCTTCACAACCCGGAGAAGATCCAGCGCGCCGAGCGCGAC
CCCAAGCTCAAGATGTCGCTGTGCTTTCGCTGGTACCTGAGCCTGGCGAGCCGCTGGGC
CAACACTGGAGCTTCCGATCGCGTCATGGACTACCAGGTCTGGTGCGGTCCTGCCATTG
GTTCCTTCAACGATTTCATCAAGGGAACTTACCTTGATCCGGCCGTCGCAAACGAGTAC
CCGTGCGTCGTTCAGATTAACAAGCAGATCCTTCGTGGAGCGTGCTTCTTGCGCCGTCT
CGAAATTCTGCGCAACGCACGCCTTTCCGATGGCGCTGCCGCTCTTGTGGCCAGCATCG
ATGACACATACGTCCCGGCCGAGAAGCTGTAAGTAAGCTCTCATATATGTTAGTTGCGT
GAGACCGACACGAAGATAATATCACATACGCTTTTGTTTGTTCTTTCAATTATTTGTCT
GTGCTTCATGTTGCTCCTCAGTATCTAGCTGGCGGCTCTTATCTTCTTTTAAAATATCT
GGACAAGGACAAAAACAAGAATAAAGGCGAGAAGATGTGAATTTCATTTCGACTTGAGA
```

FIG. 27B-2

ACTCGAAGAGCATTGATGCGGTTAGTATATGGGTATTTTCCAGACACTTTTCATCATCA
TCATCATCATCATCATTATGAAGAAGTAGTAGCTGATAAAGTAGACTCACTGTTTGCAG
CGAGAAAAAAAAAAAAAAAAAAAA

FIG. 27B-3

```
CGAGCAGAGGCCGGCCGCGAGCCCGAGCCCGCGCCGCAGATCACTAGTACCGCTGCGGA
ATCACAGCAGCAGCAGCAGCAGCAGCAGCAGCAGCAGCAGCAGCAGCAGCCACGAGAGG
GAGATAAAGAAAAGCGGCAGAGACGATGGCGCTCCGTGTCAAGACGAACAAGAAGCCA
TGCTGGGAGATGACCAAGGAGGAGCTGACCAGCGGCAAGACCGAGGTGTTCAACTATGA
GGAACTCCTCGAGTTCGCAGAGGGCGACATCGCCAAGGTCTTCGGACCCGAGTTCGCCG
TCATCGACAAGTACCCGCGCCGCGTGCGCCTGCCCGCCCGCGAGTACCTGCTCGTGACC
CGCGTCACCCTCATGGACGCCGAGGTCAACAACTACCGCGTCGGCGCCCGCATGGTCAC
CGAGTACGATCTCCCCGTCAACGGAGAGCTCTCCGAGGGCGGAGACTGCCCCTGGGCCG
TCCTGGTCGAGAGTGGCCAGTGCGATCTCATGCTCATCTCCTACATGGGCATTGACTTC
CAGAACCAGGGCGACCGCGTCTACCGCCTGCTCAACACCACGCTCACCTTTTACGGCGT
GGCCCACGAGGGCGAGACCCTCGAGTACGACATTCGCGTCACCGGCTTCGCCAAGCGTC
TCGACGGCGGCATCTCCATGTTCTTCTTCGAGTACGACTGCTACGTCAACGGCCGCCTC
CTCATCGAGATGCGCGATGGCTGCGCCGGCTTCTTCACCAACGAGGAGCTCGACGCCGG
CAAGGGCGTCGTCTTCACCCGCGGCGACCTCGCCGCCCGCGCCAAGATCCCAAAGCAGG
ACGTCTCCCCCTACGCCGTCGCCCCTGCCTCCACAAGACCAAGCTCAACGAAAGGAG
ATGCAGACCCTCGTCGACAAGGACTGGGCATCCGTCTTTGGCTCCAAGAACGGCATGCC
GGAAATCAACTACAAACTCTGCGCGCGTAAGATGCTCATGATTGACCGCGTCACCAGCA
TTGACCACAAGGGCGGTGTCTACGGCCTCGGTCAGCTCGTCGGTGAAAAGATCCTCGAG
CGCGACCACTGGTACTTTCCCTGCCACTTTGTCAAGGATCAGGTCATGGCCGGATCCCT
CGTCTCCGACGGCTGCAGCCAGATGCTCAAGATGTACATGATCTGGCTCGGCCTCCACC
TCACCACCGGACCCTTTGACTTCCGCCCGGTCAACGGCCACCCCAACAAGGTCCGCTGC
CGCGGCCAAATCTCCCCGCACAAGGGCAAGCTCGTCTACGTCATGGAGATCAAGGAGAT
GGGCTTCGACGAGGACAACGACCCGTACGCCATTGCCGACGTCAACATCATTGATGTCG
ACTTCGAAAAGGGCCAGGACTTTAGCCTCGACCGCATCAGCGACTACGGCAAGGGCGAC
CTCAACAAGAAGATCGTCGTCGACTTTAAGGGCATCGCTCTCAAGATGCAGAAGCGCTC
CACCAACAAGAACCCCTCCAAGGTTCAGCCCGTCTTTGCCAACGGCGCCGCCACTGTCG
GCCCCGAGGCCTCCAAGGCTTCCTCCGGCGCCAGCGCCAGCGCCAGCGCCGCCCCGGCC
AAGCCTGCCTTCAGCGCCGATGTTCTTGCGCCCAAGCCCGTTGCCCTTCCCGAGCACAT
CCTCAAGGGCGACGCCCTCGCCCCAAGGAGATGTCCTGGCACCCCATGGCCCGCATCC
CGGGCAACCCGACGCCCTCTTTTGCGCCCTCGGCCTACAAGCCGCGCAACATCGCCTTT
ACGCCCTTCCCCGGCAACCCCAACGATAACGACCACACCCCGGGCAAGATGCCGCTCAC
CTGGTTCAACATGGCCGAGTTCATGGCCGGCAAGGTCAGCATGTGCCTCGGCCCCGAGT
TCGCCAAGTTCGACGACTCGAACACCAGCCGCAGCCCCGCTTGGGACCTCGCTCTCGTC
ACCCGCGCCGTGTCTGTGTCTGACCTCAAGCACGTCAACTACGCAACATCGACCTCGA
CCCCTCCAAGGGTACCATGGTCGGCGAGTTCGACTGCCCCGCGGACGCCTGGTTCTACA
AGGGCGCCTGCAACGATGCCCACATGCCGTACTCGATCCTCATGGAGATCGCCCTCCAG
ACCTCGGGTGTGCTCACCTCGGTGCTCAAGGCGCCCTGACCATGGAGAAGGACGACAT
CCTCTTCCGCAACCTCGACGCCAACGCCGAGTTCGTGCGCGCCGACCTCGACTACGCG
GCAAGACTATCCGCAACGTCACCAAGTGCACTGGCTACAGCATGCTCGGCGAGATGGGC
GTCCACCGCTTCACCTTTGAGCTCTACGTCGATGATGTGCTCTTTTACAAGGGCTCGAC
CTCGTTCGGCTGGTTCGTGCCCGAGGTYTTTGCCGCCCAGGCCGGCCTCGACAACGGCC
GCAAGTCGGAGCCCTGGTTCATTGAGAACAAGGTTCCGGCCTCGCAGGTCTCCTCCTTT
GACGTGCGCCCCAACGGCAGCGGCCGCACCGCCATCTTCGCCAACGCCCCCAGCGGCGC
```

FIG. 27C-1

```
CCAGCTCAACCGCCGCACGGACCAGGGCCAGTACCTCGACGCCGTCGACATTGTCTCCG
GCAGCGGCAAGAAGAGCCTCGGCTACGCCCACGGTTCCAAGACGGTCAACCCGAACGAC
TGGTTCTTCTCGTGCCACTTTTGGTTTGACTCGGTCATGCCCGGAAGTCTCGGTGTCGA
GTCCATGTTCCAGCTCGTCGAGGCCATCGCCGCCCACGAGGATCTCGCTGGCAAAGCAC
GGCATTGCCAACCCCACCTTTGTGCACGCCCCGGGCAAGATCAAGCTGGAAGTACCGC
GGSCAGCTCACGCCCAAGAGCAAGAAGATGGACTCGGAGGTCCACATCGTGTCCGTGGA
CGCCCACGACGGCGTTGTCGACCTCGTCGCCGACGGCTTCCTCTGGGCCGACAGCCTCC
GCGTCTACTCGGTGAGCAACATTCGCGTGCGCATCGCCTCCGGTGAGGCCCCTGCCGCC
GCCTCCTCCGCCGCCTCTGTGGGCTCCTCGGCTTCGTCCGTCGAGCGCACGCGCTCGAG
CCCCGCTGTCGCCTCCGGCCCGGCCCAGACCATCGACCTCAAGCAGCTCAAGACCGAGC
TCCTCGAGCTCGATGCCCCGCTCTACCTCTCGCAGGACCCGACCAGCGGCCAGCTCAAG
AAGCACACCGACGTGGCCTCCGGCCAGGCCACCATCGTGCAGCCCTGCACGCTCGGCGA
CCTCGGTGACCGCTCCTTCATGGAGACCTACGGCGTCGTCGCCCCGCTGTACACGGGCG
CCATGGCCAAGGGCATTGCCTCGGCGGACCTCGTCATCGCCGCCGGCAAGCGCAAGATC
CTCGGCTCCTTTGGCGCCGGCGGCCTCCCCATGCACCACGTGCGCGCCGCCCTCGAGAA
GATCCAGGCCGCCCTGCCTCAGGGCCCCTACGCCGTCAACCTCATCCACTCGCCTTTTG
ACAGCAACCTCGAGAAGGGCAACGTCGATCTCTTCCTCGAGAAGGGCGTCACTGTGGTG
GAGGCCTCGGCATTCATGACCCTCACCCCGCAGGTCGTGCGCTACCGCGCCGCCGGCCT
CTCGCGCAACGCCGACGGTTCGGTCAACATCCGCAACCGCATCATCGGCAAGGTCTCGC
GCACCGAGCTCGCCGAGATGTTCATCCGCCCGGCCCCGGAGCACCTCCTCGAGAAGCTC
ATCGCCTCGGGCGAGATCACCCAGGAGCAGGCCGAGCTCGCGCGCCGCGTTCCGTCGC
CGACGATATCGCTGTCGAGGCTGACTCGGGCGGCCACACCGACAACCGCCCCATCCACG
TCATCCTCCCGCTCATCATCAACCTCCGCAACCGCCTGCACCGCGAGTGCGGCTACCCC
GCGCACCTCCGCGTCCGCGTTGGCGCCGGCGGTGGCGTCGGCTGCCCGCAGGCCGCCGC
CGCCGCGCTCACCATGGGCGCCGCCTTCATCGTCACCGGCACTGTCAACCAGGTCGCCA
AGCAGTCCGGCACCTGCGACAACGTGCGCAAGCAGCTCTCGCAGGCCACCTACTCGGAT
ATCTGCATGGCCCCGGCCGCCGACATGTTCGAGGAGGGCGTCAAGCTCCAGGTCCTCAA
GAAGGGAACCATGTTCCCCTCGCGCGCCAACAAGCTCTACGAGCTCTTTTGCAAGTACG
ACTCCTTCGACTCCATGCCTCCTGCCGAGCTCGAGCGCATCGAGAAGCGTATCTTCAAG
CGCGCACTCCAGGAGGTCTGGAGGAGACCAAGGACTTTTACATTAACGGTCTCAAGAA
CCCGGAGAAGATCCAGCGCGCCGAGCACGACCCCAAGCTCAAGATGTCGCTCTGCTTCC
GCTGGTACCTTGGTCTTGCCAGCCGCTGGGCCAACATGGGCGCCCCGGACCGCGTCATG
GACTACCAGGTCTGGTGTGGCCCGGCCATTGGCGCCTTCAACGACTTCATCAAGGGCAC
CTACCTCGACCCCGCTGTCTCCAACGAGTACCCCTGTGTCGTCCAGATCAACCTGCAAA
TCCTCCGTGGTGCCTGCTACCTGCGCCGTCTCAACGCCCTGCGCAACGACCCGCGCATT
GACCTCGAGACCGAGGATGCTGCCTTTGTCTACGAGCCCACCAACGCGCTCTAAGAAAG
TGAACCTTGTCCTAACCCGACAGCGAATGGCGGGAGGGGCGGGCTAAAGATCGTATT
ACATAGTATTTTTCCCCTACTCTTTGTGAAAAAAAAAAAAAAAAAAA
```

FIG. 27C-2

```
RCRRVSPRRAAPPPPLARTPARLAAPAVSNELLEKAETVVMEVLAAKTGYETDMIESDM
ELETELGIDSIKRVEILSEVQAMLNVEAKDVDALSRTRTVGEVVNAMKAEIAGGSAPAP
AAAAPGPAAAAPAPAVSSELLEKAETVVMEVLAAKTGYETDMIESDMELETELGIDSIK
RVEILSEVQAMLNVEAKDVDALSRTRTVGEVVDAMKAEIAGSSASAPAAAAPAPAAAAP
APAAAAPAVSNELLEKAETVVMEVLAAKTGYETDMIESDMELETELGIDSIKRVEILSE
VQAMLNVEAKDVDALSRTRTVGEVVDAMKAEIAGGSAPAPAAAAPAPAAAAPAVSNELL
EKAETVVMEVLAAKTGYETDMIESDMELETELGIDSIKRVEILSEVQAMLNVEAKDVDA
LSRTRTVGEVVDAMKAEIAGSSAPAPAAAAPAPAAAAPAPAAAAPAVSSELLEKAETVV
MEVLAAKTGYETDMIESDMELETELGIDSIKRVEILSEVQAMLNVEAKDVDALSRTRTV
GEVVDAMKAEIAGGSAPAPAAAAPAPAAAAPAVSNELLEKAETVVMEVLAAKTGYETDM
IESDMELETELGIDSIKRVEILSEVQAMLNVEAKDVDALSRTRTVGEVVDAMKAEIAGG
SAPAPAAAAPASAGAAPAVKIDSVHGADCDDLSLMHAKVVDIRRPDELILERPENRPVL
VVDDGSELTLALVRVLGACAVVLTFEGLQLAQRAGAAAIRHVLAKDLSAESAEKAIKEA
EQRFGALGGFISQQAERFEPAEILGFTLMCAKFAKASLCTAVAGGRPAFIGVARLDGRL
GFTSQGTSDALKRAQRGAIFGLCKTIGLEWSESDVFSRGVDIAQGMHPEDAAVAIVREM
ACADIRIREVGIGANQQRCTIRAAKLETGNPQRQIAKDDVLLVSGGARGITPLCIREIT
RQIAGGKYILLGRSKVSASEPAWCAGITDEKAVQKAATQELKRAFSAGEGPKPTPRAVT
KLVGSVLGAREVRSSIAAIEALGGKAIYSSCDVNSAADVAKAVRDAESQLGARVSGIVH
ASGVLRDRLIEKKLPDEFDAVFGTKVTGLENLLAAVDRANLKHMVLFSSLAGFHGNVGQ
SDYAMANEALNKMGLELAKDVSVKSICFGPWDGGMVTPQLKKQFQEMGVQIIPREGGAD
TVARIVLGSSPAEILVGNWRTPSKKVGSDTITLHRKISAKSNPFLEDHVIQGRRVLPMT
LAIGSLAETCLGLFPGYSLWAIDDAQLFKGVTVDGDVNCEVTLTPSTAPSGRVNVQATL
KTFSSGKLVPAYRAVIVLSNQGAPPANATMQPPSLDADPALQGSVYDGKTLFHGPAFRG
IDDVLSCTKSQLVAKCSAVPGSDAARGEFATDTDAHDPFVNDLAFQAMLVWVRRTLGQA
ALPNSIQRIVQHRPVPQDKPFYITLRSNQSGGHSQHKALQFHNEQGDLFIDVQASVIA
TDSLAF
```

FIG. 29A

AVFEEHDPSNAACTGHDSISALSARCGGESNMRIAITGMDATFGALKGLDAFERAIYTG
AHGAIPLPEKRWRFLGKDKDFLDLCGVKATPHGCYIEDVEVDFQRLRTPMTPEDMLLPQ
QLLAVTTIDRAILDSGMKKGGNVAVFVGLGTDLELYRHRARVALKERVRPEASKKLNDM
MQYINDCGTSTSYTSYIGNLVATRVSSQWGFTGPSFTITEGNNSVYRCAELGKYLLETG
EVDGVVVAGVDLCGSAENLYVKSRRFKVSTDTPRASFDAAADGYFVGEGCGAFVLKRE
TSCTKDDRIYACMDAIVPGNVPSACLREALDQARVKPGDIEMLELSADSARHLKDPSVL
PKELTAEEEIGGLQTILRDDDKLPRNVATGSVKATVGDTGYASGAASLIKAALCIYNRY
LPSNGDDWDEPAPEAPWDSTLFACQTSRAWLKNPGERRYAAVSGVSETRSCYSVLLSEA
EGHYERENRISLDEEAPKLIVLRADSHEEILGRLDKIRERFLQPTGAAPRESELKAQAR
RIFLELLGETLAQDAASSGSQKPLALSLVSTPSKLQREVELAAKGIPRCLKMRRDWSSP
AGSRYAPEPLASDRVAFMYGEGRSPYYGITQDIHRIWPELHEVINEKTNRLWAEGDRWV
MPRASFKSELESQQQEFDRNMIEMFRLGILTSIAFTNLARDVLNITPKAAFGLSLGEIS
MIFAFSKKNGLISDQLTKDLRESDVWNKALAVEFNALREAWGIPQSVPKDEFWQGYIVR
GTKQDIEAAIAPDSKYVRLTIINDANTALISGKPDACKAAIARLGGNIPALPVTQGMCG
HCPEVGPYTKDIAKIHANLEFPVVDGLDLWTTINQKRLVPRATGAKDEWAPSSFGEYAG
QLYEKQANFPQIVETIYKQNYDVFVEVGPNNHRSTAVRTTLGPQRNHLAGAIDKQNEDA
WTTIVKLVASLKAHLVPGVTISPLYHSKLVAEAQACYAALCKGEKPKKNKFVRKIQLNG
RFNSKADPISSADLASFPPADPAIEAAISSRIMKPVAPKFYARLNIDEQDETRDPILNK
DNAPSSSSSSSSSSSSSSSPSPAPSAPVQKKAAPAAETKAVASADALRSALLDLDSMLA
LSSASASGNLVETAPSDASVIVPPCNIADLGSRAFMKTYGVSAPLYTGAMAKGIASADL
VIAAGRQGILASFGAGGLPMQVVRESIEKIQAALPNGPYAVNLIHSPFDSNLEKGNVDL
FLEKGVTFVEASAFMTLTPQVVRYRAAGLTRNADGSVNIRNRIIGKVSRTELAEMFMRP
APEHLLQKLIASGEINQEQAELARRVPVADDIAVEADSGGHTDNRPIHVILPLIINLRD
RLHRECGYPANLRVRVGAGGGIGCPQAALATFNMGASFIVTGTVNQVAKQSGTCDNVRK
QLAKATYSDVCMAPAADMFEEGVKLQVLKKGTMFPSRANKLYELFCKYDSFESMPPAEL
ARVEKRIFSRALEEVWDETKNFYINRLHNPEKIQRAERDPKLKMSLCFRWYLSLASRWA
NTGASDRVMDYQVWCGPAIGSFNDFIKGTYLDPAVANEYPCVVQINKQILRGACFLRRL
EILRNARLSDGAAALVASIDDTYVPAEKL

FIG. 29B

```
RAEAGREPEPAPQITSTAAESQQQQQQQQQQQQQQQPREGDKEKAAETMALRVKTNKKPCWEMT
KEELTSGKTEVFNYEELLEFAEGDIAKVFGPEFAVIDKYPRRVRLPAREYLLVTRVTLMDAEVN
NYRVGARMVTEYDLPVNGELSEGGDCPWAVLVESGQCDLMLISYMGIDFQNQGDRVYRLLNTTL
TFYGVAHEGETLEYDIRVTGFAKRLDGGISMFFFEYDCYVNGRLLIEMRDGCAGFFTNEELDAG
KGVVFTRGDLAARAKIPKQDVSPYAVAPCLHKTKLNEKEMQTLVDKDWASVFGSKNGMPEINYK
LCARKMLMIDRVTSIDHKGGVYGLGQLVGEKILERDHWYFPCHFVKDQVMAGSLVSDGCSQMLK
MYMIWLGLHLTTGPFDFRPVNGHPNKVRCRGQISPHKGKLVYVMEIKEMGFDEDNDPYAIADVN
IIDVDFEKGQDFSLDRISDYGKGDLNKKIVVDFKGIALKMQKRSTNKNPSKVQPVFANGAATVG
PEASKASSGASASASAAPAKPAFSADVLAPKPVALPEHILKGDALAPKEMSWHPMARIPGNPTP
SFAPSAYKPRNIAFTPFPGNPNDNDHTPGKMPLTWFNMAEFMAGKVSMCLGPEFAKFDDSNTSR
SPAWDLALVTRAVSVSDLKHVNYRNIDLDPSKGTMVGEFDCPADAWFYKGACNDAHMPYSILME
IALQTSGVLTSVLKAPLTMEKDDILFRNLDANAEFVRADLDYRGKTIRNVTKCTGYSMLGEMGV
HRFTFELYVDDVLFYKGSTSFGWFVPEVFAAQAGLDNGRKSEPWFIENKVPASQVSSFDVRPNG
SGRTAIFANAPSGAQLNRRTDQGQYLDAVDIVSGSGKKSLGYAHGSKTVNPNDWFFSCHFWFDS
VMPGSLGVESMFQLVEAIAAHEDLAGKARHCQPHLCARPRARSSWKYRGQLTPKSKKMDSEVHI
VSVDAHDGVVDLVADGFLWADSLRVYSVSNIRVRIASGEAPAAASSAASVGSSASSVERTRSSP
AVASGPAQTIDLKQLKTELLELDAPLYLSQDPTSGQLKKHTDVASGQATIVQPCTLGDLGDRSF
METYGVVAPLYTGAMAKGIASADLVIAAGKRKILGSFGAGGLPMHHVRAALEKIQAALPQGPYA
VNLIHSPFDSNLEKGNVDLFLEKGVTVVEASAFMTLTPQVVRYRAAGLSRNADGSVNIRNRIIG
KVSRTELAEMFIRPAPEHLLEKLIASGEITQEQAELARRVPVADDIAVEADSGGHTDNRPIHVI
LPLIINLRNRLHRECGYPAHLRVRVGAGGVGCPQAAAAALTMGAAFIVTGTVNQVAKQSGTCD
NVRKQLSQATYSDICMAPAADMFEEGVKLQVLKKGTMFPSRANKLYELFCKYDSFDSMPPAELE
RIEKRIFKRALQEVWEETKDFYINGLKNPEKIQRAEHDPKLKMSLCFRWYLGLASRWANMGAPD
RVMDYQVWCGPAIGAFNDFIKGTYLDPAVSNEYPCVVQINLQILRGACYLRRLNALRNDPRIDL
ETEDAAFVYEPTNAL
```

FIG. 29C

SCHIZOCHYTRIUM PKS GENES

CROSS-REFERENCE TO RELATED APPLICATION

This application is a continuation-in-part of U.S. Ser. No. 09/090,793, filed Jun. 4, 1998, which is a continuation-in-part of provisional application U.S. Ser. No. 60/048,650, filed Jun. 4, 1997, which is incorporated herein by reference.

INTRODUCTION

1. Field of the Invention

This invention relates to modulating levels of enzymes and/or enzyme components capable of modifying long chain poly-unsaturated fatty acids (PUFAs) in a host cell, and constructs and methods for producing PUFAs in a host cell. The invention is exemplified by production of eicosapentenoic acid (EPA) using genes derived from *Shewanella putrefaciens* and *Vibrio marinus*.

2. Background

Two main families of poly-unsaturated fatty acids (PUFAs) are the ω3 fatty acids, exemplified by eicosapentenoic acid, and the ω6 fatty acids, exemplified by arachidonic acid. PUFAs are important components of the plasma membrane of the cell, where they can be found in such forms as phospholipids, and also can be found in triglycerides. PUFAs also serve as precursors to other molecules of importance in human beings and animals, including the prostacyclins, leukotrienes and prostaglandins. Long chain PUFAs of importance include docosahexenoic acid (DHA) and eicosapentenoic acid (EPA), which are found primarily in different types of fish oil, gamma-linolenic acid (GLA), which is found in the seeds of a number of plants, including evening primrose (*Oenothera biennis*), borage (*Borago officinalis*) and black currants (*Ribes nigrum*), stearidonic acid (SDA), which is found in marine oils and plant seeds, and arachidonic acid (ARA), which along with GLA is found in filamentous fungi. ARA can be purified from animal tissues including liver and adrenal gland. Several genera of marine bacteria are known which synthesize either EPA or DHA. DHA is present in human milk along with ARA.

PUFAs are necessary for proper development, particularly in the developing infant brain, and for tissue formation and repair. As an example, DHA, is an important constituent of many human cell membranes, in particular nervous cells (gray matter), muscle cells, and spermatozoa and believed to affect the development of brain functions in general and to be essential for the development of eyesight. EPA and DHA have a number of nutritional and pharmacological uses. As an example adults affected by diabetes (especially non insulin-dependent) show deficiencies and imbalances in their levels of DHA which are believed to contribute to later coronary conditions. Therefore a diet balanced in DHA may be beneficial to diabetics.

For DHA, a number of sources exist for commercial production including a variety of marine organisms, oils obtained from cold water marine fish, and egg yolk fractions. The purification of DHA from fish sources is relatively expensive due to technical difficulties, making DHA expensive and in short supply. In algae such as Amphidinium and Schizochytrium and marine fungi such as Thraustochytrium DHA may represent up to 48% of the fatty acid content of the cell. A few bacteria also are reported to produce DHA. These are generally deep sea bacteria such as *Vibrio marinus*. For ARA, microorganisms including the genera Mortierella, Entomophthora, Phytium and Porphyridium can be used for commercial production. Commercial sources of SDA include the genera Trichodesma and Echium. Commercial sources of GLA include evening primrose, black currants and borage. However, there are several disadvantages associated with commercial production of PUFAs from natural sources. Natural sources of PUFA, such as animals and plants, tend to have highly heterogeneous oil compositions. The oils obtained from these sources can require extensive purification to separate out one or more desired PUFA or to produce an oil which is enriched in one or more desired PUFA.

Natural sources also are subject to uncontrollable fluctuations in availability. Fish stocks may undergo natural variation or may be depleted by overfishing. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large-scale fermentation of organisms such as Shewanella also is expensive. Natural animal tissues contain low amounts of ARA and are difficult to process. Microorganisms such as Porphyridium and Shewanella are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Care must be taken in providing fatty acid supplements, as overaddition may result in suppression of endogenous biosynthetic pathways and lead to competition with other necessary fatty acids in various lipid fractions in vivo, leading to undesirable results. For example, Eskimos having a diet high in ω3 fatty acids have an increased tendency to bleed (U.S. Pat. No. 4,874,603). Fish oils have unpleasant tastes and odors, which may be impossible to economically separate from the desired product, such as a food supplements. Unpleasant tastes and odors of the supplements can make such regimens involving the supplement undesirable and may inhibit compliance by the patient.

A number of enzymes have been identified as being involved in PUFA biosynthesis. Linoleic acid (LA, 18:2 Δ9, 12) is produced from oleic acid (18:1 Δ9) by a Δ12-desaturase. GLA (18:3 Δ9, 12) is produced from linoleic acid (LA, 18:2 Δ9, 12) by a Δ6-desaturase. ARA (20:4 Δ5, 8, 11, 14) is produced from DGLA (20:3 Δ8, 11, 14), catalyzed by a Δ5-desaturase. Eicosapentenoic acid (EPA) is a 20 carbon, omega 3 fatty acid containing 5 double bonds (Δ5, 8, 11, 14, 17), all in the cis configuration. EPA, and the related DHA (Δ4, 7, 10, 13, 16, 19, C22:6) are produced from oleic acid by a series of elongation and desaturation reactions. Additionally, an elongase (or elongases) is required to extend the 18 carbon PUFAs out to 20 and 22 carbon chain lengths. However, animals cannot convert oleic acid (18:1 Δ9) into linoleic acid (18:2 Δ9, 12). Likewise, μ-linolenic acid (ALA, 18:3 Δ9, 12, 15) cannot be synthesized by mammals. Other eukaryotes, including fungi and plants, have enzymes which desaturate at positions Δ12 and Δ15. The major poly-unsaturated fatty acids of animals therefore are either derived from diet and/or from desaturation and elongation of linoleic acid (18:2 Δ9, 12) or µ-linolenic acid (18:3 Δ9, 12, 15).

Poly-unsaturated fatty acids are considered to be useful for nutritional, pharmaceutical, industrial, and other purposes. An expansive supply of poly-unsaturated fatty acids from natural sources and from chemical synthesis are not sufficient for commercial needs. Because a number of separate desaturase and elongase enzymes are required for fatty acid synthesis from linoleic acid (LA, 18:2 Δ9, 12), common in most plant species, to the more saturated and longer chain PUFAs, engineering plant host cells for the expression of EPA and DHA may require expression of five or six separate enzyme activities to achieve expression, at least for EPA and DHA, and for production of quantities of such PUFAs additional engineering efforts may be required, for instance the down regulation of enzymes competing for substrate, engineering of higher enzyme activities such as by mutagenesis or targeting of enzymes to plastid organelles. Therefore it is of interest to obtain genetic material involved in PUFA biosynthesis from species that naturally produce these fatty acids and to express the isolated material alone or in combination in a heterologous system which can be manipulated to allow production of commercial quantities of PUFAs.

Relevant Literature

Several genera of marine bacteria have been identified which synthesize either EPA or DHA (DeLong and Vayanos, *Applied and Environmental Microbiology* (1986) 51: 730–737). Researchers of the Sagami Chemical Research Institute have reported EPA production in *E. coli* which have been transformed with a gene cluster from the marine bacterium, *Shewanella putrefaciens*. A minimum of 5 open reading frames (ORFs) are required for fatty acid synthesis of EPA in *E. coli*.To date, extensive characterization of the functions of the proteins encoded by these genes has not been reported (Yazawa (1996) Lipids 31, S-297; WO 93/23545; WO 96/21735).

The protein sequence of open reading frame (ORF) 3 as published by Yazawa, U.S. Pat. No. 5,683,898 is not a functional protein. Yazawa defines the protein as initiating at the methionine codon at nucleotides 9016–9014 of the Shewanella PKS-like cluster (Genbank accession U73935) and ending at the stop codon at nucleotides 8185–8183 of the Shewanella PKS-like cluster. However, when this ORF is expressed under control of a heterologous promoter in an *E. Coli* strain containing the entire PKS-like cluster except ORF 3, the recombinant cells do not produce EPA.

Polyketides are secondary metabolites the synthesis of which involves a set of enzymatic reactions analogous to those of fatty acid synthesis (see reviews: Hopwood and Shernan, *Annu. Rev. Genet.* (1990) 24: 37–66, and Katz and Donadio, in *Annual Review of Microbiology* (1993) 47: 875–912). It has been proposed to use polyketide synthases to produce novel antibiotics (Hutchinson and Fujii, *Annual Review of Microbiology* (1995) 49:201–238).

SUMMARY OF THE INVENTION

Novel compositions and methods are provided for preparation of long chain poly-unsaturated fatty acids (PUFAs) using polyketide-like synthesis (PKS-like) genes in plants and plant cells. In contrast to the known and proposed methods for production of PUFAs by means of fatty acid synthesis genes, by the invention constructs and methods are provided for producing PUFAs by utilizing genes of a PKS-like system. The methods involve growing a host cell of interest transformed with an expression cassette functional in the host cell, the expression cassette comprising a transcriptional and translational initiation regulatory region, joined in reading frame 5' to a DNA sequence to a gene or component of a PKS-like system capable of modulating the production of PUFAs (PKS-like gene). An alteration in the PUFA profile of host cells is achieved by expression following introduction of a complete PKS-like system responsible for a PUFA biosynthesis into host cells. The invention finds use for example in the large scale production of DHA and EPA and for modification of the fatty acid profile of host cells and edible plant tissues and/or plant parts.

BRIEF DESCRIPTION OF THE DRAWINGS

FIG. 1 provides designations for the ORFs of the EPA gene cluster of Shewanella.

FIG. 2 provides the Shewanella PKS-like domain structure, motifs and 'Blast' matches of ORF 6 (FIG. 2A), ORF 7 (FIG. 2B), ORF 8 (FIG. 2C), ORF 9 (FIG. 2D) and ORF 3 (FIG. 2E).

FIG. 4A shows the DNA sequence (SEQ ID NO:1) for the PKS-like cluster found in Shewanella, containing ORF's 3–9. FIG. 4B shows the amino acid sequence (SEQ ID NO:2) of ORF 2, which is coded by nucleotides 6121–8103 of the sequence shown in FIG. 4A. FIG. 4C shows the amino acid sequence (SEQ ID NO:3) of the published, inactive ORF3, translated from the strand complementary to that shown in FIG. 4A, nucleotides 9016–8186. FIG. 4D shows the nucleotide sequence 8186–9157 (SEQ ID NO:4); its complementary strand codes for ORF 3 active in EPA synthesis. FIGS. 4E–J show the amino acid sequences (SEQ ID NOS:5–10) corresponding to ORF's 4–9, which are encoded by nucleotides 9681–12590 (SEQ ID NO:81), 13040–13903 (SEQ ID NO:82), 13906–22173 (SEQ ID NO:83), 22203–24515 (SEQ ID NO:84), 24518–30529 (SEQ ID NO:85) and 30730–32358 (SEQ ID NO:86), respectively, of FIG. 4A. FIG. 4K shows the amino acid sequence (SEQ ID NO:11) corresponding to nucleotides 32834–34327.

FIG. 5 shows the sequence (SEQ ID NO:12) for the PKS-like cluster in an approximately 40 kb DNA fragment of *Vibrio marinus*, containing ORFs 6, 7, 8 and 9. The start and last codons for each ORF are as follows: ORF 6: 17394, 25352; ORF 7: 25509, 28160; ORF 8: 28209, 34265; ORF 9: 34454, 36118.

FIG. 6 shows the sequence (SEQ ID NO:13) for an approximately 19 kb portion of the PKS-like cluster of FIG. 5 which contains the ORFs 6, 7, 8 and 9. The start and last codons for each ORF are as follows: ORF 6: 411, 8369 (SEQ ID NO:77); ORF 7: 8526, 11177 (SEQ ID NO:78); ORF 8: 11226, 17282 (SEQ ID NO:79); ORF 9: 17471, 19135 (SEQ ID NO:80).

FIG. 10 demonstrates sequence homology of ORF 7 of *Shewanella putrefaciens* and *Vibrio marinus*. The Shewanella ORF 7 is depicted on the vertical axis, and the Vibrio ORF 7 is depicted on the horizontal axis. Lines indicate regions of the proteins that have a 60% identity.

FIG. 12 demonstrates sequence homology of ORF 9 of *Shewanella putrefaciens* and *Vibrio marinus*. The Shewanella ORF 9 is depicted on the vertical axis, and the Vibrio ORF 9 is depicted on the horizontal axis. Lines indicate regions of the proteins that have a 60% identity.

FIG. 16 is a table of PUFA values from the ORF 8 complementation experiment, the chromatogram of which is shown in FIG. 15.

FIG. 24 shows the translated DNA sequence (SEQ ID NO:14) upstream of the published ORF 3 and the corresponding amino acids for which they code (SEQ ID NO:15). The ATG start codon at position 9016 is the start codon for the protein described by Yazawa et al (1996) supra. The other arrows depict TTG or ATT codons that can also serve as start codons in bacteria. When ORF 3 is started from the published ATG codon at 9016, the protein is not functional in making EPA. When ORF 3 is initiated at the TTG codon at position 9157, the protein is capable of facilitating EPA synthesis.

FIG. 25 shows the PCR product (SEQ ID NO:16) for SS9 Photobacter using primers in Example 1.

FIG. 26 shows probe sequences (SEQ ID NOS:17–31) resulting from PCR with primers presented in Example 1.

FIG. 27 shows the nucleotide sequence of Schizochytrium EST clones A. LIB3033-047-B5, LIB3033-046-E6 and a bridging PCR product have now been assembled into a partial cDNA sequence (ORF6 homolog), B. LIB3033–046-D2 (hglc/ORF7/ORF8/ORF9 homolog), C. LIB81–015-D5, LIB81–042-B9 and a bridging PCR product have now been assembled into a partial cDNA sequence (ORF8/ORF9 homolog).

FIG. 29 shows the amino acid sequences inferred from Schizochytrium EST clones A. ORF6 homolog, B. hglc/ORF7/ORF8/ORF9 homolog, C. ORF8/0RF9 homolog.

DESCRIPTION OF THE PREFERRED EMBODIMENTS

Figure 1A:
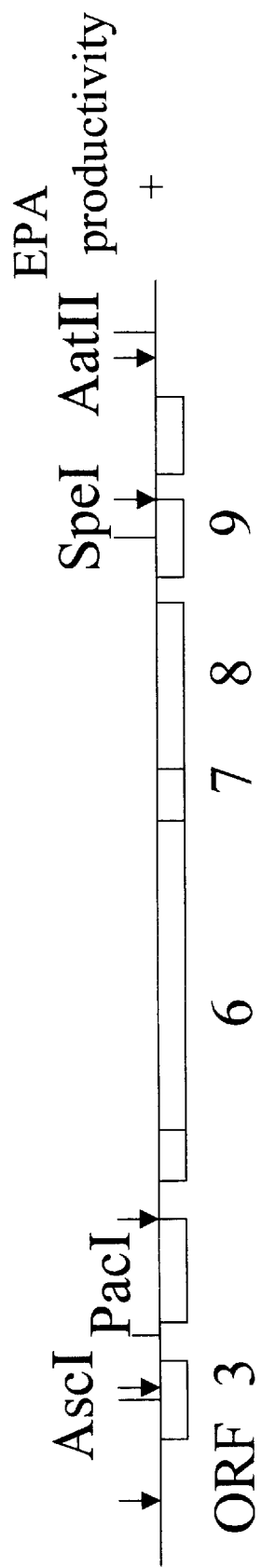
FIG. 1A shows the organization of the genes; those ORFs essential for EPA production in *E. coli* are numbered.

In accordance with the subject invention, novel DNA sequences, DNA constructs and methods are provided, which include some or all of the polyketide-like synthesis (PKS-like) pathway genes from Shewanella, Vibrio, Schizochytrium or other microorganisms, for modifying the poly-unsaturated long chain fatty acid content of host cells, particularly host plant cells. The present invention demonstrates that EPA synthesis genes in *Shewanella putrefaciens* constitute a polyketide-like synthesis pathway. Functions are ascribed to the Shewanella, Schizochytrium and Vibrio genes and methods are provided for the production of EPA and DHA in host cells. The method includes the step of transforming cells with an expression cassette comprising a DNA encoding a polypeptide capable of increasing the amount of one or more PUFA in the host cell. Desirably, integration constructs are prepared which provide for integration of the expression cassette into the genome of a host cell. Host cells are manipulated to express a sense or antisense DNA encoding a polypeptide(s) that has PKS-like gene activity. By "PKS-like gene" is intended a polypeptide which is responsible for any one or more of the functions of a PKS-like activity of interest. By "polypeptide" is meant any chain of amino acids, regardless of length or post-translational modification, for example, glycosylation or phosphorylation. Depending upon the nature of the host cell, the substrate(s) for the expressed enzyme may be produced by the host cell or may be exogenously supplied. Of particular interest is the selective control of PUFA production in plant tissues and/or plant parts such as leaves, roots, fruits and seeds. The invention can be used to synthesize EPA, DHA, and other related PUFAs in host cells.

There are many advantages to transgenic production of PUFAs. As an example, in transgenic *E. coli* as in Shewanella, EPA accumulates in the phospholipid fraction, specifically in the sn-2 position. It may be possible to produce a structured lipid in a desired host cell which differs substantially from that produced in either Shewanella or *E. coli*. Additionally transgenic production of PUFAs in particular host cells offers several advantages over purification from natural sources such as fish or plants. In transgenic plants, by utilizing a PKS-like system, fatty acid synthesis of PUFAs is achieved in the cytoplasm by a system which produces the PUFAs through de novo production of the fatty acids utilizing malonyl Co-A and acetyl Co-A as substrates. In this fashion, potential problems, such as those associated with substrate competition and diversion of normal products of fatty acid synthesis in a host to PUFA production, are avoided.

Production of fatty acids from recombinant plants provides the ability to alter the naturally occurring plant fatty acid profile by providing new synthetic pathways in the host or by suppressing undesired pathways, thereby increasing levels of desired PUFAs, or conjugated forms thereof, and decreasing levels of undesired PUFAs. Production of fatty acids in transgenic plants also offers the advantage that expression of PKS-like genes in particular tissues and/or plant parts means that greatly increased levels of desired PUFAs in those tissues and/or parts can be achieved, making recovery from those tissues more economical. Expression in a plant tissue and/or plant part presents certain efficiencies, particularly where the tissue or part is one which is easily harvested, such as seed, leaves, fruits, flowers, roots, etc. For example, the desired PUFAs can be expressed in seed; methods of isolating seed oils are well established. In addition to providing a source for purification of desired PUFAs, seed oil components can be manipulated through expression of PKS-like genes, either alone or in combination with other genes such as elongases, to provide seed oils having a particular PUFA profile in concentrated form. The concentrated seed oils then can be added to animal milks and/or synthetic or semisynthetic milks to serve as infant formulas where human nursing is impossible or undesired, or in cases of malnourishment or disease in both adults and infants.

Transgenic microbial production of fatty acids offers the advantages that many microbes are known with greatly simplified oil compositions as compared with those of higher organisms, making purification of desired components easier. Microbial production is not subject to fluctuations caused by external variables such as weather and food supply. Microbially produced oil is substantially free of contamination by environmental pollutants. Additionally, microbes can provide PUFAs in particular forms which may have specific uses. For example, Spirulina can provide PUFAs predominantly at the first and third positions of triglycerides; digestion by pancreatic lipases preferentially releases fatty acids from these positions. Following human or animal ingestion of triglycerides derived from Spirulina, these PUFAs are released by pancreatic lipases as free fatty acids and thus are directly available, for example, for infant brain development. Additionally, microbial oil production can be manipulated by controlling culture conditions, notably by providing particular substrates for microbially expressed enzymes, or by addition of compounds which suppress undesired biochemical pathways. In addition to these advantages, production of fatty acids from recombinant microbes provides the ability to alter the naturally occurring microbial fatty acid profile by providing new synthetic pathways in the host or by suppressing undesired pathways, thereby increasing levels of desired PUFAs, or conjugated forms thereof, and decreasing levels of undesired PUFAs.

Production of fatty acids in animals also presents several advantages. Expression of desaturase genes in animals can produce greatly increased levels of desired PUFAs in animal tissues, making recovery from those tissues more economical. For example, where the desired PUFAs are expressed in the breast milk of animals, methods of isolating PUFAs from animal milk are well established. In addition to providing a source for purification of desired PUFAs, animal breast milk can be manipulated through expression of desaturase genes, either alone or in combination with other human genes, to provide animal milks with a PUFA composition substantially similar to human breast milk during the different stages of infant development. Humanized animal milks could serve as infant formulas where human nursing is impossible or undesired, or in the cases of malnourishment or disease.

DNAs encoding desired PKS-like genes can be identified in a variety of ways. In one method, a source of a desired PKS-like gene, for example genomic libraries from a Shewanella, Schizochytrium or Vibrio spp., is screened with detectable enzymatically- or chemically-synthesized probes. Sources of ORFs having PKS-like genes are those organisms which produce a desired PUFA, including DHA-producing or EPA-producing deep sea bacteria growing preferentially under high pressure or at relatively low temperature. Microorgansims such as Shewanella which produce EPA or DHA also can be used as a source of PKS-like genes. The probes can be made from DNA, RNA, or non-naturally occurring nucleotides, or mixtures thereof. Probes can be enzymatically synthesized from DNAs of known PKS-like genes for normal or reduced-stringency hybridization methods. For discussions of nucleic acid probe design and annealing conditions, see, for example, Sambrook et al, *Molecular Cloning: A Laboratory Manual* ($2^{nd}$ ed.), Vols. 1–3, *Cold Spring Harbor Laboratory*, (1989) or *Current Protocols in Molecular Biology*, F. Ausubel et al, ed., Greene Publishing and Wiley-Interscience, New York (1987), each of which is incorporated herein by reference. Techniques for manipulation of nucleic acids encoding PUFA enzymes such as subcloning nucleic acid sequences encoding polypeptides into expression vectors, labelling probes, DNA hybridization, and the like are described generally in Sambrook, supra.

Oligonucleotide probes also can be used to screen sources and can be based on sequences of known PKS-like genes, including sequences conserved among known PKS-like genes, or on peptide sequences obtained from a desired purified protein. Oligonucleotide probes based on amino acid sequences can be degenerate to encompass the degeneracy of the genetic code, or can be biased in favor of the preferred codons of the source organism. Alternatively, a desired protein can be entirely sequenced and total synthesis of a DNA encoding that polypeptide performed.

Once the desired DNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA can also be employed.

For the most part, some or all of the coding sequences for the polypeptides having PKS-like gene activity are from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having PKS-like gene activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable to the desired host cell. Methods for synthesizing sequences and bringing sequences together are well established in the literature. In vitro mutagenesis and selection, site-directed mutagenesis, or other means can be employed to obtain mutations of naturally occurring PKS-like genes to produce a polypeptide having PKS-like gene activity in vivo with more desirable physical and kinetic parameters for function in the host cell, such as a longer half-life or a higher rate of production of a desired polyunsaturated fatty acid.

Of particular interest are the *Shewanella putrefaciens* ORFs and the corresponding ORFs of *Vibrio marinus* and Schizochytrium. The *Shewanella putrefaciens* PKS-like genes can be expressed in transgenic plants to effect biosynthesis of EPA. Other DNAs which are substantially identical in sequence to the *Shewanella putrefaciens* PKS-like genes, or which encode polypeptides which are substantially similar to PKS-like genes of *Shewanella putrefaciens* can be used, such as those identified from *Vibrio marinus* or Schizochytrium. By substantially identical in sequence is intended an amino acid sequence or nucleic acid sequence exhibiting in order of increasing preference at least 60%, 80%, 90% or 95% homology to the DNA sequence of the *Shewanella putrefaciens* PKS-like genes or nucleic acid sequences encoding the amino acid sequences for such genes. For polypeptides, the length of comparison sequences generally is at least 16 amino acids, preferably at least 20 amino acids, and most preferably 35 amino acids. For nucleic acids, the length of comparison sequences generally is at least 50 nucleotides, preferably at least 60 nucleotides, and more preferably at least 75 nucleotides, and most 20 preferably, 110 nucleotides.

Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). BLAST (National Center for Biotechnology Information (WCBI) www.ncbi.nlm.gov; FASTA:(Pearson and Lipman, *Science* (1985) 227:1435–1446). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* (1982) 157: 105–132), or on the basis of the ability to assume similar polypeptide secondary structure (Chou and Fasman, *Adv. Enzymol.* (1978) 47: 45–148, 1978). A related protein to the probing sequence is identified when $p \geq 0.01$, preferably $p \geq 10^{-7}$ or $10^{-8}$.

Encompassed by the present invention are related PKS-like genes from the same or other organisms. Such related PKS-like genes include variants of the disclosed PKS-like ORFs that occur naturally within the same or different species of Shewanella, as well as homologues of the disclosed PKS-like genes from other species and evolutionarily related proteins having analogous function and activity. Also included are PKS-like genes which, although not substantially identical to the *Shewanella putrefaciens* PKS-like genes, operate in a similar fashion to produce PUFAs as part of a PKS-like system. Related PKS-like genes can be identified by their ability to function substantially the same as the disclosed PKS-like genes; that is, they can be substituted for corresponding ORFs of Shewanella, Schizochytrium or Vibrio and still effectively produce EPA or DHA. Related PKS-like genes also can be identified by screening sequence databases for sequences homologous to the disclosed PKS-like genes, by hybridization of a probe based on the disclosed PKS-like genes to a library constructed from the source organism, or by RT-PCR using mRNA from the source organism and primers based on the disclosed PKS-like gene. Thus, the phrase "PKS-like genes" refers not only to the nucleotide sequences disclosed herein, but also to other nucleic acids that are allelic or species variants of these nucleotide sequences. It is also understood that these terms include nonnatural mutations introduced by deliberate mutation using recombinant technology such as single site mutation or by excising short sections of DNA open reading frames coding for PUFA enzymes or by substituting new codons or adding new codons. Such minor alterations substantially maintain the immunoidentity of the original expression product and/or its biological activity. The biological properties of the altered PUFA enzymes can be determined by expressing the enzymes in an appropriate cell line and by determining the ability of the enzymes to synthesize PUFAs. Particular enzyme modifications considered minor would include substitution of amino acids of similar chemical properties, e.g., glutamic acid for aspartic acid or glutamine for asparagine.

When utilizing a PUFA PKS-like system from another organism, the regions of a PKS-like gene polypeptide important for PKS-like gene activity can be determined through routine mutagenesis, expression of the resulting mutant polypeptides and determination of their activities. The coding region for the mutants can include deletions, insertions and point mutations, or combinations thereof. A typical functional analysis begins with deletion mutagenesis to determine the N- and C-terminal limits of the protein necessary for function, and then internal deletions, insertions or point mutants are made in the open ready frame to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such. as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a PKS-like gene polypeptide important for activity. A mutated construct is expressed, and the ability of the resulting altered protein to function as a PKS-like gene is assayed. Such structure-function analysis can determn e which regions may be deleted, which regions tolerate insertions, and which point mutations allow the mutant protein to function in substantially the same way as the native PKS-like gene. All such mutant proteins and nucleotide sequences encoding them are within the scope of the present invention. EPA is produced in Shewanella as the product of a PKS-like system, such that the EPA genes encode components of this system. In Vibrio, DHA is produced by a similar system. The enzymes which synthesize these fatty acids are encoded by a cluster of genes which are distinct from the fatty acid synthesis genes encoding the enzymes involved in synthesis of the C16 and C18 fatty acids typically found in bacteria and in plants. As the Shewanella EPA genes represent a PKS-like gene cluster, EPA production is, at least to some extent, independent of the typical bacterial type II FAS system. Thus, production of EPA in the cytoplasm of plant cells can be achieved by expression of the PKS-like pathway genes in plant cells under the control of appropriate plant regulatory signals.

EPA production in *E. coli* transformed with the Shewanella EPA genes proceeds during anaerobic growth, indicating that $O_2$-dependent desaturase reactions are not involved. Analyses of the proteins encoded by the ORFs essential for EPA production reveals the presence of domain structures characteristic of PKS-like systems. FIG. 2A shows a summary of the domains, motifs, and also key homologies detected by "BLAST" data bank searches. Because EPA is different from many of the other substances produced by PKS-like pathways, i.e., it contains 5, cis double bonds, spaced at 3 carbon intervals along the molecule, a PKS-like system for synthesis of EPA is not expected.

Figure 2F:
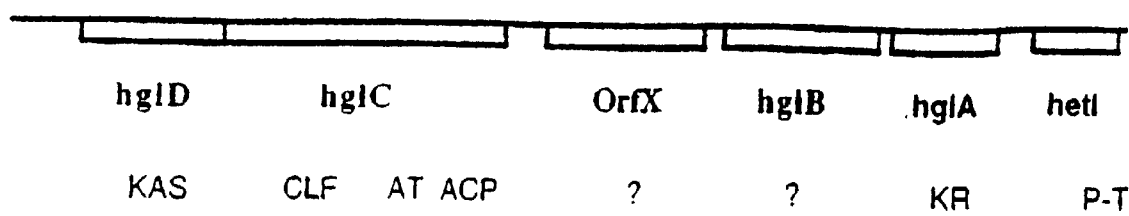
FIG. 2F shows the structure of the region of the Anabeana chromosome that is related to domains present in Shewanella EPA ORFs.

Further, BLAST searches using the domains present in the Shewanella EPA ORFs reveal that several are related to proteins encoded by a PKS-like gene cluster found in Anabeana. The structure of that region of the Anabeana chromosome is shown in FIG. 2F. The Anabeana PKS-like genes have been linked to the synthesis of a long-chain (C26), hydroxy-fatty acid found in a glycolipid layer of heterocysts. The EPA protein domains with homology to the Anabeana proteins are indicated in FIG. 2F.

ORF 6 of Shewanella contains a KAS domain which includes an active site motif (DXAC*), SEQ ID NO:32, as well as a "GFGG", SEQ ID NO:33, motif which is present at the end of many Type II KAS proteins (see FIG. 2A). Extended motifs are present but not shown here. Next is a malonyl-CoA:ACP acyl transferase (AT) domain. Sequences near the active site motif (GHS*XG), SEQ ID NO:34, suggest it transfers malonate rather than methylmalonate, i.e., it resembles the acetate-like ATs. Following a linker region, there is a cluster of 6 repeating domains, each ~100 amino acids in length, which are homologous to PKS-like ACP sequences. Each contains a pantetheine binding site motif 2S (LGXDS*(L/I)), SEQ ID NOS:35 and 36. The presence of 6 such ACP domains has not been observed previously in fatty acid synthases (FAS) or PKS-like systems. Near the end of the protein is a region which shows homology to β-keto-ACP reductases (KR). It contains a pyridine nucleotide binding site motif "GXGXX (G/A/P)", SEQ ID NOS:37, 38 and 39.

The Shewanella ORF 8 begins with a KAS domain, including active site and ending motifs (FIG. 2C). The best match in the data banks is with the Anabeana HglD. There is also a domain which has sequence homology to the N-terminal one half of the Anabeana HglC. This region also shows weak homology to KAS proteins although it lacks the active site and ending motifs. It has the characteristics of the so-called chain length factors (CLF) of Type II PKS-like systems. ORF 8 appears to direct the production of EPA versus DHA by the PKS-like system. ORF 8 also has two domains with homology to β-hydroxyacyl-ACP dehydrases (DH). The best match for both domains is with *E. coli* FabA, a bi-functional enzyme which carries out both the dehydrase reaction and an isomerization (trans to cis) of the resulting double bond. The first DH domain contains both the active site histidine (H) and an adjacent cysteine (C) implicated in FabA catalysis. The second DH domain has the active site H but lacks the adjacent C (FIG. 2C). Blast searches with the second DH domain also show matches to FabZ, a second *E. coli* DH, which does not possess isomerase activity.

The N-terminal half of ORF 7 (FIG. 2B) has no significant matches in the data banks. The best match of the C-terminal half is with a C-terminal portion of the Anabeana HglC. This domain contains an acyl-transferase (AT) motif (GXSXG), SEQ ID NO:40. Comparison of the extended active site sequences, based on the crystal structure of the *E. coli* malonyl-CoA:ACP AT, reveals that ORF 7 lacks two residues essential for exclusion of water from the active site (*E. coli* nomenclature; Q11 and R117). These data suggest that ORF 7 may function as a thioesterase.

Figure 3:
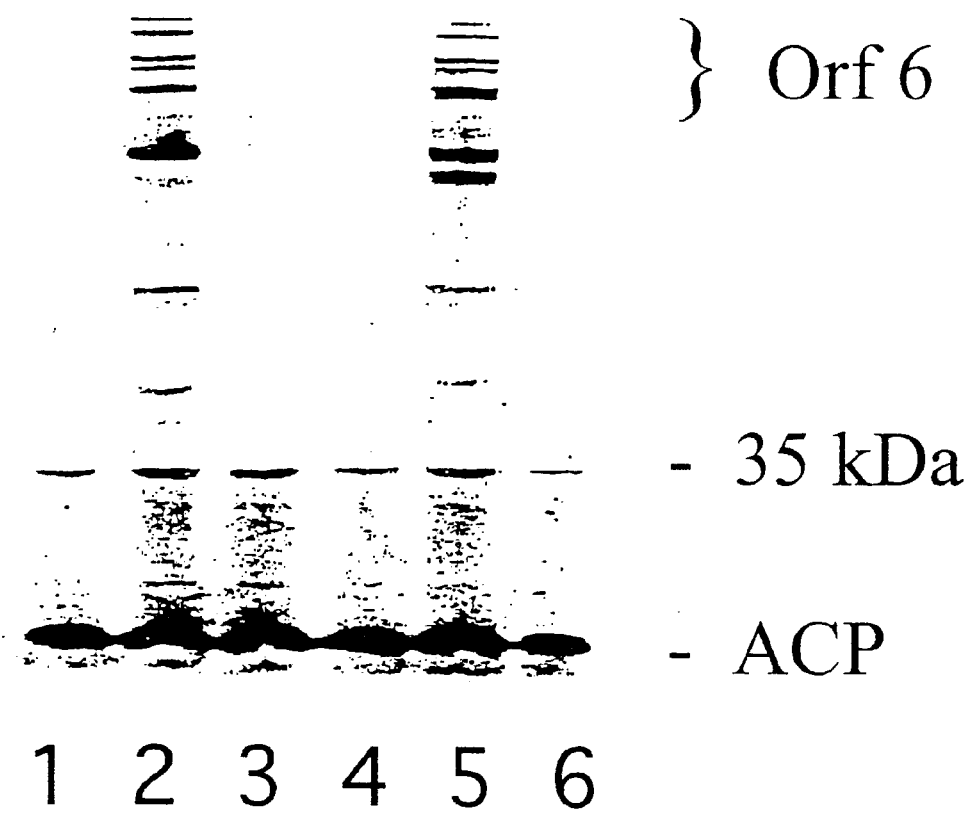
FIG. 3 shows results for pantethenylation—ORF 3 in *E. coli* strain SJ16. The image shows $[C^{14}]$ β-Alanine labelled proteins from *E. coli* (strain SJ16) cells transformed with the listed plasmids. Lane 1 represents pUC19, lane 2 represents pPA-NEB (ΔORF 3), lane 3 represents pAA-Neb (EPA+), lane 4 represents ORF 6 subclone, lane 5 represents ORF 6+ORF 3 subclones, and lane 6 represents ORF 3 subclone. ACP and an unknown (but previously observed) 35 kD protein were labelled in all of the samples. The high molecular mass proteins detected in lanes 2 and 5 are full-length (largest band) and truncated products of the Shewanella ORF-6 gene (confirmed by Western analysis). *E. Coli* strain SJ16 is conditionally blocked in β-alanine synthesis.

ORF 9 (FIG. 2D) is homologous to an ORF of unknown function in the Anabeana Hgl cluster. It also exhibits a very weak homology to NIFA, a regulatory protein in nitrogen fixing bacteria. A regulatory role for the ORF 9 protein has not been excluded. ORF 3 (FIG. 2E) is homologous to the Anabeana HetI as well as EntD from *E. coli* and Sfp of Bacillus. Recently, a new enzyme family of phosphopantetheinyl transferases has been identified that includes HetI, EntD and Sfp (Lamblot RH, et al. (1996) A new enzyme superfamily—the phophopantetheinyl transferases. *Chemistry & Biology*, Vol 3, #11, 923–936 ). The data of FIG. 3 demonstrates that the presence of ORF 3 is required for addition of β-alanine (i.e. pantetheine) to the ORF 6 protein. Thus, ORF 3 encodes the phosphopantetheinyl transferase specific for the ORF 6 ACP domains. (See, Haydock SF et al. (1995) Divergent sequence motifs correlated with the substrate specificity of (methyl)malonyl-CoA:acyl carrier protein transacylase domains in modular polyketide synthases, *FEBS Lett.*, 374, 246–248). Malonate is the source of the carbons utilized in the extension reactions of EPA synthesis. Additionally, malonyl-CoA rather than malonyl-ACP is the AT substrate, i.e., the AT region of ORF 6 uses malonyl Co-A.

Once the DNA sequences encoding the PKS-like genes of an organism responsible for PUFA production have been obtained, they are placed in a vector capable of replication in a host cell, or propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. A PUFA synthesis enzyme or a homologous protein can be expressed in a variety of recombinantly engineered cells. Numerous expression systems are available for expression of DNA encoding a PUFA enzyme. The expression of natural or synthetic nucleic acids encoding PUFA enzyme is typically achieved by opera bly linking the DNA to a promoter (which is either constitutive or inducible) within an expression vector. By expression vector is meant a DNA molecule, linear or circular, that comprises a segment encoding a PUFA enzyme, operably linked to additional segments that provide for its transcription. Such additional segments include promoter and terminator sequences. An expression vector also may include one or more origins of replication, one or more selectable markers, an enhancer, a polyadenylation signal, etc. Expression vectors generally are derived from plasmid or viral DNA, and can contain elements of both. The term "operably linked" indicates that the segments are arranged so that they function in concert for their intended purposes, for example, transcription initiates in the promoter and proceeds through the coding segment to the terminator. See Sambrook et al, supra.

The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell. In vitro expression can be accomplished, for example, by placing the coding region for the desaturase polypeptide in an expression vector designed for in vitro use and adding rabbit reticulocyte lysate and cofactors; labeled amino acids can be incorporated if desired. Such in vitro expression vectors may provide some or all of the expression signals necessary in the system used. These methods are well known in the art and the components of the system are commercially available. The: reaction mixture can then be assayed directly for PKS-like enzymes for example by determining their activity, or the synthesized enzyme can be purified and then assayed.

Expression in a host cell can be accomplished in a transient or stable fashion. Transient expression can occur from introduced constructs which contain expression signals functional in the host cell, but which constructs do not replicate and rarely integrate in the host cell, or:where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a nucleic acid construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus. To achieve expression in a host cell, the transformed DNA is operably associated with transcriptional and translational initiation and termination regulatory regions that are functional in the host cell.

Transcriptional and translational initiation and termination regions are derived from a variety of nonexclusive sources, including the DNA to be expressed, genes known or suspected to be capable of expression in the desired system, expression vectors, chemical synthesis The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property. When expressing more than one PKS-like ORF in the same cell, appropriate regulatory regions and expression methods should be used. Introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

A variety of procaryotic expression systems can be used to express PUFA enzyme. Expression vectors: can be constructed which contain a promoter to direct transcription, a ribosome binding site, and a transcriptional terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018–1024 and the leftward promoter of phage lambda (Pλ) as described by Herskowitz and Hagen, (1980) *Ann. Rev. Genet.*, 14:399–445. The inclusion of selection markers in DNA vectors transformed in *E. coli* is also useful. Examples of such markers include genes specifying resistance to ampicillin, tetracycline, or chloramphenicol. Vectors used for expressing foreign genes in bacterial hosts generally will contain a selectable marker, such as a gene for antibiotic resistance, and a promoter which functions in the host cell. Plasmids useful for transforming bacteria include pBR322 (Bolivar, et al, (1977) *Gene* 2:95–113), the pUC plasmids (Messing.(1983) *Meth. Enzymol.* 101:20–77, Vieira and Messing, (1982) *Gene* 19:259–268), pCQV2 (Queen, ibid.), and derivatives thereof. Plasmids may contain both viral and bacterial elements. Methods for the recovery of the proteins in biologically active form are discussed in U.S. Pat. Nos. 4,966,963 and 4,999,422, which are incorporated herein by reference. See Sambrook, et al for a description of other prokaryotic expression systems.

For expression in eukaryotes, host cells for use in practicing the present invention include mammalian, avian, plant, insect, and fungal cells. As an example, for plants, the choice of a promoter will depend in part upon whether constitutive or inducible expression is desired and whether it is desirable to produce the PUFAs at a particular stage of plant development and/or in a particular tissue. Considerations for choosing a specific tissue and/or developmental stage for expression of the ORFs may depend on competing substrates or the ability of the host cell to tolerate expression of a particular PUFA. Expression can be targeted to a particular location within a host plant such as seed, leaves, fruits, flowers, and roots, by using specific regulatory sequences, such as those described in U.S. Pat. No. 5,463,174, U.S. Pat. No. 4,943,674, U.S. Pat. No. 5,106,739, U.S. Pat. No. 5,175,095, U.S. Pat. No. 5,420,034, U.S. Pat. No. 5,188,958, and U.S. Pat. No. 5,589,379. Where the host cell is a yeast, transcription and translational regions functional in yeast cells are provided, particularly from the host species. The transcriptional initiation regulatory regions can be obtained, for example from genes in the glycolytic pathway, such as alcohol dehydrogenase, glyceraldehyde-3-phosphate dehydrogenase (GPD), phosphoglucoisomerase, phosphoglycerate kinase, etc. or regulatable genes such as acid phosphatase, lactase, metallothionein, glucoamylase, etc. Any one of a number of regulatory sequences can be used in a particular situation, depending upon whether constitutive or induced transcription is desired, the particular efficiency of the promoter in conjunction with the open-reading frame of interest, the ability to join a strong promoter with a control region from a different promoter which allows for inducible transcription, ease of construction, and the like. Of particular interest are promoters which are activated in the presence of galactose. Galactose-inducible promoters (GAL1, GAL7, and GAL10) have been extensively utilized for high level and regulated expression of protein in yeast (Lue et al, (1987) *Mol. Cell. Biol.* 7:3446; Johnston, (1987) *Microbiol. Rev.* 51:458). Transcription from the GAL promoters is activated by the GAL4 protein, which binds to the promoter region and activates transcription when galactose is present. In the absence of galactose, the antagonist GAL80 binds to GAL4 and prevents GAL4 from activating transcription. Addition of galactose prevents GAL80 from inhibiting activation by GAL4. Preferably, the termination region is derived from a yeast gene, particularly Saccharomyces, Schizosaccharomyces, Candida or Kluyveromyces. The 3' regions of two mammalian genes, γ interferon and α2 interferon, are also known to function in yeast.

Nucleotide sequences surrounding the translational initiation codon ATG have been found to affect expression in yeast cells. If the desired polypeptide is poorly expressed in yeast, the nucleotide sequences of exogenous genes can be modified to include an efficient yeast translation initiation sequence to obtain optimal gene expression. For expression in Saccharomyces, this can be done by site-directed mutagenesis of an inefficiently expressed gene by fusing it in-frame to an endogenous Saccharomyces gene, preferably a highly expressed gene, such as the lactase gene.

As an alternative to expressing the PKS-like genes in the plant cell cytoplasm, is to target the enzymes to the chloroplast. One method to target proteins to the chloroplast entails use of leader peptides attached to the N-terrnini of the proteins. Commonly used leader peptides are derived from the small subunit of plant ribulose bis phosphate carboxylase. Leader sequences from other chloroplast proteins may also be used. Another method for targeting proteins to the chloroplast is to transform the chloroplast genome (Stable transformation of chloroplasts of *Chlamydomonas reinhardtii* (1 green alga) using bombardment of recipient cells with high-velocity tungsten microprojectiles coated with foreign DNA has been described. See, for example, Blowers et al *Plant Cell* (1989) 1:123–132 and Debuchy et al *EMBO J* (1989) 8:2803–2809. The transformation technique, using tungsten microprojectiles, is described by Kline et al, *Nature* (London) (1987) 327:70–73). The most common method of transforming chloroplasts involves using biolistic techniques, but other techniques developed for the purpose may also be used. (Methods for targeting foreign gene products into chloroplasts (Shrier et al *EMBO J.* (1985) 4:25–32) or mitochnodria (Boutry et al, supra) have been described. See also Tomai et al *Gen. Biol. Chem.* (1988) 263:15104–15109 and U.S. Pat. No. 4,940,835 for the use of transit peptides for translocating nuclear gene products into the chloroplast. Methods for directing the transport of proteins to the chloroplast are reviewed in Kenauf TIBTECH (1987) 5:40–47.

For producing PUFAs in avian species and cells, gene transfer can be performed by introducing a nucleic acid sequence encoding a PUFA enzyme into the cells following procedures known in the art. If a transgenic animal is desired, pluripotent stem cells of embryos can be provided with a vector carrying a PUFA enzyme encoding transgene and developed into adult animal (U.S. Pat. No. 5,162,215; Ono et al. (1996) *Comparative Biochemistry and Physiolog A* 113(3):287–292; WO 9612793; WO 9606160). In most cases, the transgene is modified to express high levels of the PKS-like enzymes in order to increase production of PUFAs. The transgenes can be modified, for example, by providing transcriptional and/or translational regulatory regions that function in avian cells, such as promoters which direct expression in particular tissues and egg parts such as yolk. The gene regulatory regions can be obtained from a variety of sources, including chicken anemia or avian leukosis viruses or avian genes such as a chicken ovalbumin gene.

Production of PUFAs in insect cells can be conducted using baculovirus expression vectors harboring PKS-like transgenes. Baculovirus expression vectors are available from several commercial sources such as Clonetech. Methods for producing hybrid and transgenic strains of algae, such as marine algae, which contain and express a desaturase transgene also are provided. For example, transgenic marine algae can be prepared as described in U.S. Pat. No. 5,426,040. As with the other expression systems described above, the timing, extent of expression and activity of the desaturase transgene can be regulated by fitting the polypeptide coding sequence with the appropriate transcriptional and translational regulatory regions selected for a particular use. Of particular interest are promoter regions which can be induced under preselected growth conditions. For example, introduction of temperature sensitive and/or metabolite responsive mutations into the desaturase transgene coding sequences, its regulatory regions, and/or the genome of cells into which the transgene is introduced can be used for this purpose.

The transformed host cell is grown under appropriate conditions adapted for a desired end result. For host cells grown in culture, the conditions are typically optimized to produce the greatest or most economical yield of PUFAs, which relates to the selected desaturase activity. Media conditions which may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection. Microorganisms such as yeast, for example, are preferably grown using selected media of interest, which include yeast peptone broth (YPD) and minimal media (contains amino acids, yeast nitrogen base, and ammonium sulfate, and lacks a component for selection, for example uracil). Desirably, substrates to be added are first dissolved in ethanol. Where necessary, expression of the polypeptide of interest may be induced, for example by including or adding galactose to induce expression from a GAL promoter.

When increased expression of the PKS-like gene polypeptide in a host cell which expresses PUFA from a PKS-like system is desired, several methods can be employed. Additional genes encoding the PKS-like gene polypeptide can be introduced into the host organism. Expression from the native PKS-like gene locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (see U.S. Pat. No. 4,910,141 and U.S. Pat. No. 5,500,365). Thus, the subject host will have at least have one copy of the expression construct and may have two or more, depending upon whether the gene is integrated into the genome, amplified, or is present on an extrachromosomal element having multiple copy numbers. Where the subject host is a yeast, four principal types of yeast plasmid vectors can be used: Yeast Integrating plasmids (YIps), Yeast Replicating plasmids (YRps), Yeast Centromere plasmids (YCps), and Yeast Episomal plasmids (YEps). YIps lack a yeast replication origin and must be propagated as integrated elements in the yeast genome. YRps have a chromosomally derived autonomously replicating sequence and are propagated as medium copy number (20 to 40), autonomously replicating, unstably segregating plasmids. YCps have both a replication origin and a centromere sequence and propagate as low copy number (10–20), autonomously replicating, stably segregating plasmids. YEps have an origin of replication from the yeast 2 $\mu$m plasmid and are propagated as high copy number, autonomously replicating, irregularly segregating plasmids. The presence of the plasmids in yeast can be ensured by maintaining selection for a marker on the plasmid. Of particular interest are the yeast vectors pYES2 (a YEp plasmid available from Invitrogen, confers uracil prototrophy and a GAL1 galactose-inducible promoter for expression), and pYX424 (a YEp plasmid having a constitutive TP1 promoter and conferring leucine prototrophy; (Alber and Kawasaki (1982). *J. Mol. & Appl. Genetics* 1:419).

Figure 1B:
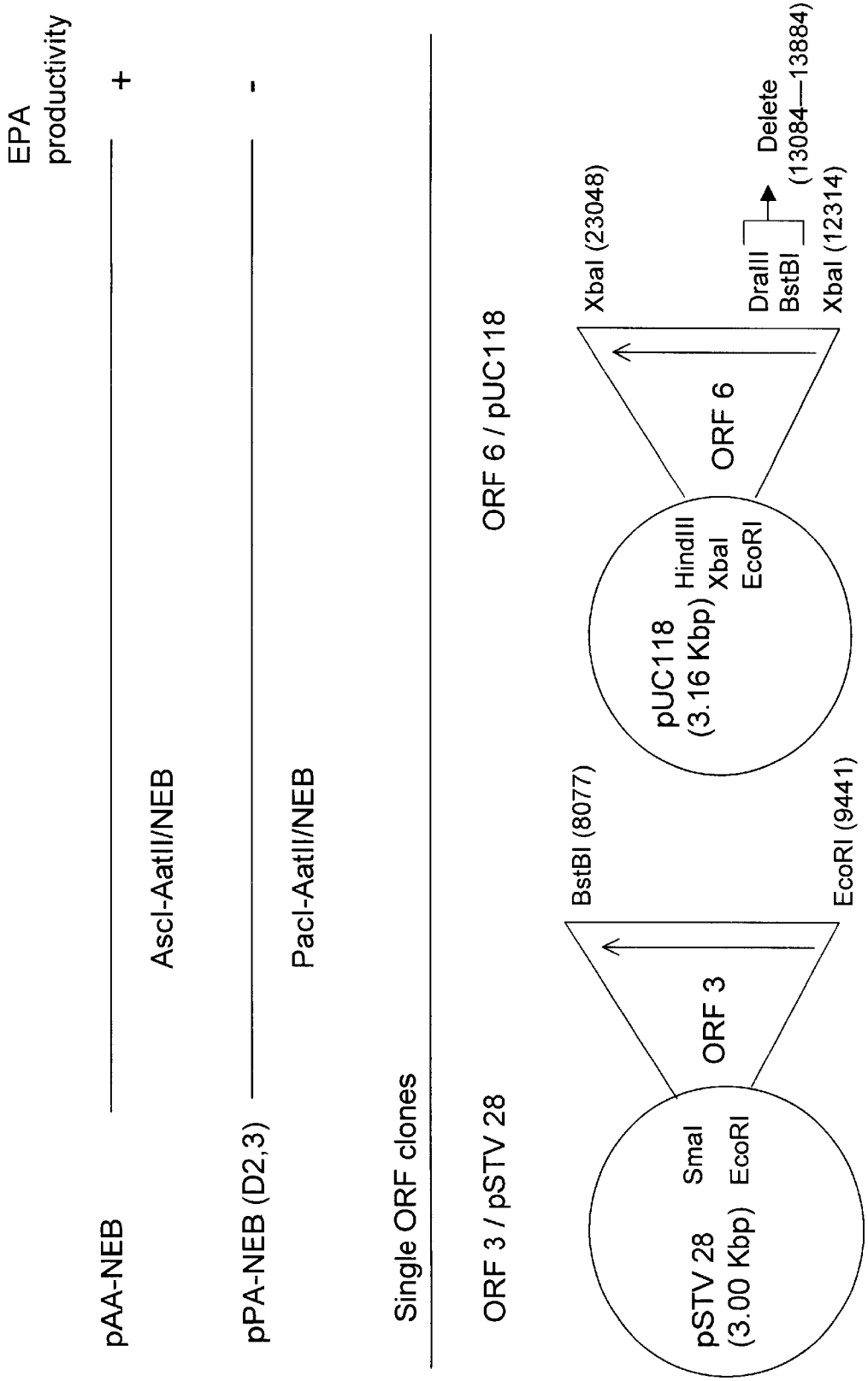
FIG. 1B shows the designations given to subclones.

The choice of a host cell is influenced in part by the desired PUFA profile of the transgenic cell, and the native profile of the host cell. Even where the host cell expresses PKS-like gene activity for o ne PUFA, expression of PKS-like genes of another PKS-like system can provide for production of a novel PUFA not produced by the host cell. In particular instances where expression of PKS-like gene activity is coupled with expression of an ORF 8 PKS-like gene of an organism which produces a different PUFA, it can be desirable that the host cell naturally have, or be mutated to have, low PKS-like gene activity for ORF 8. As an example, for production of EPA, the DNA sequence used encodes the polypeptide having PKS-like gene activity of an organism which produces EPA, while for production of DHA, the DNA sequences used are those from an organism which produces DHA. For use in a host cell which already expresses PKS-like gene activity it can be necessary to utilize an expression cassette which provides for overexpression of the desired PKS-like genes alone or with a construct to downregulate the activity of an existing ORF of the existing PKS-like system, such as by antisense or co-suppression. Similarly, a; combination of ORFs derived from separate organisms which produce the same or different PUFAs using PKS-like systems may be used. For instance, the ORF 8 of Vibrio directs the expression of DHA in a host cell, even when ORFs 3, 6, 7 and 9 are from Shewanella, which produce EPA when coupled to ORF 8 of Shewanella. Therefore, for: production of eicosapentanoic acid (EPA), the expression cassettes used generally include one or more cassettes which include ORFs 3, 6, 7, 8 and 9 from a PUFA-producing organism such as the marine bacterium *Shewanella putrefaciens* (for EPA production) or *Vibrio marinus* (for DHA production). ORF 8 can be used for induction of DHA production, and ORF 8 of Vibrio can be used in conjunction with ORFs 3, 6, 7 and 9 of Shewanella to produce DHA. The organization and numbering scheme of the ORFs identified in the Shewanella gene cluster are shown in FIG. 1A. Maps of several subclones referred to in this study are shown in FIG. 1B. For expression of a PKS-like gene polypeptide, transcriptional and translational initiation and termination regions functional in the host cell are operably linked to the DNA encoding the PKS-like gene polypeptide.

Constructs comprising the PKS-like ORFs of interest can be introduced into a host cell by any of a variety of standard techniques, depending in part upon the type of host cell. These techniques include transfection, infection, bolistic impact, electroporation, microinjection, scraping, or any other method which introduces the gene of interest into the host cell (see U.S. Pat. No. 4,743,548, U.S. Pat. No. 4,795,855, U.S. Pat. No. 5,068,193, U.S. Pat. No. 5,188,958, U.S. Pat. No. 5,463,174, U.S. Pat. No. 5,565,346 and U.S. Pat. No. 5,565,347). Methods of transformation which are used include lithium acetate transformation (*Methods in Enzymology*, (1991) 194:186–187). For convenience, a host cell which has been manipulated by any method to take up a DNA sequence or construct will be referred to as "transformed" or "recombinant" herein. The subject host will have at least have one copy of the expression construct and may have two or more, depending upon whether the gene is integrated into the genome, amplified, or is present on an extrachromosomal element having multiple copy numbers.

For production of PUFAs, depending upon the host cell, the several polypeptides produced by pEPA, ORFs 3, 6, 7, 8 and 9, are introduced as individual expression constructs or can be combined into two or more cassettes which are introduced individually or co-transformed into a host cell. A standard transformation protocol is used. For plants, where less than all PKS-like genes required for PUFA synthesis have been inserted into a single plant, plants containing a complementing gene or genes can be crossed to obtain plants containing a full complement of PKS-like genes to synthesize a desired PUFA.

The PKS-like-mediated production of PUFAs can be performed in either prokaryotic or eukaryotic host cells. The cells can be cultured or formed as part or all of a host organism including an animal. Viruses and bacteriophage also can be used with appropriate cells in the production of PUFAs, particularly for gene transfer, cellular targeting and selection. Any type of plant cell can be used for host cells, including dicotyledonous plants, monocotyledonous plants, and cereals. Of particular interest are crop plants such as Brassica, Arabidopsis, soybean, corn, and the like. Prokaryotic cells of interest include Eschericia, Baccillus, Lactobaccillus, cyanobacteria and the like. Eukaryotic cells include plant cells, mammalian cells such as those of lactating animals, avian cells such as of chickens, and other cells amenable to genetic manipulation including insect, fungal, and algae cells. Examples of host animals include mice, rats, rabbits, chickens, quail, turkeys, cattle, sheep, pigs, goats, yaks, etc., which are amenable to genetic manipulation and cloning for rapid expansion of a transgene expressing population. For animals, PKS-like transgenes can be adapted for expression in target organelles, tissues and body fluids through modification of the gene regulatory regions. Of particular interest is the production of PUFAs in the breast milk of the host animal.

Examples of host microorganisms include *Saccharomyces cerevisiae, Saccharomyces carlsbergensis*, or other yeast such as Candida, Kluyveromyces or other fungi, for example, filamentous fungi such as Aspergillus, Neurospora, Penicillium, etc. Desirable characteristics of a host microorganism are, for example, that it is genetically well characterized, can be used for high level expression of the product using ultra-high density fermentation, and is on the GRAS (generally recognized as safe) list since the proposed end product is intended for ingestion by humans. Of particular interest is use of a yeast, more particularly baker's yeast (*S. cerevisiae*), as a cell host in the subject invention. Strains of particular interest are SC334 (Mat αpep4-3 prbl-1122 ura3-52 leu2-3, 112 regl-501 gal1; (Hovland et al (1989) Gene 83:57–64); BJ1995 (Yeast Genetic Stock Centre, 1021 Donner Laboratory, Berkeley, Calif. 94720), INVSC1 (Mat αhiw3Δ1 leu2 trp1-289 ura3-52 (Invitrogen, 1600 Faraday Ave., Carlsbad, Calif. 92008) and INVSC2 (Mat αhis3Δ200 ura3-167; (Invitrogen). Bacterial cells also may be used as hosts. This includes *E. coli*, which can be useful in fermentation processes. Alternatively, a host such as a Lactobacillus species can be used as a host for introducing the products of the PKS-like pathway into a product such as yogurt.

The transformed host cell can be identified by selection for a marker contained on the introduced construct. Alternatively, a separate marker construct can be introduced with the desired construct, as many transformation techniques introduce multiple DNA molecules into host cells. Typically, transformed hosts are selected for their ability to grow on selective media. Selective media can incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host cell. Desirably, resistance to kanamycin and the amino glycoside G418 are of particular interest (see U.S. Pat. No. 5,034,322). For yeast transformants, any marker that functions in yeast can be used, such as the ability to grow on media lacking uracil, lencine, lysine or tryptophan.

Selection of a transformed host also can occur when the expressed marker protein can be detected, either directly or indirectly. The marker protein can be expressed alone or as a fusion to another protein. The marker protein can be one which is detected by its enzymatic activity; for example β-galactosidase can convert the substrate X-gal to a colored product, and luciferase can convert luciferin to a light-emitting product. The marker protein can be one which is detected by its light-producing or modifying characteristics; for example, the green fluorescent protein of *Aequorea Victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies.

The PUFAs produced using the subject methods and compositions are found in the host plant tissue and/or plant part as free fatty acids and/or in conjugated forms such as acylglycerols, phospholipids, sulfolipids or glycolipids, and can be extracted from the host cell through a variety of means well-known in the art. Such means include extraction with organic solvents, sonication, supercritical fluid extraction using for example carbon dioxide, and physical means such as presses, or combinations thereof. Of particular interest is extraction with methanol and chloroform. Where appropriate, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products are enzymatically or chemically cleaved to release the free fatty acid or a less complex conjugate of interest, and are then subjected to further manipulations to produce a desired end product. Desirably, conjugated forms of fatty acids are cleaved with potassium hydroxide.

If further purification is necessary, standard methods can be employed. Such methods include extraction, treatment with urea, fractional crystallization, HPLC, fractional distillation, silica gel chromatography, high speed centrifugation or distillation, or combinations of these techniques. Protection of reactive groups, such as the acid or alkenyl groups, can be done at any step through known techniques, for example alkylation or iodination. Methods used include methylation of the fatty acids to produce methyl esters. Similarly, protecting groups can be removed at any step. Desirably, purification of fractions containing DHA and EPA is accomplished by treatment with urea and/or fractional distillation.

The uses of the subject invention are several. Probes based on the DNAs of the present invention find use in methods for isolating related molecules or in methods to detect organisms expressing PKS-like genes. When used as probes, the DNAs or oligonucleotides need to be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practicable to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of a probe to a target via isothermal titration calorimetry, or by coating the probe or target on a surface and detecting the change in scattering of light from the surface produced by binding of a target or a probe, respectively, is done with the BIAcore system.

PUFAs produced by recombinant means find applications in a wide variety of areas. Supplementation of humans or animals with PUFAs in various forms can result in increased levels not only of the added PUFAs, but of their metabolic progeny as well.

Complex regulatory mechanisms can make it desirable to combine various PUFAs, or to add different conjugates of PUFAS, in order to prevent, control or overcome such mechanisms to achieve the desired levels of specific PUFAs in an individual. In the present case, expression of PKS-like gene genes, or antisense PKS-like gene transcripts, can alter the levels of specific PUFAs, or derivatives thereof, found in plant parts and/or plant tissues. The PKS-like gene polypeptide coding region is expressed either by itself or with other genes, in order to produce tissues and/or plant parts containing higher proportions of desired PUFAs or containing a PUFA composition which more closely resembles that of human breast milk (Prieto et al., PCT publication WO 95/24494) than does the unmodified tissues; and/or plant parts.

PUFAs, or derivatives thereof, made by the disclosed method can be used as dietary supplements for patients undergoing intravenous feeding or for preventing or treating malnutrition. For dietary supplementation, the purified PUFAs, or derivatives thereof, can be incorporated into cooking oils, fats or margarines formulated so that in normal use the recipient receives a desired amount of PUFA. The PUFAs also can be incorporated into infant formulas, nutritional supplements or other food products, and find use as anti-inflammatory or cholesterol lowering agents.

Particular fatty acids: such as EPA can be used to alter the composition of infant formulas to better replicate the PUFA composition of human breast milk. The predominant triglyceride in human milk is reported to be 1,3-di-oleoyl-2-palmitoyl, with 2-palmitoyl glycerides reported as better absorbed than 2-oleoyl or 2-lineoyl glycerides (see U.S. Pat. No. 4,876,107). Typically, human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. A preferred ratio of GLA:DGLA:ARA in infant formulas is from about 1:1:4 to about 1:1:1, respectively. Amounts of oils providing these ratios of PUFA can be determined without undue experimentation by one of skill in the art. PUFAs, or host cells containing them, also can be used as animal food supplements to alter an animal's tissue or milk fatty acid composition to one more desirable for human or animal consumption.

For pharmaceutical use (human or veterinary), the compositions generally are administered orally but can be administered by any route by which they may be successfully absorbed, e.g., parenterally (i.e. subcutaneously, intramuscularly or intravenously), rectally or vaginally or topically, for example, as a skin ointment or lotion. Where available, gelatin capsules are the preferred form of oral administration. Dietary supplementation as set forth above also can provide an oral route of administration. The unsaturated acids of the present invention can be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, described in PCT publication WO 96/33155. Preferred esters are the ethyl esters.

The PUFAs of the present invention can be administered alone or in combination with a pharmaceutically acceptable carrier or excipient. As solid salts, the PUFAs can also be administered in tablet form. For intravenous administration, the PUFAs or derivatives thereof can be incorporated into commercial formulations such as Intralipids. Where desired, the individual components of formulations can be individually provided in kit form, for single or multiple use. A typical dosage of a particular fatty acid is from 0.1 mg to 20 g, or even 100 g daily, and is preferably from 10 mg to 1, 2, 5 or 10 g daily as required, or molar equivalent amounts of derivative forms thereof. Parenteral nutrition compositions comprising from about 2 to about 30 weight percent fatty acids calculated as triglycerides are encompassed by the present invention. Other vitamins, and particularly fat-soluble vitamins such as vitamin A, D, E and L-carnitine optionally can be included. Where desired, a preservative such as a tocopherol can be added, typically at about 0.1% by weight.

The following examples are presented by way of illustration, not of limitation.

EXAMPLES

Example 1

The Identity of ORFs Derived from *Vibrio marinus*

Using polymerase chain reaction (PCR) with primers based on ORF 6 of Shewanella (Sp ORF 6) sequences (FW 5' primers CUACUACUACUACCAAGCT AAAGCACTTAACCGTG, SEQ ID NO:41, and CUAC-UACUACUAACAGCGAAATG CTTATCAAG, SEQ ID NO:42, for Vibrio and SS9 respectively and 3' BW primers: CAUCAUCAUCAUGCGACCAAAACCAAATGAGCTA ATAC, SEQ ID NO:43, for both Vibrio and SS9) and genomic DNAs templates from Vibrio and a borophyllic photobacter producing EPA (provided by Dr. Bartlett, UC San Diego), resulted in PCR products of ca. 400 bases for *Vibrio marinus* (Vibrio) and ca. 900 bases for SS9 presenting more than 75% homology with corresponding fragments of Sp ORF 6 (see FIG. 25) as determined by direct counting of homologous amino acids.

A Vibrio cosmid library was then prepared and using the Vibrio ORF 6 PCR product as a probe (see FIG. 26); clones containing at least ORF 6 were selected by colony hybridization.

Figure 7A:
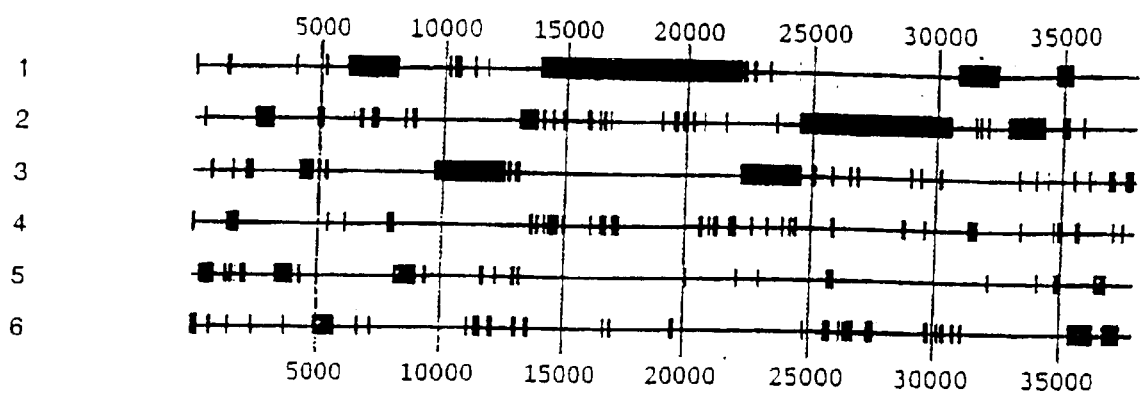
FIG. 7 shows a comparison of the PKS-like gene clusters of *Shewanella putrefaciens* and *Vibrio marinus*.
FIG. 7B is the *Vibrio marinus* operon sequence.
Figure 7B:
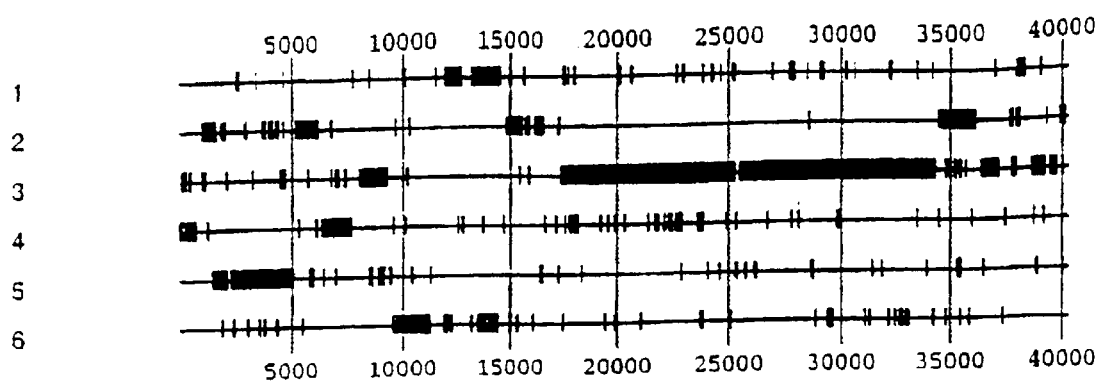

Through additional sequences of the selected cosmids such as cosmid #9 and cosmid #21, a Vibrio cluster (FIG. 5) with ORFs homologous to, and organized in the same sequential order (ORFs 6–9) as ORFs 6–9 of Shewanella, was obtained (FIG. 7). The Vibrio ORFs from this sequence are found at 17394 to 36115 and comprehend ORFs 6–9.

TABLE

| Vibrio operon figures | |
|---|---|
| 17394 to 25349 | length = 7956 nt |
| 25509 to 28157 | length = 2649 nt |
| 28209 to 34262 | length = 6054 nt |
| 34454 to 36115 | length = 1662 nt |

The ORF designations for the Shewanella genes are based on those disclosed in FIG. 4, and differ from those published for the Shewanella cluster (Yazawa et al, U.S. Pat. No.

5,683,898). For instance, ORF 3 of FIG. 4 is read in the opposite direction from the other ORFs and is not disclosed in Yazawa et al U.S. Pat. No. 5,683,898 (See FIG. 24) for comparison with Yazawa et al U.S. Pat. No. 5,683,898.

Sequences homologous to ORF 3, were not found in the proximity of ORF 6 (17000 bases upstream of ORF 6) or of ORF 9 (ca. 4000 bases downstream of ORF 9). Motifs characteristic of phosphopantethenyl transferases (Lambalot et al (1996) Current Biology 3:923–936) were absent from the Vibrio sequences screened for these motifs. In addition, there was no match to Sp ORF 3 derived probes in genomic digests of Vibrio and of SC2A Shewanella (another bacterium provided by the University of San Diego and also capable of producing EPA). Although ORF 3 may exist in Vibrio, its DNA may not be homologous to that of Sp ORF 3 and/or could be located in portions of the genome that were not sequenced.

Figure 8:
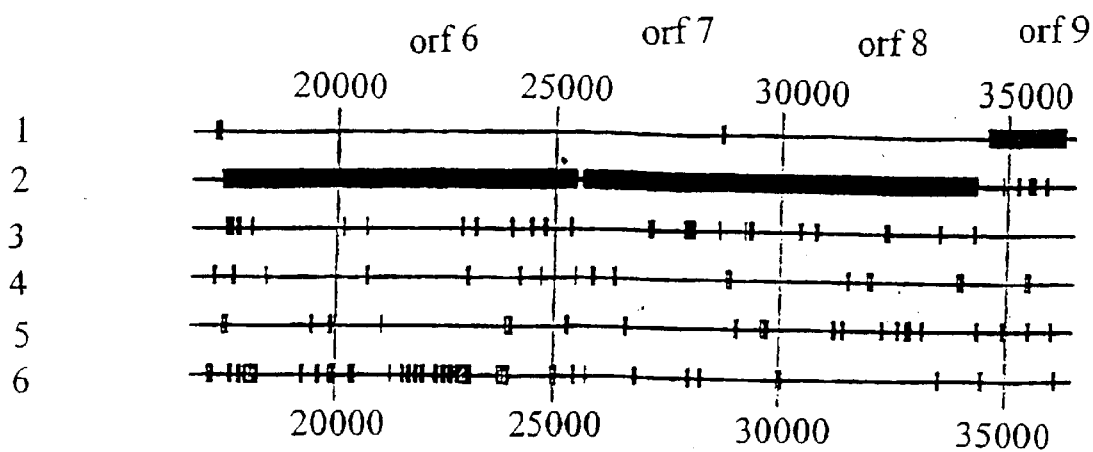
FIG. 8 is an expanded view of the PKS-like gene cluster portion of *Vibrio marinus* shown in FIG. 7B showing that ORFs 6, 7 and 8 are in reading frame 2, while ORF 9 is in reading frame 3.
Figure 9:
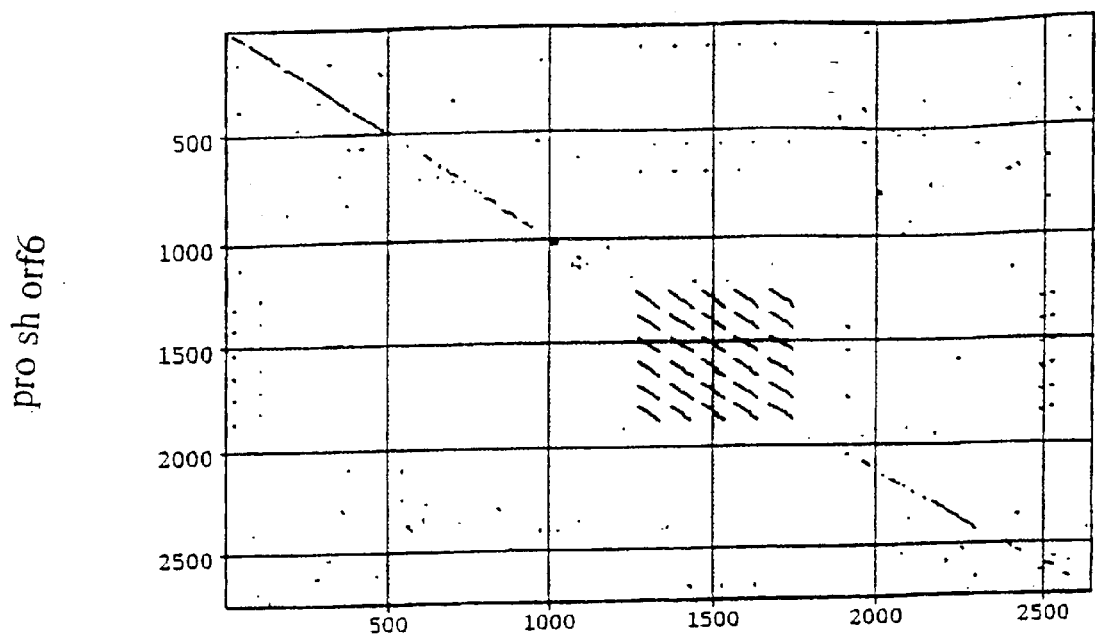
FIG. 9 demonstrates sequence homology of ORF 6 of *Shewanella putrefaciens* and *Vibrio marinus*. The Shewanella ORF 6 is depicted on the vertical axis, and the Vibrio ORF 6 is depicted on the horizontal axis. Lines indicate regions of the proteins that have a 60% identity. The repeated lines in the middle correspond to the multiple ACP domains found in ORF 6.
Figure 10:
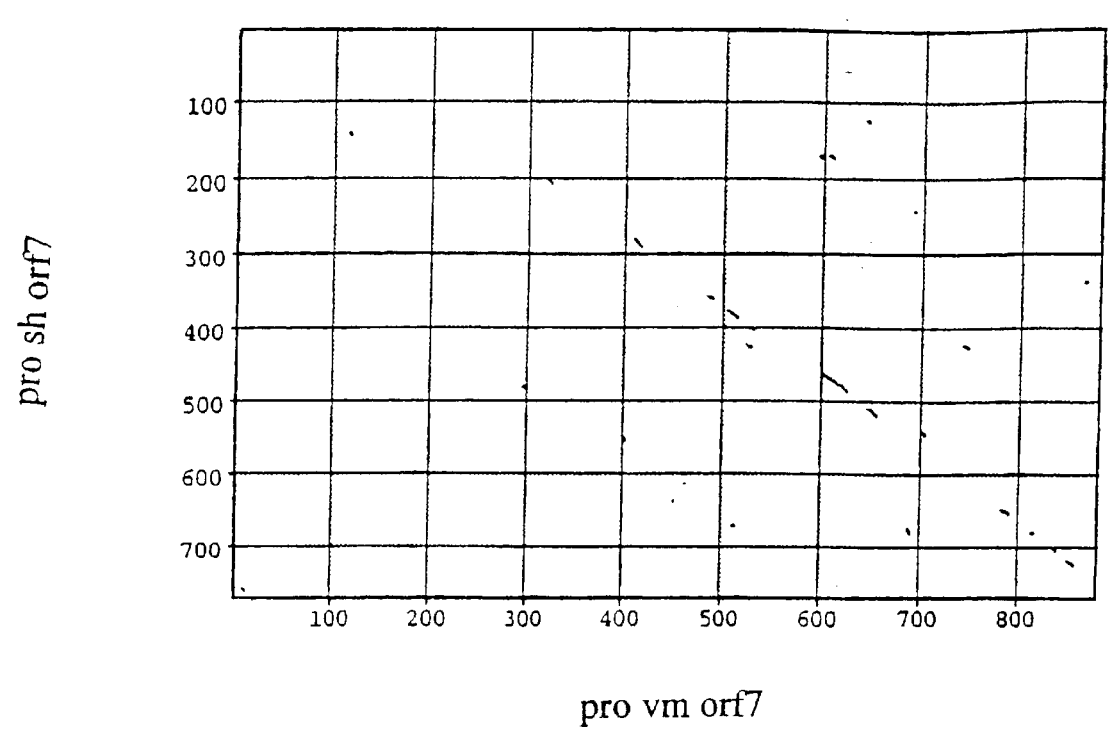
Figure 11:
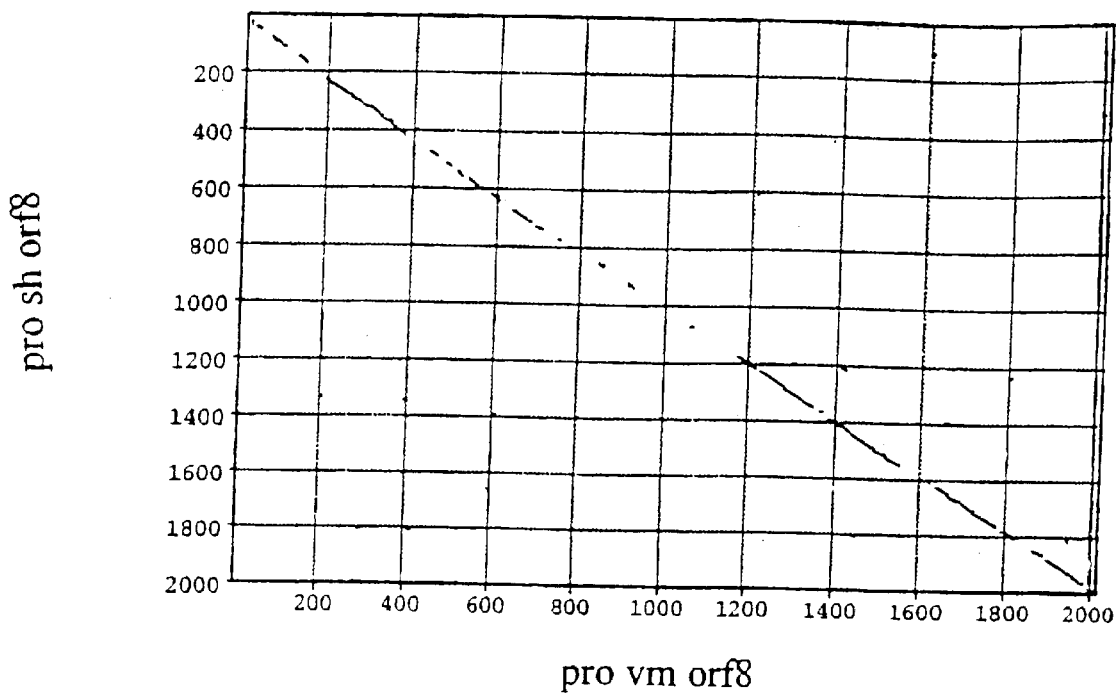
FIG. 11 demonstrates sequence homology of ORF 8 of *Shewanella putrefaciens* and *Vibrio marinus*. The Shewanella ORF 8 is depicted on the vertical axis, and the Vibro. ORF 8 is depicted on the horizontal axis. Lines indicate regions of the proteins that have a 60% identity.
Figure 12:
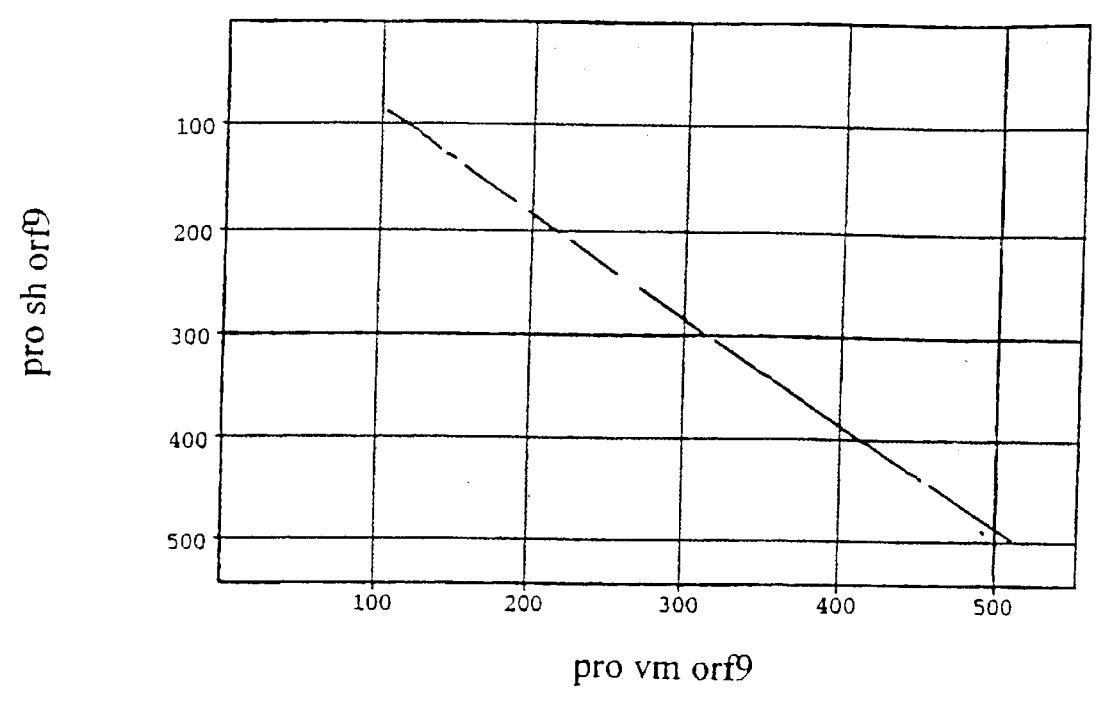

FIG. 6 provides the sequence of an approximately 19 kb Vibrio clone comprising ORFs 6–9. FIGS. 7 and 8 compare the gene cluster organizations of the PKS-like systems of *Vibrio marinus* and *Shewanella putrefacians*. FIGS. 9 through 12 show the levels of sequence. homology between the corresponding ORFs 6, 7, 8 and 9, respectively.

Example 2

ORF 8 Directs DHA Production

As described in example 1, DNA homologous to Sp ORF 6 was found in an unrelated species, SS9 Photobacter, which also is capable of producing EPA. Additionally, ORFs homologous to Sp ORF 6–9 were found in the DHA producing Vbrio marinus (Vibrio). From these ORFs a series of experiments was designed in which deletions in each of Sp ORFs 6–9 that suppressed EPA synthesis in *E. coli* (Yazawa (1996) supra) were complemented by the corresponding homologous genes from Vibrio.

Figure 13:
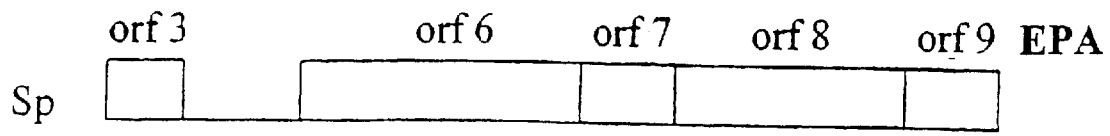
FIG. 13 is a depiction of various complementation experiments, and resulting PUFA production. On the right, is shown the longest PUFA made in the *E. coli* strain containing the Vibrio and Shewanella genes depicted on the left. The hollow boxes indicate ORFs from Shewanella. The solid boxes indicate ORFs from Vibrio.
Figure 13:
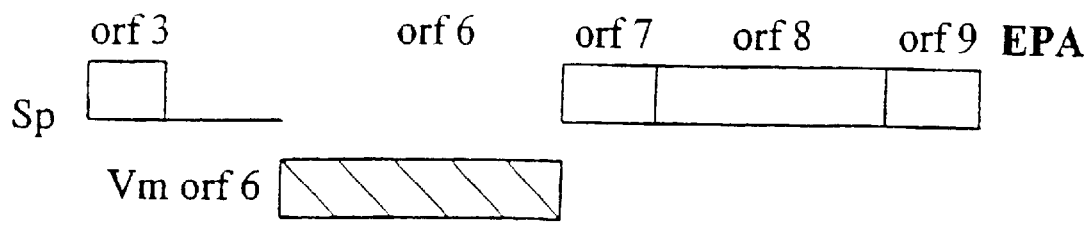
Figure 13:
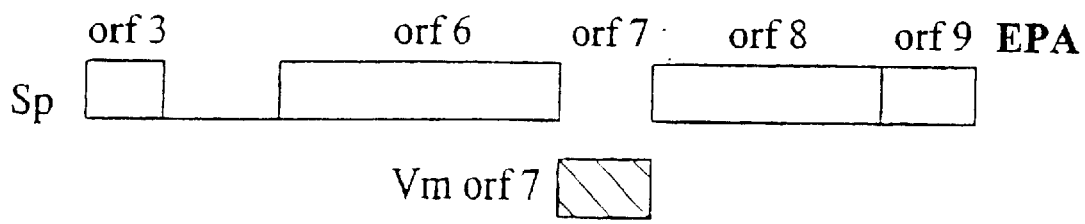
Figure 13:
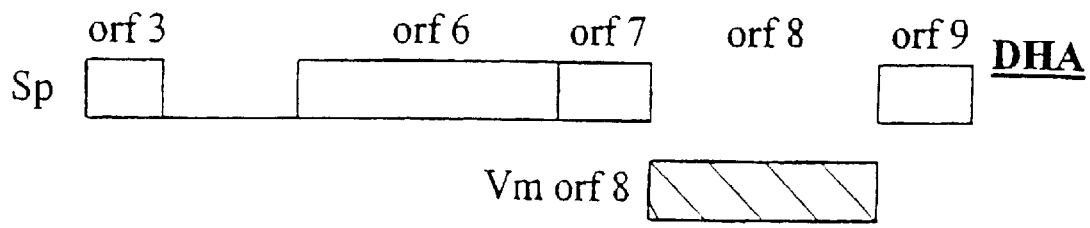

The Sp EPA cluster was used to determine if any of the Vibrio ORFs 6–9 was responsible for the production of DHA. Deletion mutants provided for each of the Sp ORFs are EPA and DHA null. Each deletion was then complemented by the corresponding Vibrio ORF expressed behind a lac promoter (FIG. 13).

Figure 14:
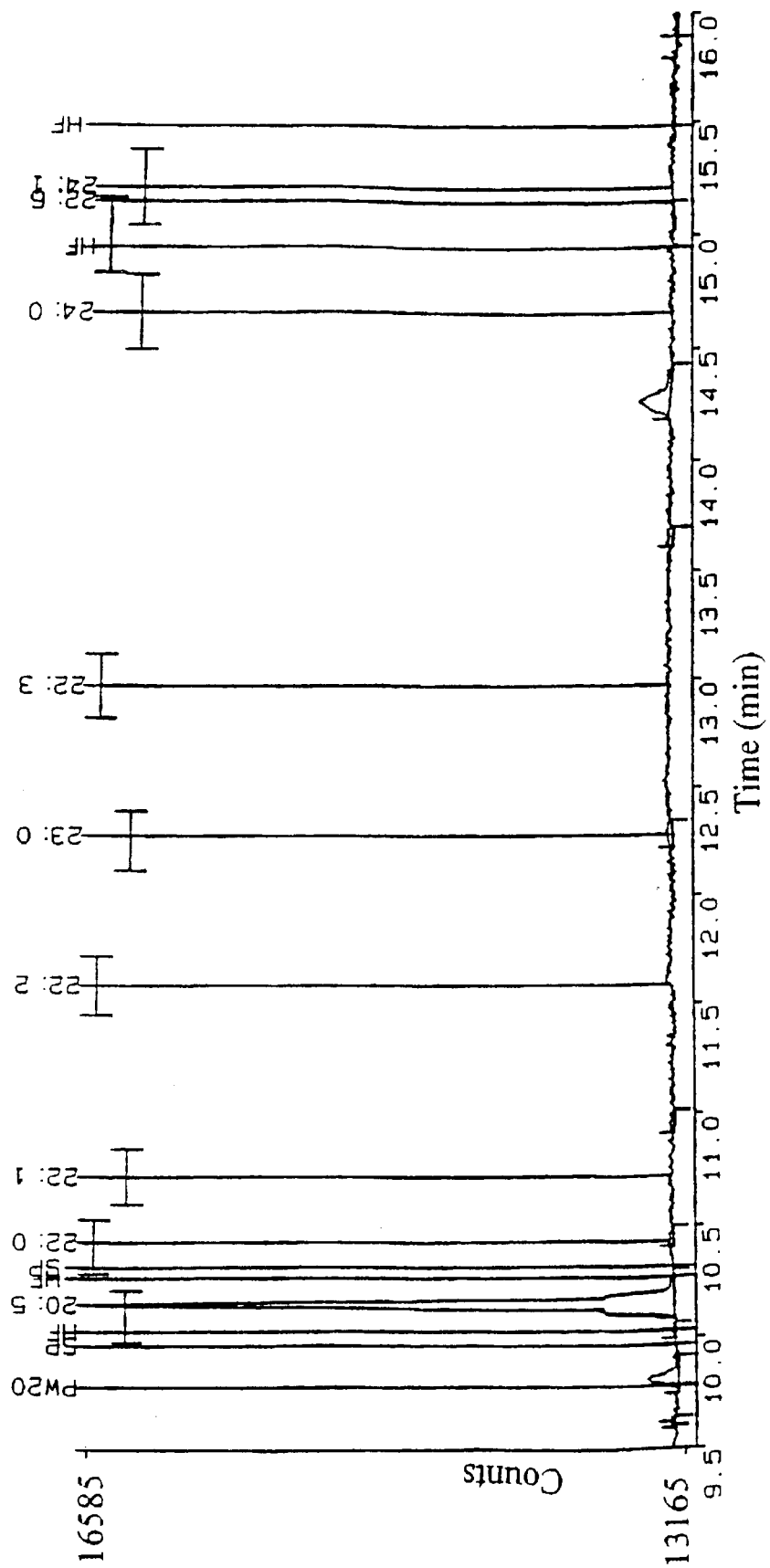
FIG. 14 is a chromatogram showing fatty acid production from complementation of pEPAD8 from Shewanella (deletion ORF 8) with ORF 8 from Shewanella, in *E. coli* Fad E-. The chromatogram presents an EPA (20:5) peak.
Figure 15:
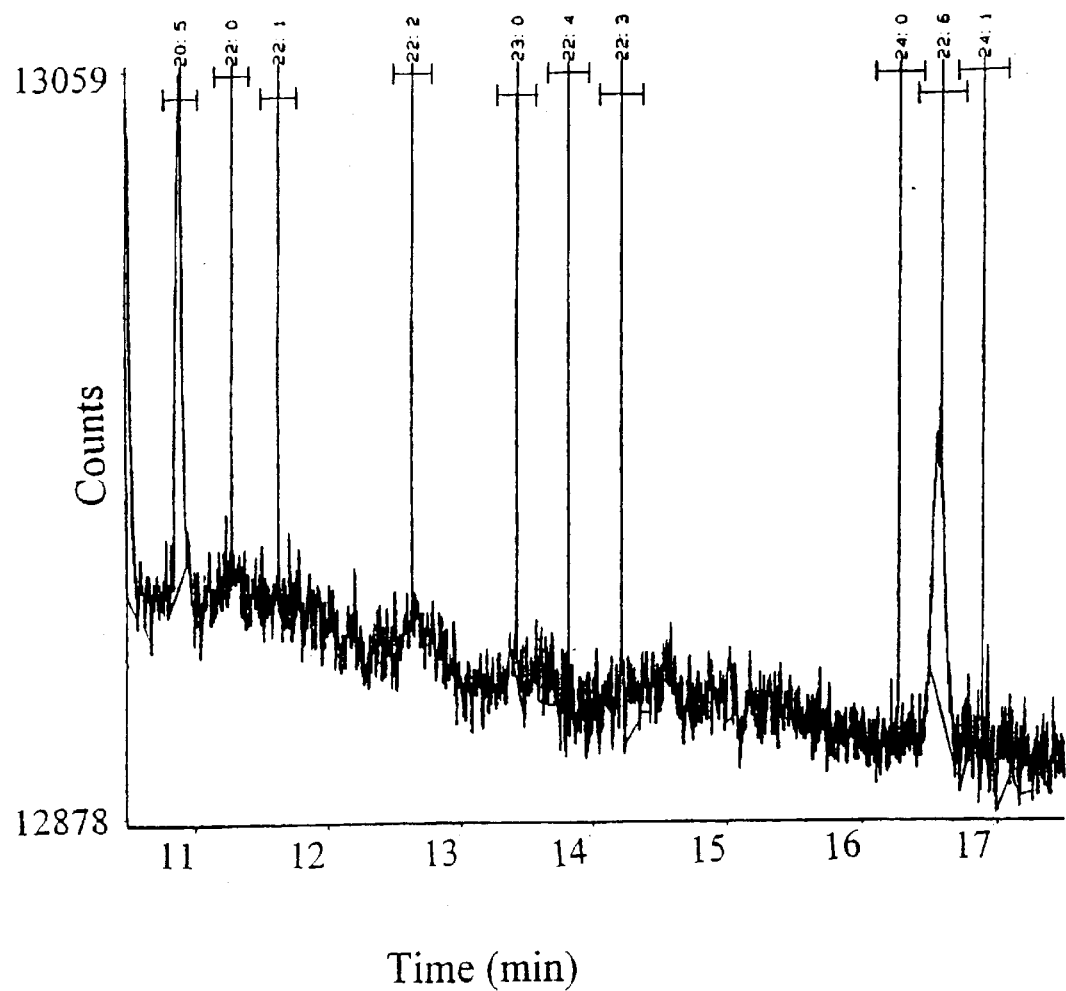
FIG. 15 is a chromatogram showing fatty acid production from complementation of pEPAD8 from Shewanella (deletion ORF 8) with ORF 8 from *Vibrio marinus*, in *E. coil* Fad E-. The chromatograph presents EPA (20:5) and DHA (22:6) peaks.

The complementation of a Sp ORF 6 deletion by a Vibrio ORF 6 reestablished the production of EPA. Similar results were obtained by complementing the Sp ORF 7 and ORF 9 deletions. By contrast, the complementation of a Sp ORF 8 deletion resulted in the production of C22:6. Vibrio ORF 8 therefore appears to be a key element in the synthesis of DHA. FIGS. 14 and 15 show chromatograms of fatty acid profiles from the respective complementations of Sp del ORF 6 with Vibrio ORF 6 (EPA and no DHA) and Sp del ORF 8 with Vibrio ORF 8 (DHA). FIG. 16 shows the fatty acid percentages for the ORF 8 complementation, again demonstrating that ORF 8 is responsible for DHA production.

These data show that polyketide-like synthesis genes with related or similar ORFs can be combined and expressed in a heterologous system and used to produce a distinct PUFA species in the host system, and that ORF 8 has a role in determining the ultimate chain length. The Vibrio ORFs 6, 7, 8, and 9 reestablish EPA synthesis. In the case of Vibrio ORF 8, DHA is also present (ca. 0.7%) along with EPA (ca. 0.6%) indicating that this gene plays a significant role in directing synthesis of DHA vs EPA for these systems.

Example 3

Requirements for Production of DHA

To determine how Vibrio ORFs of the cluster ORF 6–9 are used in combination with Vibrio ORF 8, some combinations of Vibrio ORF 8 with some or all of the other Vibrio ORFS 6–9 cluster were created to explain the synthesis of DHA.

Vibrio ORFs 6–9 were complemented with Sp ORF 3. The results of this complementation are presented in FIGS. 16b and 16c. The significant amounts of DHA measured (greater than about 9%) and the absence of EPA suggest that no ORFs other than those of Vibrio ORFs 6–9 are required for DHA synthesis when combined with Sp ORF 3. This suggests that Sp ORF 3 plays a general function in the synthesis of bacterial PUFAs.

With respect to the DHA vs EPA production, it may be necessary to combine Vibrio ORF 8 with other Vibrio ORFs of the 6–9 cluster in order to specifically produce DHA. The roles of Vibrio ORF 9 and each of the combinations of Vibrio ORFs (6,8), (7,8), (8,9), etc in the synthesis of DHA are being studied.

Example 4

Plant Expression Constructs

A cloning vector with very few restriction sites was designed to facilitate the cloning of large fragments and their subsequent manipulation. An adapter was assembled by annealing oligonucleotides with the sequences AAGCCCGGGCTT, SEQ ID NO:44, and GTACAAGCCCGGGCTTAGCT, SEQ ID NO:45. This adapter was ligated to the vector pBluescript II SK+ (Stratagene) after digestion of the vector with the restriction endonucleases Asp718 and SstI. The resulting vector, pCGN7769 had a single SrfI (and embedded SmaI) cloning site for the cloning of blunt ended DNA fragments.

Figure 17:
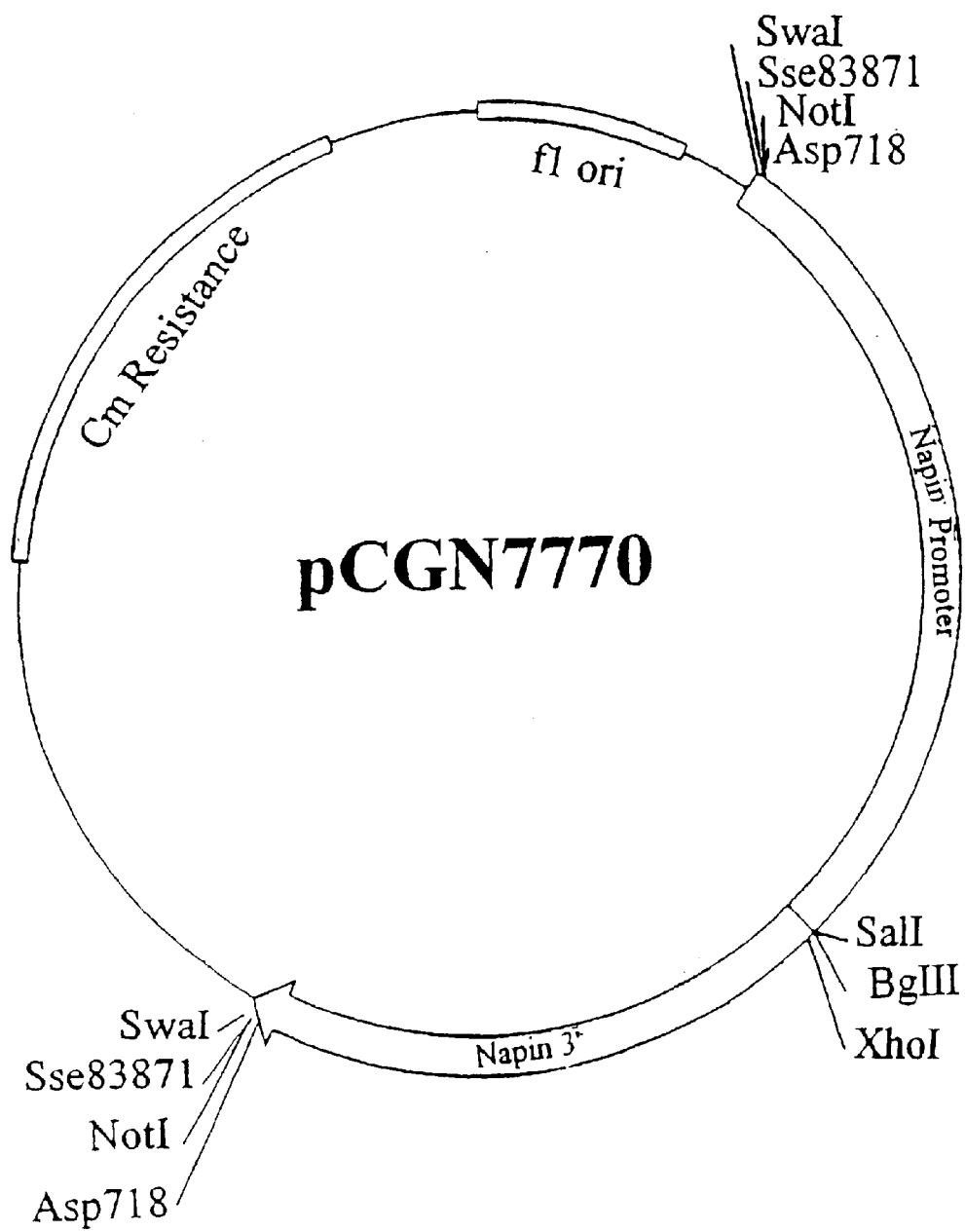
FIG. 17 is a plasmid map showing the elements of pCGN7770.

A plasmid containing the napin cassette from pCGN3223, (U.S. Pat. No. 5,639,790) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATGGCGCGCCCTGCAG-GCGGCCGCCTGCAGGGCGC GCCATTTAAAT, SEQ ID NO:46, was ligated into the vector pBC SK+ (Stratagene) after digestion of the vector with the restriction endonuclease BssHII to construct vector pCGN7765. Plamids pCGN3223 and pCGN7765 were digested with NotI and ligated together. The resultant vector, pCGN7770 (FIG. 17), contains the pCGN7765 backbone and the napin seed specific expression cassette from pCGN3223.

Shewanella Constructs

Genes encoding the Shewanella proteins were mutagenized to introduce suitable cloning sites 5' and 3' ORFs using PCR. The template for the PCR reactions was DNA of the cosmid pEPA (Yazawa et al, supra). PCR reactions were performed using Pfu DNA polymerase according to the manufacturers' protocols. The PCR products were cloned into SrfI digested pCGN7769. The primers CTGCAGCTCGAGACAATGTTGATTTCCTTATACTTC TGTCC, SEQ ID NO:47, and GGATCCAG ATCTCTAGCTAGTCTTAGCTGAAGCTCGA, SEQ ID NO:48, were used to amplify ORF 3, and to generate plasmid pCGN8520. The primers TCTAGACTC GAGACAATGAGCCAGACCTCTAAACCTACA, SEQ ID NO:49, and CCCGGGCTCGAGCTAATTCGCCTCAC TGTCGTTTGCT, SEQ ID NO:50, were used to amplify ORF 6, and generate plasmid pCGN7776. The primers GAATTCCTCGAGACAATGCCGCTGCGCATCGCAC TTATC, SEQ ID NO:51, and GGTACCAGATCTTTA- GACTTCCCCTTG AAGTAAATGG, SEQ ID NO:52, were used to amplify ORF 7, and generate plasmid pCGN7771. The primers GAATTCGTCGACACAATGTCATTACCA GACAATGCTTCT, SEQ ID NO:53, and TCTAGAGTC-GACTTATACAGATTCTTCGATGCTG ATAG, SEQ ID NO:54, were used to amplify ORF 8, and generate plasmid pCGN7775. The primers GAATTCGTCGACACAAT-GAATC CTACAGCAACTAACGAA, SEQ ID NO:55, and TCTAGAGGATCCTTAGGCCATTCTTTGGTTTGGCTTC, SEQ ID NO:56, were used to amplify ORF 9, and generate plasmid pCGN7773.

The integrity of the PCR products was verified by DNA sequencing of the inserts of pCGN7771, PCGN8520, and pCGN7773. ORF 6 and ORF 8 were quite large in size. In order to avoid sequencing the entire clones, the center portions of the ORFs were replaced with restriction fragments of pEPA. The 6.6 kilobase PacI/BamHI fragment of pEPA containing the central portion of ORF 6 was ligated into PacI/BamHI digested pCGN7776 to yield pCGN7776B4. The 4.4 kilobase BamHI/BglII fragment of pEPA containing the central portion of ORF 8 was ligated into BamHI/BglII digested pCGN7775 to yield pCGN7775A. The regions flanking the pEPA fragment and the cloning junctions were verified by DNA sequencing.

Plasmid pCGN7771 was cut with XhoI and BglII and ligated to pCGN7770 after digestion with SalI and BglII. The resultant napin/ORF 7 gene fusion plasmid was designated pCGN7783. Plasmid pCGN8520 was cut with XhoI and BglII and ligated to pCGN7770 after digestion with SalI and BglII. The resultant napin/ORF 3 gene fusion plasmid was designated pCGN8528. Plasmid pCGN7773 was cut with SalI and BamHI and ligated to pCGN7770 after digestion with SalI and BglII. The resultant napin/ORF 9 gene fusion plasmid was designated pCGN7785. Plasmid pCGN7775A was cut with SalI and ligated to pCGN7770 after digestion with SalI. The resultant napin/ORF 8 gene fusion plasmid was designated pCGN7782. Plasmid pCGN7776B4 was cut with XhoI and ligated to pCGN7770 after digestion with SalI. The resultant napin/ORF 6 gene fusion plasmid was designated pCGN7786B4.

Figure 18:
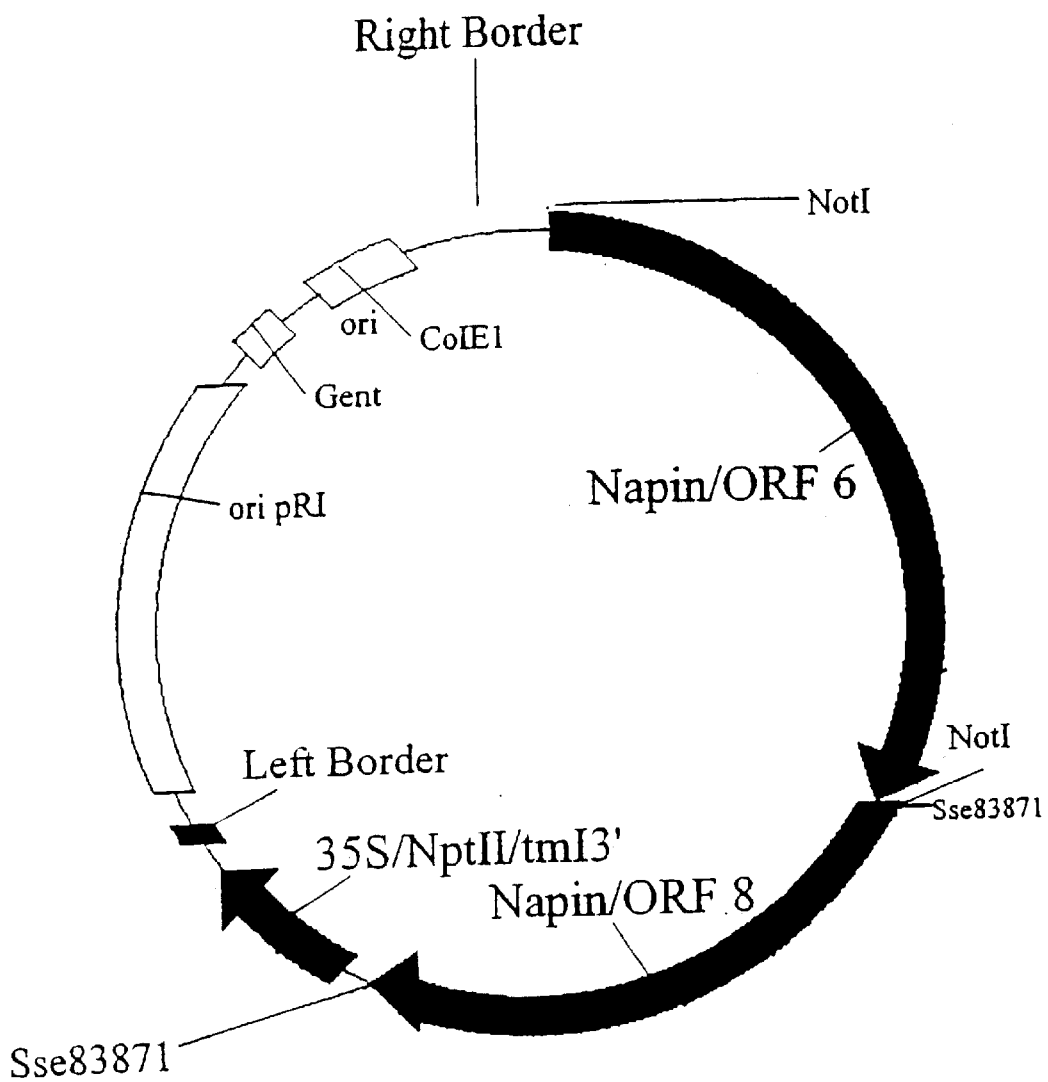
FIG. 18 is a plasmid map showing the elements of pCGN8535.

A binary vector for plant transformation, pCGN5139, was constructed from pCGN1558 (McBride and Summerfelt (1990) *Plant Molecular Biology*, 14:269–276). The polylinker of pCGN 1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139. PCGN5139 was digested with NotI and ligated with NotI digested pCGN7786B4. The resultant binary vector containing the napin/ORF 6 gene fusion was designated pCGN8533. Plasmid pCGN8533 was digested with Sse8387I and ligated with Sse8387I digested pCGN7782. The resultant binary vector containing the napin/ORF 6 gene fusion and the napin/ORF 8 gene fusion was designated pCGN8535 (FIG. 18).

Figure 19:
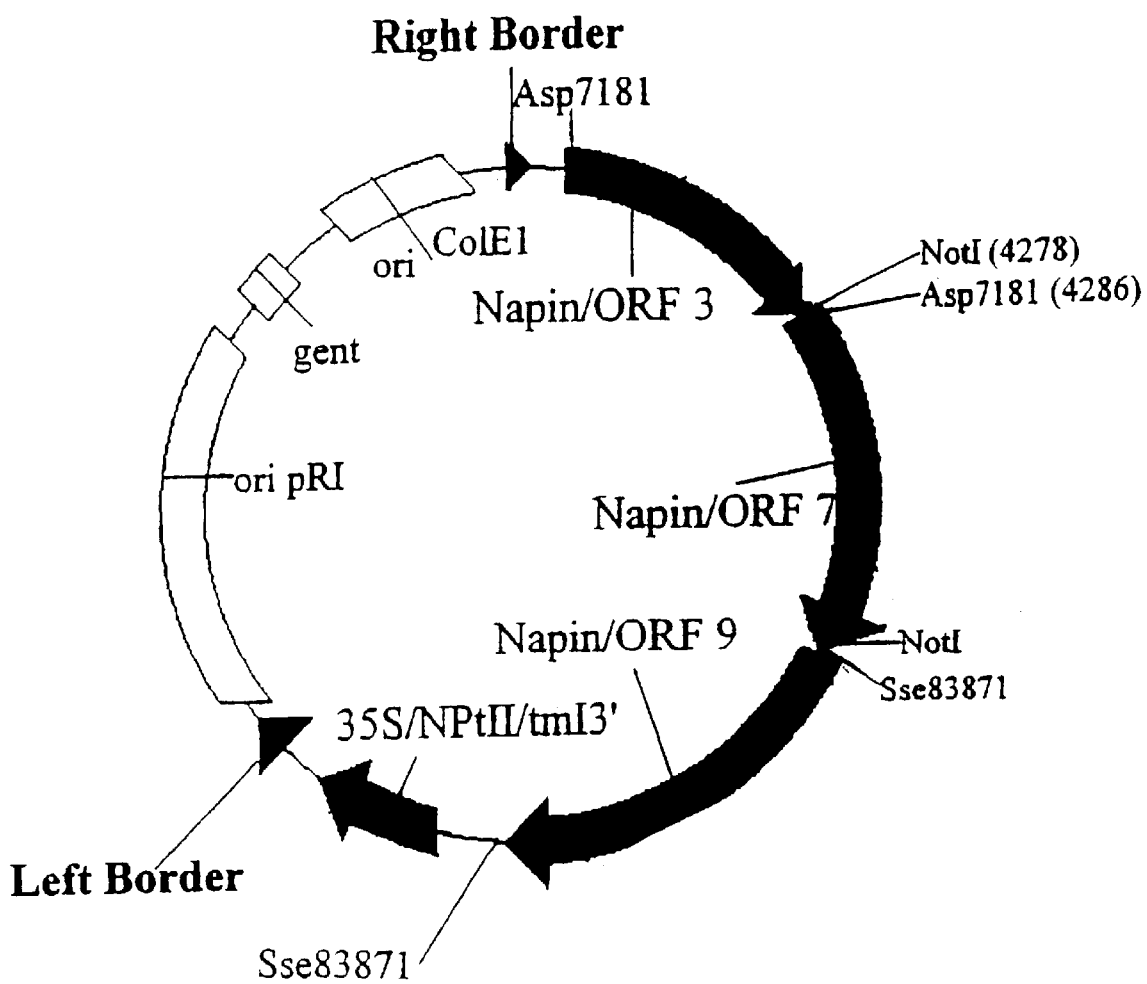
FIG. 19 is a plasmid map showing the elements of pCGN8537.
Figure 20:
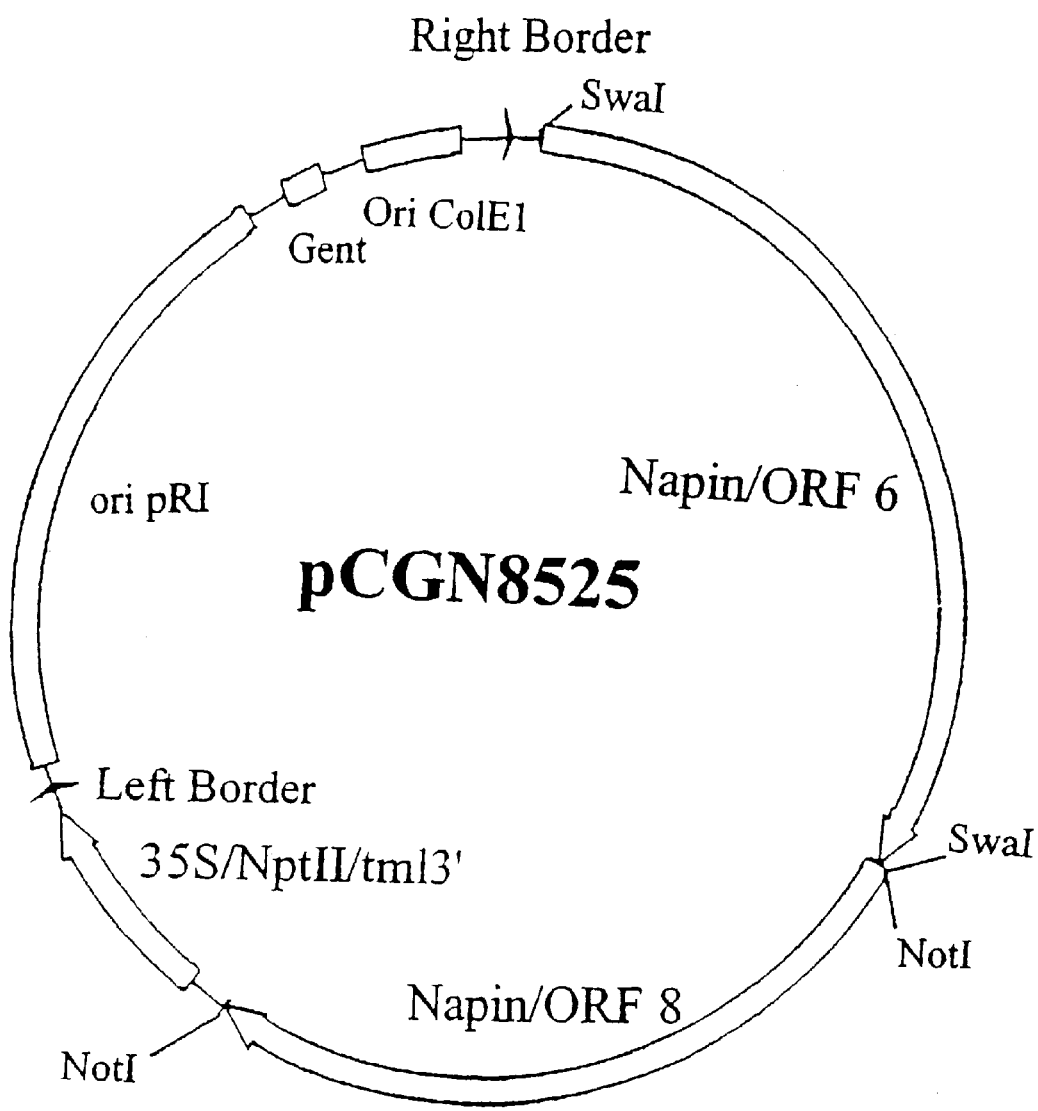
FIG. 20 is a plasmid map showing the elements of pCGN8525.
Figure 21:
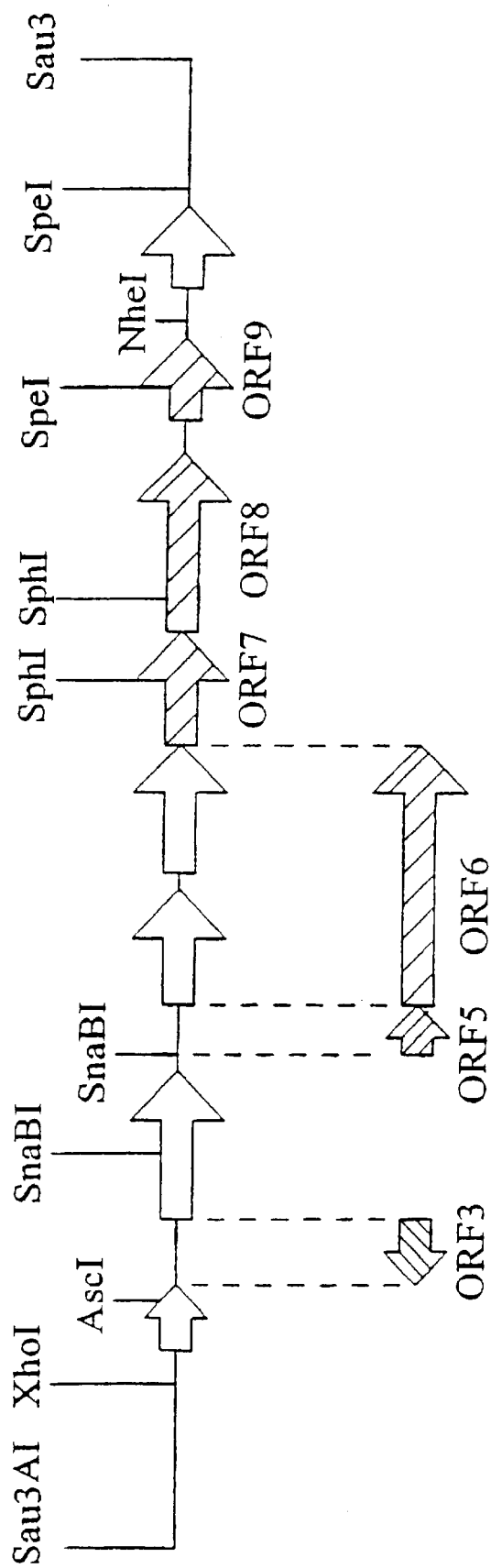
FIG. 21 is a comparison of the Shewanella ORFs as defined by Yazawa (1996) supra, and those disclosed in FIG. 4. When a protein starting at the leucine (TTG) codon at nucleotides 9157–9155 and ending at the stop codon at nucleotides 8185–8183 is expressed under control of a heterologous promoter in an *E. coli* strain containing the entire PKS-like cluster except ORF 3, the recombinant cells do produce EPA. Thus, the published protein sequence is likely to be wrong, and the coding sequence for the protein may start at the TTG codon at nucleotides 9157–9155 or the TTG codon at nucleotides 9172–9170. This information is critical to the expression of a functional PKS-like cluster heterologous system.

The plant binary transformation vector, pCGN5 139, was digested with Asp718 and ligated with Asp718 digested pCGN8528. The resultant binary vector containing the napin/ORF 3 gene fusion was designated pCGN8532. Plasmid pCGN8532 was digested with NotI and ligated with NotI digested pCGN7783. The resultant binary vector containing the napin/ORF 3 gene fusion and the napin/ORF 7 gene fusion was designated pCGN8534. Plasmid pCGN8534 was digested with Sse8387I and ligated with Sse8387I digested pCGN7785. The resultant binary vector containing the napin/ORF 3 gene fusion, the napin/ORF 7 gene fusion and the napin/ORF 9 gene fusion was designated pCGN8537 (FIG. 19).

Vibrio Constructs

The Vibrio ORFs for plant expression were all obtained using Vibrio cosmid #9 as a starting molecule. Vibrio cosmid #9 was one of the cosmids isolated from the Vibrio cosmid library using the Vibrio ORF 6 PCR product described in Example 1.

A gene encoding Vibrio ORF 7 (FIG. 6) was mutagenized to introduce a SalI site upstream of the open reading frame and BamHI site downstream of the open reading frame using the PCR primers: TCTAGAGTCGACACAATGGCGG AATTAGCTGTTATTGGT, SEQ ID NO:57, and GTCGACGGATCCCTATTTGTTCGTGTTTGCTATATG, SEQ ID NO:58. A gene encoding Vibrio ORF 9 (FIG. 6) was mutagenized to introduce a BamHI site upstream of the open reading frame and an XhoHI site downstream of the open reading frame using the PCR primers: GTCGACGGATC-CACAATGAATATAGTAAGTAATCATTCGGCA, SEQ ID NO:59, and GTCGACCTCGAGTTAATCACTCG-TACG ATAACTTGCC, SEQ ID NO:60. The restriction sites were introduced using PCR, and the integrity of the mutagenized plasmids was verified by DNA sequence. The Vibrio ORF 7 gene was cloned as a SalI-BamHI fragment into the napin cassette of Sal-BglI digested pCGN7770 (FIG. 17) to yield pCGN8539. The Vibrio ORF 9 gene was cloned as a SalI-BamHI fragment into the napin cassette of Sal-BalI digested pCGN7770 (FIG. 17) to yield pCGN8543.

Genes encoding the Vibrio ORF 6 and ORF 8 were mutagenized to introduce SalI sites flanking the open reading frames. The SalI sites flanking ORF 6 were introduced using PCR. The primers used were: CCCGGGTCGACA-CAATGGCTAAAAAGAACA CCACATCGA, SEQ ID NO:61, and CCCGGGTCGACTCATGACATATCGT-TCAAA ATGTCACTGA, SEQ ID NO:62. The central 7.3 kb BamHI-XhoI fragment of the PCR product was replaced with the corresponding fragment from Vibrio cosmid #9. The mutagenized ORF 6 were cloned into the SalI site of the napin cassette of pCGN7770 to yield plasmid pCGN8554.

The mutagenesis of ORF 8 used a different strategy. A BamHI fragment containing ORF 8 was subcloned into plasmid pHC79 to yield cosmid #9". A SalI site upstream of the coding region was introduced on and adapter comprised of the oligonucleotides TCGACATGGAAA ATATTGCAGTAGTAGGTATTGCTAATTTGTTC, SEQ ID NO:63, and CCGGGAACAAATTAGCAATA CCTACTACTGCAATATTTTCCATG, SEQ ID NO:64. The adapter was ligated to cosmid #9" after digestion with SalI and XmaI. A SalI site was introduced downstream of the stop codon by using PCR for mutagenesis. A DNA fragment containing the stop codon was generated using cosmid #9" as a template with the primers TCAGATGAACTTTATCGATAC, SEQ ID NO:65 and TCATGAGACGTCGTCGACTTACGCTTCAACAATACT, SEQ ID NO:66. The PCR product was digested with the restriction endonucleases ClaI and AatII and was cloned into the cosmid 9" derivative digested with the same enzymes to yield plasmid 8P3. The SalI fragment from 8P3 was cloned into SalI digested pCGN7770 to yield pCGN8515.

PCGN8532, a binary plant transformation vector that contains a Shewannella ORF 3 under control of the napin promoter was digested with NotI, and a NotI fragment of pCGN8539 containing a napin Vibrio ORF 7 gene fusion was inserted to yield pCGN8552. Plasmid pCGN8556 (FIG.

23), which contains Shewannella ORF 3, and Vibrio ORFs 7 and 9 under control of the napin promoter was constructed by cloning the Sse8357 fragment from pCGN8543 into Sse8387 digested pCGN8552.

Figure 22:
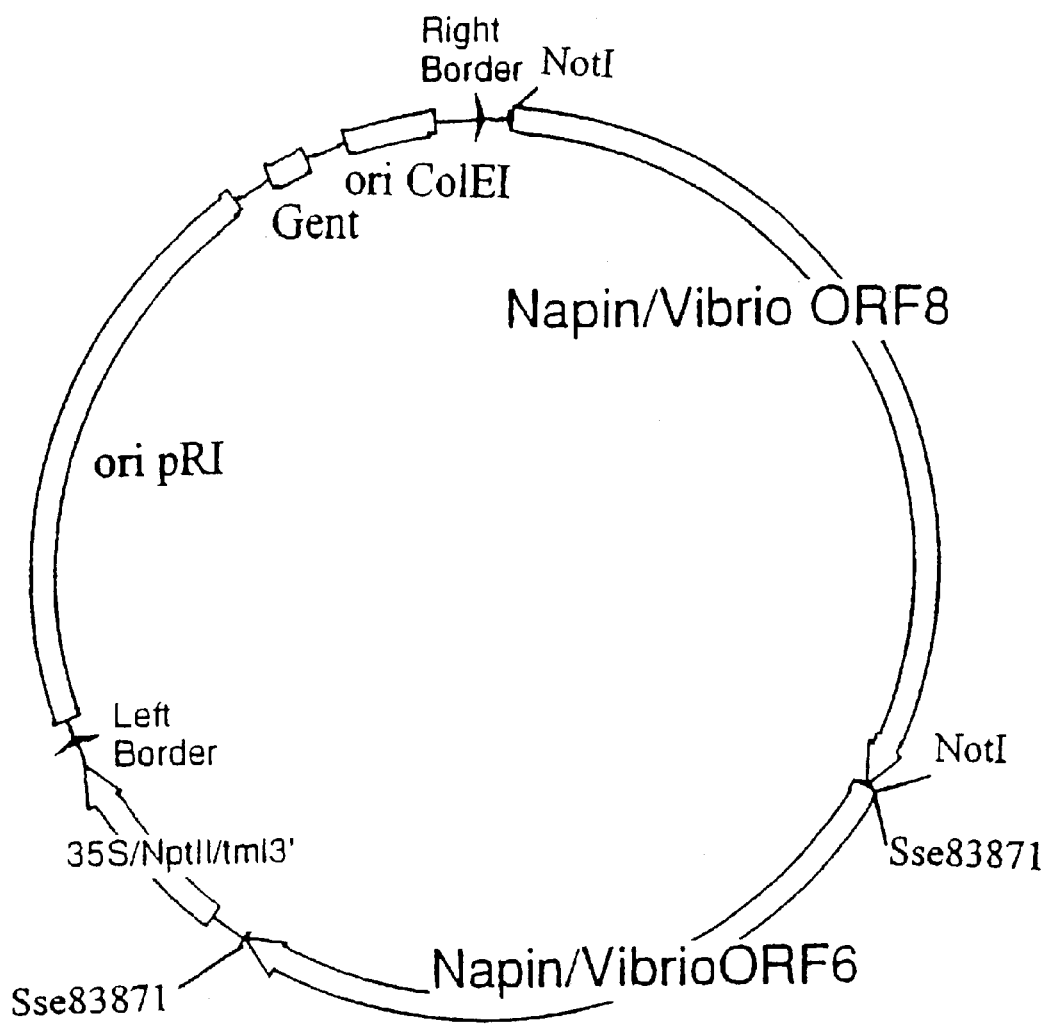
FIG. 22 is a plasmid map showing the elements of pCGN8560.
Figure 23:
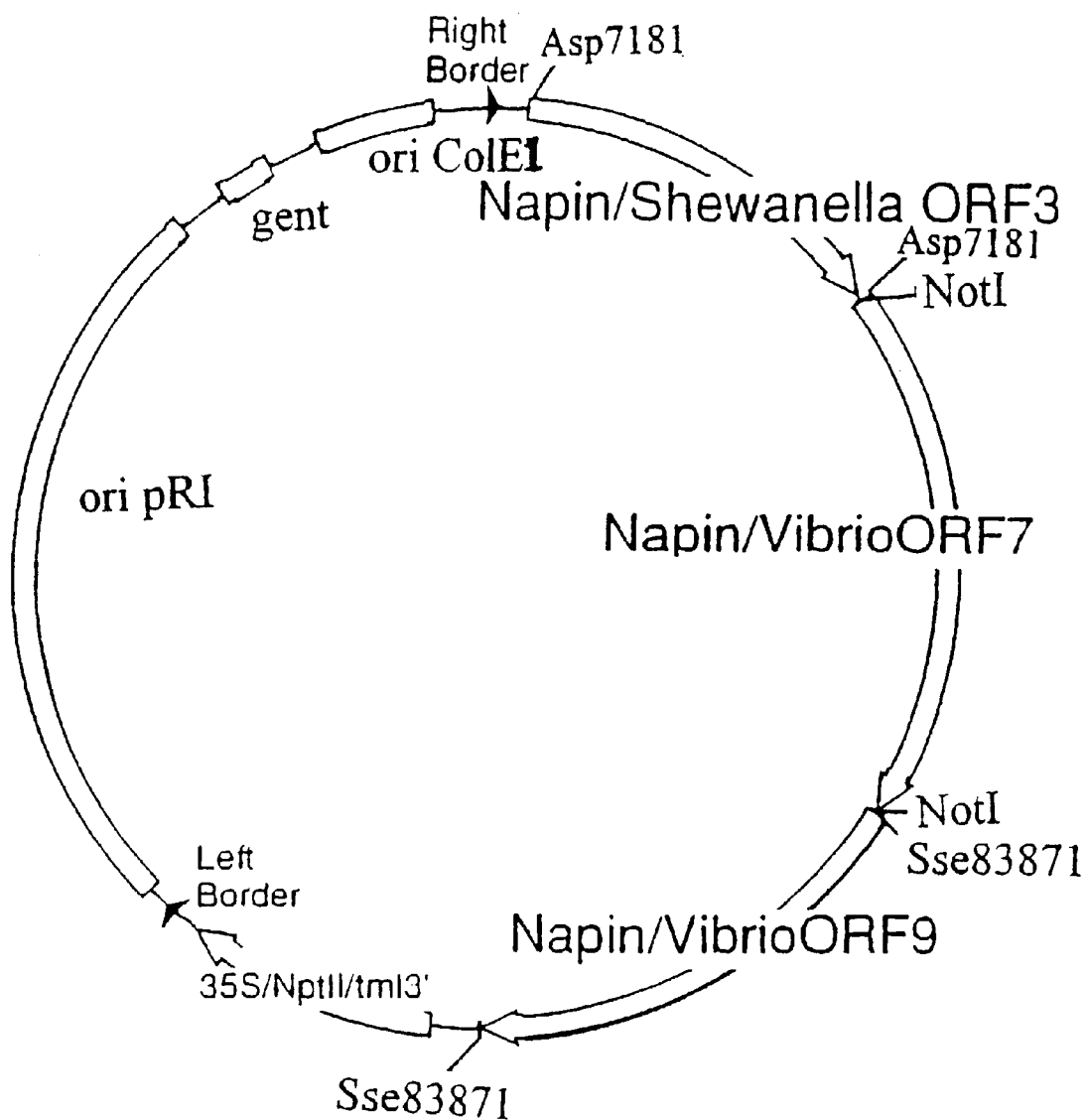
FIG. 23 is plasmid map showing the elements of pCGN8556.

The NotI digested napin/ORF 8 gene from plasmid pCGN8515 was cloned into a NotI digested plant binary transformation vector pCGN5139 to yield pCGN8548. The Sse8387 digested napin/ORF 6 gene from pCGN8554 was subsequently cloned into the Sse8387 site of pCGN8566. The resultant binary vector containing the napin/ORF 6 gene fusion and napin/ORF 8 gene fusion was designated pCGN8560 (FIG. 22).

Example 5

Plant Transformation and PUFA Production
EPA Production

The Shewanella constructs pCGN8535 and pCGN8537 can be transformed into the same or separate plants. If separate plants are used, the transgenic plants can be crossed resulting in heterozygous seed which contains both constructs.

pCGN8535 and pCGN8537 are separately transformed into Brassica napus. Plants are selected on media containing kanamycin and transformation by full length inserts of the constructs is verified by Southern analysis. Immature seeds also can be tested for protein expression of the enzyme encoded by ORFs 3, 6, 7, 8, or 9 using western analysis, in which case, the best expressing pCGNE8535 and pCGN8537 $T_1$ transformed plants are chosen and are grown out for further experimentation and crossing. Alternatively, the $T_1$ transformed plants showing insertion by Southern are crossed to one another producing $T_2$ seed which has both insertions. In this seed, half seeds may be analyzed directly from expression of EPA in the fatty acid fraction. Remaining half-seed of events with the best EPA production are grown out and developed through conventional breeding techniques to provide Brassica lines for production of EPA.

Plasmids pCGN7792 and pCGN7795 also are simultaneously introduced into Brassica napus host cells. A standard transformation protocol is used (see for example U.S. Pat. No. 5,463,174 and U.S. Pat. No. 5,750,871, however Agrobacteria containing both plasmids are mixed together and incubated with Brassica cotyledons during the cocultivation step. Many of the resultant plants are transformed with both plasmids.

DHA Production

A plant is transformed for production of DHA by introducing pCGN8556 and pCGN8560, either into separate plants or simultaneously into the same plants as described for EPA production.

Alternatively, the Shewanella ORFs can be used in a concerted fashion with ORFs 6 and 8 of Vibrio, such as by transforming with a plant the constructs pCGN8560 and pCGN7795, allowing expression of the corresponding ORFs in a plant cell. This combination provides a PKS-like gene arrangement comprising ORFs 3, 7 and 9 of Shewanella, with an ORF 6 derived from Vibrio and also an OFR 8 derived from Vibrio. As described above, ORF 8 is the PKS-like gene which controls the identity of the final PUFA product. Thus, the resulting transformed plants produce DHA in plant oil.

Example 6

Transgenic Plants Containing the Shewanella PUFA Genes

Brassica Plants

Fifty-two plants cotransformed with plasmids pCGN8535 andpCGN8537 were analyzed using PCR to determine if the Shewanella ORFs were present in the transgenic plants. Forty-one plants contained plasmid pCGN8537, and thirty-five plants contained pCGN8535. 11 of the plants contained all five ORFs required for the synthesis of EPA. Several plants contained genes from both of the binary plasmids but appeared to be missing at least one of the ORFs. Analysis is currently being performed on approximately twenty additional plants.

Twenty-three plants transformed with pCGN8535 alone were analyzed using PCR to determine if the Shewanella ORFs were present in the transgenic plants. Thirteen of these plants contained both Shewanella ORF 6 and Shewanella ORF 8. Six of the plants contained only one ORF.

Nineteen plants transformed with pCGN8537 were alone analyzed using PCR to determine if the Shewanella ORFs were present in the transgenic plants. Eighteen of the plants contained Shewanella ORF 3, Shewanella ORF 7, and Shewanella ORF 9. One plant contained Shewanella ORFs 3 and 7.

Arabidopsis

More than 40 transgenic Arabidopsis plants cotransformed with plasmids pCGN8535 and pCGN8537 are growing in our growth chambers. PCR analysis to determine which of the ORFs are present in the plants is currently underway.

Example 7

Evidence of A PKS System of PUFA Synthesis In Schizochytrium

The purpose of this experiment was to identify additional sources of PKS genes. Polyunsaturated long chain fatty acids were identified in Schizochytrium oil. Furthermore, production of polyunsaturated fatty acids was. detected in a culture of Schizochytrium. A freshly diluted culture of Schizochytrium was incubated at 24° C. in the presence of [$^{14}$C]-acetate (5uCi/mL) for 30 min with shaking (150 rpm). The cells were then collected by centrifugation, lyophilized and subjected to a transesterification protocol that involved heating to 90° C. for 90 minutes in the presence of acidic (9% $H_2SO_4$) methanol with toluene (1 volume of toluene per two volumes of acidic methanol) as a second solvent. The resulting methylesters were extracted with an organic solvent (hexane) and separated by TLC (silica gel G, developed three times with hexane:diethyl ether (19:1)). Radioactivity on the TLC plate was detected using a scanner (AMBIS). Two prominent bands were detected on the TLC plate. These bands migrated on the TLC plate in positions expected for short chain (14 to 16 carbon), saturated methyl esters (the upper band) and with methylesters of polyunsaturated long chain (20 to 22 carbon) fatty acids (the lower band). These were also the major types of fatty acids detected by GC analysis of FAMEs of Schizochytrium oil.

In a parallel experiment thiolactomycin, a well known inhibitor of Type II fatty acid synthesis systems as well as several polyketide synthesis systems including EPA to the test tubes of varying concentrations (0, 1, 10 and 100 μg/ml) prior to addition of the Schizochytrium cell cultures and [$^{14}$C] acetate. Analysis of incorporation of [$^{14}$C] acetate, as described above, revealed that 100 ug/mL thiolactomycin completely blocked synthesis of polyunsaturated fatty acids, while partial inhibition of synthesis of polyunsaturated fatty acids was observed at 10 ug/mL thiolactomycin. Synthesis of the short chain saturated fatty acids was unaffected at all tested thiolactomycin concentrations. Thiolactomycin does not inhibit Type I fatty acid synthesis systems and is not toxic to mice, suggesting that it does not inhibit the elongation system leading to EPA or DHA formation. Furthermore, thiolactomycin did not inhibit the elongation system leading to PUFA synthesis in *Phaeodactylum tricornutum*. Therefore, although Schizochytrium is known to possess a Type I fatty acid synthesis system, the data suggested that the polyunsaturated fatty acids produced in this organism were derived from a system which was distinct from the Type I fatty acid synthesis system which produced short chain fatty acids, and from a system that was similar to the elongation/desaturation pathway found in mice and Phaeodactylum. The data are consistent with DHA formation being a result of a PKS pathway as found in Vibrio marinus and Shewanella putrefaciens.

Example 8

PKS Related Sequences From Schizochytrium

The purpose of this experiment was to identify sequences from Schizochytrium that encoded PKS genes. A CDNA library from Schizochytrium was constructed and approximately 8,000 random clones (ESTS) were sequenced. The protein sequence encoded by Shewanella EPA synthesis genes was compared to the predicted amino acid sequences of the Schizochytrium ESTs using a Smith/Waterman alignment algorithm. When the protein sequence of ORF6 (Shewanella) was compared with the amino acid sequences from Schizochytrium ESTs, 38 EST clones showed a significant degree of identity (P<0.01). When the protein sequence of ORF7 was compared by Schizochytrium ESTs, 4 EST clones showed significant identity (P<0.01) suggesting that the molecules were homologous. When the protein sequence of ORF8 and ORF9 were compared with the Schizochytrium ESTs, 7 and 14 clones respectively showed significant identity (P<0.01).

Example 9

Analysis of Schizochytrium CDNA Clones

Figure 28:
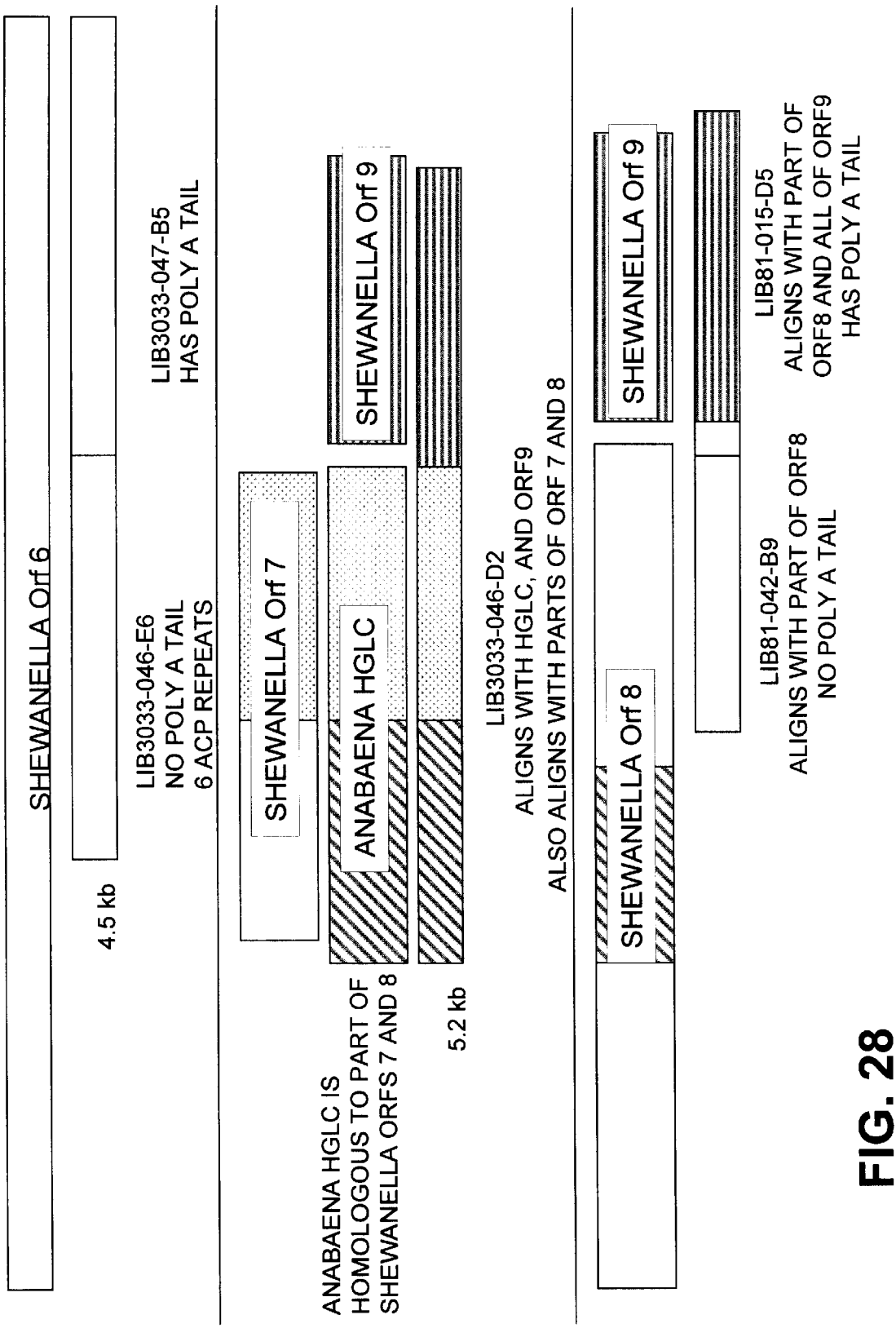
FIG. 28 shows a schematic of the similarities between Shewanella PKS sequences and Schizochytrium sequences.

Restriction enzyme analysis of the Schizochytrium EST clones was used to determine the longest clones, which were subsequently sequenced in their entirety. All of the EST sequences described in Example 8 were determined to be part of 5 cDNA clones. Two of the cDNA clones were homologous to Shewanella ORF6. LIB3033-047-B5 was homologous to the C-terminus of ORF6. The sequence of LIB3033-047-B5 could be aligned with Shewanella ORF6 from amino acids 2093 onwards. The open reading frame of LIB3033-047-B5 extended all the way to the 5' end of the sequence, thus this clone was not likely to be full length. LIB3033-046-E6 shared homology to the ACP domain of ORF6. It contained 6 ACP repeats. This cDNA clone did not have a poly-A-tail, and therefore, it was likely to be a partial cDNA with additional regions of the cDNA found downstream of the sequence. The PCR primers GTGAT-GATCTTTCCCTGATGCACGCCAAGG (SEQ ID NO:67) and AGCTCGAGACCGGCAACCCGCAGCGCCAGA (SEQ ID NO:68) were used to amplify a fragment of approximately 500 nucleotides from Schizochytrium genomic DNA. Primer GTGATGATCTTTCCCTGATG-CACGCCAAGG was derived from LIB3033-046-E6, and primer AGCTCGAGACCGGCAACCCGCAGCGCCAGA was derived from LIB3033-047-B5. Thus, LIB3033-046-E6 and LIB3033-047-B5 represented different portions of the same mRNA (see FIG. 28) and could be assembled into a single partial cDNA sequence (see FIG. 27A), SEQ ID NO:69, that was predicted to encode a protein with the sequence in FIG. 29A (SEQ ID NO:70). The open reading frame extended all the way to the 5' end of the sequence, thus this partial cDNA was not likely to be full length. Analysis of additional cDNA or genomic clones will allow the determination of the full extent of the mRNA represented by clones LIB3033-046-E6 and LIB033-047-B5. It may contain condensing enzyme related domains similar to those found near the N-terminus of Shewanella ORF6.

One of the cDNA clones, LIB3033-046-D2, was homologous to Shewanella ORF9 at its 3' end. This clone was homologous to the chain length factor region of Shewanella ORF8 at its 5' end. This clone was also homologous to the entire open reading frame of the Anabaena HglC ORF. The Anabaena HglC ORF is homologous to the chain length factor region of Shewanella ORF8 and Shewanella ORF7. Thus this cDNA (FIG. 27B), SEQ ID NO:71, was homologous to part of Shewanella ORF8, Shewanella ORF7 and Shewanella ORF9 (see FIG. 28). The amino acid sequence (FIG. 29B), SEQ ID NO:72, encoded by the open reading frame of LIB3033-046-D2 extended all the way to the 5' end of the sequence; thus this clone was not likely to be full length. Analysis of additional cDNA or genomic clones will allow the determination of the full extent of the mRNA represented by LIB3033-046-E6. It may contain condensing enzyme related domains similar to those found near the N-terminus of Shewanella ORF8.

Two additional cDNA clones were homologous to Shewanella ORF8. LIB81-015-D5 was homologous to the C-terminus of ORF8. The 5' sequence of LIB81-015-D5 could be aligned with Shewanella ORF8 from amino acids 1900 onwards. The 3' end of LIB81-015-D5 could be aligned with Shewanella ORF9 (see FIG. 28). The amino acid sequence (FIG. 29C), SEQ ID NO:73, encoded by the open reading frame of LIB81-015-D5 extended all the way to the 5' end of the sequence; thus this clone was not likely to be full length. LIB81-042-B9 was homologous to amino acids 1150 to 1850 of Shewanella ORF8. LIB81-042-B9 did not have a poly-A-tail, and therefore, it was likely to be a partial cDNA with additional regions of the cDNA found downstream of the sequence. The PCR primers TACCGCG-GCAAGACTATCCGCAACGTCACC (SEQ ID NO:74) and GCCGTCGTGGGCGTCCACGGACACGATGTG (SEQ ID NO:75) were used to amplify a fragment of approximately 500 nucleotides from Schizochytrium genomic DNA. Primer TACCGCGGCAAGACTATCCG-CAACGTCACC was derived from LIB81-042-B9, and primer GCCGTCGTGGGCGTCCACGGACACGATGTG was derived from LIB81-015-D5. Thus, LIB81-042-and LIB81-015-D5 represented different portions of the same mRNA and were assembled into a single partial cDNA sequence (see FIG. 27C), SEQ ID NO:76. The open reading frame of LIB81-042-B9 also extended all the way to the 5' end of the sequence, thus this clone was also not likely to be full length. Analysis of additional cDNA or genomic clones will allow the determination of the full extent of the mRNA represented by LIB81-042-B9.

By the present invention PKS-like genes from various organisms can now be used to transform plant cells and modify the fatty acid compositions of plant cell membranes or plant seed oils through the biosynthesis of PUFAs in the transformed plant cells. Due to the nature of the PKS-like systems, fatty acid end-products produced in the plant cells can be selected or designed to contain a number of specific chemical structures. For example, the fatty acids can comprise the following variants: Variations in the numbers of keto or hydroxyl groups at various positions along the carbon chain; variations in the numbers and types (cis or trans) of double bonds; variations in the numbers and types of branches off of the linear carbon chain (methyl, ethyl, or longer branched moieties); and variations in saturated carbons. In addition, the particular length of the end-product fatty acid can be controlled by the particular PKS-like genes utilized.

All publications and patent applications mentioned in this specification are indicative of the level of skill of those skilled in the art to which this invention pertains.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated nucleic acid molecule comprising a nucleic acid sequence selected from the group consisting of:
   (a) a nucleic acid sequence encoding SEQ ID NO:73, or a portion thereof comprising at least one functional domain of SEQ ID NO:73;
   (b) a nucleic acid sequence encoding an amino acid sequence that is at least 60% identical to the amino acid sequence of (a), wherein said nucleic acid sequence encodes a protein having the biological activity of at least one functional domain of SEQ ID NO:73;
   (c) a nucleic acid sequence that is fully complementary to the nucleic acid sequence of (a) or (b).

2. The isolated nucleic acid molecule of claim 1, wherein said nucleic acid molecule comprises a nucleic acid sequence encoding at least about 20 contiguous amino acid residues of SEQ ID NO:73.

3. The isolated nucleic acid molecule of claim 1, wherein said nucleic acid molecule comprises a nucleic acid sequence encoding at least about 35 contiguous amino acid residues of SEQ ID NO:73.

4. The isolated nucleic acid molecule of claim 1, wherein said nucleic acid molecule comprises a nucleic acid sequence comprising at least about 50 contiguous nucleotides of SEQ ID NO:76.

5. The isolated nucleic acid molecule of claim 1, wherein said nucleic acid molecule comprises a nucleic acid sequence comprising at least about 60 contiguous nucleotides of SEQ ID NO:76.

6. The isolated nucleic acid molecule of claim 1, wherein said nucleic acid molecule comprises a nucleic acid sequence comprising at least about 75 contiguous nucleotides of SEQ ID NO:76.

7. The isolated nucleic acid molecule of claim 1, wherein said nucleic acid molecule comprises a nucleic acid sequence comprising at least about 110 contiguous nucleotides of SEQ ID NO:76.

8. The isolated nucleic acid molecule of claim 1, wherein said nucleic acid molecule comprises a nucleic acid sequence encoding SEQ ID NO:73.

9. The isolated nucleic acid molecule of claim 1, wherein said nucleic acid molecule comprises SEQ ID NO:76.

10. The isolated nucleic acid molecule of claim 1, wherein said nucleic acid molecule, when expressed by a host cell, modulates the production of a long chain polyunsaturated fatty acid.

11. The isolated nucleic acid molecule of claim 1, wherein said nucleic acid molecule, when expressed by a host cell, modulates the production of docosahexaenoic acid.

12. The isolated nucleic acid molecule of claim 1, wherein said nucleic acid molecule, when exressed by a host cell, modulates the production of eicosapentaenoic acid.

13. The isolated nucleic acid molecule of claim 1, wherein said nucleic acid sequence encodes an amino acid sequence that is at least 80% identical to SEQ ID NO:73, wherein said nucleic acid sequence encodes a protein having the biological activity of at least one functional domain of SEQ ID NO:73.

14. The isolated nucleic acid molecule of claim 1, wherein said nucleic acid sequence encodes an amino acid sequence that is at least about 90% identical to SEQ ID NO:73, wherein said nucleic acid sequence encodes at least one protein having the biological activity of at least one functional domain of SEQ ID NO:73.

15. The isolated nucleic acid molecule of claim 1, wherein said nucleic acid sequence encodes an amino acid sequence that is at least about 95% identical to SEQ ID NO:73, wherein said nucleic acid sequence encodes at least one protein having the biological activity of at least one functional domain of SEQ ID NO:73.

16. A recombinant nucleic acid molecule comprising the isolated nucleic acid molecule of claim 1, operably linked to a promoter.

17. A recombinant microbial cell comprising at least one copy of an isolated nucleic acid molecule according to claim 1.

18. The recombinant microbial cell of claim 17, wherein said microbial cell comprises a nucleic acid molecule derived from two or more polyketide synthase systems.

19. The recombinant microbial cell of claim 17, wherein said microbial cell is a fungal cell.

20. The recombinant microbial cell of claim 17, wherein said fungal cell is a yeast cell.

21. The recombinant microbial cell of claim 17, wherein said microbial cell is an algal cell.

22. The recombinant microbial cell of claim 17, wherein said algal cell is a marine algal cell.

23. The recombinant microbial cell of claim 17, wherein said cell is a bacterial cell or a cyanobacterial cell.

24. The recombinant microbial cell of claim 17, wherein said bacterial cell is a Lactobacillus cell.

25. The recombinant microbial cell of claim 17, wherein said recombinant microbial cell is enriched for 22:6 fatty acids as compared to a non-recombinant microbial cell which is devoid of said isolated nucleic acid.

26. A method for production of a long chain polyunsaturated fatty acid in a microbial cell culture, said method comprising growing a microbial cell culture having a plurality of recombinant microbial cells as set forth in claim 17, under conditions whereby a long chain polyunsaturated fatty acid is produced by said microbial cell culture.

27. A recombinant plant cell comprising at least one copy of an isolated nucleic acid molecule according to claim 1.

28. The recombinant plant cell of claim 27, wherein said recombinant plant cell is a recombinant seed cell.

29. The recombinant plant cell of claim 27, wherein said recombinant seed cell is a recombinant embryo cell.

30. The recombinant plant cell of claim 27, wherein said recombinant plant cell is from a plant selected from the group consisting of Brassica, soybean, safflower, Arabidopsis, corn and sunflower.

31. A method for production of a long chain polyunsaturated fatty acid in a plant cell, said method comprising growing a plant having a plurality of recombinant plant cells as set forth in claim 27, under conditions whereby a long chain polyunsaturated fatty acid is produced in said plant cells.

32. The method of claim 31, wherein said long chain polyunsaturated fatty acid produced in said plant cells is a 20:5 and 22:6 fatty acid.

33. The method of claim 31, therein said long chain polyunsaturated fatty acid is eicosapentaenoic acid.

34. The method of claim 31, wherein said long chain polyusaturated fatty acid is docosaheyaenoic acid.

35. The nucleic acid molecule of claim 1, wherein said biological activity is dehydrase activity.

36. An oligonucleotide probe comprising at least 50 nucleotides of SEQ ID NO:76 or the complement thereof.

* * * * *

SEQUENCE LISTING

<160> NUMBER OF SEQ ID NOS: 86

<210> SEQ ID NO 1
<211> LENGTH: 37895
<212> TYPE: DNA
<213> ORGANISM: Shewanella putrefaciens

<400> SEQUENCE: 1

```
gatctcttac aaagaaacta tctcaatgtg aatttaacct taattccgtt taattacggc      60
ctgatagagc atcacccaat cagccataaa actgtaaagt gggtactcaa aggtggctgg     120
gcgattcttc tcaaatacaa agtgcccaac ccaagcaaat ccatatccga taacaggtaa     180
aagtagcaat aaacccagc gctgagttag taatacataa gcgaataata ggatcactaa      240
actactgccg aaatagtgta atattcgaca gtttctatgc tgatgttgag ataaataaaa     300
agggtaaaat tcagcaaaag aacgatagcg cttactcatt actcacacct cggtaaaaaa     360
gcaactcgcc attaacttgg ccaatcgtca gttgttctat cgtctcaaag ttatgccgac     420
taaataactc tatatgtgca ttatgattag caaaaactcc gataccatca agatgaagtt     480
gttcatcaca ccaactcaaa actgcgtcga taagcttact gccatagccc ttgccttgct     540
ccacatttgc gatagcaata aactgtaaaa tgccacattg gccacttggt aagctctcta     600
taatctgatt ttctttgtta ataagtgcct gagttgaata ccaaccagta cttaacaaca     660
tctttaaacg ccaatgccaa aaacgcgctt cacctaaggg aacctgctga gtcactatgc     720
aggctacgcc tatcaatcta tccccaacga acataccaat aagtgcttgc tcctgttgcc     780
agagctcatt gagttcttct cgaatagccc cgcgaagctt ttgctcatac tgcgcttgat     840
caccactaaa aagtgtttcg ataaaaaagg gatcatcatg ataggcgtta tagagaatag     900
aggctgctat gcgtaaatct tctgccgtga gataaactgc acgacactct tccatggctt     960
gatcttccat tgttattgtc cttgaccttg atcacacaac accaatgtaa caagactgta    1020
tagaagtgca attaataatc aattcgtgca ttaagcaggt cagcatttct ttgctaaaca    1080
agctttattg gctttgacaa aactttgcct agactttaac gatagaaatc ataatgaaag    1140
agaaaagcta caacctagag gggaataatc aaacaactgc taagatctag ataatgtaat    1200
aaacaccgag tttatcgacc atacttagat agagtcatag caacgagaat agttatggat    1260
acaacgccgc aagatctatc acacctgttt ttacagctag gattagcaaa tgatcaaccc    1320
gcaattgaac agtttatcaa tgaccatcaa ttagcggaca atatattgct acatcaagca    1380
agcttttgga gcccatcgca aaagcacttc ttaattgagt catttaatga agatgcccag    1440
tggaccgaag tcatcgacca cttagacacc ttattaagaa aaaactaacc attacaacag    1500
caactttaaa ttttgccgta agccatctcc ccccacccca caacagcgtt gttgcttatg    1560
accactggag tacattcgtc tttagtcgtt ttaccatcac catgggtacg ttgagtgcga    1620
```

```
taaaaaagca cataaacttc tttatcggcc tgaatatagg cttcgttaaa atcagctgtt      1680
cccattaaag taaccacttg ctctttactc atgcctagag atatctttgt caaattgtca      1740
cggtttttat cttgagtttt ctcccaagca ccgtgattat cccagtcaga ttccccatca      1800
ccaacattga ccacacagcc cgttagccct aagcttgcaa tcccaaaaca tgctaaacct      1860
aataatttat ttttcatttt aacttcctgt tatgacatta ttttttgctta gaagaaaagc     1920 aacttacatg ccaaaacaca agctgttgtt ttaaatgact ttatttatta ttagcctttt     1980
aggatatgcc tagagcaata ataattacca atgtttaagg aatttgacta actatgagtc     2040
cgattgagca agtgctaaca gctgctaaaa aaatcaatga acaaggtaga gaaccaacat     2100
tagcattgat taaaaccaaa cttggtaata gcatcccaat gcgcgagtta atccaaggtt     2160
tgcaacagtt taagtctatg agtgcagaag aaagacaagc aatacctagc agcttagcaa     2220
cagcaaaaga aactcaatat ggtcaatcaa gcttatctca atctgaacaa gctgatagga     2280
tcctccagct agaaaacgcc ctcaatgaat taagaaacga atttaatggg ctaaaaagtc     2340
aatttgataa cttacaacaa aacctgatga ataaagagcc tgacaccaaa tgcatgtaat     2400
tgaactacga tttgaatgtt ttgataacac cacgattact gcagcagaaa aagccattaa     2460
tggtttgctt gaagcttatc gagccaatgg ccaggttcta ggtcgtgaat ttgccgttgc     2520
atttaacgat ggtgagttta agcacgcat gttaaccca gaaaaaagca gcttatctaa      2580
acgctttaat agtccttggg taatagtgc actcgaagag ctaaccgaag ccaaattgct     2640
tgcgccacgt gaaaagtata ttggccaaga tattaattct gaagcatcta gccaagacac     2700
accaagttgg cagctacttt acacaagtta tgtgcacatg tgctcaccac taagaaatgg     2760
cgacaccttg cagcctattc cactgtatca aattccagca actgccaacg gcgatcataa     2820
acgaatgatc cgttggcaaa cagaatggca agcttgtgat gaattgcaaa tggccgcagc     2880
tactaaagct gaatttgccg cacttgaaga gctaaccagt catcagagtg atctatttag     2940
gcgtggttgg gacttacgtg gcagagtcga atacttgacg aaaattccga cctattacta     3000
tttataccgt gttggcggtg aaagcttagc agtagaaaag cagcgctctt gtcctaagtg     3060
tggcagtcaa gaatggctgc tcgataaacc attattggat atgttccatt ttcgctgtga     3120
cacctgccgc atcgtatcta atatctcttg ggaccatta taactcttcc gagtcttatc     3180
acactagagt ttagtcagca taaaaatggc gcttatattt caattaaaag aaatataagc     3240
gccattttca tcgatactat atatcagcag actattttcc gcgtaaatta gcccacatta     3300
atttcattct ttgccagatc cctggatgat ctagttgtgg catcgactct tcaataggtt     3360
taaccgcagg tgtaaccctt ggagtcaatt cgttataaa ctcgtttaaa ctgtcactta      3420
atttaacgct ttgtacttca cctggaattt caatccatac gctgccatca ctattattaa     3480
ccgtcaacat tttatcttca tcatcaagaa taccaataaa ccaagtcggc tcttgcttaa     3540
gctttctctt catcattaaa tgaccaatga tgttttgttg taagtattca aaatcagttt     3600
gatcccacac ttggattagc tcaccttggc cccattgtga gtcaaaaaat agcggtgcag     3660
aaaaatgact gccaaaaaat ggattaattt ctgcagataa tgtcatttca agtgctgttt     3720
caacattagc aaattcacca ggttgttgac gtacaaccga ttgccaaaac actgcgccat     3780
cggagcccgc ttcggcgaca acacactcag acttttgtcc ttgcgcataa tatcttggct     3840
gttcaccaag cttatccatg taggcttgtt gatatttaga taaaaaaaga tctaaagcag     3900
gtaaagaaga cacttaagcc agttccaaaa tcagttataa tagggtctcta ttttgacatg     3960
```

```
gaaaccgtat tgatgacaca acatcatgat ccctacagta acgcccccga actttctgaa   4020
ttaactttag gaaagtcgac cggttatcaa gagcagtatg atgcatcttt actacaagcg   4080
tgccgcgtaa attaaaccgt gatgctatcg gtctaaccaa tgagctacct tttcatggct   4140
gtgatatttg gactggctac gaactgtctt ggctaaatgc taaaggcaag ccaatgattg   4200
ctattgcaga ctttaaccta agttttgata gtaaaaatct gatcgagtct aagtcgttta   4260
agctgtattt aaacagctat aaccaaacac gatttgatag cgttcaagcg gttcaagaac   4320
gtttaactga agacttaagc gcctgtgccc aaggcacagt tacggtaaaa gtgattgaac   4380
ctaagcaatt taaccacctg agagtggttg atatgccagg tacctgcatt gacgatttag   4440
atattgaagt tgatgactat agctttaact ctgactatct caccgacagt gttgatgaca   4500
aagtcatggt tgctgaaacg ctaacgtcaa acttattgaa atcaaactgc taatcactt    4560 ctcagcctga ctgggtaca gtgatgatcc gttatcaagg gcctaagata gaccgtgaaa    4620
agctacttag atatctgatt tcatttagac agcacaatga atttcatgag cagtgtgttg   4680
agcgtatatt tgttgattta aagcactatt gccaatgtgc caaacttact gtctatgcac   4740
gttatacccg ccgtggtggt ttagatatca acccatatcg tagcgacttt gaaaaccctg   4800
cagaaaatca gcgcctagcg agacagtaat tgattgcagt acctacaaaa aacaatgcct   4860
ataagccaag cttatgggca tttttatatt atcaacttgt catcaaacct cagccgccaa   4920 gcctttttagt tttatcgcta aattaagccg ctctctcagc caaatatttg caggattttg   4980
ctgtaattta tggctccaca ccatgaaata ctctatcggc tctaccgcaa aagtaagtc    5040 aaatacctgt aagccaaaca gcttggcata ttcgtcagtg tgggcttttg acgcgatagc   5100
taacgcatca cttttttgagg caaccgacat catacttaat attgatgatt gctcgctgtg   5160
catttgcctt gccggtaaca cctgtttagt cagcaagtcg gcaacactta aattgtagcg   5220
gcgcatctta aaaataatat gcttttcatt aaagtattgc tcttgcgtca cccaccttg    5280 gatccttggg tgagcatttc gtgccacaca aactaattta tcctgcatta cttttttgact 5340 cttaaatgcc gcagattctg gcagccaaat atctaaggct aaatccacct tttctagttg   5400
taggtccatc tgcaactctt cttcaatgag cggcggctca cgaaatacaa tattaattgc   5460
agtgccctgt aacacttgct caatttgatc ttgcaagagt tgtattgccg actcgctggc   5520
atacacataa aaagttcgct cacttgaagt ggggtcaaat gcttcaaagc tagtcgcaac   5580
ttgctcaatt gttgacatag cgcccgcgag ctgttgataa agcgtcatcg cacttgcggt   5640
aggtttaact cccctaccca ctcgagtaaa caactcttct ccaacaatac tttttagcct   5700
cgaaatcgca ttactaaccg acgactgagt caaatccagc tcttctgccg cccggctaaa   5760
agatgaggtg cgatacaccg cagtaaaaac gcgaaataaa ttaagatcaa aagcttttttg 5820 ctgcgacata aatcagctat ctccttatcc ttatccttat ccttataaaa agttagctcc   5880
agagcactct agctcaaaaa caactcagcg tattaagcca atattttggg aactcaatta   5940
atattcataa taaagtatt cataatataa ataccaagtc ataatttagc cctaattatt    6000
aatcaattca agttacctat actggcctca attaagcaaa tgtctcatca gtctccctgc   6060
aactaaatgc aatattgaga cataaagctt tgaactgatt caatcttacg agggtaactt   6120
atgaaacaga ctctaatggc tatctcaatc atgtcgcttt tttcattcaa tgcgctagca   6180
gcgcaacatg aacatgacca catcactgtt gattacgaag ggaaagccgc aacagaacac   6240
accatagctc acaaccaagc tgtagctaaa acacttaact ttgccgacac gcgtgcattt   6300
gagcaatcgt ctaaaaatct agtcgccaag tttgataaag caactgccga tatattacgt   6360
```

```
gccgaatttg cttttattag cgatgaaatc cctgactcgg ttaacccgtc tctctaccgt    6420
caggctcagc ttaatatggt gcctaatggt ctgtataaag tgagcgatgg catttaccag    6480
gtccgcggta ccgacttatc taaccttaca cttatccgca gtgataacgg ttggatagca    6540
tacgatgttt tgttaaccaa agaagcagca aaagcctcac tacaatttgc gttaaagaat    6600
ctacctaaag atggcgattt acccgttgtt gcgatgattt actcccatag ccatgcggac    6660
cactttggcg gagctcgcgg tgttcaagag atgttccctg atgtcaaagt ctacggctca    6720
gataacatca ctaaagaaat tgtcgatgag aacgtacttg ccggtaacgc catgagccgc    6780
cgcgcagctt atcaatacgg cgcaacactg gcaaacatg accacggtat tgttgatgct    6840
gcgctaggta aaggtctatc aaaaggtgaa atcacttacg tcgccccaga ctacaccttta   6900 aacagtgaag gcaaatggga aacgctgacg attgatggtc tagagatggt gtttatggat    6960
gcctcgggca ccgaagctga gtcagaaatg atcacttata ttccctctaa aaagcgctc    7020 tggacggcgg agcttaccta tcaaggtatg cacaacattt atacgctgcg cggcgctaaa    7080
gtacgtgatg cgctcaagtg gtcaaaagat atcaacgaaa tgatcaatgc ctttggtcaa    7140
gatgtcgaag tgctgtttgc ctcgcactct gcgccagtgt ggggtaacca agcgatcaac    7200
gatttcttac gcctacagcg tgataactac ggcctagtgc acaatcaaac cttgagactt    7260
gccaacgatg gtgtcggtat acaagatatt ggcgatgcga ttcaagacac gattccagag    7320
tctatctaca gacgtggca taccaatggt taccacggca cttatagcca taacgctaaa    7380
gcggtttata caagtatct aggctacttc gatatgaacc cagccaacct taatccgctg    7440
ccaaccaagc aagaatctgc caagtttgtc gaatacatgg gcggcgcaga tgccgcaatt    7500
aagcgcgcta agatgatta cgctcaaggt gaataccgct tgttgcaac ggcattaaat    7560 aaggtggtga tggccgagcc agaaaatgac tccgctcgtc aattgctagc cgatacctat    7620
gagcaacttg gttatcaagc agaaggggct ggctggagaa acatttactt aactggcgca    7680
caagagctac gagtaggtat tcaagctggc gcgcctaaaa ccgcatcggc agatgtcatc    7740
agtgaaatgg acatgccgac tctatttgac ttcctcgcgg tgaagattga tagtcaacag    7800
gcggctaagc acggcttagt taagatgaat gttatcaccc ctgatactaa agatattctc    7860
tatattgagc taagcaacgg taacttaagc aacgcagtgg tcgacaaaga gcaagcagct    7920
gacgcaaacc ttatggttaa taaagctgac gttaaccgca tcttacttgg ccaagtaacc    7980
ctaaaagcgt tattagccag cggcgatgcc aagctcactg gtgataaaac ggcatttagt    8040
aaaatagccg atagcatggt cgagtttaca cctgacttcg aaatcgtacc aacgcctgtt    8100
aaatgaggca ttaatctcaa caagtgcaag ctagacataa aaatgggcg attagacgcc    8160 ccatttttta tgcaatttg aactagctag tcttagctga agctcgaaca acagctttaa    8220
aattcacttc ttctgctgca atacttattt gctgacactg accaatactc agtgcaaaac    8280
gataactatc atcaagatgg cccagtaaac aatgccaatt atcagcagcg ttcatttgct    8340
gttctttagc ctcaatcaaa cctaaaccag acttttgtgg ctcagcgtta ggcttattag    8400
aactcgactc tagtaaagca agaccaatat cttgttttaa caaaacctgt cgctgattaa    8460
gttgatgctc aaccttgtga tccgcaatag catcggaaat atcaacacaa tggctcaagc    8520
ttttaggtgc attaactcca agaaagtttt cgctcagtgc agagaagtca acgcaaaag    8580 attttagcga taatgccagc ccaagtcctt tcgctttaat gtaagactcc ttgagcgccc    8640
acaaatcaaa aaagcggtct cgctgcaagg cctctggtaa cgctaacaag gctcgctttt    8700
```

```
ctgattcaga gaaataatga ctaagaatag agtggatatt ggtgctgtta cggcaacgct   8760
caatgtcgac gccaaactca atactagcag agtcagtttc ctccttgctt gcctgactgg   8820
cgcctttatt atcagcagtg caaatgccta ctaatagcca atctccacta tgactcacat   8880
taaagtggac cccggtttga gcaaattgcg catcactcaa tctaggctta cctttgtcgc   8940
catattcaaa gcgccattca ttggggcgta tttcactatg ttgtgacaat aaagcgcgca   9000
aatagcctct taccattaaa ccttgagttt tagcttcttg tttaatgtag cgattaacct   9060
taattaactc atcttcaggc agccatgact taaccaactc tgtagtctgg ttatcgcact   9120
cttgtattgt taacggacag aagtataagg aaatcaatcg agaagttagc aattttttcag  9180
gacactcttt aaagcaacaa acataacccc tattttttacc aatttaagat caaaactaaa   9240
gccaaaacta attgagaata gtgtcaaact agctttaaag gaaaaaaata taaaaagaac   9300
attatacttg tataaattat tttacacacc aaagccatga tcttcacaaa attagctccc   9360
tctccctaaa acaagattga ataaaaaaat aaaccttaac tttcatatag ataaaacaaa   9420
ccaatgggat aaagtatatt gaattcattt ttaaggaaaa attcaaattg aattcaagct   9480
cttcagtaaa agcatatttt gccgttagtg tgaaaaaaaa caaatttaaa aaccaacata   9540
gaacaaataa gcagacaata aaaccaaggc gcaacacaaa caacgcgctt acaattttca   9600
caaaaaagca acaagagtaa cgtttagtat ttggatatgg ttattgtaat tgagaatttt   9660
ataacaatta tattaaggga atgagtatgt ttttaaattc aaaactttcg cgctcagtca   9720
aacttgccat atccgcaggc ttaacagcct cgctagctat gcctgttttt gcagaagaaa   9780
ctgctgctga agaacaaata gaaagagtcg cagtgaccgg atcgcgaatc gctaaagcag   9840
agctaactca accagctcca gtcgtcagcc tttcagccga agaactgaca aaatttggta   9900
atcaagattt aggtagcgta ctagcagaat tacctgctat tggtgcaacc aacactatta   9960
ttggtaataa caatagcaac tcaagcgcag gtgttagctc agcagacttg cgtcgtctag  10020
gtgctaacag aaccttagta ttagtcaacg gtaagcgcta cgttgccggc caaccgggct  10080
cagctgaggt agatttgtca actataccaa ctagcatgat ctcgcgagtt gagattgtaa  10140
ccggcggtgc ttcagcaatt tatggttcgg acgctgtatc aggtgttatc aacgttatcc  10200
ttaaagaaga ctttgaaggc tttgagttta acgcacgtac tagcggttct actgaaagtg  10260
taggcactca agagcactct tttgacattt tgggtggtgc aaacgttgca gatggacgtg  10320
gtaatgtaac cttctacgca ggttatgaac gtacaaaaga agtcatggct accgacattc  10380
gccaattcga tgcttgggga acaattaaaa acgaagccga tggtggtgaa gatgatggta  10440
ttccagacag actacgtgta ccacgagttt attctgaaat gattaatgct accggtgtta  10500
tcaatgcatt tggtggtgga attggtcgct caacctttga cagtaacggc aatcctattg  10560
cacaacaaga acgtgatggg actaacagct ttgcatttgg ttcattccct aatggctgtg  10620
acacatgttt caacactgaa gcatacgaaa actatattcc agggtagaa agaataaacg   10680
ttggctcatc attcaacttt gattttaccg ataacattca attttacact gacttcagat  10740
atgtaaagtc agatattcag caacaatttc agccttcatt ccgttttggt aacattaata  10800
tcaatgttga agataacgcc ttttgaatg acgacttgcg tcagcaaatg ctcgatgcgg  10860
gtcaaaccaa tgctagtttt gccaagtttt ttgatgaatt aggaaatcgc tcagcagaaa  10920
ataaacgcga acttttccgt tacgtaggtg gctttaaagg tggctttgat attagcgaaa  10980
ccatatttga ttacgacctt tactatgttt atggcgagac taataaccgt cgtaaaaccc  11040
ttaatgacct aattcctgat aactttgtcg cagctgtcga ctctgttatt gatcctgata  11100
```

```
ctggcttagc agcgtgtcgc tcacaagtag caagcgctca aggcgatgac tatacagatc   11160
ccgcgtctgt aaatggtagc gactgtgttg cttataaccc atttggcatg ggtcaagctt   11220
cagcagaagc ccgcgactgg gtttctgctg atgtgactcg tgaagacaaa ataactcaac   11280
aagtgattgg tggtactctc ggtaccgatt ctgaagaact atttgagctt caaggtggtg   11340
caatcgctat ggttgttggt tttgaatacc gtgaagaaac gtctggttca acaaccgatg   11400
aatttactaa agcaggtttc ttgacaagcg ctgcaacgcc agattcttat ggcgaatacg   11460
acgtgactga gtattttgtt gaggtgaaca tcccagtact aaaagaatta ccttttgcac   11520
atgagttgag ctttgacggt gcataccgta atgctgatta ctcacatgcc ggtaagactg   11580
aagcatggaa agctggtatg ttctactcac cattagagca acttgcatta cgtggtacgg   11640
taggtgaagc agtacgagca ccaaacattg cagaagcctt tagtccacgc tctcctggtt   11700
ttggccgcgt ttcagatcca tgtgatgcag ataacattaa tgacgatccg gatcgcgtgt   11760
caaactgtgc agcattgggg atccctccag gattccaagc taatgataac gtcagtgtag   11820
ataccttatc tggtggtaac ccagatctaa aacctgaaac atcaacatcc tttacaggtg   11880
gtcttgtttg gacaccaacg tttgctgaca atctatcatt cactgtcgat tattatgata   11940
ttcaaattga ggatgctatt ttgtcagtag ccacccagac tgtggctgat aactgtgttg   12000
actcaactgg cggacctgac accgacttct gtagtcaagt tgatcgtaat ccaacgacct   12060
atgatattga acttgttcgc tctggttatc taaatgccgc ggcattgaat accaaaggta   12120
ttgaatttca agctgcatac tcattagatc tagagtcttt caacgcgcct ggtgaactac   12180
gcttcaacct attggggaac caattacttg aactagaacg tcttgaattc caaaatcgtc   12240
ctgatgagat taatgatgaa aaaggcgaag taggtgatcc agagctgcag ttccgcctag   12300
gcatcgatta ccgtctagat gatcaagtg ttagctggaa cacgcgttat attgatagcg   12360
tagtaactta tgatgtctct gaaaatggtg gctctcctga agatttatat ccaggccaca   12420
taggctcaat gacaactcat gacttgagcg ctacatacta catcaatgag aacttcatga   12480
ttaacggtgg tgtacgtaac ctatttgacg cacttccacc tggatacact aacgatgcgc   12540
tatatgatct agttggtcgc cgtgcattcc taggtattaa ggtaatgatg taattaatta   12600
ttacgcctct aactaataaa aatgcaatct cttcgtagag attgcatttt tttatgaaat   12660
ccaatcttaa actggttctc cgagcatctt acgccttaaa aaccccgccc ctcaatgtaa   12720
cgccaaagtt aattgcttac acgcacttac acaaacgaac aatttcatta acacgagaca   12780
cagctcacgc ttttatttt acccttgatt ttactacata aaattgcgtt ttagcgcaca   12840
agtgttctcc caagctggtc gtatctgtaa ttattcagtc ccaggtgatt gtattgaccc   12900
ataagctcag gtagtctgct ctgccattag ctaaacaata ttgacaaaat ggcgataaaa   12960
tgtggcttag cgctaagttc accgtaagtt ttatcggcat taagtcccaa cagattatta   13020
acggaaaccc gctaaactga tggcaaaaat aaatagtgaa cacttggatg aagctactat   13080
tacttcgaat aagtgtacgc aaacagagac tgaggctcgg catagaaatg ccactacaac   13140
acctgagatg cgccgattca tacaagagtc ggatctcagt gttagccaac tgtctaaaat   13200
attaaatatc agtgaagcta ccgtacgtaa gtggcgcaag cgtgactctg tcgaaaactg   13260
tcctaatacc ccgcaccatc tcaataccac gctaacccct ttgcaagaat atgtggttgt   13320
gggcctgcgt tatcaattga aaatgccatt agacagattg ctcaaagcaa cccaagagtt   13380
tatcaatcca aacgtgtcgc gctcaggttt agcaagatgt ttgaagcgtt atggcgtttc   13440
```

```
acgggtgagt gatatccaaa gcccacacgt accaatgcgc tactttaatc aaattccagt   13500
cactcaaggc agcgatgtgc aaacctacac cctgcactat gaaacgctgg caaaaacctt   13560
agccttacct agtaccgatg gtgacaatgt ggtgcaagtg gtgtctctca ccattccacc   13620
aaagttaacc gaagaagcac ccagttcaat tttgctcggc attgatcctc atagcgactg   13680
gatctatctc gacatatacc aagatggcaa tacacaagcc acgaatagat atatggctta   13740
tgtgctaaaa cacgggccat tccatttacg aaagttactc gtgcgtaact atcacacctt   13800
tttacagcgc tttcctggag cgacgcaaaa tcgccgcccc tctaaagata tgcctgaaac   13860
aatcaacaag acgcctgaaa cacaggcacc cagtggagac tcataatgag ccagacctct   13920
aaacctacaa actcagcaac tgagcaagca caagactcac aagctgactc tcgtttaaat   13980
aaacgactaa aagatatgcc aattgctatt gttggcatgg cgagtatttt tgcaaactct   14040
cgctatttga ataagttttg ggacttaatc agcgaaaaaa ttgatgcgat tactgaatta   14100
ccatcaactc actggcagcc tgaagaatat tacgacgcag ataaaaccgc agcagacaaa   14160
agctactgta aacgtggtgg cttttttgcca gatgtagact tcaacccaat ggagtttggc   14220
ctgccgccaa acattttgga actgaccgat tcatcgcaac tattatcact catcgttgct   14280
aaagaagtgt tggctgatgc taacttacct gagaattacg accgcgataa aattggtatc   14340
accttaggtg tcggcggtgg tcaaaaaatt agccacagcc taacagcgcg tctgcaatac   14400
ccagtattga agaaagtatt cgccaatagc ggcattagtg acaccgacag cgaaatgctt   14460
atcaagaaat tccaagacca atatgtacac tgggaagaaa actcgttccc aggttcactt   14520
ggtaacgtta ttgcgggccg tatcgccaac cgcttcgatt ttggcggcat gaactgtgtg   14580
gttgatgctg cctgtgctgg atcacttgct gctatgcgta tggcgctaac agagctaact   14640
gaaggtcgct ctgaaatgat gatcaccggt ggtgtgtgta ctgataactc accctctatg   14700
tatatgagct tttcaaaaac gcccgccttt accactaacg aaaccattca gccatttgat   14760
atcgactcaa aaggcatgat gattggtgaa ggtattggca tggtggcgct aaagcgtctt   14820
gaagatgcag agcgcgatgg cgaccgcatt tactctgtaa ttaaaggtgt gggtgcatca   14880
tctgacggta agtttaaatc aatctatgcc cctcgcccat caggccaagc taaagcactt   14940
aaccgtgcct atgatgacgc aggttttgcg ccgcatacct taggtctaat tgaagctcac   15000
ggaacaggta ctgcagcagg tgacgcggca gagtttgccg gcctttgctc agtatttgct   15060
gaaggcaacg ataccaagca acacattgcg ctaggttcag ttaaatcaca aattggtcat   15120
actaaatcaa ctgcaggtac agcaggttta attaaagctg ctcttgcttt gcatcacaag   15180
gtactgccgc cgaccattaa cgttagtcag ccaagcccta aacttgatat cgaaaactca   15240
ccgtttatc taaacactga gactcgtcca tggttaccac gtgttgatgg tacgccgcgc   15300
cgcgcgggta ttagctcatt tggttttggt ggcactaact tccattttgt actagaagag   15360
tacaaccaag aacacagccg tactgatagc gaaaaagcta agtatcgtca acgccaagtg   15420
gcgcaaagct tccttgttag cgcaagcgat aaagcatcgc taattaacga gttaaacgta   15480
ctagcagcat ctgcaagcca agctgagttt atcctcaaag atgcagcagc aaactatggc   15540
gtacgtgagc ttgataaaaa tgcaccacgg atcggtttag ttgcaaacac agctgaagag   15600
ttagcaggcc taattaagca agcacttgcc aaactagcag ctagcgatga taacgcatgg   15660
cagctacctg gtggcactag ctaccgcgcc gctgcagtag aaggtaaagt tgccgcactg   15720
tttgctggcc aaggttcaca atatctcaat atgggccgtg accttacttg ttattaccca   15780
gagatgcgtc agcaatttgt aactgcagat aaagtatttg ccgcaaatga taaaacgccg   15840
```

-continued

```
ttatcgcaaa ctctgtatcc aaagcctgta tttaataaag atgaattaaa ggctcaagaa   15900
gccattttga ccaataccgc caatgcccaa agcgcaattg gtgcgatttc aatgggtcaa   15960
tacgatttgt ttactgcggc tggctttaat gccgacatgt tgcaggcca tagctttggt    16020 gagctaagtg cactgtgtgc tgcaggtgtt atttcagctg atgactacta caagctggct   16080
tttgctcgtg gtgaggctat ggcaacaaaa gcaccggcta agacggcgt tgaagcagat    16140 gcaggagcaa tgtttgcaat cataaccaag agtgctgcag accttgaaac cgttgaagcc   16200
accatcgcta aatttgatgg ggtgaaagtc gctaactata acgcgccaac gcaatcagta   16260
attgcaggcc aacagcaac taccgctgat gcggctaaag cgctaactga gcttggttac    16320
aaagcgatta acctgccagt atcaggtgca ttccacactg aacttgttgg tcacgctcaa   16380
gcgccatttg ctaaagcgat tgacgcagcc aaatttacta aaacaagccg agcactttac   16440
tcaaatgcaa ctggcggact ttatgaaagc actgctgcaa agattaaagc ctcgtttaag   16500
aaacatatgc ttcaatcagt gcgctttact agccagctag aagccatgta caacgacggc   16560
gcccgtgtat ttgttgaatt tggtccaaag aacatcttac aaaaattagt tcaaggcacg   16620
cttgtcaaca ctgaaaatga gtttgcact atctctatca accctaatcc taaagttgat    16680
agtgatctgc agcttaagca agcagcaatg cagctagcgg ttactggtgt ggtactcagt   16740
gaaattgacc cataccaagc cgatattgcc gcaccagcga aaaagtcgcc aatgagcatt   16800
tcgcttaatg ctgctaacca tatcagcaaa gcaactcgcg ctaagatggc caagtctta    16860 gagacaggta tcgtcacctc gcaaatagaa catgttattg aagaaaaaat cgttgaagtt   16920
gagaaactgg ttgaagtcga aaagatcgtc gaaaaagtgg ttgaagtaga aaagttgtt    16980 gaggttgaag ctcctgttaa ttcagtgcaa gccaatgcaa ttcaaacccg ttcagttgtc   17040
gctccagtaa tagagaacca agtcgtgtct aaaaacagta agccagcagt ccagagcatt   17100
agtggtgatg cactcagcaa cttttttgct gcacagcagc aaaccgcaca gttgcatcag   17160
cagttcttag ctattccgca gcaatatggt gagacgttca ctacgctgat gaccgagcaa   17220
gctaaactgg caagttctgg tgttgcaatt ccagagagtc tgcaacgctc aatggagcaa   17280
ttccaccaac tacaagcgca aacactacaa agccacaccc agttccttga gatgcaagcg   17340
ggtagcaaca ttgcagcgtt aaacctactc aatagcagcc aagcaactta cgctccagcc   17400
attcacaatg aagcgattca aagccaagtg gttcaaagcc aaactgcagt ccagccagta   17460
atttcaacac aagttaacca tgtgtcagag cagccaactc aagctccagc tccaaaagcg   17520
cagccagcac ctgtgacaac tgcagttcaa actgctccgg cacaagttgt tcgtcaagcc   17580
gcaccagttc aagccgctat tgaaccgatt aatacaagtg ttgcgactac aacgccttca   17640
gccttcagcg ccgaaacagc cctgagcgca acaaaagtcc aagccactat gcttgaagtg   17700
gttgctgaga aaaccggtta cccaactgaa atgctagagc ttgaaatgga tatggaagcc   17760
gatttaggca tcgattctat caagcgtgta gaaattcttg gcacagtaca agatgagcta   17820
ccgggtctac ctgagcttag ccctgaagat ctagctgagt gtcgaacgct aggcgaaatc   17880
gttgactata tgggcagtaa actgccggct gaaggctcta tgaattctca gctgtctaca   17940
ggttccgcag ctgcgactcc tgcagcgaat ggtctttctg cggagaaagt tcaagcgact   18000
atgatgtctg tggttgccga aaagactggc tacccaactg aaatgctaga gcttgaaatg   18060
gatatggaag ccgatttagg catagattct atcaagcgcg ttgaaattct tggcacagta   18120
caagatgagc taccgggtct acctgagctt agccctgaag atctagctga gtgtcgtact   18180
```

```
ctaggcgaaa tcgttgacta tatgaactct aaactcgctg acggctctaa gctgccggct    18240
gaaggctcta tgaattctca gctgtctaca agtgccgcag ctgcgactcc tgcagcgaat    18300
ggtctctctg cggagaaagt tcaagcgact atgatgtctg tggttgccga aaagactggc    18360
tacccaactg aaatgctaga acttgaaatg gatatggaag ctgaccttgg catcgattca    18420
atcaagcgcg ttgaaattct tggcacagta caagatgagc taccgggttt acctgagcta    18480
aatccagaag atttggcaga gtgtcgtact cttggcgaaa tcgtgactta tatgaactct    18540
aaactcgctg acggctctaa gctgccagct gaaggctcta tgcactatca gctgtctaca    18600
agtaccgctg ctgcgactcc tgtagcgaat ggtctctctg cagaaaaagt tcaagcgacc    18660
atgatgtctg tagttgcaga taaaactggc tacccaactg aaatgcttga acttgaaatg    18720
gatatggaag ccgatttagg tatcgattct atcaagcgcg ttgaaattct tggcacagta    18780
caagatgagc taccgggttt acctgagcta aatccagaag atctagcaga gtgtcgcacc    18840
ctaggcgaaa tcgttgacta tatgggcagt aaactgccgg ctgaaggctc tgctaataca    18900
agtgccgctg cgtctcttaa tgttagtgcc gttgcggcgc ctcaagctgc tgcgactcct    18960
gtatcgaacg gtctctctgc agagaaagtg caaagcacta tgatgtcagt agttgcagaa    19020
aagaccggct acccaactga aatgctagaa cttggcatgg atatgaagc cgatttaggt    19080 atcgactcaa ttaaacgcgt tgagattctt ggcacagtac aagatgagct accgggtcta    19140
ccagagctta atcctgaaga tttagctgag tgccgtacgc tgggcgaaat cgttgactat    19200
atgaactcta agctggctga cggctctaag cttccagctg aaggctctgc taatacaagt    19260
gccactgctg cgactcctgc agtgaatggt ctttctgctg acaaggtaca ggcgactatg    19320
atgtctgtag ttgctgaaaa gaccggctac ccaactgaaa tgctagaact tggcatggat    19380
atggaagcag accttggtat tgattctatt aagcgcgttg aaattcttgg cacagtacaa    19440
gatgagctcc caggtttacc tgagcttaat cctgaagatc tcgctgagtg ccgcacgctt    19500
ggcgaaatcg ttagctatat gaactctcaa ctggctgatg gctctaaact ttctacaagt    19560
gcggctgaag gctctgctga tacaagtgct gcaaatgctg caaagccggc agcaatttcg    19620
gcagaaccaa gtgttgagct tcctcctcat agcgaggtag cgctaaaaaa gcttaatgcg    19680
gcgaacaagc tagaaaattg tttcgccgca gacgcaagtt ttgtgattaa cgatgatggt    19740
cacaacgcag gcgttttagc tgagaaactt attaaacaag gcctaaaagt agccgttgtg    19800
cgtttaccga aaggtcagcc tcaatcgcca ctttcaagcg atgttgctag ctttgagctt    19860
gcctcaagcc aagaatctga gcttgaagcc agtatcactg cagttatcgc gcagattgaa    19920
actcaggttg gcgctattgg tggctttatt cacttgcaac cagaagcgaa tacagaagag    19980
caaacggcag taaacctaga tgcgcaaagt tttactcacg ttagcaatgc gttcttgtgg    20040
gccaaattat tgcaaccaaa gctcgttgct ggagcagatg cgcgtcgctg ttttgtaaca    20100
gtaagccgta tcgacggtgg ctttggttac ctaaatactg acgccctaaa agatgctgag    20160
ctaaaccaag cagcattagc tggtttaact aaaaaccttaa gccatgaatg gccacaagtg    20220
ttctgtcgcg cgctagatat tgcaacagat gttgatgcaa cccatcttgc tgatgcaatc    20280
accagtgaac tatttgatag ccaagctcag ctacctgaag tgggcttaag cttaattgat    20340
ggcaaagtta accgcgtaac tctagttgct gctgaagctg cagataaaac agcaaaagca    20400
gagcttaaca gcacagataa aatcttagtg actggtgggg caaaaggggt gacatttgaa    20460
tgtgcactgg cattagcatc tcgcagccag tctcacttta tcttagctgg gcgcagtgaa    20520
ttacaagctt taccaagctg ggctgagggt aagcaaaacta gcgagctaaa atcagctgca    20580
```

```
atcgcacata ttatttctac tggtcaaaag ccaacgccta agcaagttga agccgctgtg    20640
tggccagtgc aaagcagcat tgaaattaat gccgccctag ccgcctttaa caaagttggc    20700
gcctcagctg aatacgtcag catggatgtt accgatagcg ccgcaatcac agcagcactt    20760
aatggtcgct caaatgagat caccggtctt attcatggcg caggtgtact agccgacaag    20820
catattcaag acaagactct tgctgaactt gctaaagttt atggcactaa agtcaacggc    20880
ctaaaagcgc tgctcgcggc acttgagcca agcaaaatta aattacttgc tatgttctca    20940
tctgcagcag gtttttacgg taatatcggc caaagcgatt acgcgatgtc gaacgatatt    21000
cttaacaagg cagcgctgca gttcaccgct cgcaacccac aagctaaagt catgagcttt    21060 aactgggtc cttgggatgg cggcatggtt aacccgcgc ttaaaaagat gtttaccgag    21120
cgtggtgtgt acgttattcc actaaaagca ggtgcagagc tatttgccac tcagctattg    21180
gctgaaactg gcgtgcagtt gctcattggt acgtcaatgc aaggtggcag cgacactaaa    21240
gcaactgaga ctgcttctgt aaaaaagctt aatgcgggtg aggtgctaag tgcatcgcat    21300
ccgcgtgctg gtgcacaaaa aacaccacta caagctgtca ctgcaacgcg tctgttaacc    21360
ccaagtgcca tggtcttcat tgaagatcac cgcattggcg gtaacagtgt gttgccaacg    21420
gtatgcgcca tcgactggat gcgtgaagcg gcaagcgaca tgcttggcgc tcaagttaag    21480
gtacttgatt acaagctatt aaaaggcatt gtatttgaga ctgatgagcc gcaagagtta    21540
acacttgagc taacgccaga cgattcagac gaagctacgc tacaagcatt aatcagctgt    21600
aatgggcgtc cgcaatacaa ggcgacgctt atcagtgata tgccgatat taagcaactt    21660 aacaagcagt ttgatttaag cgctaaggcg attaccacag caaaagagct ttatagcaac    21720
ggcaccttgt tccacggtcc gcgtctacaa gggatccaat ctgtagtgca gttcgatgat    21780
caaggcttaa ttgctaaagt cgctctgcct aaggttgaac ttagcgattg tggtgagttc    21840
ttgccgcaaa cccacatggg tggcagtcaa ccttttgctg aggacttgct attacaagct    21900
atgctggttt gggctcgcct taaaactggc tcggcaagtt tgccatcaag cattggtgag    21960
tttacctcat accaaccaat ggcctttggt gaaactggta ccatagagct tgaagtgatt    22020
aagcacaaca aacgctcact tgaagcgaat gttgcgctat atcgtgacaa cggcgagtta    22080
agtgccatgt ttaagtcagc taaaatcacc attagcaaaa gcttaaattc agcattttta    22140
cctgctgtct tagcaaacga cagtgaggcg aattagtgga acaaacgcct aaagctagtg    22200
cgatgccgct gcgcatcgca cttatcttac tgccaacacc gcagtttgaa gttaactctg    22260
tcgaccagtc agtattagcc agctatcaaa cactgcagcc tgagctaaat gccctgctta    22320
atagtgcgcc gacacctgaa atgctcagca tcactatctc agatgatagc gatgcaaaca    22380
gctttgagtc gcagctaaat gctgcgacca acgcaattaa caatggctat atcgtcaagc    22440
ttgctacggc aactcacgct ttgttaatgc tgcctgcatt aaaagcggcg caaatgcgga    22500
tccatcctca tgcgcagctt gccgctatgc agcaagctaa atcgacgcca atgagtcaag    22560
tatctggtga gctaaagctt ggcgctaatg cgctaagcct agctcagact aatgcgctgt    22620
ctcatgcttt aagccaagcc aagcgtaact taactgatgt cagcgtgaat gagtgttttg    22680
agaacctcaa aagtgaacag cagttcacag aggtttattc gcttattcag caacttgcta    22740
gccgcaccca tgtgagaaaa gaggttaatc aaggtgtgga acttggccct aaacaagcca    22800
aaagccacta ttggtttagc gaatttcacc aaaaccgtgt tgctgccatc aactttatta    22860
atggccaaca agcaaccagc tatgtgctta ctcaaggttc aggattgtta gctgcgaaat    22920
```

```
caatgctaaa ccagcaaaga ttaatgttta tcttgccggg taacagtcag caacaaataa   22980
ccgcatcaat aactcagtta atgcagcaat tagagcgttt gcaggtaact gaggttaatg   23040
agctttctct agaatgccaa ctagagctgc tcagcataat gtatgacaac ttagtcaacg   23100
cagacaaact cactactcgc gatagtaagc ccgcttatca ggctgtgatt caagcaagct   23160
ctgttagcgc tgcaaagcaa gagttaagcg cgcttaacga tgcactcaca cgcgctgtttg  23220 ctgagcaaac aaacgccaca tcaacgaata aaggcttaat ccaatacaaa acaccggcgg   23280
gcagttactt aaccctaaca ccgcttggca gcaacaatga caacgcccaa gcgggtcttg   23340
cttttgtcta tccgggtgtg ggaacggttt acgccgatat gcttaatgag ctgcatcagt   23400
acttccctgc gctttacgcc aaacttgagc gtgaaggcga tttaaaggcg atgctacaag   23460
cagaagatat ctatcatctt gaccctaaac atgctgccca aatgagctta ggtgacttag   23520
ccattgctgg cgtgggggagc agctaccgtg taactcagct gctcaccgat gagtttaata   23580
ttaagcctaa ttttgcatta ggttactcaa tgggtgaagc atcaatgtgg gcaagcttag   23640
gcgtatggca aaacccgcat gcgctgatca gcaaaaccca aaccgacccg ctatttactt   23700
ctgctatttc cggcaaattg accgcggtta gacaagcttg gcagcttgat gataccgcag   23760
cggaaatcca gtggaatagc tttgtggtta gaagtgaagc agcgccgatt gaagccttgc   23820
taaaagatta cccacacgct tacctcgcga ttattcaagg ggatacctgc gtaatcgctg   23880
gctgtgaaat ccaatgtaaa gcgctacttg cagcactggg taaacgcggt attgcagcta   23940
atcgtgtaac ggcgatgcat acgcagcctg cgatgcaaga gcatcaaaat gtgatggatt   24000
tttatctgca accgttaaaa gcagagcttc ctagtgaaat aagctttatc agcgccgctg   24060
atttaactgc caagcaaacg gtgagtgagc aagcacttag cagccaagtc gttgctcagt   24120
ctattgccga caccttctgc caaaccttgg actttaccgc gctagtacat cacgcccaac   24180
atcaaggcgc taagctgttt gttgaaattg gcgcggatag acaaaactgc accttgatag   24240
acaagattgt taaacaagat ggtgccagca gtgtacaaca tcaaccttgt tgcacagtgc   24300
ctatgaacgc aaaaggtagc caagatatta ccagcgtgat taaagcgctt ggccaattaa   24360
ttagccatca ggtgccatta tcggtgcaac catttattga tggactcaag cgcgagctaa   24420
cactttgcca attgaccagc caacagctgg cagcacatgc aaatgttgac agcaagtttg   24480
agtctaacca agaccattta cttcaagggg aagtctaatg tcattaccag acaatgcttc   24540
taaccacctt tctgccaacc agaaaggcgc atctcaggca agtaaaacca gtaagcaaag   24600
caaaatcgcc attgtcggtt tagccactct gtatccagac gctaaaaccc gcaagaatt   24660 ttggcagaat ttgctggata aacgcgactc tcgcagcacc ttaactaacg aaaaactcgg   24720
cgctaacagc caagattatc aaggtgtgca aggccaatct gaccgttttt attgtaataa   24780
aggcggctac attgagaact tcagctttaa tgctgcaggc tacaaattgc cggagcaaag   24840
cttaaatggc ttggacgaca gcttcctttg ggcgctcgat actagccgta acgcactaat   24900
tgatgctggt attgatatca acggcgctga tttaagccgc gcaggtgtag tcatgggcgc   24960
gctgtcgttc ccaactaccc gctcaaacga tctgttttgg ccaatttatc acagcgccgt   25020
tgaaaaagcc ctgcaagata aactaggcgt aaaggcattt aagctaagcc caactaatgc   25080
tcataccgct cgcgcggcaa atgagagcag cctaaatgca gccaatggtg ccattgccca   25140
taacagctca aaagtggtgg ccgatgcact tggccttggc ggcgcacaac taagcctaga   25200
tgctgcctgt gctagttcgg tttactcatt aaagcttgcc tgcgattacc taagcactgg   25260
caaagccgat atcatgctag caggcgcagt atctggcgcg gatccttttct ttattaatat   25320
```

-continued

```
gggattctca atcttccacg cctacccaga ccatggtatc tcagtaccgt ttgatgccag     25380
cagtaaaggt ttgtttgctg gcgaaggcgc tggcgtatta gtgcttaaac gtcttgaaga     25440
tgccgagcgc gacaatgaca aaatctatgc ggttgttagc ggcgtaggtc tatcaaacga     25500
cggtaaaggc cagtttgtat taagccctaa tccaaaaggt caggtgaagg cctttgaacg     25560
tgcttatgct gccagtgaca ttgagccaaa agacattgaa gtgattgagt gccacgcaac     25620
aggcacaccg cttggcgata aaattgagct cacttcaatg gaaaccttct ttgaagacaa     25680
gctgcaaggc accgatgcac cgttaattgg ctcagctaag tctaacttag ccacctatt      25740 aactgcagcg catgcgggga tcatgaagat gatcttcgcc atgaaagaag gttacctgcc     25800
gccaagtatc aatattagtg atgctatcgc ttcgccgaaa aaactcttcg gtaaaccaac     25860
cctgcctagc atggttcaag gctggccaga taagccatcg aataatcatt ttggtgtaag     25920
aacccgtcac gcaggcgtat cggtatttgg ctttggtggc tgtaacgccc atctgttgct     25980
tgagtcatac aacggcaaag gaacagtaaa ggcagaagcc actcaagtac cgcgtcaagc     26040
tgagccgcta aaagtggttg gccttgcctc gcactttggg cctcttagca gcattaatgc     26100
actcaacaat gctgtgaccc aagatgggaa tggctttatc gaactgccga aaaagcgctg     26160
gaaaggcctt gaaaagcaca gtgaactgtt agctgaattt ggcttagcat ctgcgccaaa     26220
aggtgcttat gttgataact tcgagctgga cttttttacgc tttaaactgc cgccaaacga     26280
agatgaccgt ttgatctcac agcagctaat gctaatgcga gtaacagacg aagccattcg     26340
tgatgccaag cttgagccgg ggcaaaaagt agctgtatta gtggcaatgg aaactgagct     26400
tgaactgcat cagttccgcg gccggggttaa cttgcatact caattagcgc aaagtcttgc     26460
cgccatgggc gtgagtttat caacggatga ataccaagcg cttgaagcca tcgccatgga     26520
cagcgtgctt gatgctgcca agctcaatca gtacaccagc tttattggta atattatggc     26580
gtcacgcgtg gcgtcactat gggactttaa tggcccagcc ttcactattt cagcagcaga     26640
gcaatctgtg agccgctgta tcgatgtggc gcaaaacctc atcatggagg ataacctaga     26700
tgcggtggtg attgcagcgg tcgatctctc tggtagcttt gagcaagtca ttcttaaaaa     26760
tgccattgca cctgtagcca ttgagccaaa cctcgaagca agccttaatc caacatcagc     26820
aagctggaat gtcggtgaag gtgctggcgc ggtcgtgctt gttaaaaatg aagctacatc     26880
gggctgctca tacggccaaa ttgatgcact tggctttgct aaaactgccg aaacagcgtt     26940
ggctaccgac aagctactga gccaaactgc cacagacttt aataaggtta aagtgattga     27000
aactatggca gcgcctgcta gccaaattca attagcgcca atagttagct ctcaagtgac     27060
tcacactgct gcagagcagc gtgttggtca ctgctttgct gcagcgggta tggcaagcct     27120
attacacggc ttacttaact taaatactgt agcccaaacc aataaagcca attgcgcgct     27180
tatcaacaat atcagtgaaa accaattatc acagctgttg attagccaaa cagcgagcga     27240
acaacaagca ttaaccgcgc gtttaagcaa tgagcttaaa tccgatgcta acaccaact     27300 ggttaagcaa gtcaccttag gtggccgtga tatctaccag catattgttg atacaccgct     27360
tgcaagcctt gaaagcatta ctcagaaatt ggcgcaagcg acagcatcga cagtggtcaa     27420
ccaagttaaa cctattaagg ccgctggctc agtcgaaatg gctaactcat tcgaaacgga     27480
aagctcagca gagccacaaa taacaattgc agcacaacag actgcaaaca ttggcgtcac     27540
cgctcaggca accaaacgtg aattaggtac cccaccaatg acaacaaata ccattgctaa     27600
tacagcaaat aatttagaca agactcttga gactgttgct ggcaatactg ttgctagcaa     27660
```

```
ggttggctct ggcgacatag tcaattttca acagaaccaa caattggctc aacaagctca   27720
cctcgccttt cttgaaagcc gcagtgcggg tatgaaggtg gctgatgctt tattgaagca   27780
acagctagct caagtaacag gccaaactat cgataatcag gccctcgata ctcaagccgt   27840
cgatactcaa acaagcgaga atgtagcgat tgccgcagaa tcaccagttc aagttacaac   27900
acctgttcaa gttacaacac ctgttcaaat cagtgttgtg gagttaaaac cagatcacgc   27960
taatgtgcca ccatacacgc cgccagtgcc tgcattaaag ccgtgtatct ggaactatgc   28020
cgatttagtt gagtacgcag aaggcgatat cgccaaggta tttggcagtg attatgccat   28080
tatcgacagc tactcgcgcc gcgtacgtct accgaccact gactacctgt tggtatcgcg   28140
cgtgaccaaa cttgatgcga ccatcaatca atttaagcca tgctcaatga ccactgagta   28200
cgacatccct gttgatgcgc cgtacttagt agacggacaa atcccttggg cggtagcagt   28260
agaatcaggc caatgtgact tgatgcttat tagctatctc ggtatcgact ttgagaacaa   28320
aggcgagcgg gtttatcgac tactcgattg taccctcacc ttcctaggcg acttgccacg   28380
tggcggagat accctacgtt acgacattaa gatcaataac tatgctcgca acggcgacac   28440
cctgctgttc ttcttctcgt atgagtgttt tgttggcgac aagatgatcc tcaagatgga   28500
tggcggctgc gctggcttct tcactgatga agagcttgcc gacggtaaag gcgtgattcg   28560
cacagaagaa gagattaaag ctcgcagcct agtgcaaaag caacgcttta atccgttact   28620
agattgtcct aaaacccaat ttagttatgg tgatattcat aagctattaa ctgctgatat   28680
tgagggttgt tttggcccaa gccacagtgg cgtccaccag ccgtcacttt gtttcgcatc   28740
tgaaaaattc ttgatgattg aacaagtcag caaggttgat cgcactggcg gtacttgggg   28800
acttggctta attgagggtc ataagcagct tgaagcagac cactggtact cccatgtca    28860
tttcaagggc gaccaagtga tggctggctc gctaatggct gaaggttgtg ccagttatt    28920
gcagttctat atgctgcacc ttggtatgca tacccaaact aaaaatggtc gtttccaacc   28980
tcttgaaaac gcctcacagc aagtacgctg tcgcggtcaa gtgctgccac aatcaggcgt   29040
gctaacttac cgtatggaag tgactgaaat cggtttcagt ccacgcccat atgctaaagc   29100
taacatcgat atcttgctta atggcaaagc ggtagtggat ttccaaaacc tagggtgat    29160
gataaaagag gaagatgagt gtactcgtta tccacttttg actgaatcaa caacggctag   29220
cactgcacaa gtaaacgctc aaacaagtgc gaaaaaggta tacaagccag catcagtcaa   29280
tgcgccatta atggcacaaa ttcctgatct gactaaagag ccaaacaagg gcgttattcc   29340
gatttcccat gttgaagcac caattacgcc agactacccg aaccgtgtac ctgatacagt   29400
gccattcacg ccgtatcaca tgtttgagtt tgctacaggc aatatcgaaa actgtttcgg   29460
gccagagttc tcaatctatc gcggcatgat cccaccacgt acaccatgcg gtgacttaca   29520
agtgaccaca cgtgtgattg aagttaacgg taagcgtggc gactttaaaa agccatcatc   29580
gtgtatcgct gaatatgaag tgcctgcaga tgcgtggtat ttcgataaaa acagccacgg   29640
cgcagtgatg ccatattcaa ttttaatgga gatctcactg caacctaacg gctttatctc   29700
aggttacatg ggcacaaccc taggcttccc tggccttgag ctgttcttcc gtaacttaga   29760
cggtagcggt gagttactac gtgaagtaga tttacgtggt aaaaccatcc gtaacgactc   29820
acgtttatta tcaacagtga tggccggcac taacatcatc caaagcttta gcttcgagct   29880
aagcactgac ggtgagcctt tctatcgcgg cactgcggta tttggctatt ttaaaggtga   29940
cgcacttaaa gatcagctag gcctagataa cggtaaagtc actcagccat ggcatgtagc   30000
taacggcgtt gctgcaagca ctaaggtgaa cctgcttgat aagagctgcc gtcactttaa   30060
```

```
tgcgccagct aaccagccac actatcgtct agccggtggt cagctgaact ttatcgacag   30120
tgttgaaatt gttgataatg gcggcaccga aggtttaggt tacttgtatg ccgagcgcac   30180
cattgaccca agtgattggt tcttccagtt ccacttccac caagatccgg ttatgccagg   30240
ctccttaggt gttgaagcaa ttattgaaac catgcaagct tacgctatta gtaaagactt   30300
gggcgcagat ttcaaaaatc ctaagtttgg tcagatttta tcgaacatca agtggaagta   30360
tcgcggtcaa atcaatccgc tgaacaagca gatgtctatg gatgtcagca ttacttcaat   30420
caaagatgaa gacggtaaga aagtcatcac aggtaatgcc agcttgagta agatggtct   30480 gcgcatatac gaggtcttcg atatagctat cagcatcgaa gaatctgtat aaatcggagt   30540
gactgtctgg ctattttact caatttctgt gtcaaaagtg ctcacctata ttcataggct   30600
gcgcgctttt ttctggaaat tgagcaaaag tatctgcgtc ctaactcgat ttataagaat   30660
ggtttaattg aaaagaacaa cagctaagag ccgcaagctc aatataaata attaagggtc   30720
ttacaaataa tgaatcctac agcaactaac gaaatgcttt ctccgtggcc atgggctgtg   30780
acagagtcaa atatcagttt tgacgtgcaa gtgatggaac acaacttaa agattttagc   30840 cgggcatgtt acgtggtcaa tcatgccgac cacggctttg gtattgcgca aactgccgat   30900
atcgtgactg aacaagcggc aaacagcaca gatttacctg ttagtgcttt tactcctgca   30960
ttaggtaccg aaagcctagg cgacaataat ttccgccgcg ttcacggcgt taaatacgct   31020
tattacgcag cgctatggc aaacggtatt tcatctgaag agctagtgat tgccctaggt   31080
caagctggca ttttgtgtgg ttcgtttgga gcagccggtc ttattccaag tcgcgttgaa   31140
gcggcaatta accgtattca agcagcgctg ccaaatggcc cttatatgtt taaccttatc   31200
catagtccta gcgagccagc attagagcgt ggcagcgtag agctattttt aaagcataag   31260
gtacgcaccg ttgaagcatc agcttcttta ggtctaacac cacaaatcgt ctattaccgt   31320
gcagcaggat tgagccgaga cgcacaaggt aaagttgtgg ttggtaacaa ggttatcgct   31380
aaagtaagtc gcaccgaagt ggctgaaaag tttatgatgc cagcgcccgc aaaaatgcta   31440
caaaaactag ttgatgacgg ttcaattacc gctgagcaaa tggagctggc gcaacttgta   31500
cctatggctg acgacatcac tgcagaggcc gattcaggtg gccatactga taaccgtcca   31560
ttagtaacat tgctgccaac catttttagcg ctgaaagaag aaattcaagc taaataccaa   31620
tacgacactc ctattcgtgt cggttgtggt ggcggtgtgg gtacgcctga tgcagcgctg   31680
gcaacgttta acatgggcgc ggcgtatatt gttaccggct ctatcaacca agcttgtgtt   31740
gaagcgggcg caagtgatca cactcgtaaa ttacttgcca ccactgaaat ggccgatgtg   31800
actatggcac cagctgcaga tatgttcgag atgggcgtaa aactgcaggt ggttaagcgc   31860
ggcacgctat tcccaatgcg cgctaacaag ctatatgaga tctacacccg ttacgattca   31920
atcgaagcga tcccattaga cgagcgtgaa aagcttgaga acaagtatt ccgctcaagc   31980 ctagatgaaa tatgggcagg tacagtggcg cactttaacg agcgcgaccc taagcaaatc   32040
gaacgcgcag agggtaaccc taagcgtaaa atggcattga ttttccgttg gtacttaggt   32100
ctttctagtc gctggtcaaa ctcaggcgaa gtgggtcgtg aaatggatta tcaaatttgg   32160
gctggccctg ctctcggtgc atttaaccaa tgggcaaaag gcagttactt agataactat   32220
caagaccgaa atgccgtcga tttggcaaag cacttaatgt acggcgcggc ttacttaaat   32280
cgtattaact cgctaacggc tcaaggcgtt aaagtgccag cacagttact tcgctggaag   32340
ccaaaccaaa gaatggccta atacacttac aaagcaccag tctaaaaagc cactaatctt   32400
```

-continued

```
gattagtggc ttttttttatt gtggtcaata tgaggctatt tagcctgtaa gcctgaaaat   32460
atcagcactc tgactttaca agcaaattat aattaaggca gggctctact catttatact   32520
gctagcaaac aagcaagttg cccagtaaaa caacaaggta cctgatttat atcgtcataa   32580
aagttggcta gagattcgtt attgatcttt actgattaga gtcgctctgt ttggaaaaag   32640
gtttctcgtt atcatcaaaa tacactctca aacctttaat caattacaac ttaggctttc   32700
tgcgggcatt tttatcttat ttgccacagc tgtatttgcc tttaggtttt gggtgcaact   32760
accattaatt gaggcctcat tagttaaatt atctgagcaa gagctcacct ctttaaatta   32820
cgcttttcag caaatgagaa agccactaca aaccattaat tacgactatg cggtgtggga   32880
cagaacctac agctatatga aatcaaactc agcgagcgct aaaaggtact atgaaaaaca   32940
tgagtaccca gatgatacgt tcaagagttt aaaagtcgac ggagtattta tattcaaccg   33000
tacaaatcag ccagttttta gtaaaggttt taatcataga aatgatatac cgctggtctt   33060
tgaattaact gactttaaac aacatccaca aaacatcgca ttatctccac aaaccaaaca   33120
ggcacaccca ccggcaagta agccgttaga ctcccctgat gatgtgcctt ctacccatgg   33180
ggttatcgcc acacgatacg gtccagcaat ttatagctct accagcattt taaaatctga   33240
tcgtagcggc tcccaacttg gttatttagt cttcattagg ttaattgatg aatggttcat   33300
cgctgagcta tcgcaataca ctgccgcagg tgttgaaatc gctatggctg atgccgcaga   33360
cgcacaatta gcgagattag cgcaaacac taagcttaat aaagtaaccg ctacatccga   33420
acggttaata actaatgtcg atggtaagcc tctgttgaag ttagtgcttt accataccaa   33480
taaccaaccg ccgccgatgc tagattacag tataataatt ctattagttg agatgtcatt   33540
tttactgatc ctcgcttatt tcctttactc ctacttctta gtcaggccag ttagaaagct   33600
ggcttcagat attaaaaaaa tggataaaag tcgtgaaatt aaaaagctaa ggtatcacta   33660
ccctattact gagctagtca aagttgcgac tcacttcaac gccctaatgg ggacgattca   33720
ggaacaaact aaacagctta atgaacaagt ttttattgat aaattaacca atattcccaa   33780
tcgtcgcgct tttgagcagc gacttgaaac ctattgccaa ctgctagccc ggcaacaaat   33840
tggctttact ctcatcattg ccgatgtgga tcattttaaa gagtacaacg atactcttgg   33900
gcaccttgct ggggatgaag cattaataaa agtggcacaa acactatcgc aacagtttta   33960
ccgtgcagaa gatatttgtg cccgttttgg tggtgaagaa tttattatgt tatttcgaga   34020
catacctgat gagcccttgc agagaaagct cgatgcgatg ctgcactctt ttgcagagct   34080
caacctacct catccaaact catcaaccgc taattacgtt actgtgagcc ttggggtttg   34140
cacagttgtt gctgttgatg attttgaatt taaaagtgag tcgcatatta ttggcagtca   34200
ggctgcatta atcgcagata aggcgcttta tcatgctaaa gcctgtggtc gtaaccagtt   34260
gtcaaaaact actattactg ttgatgagat tgagcaatta gaagcaaata aaatcggtca   34320
tcaagcctaa actcgttcga gtactttccc ctaagtcaga gctatttgcc acttcaagat   34380
gtggctacaa ggcttactct ttcaaaacct gcatcaatag aacacagcaa aatacaataa   34440
tttaagtcaa tttagcctat taaacagagt taatgacagc tcatggtcgc aacttattag   34500
ctatttctag caatataaaa acttatccat tagtagtaac caataaaaaa actaatatat   34560
aaaactattt aatcattatt ttacagatga ttagctacca cccaccttaa gctggctata   34620
ttcgcactag taaaaataaa cattagatcg ggttcagatc aatttacgag tctcgtataa   34680
aatgtacaat aattcactta atttaatact gcatattttt acaagtagag agcggtgatg   34740
aaacaaaata cgaaaggctt tacattaatt gaattagtca tcgtgattat tattctcggt   34800
```

```
atacttgctg ctgtggcact gccgaaattc atcaatgttc aagatgacgc taggatctct    34860
gcgatgagcg gtcagttttc atcatttgaa agtgccgtaa aactatacca tagcggttgg    34920
ttagccaaag gctacaacac tgcggttgaa aagctctcag gctttggcca aggtaatgtt    34980
gcatcaagtg acacaggttt tccgtactca acatcaggca cgagtactga tgtgcataaa    35040
gcttgtggtg aactatggca tggcattacc gatacagact tcacaattgg tgcggttagt    35100
gatggcgatc taatgactgc agatgtcgat attgcttaca cctatcgtgg tgatatgtgt    35160
atctatcgcg atctgtattt tattcagcgc tcattaccta ctaaggtgat gaactacaaa    35220
tttaaaactg gtgaaataga aattattgat gctttctaca accctgacgg ctcaactggt    35280
caattaccat aaatttggcg cttatctaag ttgtacttgc tctgaccgac acaaataatg    35340
tcgtttctca gcatatatca aaatacacag caaaaatttg gggttagcta tatagctaac    35400
cccaaatcat atctaacttt acactgcatc taattccaaa cagtatccag ccaaaagcct    35460
aaactattgt tgactcagcg ctaaaatatg cgatgcaaca aacaagtctt ggatcgcaat    35520
acctgagcta tcaaaaatgg tcacctcatc agcactttga cgtcctgttg cggactcgtt    35580
tatcacctga ccaatctcaa ttatcggcgt atttctgcta tgttgaaact caccaataac    35640
aatagattga gaagcaaagt cgcaaaacaa gcgagcatga ctatataggt cagttggcaa    35700
ctcttgctta cccactttat cagcgcccat gcagaaaata tgcgttcctg cttgtaccca    35760
ctgcgcttca aataaaggcg cttgagctgt ggttgctgtg ataataatat ctgcttgttc    35820
acaagcagct tgtgcatcac aagcttcggc attaatgcct ttttctaata aacgcttaac    35880
caagttttca gttttgctag cactacggcc aactaccaat accttagtta atgaacgaac    35940
cttgctcact gctagcactt catattcagc ctgatgaccg gtaccaaaaa cagttaatac    36000
cgtagcatct tctctcgcga ggtaactcac tgctactgca tcggcagcac cagtgcggta    36060
agcattaacg gtagtggcag caatcaccgn ctgcaacata ccggttaatg gatcgagtaa    36120
aaatacgtta gtgccgtggc atggtaaacc atgtttatgg ttatcaggcc aatagctgcc    36180
tgttttccag ccgacaaggt ttggcgttga agccgacttt aatgagaaca tttcattaag    36240
gttcgcgccc tgtgcattaa ctaccgggaa caaggttgct ttatcatcta cggcagcgac    36300
aaacgcttct ttaacagcga tataagccag ctcatgggag atgagctttg atgtttgcgc    36360
ttcagttaaa tagatcatat taccacccct gcactcgatt ccagatctca tagccaccat    36420
tatcaccatc agtatcaaat acatggtact gagcgtgcat tgaagctgtt gcacaggcgt    36480
ggttcggcaa aatatgtaga cgactaccta ccgggaactg cgctaaatca ataacgccgc    36540
catcaactgc ttcaataatg ccgtgctctt gattaacagt tataacctgt agacctgata    36600
acacgtgacc gctgtcgtca cacactaaac cataaccaca atcttttggc tgctctgcag    36660
tacctctatc acccgaaaga gccatccaac ccgcatcaat gaaaatccag ttttttatcag   36720
gattatgacc aataacactg gtcactaccg ttgcggcaat atcagttaac tgacacacgt    36780
ttagccctgc catgactaaa tcgaagaagg tgtacacacc cgctctaacc tcggtgatcc    36840
catcaaggtt ttgatagctt tgcgctgttg gtgttgaacc aatactaacg atgtcacatt    36900
gcatacccgc tgcgcgaatg cgtcagcagc ttgtacagcc gctgcaactt cattttgcgc    36960
cgcatcaatt aattgctgtt tttcaaaaca ttgatatgac tcaccagcgt gagtnagtac    37020
gccgtgaaaa ctcgctgcgc cagacgttag tatctgagca atttcaatca acttatcggc    37080
ttccggtgga ataccaccac gatggccatc acaatcaatt tcaattaatg ctggtatttg    37140
```

-continued

```
gcagtcataa gaaccacaga aatgatttag ctgatgcgct tgctcaacac tatcaagtaa      37200
aactcttgca ttaataccct ggtccaacat tttagcaata cgcggcaact taccatcggc      37260
aatacctact gcataaataa tgtctgtgta acctttagat gctaaggcct cggcctcttt      37320
taccgttgat acagtgactg gtgagttttt agtgggtaat aaaaactcgg ctgcttcaag      37380
tgatcttaac gttttaaaat gcggtcttag gtttgcacct aatccttcaa ttttttggcg      37440
tagttgactg aggttattaa taaatactgg cttatttaca tataaaaacg gtgtatcaat      37500
tgcttgatac tgactttgct gagtcgtgga aagtatttga gtagatggca tctttaatat      37560
cctagttcat caatcaatct aacaagtttg atgcctagcc acagtggctt gtattcatga      37620
tgctttggaa aatgcttata ttcaaagtat ttgaaagaca tcaaacttct tgtttaatgc      37680
tcagtatcca ccagcacgca tttattttat attaactatt atcaagatat agattaggtt      37740
caaaccaaat gattagtact gaagatctac gttttatcag cgtaatcgcc agtcatcgca      37800
ccttagctga tgccgctaga acactaaata tcacgccacc atcagtgaca ttaaggttgc      37860
agcatattga aaagaaacta tcgattagcc tgatc                                 37895
```

```
<210> SEQ ID NO 2
<211> LENGTH: 654
<212> TYPE: PRT
<213> ORGANISM: Shewanella putrefaciens

<400> SEQUENCE: 2
```

| | | | | | | | | | | | | | | |
|---|---|---|---|---|---|---|---|---|---|---|---|---|---|---|
| Met | Lys | Gln | Thr | Leu | Met | Ala | Ile | Ser | Ile | Met | Ser | Leu | Phe | Ser | Phe |
| 1 | | | | 5 | | | | | 10 | | | | | 15 | |

Met Lys Gln Thr Leu Met Ala Ile Ser Ile Met Ser Leu Phe Ser Phe
1               5                   10                  15

Asn Ala Leu Ala Ala Gln His Glu His Asp His Ile Thr Val Asp Tyr
            20                  25                  30

Glu Gly Lys Ala Ala Thr Glu His Thr Ile Ala His Asn Gln Ala Val
        35                  40                  45

Ala Lys Thr Leu Asn Phe Ala Asp Thr Arg Ala Phe Glu Gln Ser Ser
    50                  55                  60

Lys Asn Leu Val Ala Lys Phe Asp Lys Ala Thr Ala Asp Ile Leu Arg
65                  70                  75                  80

Ala Glu Phe Ala Phe Ile Ser Asp Glu Ile Pro Asp Ser Val Asn Pro
                85                  90                  95

Ser Leu Tyr Arg Gln Ala Gln Leu Asn Met Val Pro Asn Gly Tyr Lys
            100                 105                 110

Val Ser Asp Gly Ile Tyr Gln Val Arg Gly Thr Asp Leu Ser Asn Leu
        115                 120                 125

Thr Leu Ile Arg Ser Asp Asn Gly Trp Ile Ala Tyr Asp Val Leu Leu
    130                 135                 140

Thr Lys Glu Ala Ala Lys Ala Ser Leu Gln Phe Ala Leu Lys Asn Leu
145                 150                 155                 160

Pro Lys Asp Gly Asp Pro Val Val Ala Met Ile Tyr Ser His Ser His
                165                 170                 175

Ala Asp His Phe Gly Gly Ala Arg Gly Val Gln Glu Met Phe Pro Asp
            180                 185                 190

Val Lys Val Tyr Gly Ser Asp Asn Ile Thr Lys Glu Ile Val Asp Glu
        195                 200                 205

Asn Val Leu Ala Gly Asn Ala Met Ser Arg Arg Ala Ala Tyr Gln Tyr
    210                 215                 220

Gly Ala Thr Leu Gly Lys His Asp His Gly Ile Val Asp Ala Ala Leu
225                 230                 235                 240

-continued

```
Gly Lys Gly Leu Ser Lys Gly Glu Ile Thr Tyr Val Ala Pro Asp Tyr
                245                 250                 255

Thr Leu Asn Ser Glu Gly Lys Trp Glu Thr Leu Thr Ile Asp Gly Leu
            260                 265                 270

Glu Met Val Phe Met Asp Ala Ser Gly Thr Glu Ala Glu Ser Glu Met
        275                 280                 285

Ile Thr Tyr Ile Pro Ser Lys Lys Ala Leu Trp Thr Ala Glu Leu Thr
    290                 295                 300

Tyr Gln Gly Met His Asn Ile Tyr Thr Leu Arg Gly Ala Lys Val Arg
305                 310                 315                 320

Asp Ala Leu Lys Trp Ser Lys Asp Ile Asn Glu Met Ile Asn Ala Phe
                325                 330                 335

Gly Gln Asp Val Glu Val Leu Phe Ala Ser His Ser Ala Pro Val Trp
            340                 345                 350

Gly Asn Gln Ala Ile Asn Asp Phe Leu Arg Leu Gln Arg Asp Asn Tyr
        355                 360                 365

Gly Leu Val His Asn Gln Thr Leu Arg Leu Ala Asn Asp Gly Val Gly
    370                 375                 380

Ile Gln Asp Ile Gly Asp Ala Ile Gln Asp Thr Ile Pro Glu Ser Ile
385                 390                 395                 400

Tyr Lys Thr Trp His Thr Asn Gly Tyr His Gly Thr Tyr Ser His Asn
                405                 410                 415

Ala Lys Ala Val Tyr Asn Lys Tyr Leu Gly Tyr Phe Asp Met Asn Pro
            420                 425                 430

Ala Asn Leu Asn Pro Leu Pro Thr Lys Gln Glu Ser Ala Lys Phe Val
        435                 440                 445

Glu Tyr Met Gly Gly Ala Asp Ala Ala Ile Lys Arg Ala Lys Asp Asp
    450                 455                 460

Tyr Ala Gln Gly Glu Tyr Arg Phe Val Ala Thr Ala Leu Asn Lys Val
465                 470                 475                 480

Val Met Ala Glu Pro Glu Asn Asp Ser Ala Arg Gln Leu Leu Ala Asp
                485                 490                 495

Thr Tyr Glu Gln Leu Gly Tyr Gln Ala Glu Gly Ala Gly Trp Arg Asn
            500                 505                 510

Ile Tyr Leu Thr Gly Ala Gln Glu Leu Arg Val Gly Ile Gln Ala Gly
        515                 520                 525

Ala Pro Lys Thr Ala Ser Ala Asp Val Ile Ser Glu Met Asp Met Pro
    530                 535                 540

Thr Leu Phe Asp Phe Leu Ala Val Lys Ile Asp Ser Gln Gln Ala Ala
545                 550                 555                 560

Lys His Gly Leu Val Lys Met Asn Val Ile Thr Pro Asp Thr Lys Asp
                565                 570                 575

Ile Leu Tyr Ile Glu Leu Ser Asn Gly Asn Leu Ser Asn Ala Val Val
            580                 585                 590

Asp Lys Glu Gln Leu Met Val Asn Lys Ala Asp Val Asn Arg Ile Leu
        595                 600                 605

Leu Gly Gln Val Thr Leu Lys Ala Leu Leu Ala Ser Gly Asp Ala Lys
    610                 615                 620

Leu Thr Gly Asp Lys Thr Ala Phe Ser Lys Ile Ala Asp Ser Met Val
625                 630                 635                 640

Glu Phe Thr Pro Asp Phe Glu Ile Val Pro Thr Pro Val Lys
                645                 650
```

<210> SEQ ID NO 3
<211> LENGTH: 277
<212> TYPE: PRT
<213> ORGANISM: Shewanella putrefaciens

<400> SEQUENCE: 3

```
Ser Thr Lys Ala Ser Ala Arg Val Val Ala Lys Phe Asn Val Glu Glu
  1               5                  10                  15

Ala Ala Ile Ser Ile Gln Gln Cys Gln Gly Ile Ser Leu Ala Phe Arg
             20                  25                  30

Tyr Ser Asp Asp Leu His Gly Leu Leu Cys His Trp Asn Asp Ala Ala
         35                  40                  45

Asn Met Gln Gln Glu Lys Ala Glu Ile Leu Gly Leu Gly Ser Lys Gln
 50                  55                  60

Pro Glu Ala Asn Pro Lys Asn Ser Ser Glu Leu Leu Ala Leu Gly
 65                  70                  75                  80

Ile Asp Gln Lys Leu Leu Val Gln Arg Gln Asn Leu Gln His Glu Val
                 85                  90                  95

Lys His Asp Ala Ile Ala Asp Ser Ile Asp Val Cys His Ser Leu Ser
            100                 105                 110

Lys Pro Ala Asn Val Gly Leu Phe Thr Glu Ser Leu Ala Ser Phe Asp
        115                 120                 125

Phe Ala Phe Ser Lys Leu Ser Leu Ala Leu Gly Leu Gly Lys Ala Lys
130                 135                 140

Ile Tyr Ser Glu Lys Leu Ala Trp Leu Asp Phe Phe Arg Asp Arg Gln
145                 150                 155                 160

Leu Ala Glu Pro Leu Ala Leu Leu Ala Arg Lys Glu Ser Glu Ser Phe
                165                 170                 175

Tyr His Ser Leu Ile Ser His Ile Asn Thr Ser Asn Arg Cys Arg Glu
            180                 185                 190

Ile Asp Val Gly Phe Glu Ile Ser Ala Ser Asp Thr Glu Lys Ser
        195                 200                 205

Ala Gln Ser Ala Gly Lys Asn Asp Ala Thr Cys Ile Gly Val Leu Leu
    210                 215                 220

Trp Asp Gly Ser His Ser Val Asn Phe His Val Gly Thr Gln Ala Phe
225                 230                 235                 240

Gln Ala Asp Ser Leu Arg Pro Lys Gly Lys Asp Gly Tyr Glu Phe Arg
                245                 250                 255

Trp Glu Asn Pro Arg Ile Glu Ser His Gln Ser Leu Leu Ala Arg Leu
            260                 265                 270

Tyr Gly Arg Val Met
        275
```

<210> SEQ ID NO 4
<211> LENGTH: 1480
<212> TYPE: DNA
<213> ORGANISM: Shewanella putrefaciens

<400> SEQUENCE: 4

```
gctagtctta gctgasrthr ysaasragct cgaacaacag ctttaaaatt cacttcttct    60
gctgcaatac ttatttgctg acactgacca atactcagtg caaaacgata actatcatca   120
agatggaaar gvavaaaysh asnvaggaaa asrgngncys gngysraaha rgtyrsrasa   180
shscccagta acaatgcca attatcagca gcgttcattt gctgttcttt agcctcaatc    240
aaacctaaac cagactttg tggctcagcg ttaggcttat taggycyshs trasnasaaa    300
```

-continued aasnmtgngn gysaaggygy srysgnrgaa asnrysasns raactcgact ctagtaaagc 360
aagaccaata tcttgtttta acaaaacctg tcgctgatta agttgatgct caaccttgtg 420
atccgcaata gcatcggaaa tsrsrgaagy asgnysvagn arggnasngn hsgvayshsa 480
saaaaassra tcaacacaat ggctcaagct tttaggtgca ttaactccaa gaaaagtttc 540
gctcagtgca gagaagtcaa acgcaaaaga ttttagcgat aatgccagca svacyshssr 600
srysraaasn vagyhthrgs raasrhasha ahsryssraa ccaagtcctt tcgctttaat 660
gtaagactcc ttgagcgccc acaaatcaaa aaagcggtct cgctgcaagg cctctggtaa 720
cgctaacaag gctcgctttt gygyysaays tyrsrgysaa trashharga sarggnaagr 780
aaaaargysg ctgattcaga gaaataatga ctaagaatag agtggatatt ggtgctgtta 840
cggcaacgct caatgtcgac gccaaactca atactagcag agtcagtttc srgsrhtyrh 900
ssrsrhsasn thrsrasnar gcysarggas vagyhgsraa srasthrgct ccttgcttgc 960
ctgactggcg cctttattat cagcagtgca aatgcctact aatagccaat ctccactatg 1020
actcacatta aagtggaccc cggtttgagy ssraagnsra agyysasnas aathrcysgy 1080
vatrasgysr hssrvaasnh hsvagythrg ngcaaattgc gcatcactca atctaggctt 1140
acctttgtcg ccatattcaa agcgccattc attggggcgt atttcactat gttgtgacaa 1200
taaagcgcgc aaahgnaaas srargrysgy ysasgytyrg hargtrgasn rarggsrhsg 1260
nsraaargaa tagcctctta ccattaaacc ttgagtttta gcttcttgtt taatgtagcg 1320
attaacctta attaactcat cttcaggcag ccatgactta accaactcty rgyargvamt 1380
gygnthrysa aggnystyra rgasnvaysg asgrtrsrys vagtgtagtc tggttatcgc 1440
actcttgtat tgttaacgga cagaagtata aggaaatcaa 1480

<210> SEQ ID NO 5
<211> LENGTH: 970
<212> TYPE: PRT
<213> ORGANISM: Shewanella putrefaciens

<400> SEQUENCE: 5

Met Ser Met Phe Leu Asn Ser Lys Leu Ser Arg Ser Val Lys Leu Ala
1 5 10 15

Ile Ser Ala Gly Leu Thr Ala Ser Leu Ala Met Pro Val Phe Ala Glu
20 25 30

Glu Thr Ala Ala Glu Glu Gln Ile Glu Arg Val Ala Val Thr Gly Ser
35 40 45

Arg Ile Ala Lys Ala Glu Leu Thr Gln Pro Ala Pro Val Val Ser Leu
50 55 60

Ser Ala Glu Glu Leu Thr Lys Phe Gly Asn Gln Asp Leu Gly Ser Val
65 70 75 80

Leu Ala Glu Leu Pro Ala Ile Gly Ala Thr Asn Thr Ile Ile Gly Asn
85 90 95

Asn Asn Ser Asn Ser Ser Ala Gly Val Ser Ser Ala Asp Leu Arg Arg
100 105 110

Leu Gly Ala Asn Arg Thr Leu Val Leu Val Asn Gly Lys Arg Tyr Val
115 120 125

Ala Gly Gln Pro Gly Ser Ala Glu Val Asp Leu Ser Thr Ile Pro Thr
130 135 140

Ser Met Ile Ser Arg Val Glu Ile Val Thr Gly Gly Ala Ser Ala Ile
145 150 155 160

Tyr Gly Ser Asp Ala Val Ser Gly Val Ile Asn Val Ile Leu Lys Glu

-continued

```
                165                 170                 175
Asp Phe Glu Gly Phe Glu Phe Asn Ala Arg Thr Ser Gly Ser Thr Glu
                180                 185                 190
Ser Val Gly Thr Gln Glu His Ser Phe Asp Ile Leu Gly Gly Ala Asn
            195                 200                 205
Val Ala Asp Gly Arg Gly Asn Val Thr Phe Tyr Ala Gly Tyr Glu Arg
210                 215                 220
Thr Lys Glu Val Met Ala Thr Asp Ile Arg Gln Phe Asp Ala Trp Gly
225                 230                 235                 240
Thr Ile Lys Asn Glu Ala Asp Gly Gly Glu Asp Gly Ile Pro Asp
                245                 250                 255
Arg Leu Arg Val Pro Arg Val Tyr Ser Glu Met Ile Asn Ala Thr Gly
                260                 265                 270
Val Ile Asn Ala Phe Gly Gly Ile Gly Arg Ser Thr Phe Asp Ser
            275                 280                 285
Asn Gly Asn Pro Ile Ala Gln Gln Glu Arg Asp Gly Thr Asn Ser Phe
290                 295                 300
Ala Phe Gly Ser Phe Pro Asn Gly Cys Asp Thr Cys Phe Asn Thr Glu
305                 310                 315                 320
Ala Tyr Glu Asn Tyr Ile Pro Gly Val Glu Arg Ile Asn Val Gly Ser
                325                 330                 335
Ser Phe Asn Phe Asp Phe Thr Asp Asn Ile Gln Phe Tyr Thr Asp Phe
                340                 345                 350
Arg Tyr Val Lys Ser Asp Ile Gln Gln Gln Phe Gln Pro Ser Phe Arg
            355                 360                 365
Phe Gly Asn Ile Asn Ile Asn Val Glu Asp Asn Ala Phe Leu Asn Asp
            370                 375                 380
Asp Leu Arg Gln Gln Met Leu Asp Ala Gly Gln Thr Asn Ala Ser Phe
385                 390                 395                 400
Ala Lys Phe Phe Asp Glu Leu Gly Asn Arg Ser Ala Glu Asn Lys Arg
                405                 410                 415
Glu Leu Phe Arg Tyr Val Gly Gly Phe Lys Gly Phe Asp Ile Ser
            420                 425                 430
Glu Thr Ile Phe Asp Tyr Asp Leu Tyr Tyr Val Tyr Gly Glu Thr Asn
            435                 440                 445
Asn Arg Arg Lys Thr Leu Asn Asp Leu Ile Pro Asp Asn Phe Val Ala
450                 455                 460
Ala Val Asp Ser Val Ile Asp Pro Asp Thr Gly Leu Ala Ala Cys Arg
465                 470                 475                 480
Ser Gln Val Ala Ser Ala Gln Gly Asp Asp Tyr Thr Asp Pro Ala Ser
                485                 490                 495
Val Asn Gly Ser Asp Cys Val Ala Tyr Asn Pro Phe Gly Met Gly Gln
            500                 505                 510
Ala Ser Ala Glu Ala Arg Asp Trp Val Ser Ala Asp Val Thr Arg Glu
            515                 520                 525
Asp Lys Ile Thr Gln Gln Val Ile Gly Gly Thr Leu Gly Thr Asp Ser
        530                 535                 540
Glu Glu Leu Phe Glu Leu Gln Gly Gly Ala Ile Ala Met Val Val Gly
545                 550                 555                 560
Phe Glu Tyr Arg Glu Glu Thr Ser Gly Ser Thr Thr Asp Glu Phe Thr
                565                 570                 575
Lys Ala Gly Phe Leu Thr Ser Ala Ala Thr Pro Asp Ser Tyr Gly Glu
            580                 585                 590
```

-continued

```
Tyr Asp Val Thr Glu Tyr Phe Val Glu Val Asn Ile Pro Val Leu Lys
            595                 600                 605

Glu Leu Pro Phe Ala His Glu Leu Ser Phe Asp Gly Ala Tyr Arg Asn
    610                 615                 620

Ala Asp Tyr Ser His Ala Gly Lys Thr Glu Ala Trp Lys Ala Gly Met
625                 630                 635                 640

Phe Tyr Ser Pro Leu Glu Gln Leu Ala Leu Arg Gly Thr Val Gly Glu
                645                 650                 655

Ala Val Arg Ala Pro Asn Ile Ala Glu Ala Phe Ser Pro Arg Ser Pro
            660                 665                 670

Gly Phe Gly Arg Val Ser Asp Pro Cys Asp Ala Asp Asn Ile Asn Asp
        675                 680                 685

Asp Pro Asp Arg Val Ser Asn Cys Ala Ala Leu Gly Ile Pro Pro Gly
    690                 695                 700

Phe Gln Ala Asn Asp Asn Val Ser Val Asp Thr Leu Ser Gly Gly Asn
705                 710                 715                 720

Pro Asp Leu Lys Pro Glu Thr Ser Thr Ser Phe Thr Gly Gly Leu Val
                725                 730                 735

Trp Thr Pro Thr Phe Ala Asp Asn Leu Ser Phe Thr Val Asp Tyr Tyr
            740                 745                 750

Asp Ile Gln Ile Glu Asp Ala Ile Leu Ser Val Ala Thr Gln Thr Val
        755                 760                 765

Ala Asp Asn Cys Val Asp Ser Thr Gly Pro Asp Thr Asp Phe Cys
770                 775                 780

Ser Gln Val Asp Arg Asn Pro Thr Thr Tyr Asp Ile Glu Leu Val Arg
785                 790                 795                 800

Ser Gly Tyr Leu Asn Ala Ala Leu Asn Thr Lys Gly Ile Glu Phe
                805                 810                 815

Gln Ala Ala Tyr Ser Leu Asp Leu Glu Ser Phe Asn Ala Pro Gly Glu
            820                 825                 830

Leu Arg Phe Asn Leu Leu Gly Asn Gln Leu Leu Glu Leu Glu Arg Leu
        835                 840                 845

Glu Phe Gln Asn Arg Pro Asp Glu Ile Asn Asp Glu Lys Gly Glu Val
    850                 855                 860

Gly Asp Pro Glu Leu Gln Phe Arg Leu Gly Ile Asp Tyr Arg Leu Asp
865                 870                 875                 880

Asp Leu Ser Val Ser Trp Asn Thr Arg Tyr Ile Asp Ser Val Val Thr
                885                 890                 895

Tyr Asp Val Ser Glu Asn Gly Gly Ser Pro Glu Asp Leu Tyr Pro Gly
            900                 905                 910

His Ile Gly Ser Met Thr Thr His Asp Leu Ser Ala Thr Tyr Tyr Ile
        915                 920                 925

Asn Glu Asn Phe Met Ile Asn Gly Gly Val Arg Asn Leu Phe Asp Ala
    930                 935                 940

Leu Pro Pro Gly Tyr Thr Asn Asp Ala Leu Tyr Asp Leu Val Gly Arg
945                 950                 955                 960

Arg Ala Phe Leu Gly Ile Lys Val Met Met
                965                 970
```

<210> SEQ ID NO 6
<211> LENGTH: 288
<212> TYPE: PRT
<213> ORGANISM: Shewanella putrefaciens

```
<400> SEQUENCE: 6

Met Ala Lys Ile Asn Ser Glu His Leu Asp Glu Ala Thr Ile Thr Ser
 1               5                  10                  15

Asn Lys Cys Thr Gln Thr Glu Thr Glu Ala Arg His Arg Asn Ala Thr
            20                  25                  30

Thr Thr Pro Glu Met Arg Arg Phe Ile Gln Glu Ser Asp Leu Ser Val
        35                  40                  45

Ser Gln Leu Ser Lys Ile Leu Asn Ile Ser Glu Ala Thr Val Arg Lys
    50                  55                  60

Trp Arg Lys Arg Asp Ser Val Glu Asn Cys Pro Asn Thr Pro His His
 65                  70                  75                  80

Leu Asn Thr Thr Leu Thr Pro Leu Gln Glu Tyr Val Val Gly Leu
                85                  90                  95

Arg Tyr Gln Leu Lys Met Pro Leu Asp Arg Leu Leu Lys Ala Thr Gln
                100                 105                 110

Glu Phe Ile Asn Pro Asn Val Ser Arg Ser Gly Leu Ala Arg Cys Leu
                115                 120                 125

Lys Arg Tyr Gly Val Ser Arg Val Ser Asp Ile Gln Ser Pro His Val
        130                 135                 140

Pro Met Arg Tyr Phe Asn Gln Ile Pro Val Thr Gln Gly Ser Asp Val
145                 150                 155                 160

Gln Thr Tyr Thr Leu His Tyr Glu Thr Leu Ala Lys Thr Leu Ala Leu
                165                 170                 175

Pro Ser Thr Asp Gly Asp Asn Val Val Gln Val Val Ser Leu Thr Ile
                180                 185                 190

Pro Pro Lys Leu Thr Glu Glu Ala Pro Ser Ser Ile Leu Leu Gly Ile
            195                 200                 205

Asp Pro His Ser Asp Trp Ile Tyr Leu Asp Ile Tyr Gln Asp Gly Asn
    210                 215                 220

Thr Gln Ala Thr Asn Arg Tyr Met Ala Tyr Val Leu Lys His Gly Pro
225                 230                 235                 240

Phe His Leu Arg Lys Leu Leu Val Arg Asn Tyr His Thr Phe Leu Gln
                245                 250                 255

Arg Phe Pro Gly Ala Thr Gln Asn Arg Arg Pro Ser Lys Asp Met Pro
                260                 265                 270

Glu Thr Ile Asn Lys Thr Pro Glu Thr Gln Ala Pro Ser Gly Asp Ser
                275                 280                 285

<210> SEQ ID NO 7
<211> LENGTH: 2756
<212> TYPE: PRT
<213> ORGANISM: Shewanella putrefaciens

<400> SEQUENCE: 7

Met Ser Gln Thr Ser Lys Pro Thr Asn Ser Ala Thr Glu Gln Ala Gln
 1               5                  10                  15

Asp Ser Gln Ala Asp Ser Arg Leu Asn Lys Arg Leu Lys Asp Met Pro
            20                  25                  30

Ile Ala Ile Val Gly Met Ala Ser Ile Phe Ala Asn Ser Arg Tyr Leu
            35                  40                  45

Asn Lys Phe Trp Asp Leu Ile Ser Glu Lys Ile Asp Ala Ile Thr Glu
    50                  55                  60

Leu Pro Ser Thr His Trp Gln Pro Glu Gly Tyr Tyr Asp Ala Asp Lys
 65                  70                  75                  80
```

-continued

Thr Ala Ala Asp Lys Ser Tyr Cys Lys Arg Gly Gly Phe Leu Pro Asp
                85                  90                  95

Val Asp Phe Asn Pro Met Glu Phe Gly Leu Pro Pro Asn Ile Leu Glu
            100                 105                 110

Leu Thr Asp Ser Ser Gln Leu Leu Ser Leu Ile Val Ala Lys Glu Val
        115                 120                 125

Leu Ala Asp Ala Asn Leu Pro Glu Asn Tyr Asp Arg Asp Lys Ile Gly
    130                 135                 140

Ile Thr Leu Gly Val Gly Gly Gln Lys Ile Ser His Ser Leu Thr
145                 150                 155                 160

Ala Arg Leu Gln Tyr Pro Val Leu Lys Lys Val Phe Ala Asn Ser Gly
                165                 170                 175

Ile Ser Asp Thr Asp Ser Glu Met Leu Ile Lys Lys Phe Gln Asp Gln
            180                 185                 190

Tyr Val His Trp Glu Glu Asn Ser Phe Pro Gly Ser Leu Gly Asn Val
        195                 200                 205

Ile Ala Gly Arg Ile Ala Asn Arg Phe Asp Phe Gly Gly Met Asn Cys
    210                 215                 220

Val Val Asp Ala Ala Cys Ala Gly Ser Leu Ala Ala Met Arg Met Ala
225                 230                 235                 240

Leu Thr Glu Leu Thr Glu Gly Arg Ser Glu Met Met Ile Thr Gly Gly
                245                 250                 255

Val Cys Thr Asp Asn Ser Pro Ser Met Tyr Met Ser Phe Ser Lys Thr
            260                 265                 270

Pro Ala Phe Thr Thr Asn Glu Thr Ile Gln Pro Phe Asp Ile Asp Ser
        275                 280                 285

Lys Gly Met Met Ile Gly Glu Gly Ile Gly Met Val Ala Leu Lys Arg
    290                 295                 300

Leu Glu Asp Ala Glu Arg Asp Gly Asp Arg Ile Tyr Ser Val Ile Lys
305                 310                 315                 320

Gly Val Gly Ala Ser Ser Asp Gly Lys Phe Lys Ser Ile Tyr Ala Pro
                325                 330                 335

Arg Pro Ser Gly Gln Ala Lys Ala Leu Asn Arg Ala Tyr Asp Asp Ala
            340                 345                 350

Gly Phe Ala Pro His Thr Leu Gly Leu Ile Glu Ala His Gly Thr Gly
        355                 360                 365

Thr Ala Ala Gly Asp Ala Ala Glu Phe Ala Gly Leu Cys Ser Val Phe
    370                 375                 380

Ala Glu Gly Asn Asp Thr Lys Gln His Ile Ala Leu Gly Ser Val Lys
385                 390                 395                 400

Ser Gln Ile Gly His Thr Lys Ser Thr Ala Gly Thr Ala Gly Leu Ile
                405                 410                 415

Lys Ala Ala Leu Ala Leu His His Lys Val Leu Pro Pro Thr Ile Asn
            420                 425                 430

Val Ser Gln Pro Ser Pro Lys Leu Asp Ile Glu Asn Ser Pro Phe Tyr
        435                 440                 445

Leu Asn Thr Glu Thr Arg Pro Trp Leu Pro Arg Val Asp Gly Thr Pro
    450                 455                 460

Arg Arg Ala Gly Ile Ser Ser Phe Gly Phe Gly Gly Thr Asn Phe His
465                 470                 475                 480

Phe Val Leu Glu Glu Tyr Asn Gln Glu His Ser Arg Thr Asp Ser Glu
                485                 490                 495

Lys Ala Lys Tyr Arg Gln Arg Gln Val Ala Gln Ser Phe Leu Val Ser

-continued

```
                    500                 505                 510
Ala Ser Asp Lys Ala Ser Leu Ile Asn Glu Leu Asn Val Leu Ala Ala
            515                 520                 525

Ser Ala Ser Gln Ala Glu Phe Ile Leu Lys Asp Ala Ala Asn Tyr
    530                 535                 540

Gly Val Arg Glu Leu Asp Lys Asn Ala Pro Arg Ile Gly Leu Val Ala
545                 550                 555                 560

Asn Thr Ala Glu Glu Leu Ala Gly Leu Ile Lys Gln Ala Leu Ala Lys
                565                 570                 575

Leu Ala Ala Ser Asp Asp Asn Ala Trp Gln Leu Pro Gly Gly Thr Ser
            580                 585                 590

Tyr Arg Ala Ala Ala Val Glu Gly Lys Val Ala Ala Leu Phe Ala Gly
        595                 600                 605

Gln Gly Ser Gln Tyr Leu Asn Met Gly Arg Asp Leu Thr Cys Tyr Tyr
        610                 615                 620

Pro Glu Met Arg Gln Gln Phe Val Thr Ala Asp Lys Val Phe Ala Ala
625                 630                 635                 640

Asn Asp Lys Thr Pro Leu Ser Gln Thr Leu Tyr Pro Lys Pro Val Phe
                645                 650                 655

Asn Lys Asp Glu Leu Lys Ala Gln Glu Ala Ile Leu Thr Asn Thr Ala
                660                 665                 670

Asn Ala Gln Ser Ala Ile Gly Ala Ile Ser Met Gly Gln Tyr Asp Leu
            675                 680                 685

Phe Thr Ala Ala Gly Phe Asn Ala Asp Met Val Ala Gly His Ser Phe
        690                 695                 700

Gly Glu Leu Ser Ala Leu Cys Ala Ala Gly Val Ile Ser Ala Asp Asp
705                 710                 715                 720

Tyr Tyr Lys Leu Ala Phe Ala Arg Gly Glu Ala Met Ala Thr Lys Ala
                725                 730                 735

Pro Ala Lys Asp Gly Val Glu Ala Asp Ala Gly Ala Met Phe Ala Ile
            740                 745                 750

Ile Thr Lys Ser Ala Ala Asp Leu Glu Thr Val Glu Ala Thr Ile Ala
        755                 760                 765

Lys Phe Asp Gly Val Lys Val Ala Asn Tyr Asn Ala Pro Thr Gln Ser
        770                 775                 780

Val Ile Ala Gly Pro Thr Ala Thr Ala Asp Ala Ala Lys Ala Leu
785                 790                 795                 800

Thr Glu Leu Gly Tyr Lys Ala Ile Asn Leu Pro Val Ser Gly Ala Phe
                805                 810                 815

His Thr Glu Leu Val Gly His Ala Gln Ala Pro Phe Ala Lys Ala Ile
                820                 825                 830

Asp Ala Ala Lys Phe Thr Lys Thr Ser Arg Ala Leu Tyr Ser Asn Ala
            835                 840                 845

Thr Gly Gly Leu Tyr Glu Ser Thr Ala Ala Lys Ile Lys Ala Ser Phe
        850                 855                 860

Lys Lys His Met Leu Gln Ser Val Arg Phe Thr Ser Gln Leu Glu Ala
865                 870                 875                 880

Met Tyr Asn Asp Gly Ala Arg Val Phe Val Glu Phe Gly Pro Lys Asn
                885                 890                 895

Ile Leu Gln Lys Leu Val Gln Gly Thr Leu Val Asn Thr Glu Asn Glu
            900                 905                 910

Val Cys Thr Ile Ser Ile Asn Pro Asn Pro Lys Val Asp Ser Asp Leu
        915                 920                 925
```

-continued

```
Gln Leu Lys Gln Ala Ala Met Gln Leu Ala Val Thr Gly Val Val Leu
        930                 935                 940
Ser Glu Ile Asp Pro Tyr Gln Ala Asp Ile Ala Ala Pro Ala Lys Lys
945                 950                 955                 960
Ser Pro Met Ser Ile Ser Leu Asn Ala Ala Asn His Ile Ser Lys Ala
                965                 970                 975
Thr Arg Ala Lys Met Ala Lys Ser Leu Glu Thr Gly Ile Val Thr Ser
            980                 985                 990
Gln Ile Glu His Val Ile Glu Glu Lys Ile Val Glu Val Glu Lys Leu
        995                 1000                1005
Val Glu Val Glu Lys Ile Val Glu Lys Val Glu Val Glu Lys Val
    1010                1015                1020
Val Glu Val Glu Ala Pro Val Asn Ser Val Gln Ala Asn Ala Ile Gln
1025                1030                1035                1040
Thr Arg Ser Val Val Ala Pro Val Ile Glu Asn Gln Val Val Ser Lys
                1045                1050                1055
Asn Ser Lys Pro Ala Val Gln Ser Ile Ser Gly Asp Ala Leu Ser Asn
            1060                1065                1070
Phe Phe Ala Ala Gln Gln Gln Thr Ala Gln Leu His Gln Gln Phe Leu
        1075                1080                1085
Ala Ile Pro Gln Gln Tyr Gly Glu Thr Phe Thr Thr Leu Met Thr Glu
    1090                1095                1100
Gln Ala Lys Leu Ala Ser Ser Gly Val Ala Ile Pro Glu Ser Leu Gln
1105                1110                1115                1120
Arg Ser Met Glu Gln Phe His Gln Leu Gln Ala Gln Thr Leu Gln Ser
                1125                1130                1135
His Thr Gln Phe Leu Glu Met Gln Ala Gly Ser Asn Ile Ala Ala Leu
            1140                1145                1150
Asn Leu Leu Asn Ser Ser Gln Ala Thr Tyr Ala Pro Ala Ile His Asn
        1155                1160                1165
Glu Ala Ile Gln Ser Gln Val Val Gln Ser Gln Thr Ala Val Gln Pro
    1170                1175                1180
Val Ile Ser Thr Gln Val Asn His Val Ser Glu Gln Pro Thr Gln Ala
1185                1190                1195                1200
Pro Ala Pro Lys Ala Gln Pro Ala Pro Val Thr Thr Ala Val Gln Thr
                1205                1210                1215
Ala Pro Ala Gln Val Val Arg Gln Ala Ala Pro Val Gln Ala Ala Ile
            1220                1225                1230
Glu Pro Ile Asn Thr Ser Val Ala Thr Thr Thr Pro Ser Ala Phe Ser
        1235                1240                1245
Ala Glu Thr Ala Leu Ser Ala Thr Lys Val Gln Ala Thr Met Leu Glu
    1250                1255                1260
Val Val Ala Glu Lys Thr Gly Tyr Pro Thr Glu Met Leu Glu Leu Glu
1265                1270                1275                1280
Met Asp Met Glu Ala Asp Leu Gly Ile Asp Ser Ile Lys Arg Val Glu
                1285                1290                1295
Ile Leu Gly Thr Val Gln Asp Glu Leu Pro Gly Leu Pro Glu Leu Ser
            1300                1305                1310
Pro Glu Asp Leu Ala Glu Cys Arg Thr Leu Gly Glu Ile Val Asp Tyr
        1315                1320                1325
Met Gly Ser Lys Leu Pro Ala Glu Gly Ser Met Asn Ser Gln Leu Ser
    1330                1335                1340
```

-continued

```
Thr Gly Ser Ala Ala Ala Thr Pro Ala Ala Asn Gly Leu Ser Ala Glu
1345                1350                1355                1360

Lys Val Gln Ala Thr Met Met Ser Val Val Ala Glu Lys Thr Gly Tyr
            1365                1370                1375

Pro Thr Glu Met Leu Glu Leu Glu Met Asp Met Glu Ala Asp Leu Gly
        1380                1385                1390

Ile Asp Ser Ile Lys Arg Val Glu Ile Leu Gly Thr Val Gln Asp Glu
    1395                1400                1405

Leu Pro Gly Leu Pro Glu Leu Ser Pro Glu Asp Leu Ala Glu Cys Arg
1410                1415                1420

Thr Leu Gly Glu Ile Val Asp Tyr Met Asn Ser Lys Leu Ala Asp Gly
1425                1430                1435                1440

Ser Lys Leu Pro Ala Glu Gly Ser Met Asn Ser Gln Leu Ser Thr Ser
            1445                1450                1455

Ala Ala Ala Ala Thr Pro Ala Ala Asn Gly Leu Ser Ala Glu Lys Val
        1460                1465                1470

Gln Ala Thr Met Met Ser Val Val Ala Glu Lys Thr Gly Tyr Pro Thr
    1475                1480                1485

Glu Met Leu Glu Leu Glu Met Asp Met Glu Ala Asp Leu Gly Ile Asp
1490                1495                1500

Ser Ile Lys Arg Val Glu Ile Leu Gly Thr Val Gln Asp Glu Leu Pro
1505                1510                1515                1520

Gly Leu Pro Glu Leu Asn Pro Glu Asp Leu Ala Glu Cys Arg Thr Leu
            1525                1530                1535

Gly Glu Ile Val Thr Tyr Met Asn Ser Lys Leu Ala Asp Gly Ser Lys
        1540                1545                1550

Leu Pro Ala Glu Gly Ser Met His Tyr Gln Leu Ser Thr Ser Thr Ala
    1555                1560                1565

Ala Ala Thr Pro Val Ala Asn Gly Leu Ser Ala Glu Lys Val Gln Ala
1570                1575                1580

Thr Met Met Ser Val Val Ala Asp Lys Thr Gly Tyr Pro Thr Glu Met
1585                1590                1595                1600

Leu Glu Leu Glu Met Asp Met Glu Ala Asp Leu Gly Ile Asp Ser Ile
            1605                1610                1615

Lys Arg Val Glu Ile Leu Gly Thr Val Gln Asp Glu Leu Pro Gly Leu
        1620                1625                1630

Pro Glu Leu Asn Pro Glu Asp Leu Ala Glu Cys Arg Thr Leu Gly Glu
    1635                1640                1645

Ile Val Asp Tyr Met Gly Ser Lys Leu Pro Ala Glu Gly Ser Ala Asn
1650                1655                1660

Thr Ser Ala Ala Ala Ser Leu Asn Val Ser Ala Val Ala Ala Pro Gln
1665                1670                1675                1680

Ala Ala Ala Thr Pro Val Ser Asn Gly Leu Ser Ala Glu Lys Val Gln
            1685                1690                1695

Ser Thr Met Met Ser Val Val Ala Glu Lys Thr Gly Tyr Pro Thr Glu
        1700                1705                1710

Met Leu Glu Leu Gly Met Asp Met Glu Ala Asp Leu Gly Ile Asp Ser
    1715                1720                1725

Ile Lys Arg Val Glu Ile Leu Gly Thr Val Gln Asp Glu Leu Pro Gly
1730                1735                1740

Leu Pro Glu Leu Asn Pro Glu Asp Leu Ala Glu Cys Arg Thr Leu Gly
1745                1750                1755                1760

Glu Ile Val Asp Tyr Met Asn Ser Lys Leu Ala Asp Gly Ser Lys Leu
```

-continued

```
                1765                1770                1775
Pro Ala Glu Gly Ser Ala Asn Thr Ser Ala Thr Ala Ala Thr Pro Ala
            1780                1785                1790
Val Asn Gly Leu Ser Ala Asp Lys Val Gln Ala Thr Met Met Ser Val
        1795                1800                1805
Val Ala Glu Lys Thr Gly Tyr Pro Thr Glu Met Leu Glu Leu Gly Met
    1810                1815                1820
Asp Met Glu Ala Asp Leu Gly Ile Asp Ser Ile Lys Arg Val Glu Ile
1825                1830                1835                1840
Leu Gly Thr Val Gln Asp Glu Leu Pro Gly Leu Pro Glu Leu Asn Pro
            1845                1850                1855
Glu Asp Leu Ala Glu Cys Arg Thr Leu Gly Glu Ile Val Ser Tyr Met
        1860                1865                1870
Asn Ser Gln Leu Ala Asp Gly Ser Lys Leu Ser Thr Ser Ala Ala Glu
        1875                1880                1885
Gly Ser Ala Asp Thr Ser Ala Ala Asn Ala Ala Lys Pro Ala Ala Ile
        1890                1895                1900
Ser Ala Glu Pro Ser Val Glu Leu Pro Pro His Ser Glu Val Ala Leu
1905                1910                1915                1920
Lys Lys Leu Asn Ala Ala Asn Lys Leu Glu Asn Cys Phe Ala Ala Asp
            1925                1930                1935
Ala Ser Val Val Ile Asn Asp Asp Gly His Asn Ala Gly Val Leu Ala
        1940                1945                1950
Glu Lys Leu Ile Lys Gln Gly Leu Lys Val Ala Val Val Arg Leu Pro
        1955                1960                1965
Lys Gly Gln Pro Gln Ser Pro Leu Ser Ser Asp Val Ala Ser Phe Glu
    1970                1975                1980
Leu Ala Ser Ser Gln Glu Ser Glu Leu Glu Ala Ser Ile Thr Ala Val
1985                1990                1995                2000
Ile Ala Gln Ile Glu Thr Gln Val Gly Ala Ile Gly Gly Phe Ile His
            2005                2010                2015
Leu Gln Pro Glu Ala Asn Thr Glu Glu Gln Thr Ala Val Asn Leu Asp
        2020                2025                2030
Ala Gln Ser Phe Thr His Val Ser Asn Ala Phe Leu Trp Ala Lys Leu
    2035                2040                2045
Leu Gln Pro Lys Leu Val Ala Gly Ala Asp Ala Arg Arg Cys Phe Val
    2050                2055                2060
Thr Val Ser Arg Ile Asp Gly Gly Phe Gly Tyr Leu Asn Thr Asp Ala
2065                2070                2075                2080
Leu Lys Asp Ala Glu Leu Asn Gln Ala Ala Leu Ala Gly Leu Thr Lys
            2085                2090                2095
Thr Leu Ser His Glu Trp Pro Gln Val Phe Cys Arg Ala Leu Asp Ile
        2100                2105                2110
Ala Thr Asp Val Asp Ala Thr His Leu Ala Asp Ala Ile Thr Ser Glu
    2115                2120                2125
Leu Phe Asp Ser Gln Ala Gln Leu Pro Glu Val Gly Leu Ser Leu Ile
    2130                2135                2140
Asp Gly Lys Val Asn Arg Val Thr Leu Val Ala Ala Glu Ala Ala Asp
2145                2150                2155                2160
Lys Thr Ala Lys Ala Glu Leu Asn Ser Thr Asp Lys Ile Leu Val Thr
            2165                2170                2175
Gly Gly Ala Lys Gly Val Thr Phe Glu Cys Ala Leu Ala Leu Ala Ser
        2180                2185                2190
```

-continued

```
Arg Ser Gln Ser His Phe Ile Leu Ala Gly Arg Ser Glu Leu Gln Ala
    2195                2200                2205

Leu Pro Ser Trp Ala Glu Gly Lys Gln Thr Ser Glu Leu Lys Ser Ala
    2210                2215                2220

Ala Ile Ala His Ile Ile Ser Thr Gly Gln Lys Pro Thr Pro Lys Gln
2225                2230                2235                2240

Val Glu Ala Ala Val Trp Pro Val Gln Ser Ser Ile Glu Ile Asn Ala
                2245                2250                2255

Ala Leu Ala Ala Phe Asn Lys Val Gly Ala Ser Ala Glu Tyr Val Ser
            2260                2265                2270

Met Asp Val Thr Asp Ser Ala Ala Ile Thr Ala Ala Leu Asn Gly Arg
    2275                2280                2285

Ser Asn Glu Ile Thr Gly Leu Ile His Gly Ala Gly Val Leu Ala Asp
    2290                2295                2300

Lys His Ile Gln Asp Lys Thr Leu Ala Glu Leu Ala Lys Val Tyr Gly
2305                2310                2315                2320

Thr Lys Val Asn Gly Leu Lys Ala Leu Leu Ala Ala Leu Glu Pro Ser
                2325                2330                2335

Lys Ile Lys Leu Leu Ala Met Phe Ser Ser Ala Ala Gly Phe Tyr Gly
            2340                2345                2350

Asn Ile Gly Gln Ser Asp Tyr Ala Met Ser Asn Asp Ile Leu Asn Lys
            2355                2360                2365

Ala Ala Leu Gln Phe Thr Ala Arg Asn Pro Gln Ala Lys Val Met Ser
    2370                2375                2380

Phe Asn Trp Gly Pro Trp Asp Gly Gly Met Val Asn Pro Ala Leu Lys
2385                2390                2395                2400

Lys Met Phe Thr Glu Arg Gly Val Tyr Val Ile Pro Leu Lys Ala Gly
            2405                2410                2415

Ala Glu Leu Phe Ala Thr Gln Leu Leu Ala Glu Thr Gly Val Gln Leu
            2420                2425                2430

Leu Ile Gly Thr Ser Met Gln Gly Gly Ser Asp Thr Lys Ala Thr Glu
            2435                2440                2445

Thr Ala Ser Val Lys Lys Leu Asn Ala Gly Glu Val Leu Ser Ala Ser
    2450                2455                2460

His Pro Arg Ala Gly Ala Gln Lys Thr Pro Leu Gln Ala Val Thr Ala
2465                2470                2475                2480

Thr Arg Leu Leu Thr Pro Ser Ala Met Val Phe Ile Glu Asp His Arg
                2485                2490                2495

Ile Gly Gly Asn Ser Val Leu Pro Thr Val Cys Ala Ile Asp Trp Met
            2500                2505                2510

Arg Glu Ala Ala Ser Asp Met Leu Gly Ala Gln Val Lys Val Leu Asp
    2515                2520                2525

Tyr Lys Leu Leu Lys Gly Ile Val Phe Glu Thr Asp Glu Pro Gln Glu
    2530                2535                2540

Leu Thr Leu Glu Leu Thr Pro Asp Asp Ser Asp Glu Ala Thr Leu Gln
2545                2550                2555                2560

Ala Leu Ile Ser Cys Asn Gly Arg Pro Gln Tyr Lys Ala Thr Leu Ile
            2565                2570                2575

Ser Asp Asn Ala Asp Ile Lys Gln Leu Asn Lys Gln Phe Asp Leu Ser
            2580                2585                2590

Ala Lys Ala Ile Thr Thr Ala Lys Glu Leu Tyr Ser Asn Gly Thr Leu
    2595                2600                2605
```

-continued

```
Phe His Gly Pro Arg Leu Gln Gly Ile Gln Ser Val Gln Phe Asp
    2610                2615                2620

Asp Gln Gly Leu Ile Ala Lys Val Ala Leu Pro Lys Val Glu Leu Ser
2625                2630                2635                2640

Asp Cys Gly Glu Phe Leu Pro Gln Thr His Met Gly Gly Ser Gln Pro
                2645                2650                2655

Phe Ala Glu Asp Leu Leu Leu Gln Ala Met Leu Val Trp Ala Arg Leu
                2660                2665                2670

Lys Thr Gly Ser Ala Ser Leu Pro Ser Ser Ile Gly Glu Phe Thr Ser
            2675                2680                2685

Tyr Gln Pro Met Ala Phe Gly Glu Thr Gly Thr Ile Glu Leu Glu Val
            2690                2695                2700

Ile Lys His Asn Lys Arg Ser Leu Glu Ala Asn Val Ala Leu Tyr Arg
2705                2710                2715                2720

Asp Asn Gly Glu Leu Ser Ala Met Phe Lys Ser Ala Lys Ile Thr Ile
                2725                2730                2735

Ser Lys Ser Leu Asn Ser Ala Phe Leu Pro Ala Val Leu Ala Asn Asp
                2740                2745                2750

Ser Glu Ala Asn
        2755

<210> SEQ ID NO 8
<211> LENGTH: 771
<212> TYPE: PRT
<213> ORGANISM: Shewanella putrefaciens

<400> SEQUENCE: 8

Met Pro Leu Arg Ile Ala Leu Ile Leu Leu Pro Thr Pro Gln Phe Glu
  1               5                  10                  15

Val Asn Ser Val Asp Gln Ser Val Leu Ala Ser Tyr Gln Thr Leu Gln
                20                  25                  30

Pro Glu Leu Asn Ala Leu Leu Asn Ser Ala Pro Thr Pro Glu Met Leu
            35                  40                  45

Ser Ile Thr Ile Ser Asp Asp Ser Asp Ala Asn Ser Phe Glu Ser Gln
    50                  55                  60

Leu Asn Ala Ala Thr Asn Ala Ile Asn Asn Gly Tyr Ile Val Lys Leu
65                  70                  75                  80

Ala Thr Ala Thr His Ala Leu Leu Met Leu Pro Ala Leu Lys Ala Ala
                85                  90                  95

Gln Met Arg Ile His Pro His Ala Gln Leu Ala Ala Met Gln Gln Ala
                100                 105                 110

Lys Ser Thr Pro Met Ser Gln Val Ser Gly Glu Leu Lys Leu Gly Ala
            115                 120                 125

Asn Ala Leu Ser Leu Ala Gln Thr Asn Ala Leu Ser His Ala Leu Ser
130                 135                 140

Gln Ala Lys Arg Asn Leu Thr Asp Val Ser Val Asn Glu Cys Phe Glu
145                 150                 155                 160

Asn Leu Lys Ser Glu Gln Gln Phe Thr Glu Val Tyr Ser Leu Ile Gln
                165                 170                 175

Gln Leu Ala Ser Arg Thr His Val Arg Lys Glu Val Asn Gln Gly Val
                180                 185                 190

Glu Leu Gly Pro Lys Gln Ala Lys Ser His Tyr Trp Phe Ser Glu Phe
            195                 200                 205

His Gln Asn Arg Val Ala Ala Ile Asn Phe Ile Asn Gly Gln Gln Ala
    210                 215                 220
```

```
Thr Ser Tyr Val Leu Thr Gln Gly Ser Gly Leu Leu Ala Ala Lys Ser
225                 230                 235                 240

Met Leu Asn Gln Gln Arg Leu Met Phe Ile Leu Pro Gly Asn Ser Gln
            245                 250                 255

Gln Gln Ile Thr Ala Ser Ile Thr Gln Leu Met Gln Leu Glu Arg
            260                 265                 270

Leu Gln Val Thr Glu Val Asn Glu Leu Ser Leu Glu Cys Gln Leu Glu
            275                 280                 285

Leu Leu Ser Ile Met Tyr Asp Asn Leu Val Asn Ala Asp Lys Leu Thr
    290                 295                 300

Thr Arg Asp Ser Lys Pro Ala Tyr Gln Ala Val Ile Gln Ala Ser Ser
305                 310                 315                 320

Val Ser Ala Ala Lys Gln Glu Leu Ser Ala Leu Asn Asp Ala Leu Thr
            325                 330                 335

Ala Leu Phe Ala Glu Gln Thr Asn Ala Thr Ser Thr Asn Lys Gly Leu
            340                 345                 350

Ile Gln Tyr Lys Thr Pro Ala Gly Ser Tyr Leu Thr Leu Thr Pro Leu
            355                 360                 365

Gly Ser Asn Asn Asp Asn Ala Gln Ala Gly Leu Ala Phe Val Tyr Pro
370                 375                 380

Gly Val Gly Thr Val Tyr Ala Asp Met Leu Asn Glu Leu His Gln Tyr
385                 390                 395                 400

Phe Pro Ala Leu Tyr Ala Lys Leu Glu Arg Glu Gly Asp Leu Lys Ala
                405                 410                 415

Met Leu Gln Ala Glu Asp Ile Tyr His Leu Asp Pro Lys His Ala Ala
            420                 425                 430

Gln Met Ser Leu Gly Asp Leu Ala Ile Ala Gly Val Gly Ser Ser Tyr
            435                 440                 445

Leu Leu Thr Gln Leu Leu Thr Asp Glu Phe Asn Ile Lys Pro Asn Phe
    450                 455                 460

Ala Leu Gly Tyr Ser Met Gly Glu Ala Ser Met Trp Ala Ser Leu Gly
465                 470                 475                 480

Val Trp Gln Asn Pro His Ala Leu Ile Ser Lys Thr Gln Thr Asp Pro
            485                 490                 495

Leu Phe Thr Ser Ala Ile Ser Gly Lys Leu Thr Ala Val Arg Gln Ala
            500                 505                 510

Trp Gln Leu Asp Asp Thr Ala Ala Glu Ile Gln Trp Asn Ser Phe Val
            515                 520                 525

Val Arg Ser Glu Ala Ala Pro Ile Glu Ala Leu Leu Lys Asp Tyr Pro
530                 535                 540

His Ala Tyr Leu Ala Ile Ile Gln Gly Asp Thr Cys Val Ile Ala Gly
545                 550                 555                 560

Cys Glu Ile Gln Cys Lys Ala Leu Leu Ala Leu Gly Lys Arg Gly
            565                 570                 575

Ile Ala Ala Asn Arg Val Thr Ala Met His Thr Gln Pro Ala Met Gln
            580                 585                 590

Glu His Gln Asn Val Met Asp Phe Tyr Leu Gln Pro Leu Lys Ala Glu
            595                 600                 605

Leu Pro Ser Glu Ile Ser Phe Ile Ser Ala Ala Asp Leu Thr Ala Lys
    610                 615                 620

Gln Thr Val Ser Glu Gln Ala Leu Ser Ser Gln Val Val Ala Gln Ser
625                 630                 635                 640
```

Ile Ala Asp Thr Phe Cys Gln Thr Leu Asp Phe Thr Ala Leu Val His
            645                 650                 655

His Ala Gln His Gln Gly Ala Lys Leu Phe Val Glu Ile Gly Ala Asp
            660                 665                 670

Arg Gln Asn Cys Thr Leu Ile Asp Lys Ile Val Lys Gln Asp Gly Ala
            675                 680                 685

Ser Ser Val Gln His Gln Pro Cys Cys Thr Val Pro Met Asn Ala Lys
            690                 695                 700

Gly Ser Gln Asp Ile Thr Ser Val Ile Lys Ala Leu Gly Gln Leu Ile
705                 710                 715                 720

Ser His Gln Val Pro Leu Ser Val Gln Pro Phe Ile Asp Gly Leu Lys
            725                 730                 735

Arg Glu Leu Thr Leu Cys Gln Leu Thr Ser Gln Gln Leu Ala Ala His
            740                 745                 750

Ala Asn Val Asp Ser Lys Phe Glu Ser Asn Gln Asp His Leu Leu Gln
            755                 760                 765

Gly Glu Val
        770

<210> SEQ ID NO 9
<211> LENGTH: 2004
<212> TYPE: PRT
<213> ORGANISM: Shewanella putrefaciens

<400> SEQUENCE: 9

Met Ser Leu Pro Asp Asn Ala Ser Asn His Leu Ser Ala Asn Gln Lys
  1               5                  10                  15

Gly Ala Ser Gln Ala Ser Lys Thr Ser Lys Gln Ser Lys Ile Ala Ile
             20                  25                  30

Val Gly Leu Ala Thr Leu Tyr Pro Asp Ala Lys Thr Pro Gln Glu Phe
         35                  40                  45

Trp Gln Asn Leu Leu Asp Lys Arg Asp Ser Arg Ser Thr Leu Thr Asn
     50                  55                  60

Glu Lys Leu Gly Ala Asn Ser Gln Asp Tyr Gln Gly Val Gln Gly Gln
 65                  70                  75                  80

Ser Asp Arg Phe Tyr Cys Asn Lys Gly Gly Tyr Ile Glu Asn Phe Ser
                 85                  90                  95

Phe Asn Ala Ala Gly Tyr Lys Leu Pro Glu Gln Ser Leu Asn Gly Leu
            100                 105                 110

Asp Asp Ser Phe Leu Trp Ala Leu Asp Thr Ser Arg Asn Ala Leu Ile
        115                 120                 125

Asp Ala Gly Ile Asp Ile Asn Gly Ala Asp Leu Ser Arg Ala Gly Val
    130                 135                 140

Val Met Gly Ala Leu Ser Phe Pro Thr Thr Arg Ser Asn Asp Leu Phe
145                 150                 155                 160

Leu Pro Ile Tyr His Ser Ala Val Glu Lys Ala Leu Gln Asp Lys Leu
                165                 170                 175

Gly Val Lys Ala Phe Lys Leu Ser Pro Thr Asn Ala His Thr Ala Arg
            180                 185                 190

Ala Ala Asn Glu Ser Ser Leu Asn Ala Ala Asn Gly Ala Ile Ala His
        195                 200                 205

Asn Ser Ser Lys Val Val Ala Asp Ala Leu Gly Leu Gly Gly Ala Gln
    210                 215                 220

Leu Ser Leu Asp Ala Ala Cys Ala Ser Ser Val Tyr Ser Leu Lys Leu
225                 230                 235                 240

```
Ala Cys Asp Tyr Leu Ser Thr Gly Lys Ala Asp Ile Met Leu Ala Gly
            245                 250                 255

Ala Val Ser Gly Ala Asp Pro Phe Phe Ile Asn Met Gly Phe Ser Ile
        260                 265                 270

Phe His Ala Tyr Pro Asp His Gly Ile Ser Val Pro Phe Asp Ala Ser
        275                 280                 285

Ser Lys Gly Leu Phe Ala Gly Glu Gly Ala Gly Val Leu Val Leu Lys
    290                 295                 300

Arg Leu Glu Asp Ala Glu Arg Asp Asn Asp Lys Ile Tyr Ala Val Val
305                 310                 315                 320

Ser Gly Val Gly Leu Ser Asn Asp Gly Lys Gly Gln Phe Val Leu Ser
                325                 330                 335

Pro Asn Pro Lys Gly Gln Val Lys Ala Phe Glu Arg Ala Tyr Ala Ala
                340                 345                 350

Ser Asp Ile Glu Pro Lys Asp Ile Glu Val Ile Glu Cys His Ala Thr
            355                 360                 365

Gly Thr Pro Leu Gly Asp Lys Ile Glu Leu Thr Ser Met Glu Thr Phe
        370                 375                 380

Phe Glu Asp Lys Leu Gln Gly Thr Asp Ala Pro Leu Ile Gly Ser Ala
385                 390                 395                 400

Lys Ser Asn Leu Gly His Leu Leu Thr Ala Ala His Ala Gly Ile Met
                405                 410                 415

Lys Met Ile Phe Ala Met Lys Glu Gly Tyr Leu Pro Pro Ser Ile Asn
            420                 425                 430

Ile Ser Asp Ala Ile Ala Ser Pro Lys Lys Leu Phe Gly Lys Pro Thr
        435                 440                 445

Leu Pro Ser Met Val Gln Gly Trp Pro Asp Lys Pro Ser Asn Asn His
    450                 455                 460

Phe Gly Val Arg Thr Arg His Ala Gly Val Ser Val Phe Gly Phe Gly
465                 470                 475                 480

Gly Cys Asn Ala His Leu Leu Leu Glu Ser Tyr Asn Gly Lys Gly Thr
                485                 490                 495

Val Lys Ala Glu Ala Thr Gln Val Pro Arg Gln Ala Glu Pro Leu Lys
            500                 505                 510

Val Val Gly Leu Ala Ser His Phe Gly Pro Leu Ser Ser Ile Asn Ala
        515                 520                 525

Leu Asn Asn Ala Val Thr Gln Asp Gly Asn Gly Phe Ile Glu Leu Pro
    530                 535                 540

Lys Lys Arg Trp Lys Gly Leu Glu Lys His Ser Glu Leu Leu Ala Glu
545                 550                 555                 560

Phe Gly Leu Ala Ser Ala Pro Lys Gly Ala Tyr Val Asp Asn Phe Glu
                565                 570                 575

Leu Asp Phe Leu Arg Phe Lys Leu Pro Pro Asn Glu Asp Asp Arg Leu
            580                 585                 590

Ile Ser Gln Gln Leu Met Leu Met Arg Val Thr Asp Glu Ala Ile Arg
        595                 600                 605

Asp Ala Lys Leu Glu Pro Gly Gln Lys Val Ala Val Leu Val Ala Met
    610                 615                 620

Glu Thr Glu Leu Glu Leu His Gln Phe Arg Gly Arg Val Asn Leu His
625                 630                 635                 640

Thr Gln Leu Ala Gln Ser Leu Ala Ala Met Gly Val Ser Leu Ser Thr
                645                 650                 655
```

-continued

```
Asp Glu Tyr Gln Ala Leu Glu Ala Ile Ala Met Asp Ser Val Leu Asp
            660                 665                 670

Ala Ala Lys Leu Asn Gln Tyr Thr Ser Phe Ile Gly Asn Ile Met Ala
        675                 680                 685

Ser Arg Val Ala Ser Leu Trp Asp Phe Asn Gly Pro Ala Phe Thr Ile
    690                 695                 700

Ser Ala Ala Glu Gln Ser Val Ser Arg Cys Ile Asp Val Ala Gln Asn
705                 710                 715                 720

Leu Ile Met Glu Asp Asn Leu Asp Ala Val Ile Ala Ala Val Asp
            725                 730                 735

Leu Ser Gly Ser Phe Glu Gln Val Ile Leu Lys Asn Ala Ile Ala Pro
        740                 745                 750

Val Ala Ile Glu Pro Asn Leu Glu Ala Ser Leu Asn Pro Thr Ser Ala
    755                 760                 765

Ser Trp Asn Val Gly Glu Gly Ala Gly Ala Val Leu Val Lys Asn
    770                 775                 780

Glu Ala Thr Ser Gly Cys Ser Tyr Gly Gln Ile Asp Ala Leu Gly Phe
785                 790                 795                 800

Ala Lys Thr Ala Glu Thr Ala Leu Ala Thr Asp Lys Leu Leu Ser Gln
            805                 810                 815

Thr Ala Thr Asp Phe Asn Lys Val Lys Val Ile Glu Thr Met Ala Ala
        820                 825                 830

Pro Ala Ser Gln Ile Gln Leu Ala Pro Ile Val Ser Ser Gln Val Thr
    835                 840                 845

His Thr Ala Ala Glu Gln Arg Val Gly His Cys Phe Ala Ala Ala Gly
    850                 855                 860

Met Ala Ser Leu Leu His Gly Leu Leu Asn Leu Asn Thr Val Ala Gln
865                 870                 875                 880

Thr Asn Lys Ala Asn Cys Ala Leu Ile Asn Asn Ile Ser Glu Asn Gln
            885                 890                 895

Leu Ser Gln Leu Leu Ile Ser Gln Thr Ala Ser Glu Gln Gln Ala Leu
        900                 905                 910

Thr Ala Arg Leu Ser Asn Glu Leu Lys Ser Asp Ala Lys His Gln Leu
    915                 920                 925

Val Lys Gln Val Thr Leu Gly Gly Arg Asp Ile Tyr Gln His Ile Val
    930                 935                 940

Asp Thr Pro Leu Ala Ser Leu Glu Ser Ile Thr Gln Lys Leu Ala Gln
945                 950                 955                 960

Ala Thr Ala Ser Thr Val Val Asn Gln Val Lys Pro Ile Lys Ala Ala
            965                 970                 975

Gly Ser Val Glu Met Ala Asn Ser Phe Glu Thr Glu Ser Ser Ala Glu
        980                 985                 990

Pro Gln Ile Thr Ile Ala Ala Gln Gln Thr Ala Asn Ile Gly Val Thr
    995                 1000                1005

Ala Gln Ala Thr Lys Arg Glu Leu Gly Thr Pro Pro Met Thr Thr Asn
    1010                1015                1020

Thr Ile Ala Asn Thr Ala Asn Asn Leu Asp Lys Thr Leu Glu Thr Val
1025                1030                1035                1040

Ala Gly Asn Thr Val Ala Ser Lys Val Gly Ser Gly Asp Ile Val Asn
            1045                1050                1055

Phe Gln Gln Asn Gln Gln Leu Ala Gln Gln Ala His Leu Ala Phe Leu
        1060                1065                1070

Glu Ser Arg Ser Ala Gly Met Lys Val Ala Asp Ala Leu Leu Lys Gln
```

-continued

```
              1075                1080                1085
Gln Leu Ala Gln Val Thr Gly Gln Thr Ile Asp Asn Gln Ala Leu Asp
    1090                1095                1100
Thr Gln Ala Val Asp Thr Gln Thr Ser Glu Asn Val Ala Ile Ala Ala
1105                1110                1115                1120
Glu Ser Pro Val Gln Val Thr Thr Pro Val Gln Val Thr Thr Pro Val
                1125                1130                1135
Gln Ile Ser Val Val Glu Leu Lys Pro Asp His Ala Asn Val Pro Pro
        1140                1145                1150
Tyr Thr Pro Pro Val Pro Ala Leu Lys Pro Cys Ile Trp Asn Tyr Ala
    1155                1160                1165
Asp Leu Val Glu Tyr Ala Glu Gly Asp Ile Ala Lys Val Phe Gly Ser
1170                1175                1180
Asp Tyr Ala Ile Ile Asp Ser Tyr Ser Arg Arg Val Arg Leu Pro Thr
1185                1190                1195                1200
Thr Asp Tyr Leu Leu Val Ser Arg Val Thr Lys Leu Asp Ala Thr Ile
                1205                1210                1215
Asn Gln Phe Lys Pro Cys Ser Met Thr Thr Glu Tyr Asp Ile Pro Val
        1220                1225                1230
Asp Ala Pro Tyr Leu Val Asp Gly Gln Ile Pro Trp Ala Val Ala Val
    1235                1240                1245
Glu Ser Gly Gln Cys Asp Leu Met Leu Ile Ser Tyr Leu Gly Ile Asp
1250                1255                1260
Phe Glu Asn Lys Gly Glu Arg Val Tyr Arg Leu Leu Asp Cys Thr Leu
1265                1270                1275                1280
Thr Phe Leu Gly Asp Leu Pro Arg Gly Gly Asp Thr Leu Arg Tyr Asp
                1285                1290                1295
Ile Lys Ile Asn Asn Tyr Ala Arg Asn Gly Asp Thr Leu Leu Phe Phe
        1300                1305                1310
Phe Ser Tyr Glu Cys Phe Val Gly Asp Lys Met Ile Leu Lys Met Asp
    1315                1320                1325
Gly Gly Cys Ala Gly Phe Phe Thr Asp Glu Glu Leu Ala Asp Gly Lys
    1330                1335                1340
Gly Val Ile Arg Thr Glu Glu Glu Ile Lys Ala Arg Ser Leu Val Gln
1345                1350                1355                1360
Lys Gln Arg Phe Asn Pro Leu Leu Asp Cys Pro Lys Thr Gln Phe Ser
                1365                1370                1375
Tyr Gly Asp Ile His Lys Leu Leu Thr Ala Asp Ile Glu Gly Cys Phe
        1380                1385                1390
Gly Pro Ser His Ser Gly Val His Gln Pro Ser Leu Cys Phe Ala Ser
    1395                1400                1405
Glu Lys Phe Leu Met Ile Glu Gln Val Ser Lys Val Asp Arg Thr Gly
    1410                1415                1420
Gly Thr Trp Gly Leu Gly Leu Ile Glu Gly His Lys Gln Leu Glu Ala
1425                1430                1435                1440
Asp His Trp Tyr Phe Pro Cys His Phe Lys Gly Asp Gln Val Met Ala
                1445                1450                1455
Gly Ser Leu Met Ala Glu Gly Cys Gly Gln Leu Leu Gln Phe Tyr Met
        1460                1465                1470
Leu His Leu Gly Met His Thr Gln Thr Lys Asn Gly Arg Phe Gln Pro
    1475                1480                1485
Leu Glu Asn Ala Ser Gln Gln Val Arg Cys Arg Gly Gln Val Leu Pro
1490                1495                1500
```

```
Gln Ser Gly Val Leu Thr Tyr Arg Met Glu Val Thr Glu Ile Gly Phe
1505                1510                1515                1520

Ser Pro Arg Pro Tyr Ala Lys Ala Asn Ile Asp Ile Leu Leu Asn Gly
                1525                1530                1535

Lys Ala Val Val Asp Phe Gln Asn Leu Gly Val Met Ile Lys Glu Glu
            1540                1545                1550

Asp Glu Cys Thr Arg Tyr Pro Leu Leu Thr Glu Ser Thr Thr Ala Ser
        1555                1560                1565

Thr Ala Gln Val Asn Ala Gln Thr Ser Ala Lys Val Tyr Lys Pro
    1570                1575                1580

Ala Ser Val Asn Ala Pro Leu Met Ala Gln Ile Pro Asp Leu Thr Lys
1585                1590                1595                1600

Glu Pro Asn Lys Gly Val Ile Pro Ile Ser His Val Glu Ala Pro Ile
                1605                1610                1615

Thr Pro Asp Tyr Pro Asn Arg Val Pro Asp Thr Val Pro Phe Thr Pro
            1620                1625                1630

Tyr His Met Phe Glu Phe Ala Thr Gly Asn Ile Glu Asn Cys Phe Gly
        1635                1640                1645

Pro Glu Phe Ser Ile Tyr Arg Gly Met Ile Pro Pro Arg Thr Pro Cys
1650                1655                1660

Gly Asp Leu Gln Val Thr Thr Arg Val Ile Glu Val Asn Gly Lys Arg
1665                1670                1675                1680

Gly Asp Phe Lys Lys Pro Ser Ser Cys Ile Ala Glu Tyr Glu Val Pro
                1685                1690                1695

Ala Asp Ala Trp Tyr Phe Asp Lys Asn Ser His Gly Ala Val Met Pro
            1700                1705                1710

Tyr Ser Ile Leu Met Glu Ile Ser Leu Gln Pro Asn Gly Phe Ile Ser
        1715                1720                1725

Gly Tyr Met Gly Thr Thr Leu Gly Phe Pro Gly Leu Glu Leu Phe Phe
    1730                1735                1740

Arg Asn Leu Asp Gly Ser Gly Glu Leu Leu Arg Glu Val Asp Leu Arg
1745                1750                1755                1760

Gly Lys Thr Ile Arg Asn Asp Ser Arg Leu Leu Ser Thr Val Met Ala
                1765                1770                1775

Gly Thr Asn Ile Ile Gln Ser Phe Ser Phe Glu Leu Ser Thr Asp Gly
            1780                1785                1790

Glu Pro Phe Tyr Arg Gly Thr Ala Val Phe Gly Tyr Phe Lys Gly Asp
        1795                1800                1805

Ala Leu Lys Asp Gln Leu Gly Leu Asp Asn Gly Lys Val Thr Gln Pro
    1810                1815                1820

Trp His Val Ala Asn Gly Val Ala Ala Ser Thr Lys Val Asn Leu Leu
1825                1830                1835                1840

Asp Lys Ser Cys Arg His Phe Asn Ala Pro Ala Asn Gln Pro His Tyr
                1845                1850                1855

Arg Leu Ala Gly Gly Gln Leu Asn Phe Ile Asp Ser Val Glu Ile Val
            1860                1865                1870

Asp Asn Gly Gly Thr Glu Gly Leu Gly Tyr Leu Tyr Ala Glu Arg Thr
        1875                1880                1885

Ile Asp Pro Ser Asp Trp Phe Phe Gln Phe His Phe His Gln Asp Pro
    1890                1895                1900

Val Met Pro Gly Ser Leu Gly Val Glu Ala Ile Ile Glu Thr Met Gln
1905                1910                1915                1920
```

-continued

```
Ala Tyr Ala Ile Ser Lys Asp Leu Gly Ala Asp Phe Lys Asn Pro Lys
            1925                1930                1935

Phe Gly Gln Ile Leu Ser Asn Ile Lys Trp Lys Tyr Arg Gly Gln Ile
            1940                1945                1950

Asn Pro Leu Asn Lys Gln Met Ser Met Asp Val Ser Ile Thr Ser Ile
            1955                1960                1965

Lys Asp Glu Asp Gly Lys Lys Val Ile Thr Gly Asn Ala Ser Leu Ser
    1970                1975                1980

Lys Asp Gly Leu Arg Ile Tyr Glu Val Phe Asp Ile Ala Ile Ser Ile
1985                1990                1995                2000

Glu Glu Ser Val

<210> SEQ ID NO 10
<211> LENGTH: 543
<212> TYPE: PRT
<213> ORGANISM: Shewanella putrefaciens

<400> SEQUENCE: 10

Met Asn Pro Thr Ala Thr Asn Glu Met Leu Ser Pro Trp Pro Trp Ala
  1               5                  10                  15

Val Thr Glu Ser Asn Ile Ser Phe Asp Val Gln Val Met Glu Gln Gln
                 20                  25                  30

Leu Lys Asp Phe Ser Arg Ala Cys Tyr Val Val Asn His Ala Asp His
             35                  40                  45

Gly Phe Gly Ile Ala Gln Thr Ala Asp Ile Val Thr Glu Gln Ala Ala
         50                  55                  60

Asn Ser Thr Asp Leu Pro Val Ser Ala Phe Thr Pro Ala Leu Gly Thr
 65                  70                  75                  80

Glu Ser Leu Gly Asp Asn Asn Phe Arg Arg Val His Gly Val Lys Tyr
                 85                  90                  95

Ala Tyr Tyr Ala Gly Ala Met Ala Asn Gly Ile Ser Ser Glu Glu Leu
                100                 105                 110

Val Ile Ala Leu Gly Gln Ala Gly Ile Leu Cys Gly Ser Phe Gly Ala
            115                 120                 125

Ala Gly Leu Ile Pro Ser Arg Val Glu Ala Ala Ile Asn Arg Ile Gln
        130                 135                 140

Ala Ala Leu Pro Asn Gly Pro Tyr Met Phe Asn Leu Ile His Ser Pro
145                 150                 155                 160

Ser Glu Pro Ala Leu Glu Arg Gly Ser Val Glu Leu Phe Leu Lys His
                165                 170                 175

Lys Val Arg Thr Val Glu Ala Ser Ala Phe Leu Gly Leu Thr Pro Gln
            180                 185                 190

Ile Val Tyr Tyr Arg Ala Ala Gly Leu Ser Arg Asp Ala Gln Gly Lys
        195                 200                 205

Val Val Val Gly Asn Lys Val Ile Ala Lys Val Ser Arg Thr Glu Val
    210                 215                 220

Ala Glu Lys Phe Met Met Pro Ala Pro Ala Lys Met Leu Gln Lys Leu
225                 230                 235                 240

Val Asp Asp Gly Ser Ile Thr Ala Glu Gln Met Glu Leu Ala Gln Leu
                245                 250                 255

Val Pro Met Ala Asp Ile Thr Ala Glu Ala Asp Ser Gly Gly His
            260                 265                 270

Thr Asp Asn Arg Pro Leu Val Thr Leu Leu Pro Thr Ile Leu Ala Leu
        275                 280                 285
```

-continued

```
Lys Glu Glu Ile Gln Ala Lys Tyr Gln Tyr Asp Thr Pro Ile Arg Val
    290                 295                 300

Gly Cys Gly Gly Val Gly Thr Pro Asp Ala Ala Leu Ala Thr Phe
305                 310                 315                 320

Asn Met Gly Ala Ala Tyr Ile Val Thr Gly Ser Ile Asn Gln Ala Cys
                325                 330                 335

Val Glu Ala Gly Ala Ser Asp His Thr Arg Lys Leu Leu Ala Thr Thr
            340                 345                 350

Glu Met Ala Asp Val Thr Met Ala Pro Ala Ala Asp Met Phe Glu Met
        355                 360                 365

Gly Val Lys Leu Gln Val Val Lys Arg Gly Thr Leu Phe Pro Met Arg
    370                 375                 380

Ala Asn Lys Leu Tyr Glu Ile Tyr Thr Arg Tyr Asp Ser Ile Glu Ala
385                 390                 395                 400

Ile Pro Leu Asp Glu Arg Glu Lys Leu Glu Lys Gln Val Phe Arg Ser
                405                 410                 415

Ser Leu Asp Glu Ile Trp Ala Gly Thr Val Ala His Phe Asn Glu Arg
            420                 425                 430

Asp Pro Lys Gln Ile Glu Arg Ala Glu Gly Asn Pro Lys Arg Lys Met
        435                 440                 445

Ala Leu Ile Phe Arg Trp Tyr Leu Gly Leu Ser Ser Arg Trp Ser Asn
    450                 455                 460

Ser Gly Glu Val Gly Arg Glu Met Asp Tyr Gln Ile Trp Ala Gly Pro
465                 470                 475                 480

Ala Leu Gly Ala Phe Asn Gln Trp Ala Lys Gly Ser Tyr Leu Asp Asn
                485                 490                 495

Tyr Gln Asp Arg Asn Ala Val Asp Leu Ala Lys His Leu Met Tyr Gly
            500                 505                 510

Ala Ala Tyr Leu Asn Arg Ile Asn Ser Leu Thr Ala Gln Gly Val Lys
        515                 520                 525

Val Pro Ala Gln Leu Leu Arg Trp Lys Pro Asn Gln Arg Met Ala
    530                 535                 540
```

<210> SEQ ID NO 11
<211> LENGTH: 499
<212> TYPE: PRT
<213> ORGANISM: Shewanella putrefaciens

<400> SEQUENCE: 11

```
Met Arg Lys Pro Leu Gln Thr Ile Asn Tyr Asp Tyr Ala Val Trp Asp
  1               5                  10                  15

Arg Thr Tyr Ser Tyr Met Lys Ser Asn Ser Ala Ser Ala Lys Arg Tyr
                20                  25                  30

Tyr Glu Lys His Glu Tyr Pro Asp Asp Thr Phe Lys Ser Leu Lys Val
            35                  40                  45

Asp Gly Val Phe Ile Phe Asn Arg Thr Asn Gln Pro Val Phe Ser Lys
        50                  55                  60

Gly Phe Asn His Arg Asn Asp Ile Pro Leu Val Phe Glu Leu Thr Asp
65                  70                  75                  80

Phe Lys Gln His Pro Gln Asn Ile Ala Leu Ser Pro Gln Thr Lys Gln
                85                  90                  95

Ala His Pro Pro Ala Ser Lys Pro Leu Asp Ser Pro Asp Val Pro
            100                 105                 110

Ser Thr His Gly Val Ile Ala Thr Arg Tyr Gly Pro Ala Ile Tyr Tyr
        115                 120                 125
```

Ser Ser Thr Ser Ile Leu Lys Ser Asp Arg Ser Gly Ser Gln Leu Gly
130                 135                 140

Tyr Leu Val Phe Ile Arg Leu Ile Asp Glu Trp Phe Ile Ala Glu Leu
145                 150                 155                 160

Ser Gln Tyr Thr Ala Ala Gly Val Glu Ile Ala Met Ala Asp Ala Ala
                165                 170                 175

Asp Ala Gln Leu Ala Arg Leu Gly Ala Asn Thr Lys Leu Asn Lys Val
                180                 185                 190

Thr Ala Thr Ser Glu Arg Leu Ile Thr Asn Val Asp Gly Lys Pro Leu
                195                 200                 205

Leu Lys Leu Val Leu Tyr His Thr Asn Asn Gln Pro Pro Pro Met Leu
210                 215                 220

Asp Tyr Ser Ile Ile Ile Leu Leu Val Glu Met Ser Phe Leu Leu Ile
225                 230                 235                 240

Leu Ala Tyr Phe Leu Tyr Ser Tyr Phe Leu Val Arg Pro Val Arg Lys
                245                 250                 255

Leu Ala Ser Asp Ile Lys Lys Met Asp Lys Ser Arg Glu Ile Lys Lys
                260                 265                 270

Leu Arg Tyr His Tyr Pro Ile Thr Glu Leu Val Lys Val Ala Thr His
                275                 280                 285

Phe Asn Ala Leu Met Gly Thr Ile Gln Glu Gln Thr Lys Gln Leu Asn
290                 295                 300

Glu Gln Val Phe Ile Asp Lys Leu Thr Asn Ile Pro Asn Arg Arg Ala
305                 310                 315                 320

Phe Glu Gln Arg Leu Glu Thr Tyr Cys Gln Leu Leu Ala Arg Gln Gln
                325                 330                 335

Ile Gly Phe Thr Leu Ile Ile Ala Asp Val Asp His Phe Lys Glu Tyr
                340                 345                 350

Asn Asp Thr Leu Gly His Leu Ala Gly Asp Glu Ala Leu Ile Lys Val
                355                 360                 365

Ala Gln Thr Leu Ser Gln Gln Phe Tyr Arg Ala Glu Asp Ile Cys Ala
                370                 375                 380

Arg Phe Gly Gly Glu Glu Phe Ile Met Leu Phe Arg Asp Ile Pro Asp
385                 390                 395                 400

Glu Pro Leu Gln Arg Lys Leu Asp Ala Met Leu His Ser Phe Ala Glu
                405                 410                 415

Leu Asn Leu Pro His Pro Asn Ser Ser Thr Ala Asn Tyr Val Thr Val
                420                 425                 430

Ser Leu Gly Val Cys Thr Val Val Ala Val Asp Asp Phe Glu Phe Lys
                435                 440                 445

Ser Glu Ser His Ile Ile Gly Ser Gln Ala Ala Leu Ile Ala Asp Lys
                450                 455                 460

Ala Leu Tyr His Ala Lys Ala Cys Gly Arg Asn Gln Ala Leu Ser Lys
465                 470                 475                 480

Thr Thr Ile Thr Val Asp Glu Ile Glu Gln Leu Glu Ala Asn Lys Ile
                485                 490                 495

Gly His Gln

<210> SEQ ID NO 12
<211> LENGTH: 40138
<212> TYPE: DNA
<213> ORGANISM: Vibrio marinus

<400> SEQUENCE: 12

-continued

```
aatagatcga ctcgcaaaag ttgcttaaga tagtgtcaat atagcttctt atttgtaaat      60
attgttttt  atgtgtaaac atgtttagtg tgtgtaaatg ctgttaatta tccttttggg    120
attgtaatag ctgatgttgc tggctaatga gtacttttag ttcggcaata tcttgcttta    180
aatcgctaac ttcagttttt aattcaccca cacttgttgt atttttaagg ctctcttccc    240
caccatcgac aaaccaggat gatatgaaac cggtaaacgt accaaagaga ccgacacctg    300
cagtcatgag taatgccgca atgatacgtc cgccagtggt gacggggtag tagtcaccgt    360
aaccaacagt cgttattgtc acaaatgacc accaaagtgc gtcgatgccg ttattgatgt    420
tactgcctac ttgatcctgt tctaacaata aataccgat  agcaccaaag gtgacaagga    480
tgaaggatat cgcagatacc agcgaaaagg tggctttaaa ccgatgttca aaaatcattt    540
ttaagataat ttttgatgag cgtatattct aatagatct  taatactcta gcgatacgaa    600
ttatgcgaat aaactgcagt tgctcgacca tcggaatact cgacagtagg tcaatccaac    660
cccatttcat aaactgaaat ttattctcag cttggtgaaa gcgaattaca aagtcagtga    720
aaagaataa  gcaaatcgta ttatctacgc tcgttaatat ttcagtgacg ttacttgaaa    780
aggtaaaaat aagttgcagt agtgatgata cgaccacatg aagtgataaa ataagcatga    840
aaatctgaaa tggatttaca tcactgttgt ttttggtgcc acttttaagg ttcgttttca    900
caatctgctg cctcggttca ttgattttgt taatataaac cttagtcagt agcaagacaa    960
aatatattta catcaatgtc atcgtattat tcaaccgcgc gtcgtgtatt cagaccaaga   1020
tcgttgtata tgttagtcat gtagcgatga gattatcatg cgacaggaga gaattatgtt   1080
tgttattatt ttttacgtac ctaaagttaa tgttgaagaa gtaaaacagg cgttatttaa   1140
cgtcggagct ggcaccatcg gtgattatga tagttgtgct tggcaatgtt tggggactgg   1200
gcagttccaa cctttacttg gtagccagcc acatattggt aagctaaatg aggttgaatt   1260
cgttgatgag tttagagtag aaatggtttg tcgagcagaa aatgtaaggg cagcaataaa   1320
tgcacttatt gctgcgcacc cttatgaaga acctgcttat catattctgc aaacattgaa   1380
tcttgatgag ttaccttaag ttagatgcac tgcacttaat tggttcgctg tgctaggtta   1440
gcaattagca attttgacca tgttagcgat agttttggca caagtgatcg atattaaact   1500
atccgattca gatcccattt ttactgctga attaggtttc attacacttg ttctagtggt   1560
ttttcccgac aggtgtaact ctgttacttg cgtaaggttg ataatctcta ccgcattggc   1620
aggagttaca cctgcaccag gcataatact aattctacca tctgcttggt taactaacgt   1680
ttggattaag gcgcagcctt ctagcgcttg agcttgttga ccagaggtta aaatacgctc   1740
acaaccagca gtgatcaagg tctccaaggc ttgttgtgga tcattacaca agtcgaaagc   1800
gcggtggaag gttacgccga gatcacgtga tgccaccatt aagcgtttta aagctggctc   1860
gtcaatatta ccatctgctg ttaacgcgcc aataacgacc ccttggacac cgagtaactt   1920
catgaatttg atgtcggaaa ccataatatc aacttcttgt tcgctatata caaaatcacc   1980
ggcgcgaggg cgaataatgg cataaatggg gatcgttgct agatcaatag acttttgtac   2040
aaaacctgcg ttggcggtca agccacctaa tgctaatgcc gagcacaact caatacgatc   2100
ggcgccagat gcttgagccg tcagcagtga ttctatatta tcgacacata cttctattgt   2160
cattgtcata tacttctctt taaaaagttt attaaaaata ataaagccag cataagtcgt   2220
tttatacaat atgaaagggg aaaaggcgac ttagctcgcc tagatcaatt attatggcag   2280
aatactgccg tattgtgatt agaaagacag ttttttaagc tcaatagccg ttatcgcgtt   2340
```

```
gttatctacc atcgtgtaac ttttctggcc tgggtgcttt attaacactg tttcagtggc    2400
tggattaggg tgaaatgatt cttttttcaa atctgttttt ttgtatttga acgtacctgt    2460
aatgtcttgc tgctcacgaa gacgtacaaa tattggttgc gcatagcttg gtagtgccgc    2520
attgacatgt tgatagaatt cagacgctga aaattcatga ataggggcaat tcaaagtcag   2580 cgcgaccatg cctgctcggc catcgtgatg tgggagcttg acaccataag ccacactttg    2640
ctcaatttgc acaaaatcgt taacttgagc ttctacttgc gtcgtggcga cattttcacc    2700
tttccagcgg aatgtatcac ctaatctatc cacaaaggaa atatggcgat aaccttggta    2760
atgaacgaga tcgccggtat aaaataaca gtcaccgtct tttaatactg acttaaatag     2820 cttttttatta ctttcgttgt catcggtata accatcaaat ggtgaacgtt tagttatctt   2880
tgttagcagt agccctgttt ctcccgtttt tactttggtc attttccctt tcgcattata    2940
cacaggtttg tcattgtcaa tatcatattg tatgacggta aaagcaagtg gagtaacccc    3000
cgctgtatgc ggtaagttca gcgcattgga gaacacaaga ttacactcac tggcgccata    3060
gaattcatta atatgctcga tcccaaaacg ttgttggaaa tgatcccaaa tttcggggcg    3120
taatccatta cctatgattt tctttatatt atgctgtttg tctttattgc taggcggtac    3180
atttaataaa taacggcaga gctcgccgat gtaagtaaac gcagtggcat tatgagcacg    3240
aacttcatcc caaaagcgac ttgaactgaa ttttcagaa agtgcgaggg ttgctgcgct     3300
accaaacacg gcgcttaatg acactgtcag tgcattgtta tggtataggg ggagtgataa    3360
atacaataca tcatcagctg ttaagcgtaa tgatgccatc cccatgcctg ccatggattt    3420
aaaccaacgg tgatggctca ttcttgctgc ttttggcagt ccagttttc ccgaggtaaa     3480 gatataaaac gcgcaatgct taagctgtat ttgtgctgtt gattcagggt tcaatactga   3540
atatcctgcg actagtgtag atatgttttt ataaccatca ctcatgtctg gcgtttctaa    3600
agcgggtacg taaaagacat tctgttgtaa tgtcgatgac aaattggttt caatattatt    3660
aatggcggat gtgtatagtt catctgcgat gagtaaatttg gtatcgacca cgctaagact   3720
atgttcgagg attgaatccc gttgtgtcgt atttatcata caagcaatcg cgccaagctt    3780
gacaactgcg agggcaataa tgatggtttc aggcctgtta tcgagcatga tggcgacttt    3840 atcatttta ccaatgccgt attcatgaag gaaatgggca tattgatttg cttgcttatt     3900
caatgaatcg taactataac gctggtcttt aaattgtatt gcgatcaagt cagagttatt    3960
gacagcttgc tgctctagta ataaaccaat agacataaaa cgttcgggct ttgcttgttg    4020
taagtgccat aagcctttga tgattggctt tggggttttt aatagattga tggtacttt    4080 caggaattgt ttgccggtta taacagtcat aagctaattc ttttttatcaa gaagagggt    4140 tatgacacca aataaatggg tcacgcgttg gtttaatttg gttagactaa atgtgttgtt    4200
ttgctgtgat aatgcgacgt tcaaacaaac ttgagaaggt aaaaaaatag cattttaaa    4260 ttgaacatca atactaatgt gttgaatatc aatcaagttt tctaactgtg cgagcacgcg    4320
tgctttagca acatgccat gtgctattgc tgttttaaac cccattagtt tcgctgggat     4380
aaaatgtaaa tggattggat ttgtgtcttt ggagatataa gcatatttat atacgtcaaa    4440
aggactaaat ttaaacaatg aaatcggctc gtaagcataa ttcgctggcg tatttactat    4500
tttctcaccg ctggaacgtt gagatcgttg gcacgttttt cgctgtttcg ttttctgtaa    4560
gaatgtcgat gtacactccc acgcaaattg tccatctaca aacacatcaa tatgagtatc    4620
aatgaaacgt cctgtatccg ttatgtactc cttaattaca cgacatgtgc tcgtcaatat    4680
cgcgtttaat gctatcggtt gatgttgtgt tatgcgattt cgataatgga ctagtcctaa    4740
```

```
tatagatatc ggaaattgtg ttgatgtcat gagtttcatc aataatggaa agatcatcac    4800
aaatggataa gtaaccggta catagtttgt gttattaaac ccacagcatt taatatattg    4860 cttaaattt  cgctgatcta ttttttgtcc actgatacta aattgctcag tacacacttg    4920
tgtcgaccaa gtgttcatca gtgttttaac aattgtattg accactgctt tcacatataa    4980
aagcgagata atcggttgct ttgttaacag tgtgatctgg ttagcgtgca ttgaaataat    5040
tcatataaga gtatgtagca tttatgttaa tattttgttt tggaagttga attggcgaat    5100
ccgtaatcgg tttatggcag ttcggtcaaa tacttcaggt aaactcgtta ctcataccat    5160
tgatagtgtt aaagtgattg actgaataaa gaatagagct aaaagtggaa aaattatgca    5220
agatgcgggt atgttattac gcattgctta tgaggcaatg aaagagttag aggttgatgt    5280
cattgaagta ctttctcgtt gtaacataag tgaagaagta ctgaatgata aggatcttcg    5340
cacacctaat catgcacaaa cacattttg  gcaagtatta aagacatat  cacaagatcc    5400 taacatcggc atttcacttg gtgagagaat gccagtgttc acgggcagg  tattacagta    5460 tcttttctc  agtagtccta catttggtac tggctgggaa cgcgcaacaa atactttcg    5520 attaatcagt gatgcggcga gtgtttctat caagatggaa ggctgtgaag cgcgattatc    5580
tgtgaactta gatggtttag cggaagatgc gaatcgtcat ttgaatgatt gcctagtgat    5640
cggtgcattt aaattttgtt tatatgtgac agaaggcgaa tttaaagtaa gcaaaatagc    5700
ctttgctcat gctcgcccga agatattac  tgcctatacc aatgtattta catgtccgat    5760
tgagtttgct gccgaagata attatattta tttcgatgct gatttactcg aacgtccttc    5820
ttcgcatgcg gagcctgagc tattcgcctt acacgatcag cttgcaagcc gtaaaatagc    5880
caagttagaa ctgcaagatt tagtggataa agtacgtaag gttattgcac aacaacttga    5940
gtctggtgtg gtgactttag aaagtatcgc cactgaactt gacatgaaac cacgtatgct    6000
aagagcgaag ttagctgaca ttgattataa ctttaatcaa atactcgctg attttcgttg    6060
cgagttatca aaaaaactgt tggcgaatac ggacgagtct attgatcaga ttgtctatct    6120
cactggtttt tctgaaccaa gtactttta  tcgtgccttt aagcgctggg ttaaaatgac    6180
gccaattgaa tatcgccgta gcaaactcgg ggttaggcat gctaatcaac acgagtccta    6240
aaaattcgct gcttagtgca tagtgcatag tgcatagtgc tagtaagcca agtacaaagc    6300
gttaaagtta agtacttgag cgaaccatca gacaccactt actagattaa gcacctatta    6360
atgattgacc acaaattctg atcgtattgc ctgtgatccc tgcagcttga ggttgcgcaa    6420
aaaaagctat cgcttcagca acatcaactg gcttaccacc ttgttttaat gaattcatac    6480
gacgaccagc ttcacgaact gtaaatggaa tcgctgctgt catttttgtt tcaataaagc    6540
ctggtgcaac agcattaatg gtgatgtatt tgtctgcaag cggagtttgc attgcatcaa    6600
cataaccaat gactgcggcc ttagacgttg cataattagt ctgaccaaag ttacccgcaa    6660
tcccactcat cgaagacaca caaacaatgc ggccatagtc gttgagcaga tcatcattta    6720
gcagtcgctc attgattctt tccattgccg acaagttaat atccatcagt acatcccaat    6780
ggttatccgg catacgtgct agcgttttgt cttttgttac cccggcatta tggacgatga    6840
tatcaagcga ctgttctcgc acaaagtcag caatgatatt tggggcgtca gcagcggtaa    6900
tatcagcaac aatgctgcta cctttcaagc aatgagctac ttttcaaggt cctgttttta    6960
atgccggaat gtctaagcaa ataacatgtg cgccatcacg ggcgagtgtt tcagcaatag    7020
cagccccgat gccacgtgat gcaccagtga caagtgctgt cttccttgt  aatggttttg    7080
```

```
ccgtgttact tgtttcgtta ataacttcgt taataacttc gttaataact tcgttaatag   7140
ccccattaat cgaaccgggt tttacgttaa taacctgtgc tgagatatag gctgattttg   7200
ctgaggttaa gaaacgtagc ggggcctcta ataattgctc actaccaggt tgtacataga   7260
taagttgaca ggtactacca ttcttgccta tttctttggc gacactgcga caaaaccctt   7320
ctaaagatct ttgtacagtc gcgtagctta catcgtcaag atgttcactc ggatgaccta   7380
acacgatcac tctgctgcat ggcgagagct gcttaattac aggttgaaaa aaacgatgta   7440
atgcacttaa ttgcttgctg ttcttaatgc ctgaggcgtc gaagataata ccgttgaagc   7500
gatctgtttt agcgatagca ttaaggctaa taggtgtcgc gactaaagac gtttgattaa   7560
attcaatatt aagatcggct aacgctgacg tgttattagg ataagaaatc gtgacttcag   7620
catctttaaa tgtgttaaga atgggtttaa ttaatttgct gttgctggct gcgccgatga   7680
gtaagttgcc agagatgaga tcggttccct gatcgtagcg tgttaacgta accggtcgtg   7740
gcagattaag cgctttaaat aaacctgatg tccacttgcc attagcgagt tttgcgtatg   7800
tatccgtcat tttctaatcc ttgttatagt gaacagtttg aatctcgaag atgtacatgt   7860
gttaaaaatt atctgatagc tatgacttat ctgccactac gtaataataa atagaccagt   7920 tcattcatc gttaatcgat atagtataac taaatactaa gtaaattata atgataagac   7980
tgttatcgta ctcggatcaa actctgatca gcaaataatc aaattagagt ttttatttta   8040
aacttgtatc aacaatgtta cattaatgta tcttacgtct aatgtgctac gggcatattt   8100
aagtcactaa attaaaggaa taaaccatga caggtcaaac aataagaaga gtagcaatta   8160
tcggcggtaa ccgtatcccg tttgcacgtt caaatacagc gtattcaaaa ctaagtaacc   8220
aagatatgct gacggaaact atccgtggct tggtggttaa atataaccta cgtggtgaac   8280
aactggggga agttgttgct ggtgcggtaa ttaagcattc tcgtgatttt aacttaacac   8340
gtgaagccgt gctaagtgca ggtcttgcac ctgaaacgcc ttgttatgac attcaacaag   8400
cttgtggtac tggtctagct gcagctatcc aagtagcaaa caaaattgcg cttggtcaaa   8460
tagaagcggg tattgctggt ggttctgata cgacatcaga tgcaccgatt gcagtcagtg   8520
aaggcatgcg tagtgtatta cttgagctta atcgagctaa aacgggtaag caacgtttga   8580
aagcactatc tcgtctacgt ctaaaacact ttgcgccact aacgcctgca ataaagagc   8640 cgcgtaccaa aatggcgatg ggcgatcatt gtcaagtaac agcgaaagag tggaatatct   8700
cacgtgaagc acaagatgca ttggcctgcg caagtcatca aaaattagct gcagcatatg   8760
aagaaggttt ctttgatacg ttagtttcac ctatggccgg cttaacgaaa gataacgtat   8820
tacgcgcaga tacaacagtt gagaaactgg ctaaattgaa accttgtttt gataaagtaa   8880
acggcactat gacggcgggt aacagtacta accttaccga tggagcatca gctgtattac   8940
ttgcaagtga agaatgggca gcggcacata acttaccagt acaagcttat ctaacatttg   9000
gtgaaacggc cgctatcgac ttcgttgata agaaagaagg tctgttaatg gcgcctgcat   9060
acgcagtgcc aaaaatgttg aagcgtgctg gccttacatt acaagacttc gattactatg   9120
aaatacatga agcatttgct gcgcagttat tagcaacgct agcagcttgg gaagacgaaa   9180
aattctgtaa agaaaaactg ggtctagatg ctgcgcttgg ttcaattgat atgaccaagt   9240
taaacgtgaa agggagtagc ttagccacgg gtcacccatt gccgcaact ggtggtcgtg   9300 ttgtcgctac gctagcgcaa ttacttgatc agaaaggttc aggtcgtggt ttgatctcga   9360
tttgtgctgc tggtggtcaa ggtatcacgg caatttaga gaaataaacg cactgtttat   9420
tatctattga ttaagctgtc ctgagatact ggatattttt aaataaaacg ccaatactgc   9480
```

```
agagtattgg cgttttttg taataccaat tcctatataa cggtgcattt taaacactta    9540
atttccggca ttggtatcat aaaaaagcag caccgaagtg ctgcttgatt gtagattaac    9600
ctattaaaat agagaggcta gaattagtct tcgtatgctt cattatgtac gccagctgca    9660
cgacccgatg gatcagcatt gttttggaaa ctttcatccc aagctaatgc ttctacagtt    9720
gaacaagcaa cggatttacc aaacggtacg catttcgctg ctgaatcacc tgggaagtga    9780
tcttcaaaga tggcacgata gtagtaacct tctttcgtat ctggtgtgtt aattgggaac    9840
ttaaatgctg cacttgctaa catttgatca gttaccgctt cttcaacgtg tactttaagt    9900
tggtcaatcc aagaataacc aacaccatca gagaattgtt cttttttgacg ccatacaatt    9960 tcttcaggta gtaaatcttc aaatgcttct cgaatgatgt ttttctcaat gcggtcgccc   10020
gtgatcattt ttagttcagg gtttagacgc attgacgcat caacaaattc tttatctaag   10080
aaaggaacac gtgcttcgat gccccaagct gccatagatt tgtttgcacg taagcaatca   10140
aacatatgta atttatttac tttacgtacc gtctcttcat ggaattcttt cgcatttggc   10200
gctttgtgga agtacaagta accaccgaac agttcatcag caccttcacc agaaagcacc   10260
atcttaatcc ccatggcttt aattttacgt gccattaggt acataggggt tgatgcacga   10320
attgttgtta catcgtaggt ttcaatgtgg taaatcacgt cgcgtaaagc gtcgatacct   10380
tcttgcacag taaattcaat tgaatgatgg atagtaccta agtgatctgc cactttttgt   10440
gcagcggcta aatctggaga accatttagg cctacagaga aagagtgtag ttgtggccac   10500
catgcttcgg ttttaccacc gtcttcaata cgacgttttg catactgttg ggtgattgct   10560
gaaataacag atgaatctaa cccgcctgat aataatacgc cgtaaggtac atcacacatt   10620
aattgacgtt taactgcatc ttccaaacct tgcttaacaa cgcttttatc accaccattt   10680
tgtgcaacgt tatcaaaatc tttccaatca cgttgataat aaggcgtgac tacaccatcc   10740
ttactccaca ggtaatgacc tgctgggaat tcttcaattt gagtacaaat tggcactagt   10800
gctttcattt cagaggcaac ataaaagtta ccgtgttcat catagcccgt ataaagaggg   10860
atgataccga tatggtcacg gccaatcagg taagcgtcct ctgtttcgtc atataaagcg   10920
aaagcaaaaa taccatttag atcatctaaa aattgtgtgc ctttttcttt atatagcgca   10980
agtatcactt cgcaatctga ttctgtttgg aattcaaagt ctacgttcag cgttttcttt   11040
aaatctttgt ggttataaat ttcaccatta acagcaagta cgtgtgtctt ttcttcatta   11100
tatagcggct gtgcaccatt atttacatcg acaatagcaa gacgttcatg aactaaaata   11160
gcattgtcac ttgtatagat acctgaccaa tctgggccgc ggtgacgtag taactttgat   11220
agttctagtg cttgttcgcg aagaggttta atgtctgatt tgatgtctag aattccgaat   11280
attgagcaca taactaattc cttctggggc tgcgtctgca gctaactttc taaatagtgt   11340
gtctaatttg ccacattgta gatttaatgc aaacattaat gataaaacat ttataaaaaa   11400
tgtaattcaa tgtggaatcg ataatttaat ggcttaaaag tgaagatcca ttaattgtga   11460
tggcgaggtg atagaccaat gtagaccta atgaataaag caggcacgat tgaatccatt   11520
caacgcaaag tggtactaac tattgtttta aacgttataa atagtgtttt aaaggttata   11580
agtaaataat ttaaaacaa taataatcca catgcattaa atttatcatg ataaaccgct   11640
atatctcaat ggcaatttgg gataagtgta aaatatatgt aaaatgaatg agttgacttg   11700 cttttttttac actaagtgat gaaattaaag ctagatgtcg ttgttagcat tgattaataa   11760
cgtactaaaa tacgacatct agtatagaaa tttaaaaaac agttggtttt gatagcataa   11820
```

-continued

```
ctgcataaac taatcagctt attgtctgta atatttttgt aatttaaata ggtttaataa   11880
aattatatgt ctgataaata taaaccgtac gacctttcct ttaaaaagac gttttgctg    11940 cctaagtttt ggcctgtgtg gttcggggtg tttgcaatat acttattagc ttttatgcca   12000
gtaaagccgc gtgataaatt tgctcgattc atagcgaaga aattgtttag tctaaaaatg   12060
atggcaaagc gtaaaaaggt agcaaagatc aatttatcta tgtgcttccc tgaaatggat   12120
gatacggaac aagaccgtat aatcatggtc aatctagtta cttttgtca aactatctta   12180 agttatgcag agccaagtgc gcgtagtcgt gcttataacc gtgaccgtat gatagtgcat   12240
ggtggcgaga atttatttcc gctacttgaa caaggtaagg cttgtatctt attagtgccg   12300
catagcttcg ctattgattt tgcaggttta cacattgctt cttatggcgc gccattttgt   12360
actatgttta acaattctga gaatgagttg ttcgattggc tgatgacacg tcaacgcgct   12420
atgtttggag gcactgttta tcaccgcaag gcagggctag gggctctagt taaatcactt   12480
aagagcggtg aaagctgtta ttacttacct gatgaagacc atggacctaa gcgtagtgta   12540
tttgcgcctt tatttgcgac tcaaaaagca acttttacctg taatgggcaa gctagcagaa   12600
aaaacaaatg cactcgttgt tcctgtttat gcggcatata atgaatcact aggtaaattt   12660 gaaacccttta ttcgaccagc aatgcaaaac tttccatcag aaagcccaga acaagatgca   12720
gtgatgatga ataaagagat tgaagccttg attgaatgtg gtgttgatca atatatgtgg   12780
acacttagat tattgagaac acgtccggac ggtaaaaaaa tctactaata aagtttaata   12840
aacaccataa tcttcgttga atatggtgtt tacccccctg aataccctct aaattaataa   12900
caaaaaaagc catttacgta acatctaatg atgatttagc ctgcacttgc tttgttttta   12960
gtcttaagag cctaataaac ttgatctagg tatagattct gtctttcttt acgtaacgcg   13020
atctattttt tttaaccgat agttgttata attagtttca tatgaaagag atatcgtttc   13080
agtaaaagct atttcgtttc aatagataat ttatttatag tcatatttttc tgtaatgaca   13140 atcattttct catctagact atagataaga atacgaatta agtaagaaca ttaattttac   13200
aagaatataa aatatcccat cggagctata agaatgaaaa agactaaaat tgtttgtaca   13260
attggtccaa aaactgaatc agtagagaaa ctaacagagc ttgttaatgc aggcatgaac   13320
gttatgcgtt taaatttctc tcatggtaac tttgctgaac attcagtgcg tattcaaaat   13380
atccgtcaag taagtgaaaa cctgaataag aaaattgctg ttttactgga tactaaaggt   13440
ccagaaatcc gtacgattaa actagaaaac ggtgacgatg taatgttgac cgctggtcag   13500
tcattcacgt ttacaacaga cattaacgtg gtaggtaata aagactgtgt tgctgtaaca   13560
tatgctggtt ttgctaaaga ccttaatcct ggtgcaatca tccttgttga tgatggttta   13620
attgaaatgg aagttgttgc aacaactgac actgaagtta aatgtacagt attaaatact   13680
ggtgcacttg gtgaaaataa aggcgttaac ttacctaaca tcagtgtagg tctacctgca   13740
ttgtcagaaa aagataaagc tgatttagcg tttggttgtg agcaagaagt tgattttgtt   13800
gctgcatcat ttattcgtaa ggctgatgat gtaagagaaa ttcgtgaaat cctatttaat   13860
aatggtggcg aaaacattca gattatctcg aaaattgaaa accaagaagg tgtagacaat   13920
ttcgatgaaa tcttagctga atcagacggt atcatggttg ctcgtggcga tctcggtgtt   13980
gagatcccag ttgaagaagt gatcatggca cagaagatga tgatcaaaaa atgtaataaa   14040
gcaggtaaag ttgtaattac tgcaacacaa atgcttgatt caatgatcag taacccacgt   14100
ccaacacgtg cagaagcggg cgatgttgcc aatgctgtgc ttgacggtac cgacgcggta   14160
atgctttctg gtgaaactgc gaaggtaaaa tacccagttg aagctgtgtc tatcatggca   14220
```

```
aacatctgtg aacgtactga taactcaatg tcttcggatt taggtgcgaa cattgttgct    14280
aaaagcatgc gcattacaga agctgtgtgt aaaggtgcgg tagaaacaac agaaaaattg    14340
tgtgctccac ttattgttgt tgcaactcgt ggcggtaaat cagcaaaatc tgttcgtaaa    14400
tacttcccga aagcaaatat tcttgctatc acaacaaatg aaaaagcagc gcaacagtta    14460
tgcctaacta aaggcgtaag cagctgcatc gttgagcaga ttgatagcac tgatgagttc    14520
taccgtaaag gtaaagagct tgcattagca actggtttag ctaaagaagg cgatatcgtt    14580
gttatggtat caggtgcgtt agtaccatca ggtacaacga atacggcatc tgttcaccaa    14640
ctttaagttg ccatattgat attataaaaa agagagcgta tgctctcttt ttttatatct    14700
gtagtttata tgtctgtaca aaaaaatgat aaagagtaca taaactatta atatagcgta    14760
atatataatg attaacggtg atgaaagggt taaataaatg gatagtgcta aacataaaat    14820
tggcttagtc ctttctggcg gtggtgcgaa aggtattgct catcttggtg tattaaaata    14880
cctgttagag caagatataa gaccgaatgt aattgcgggt acaagtgctg gctctatggt    14940
tggtgcactt tattgctcag gacttgagat tgatgacatt ttacaattct tcatcgatgt    15000 aaaaccttt  tcttggaagt ttacccgtgc ccgtgctggc tttatagacc cggcaaaatt    15060
atatcctgaa gtgctaaaat atatccccga ggatagcttt gagtaccttc aacctgaatt    15120
gcgcattgtt gccaccaaca tgttactcgg taaagagcat atatttaaag atggctccgt    15180
gattaatgcc ttattagcat cagccagcta ccctttagtt ttttctccga tgatcattga    15240
cgatcaagtg tattcagatg gcggtattgt taatcatttc cccgtgagtg tcattgaaga    15300
tgattgcgat aaaataatcg gcgtatacgt gtcgcccatt cgtcaggtcg aagctgacga    15360
actctcgagt ataaaagacg tggtattacg tgcgttcacg ctgcagggta gtggtgctga    15420
attagataaa ctatcgcaat gtgatgtgca aatttatcca gaagcgctat tgaattacaa    15480
tacgtttgca accgatgaaa aatcattacg ggagatctac cagattggtt atgatgctgc    15540
aaaagatcaa catgacaacc ttatggcatt gaaagaaagt atcaccacca gcgaggttaa    15600
aaagaacgtc tttagcaaat ggtttggtga taaacttgct agcaacagcg gcaaatagcg    15660
gcccacacgg atttatacac taggataatg ggcgttaata gcctcactgt cgttgtgtgg    15720
tctctaattt tagctaaatc ttgtgttata ctgacttcct attaatcata aacgatttat    15780
cacggtaaac atgactcaaa taataaccc gcttcacggc atgacactcg aaaaagtaat    15840
taacagtctc gttgaacaat atggctggga tggtcttgga tactacatca acattcgttg    15900
ctttactgaa aatccaagtg ttaagtctag tcttaaattt ttacgtaaaa ccccttgggc    15960
acgtgataaa gtagaagcgc tatatatcaa aatggtgact gaaggctaac tgtctccacg    16020
ctagcgaacc gctgttttata gttaatataa gtactataag cagggctcgt taattcagta    16080
tgtaattaat cctgaatacc tccgcttatt tcaacattgt actctctaga taacactctc    16140
aacattacac cttcaacatc acagcctcca cataacatcc gatgacatag ccctgttatt    16200
tttcacattt atctatatgc tatatatttt agccatttga tcaattgagt taatttctgc    16260
aatgacaaag atataccatc atccagtaca aatttattat gaagataccg accattctgg    16320
tgttgtttac caccctaact ttttaaaata ctttgaacgt gcacgtgagc atgtgataaa    16380
tagtgactta ctagcaacat tgtggaatga acgcggttta ggttttgcgg tgtataaagc    16440
caatatgact tttcaggatg gggtcgaatt tgctgaagtg tgtgatattc gcacttcttt    16500
tgtcctagac ggtaagtaca aaacgatctg gcgccaagaa gtatggcgtc cgaatgcgac    16560
```

```
tagggctgcc gttatcggtg atattgaaat ggtgtgctta gacaaacaaa aacgtttaca   16620
gcccatccct gatgatgtgt tagctgcaat ggttagtgaa taaatggttc atgcataaat   16680
agttaataca tgattctggc ccgtcacgtt tacagataag aggcatccga tgcctccttc   16740
ctattaccaa tactactgct tatcccttc taactatctt tagcgtccat aacacactga    16800
gcatttattc tattaatcag tgattgtgat ttaattatct tctatatatg taatttaatg   16860
taattttcaa tttattttta gctacattaa ggcttacgaa tgtacgctaa aatgagatgt   16920
cagactaatt ttagcttatt aatctgttag ccgtttatat tttataaaga tgggatttaa   16980
cttaaatgca attaattatg gcgtaaatag agtgaaaaca tggctaatat tcactaagtc   17040
ctgaattta tataaagttt aatctgttat tttagcgttt acctggtctt atcagtgagg    17100
tttatagcca ttattagtgg gattgaagtg atttttaaag ctatgtatat tattgcaaat   17160
ataaattgta acaattaaga ctttggacac ttgagttcaa tttcgaattg attggcataa   17220
aatttaaaac agctaaatct acctcaatca ttttagcaaa tgtatgcagg tagatttttt   17280
tcgccattta agagtacact tgtacgctag gttttgttt agtgtgcaaa tgaacgtttt    17340
gatgagcatt gttttagag cacaaaatag atccttacag gagcaataac gcaatggcta    17400
aaagaacac cacatcgatt aagcacgcca aggatgtgtt aagtagtgat gatcaacagt    17460
taaattctcg cttgcaagaa tgtccgattg ccatcattgg tatggcatcg gttttttgcag  17520
atgctaaaaa cttggatcaa ttctgggata acatcgttga ctctgtggac gctattattg   17580
atgtgcctag cgatcgctgg aacattgacg accattactc ggctgataaa aaagcagctg   17640
acaagacata ctgcaaacgc ggtggtttca ttccagagct tgattttgat ccgatggagt   17700
ttggtttacc gccaaatatc ctcgagttaa ctgacatcgc tcaattgttg tcattaattg   17760
ttgctcgtga tgtattaagt gatgctggca ttggtagtga ttatgaccat gataaaattg   17820
gtatcacgct gggtgtcggt ggtggtcaga acaaatttc gccattaacg tcgcgcctac    17880
aaggcccggt attagaaaaa gtattaaaag cctcaggcat tgatgaagat gatcgcgcta   17940
tgatcatcga caaatttaaa aaagcctaca tcggctggga agagaactca ttcccaggca   18000
tgctaggtaa cgttattgct ggtcgtatcg ccaatcgttt tgattttggt ggtactaact   18060
gtgtggttga tgcggcatgc gctggctccc ttgcagctgt taaaatggcg atctcagact   18120
tacttgaata tcgttcagaa gtcatgatat cgggtggtgt atgttgtgat aactcgccat   18180
tcatgtatat gtcattctcg aaaacaccag catttaccac caatgatgat atccgtccgt   18240
ttgatgacga ttcaaaaggc atgctggttg gtgaaggtat tggcatgatg cgtttaaac    18300
gtcttgaaga tgctgaacgt gacggcgaca aaatttattc tgtactgaaa ggtatcggta   18360
catcttcaga tggtcgtttc aaatctattt acgctccacg cccagatggc caagcaaaag   18420
cgctaaaacg tgcttatgaa gatgccggtt ttgcccctga acatgtggt ctaattgaag    18480
gccatggtac gggtaccaaa gcgggtgatg ccgcagaatt tgctggcttg accaaacact   18540
ttggcgccgc cagtgatgaa aagcaatata tcgccttagg ctcagttaaa tcgcaaattg   18600
gtcatactaa atctgcggct ggctctgcgg gtatgattaa ggcggcatta gcgctgcatc   18660
ataaaatctt acctgcaacg atccatatcg ataaaccaag tgaagccttg gatatcaaaa   18720
acagcccgtt ataccctaaac agcgaaacgc gtccttggat gccacgtgaa gatggtattc   18780
cacgtcgtgc aggtatcagc tcatttggtt ttggcggcac caacttccat attatttttag  18840
aagagtatcg cccaggtcac gatagcgcat atcgcttaaa ctcagtgagc caaactgtgt   18900
tgatctcggc aaacgaccaa caaggtattg ttgctgagtt aaataactgg cgtactaaac   18960
```

```
tggctgtcga tgctgatcat caagggtttg tatttaatga gttagtgaca acgtggccat   19020
taaaaacccc atccgttaac caagctcgtt taggttttgt tgcgcgtaat gcaaatgaag   19080
cgatcgcgat gattgatacg gcattgaaac aattcaatgc gaacgcagat aaaatgacat   19140
ggtcagtacc taccggggtt tactatcgtc aagccggtat tgatgcaaca ggtaaagtgg   19200
ttgcgctatt ctcagggcaa ggttcgcaat acgtgaacat gggtcgtgaa ttaacctgta   19260
acttcccaag catgatgcac agtgctgcgg cgatggataa agagttcagt gccgctggtt   19320
taggccagtt atctgcagtt actttcccta tccctgttta tacggatgcc gagcgtaagc   19380
tacaagaaga gcaattacgt ttaacgcaac atgcgcaacc agcgattggt agtttgagtg   19440
ttggtctgtt caaaacgttt aagcaagcag gtttttaaagc tgattttgct gccggtcata   19500
gtttcggtga gttaaccgca ttatgggctg ccgatgtatt gagcgaaagc gattacatga   19560
tgttagcgcg tagtcgtggt caagcaatgg ctgcgccaga gcaacaagat tttgatgcag   19620
gtaagatggc cgctgttgtt ggtgatccaa agcaagtcgc tgtgatcatt gatacccttg   19680
atgatgtctc tattgctaac ttcaactcga ataaccaagt tgttattgct ggtactacgg   19740
agcaggttgc tgtagcggtt acaaccttag gtaatgctgg tttcaaagtt gtgccactgc   19800
cggtatctgc tgcgttccat acacctttag ttcgtcacgc gcaaaaacca tttgctaaag   19860
cggttgatag cgctaaattt aaagcgccaa gcattccagt gtttgctaat ggcacaggct   19920
tggtgcattc aagcaaaccg aatgacatta gaaaaaacct gaaaaaccac atgctggaat   19980
ctgttcattt caatcaagaa attgacaaca tctatgctga tggtggccgc gtatttatcg   20040
aatttggtcc aaagaatgta ttaactaaat tggttgaaaa cattctcact gaaaaatctg   20100
atgtgactgc tatcgcggtt aatgctaatc ctaaacaacc tgcggacgta caaatgcgcc   20160
aagctgcgct gcaaatggca gtgcttggtg tcgcattaga caatattgac ccgtacgacg   20220
ccgttaagcg tccacttgtt gcgccgaaag catcaccaat gttgatgaag ttatctgcag   20280
cgtcttatgt tagtccgaaa acgaagaaag cgtttgctga tgcattgact gatggctgga   20340
ctgttaagca agcgaaagct gtacctgctg ttgtgtcaca accacaagtg attgaaaaga   20400
tcgttgaagt tgaaaagata gttgaacgca ttgtcgaagt agagcgtatt gtcgaagtag   20460
aaaaaatcgt ctacgttaat gctgacggtt cgcttatatc gcaaaataat caagacgtta   20520
acagcgctgt tgttagcaac gtgactaata gctcagtgac tcatagcagt gatgctgacc   20580
ttgttgcctc tattgaacgc agtgttggtc aatttgttgc acaccaacag caattattaa   20640
atgtacatga acagtttatg caaggtccac aagactacgc gaaaacagtg cagaacgtac   20700
ttgctgcgca gacgagcaat gaattaccgg aaagtttaga ccgtacattg tctatgtata   20760
acgagttcca atcagaaacg ctacgtgtac atgaaacgta cctgaacaat cagacgagca   20820
acatgaacac catgcttact ggtgctgaag ctgatgtgct agcaaccccca ataactcagg   20880 tagtgaatac agccgttgcc actagtcaca aggtagttgc tccagttatt gctaatacag   20940
tgacgaatgt tgtatctagt gtcagtaata acgcggcggt tgcagtgcaa actgtggcat   21000
tagcgcctac gcaagaaatc gctccaacag tcgctactac gccagcaccc gcattggttg   21060
ctatcgtggc tgaacctgtg attgttgcgc atgttgctac agaagttgca ccaattacac   21120
catcagttac accagttgtc gcaactcaag cggctatcga tgtagcaact attaacaaag   21180
taatgttaga agttgttgct gataaaaccg gttatccaac ggatatgctg gaactgagca   21240
tggacatgga agctgactta ggtatcgact caatcaaacg tgttgagata ttaggcgcag   21300
```

```
tacaggaatt gatccctgac ttacctgaac ttaatcctga agatcttgct gagctacgca    21360
cgcttggtga gattgtcgat tacatgaatt caaaagccca ggctgtagct cctacaacag    21420
tacctgtaac aagtgcacct gtttcgcctg catctgctgg tattgattta gcccacatcc    21480
aaaacgtaat gttagaagtg gttgcagaca aaaccggtta cccaacagac atgctagaac    21540
tgagcatgga tatggaagct gacttaggta ttgattcaat caagcgtgtg gaaatcttag    21600
gtgcagtaca ggagatcata actgatttac ctgagctaaa ccctgaagat cttgctgaat    21660
tacgcaccct aggtgaaatc gttagttaca tgcaaagcaa agcgccagtc gctgaaagtg    21720
cgccagtggc gacggctcct gtagcaacaa gctcagcacc gtctatcgat ttgaaccaca    21780
ttcaaacagt gatgatggat gtagttcag ataagactgg ttatccaact gacatgctag     21840
aacttggcat ggacatggaa gctgatttag gtatcgattc aatcaaacgt gtggaaatat    21900
taggcgcagt gcaggagatc atcactgatt tacctgagct aaacccagaa gacctcgctg    21960
aattacgcac gctaggtgaa atcgttagtt acatgcaaag caaagcgcca gtcgctgaga    22020
gtgcgccagt agcgacggct tctgtagcaa caagctctgc accgtctatc gatttaaacc    22080
atatccaaac agtgatgatg aagtggttg cagacaaaac cggttatcca gtagacatgt      22140
tagaacttgc tatggacatg gaagctgacc taggtatcga ttcaatcaag cgtgtagaaa    22200
ttttaggtgc ggtacaggaa atcattactg acttacctga gcttaaccct gaagatcttg    22260
ctgaactacg tacattaggt gaaatcgtta gttacatgca aagcaaagcg cccgtagctg    22320
aagcgcctgc agtacctgtt gcagtagaaa gtgcacctac tagtgtaaca agctcagcac    22380
cgtctatcga tttagaccac atccaaaatg taatgatgga tgttgttgct gataagactg    22440
gttatcctgc caatatgctt gaattagcaa tggacatgga agccgacctt ggtattgatt    22500
caatcaagcg tgttgaaatt ctaggcgcgg tacaggagat cattactgat ttacctgaac    22560
taaacccaga agacttagct gaactacgta cgttagaaga aattgtaacc tacatgcaaa    22620
gcaaggcgag tggtgttact gtaaatgtag tggctagccc tgaaaataat gctgtatcag    22680
atgcatttat gcaaagcaat gtggcgacta tcacagcggc cgcagaacat aaggcggaat    22740
ttaaaccggc gccgagcgca accgttgcta tctctcgtct aagctctatc agtaaaataa    22800
gccaagattg taaaggtgct aacgccttaa tcgtagctga tggcactgat aatgctgtgt    22860
tacttgcaga ccacctattg caaactggct ggaatgtaac tgcattgcaa ccaacttggg    22920
tagctgtaac aacgacgaaa gcatttaata agtcagtgaa cctggtgact ttaaatggcg    22980
ttgatgaaac tgaaatcaac aacattatta ctgctaacgc acaattggat gcagttatct    23040
atctgcacgc aagtagcgaa attaatgcta tcgaatacc acaagcatct aagcaaggcc      23100
tgatgttagc cttcttatta gcgaaattga gtaaagtaac tcaagccgct aaagtgcgtg    23160
gcgccttta gattgttact cagcagggtg gttcattagg ttttgatgat atcgattctg      23220
ctacaagtca tgatgtgaaa acagacctag tacaaagcgg cttaaacggt ttagttaaga    23280
cactgtctca cgagtgggat aacgtattct gtcgtgcggt tgatattgct tcgtcattaa    23340
cggctgaaca agttgcaagc cttgttagtg atgaactact tgatgctaac actgtattaa    23400
cagaagtggg ttatcaacaa gctggtaaag gccttgaacg tatcacgtta actggtgtgg    23460
ctactgacag ctatgcatta acagctggca ataacatcga tgctaactcg gtatttttag    23520
tgagtggtgg cgcaaaaggt gtaactgcac attgtgttgc tcgtatagct aaagaatatc    23580
agtctaagtt catcttattg ggacgttcaa cgttctcaag tgacgaaccg agctgggcaa    23640
gtggtattac tgatgaagcg gcgttaaaga aagcagcgat gcagtctttg attacagcag    23700
```

```
gtgataaacc aacacccgtt aagatcgtac agctaatcaa accaatccaa gctaatcgtg   23760
aaattgcgca aaccttgtct gcaattaccg ctgctggtgg ccaagctgaa tatgtttctg   23820
cagatgtaac taatgcagca agcgtacaaa tggcagtcgc tccagctatc gctaagttcg   23880
gtgcaatcac tggcatcatt catggcgcgg gtgtgttagc tgaccaattc attgagcaaa   23940
aaacactgag tgattttgag tctgtttaca gcactaaaat tgacggtttg ttatcgctac   24000
tatcagtcac tgaagcaagc aacatcaagc aattggtatt gttctcgtca gcggctggtt   24060
tctacggtaa ccccggccag tctgattact cgattgccaa tgagatctta aataaaaccg   24120
cataccgctt taaatcattg cacccacaag ctcaagtatt gagctttaac tggggtcctt   24180
gggacggtgg catggtaacg cctgagctta acgtatgtt tgaccaacgt ggtgtttaca   24240
ttattccact tgatgcaggt gcacagttat tgctgaatga actagccgct aatgataacc   24300
gttgtccaca aatcctcgtg ggtaatgact tatctaaaga tgctagctct gatcaaaagt   24360
ctgatgaaaa gagtactgct gtaaaaaagc cacaagttag tcgtttatca gatgctttag   24420
taactaaaag tatcaaagcg actaacagta gctctttatc aaacaagact agtgctttat   24480
cagacagtag tgcttttcag gttaacgaaa accacttttt agctgaccac atgatcaaag   24540
gcaatcaggt attaccaacg gtatgcgcga ttgcttggat gagtgatgca gcaaaagcga   24600
cttatagtaa ccgagactgt gcattgaagt atgtcggttt cgaagactat aaattgttta   24660
aaggtgtggt ttttgatggc aatgaggcgg cggattacca aatccaattg tcgcctgtga   24720
caagggcgtc agaacaggat tctgaagtcc gtattgccgc aaagatcttt agcctgaaaa   24780
gtgacggtaa acctgtgttt cattatgcag cgacaatatt gttagcaact cagccactta   24840
atgctgtgaa ggtagaactt ccgacattga cagaaagtgt tgatagcaac aataaagtaa   24900
ctgatgaagc acaagcgtta tacagcaatg gcaccttgtt ccacggtgaa agtctgcagg   24960
gcattaagca gatattaagt tgtgacgaca agggcctgct attggcttgt cagataaccg   25020
atgttgcaac agctaagcag ggatccttcc cgttagctga caacaatatc tttgccaatg   25080
atttggttta tcaggctatg ttggtctggg tgcgcaaaca atttggtttta ggtagcttac   25140 cttcggtgac aacggcttgg actgtgtatc gtgaagtggt tgtagatgaa gtattttatc   25200
tgcaacttaa tgttgttgag catgatctat tgggttcacg cggcagtaaa gcccgttgtg   25260
atattcaatt gattgctgct gatatgcaat tacttgccga agtgaaatca gcgcaagtca   25320
gtgtcagtga cattttgaac gatatgtcat gatcgagtaa ataataacga taggcgtcat   25380
ggtgagcatg gcgtctgctt tcttcatttt ttaacattaa caatattaat agctaaacgc   25440
ggttgcttta aaccaagtaa acaagtgctt ttagctatta ctattccaaa caggatatta   25500
aagagaatat gacggaatta gctgttattg gtatggatgc taaatttagc ggacaagaca   25560
atattgaccg tgtggaacgc gctttctatg aaggtgctta tgtaggtaat gttagccgcg   25620
ttagtaccga atctaatgtt attagcaatg gcgaagaaca agttattact gccatgacag   25680
ttcttaactc tgtcagtcta ctagcgcaaa cgaatcagtt aaatatagct gatatcgcgg   25740
tgttgctgat tgctgatgta aaaagtgctg atgatcagct tgtagtccaa attgcatcag   25800
caattgaaaa acagtgtgcg agttgtgttg ttattgctga tttaggccaa gcattaaatc   25860
aagtagctga tttagttaat aaccaagact gtcctgtggc tgtaattggc atgaataact   25920
cggttaattt atctcgtcat gatcttgaat ctgtaactgc aacaatcagc tttgatgaaa   25980
ccttcaatgg ttataacaat gtagctgggt tcgcgagttt acttatcgct tcaactgcgt   26040
```

```
ttgccaatgc taagcaatgt tatatatacg ccaacattaa gggcttcgct caatcgggcg   26100
taaatgctca atttaacgtt ggaaacatta gcgatactgc aaagaccgca ttgcagcaag   26160
ctagcataac tgcagagcag gttggtttgt tagaagtgtc agcagtcgct gattcggcaa   26220
tcgcattgtc tgaaagccaa ggtttaatgt ctgcttatca tcatacgcaa actttgcata   26280
ctgcattaag cagtgcccgt agtgtgactg gtgaaggcgg gtgtttttca caggtcgcag   26340
gtttattgaa atgtgtaatt ggtttacatc aacgttatat tccggcgatt aaagattggc   26400
aacaaccgag tgacaatcaa atgtcacggt ggcggaattc accattctat atgcctgtag   26460
atgctcgacc ttggttccca catgctgatg gctctgcaca cattgccgct tatagttgtg   26520
tgactgctga cagctattgt catattcttt tacaagaaaa cgtcttacaa gaacttgttt   26580
tgaaagaaac agtcttgcaa gataatgact taactgaaag caagcttcag actcttgaac   26640
aaaacaatcc agtagctgat ctgcgcacta atggttactt tgcatcgagc gagttagcat   26700
taatcatagt acaaggtaat gacgaagcac aattacgctg tgaattagaa actattacag   26760
ggcagttaag tactactggc ataagtacta tcagtattaa acagatcgca gcagactgtt   26820
atgcccgtaa tgatactaac aaagcctata gcgcagtgct tattgccgag actgctgaag   26880
agttaagcaa agaaataacc ttggcgtttg ctggtatcgc tagcgtgttt aatgaagatg   26940
ctaaagaatg gaaaacccg aagggcagtt attttaccgc gcagcctgca aataaacagg   27000
ctgctaacag cacacagaat ggtgtcacct tcatgtaccc aggtattggt gctacatatg   27060
ttggtttagg gcgtgatcta tttcatctat tcccacagat ttatcagcct gtagcggctt   27120
tagccgatga cattggcgaa agtctaaaag atactttact taatccacgc agtattagtc   27180
gtcatagctt taaagaactc aagcagttgg atctggacct gcgcggtaac ttagccaata   27240
tcgctgaagc cggtgtgggt tttgcttgtg tgtttaccaa ggtatttgaa gaagtctttg   27300
ccgttaaagc tgactttgct acaggttata gcatgggtga agtaagcatg tatgcagcac   27360
taggctgctg gcagcaaccg ggattgatga gtgctcgcct tgcacaatcg aatacctta   27420 atcatcaact ttgcggcgag ttaagaacac tacgtcagca ttggggcatg gatgatgtag   27480
ctaacggtac gttcgagcag atctgggaaa cctataccat taaggcaacg attgaacagg   27540
tcgaaattgc ctctgcagat gaagatcgtg tgtattgcac cattatcaat acacctgata   27600
gcttgttgtt agccggttat ccagaagcct gtcagcgagt cattaagaat ttaggtgtgc   27660
gtgcaatggc attgaatatg gcgaacgcaa ttcacagcgc gccagcttat gccgaatacg   27720
atcatatggt tgagctatac catatggatg ttactccacg tattaatacc aagatgtatt   27780
caagctcatg ttatttaccg attccacaac gcagcaaagc gatttcccac agtattgcta   27840
aatgtttgtg tgatgtggtg gatttcccac gtttggttaa taccttacat gacaaaggtg   27900
cgcgggtatt cattgaaatg ggtccaggtc gttcgttatg tagctgggta gataagatct   27960
tagttaatgg cgatggcgat aataaaaagc aaagccaaca tgtatctgtt cctgtgaatg   28020
ccaaaggcac cagtgatgaa cttacttata ttcgtgcgat tgctaagtta attagtcatg   28080
gcgtgaattt gaatttagat agcttgttta acgggtcaat cctggttaaa gcaggccata   28140
tagcaaacac gaacaaatag tcaacatcga tatctagcgc tggtgagtta tacctcatta   28200
gttgaaatat ggatttaaag agagtaatta tggaaaatat tgcagtagta ggtattgcta   28260
atttgttccc gggctcacaa gcaccggatc aattttggca gcaattgctt gaacaacaag   28320
attgccgcag taaggcgacc gctgttcaaa tgggcgttga tcctgctaaa tataccgcca   28380
acaaaggtga cacagataaa ttttactgtg tgcacggcgg ttacatcagt gatttcaatt   28440
```

```
ttgatgcttc aggttatcaa ctcgataatg attatttagc cggtttagat gaccttaatc    28500
aatgggggct ttatgttacg aaacaagccc ttaccgatgc gggttattgg ggcagtactg    28560
cactagaaaa ctgtggtgtg attttaggta atttgtcatt cccaactaaa tcatctaatc    28620
agctgtttat gcctttgtat catcaagttg ttgataatgc cttaaaggcg gtattacatc    28680
ctgattttca attaacgcat tacacagcac cgaaaaaaac acatgctgac aatgcattag    28740
tagcaggtta tccagctgca ttgatcgcgc aagcggcggg tcttggtggt tcacattttg    28800
cactggatgc ggcttgtgct tcatcttgtt atagcgttaa gttagcgtgt gattacctgc    28860
atacgggtaa agccaacatg atgcttgctg gtgcggtatc tgcagcagat cctatgttcg    28920
taaatatggg tttctcgata ttccaagctt acccagctaa caatgtacat gccccgtttg    28980
accaaaattc acaaggtcta tttgccggtg aaggcgcggg catgatggta ttgaaacgtc    29040
aaagtgatgc agtacgtgat ggtgatcata tttacgccat tattaaaggc ggcgcattat    29100
cgaatgacgg taaaggcgag tttgtattaa gcccgaacac caagggccaa gtattagtat    29160
atgaacgtgc ttatgccgat gcagatgttg acccgagtac agttgactat attgaatgtc    29220
atgcaacggg cacacctaag ggtgacaatg ttgaattgcg ttcgatggaa accttttttca    29280 gtcgcgtaaa taacaaacca ttactgggct cggttaaatc taaccttggt catttgttaa    29340
ctgccgctgg tatgcctggc atgaccaaag ctatgttagc gctaggtaaa ggtcttattc    29400
ctgcaacgat taacttaaag caaccactgc aatctaaaaa cggttacttt actggcgagc    29460
aaatgccaac gacgactgtg tcttggccaa caactccggg tgccaaggca gataaaccgc    29520
gtaccgcagg tgtgagcgta tttggttttg gtggcagcaa cgcccatttg gtattacaac    29580
agccaacgca aacactcgag actaatttta gtgttgctaa accacgtgag cctttggcta    29640
ttattggtat ggacagccat tttggtagtg ccagtaattt agcgcagttc aaaacccttat    29700 taaataataa tcaaaatacc ttccgtgaat taccagaaca acgctggaaa ggcatggaaa    29760
gtaacgctaa cgtcatgcag tcgttacaat tacgcaaagc gcctaaaggc agttacgttg    29820
aacagctaga tattgatttc ttgcgtttta agtaccgcc taatgaaaaa gattgcttga    29880
tcccgcaaca gttaatgatg atgcaagtgg cagacaatgc tgcgaaagac ggaggtctag    29940
ttgaaggtcg taatgttgcg gtattagtag cgatgggcat ggaactggaa ttacatcagt    30000
atcgtggtcg cgttaatcta accacccaaa ttgaagacag cttattacag caaggtatta    30060
acctgactgt tgagcaacgt gaagaactga ccaatattgc taaagacggt gttgcctcgg    30120
ctgcacagct aaatcagtat acgagtttca ttggtaatat tatggcgtca cgtatttcgg    30180
cgttatggga tttttctggt cctgctatta ccgtatcggc tgaagaaaac tctgtttatc    30240
gttgtgttga attagctgaa atctatttc aaaccagtga tgttgaagcc gttattattg    30300
ctgctgttga tttgtctggt tcaattgaaa acattacttt acgtcagcac tacggtccag    30360
ttaatgaaaa gggatctgta agtgaatgtg gtccggttaa tgaaagcagt tcagtaacca    30420
acaatattct tgatcagcaa caatggctgg tgggtgaagg cgcagcggct attgtcgtta    30480
aaccgtcatc gcaagtcact gctgagcaag tttatgcgcg tattgatgcg gtgagttttg    30540
cccctggtag caatgcgaaa gcaattacga ttgcagcgga taaagcatta acacttgctg    30600
gtatcagtgc tgctgatgta gctagtgttg aagcacatgc aagtggtttt agtgccgaaa    30660
ataatgctga aaaaccgcg ttaccgactt tatacccaag cgcaagatc agttcggtga    30720 aagccaatat tggtcatacg tttaatgcct cgggtatggc gagtattatt aaaacggcgc    30780
```

```
tgctgttaga tcagaatacg agtcaagatc agaaaagcaa acatattgct attaacggtc    30840
taggtcgtga taacagctgc gcgcatctta tcttatcgag ttcagcgcaa gcgcatcaag    30900
ttgcaccagc gcctgtatct ggtatggcca agcaacgccc acagttagtt aaaaccatca    30960
aactcggtgg tcagttaatt agcaacgcga ttgttaacag tgcgagttca tctttacacg    31020
ctattaaagc gcagtttgcc ggtaagcact taaacaaagt taaccagcca gtgatgatgg    31080
ataacctgaa gccccaaggt attagcgctc atgcaaccaa tgagtatgtg gtgactggag    31140
ctgctaacac tcaagcttct aacattcaag catctcatgt tcaagcgtca agtcatgcac    31200
aagagatagc accaaaccaa gttcaaaata tgcaagctac agcagccgct gtaagttcac    31260 cccttctca acatcaacac acagcgcagc ccgtagcggc accgagcgtt gttggagtga    31320
ctgtgaaaca taaagcaagt aaccaaattc atcagcaagc gtctacgcat aaagcatttt    31380
tagaaagtcg tttagctgca cagaaaaacc tatcgcaact tgttgaattg caaaccaagc    31440
tgtcaatcca aactggtagt gacaatacat ctaacaatac tgcgtcaaca agcaatacag    31500
tgctaacaaa tcctgtatca gcaacgccat taacacttgt gtctaatgcg cctgtagtag    31560
cgacaaacct aaccagtaca gaagcaaaag cgcaagcagc tgctacacaa gctggttttc    31620
agataaaagg acctgttggt tacaactatc caccgctgca gttaattgaa cgttataata    31680
aaccagaaaa cgtgatttac gatcaagctg atttggttga attcgctgaa ggtgatattg    31740
gtaaggtatt tggtgctgaa tacaatatta ttgatggcta ttcgcgtcgt gtacgtctgc    31800
caacctcaga ttacttgtta gtaacacgtg ttactgaact tgatgccaag gtgcatgaat    31860
acaagaaatc atacatgtgt actgaatatg atgtgcctgt tgatgcaccg ttcttaattg    31920
atggtcagat cccttggtct gttgccgtcg aatcaggcca gtgtgatttg atgttgattt    31980
catatatcgg tattgatttc caagcgaaag gcgaacgtgt ttaccgttta cttgattgtg    32040
aattaacttt ccttgaagag atggcttttg gtggcgatac tttacgttac gagatccaca    32100
ttgattcgta tgcacgtaac ggcgagcaat tattattctt cttccattac gattgttacg    32160 tagggataa gaaggtactt atcatgcgta atggttgtgc tggtttcttt actgacgaag    32220
aactttctga tggtaaaggc gttattcata cgacaaaga caaagctgag tttagcaatg    32280
ctgttaaatc atcattcacg ccgttattac aacataaccg tggtcaatac gattataacg    32340
acatgatgaa gttggttaat ggtgatgttg ccagttgttt tggtccgcaa tatgatcaag    32400
gtggccgtaa tccatcattg aaattctcgt ctgagaagtt cttgatgatt gaacgtatta    32460
ccaagataga cccaaccggt ggtcattggg gactaggcct gttagaaggt cagaaagatt    32520
tagaccctga gcattggtat ttcccttgtc actttaaagg tgatcaagta atggctggtt    32580
cgttgatgtc ggaaggttgt ggccaaatgg cgatgttctt catgctgtct cttggtatgc    32640
ataccaatgt gaacaacgct cgtttccaac cactaccagg tgaatcacaa acggtacgtt    32700
gtcgtgggca agtactgcca cagcgcaata ccttaactta ccgtatggaa gttactgcga    32760
tgggtatgca tccacagcca ttcatgaaag ctaatattga tattttgctt gacggtaaag    32820
tggttgttga tttcaaaaac ttgagcgtga tgatcagcga acaagatgag cattcagatt    32880
accctgtaac actgccgagt aatgtggcgc ttaaagcgat tactgcacct gttgcgtcag    32940
tagcaccagc atcttcaccc gctaacagcg cggatctaga cgaacgtggt gttgaaccgt    33000
ttaagttccc tgaacgtccg ttaatgcgtg ttgagtcaga cttgtctgca ccgaaaagca    33060
aaggtgtgac accgattaag cattttgaag cgcctgctgt tgctggtcat catagagtgc    33120
ctaaccaagc accgtttaca ccttggcata tgtttgagtt tgcgacgggt aatatttcta    33180
```

```
actgtttcgg tcctgatttt gatgtttatg aaggtcgtat tccacctcgt acaccttgtg    33240
gcgatttaca agttgttact caggttgtag aagtgcaggg cgaacgtctt gatcttaaaa    33300
atccatcaag ctgtgtagct gaatactatg taccggaaga cgcttggtac tttactaaaa    33360
acagccatga aaactggatg ccttattcat taatcatgga aattgcattg caaccaaatg    33420
gctttatttc tggttacatg ggcacgacgc ttaaataccc tgaaaagat ctgttcttcc     33480 gtaaccttga tggtagcggc acgttattaa agcagattga tttacgcggc aagaccattg    33540
tgaataaatc agtcttggtt agtacggcta ttgctggtgg cgcgattatt caaagtttca    33600
cgtttgatat gtctgtagat ggcgagctat tttatactgg taaagctgta tttggttact    33660
ttagtggtga atcactgact aaccaactgg gcattgataa cggtaaaacg actaatgcgt    33720
ggtttgttga taacaatacc cccgcagcga atattgatgt gtttgattta actaatcagt    33780
cattggctct gtataaagcg cctgtggata accgcatta taaattggct ggtggtcaga    33840
tgaactttat cgatacagtg tcagtggttg aaggcggtgg taaagcgggc gtggcttatg    33900
tttatggcga acgtacgatt gatgctgatg attggttctt ccgttatcac ttccaccaag    33960
atccggtgat gccaggttca ttaggtgttg aagctattat tgagttgatg cagacctatg    34020
cgcttaaaaa tgatttgggt ggcaagtttg ctaacccacg tttcattgcg ccgatgacgc    34080
aagttgattg gaaataccgt gggcaaatta cgccgctgaa taaacagatg tcactggacg    34140
tgcatatcac tgagatcgtg aatgacgctg gtgaagtgcg aatcgttggt gatgcgaatc    34200
tgtctaaaga tggtctgcgt atttatgaag ttaaaaacat cgttttaagt attgttgaag    34260
cgtaaagggt caagtgtaac gtgcttaagc gccgcattgg ttaaagacgc tttgcacgcc    34320
gtgaatccgt ccatggaggc ttggggttgg catccatgcc aacaacagca agcttacttt    34380
aatcaatacg gcttggtgtc catttagacg cctcgaactt agtagttaat agacaaaata    34440
atttagctgt ggaatgaata tagtaagtaa tcattcggca gctacaaaaa aggaattaag    34500
aatgtcgagt ttaggtttta acaataacaa cgcaattaac tgggcttgga agtagatcc    34560 agcgtcagtt catacacaag atgcagaaat taaagcagct ttaatggatc taactaaacc    34620
tctctatgtg gcgaataatt caggcgtaac tggtatagct aatcatacgt cagtagcagg    34680
tgcgatcagc aataacatcg atgttgatgt attggcgttt gcgcaaaagt taaacccaga    34740
agatctgggt gatgatgctt acaagaaaca gcacggcgtt aaatatgctt atcatggcgg    34800
tgcgatggca aatggtattg cctcggttga attggttgtt gcgttaggta aagcagggct    34860
gttatgttca tttggtgctg caggtctagt gcctgatgcg gttgaagatg caattcgtcg    34920
tattcaagct gaattaccaa atggccctta tgcggttaac ttgatccatg caccagcaga    34980
agaagcatta gagcgtggcg cggttgaacg tttcctaaaa cttggcgtca agacggtaga    35040
ggcttcagct taccttggtt taactgaaca cattgtttgg tatcgtgctg ctggtctaac    35100
taaaaacgca gatggcagtg ttaatatcgg taacaaggtt atcgctaaag tatcgcgtac    35160
cgaagttggt cgccgcttta tggaacctgc accgcaaaaa ttactggata agttattaga    35220
acaaaataag atcacccctg aacaagctgc tttagcgttg cttgtaccta tggctgatga    35280
tattactggg gaagcggatt ctggtggtca tacagataac cgtccgtttt taacattatt    35340
accgacgatt attggtctgc gtgatgaagt gcaagcgaag tataacttct ctcctgcatt    35400
acgtgttggt gctggtggtg gtatcggaac gcctgaagca gcactcgctg catttaacat    35460
gggcgcggct tatatcgttc tgggttctgt gaatcaggcg tgtgttgaag cggtgcatc     35520
```

```
tgaatatact cgtaaactgt tatcgacagt tgaaatggct gatgtgacta tggcacctgc    35580
tgcagatatg tttgaaatgg gtgtgaagct gcaagtatta aaacgcggtt ctatgttcgc    35640
gatgcgtgcg aagaaactgt atgacttgta tgtggcttat gactcgattg aagatatccc    35700
agctgctgaa cgtgagaaga ttgaaaaaca aatcttccgt gcaaacctag acgagatttg    35760
ggatggcact atcgctttct ttactgaacg cgatccagaa atgctagccc gtgcaacgag    35820
tagtcctaaa cgtaaaatgg cacttatctt ccgttggtat cttggccttt cttcacgctg    35880
gtcaaacaca ggcgagaagg gacgtgaaat ggattatcag atttgggcag cccaagttt    35940 aggtgcattc aacagctggg tgaaaggttc ttaccttgaa gactataccc gccgtggcgc    36000
tgtagatgtt gctttgcata tgcttaaagg tgctgcgtat ttacaacgtg taaaccagtt    36060
gaaattgcaa ggtgttagct aagtacagaa attggcaagt tatcgtacga gtgattaatg    36120
ttacttgatg atatgtgaat taattaaagc gcctgagggc gcttttttg gttttaact    36180 caggtgttgt aactcgaaat tgccccttc aagttagatc gattactcac tcacaatatg    36240
ttgatatcgc acttgccata tacttgctca tccaaagccc tatattgata atggtgttaa    36300
tagtctttaa tatccgagtc tttcttcagc ataaactaa tatagagact cgaccaatgt    36360
taaacacaac aaagaatata ttcttgtgta ctgccttatt attaacgagt gcgagtacga    36420
cagctactac gctaaacaat tcgatatcag caattgaaca acgtatttct ggtcgtatcg    36480
gtgtggctgt tttagatacg caaaataaac aaacgtgggc ttacaatggt gatgcacatt    36540
ttccgatgat gagtacattc aaaaccctcg cttgcgcgaa aatgctaagt gaatcgacaa    36600
atggtaatct ggatcccagt actagctcat tgataaaggc tgaagaatta atcccttggt    36660
caccagtcac taaaacgttt gtgaataaca ctattacagt ggcgaaagcg tgtgaagcaa    36720
caatgctgac cagtgataat accgcggcta atattgtttt acagtatatc ggaggccctc    36780
aaggcgttac tgcattcttg cgagaaattg gtgatgaaga gagtcagtta gatcgtatag    36840
aacctgaatt gaatgaagct aaggtcggag acttgcgtga taccacgaca ccgaaagcca    36900
tagttaccac gctcaacaaa ctactacttg gtgatgttct acttgatttg gataaaaacc    36960
aacttaaaac atggatgcaa aataataaag tgtcagatcc tttactgcgt tctatattac    37020
cgcaaggctg gttattgcc gaccgctcag gtgcgggtgg taatggttct cgaggtataa    37080
ctgctatgct ttggcactcc gagcgtcaac cgctaatcat cagtatttat ttaaccgaaa    37140
ctgagttagc aatggcaatg cgcaatgaga ttattgttga gatcggtaag ctgatattca    37200
aagaatacgc ggtgaaataa taagttattt tttgataata ctttaacgag cgtagctatc    37260
gaagtgaggg cgtcaattag acacctttgc ttcccctaca aaatcaatg tgtattacct    37320 cggctagtac aattgcccta agttatttct gtccagcttt ggcttagtgc aattgcgtta    37380
gccaatgtga acaccaaggg actttgtcgt accataacta ccaagcgact ttgtcgtttt    37440 tatctttct tagacaaaca gaggttaaat gagtgacgcc ttccaaatca caggaatgaa    37500
tccgcatttc aataaaatct aacccgtacc aactccgtac aagttgatct ttagttgttt    37560
aaaatctata ataaattcaa ttacggaatt aatccgtaca actggaggtt ttatggctac    37620
tgcaagactt gatatccgtt tggatgaaga atcaaagct aaggctgaga agcatcagc    37680 tttactcggc ttaaaaagtt taaccgaata cgttgttcgc ttaatggacg aagattcaac    37740
taaagtagtt tctgagcatg agagtattac cgttgaagcg aatgtattcg accaatttat    37800
ggctgcttgt gatgaagcga agcccccaaa taaagcatta cttgaagccg ctgtatttac    37860
tcagaatggt gagtttaagt gagttattcc aaacgtttca aagaactgga taaatcaaaa    37920
```

```
catgacagag catcatttga ctgtggcgaa aaagagctaa atgattttat ccaaactcaa   37980
gcagccaaac atatgcaagc aggtattagc cgcactctgg ttttacctgc ttctgcgccg   38040
ttaccaaaca aaaatatcc aatttgctca ttttatagta tcgcgccaag ctcaattagc    38100
cgcgatacgt taccacaagc aatggctaaa agttaccac gttatcctat ccctgttttt    38160
cttttggctc aacttgccgt ccataaagag tttcatggga gtgggttagg caagttagc    38220
ttaattaaag cgttagagta cctttgggaa attaactctc acatgagagc ttacgccatc    38280
gttgttgatt gtttaactga acaagctgag tcattctacg ctaaatatgg tttcgacgtt    38340
ctctgcgaaa taaatggtcg agtaagaatg ttcatatcaa tgaaaacagt caatcagtta    38400
ttcacttaac agtaagagtt agtataacag ttgtatgaat taaatttatt atattcggta    38460
atctcattgc gatcacgcta gaagtgcgag cgggtcagac cgaggccaca atagcagccg    38520
ttacgtttag gggatgactt aaaaagataa ctactacgtc agtggcgatc ctagaggatt    38580
aaaggtttat gattcacaac atttatttat tgtgcttaat ttttctatc caatatgcgc     38640
aagctgtaaa tatcactgaa gtagactttt atgtcagtga tgatatccct aaagatgttg    38700
ccaaattaaa gataggtgaa tccataacga actccagcct tattctaagt aactcatcta    38760
ttccactctc gcgggagacg ggtaacatat attactcttc atcaattgct aacttgaact    38820
atgactcgat agaatttgtt atggctcaat tgatggccga agattccagc ctttacaaga    38880
tgctggtaaa tagcgatagg ttgtccgtgc tagtaatgac atcttcccag tccacagatc    38940
tctatggctc gacttactcg gcttattttc ctaatgttgc ggtcatcgat ttgaattgtg    39000
actcgctaac tttagaacat gagctcggcc atctatacgg agctgaacat gaagaaatat    39060
atgacgacta tgtcttctat gctgcgatat gtggagacta tacgactatc atgaactcta    39120
tgcagcctga aatgaaagaa aaacaaatga taaaggcata ttcattccct gaattaaaag    39180
tggatggctt gcagtgcgga aatgaaaata cgaataacaa aaaggttatt ttagacaata    39240
ttggtcggtt tagataggat tgggatatta ttctcattcg gctctactta gtgctgttat    39300
tatgagtgcc agtgcttcta tctacgatat tggtcttaac aagtatttat ctatagacgc    39360
taaggtgtta tgtatttaag ggatgttcaa gatgaaacta ggtgtaaacg atgtatagtt    39420
gtataacatt ttttcaacgg ttggaacgtt cgattctatc gggtaacaag accgcgacga    39480
tccgcgataa gtccgatagt cattacttag ttggtcagat gttagatgct tgtactcacg    39540
aagataatcg gaaaatgtgt caaatagaaa tactgagcat tgaatatgtg acgtttagtg    39600
aattaaaccg tgcgcacgcc aatgctgaag gttaccgtt tttgtttatg cttaagtgga     39660
tagttcgaaa gatttatccg acttcaaatg atttattttt cataagtttc agagttgtaa    39720
ctatcgatat cttataagtc ttagtgcaca aaacagaact atttatagcg ctcaagaagg    39780
cgataatttg ataatgaatt atcgccttgt tactattaag agactttaaa tgactgagat    39840
ataagatatg acacggaaga acatattgat cacaggcgca agttcagggt tgggccgagg    39900
tatggccatc gaatttgcaa aatcaggtca taacttagca ctttgtgcac gtagacttga    39960
taatttagtt gcactgaaag cagaactctt agccctcaat cctcacatcc aaatcgaaat    40020
aaaacctctt gatgtcaatg aacatgaaca agtcttcact gttttccatg aattcaaagc    40080
tgaatttggt acgcttgatc gtattattgt taatgctgga ttaggcaagg gtggatcc      40138
```

<210> SEQ ID NO 13
<211> LENGTH: 19227
<212> TYPE: DNA

<213> ORGANISM: Vibrio marinus

<400> SEQUENCE: 13

| | | | | | |
|---|---|---|---|---|---|
| aaatgcaatt | aattatggcg | taaatagagt | gaaaacatgg | ctaatattca | ctaagtcctg | 60 |
| aattttatat | aaagtttaat | ctgttatttt | agcgtttacc | tggtcttatc | agtgaggttt | 120 |
| atagccatta | ttagtgggat | tgaagtgatt | tttaaagcta | tgtatattat | tgcaaatata | 180 |
| aattgtaaca | attaagactt | tggacacttg | agttcaattt | cgaattgatt | ggcataaaat | 240 |
| ttaaaacagc | taaatctacc | tcaatcattt | tagcaaatgt | atgcaggtag | atttttttcg | 300 |
| ccatttaaga | gtacacttgt | acgctaggtt | tttgtttagt | gtgcaaatga | acgttttgat | 360 |
| gagcattgtt | tttagagcac | aaaatagatc | cttacaggag | caataacgca | atggctaaaa | 420 |
| agaacaccac | atcgattaag | cacgccaagg | atgtgttaag | tagtgatgat | caacagttaa | 480 |
| attctcgctt | gcaagaatgt | ccgattgcca | tcattggtat | ggcatcggtt | tttgcagatg | 540 |
| ctaaaaactt | ggatcaattc | tgggataaca | tcgttgactc | tgtggacgct | attattgatg | 600 |
| tgcctagcga | tcgctggaac | attgacgacc | attactcggc | tgataaaaaa | gcagctgaca | 660 |
| agacatactg | caaacgcggt | ggtttcattc | cagagcttga | ttttgatccg | atggagtttg | 720 |
| gtttaccgcc | aaatatcctc | gagttaactg | acatcgctca | attgttgtca | ttaattgttg | 780 |
| ctcgtgatgt | attaagtgat | gctggcattg | gtagtgatta | tgaccatgat | aaaattggta | 840 |
| tcacgctggg | tgtcggtggt | ggtcagaaac | aaatttcgcc | attaacgtcg | cgcctacaag | 900 |
| gcccggtatt | agaaaagta | ttaaaagcct | caggcattga | tgaagatgat | cgcgctatga | 960 |
| tcatcgacaa | atttaaaaaa | gcctacatcg | gctgggaaga | gaactcattc | ccaggcatgc | 1020 |
| taggtaacgt | tattgctggt | cgtatcgcca | atcgttttga | ttttggtggt | actaactgtg | 1080 |
| tggttgatgc | ggcatgcgct | ggctcccttg | cagctgttaa | aatggcgatc | tcagacttac | 1140 |
| ttgaatatcg | ttcagaagtc | atgatatcgg | gtggtgtatg | ttgtgataac | tcgccattca | 1200 |
| tgtatatgtc | attctcgaaa | acaccagcat | ttaccaccaa | tgatgatatc | cgtccgtttg | 1260 |
| atgacgattc | aaaaggcatg | ctggttggtg | aaggtattgg | catgatggcg | tttaaacgtc | 1320 |
| ttgaagatgc | tgaacgtgac | ggcgacaaaa | tttattctgt | actgaaaggt | atcggtacat | 1380 |
| cttcagatgg | tcgtttcaaa | tctatttacg | ctccacgccc | agatggccaa | gcaaaagcgc | 1440 |
| taaaacgtgc | ttatgaagat | gccggttttg | ccctgaaaac | atgtggtcta | attgaaggcc | 1500 |
| atggtacggg | taccaaagcg | ggtgatgccg | cagaatttgc | tggcttgacc | aaacactttg | 1560 |
| gcgccgccag | tgatgaaaag | caatatatcg | ccttaggctc | agttaaatcg | caaattggtc | 1620 |
| atactaaatc | tgcggctggc | tctgcgggta | tgattaaggc | ggcattagcg | ctgcatcata | 1680 |
| aaatcttacc | tgcaacgatc | catatcgata | aaccaagtga | agccttggat | atcaaaaaca | 1740 |
| gcccgttata | cctaaacagc | gaaacgcgtc | cttggatgcc | acgtgaagat | ggtattccac | 1800 |
| gtcgtgcagg | tatcagctca | tttggttttg | gcggcaccaa | cttccatatt | attttagaag | 1860 |
| agtatcgccc | aggtcacgat | agcgcatatc | gcttaaactc | agtgagccaa | actgtgttga | 1920 |
| tctcggcaaa | cgaccaacaa | ggtattgttg | ctgagttaaa | taactggcgt | actaaactgg | 1980 |
| ctgtcgatgc | tgatcatcaa | gggtttgtat | ttaatgagtt | agtgacaacg | tggccattaa | 2040 |
| aaacccccatc | cgttaaccaa | gctcgtttag | gttttgttgc | gcgtaatgca | aatgaagcga | 2100 |
| tcgcgatgat | tgatacggca | ttgaaacaat | tcaatgcgaa | cgcagataaa | atgacatggt | 2160 |
| cagtacctac | cggggtttac | tatcgtcaag | ccggtattga | tgcaacaggt | aaagtggttg | 2220 |
| cgctattctc | agggcaaggt | tcgcaatacg | tgaacatggg | tcgtgaatta | acctgtaact | 2280 |

```
tcccaagcat gatgcacagt gctgcggcga tggataaaga gttcagtgcc gctggtttag   2340
gccagttatc tgcagttact ttccctatcc ctgtttatac ggatgccgag cgtaagctac   2400
aagaagagca attacgttta acgcaacatg cgcaaccagc gattggtagt ttgagtgttg   2460
gtctgttcaa aacgtttaag caagcaggtt ttaaagctga ttttgctgcc ggtcatagtt   2520
tcggtgagtt aaccgcatta tgggctgccg atgtattgag cgaaagcgat tacatgatgt   2580
tagcgcgtag tcgtggtcaa gcaatggctg cgccagagca acaagatttt gatgcaggta   2640
agatggccgc tgttgttggt gatccaaagc aagtcgctgt gatcattgat acccttgatg   2700
atgtctctat tgctaacttc aactcgaata accaagttgt tattgctggt actacggagc   2760
aggttgctgt agcggttaca accttaggta atgctggttt caagttgtg ccactgccgg    2820 tatctgctgc gttccataca cctttagttc gtcacgcgca aaaccatttt gctaaagcgg   2880
ttgatagcgc taaatttaaa gcgccaagca ttccagtgtt tgctaatggc acaggcttgg   2940
tgcattcaag caaaccgaat gacattaaga aaaacctgaa aaccacatg ctggaatctg     3000 ttcatttcaa tcaagaaatt gacaacatct atgctgatgg tggccgcgta tttatcgaat   3060
ttggtccaaa gaatgtatta actaaattgg ttgaaaacat tctcactgaa aaatctgatg   3120
tgactgctat cgcggttaat gctaatccta acaacctgc ggacgtacaa atgcgccaag     3180
ctgcgctgca aatggcagtg cttggtgtcg cattagacaa tattgacccg tacgacgccg   3240
ttaagcgtcc acttgttgcg ccgaaagcat caccaatgtt gatgaagtta tctgcagcgt   3300
cttatgttag tccgaaaacg aagaaagcgt ttgctgatgc attgactgat ggctggactg   3360
ttaagcaagc gaaagctgta cctgctgttg tgtcacaacc acaagtgatt gaaaagatcg   3420
ttgaagttga aaagatagtt gaacgcattg tcgaagtaga gcgtattgtc gaagtagaaa   3480
aaatcgtcta cgttaatgct gacggttcgc ttatatcgca aaataatcaa gacgttaaca   3540
gcgctgttgt tagcaacgtg actaatagct cagtgactca tagcagtgat gctgaccttg   3600
ttgcctctat tgaacgcagt gttggtcaat ttgttgcaca ccaacagcaa ttattaaatg   3660
tacatgaaca gtttatgcaa ggtccacaag actacgcgaa aacagtgcag aacgtacttg   3720
ctgcgcagac gagcaatgaa ttaccggaaa gtttagaccg tacattgtct atgtataacg   3780
agttccaatc agaaacgcta cgtgtacatg aaacgtacct gaacaatcag acgagcaaca   3840
tgaacaccat gcttactggt gctgaagctg atgtgctagc aaccccaata actcaggtag   3900
tgaatacagc cgttgccact agtcacaagg tagttgctcc agttattgct aatacagtga   3960
cgaatgttgt atctagtgtc agtaataacg cggcggttgc agtgcaaact gtggcattag   4020
cgcctacgca agaaatcgct ccaacagtcg ctactacgcc agcacccgca ttggttgcta   4080
tcgtggctga acctgtgatt gttgcgcatg ttgctacaga agttgcacca attacaccat   4140
cagttacacc agttgtcgca actcaagcgg ctatcgatgt agcaactatt aacaaagtaa   4200
tgttagaagt tgttgctgat aaaaccggtt atccaacgga tatgctggaa ctgagcatgg   4260
acatggaagc tgacttaggt atcgactcaa tcaaacgtgt tgagatatta ggcgcagtac   4320
aggaattgat ccctgactta cctgaactta atcctgaaga tcttgctgag ctacgcacgc   4380
ttggtgagat tgtcgattac atgaattcaa agcccaggc tgtagctcct acaacagtac    4440
ctgtaacaag tgcacctgtt tcgcctgcat ctgctggtat tgatttagcc cacatccaaa   4500
acgtaatgtt agaagtggtt gcagacaaaa ccggttaccc aacagacatg ctagaactga   4560
gcatggatat ggaagctgac ttaggtattg attcaatcaa gcgtgtggaa atcttaggtg   4620
```

```
cagtacagga gatcataact gatttacctg agctaaaccc tgaagatctt gctgaattac    4680
gcaccctagg tgaaatcgtt agttacatgc aaagcaaagc gccagtcgct gaaagtgcgc    4740
cagtggcgac ggctcctgta gcaacaagct cagcaccgtc tatcgatttg aaccacattc    4800
aaacagtgat gatggatgta gttgcagata agactggtta tccaactgac atgctagaac    4860
ttggcatgga catggaagct gatttaggta tcgattcaat caaacgtgtg gaaatattag    4920
gcgcagtgca ggagatcatc actgatttac ctgagctaaa cccagaagac ctcgctgaat    4980
tacgcacgct aggtgaaatc gttagttaca tgcaaagcaa agcgccagtc gctgagagtg    5040
cgccagtagc gacggcttct gtagcaacaa gctctgcacc gtctatcgat ttaaaccata    5100
tccaaacagt gatgatggaa gtggttgcag acaaaaccgg ttatccagta gacatgttag    5160
aacttgctat ggacatggaa gctgacctag gtatcgattc aatcaagcgt gtagaaattt    5220
taggtgcggt acaggaaatc attactgact tacctgagct taaccctgaa gatcttgctg    5280
aactacgtac attaggtgaa atcgttagtt acatgcaaag caaagcgccc gtagctgaag    5340
cgcctgcagt acctgttgca gtagaaagtg cacctactag tgtaacaagc tcagcaccgt    5400
ctatcgattt agaccacatc caaaatgtaa tgatggatgt tgttgctgat aagactggtt    5460
atcctgccaa tatgcttgaa ttagcaatgg acatggaagc cgaccttggt attgattcaa    5520
tcaagcgtgt tgaaattcta ggcgcggtac aggagatcat tactgattta cctgaactaa    5580
acccagaaga cttagctgaa ctacgtacgt tagaagaaat tgtaacctac atgcaaagca    5640
aggcgagtgg tgttactgta aatgtagtgg ctagccctga aaataatgct gtatcagatg    5700
catttatgca aagcaatgtg gcgactatca cagcggccgc agaacataag gcggaattta    5760
aaccggcgcc gagcgcaacc gttgctatct ctcgtctaag ctctatcagt aaaataagcc    5820
aagattgtaa aggtgctaac gccttaatcg tagctgatgg cactgataat gctgtgttac    5880
ttgcagacca cctattgcaa actggctgga atgtaactgc attgcaacca acttgggtag    5940
ctgtaacaac gacgaaagca tttaataagt cagtgaacct ggtgacttta aatggcgttg    6000
atgaaactga aatcaacaac attattactg ctaacgcaca attggatgca gttatctatc    6060
tgcacgcaag tagcgaaatt aatgctatcg aatacccaca agcatctaag caaggcctga    6120
tgttagcctt cttattagcg aaattgagta agtaactca agccgctaaa gtgcgtggcg    6180
cctttatgat tgttactcag cagggtggtt cattaggttt tgatgatatc gattctgcta    6240
caagtcatga tgtgaaaaca gacctagtac aaagcggctt aaacggttta gttaagacac    6300
tgtctcacga gtgggataac gtattctgtc gtgcggttga tattgcttcg tcattaacgg    6360
ctgaacaagt tgcaagcctt gttagtgatg aactacttga tgctaacact gtattaacag    6420
aagtgggtta tcaacaagct ggtaaaggcc ttgaacgtat cacgttaact ggtgtggcta    6480
ctgacagcta tgcattaaca gctggcaata acatcgatgc taactcggta ttttttagtga    6540 gtggtggcgc aaaaggtgta actgcacatt gtgttgctcg tatagctaaa gaatatcagt    6600
ctaagttcat cttattggga cgttcaacgt tctcaagtga cgaaccgagc tgggcaagtg    6660
gtattactga tgaagcggcg ttaaagaaag cagcgatgca gtctttgatt acagcaggtg    6720
ataaaccaac acccgttaag atcgtacagc taatcaaacc aatccaagct aatcgtgaaa    6780
ttgcgcaaac cttgtctgca attaccgctg ctggtggcca agctgaatat gtttctgcag    6840
atgtaactaa tgcagcaagc gtacaaatgc agtcgctcc agctatcgct aagttcggtg    6900
caatcactgg catcattcat ggcgcgggtg tgttagctga ccaattcatt gagcaaaaaa    6960
cactgagtga ttttgagtct gtttacagca ctaaaattga cggtttgtta tcgctactat    7020
```

```
cagtcactga agcaagcaac atcaagcaat tggtattgtt ctcgtcagcg gctggtttct    7080
acggtaaccc cggccagtct gattactcga ttgccaatga gatcttaaat aaaaccgcat    7140
accgctttaa atcattgcac ccacaagctc aagtattgag ctttaactgg ggtccttggg    7200
acggtggcat ggtaacgcct gagcttaaac gtatgtttga ccaacgtggt gtttacatta    7260
ttccacttga tgcaggtgca cagttattgc tgaatgaact agccgctaat gataaccgtt    7320
gtccacaaat cctcgtgggt aatgacttat ctaaagatgc tagctctgat caaaagtctg    7380
atgaaaagag tactgctgta aaaaagccac aagttagtcg tttatcagat gctttagtaa    7440
ctaaaagtat caaagcgact aacagtagct ctttatcaaa caagactagt gctttatcag    7500
acagtagtgc ttttcaggtt aacgaaaacc acttttttagc tgaccacatg atcaaaggca    7560
atcaggtatt accaacggta tgcgcgattg cttggatgag tgatgcagca aaagcgactt    7620
atagtaaccg agactgtgca ttgaagtatg tcggtttcga agactataaa ttgtttaaag    7680
gtgtggtttt tgatggcaat gaggcggcgg attaccaaat ccaattgtcg cctgtgacaa    7740
gggcgtcaga acaggattct gaagtccgta ttgccgcaaa gatctttagc ctgaaaagtg    7800
acggtaaacc tgtgtttcat tatgcagcga caatattgtt agcaactcag ccacttaatg    7860
ctgtgaaggt agaacttccg acattgacag aaagtgttga tagcaacaat aaagtaactg    7920
atgaagcaca agcgttatac agcaatggca ccttgttcca cggtgaaagt ctgcagggca    7980
ttaagcagat attaagttgt gacgacaagg gcctgctatt ggcttgtcag ataaccgatg    8040
ttgcaacagc taagcaggga tccttcccgt tagctgacaa caatatcttt gccaatgatt    8100
tggtttatca ggctatgttg gtctgggtgc gcaaacaatt tggtttaggt agcttacctt    8160
cggtgacaac ggcttggact gtgtatcgtg aagtggttgt agatgaagta ttttatctgc    8220
aacttaatgt tgttgagcat gatctattgg gttcacgcgg cagtaaagcc cgttgtgata    8280
ttcaattgat tgctgctgat atgcaattac ttgccgaagt gaaatcagcg caagtcagtg    8340
tcagtgacat tttgaacgat atgtcatgat cgagtaaata taacgatag gcgtcatggt    8400 gagcatggcg tctgctttct tcatttttta acattaacaa tattaatagc taaacgcggt    8460
tgctttaaac caagtaaaca agtgctttta gctattacta ttccaaacag gatattaaag    8520
agaatatgac ggaattagct gttattggta tggatgctaa atttagcgga caagacaata    8580
ttgaccgtgt ggaacgcgct ttctatgaag gtgcttatgt aggtaatgtt agccgcgtta    8640
gtaccgaatc taatgttatt agcaatggcg aagaacaagt tattactgcc atgacagttc    8700
ttaactctgt cagtctacta gcgcaaacga atcagttaaa tatagctgat atcgcggtgt    8760
tgctgattgc tgatgtaaaa agtgctgatg atcagcttgt agtccaaatt gcatcagcaa    8820
ttgaaaaaca gtgtgcgagt tgtgttgtta ttgctgattt aggccaagca ttaaatcaag    8880
tagctgattt agttaataac caagactgtc ctgtggctgt aattggcatg aataactcgg    8940
ttaatttatc tcgtcatgat cttgaatctg taactgcaac aatcagcttt gatgaaacct    9000
tcaatggtta taacaatgta gctgggttcg cgagtttact tatcgcttca actgcgtttg    9060
ccaatgctaa gcaatgttat atatacgcca acattaaggg cttcgctcaa tcgggcgtaa    9120
atgctcaatt taacgttgga aacattagcg atactgcaaa gaccgcattg cagcaagcta    9180
gcataactgc agagcaggtt ggtttgttag aagtgtcagc agtcgctgat tcggcaatcg    9240
cattgtctga aagccaaggt ttaatgtctg cttatcatca tacgcaaact ttgcatactg    9300
cattaagcag tgcccgtagt gtgactggtg aaggcgggtg ttttttcacag gtcgcaggtt    9360
```

```
tattgaaatg tgtaattggt ttacatcaac gttatattcc ggcgattaaa gattggcaac   9420
aaccgagtga caatcaaatg tcacggtggc ggaattcacc attctatatg cctgtagatg   9480
ctcgaccttg gttcccacat gctgatggct ctgcacacat tgccgcttat agttgtgtga   9540
ctgctgacag ctattgtcat attcttttac aagaaaacgt cttacaagaa cttgttttga   9600
aagaaacagt cttgcaagat aatgacttaa ctgaaagcaa gcttcagact cttgaacaaa   9660
acaatccagt agctgatctg cgcactaatg gttactttgc atcgagcgag ttagcattaa   9720
tcatagtaca aggtaatgac gaagcacaat tacgctgtga attagaaact attacagggc   9780
agttaagtac tactggcata agtactatca gtattaaaca gatcgcagca gactgttatg   9840
cccgtaatga tactaacaaa gcctatagcg cagtgcttat tgccgagact gctgaagagt   9900
taagcaaaga aataaccttg gcgtttgctg gtatcgctag cgtgtttaat gaagatgcta   9960
aagaatggaa accccgaagg gcagttattt ttaccgcgca gcctgcaaat aaacaggctg  10020
ctaacagcac acagaatggt gtcaccttca tgtacccagg tattggtgct acatatgttg  10080
gtttagggcg tgatctattt catctattcc cacagattta tcagcctgta gcggcttttag  10140 ccgatgacat tggcgaaagt ctaaaagata ctttacttaa tccacgcagt attagtcgtc  10200
atagctttaa agaactcaag cagttggatc tggacctgcg cggtaactta gccaatatcg  10260
ctgaagccgg tgtgggtttt gcttgtgtgt ttaccaaggt atttgaagaa gtctttgccg  10320
ttaaagctga ctttgctaca ggttatagca tgggtgaagt aagcatgtat gcagcactag  10380
gctgctggca gcaaccggga ttgatgagtg ctcgccttgc acaatcgaat accttaatc  10440 atcaactttg cggcgagtta agaacactac gtcagcattg gggcatggat gatgtagcta  10500
acggtacgtt cgagcagatc tgggaaacct ataccattaa ggcaacgatt gaacaggtcg  10560
aaattgcctc tgcagatgaa gatcgtgtgt attgcaccat tatcaataca cctgatagct  10620
tgttgttagc cggttatcca gaagcctgtc agcgagtcat taagaattta ggtgtgcgtg  10680
caatggcatt gaatatggcg aacgcaattc acagcgcgcc agcttatgcc gaatacgatc  10740
atatggttga gctataccat atggatgtta ctccacgtat taataccaag atgtattcaa  10800
gctcatgtta tttaccgatt ccacaacgca gcaaagcgat ttcccacagt attgctaaat  10860
gtttgtgtga tgtggtggat ttcccacgtt tggttaatac cttacatgac aaaggtgcgc  10920
gggtattcat tgaaatgggt ccaggtcgtt cgttatgtag ctgggtagat aagatcttag  10980
ttaatggcga tggcgataat aaaaagcaaa gccaacatgt atctgttcct gtgaatgcca  11040
aaggcaccag tgatgaactt acttatattc gtgcgattgc taagttaatt agtcatggcg  11100
tgaatttgaa tttagatagc ttgtttaacg ggtcaatcct ggttaaagca ggccatatag  11160
caaacacgaa caaatagtca acatcgatat ctagcgctgg tgagttatac ctcattagtt  11220
gaaatatgga tttaaagaga gtaattatgg aaaatattgc agtagtaggt attgctaatt  11280
tgttcccggg ctcacaagca ccggatcaat tttggcagca attgcttgaa caacaagatt  11340
gccgcagtaa ggcgaccgct gttcaaatgg gcgttgatcc tgctaaatat accgccaaca  11400
aaggtgacac agataaattt tactgtgtgc acggcggtta catcagtgat ttcaatttg  11460 atgcttcagg ttatcaactc gataatgatt atttagccgg tttagatgac cttaatcaat  11520
gggggcttta tgttacgaaa caagccctta ccgatgcggg ttattggggc agtactgcac  11580
tagaaaactg tggtgtgatt ttaggtaatt tgtcattccc aactaaatca tctaatcagc  11640
tgtttatgcc tttgtatcat caagttgttg ataatgcctt aaaggcggta ttacatcctg  11700
attttcaatt aacgcattac acagcaccga aaaaaacaca tgctgacaat gcattagtag  11760
```

```
caggttatcc agctgcattg atcgcgcaag cggcgggtct tggtggttca cattttgcac   11820
tggatgcggc ttgtgcttca tcttgttata gcgttaagtt agcgtgtgat tacctgcata   11880
cgggtaaagc caacatgatg cttgctggtg cggtatctgc agcagatcct atgttcgtaa   11940
atatgggttt ctcgatattc caagcttacc cagctaacaa tgtacatgcc ccgtttgacc   12000
aaaattcaca aggtctattt gccggtgaag gcgcgggcat gatggtattg aaacgtcaaa   12060
gtgatgcagt acgtgatggt gatcatattt acgccattat taaaggcggc gcattatcga   12120
atgacggtaa aggcgagttt gtattaagcc cgaacaccaa gggccaagta ttagtatatg   12180
aacgtgctta tgccgatgca gatgttgacc cgagtacagt tgactatatt gaatgtcatg   12240
caacgggcac acctaagggt gacaatgttg aattgcgttc gatggaaacc tttttcagtc   12300
gcgtaaataa caaaccatta ctgggctcgg ttaaatctaa ccttggtcat tgttaactg    12360 ccgctggtat gcctggcatg accaaagcta tgttagcgct aggtaaaggt cttattcctg   12420
caacgattaa cttaaagcaa ccactgcaat ctaaaaacgg ttactttact ggcgagcaaa   12480
tgccaacgac gactgtgtct tggccaacaa ctccgggtgc caaggcagat aaaccgcgta   12540
ccgcaggtgt gagcgtattt ggttttggtg gcagcaacgc ccatttggta ttacaacagc   12600
caacgcaaac actcgagact aattttagtg ttgctaaacc acgtgagcct ttggctatta   12660
ttggtatgga cagccatttt ggtagtgcca gtaatttagc gcagttcaaa accttattaa   12720
ataataatca aaataccttc cgtgaattac cagaacaacg ctggaaaggc atggaaagta   12780
acgctaacgt catgcagtcg ttacaattac gcaaagcgcc taaaggcagt tacgttgaac   12840
agctagatat tgatttcttg cgttttaaag taccgcctaa tgaaaaagat tgcttgatcc   12900
cgcaacagtt aatgatgatg caagtggcag acaatgctgc gaaagacgga ggtctagttg   12960
aaggtcgtaa tgttgcggta ttagtagcga tgggcatgga actggaatta catcagtatc   13020
gtggtcgcgt taatctaacc acccaaattg aagacagctt attacagcaa ggtattaacc   13080
tgactgttga gcaacgtgaa gaactgacca atattgctaa agacggtgtt gcctcggctg   13140
cacagctaaa tcagtatacg agtttcattg gtaatattat ggcgtcacgt atttcggcgt   13200
tatgggattt ttctggtcct gctattaccg tatcggctga agaaaactct gtttatcgtt   13260
gtgttgaatt agctgaaaat ctatttcaaa ccagtgatgt tgaagccgtt attattgctg   13320
ctgttgattt gtctggttca attgaaaaca ttactttacg tcagcactac ggtccagtta   13380
atgaaaaggg atctgtaagt gaatgtggtc cggttaatga aagcagttca gtaaccaaca   13440
atattcttga tcagcaacaa tggctggtgg gtgaaggcgc agcggctatt gtcgttaaac   13500
cgtcatcgca agtcactgct gagcaagttt atgcgcgtat tgatgcggtg agttttgccc   13560
ctggtagcaa tgcgaaagca attacgattg cagcggataa agcattaaca cttgctggta   13620
tcagtgctgc tgatgtagct agtgttgaag cacatgcaag tggttttagt gccgaaaata   13680
atgctgaaaa aaccgcgtta ccgactttat acccaagcgc aagtatcagt tcggtgaaag   13740
ccaatattgg tcatacgttt aatgcctcgg gtatggcgag tattattaaa acggcgctgc   13800
tgttagatca gaatacgagt caagatcaga aaagcaaaca tattgctatt aacggtctag   13860
gtcgtgataa cagctgcgcg catcttatct tatcgagttc agcgcaagcg catcaagttg   13920
caccagcgcc tgtatctggt atggccaagc aacgcccaca gttagttaaa accatcaaac   13980
tcggtggtca gttaattagc aacgcgattg ttaacagtgc gagttcatct ttacacgcta   14040
ttaaagcgca gtttgccggt aagcacttaa acaaagttaa ccagccagtg atgatggata   14100
```

```
acctgaagcc ccaaggtatt agcgctcatg caaccaatga gtatgtggtg actggagctg    14160
ctaacactca agcttctaac attcaagcat ctcatgttca agcgtcaagt catgcacaag    14220
agatagcacc aaaccaagtt caaaatatgc aagctacagc agccgctgta agttcacccc    14280
tttctcaaca tcaacacaca gcgcagcccg tagcggcacc gagcgttgtt ggagtgactg    14340
tgaaacataa agcaagtaac caaattcatc agcaagcgtc tacgcataaa gcattttag    14400 aaagtcgttt agctgcacag aaaaacctat cgcaacttgt tgaattgcaa accaagctgt    14460
caatccaaac tggtagtgac aatacatcta acaatactgc gtcaacaagc aatacagtgc    14520
taacaaatcc tgtatcagca acgccattaa cacttgtgtc taatgcgcct gtagtagcga    14580
caaacctaac cagtacagaa gcaaagcgc aagcagctgc tacacaagct ggttttcaga    14640
taaaaggacc tgttggttac aactatccac cgctgcagtt aattgaacgt tataataaac    14700
cagaaaacgt gatttacgat caagctgatt tggttgaatt cgctgaaggt gatattggta    14760
aggtatttgg tgctgaatac aatattattg atggctattc gcgtcgtgta cgtctgccaa    14820
cctcagatta cttgttagta acacgtgtta ctgaacttga tgccaaggtg catgaataca    14880
agaaatcata catgtgtact gaatatgatg tgcctgttga tgcaccgttc ttaattgatg    14940
gtcagatccc ttggtctgtt gccgtcgaat caggccagtg tgatttgatg ttgatttcat    15000
atatcggtat tgatttccaa gcgaaaggcg aacgtgttta ccgtttactt gattgtgaat    15060
taactttcct tgaagagatg gcttttggtg gcgatacttt acgttacgag atccacattg    15120
attcgtatgc acgtaacggc gagcaattat tattcttctt ccattacgat tgttacgtag    15180
gggataagaa ggtacttatc atgcgtaatg gttgtgctgg tttctttact gacgaagaac    15240
tttctgatgg taaaggcgtt attcataacg acaaagacaa agctgagttt agcaatgctg    15300
ttaaatcatc attcacgccg ttattacaac ataaccgtgg tcaatacgat tataacgaca    15360
tgatgaagtt ggttaatggt gatgttgcca gttgttttgg tccgcaatat gatcaaggtg    15420
gccgtaatcc atcattgaaa ttctcgtctg agaagttctt gatgattgaa cgtattacca    15480
agatagaccc aaccggtggt cattggggac taggcctgtt agaaggtcag aaagatttag    15540
accctgagca ttggtatttc ccttgtcact ttaaaggtga tcaagtaatg gctggttcgt    15600
tgatgtcgga aggttgtggc caaatggcga tgttcttcat gctgtctctt ggtatgcata    15660
ccaatgtgaa caacgctcgt ttccaaccac taccaggtga atcacaaacg gtacgttgtc    15720
gtgggcaagt actgccacag cgcaatacct aacttaccg tatggaagtt actgcgatgg    15780
gtatgcatcc acagccattc atgaaagcta atattgatat tttgcttgac ggtaaagtgg    15840
ttgttgattt caaaaacttg agcgtgatga tcagcgaaca agatgagcat tcagattacc    15900
ctgtaacact gccgagtaat gtggcgctta agcgattac tgcacctgtt gcgtcagtag    15960
caccagcatc ttcacccgct aacagcgcgg atctagacga acgtggtgtt gaaccgtttta    16020 agtttcctga acgtccgtta atgcgtgttg agtcagactt gtctgcaccg aaaagcaaag    16080
gtgtgacacc gattaagcat tttgaagcgc ctgctgttgc tggtcatcat agagtgccta    16140
accaagcacc gtttacacct tggcatatgt ttgagtttgc gacgggtaat atttctaact    16200
gtttcggtcc tgattttgat gtttatgaag gtcgtattcc acctcgtaca ccttgtggcg    16260
atttacaagt tgttactcag gttgtagaag tgcagggcga acgtcttgat cttaaaaatc    16320
catcaagctg tgtagctgaa tactatgtac cggaagacgc ttggtacttt actaaaaaca    16380
gccatgaaaa ctggatgcct tattcattaa tcatggaaat tgcattgcaa ccaaatggct    16440
ttatttctgg ttacatgggc acgacgctta aatacccctga aaaagatctg ttcttccgta    16500
```

```
accttgatgg tagcggcacg ttattaaagc agattgattt acgcggcaag accattgtga   16560
ataaatcagt cttggttagt acggctattg ctggtggcgc gattattcaa agtttcacgt   16620
ttgatatgtc tgtagatggc gagctatttt atactggtaa agctgtattt ggttacttta   16680
gtggtgaatc actgactaac caactgggca ttgataacgg taaaacgact aatgcgtggt   16740
ttgttgataa caatacccccc gcagcgaata ttgatgtgtt tgatttaact aatcagtcat   16800
tggctctgta taaagcgcct gtggataaac cgcattataa attggctggt ggtcagatga   16860
actttatcga tacagtgtca gtggttgaag gcggtggtaa agcgggcgtg gcttatgttt   16920
atggcgaacg tacgattgat gctgatgatt ggttcttccg ttatcacttc caccaagatc   16980
cggtgatgcc aggttcatta ggtgttgaag ctattattga gttgatgcag acctatgcgc   17040
ttaaaaatga tttgggtggc aagtttgcta acccacgttt cattgcgccg atgacgcaag   17100
ttgattggaa ataccgtggg caaattacgc cgctgaataa acagatgtca ctggacgtgc   17160
atatcactga gatcgtgaat gacgctggtg aagtgcgaat cgttggtgat gcgaatctgt   17220
ctaaagatgg tctgcgtatt tatgaagtta aaaacatcgt tttaagtatt gttgaagcgt   17280
aaagggtcaa gtgtaacgtg cttaagcgcc gcattggtta agacgctttt gcacgccgtg   17340
aatccgtcca tggaggcttg gggttggcat ccatgccaac aacagcaagc ttactttaat   17400
caatacggct tggtgtccat ttagacgcct cgaacttagt agttaataga caaaataatt   17460
tagctgtgga atgaatatag taagtaatca ttcggcagct acaaaaaagg aattaagaat   17520
gtcgagttta ggttttaaca ataacaacgc aattaactgg gcttggaaag tagatccagc   17580
gtcagttcat acacaagatg cagaaattaa agcagcttta atggatctaa ctaaacctct   17640
ctatgtggcg aataattcag gcgtaactgg tatagctaat catacgtcag tagcaggtgc   17700
gatcagcaat aacatcgatg ttgatgtatt ggcgtttgcg caaaagttaa acccagaaga   17760
tctgggtgat gatgcttaca agaaacagca cggcgttaaa tatgcttatc atggcggtgc   17820
gatggcaaat ggtattgcct cggttgaatt ggttgttgcg ttaggtaaag cagggctgtt   17880
atgttcattt ggtgctgcag gtctagtgcc tgatgcggtt gaagatgcaa ttcgtcgtat   17940
tcaagctgaa ttaccaaatg gcccttatgc ggttaacttg atccatgcac cagcagaaga   18000
agcattagag cgtggcgcgg ttgaacgttt cctaaaactt ggcgtcaaga cggtagaggc   18060
ttcagcttac cttggtttaa ctgaacacat tgtttggtat cgtgctgctg gtctaactaa   18120
aaacgcagat ggcagtgtta atatcggtaa caaggttatc gctaaagtat cgcgtaccga   18180
agttggtcgc cgctttatgg aacctgcacc gcaaaaatta ctggataagt tattagaaca   18240
aaataagatc acccctgaac aagctgcttt agcgttgctt gtacctatgg ctgatgatat   18300
tactggggaa gcggattctg gtggtcatac agataaccgt ccgtttttaa cattattacc   18360
gacgattatt ggtctgcgtg atgaagtgca agcgaagtat aacttctctc ctgcattacg   18420
tgttggtgct ggtggtggta tcggaacgcc tgaagcagca ctcgctgcat ttaacatggg   18480
cgcggcttat atcgttctgg gttctgtgaa tcaggcgtgt gttgaagcgg gtgcatctga   18540
atatactcgt aaactgttat cgacagttga atggctgat gtgactatgg cacctgctgc   18600
agatatgttt gaaatgggtg tgaagctgca agtattaaaa cgcggttcta tgttcgcgat   18660
gcgtgcgaag aaactgtatg acttgtatgt ggcttatgac tcgattgaag atatcccagc   18720
tgctgaacgt gagaagattg aaaaacaaat cttccgtgca aacctagacg agatttggga   18780
tggcactatc gctttctta ctgaacgcga tccagaaatg ctagcccgtg caacgagtag   18840
```

-continued

```
tcctaaacgt aaaatggcac ttatcttccg ttggtatctt ggccttcctt cacgctggtc     18900
aaacacaggc gagaagggac gtgaaatgga ttatcagatt tgggcaggcc caagtttagg     18960
tgcattcaac agctgggtga aggttctta ccttgaagac tatacccgcc gtggcgctgt     19020
agatgttgct ttgcatatgc ttaaaggtgc tgcgtattta caacgtgtaa accagttgaa     19080
attgcaaggt gttagcttaa gtacagaatt ggcaagttat cgtacgagtg attaatgtta     19140
cttgatgata tgtgaattaa ttaaagcgcc tgagggcgct ttttttggtt tttaactcag     19200
gtgttgtaac tcgaaattgc ccctttc                                        19227
```

<210> SEQ ID NO 14
<211> LENGTH: 217
<212> TYPE: DNA
<213> ORGANISM: Shewanella putrefaciens

<400> SEQUENCE: 14

```
attggtaaaa atagggtta tgtttgttgc tttaaagagt gtcctgaaaa attgctaact       60
tctcgattga tttccttata cttctgtccg ttaacaatac aagagtgcga taaccagact      120
acagagttgg ttaagtcatg gctgcctgaa gatgagttaa ttaaggttaa tcgctacatt      180
aaacaagaag ctaaaactca aggtttaatg gtaagag                              217
```

<210> SEQ ID NO 15
<211> LENGTH: 72
<212> TYPE: PRT
<213> ORGANISM: Shewanella putrefaciens

<400> SEQUENCE: 15

```
Ile Gly Lys Asn Arg Gly Tyr Val Cys Cys Phe Lys Glu Cys Pro Glu
  1               5                  10                  15

Lys Leu Leu Thr Ser Arg Leu Ile Ser Leu Tyr Phe Cys Pro Leu Thr
             20                  25                  30

Ile Gln Glu Cys Asp Asn Gln Thr Thr Glu Leu Val Lys Ser Trp Leu
         35                  40                  45

Pro Glu Asp Glu Leu Ile Lys Val Asn Arg Tyr Ile Lys Gln Glu Ala
     50                  55                  60

Lys Thr Gln Gly Leu Met Val Arg
 65                  70
```

<210> SEQ ID NO 16
<211> LENGTH: 885
<212> TYPE: DNA
<213> ORGANISM: Shewanella putrefaciens

<400> SEQUENCE: 16

```
agcgaaatgc ttatcaagaa attccaagat caatacatca ctgggaagaa aattcattcc       60
ctggttcact gggtaacgtt atttccggcc gtattgctaa ccgcttcgac cttggtggca      120
tgaactgtgt cgttgatgca gcatgtgcag ccctcttgc tgcattgcgt atggcattaa      180
gcgagcttgt tgaaggccgc agcgaaatga tgattacagg tggtgtgtgt accgataact      240
caccaaccat gtacatgagc ttctctaaaa caccggcatt cacgacaaac gaaacaattc      300
aaccattcga tattgactcg aaaggtatga tgattggtga aggtatcggt atgattgcgc      360
ttaaacgtct tgaagacgca gagcgtgatg gcgaccgtat ctattccgtg attaaaggtg      420
ttgggtgcat cttcagacgg taatttatta agagtantta tgcgcntcgt cctgaaggtc      480
aggctaaggc acttaaacgt gcttacgacg atgcaggttt cgcaccgcac acacttggct      540
```

-continued

```
tacttgaagc ccacggcaca ggcacagcag caggtgatgt ggcagaattc agtggtctta      600
actctgtatt cagtgaaggc aatgacgaaa agcaacacat cgcattaggt tcagtgaaat      660
cacagattgg tcacactaaa tcaacagcgg gtactgcggg tctaatcaaa gcgtctttag      720
cactgcacca taaagtactg ccgccaacaa tcaatgtaac cagccctaac cctaaactga      780
atattgaaga ctcgcctttc tacctcaata cacagacgcg tccatggatg caacgtgtcg      840
atggtacacc gcgtcgtgct ggtattagct catttggttt tggtg                     885
```

<210> SEQ ID NO 17
<211> LENGTH: 409
<212> TYPE: DNA
<213> ORGANISM: Shewanella putrefaciens

<400> SEQUENCE: 17

```
ccaagctaaa gcacttaacc gtgcttatga agatgccggt tttgcccctg aaacatgtgg       60
tctaattgaa ggccatggta cgggtaccaa agcgggtgat gccgcagaat ttgctggctt      120
gaccaaacac tttggcgccg ccagtgatga aaagcaatat atcgcttag gctcagttaa      180 atcgcaaatt ggtcatacta atctgcggc tggctctgcg gtatgatta aggcggcatt      240 agcgctgcat cataaaatct tacctgcaac gatccatatc gataaaccaa gtgaagcctt      300
ggatatcaaa aacagcccgt tatacctaaa cagcgaaacg cgtccttgga tgccacgtga      360
agatggtatt ccacgtcgtg caggtattag ctcatttggt tttggtggc                 409
```

<210> SEQ ID NO 18
<211> LENGTH: 81
<212> TYPE: DNA
<213> ORGANISM: Artificial Sequence
<220> FEATURE:
<223> OTHER INFORMATION: Description of Artificial Sequence: SYNTHETIC

<400> SEQUENCE: 18

```
ccaagctaaa gcacttaacc gtgcctatga tgatgccggt tttgcccctg aaacatgtgg       60
tctaattgaa ggccatggta c                                                81
```

<210> SEQ ID NO 19
<211> LENGTH: 81
<212> TYPE: DNA
<213> ORGANISM: Artificial Sequence
<220> FEATURE:
<223> OTHER INFORMATION: Description of Artificial Sequence: SYNTHETIC

<400> SEQUENCE: 19

```
ccaagctaaa gcacttaacc gtgcttatga agatgccggt tttgcccctg aaacatgtgg       60
tctaattgaa ggccatggta c                                                81
```

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: SYNTHETIC

<400> SEQUENCE: 20

```
agaacgcaaa gttgccgcac tgtttggtcg ccaaggttca caa                        43
```

<210> SEQ ID NO 21
<211> LENGTH: 43
<212> TYPE: DNA
<213> ORGANISM: Artificial Sequence

```
<220> FEATURE:
<223> OTHER INFORMATION: Description of Artificial Sequence: SYNTHETIC

<400> SEQUENCE: 21
caaagcgggt gatgccgcac tgtttggtcg cttgacctaa cac                    43

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: SYNTHETIC

<400> SEQUENCE: 22
cattgcgcta ggttcagtta aatcacaaat tggtcatact aaatcaactg caggt       55

<210> SEQ ID NO 23
<211> LENGTH: 55
<212> TYPE: DNA
<213> ORGANISM: Artificial Sequence
<220> FEATURE:
<223> OTHER INFORMATION: Description of Artificial Sequence: SYNTHETIC

<400> SEQUENCE: 23
tatcgcctta ggctcagtta aatcgcaaat tggtcatact aaatctgcgg ctggc       55

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 24
cggcttcgat tttggcggca tgaacggtg                                    29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 25
cgcgtatgat taaggcggca ttagcgctg                                    29

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: SYNTHETIC

<400> SEQUENCE: 26
gcactgctgc aagcatgaac gcgtcgtt                                     28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: SYNTHETIC

<400> SEQUENCE: 27
gctctgcggc tatcattaac gcggcatt                                     28
```

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 28
tccctggtgc taaccatatc agcaaacca                                29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 29
tacctgcaac gatccatatc gataaacca                                29

<210> SEQ ID NO 30
<211> LENGTH: 98
<212> TYPE: DNA
<213> ORGANISM: Artificial Sequence
<220> FEATURE:
<223> OTHER INFORMATION: Description of Artificial Sequence: SYNTHETIC

<400> SEQUENCE: 30
ctcacctttg tatctaaaca ctgagacttc gtccatggtt accacgtgtt gatggtacgc    60
cgcgccgcgc gggtattagc tcatttggtt ttggtggc                            98

<210> SEQ ID NO 31
<211> LENGTH: 98
<212> TYPE: DNA
<213> ORGANISM: Artificial Sequence
<220> FEATURE:
<223> OTHER INFORMATION: Description of Artificial Sequence: SYNTHETIC

<400> SEQUENCE: 31
cagcccgtta tacctaaaca gcgaaacggc gtccttggat gccacgtgaa gatggtattc    60
cacgtcgtgc aggtattagc tcatttggtt ttggtggc                            98

<210> SEQ ID NO 32
<211> LENGTH: 4
<212> TYPE: PRT
<213> ORGANISM: Shewanella putrefaciens

<400> SEQUENCE: 32

Asp Xaa Ala Cys
 1

<210> SEQ ID NO 33
<211> LENGTH: 4
<212> TYPE: PRT
<213> ORGANISM: Shewanella putrefaciens

<400> SEQUENCE: 33

Gly Phe Gly Gly
 1

<210> SEQ ID NO 34
<211> LENGTH: 5
<212> TYPE: PRT
<213> ORGANISM: Shewanella putrefaciens -continued

```
<400> SEQUENCE: 34

Gly His Ser Xaa Gly
 1               5

<210> SEQ ID NO 35
<211> LENGTH: 6
<212> TYPE: PRT
<213> ORGANISM: Shewanella putrefaciens

<400> SEQUENCE: 35

Leu Gly Xaa Asp Ser Leu
 1               5

<210> SEQ ID NO 36
<211> LENGTH: 6
<212> TYPE: PRT
<213> ORGANISM: Shewanella putrefaciens

<400> SEQUENCE: 36

Leu Gly Xaa Asp Ser Ile
 1               5

<210> SEQ ID NO 37
<211> LENGTH: 6
<212> TYPE: PRT
<213> ORGANISM: Shewanella putrefaciens

<400> SEQUENCE: 37

Gly Xaa Gly Xaa Xaa Gly
 1               5

<210> SEQ ID NO 38
<211> LENGTH: 6
<212> TYPE: PRT
<213> ORGANISM: Shewanella putrefaciens

<400> SEQUENCE: 38

Gly Xaa Gly Xaa Xaa Ala
 1               5

<210> SEQ ID NO 39
<211> LENGTH: 6
<212> TYPE: PRT
<213> ORGANISM: 'Axial Seamount' polynoid polychaete

<400> SEQUENCE: 39

Gly Xaa Gly Xaa Xaa Pro
 1               5

<210> SEQ ID NO 40
<211> LENGTH: 5
<212> TYPE: PRT
<213> ORGANISM: Shewanella putrefaciens

<400> SEQUENCE: 40

Gly Xaa Ser Xaa Gly
 1               5

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: synthetic
```

<400> SEQUENCE: 41
cuacuacuac uaccaagcua aagcacuuaa ccgug                          35

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: synthetic

<400> SEQUENCE: 42
cuacuacuac uaacagcgaa augcuuauca ag                             32

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: synthetic

<400> SEQUENCE: 43
cuacuacuac uagcgaccaa aaccaaauga gcuaauac                       38

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: synthetic

<400> SEQUENCE: 44
aagcccgggc tt                                                   12

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 45
gtacaagccc gggcttagct                                           20

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: synthetic

<400> SEQUENCE: 46
cgcgatttaa atggcgcgcc ctgcaggcgg ccgcctgcag ggcgcgccat ttaaat    56

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: synthetic

<400> SEQUENCE: 47
ctgcagctcg agacaatgtt gatttcctta tacttctgtc c                   41

<210> SEQ ID NO 48

<210> SEQ ID NO 49
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 48
ggatccagat ctctagctag tcttagctga agctcga                    37

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 49
tctagactcg agacaatgag ccagacctct aaacctaca                  39

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 50
cccgggctcg agctaattcg cctcactgtc gtttgct                    37

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 51
gaattcctcg agacaatgcc gctgcgcatc gcacttatc                  39

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 52
ggtaccagat ctttagactt ccccttgaag taaatgg                    37

<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 53
gaattcgtcg acacaatgtc attaccagac aatgcttct                  39

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: synthetic

<400> SEQUENCE: 54

```
tctagagtcg acttatacag attcttcgat gctgatag                          38

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 55
gaattcgtcg acacaatgaa tcctacagca actaacgaa                         39

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 56
tctagaggat ccttaggcca ttctttggtt tggcttc                           37

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 57
tctagagtcg acacaatggc ggaattagct gttattggt                         39

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 58
gtcgacggat ccctatttgt tcgtgtttgc tatatg                            36

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: synthetic

<400> SEQUENCE: 59
gtcgacggat ccacaatgaa tatagtaagt aatcattcgg ca                     42

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 60
gtcgacctcg agttaatcac tcgtacgata acttgcc                           37

<210> SEQ ID NO 61
<211> LENGTH: 39
<212> TYPE: DNA
```

```
<213> ORGANISM: Artificial Sequence
<220> FEATURE:
<223> OTHER INFORMATION: Description of Artificial Sequence: synthetic

<400> SEQUENCE: 61
cccgggtcga cacaatggct aaaaagaaca ccacatcga                              39

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: synthetic

<400> SEQUENCE: 62
cccgggtcga ctcatgacat atcgttcaaa atgtcactga                             40

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: synthetic

<400> SEQUENCE: 63
tcgacatgga aaatattgca gtagtaggta ttgctaatttt gttc                       44

<210> SEQ ID NO 64
<211> LENGTH: 44
<212> TYPE: DNA
<213> ORGANISM: Artificial Sequence
<220> FEATURE:
<223> OTHER INFORMATION: Description of Artificial Sequence: synthetic

<400> SEQUENCE: 64
ccgggaacaa attagcaata cctactactg caatattttc catg                        44

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: synthetic

<400> SEQUENCE: 65
tcagatgaac tttatcgata c                                                 21

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 66
tcatgagacg tcgtcgactt acgcttcaac aatact                                 36

<210> SEQ ID NO 67
<211> LENGTH: 30
<212> TYPE: DNA
<213> ORGANISM: Schizochytrium aggregatum

<400> SEQUENCE: 67
gtgatgatct ttccctgatg cacgccaagg                                        30
```

```
<210> SEQ ID NO 68
<211> LENGTH: 30
<212> TYPE: DNA
<213> ORGANISM: Schizochytrium aggregatum

<400> SEQUENCE: 68
agctcgagac cggcaacccg cagcgccaga                                        30

<210> SEQ ID NO 69
<211> LENGTH: 4446
<212> TYPE: DNA
<213> ORGANISM: Schizochytrium aggregatum

<400> SEQUENCE: 69
cgctgccgcc gcgtctcgcc gcgccgcgcc gcgccgccgc cgccgctcgc gcgcacgccc        60
gcgcgtctcg ccgcgcctgc tgtctcgaac gagcttctcg agaaggccga gaccgtcgtc       120
atggaggtcc tcgccgccaa gactggctac gagactgaca tgatcgagtc cgacatggag       180
ctcgagactg agctcggcat tgactccatc aagcgtgtcg agatcctctc cgaggttcag       240
gccatgctca acgtcgaggc caaggacgtc gacgctctca ccgcactcg cactgtgggt        300
gaggtcgtca acgccatgaa ggctgagatc gctggtggct ctgccccggc gcctgccgcc       360
gctgccccag gtccggctgc tgccgcccct gcgcctgctg tctcgagcga gcttctcgag       420
aaggccgaga ctgtcgtcat ggaggtcctc gccgccaaga ctggctacga gactgacatg       480
attgagtccg acatggagct cgagaccgag ctcggcattg actccatcaa gcgtgtcgag       540
attctctccg aggttcaggc catgctcaac gtcgaggcca aggacgtcga cgctctcagc       600
cgcactcgca ctgttggtga ggtcgtcgat gccatgaagg ctgagatcgc tggcagctcc       660
gcctcggcgc ctgccgccgc tgctcctgct ccggctgctg ccgctcctgc gccgctgcc        720
gccgccctg ctgtctcgaa cgagcttctc gagaaagccg agactgtcgt catggaggtc        780
ctcgccgcca agactggcta cgagactgac atgatcgagt ccgacatgga gctcgagact       840
gagctcggca ttgactccat caagcgtgtc gagatcctct ccgaggttca ggccatgctc       900
aacgtcgagg ccaaggacgt cgatgccctc agccgcaccc gcactgttgg cgaggttgtc       960
gatgccatga aggccgagat cgctggtggc tctgccccgg cgcctgccgc cgctgccccct     1020
gctccggctg ccgccgcccc tgctgtctcg aacgagcttc ttgagaaggc cgagactgtc      1080
gtcatggagg tcctcgccgc caagactggc tacgagaccg acatgatcga gtccgacatg      1140
gagctcgaga ccgagctcgg cattgactcc atcaagcgtg tcgagattct ctccgaggtt      1200
caggccatgc tcaacgtcga ggccaaggac gtcgatgctc tcagccgcac tcgcactgtt      1260
ggcgaggtcg tcgatgccat gaaggctgag atcgccggca gctccgcccc ggcgcctgcc      1320
gccgctgctc ctgctccggc tgctgccgct cctgcgcccg ctgccgctgc cctgctgtc       1380
tcgagcgagc ttctcgagaa ggccgagacc gtcgtcatgg aggtcctcgc cgccaagact      1440
ggctacgaga ctgacatgat tgagtccgac atggagctcg agactgagct cggcattgac      1500
tccatcaagc gtgtcgagat cctctccgag gttcaggcca tgctcaacgt cgaggccaag      1560
gacgtcgatg ccctcagccg cacccgcact gttggcgagg ttgtcgatgc catgaaggcc      1620
gagatcgctg tggctctgc ccggcgcct gccgccgctg ccctgctcc ggctgccgcc          1680
gccctgctg tctcgaacga gcttcttgag aaggccgaga ccgtcgtcat ggaggtcctc       1740
gccgccaaga ctggctacga gaccgacatg atcgagtccg acatggagct cgagaccgag      1800
ctcggcattg actccatcaa gcgtgtcgag attctctccg aggttcaggc catgctcaac     1860
```

```
gtcgaggcca aggacgtcga cgctctcagc cgcactcgca ctgttggcga ggtcgtcgat  1920
gccatgaagg ctgagatcgc tggtggctct gccccggcgc ctgccgccgc tgctcctgcc  1980
tcggctggcg ccgcgcctgc ggtcaagatt gactcggtcc acggcgctga ctgtgatgat  2040 cttccctga tgcacgccaa ggtggttgac atccgccgcc cggacgagct catcctggag  2100
cgccccgaga accgccccgt tctcgttgtc gatgacggca cgagctcac cctcgccctg  2160 gtccgcgtcc tcggcgcctg cgccgttgtc ctgacctttg agggtctcca gctcgctcag  2220
cgcgctggtg ccgctgccat ccgccacgtg ctcgccaagg atctttccgc ggagagcgcc  2280
gagaaggcca tcaaggaggc cgagcagcgc tttggcgctc tcggcggctt catctcgcag  2340
caggcggagc gcttcgagcc cgccgaaatc ctcggcttca cgctcatgtg cgccaagttc  2400
gccaaggctt ccctctgcac ggctgtggct ggcggccgcc cggcctttat cggtgtggcg  2460
cgccttgacg gccgcctcgg attcacttcg cagggcactt ctgacgcgct caagcgtgcc  2520
cagcgtggtg ccatctttgg cctctgcaag accatcggcc tcgagtggtc cgagtctgac  2580
gtcttttccc gcggcgtgga cattgctcag ggcatgcacc ccgaggatgc cgccgtggcg  2640
attgtgcgcg agatggcgtg cgctgacatt cgcattcgcg aggtcggcat tggcgcaaac  2700
cagcagcgct gcacgatccg tgccgccaag ctcgagaccg gcaacccgca gcgccagatc  2760
gccaaggacg acgtgctgct cgtttctggc ggcgctcgcg gcatcacgcc tctttgcatc  2820
cgggagatca cgcgccagat cgcgggcggc aagtacattc tgcttggccg cagcaaggtc  2880
tctgcgagcg aaccggcatg gtgcgctggc atcactgacg agaaggctgt gcaaaaggct  2940
gctacccagg agctcaagcg cgcctttagc gctggcgagg gccccaagcc cacgccccgc  3000
gctgtcacta gcttgtggg ctctgttctt ggcgctcgcg aggtgcgcag ctctattgct  3060
gcgattgaag cgctcggcgg caaggccatc tactcgtcgt gcgacgtgaa ctctgccgcc  3120
gacgtggcca aggccgtgcg cgatgccgag tcccagctcg gtgcccgcgt ctcgggcatc  3180
gttcatgcct cgggcgtgct ccgcgaccgt ctcatcgaga agaagctccc cgacgagttc  3240
gacgccgtct ttggcaccaa ggtcaccggt ctcgagaacc tcctcgccgc cgtcgaccgc  3300
gccaacctca agcacatggt cctcttcagc tcgctcgccg gcttccacgg caacgtcggc  3360
cagtctgact acgccatggc caacgaggcc cttaacaaga tgggcctcga gctcgccaag  3420
gacgtctcgg tcaagtcgat ctgcttcggt ccctgggacg gtggcatggt gacgccgcag  3480
ctcaagaagc agttccagga gatgggcgtg cagatcatcc ccgcgagggg cggcgctgat  3540
accgtggcgc gcatcgtgct cggctcctcg ccggctgaga tccttgtcgg caactggcgc  3600
accccgtcca gaaggtcgg ctcggacacc atcaccctgc accgcaagat ttccgccaag  3660 tccaaccct tcctcgagga ccacgtcatc cagggccgcc gcgtgctgcc catgacgctg  3720
gccattggct cgctcgcgga gacctgcctc ggcctcttcc ccggctactc gctctgggcc  3780
attgacgacg cccagctctt caagggtgtc actgtcgacg gcgacgtcaa ctgcgaggtg  3840
accctcaccc cgtcgacggc gccctcgggc gcgtcaacg tccaggccac gctcaagacc  3900 tttccagcg gcaagctggt cccggcctac gcgcgccgtca tcgtgctctc caaccagggc  3960
gcgcccccgg ccaacgccac catgcagccg cctcgctcg atgccgatcc ggcgctccag  4020
ggctccgtct acgacggcaa gaccctcttc cacgcccgg ccttccgcgg catcgatgac  4080
gtgctctcgt gcaccaagag ccagcttgtg ccaagtgca gcgctgtccc cggctccgac  4140
gccgctcgcg gcgagtttgc cacggacact gacgcccatg acccttcgt gaacgacctg  4200 gcctttcagg ccatgctcgt ctgggtgcgc cgcacgctcg gccaggctgc gctccccaac  4260
```

```
tcgatccagc gcatcgtcca gcaccgcccg gtcccgcagg acaagcccct ctacattacc   4320
ctccgctcca accagtcggg cggtcactcc cagcacaagc acgcccttca gttccacaac   4380
gagcagggcg atctcttcat tgatgtccag gcttcggtca tcgccacgga cagccttgcc   4440
ttctaa                                                              4446
```

<210> SEQ ID NO 70
<211> LENGTH: 1481
<212> TYPE: PRT
<213> ORGANISM: Schizochytrium aggregatum

<400> SEQUENCE: 70

```
Arg Cys Arg Arg Val Ser Pro Arg Arg Ala Pro Pro Pro Leu
 1               5                  10                  15

Ala Arg Thr Pro Ala Arg Leu Ala Ala Pro Ala Val Ser Asn Glu Leu
            20                  25                  30

Leu Glu Lys Ala Glu Thr Val Val Met Glu Val Leu Ala Ala Lys Thr
        35                  40                  45

Gly Tyr Glu Thr Asp Met Ile Glu Ser Asp Met Glu Leu Glu Thr Glu
    50                  55                  60

Leu Gly Ile Asp Ser Ile Lys Arg Val Glu Ile Leu Ser Glu Val Gln
65                  70                  75                  80

Ala Met Leu Asn Val Glu Ala Lys Asp Val Asp Ala Leu Ser Arg Thr
                85                  90                  95

Arg Thr Val Gly Glu Val Val Asn Ala Met Lys Ala Glu Ile Ala Gly
            100                 105                 110

Gly Ser Ala Pro Ala Pro Ala Ala Ala Pro Gly Pro Ala Ala Ala
        115                 120                 125

Ala Pro Ala Pro Ala Val Ser Ser Glu Leu Leu Glu Lys Ala Glu Thr
    130                 135                 140

Val Val Met Glu Val Leu Ala Ala Lys Thr Gly Tyr Glu Thr Asp Met
145                 150                 155                 160

Ile Glu Ser Asp Met Glu Leu Glu Thr Glu Leu Gly Ile Asp Ser Ile
                165                 170                 175

Lys Arg Val Glu Ile Leu Ser Glu Val Gln Ala Met Leu Asn Val Glu
            180                 185                 190

Ala Lys Asp Val Asp Ala Leu Ser Arg Thr Arg Thr Val Gly Glu Val
        195                 200                 205

Val Asp Ala Met Lys Ala Glu Ile Ala Gly Ser Ser Ala Ser Ala Pro
    210                 215                 220

Ala Ala Ala Ala Pro Ala Pro Ala Ala Ala Pro Ala Pro Ala Ala
225                 230                 235                 240

Ala Ala Pro Ala Val Ser Asn Glu Leu Leu Glu Lys Ala Glu Thr Val
                245                 250                 255

Val Met Glu Val Leu Ala Ala Lys Thr Gly Tyr Glu Thr Asp Met Ile
            260                 265                 270

Glu Ser Asp Met Glu Leu Glu Thr Glu Leu Gly Ile Asp Ser Ile Lys
        275                 280                 285

Arg Val Glu Ile Leu Ser Glu Val Gln Ala Met Leu Asn Val Glu Ala
    290                 295                 300

Lys Asp Val Asp Ala Leu Ser Arg Thr Arg Thr Val Gly Glu Val Val
305                 310                 315                 320

Asp Ala Met Lys Ala Glu Ile Ala Gly Gly Ser Ala Pro Ala Pro Ala
                325                 330                 335
```

-continued

```
Ala Ala Ala Pro Ala Pro Ala Ala Ala Pro Ala Val Ser Asn Glu
            340             345             350

Leu Leu Glu Lys Ala Glu Thr Val Val Met Glu Val Leu Ala Ala Lys
            355             360             365

Thr Gly Tyr Glu Thr Asp Met Ile Glu Ser Asp Met Glu Leu Glu Thr
            370             375             380

Glu Leu Gly Ile Asp Ser Ile Lys Arg Val Glu Ile Leu Ser Glu Val
385             390             395             400

Gln Ala Met Leu Asn Val Glu Ala Lys Asp Val Asp Ala Leu Ser Arg
            405             410             415

Thr Arg Thr Val Gly Glu Val Val Asp Ala Met Lys Ala Glu Ile Ala
            420             425             430

Gly Ser Ser Ala Pro Ala Pro Ala Ala Ala Pro Ala Pro Ala Ala
            435             440             445

Ala Ala Pro Ala Pro Ala Ala Ala Pro Ala Val Ser Ser Glu Leu
            450             455             460

Leu Glu Lys Ala Glu Thr Val Val Met Glu Val Leu Ala Ala Lys Thr
465             470             475             480

Gly Tyr Glu Thr Asp Met Ile Glu Ser Asp Met Glu Leu Glu Thr Glu
            485             490             495

Leu Gly Ile Asp Ser Ile Lys Arg Val Glu Ile Leu Ser Glu Val Gln
            500             505             510

Ala Met Leu Asn Val Glu Ala Lys Asp Val Asp Ala Leu Ser Arg Thr
            515             520             525

Arg Thr Val Gly Glu Val Val Asp Ala Met Lys Ala Glu Ile Ala Gly
            530             535             540

Gly Ser Ala Pro Ala Pro Ala Ala Ala Pro Ala Pro Ala Ala Ala
545             550             555             560

Ala Pro Ala Val Ser Asn Glu Leu Leu Glu Lys Ala Glu Thr Val Val
            565             570             575

Met Glu Val Leu Ala Ala Lys Thr Gly Tyr Glu Thr Asp Met Ile Glu
            580             585             590

Ser Asp Met Glu Leu Glu Thr Glu Leu Gly Ile Asp Ser Ile Lys Arg
            595             600             605

Val Glu Ile Leu Ser Glu Val Gln Ala Met Leu Asn Val Glu Ala Lys
            610             615             620

Asp Val Asp Ala Leu Ser Arg Thr Arg Thr Val Gly Glu Val Val Asp
625             630             635             640

Ala Met Lys Ala Glu Ile Ala Gly Gly Ser Ala Pro Ala Pro Ala Ala
            645             650             655

Ala Ala Pro Ala Ser Ala Gly Ala Ala Pro Ala Val Lys Ile Asp Ser
            660             665             670

Val His Gly Ala Asp Cys Asp Leu Ser Leu Met His Ala Lys Val
            675             680             685

Val Asp Ile Arg Arg Pro Asp Glu Leu Ile Leu Glu Arg Pro Glu Asn
            690             695             700

Arg Pro Val Leu Val Asp Asp Gly Ser Glu Leu Thr Leu Ala Leu
705             710             715             720

Val Arg Val Leu Gly Ala Cys Ala Val Val Leu Thr Phe Glu Gly Leu
            725             730             735

Gln Leu Ala Gln Arg Ala Gly Ala Ala Ile Arg His Val Leu Ala
            740             745             750
```

-continued

```
Lys Asp Leu Ser Ala Glu Ser Ala Glu Lys Ala Ile Lys Glu Ala Glu
            755                 760                 765

Gln Arg Phe Gly Ala Leu Gly Gly Phe Ile Ser Gln Gln Ala Glu Arg
        770                 775                 780

Phe Glu Pro Ala Glu Ile Leu Gly Phe Thr Leu Met Cys Ala Lys Phe
785                 790                 795                 800

Ala Lys Ala Ser Leu Cys Thr Ala Val Ala Gly Gly Arg Pro Ala Phe
                805                 810                 815

Ile Gly Val Ala Arg Leu Asp Gly Arg Leu Gly Phe Thr Ser Gln Gly
            820                 825                 830

Thr Ser Asp Ala Leu Lys Arg Ala Gln Arg Gly Ala Ile Phe Gly Leu
        835                 840                 845

Cys Lys Thr Ile Gly Leu Glu Trp Ser Glu Ser Asp Val Phe Ser Arg
850                 855                 860

Gly Val Asp Ile Ala Gln Gly Met His Pro Glu Asp Ala Ala Val Ala
865                 870                 875                 880

Ile Val Arg Glu Met Ala Cys Ala Asp Ile Arg Ile Arg Glu Val Gly
                885                 890                 895

Ile Gly Ala Asn Gln Gln Arg Cys Thr Ile Arg Ala Ala Lys Leu Glu
            900                 905                 910

Thr Gly Asn Pro Gln Arg Gln Ile Ala Lys Asp Asp Val Leu Leu Val
        915                 920                 925

Ser Gly Gly Ala Arg Gly Ile Thr Pro Leu Cys Ile Arg Glu Ile Thr
    930                 935                 940

Arg Gln Ile Ala Gly Gly Lys Tyr Ile Leu Leu Gly Arg Ser Lys Val
945                 950                 955                 960

Ser Ala Ser Glu Pro Ala Trp Cys Ala Gly Ile Thr Asp Glu Lys Ala
                965                 970                 975

Val Gln Lys Ala Ala Thr Gln Glu Leu Lys Arg Ala Phe Ser Ala Gly
            980                 985                 990

Glu Gly Pro Lys Pro Thr Pro Arg Ala Val Thr Lys Leu Val Gly Ser
        995                 1000                1005

Val Leu Gly Ala Arg Glu Val Arg Ser Ser Ile Ala Ala Ile Glu Ala
    1010                1015                1020

Leu Gly Gly Lys Ala Ile Tyr Ser Ser Cys Asp Val Asn Ser Ala Ala
1025                1030                1035                1040

Asp Val Ala Lys Ala Val Arg Asp Ala Glu Ser Gln Leu Gly Ala Arg
                1045                1050                1055

Val Ser Gly Ile Val His Ala Ser Gly Val Leu Arg Asp Arg Leu Ile
            1060                1065                1070

Glu Lys Lys Leu Pro Asp Glu Phe Asp Ala Val Phe Gly Thr Lys Val
        1075                1080                1085

Thr Gly Leu Glu Asn Leu Leu Ala Ala Val Asp Arg Ala Asn Leu Lys
    1090                1095                1100

His Met Val Leu Phe Ser Ser Leu Ala Gly Phe His Gly Asn Val Gly
1105                1110                1115                1120

Gln Ser Asp Tyr Ala Met Ala Asn Glu Ala Leu Asn Lys Met Gly Leu
                1125                1130                1135

Glu Leu Ala Lys Asp Val Ser Val Lys Ser Ile Cys Phe Gly Pro Trp
            1140                1145                1150

Asp Gly Gly Met Val Thr Pro Gln Leu Lys Lys Gln Phe Gln Glu Met
        1155                1160                1165

Gly Val Gln Ile Ile Pro Arg Glu Gly Gly Ala Asp Thr Val Ala Arg
```

Ile Val Leu Gly Ser Ser Pro Ala Glu Ile Leu Val Gly Asn Trp Arg
1185                1190                1195                1200

Thr Pro Ser Lys Lys Val Gly Ser Asp Thr Ile Thr Leu His Arg Lys
                1205                1210                1215

Ile Ser Ala Lys Ser Asn Pro Phe Leu Glu Asp His Val Ile Gln Gly
                1220                1225                1230

Arg Arg Val Leu Pro Met Thr Leu Ala Ile Gly Ser Leu Ala Glu Thr
                1235                1240                1245

Cys Leu Gly Leu Phe Pro Gly Tyr Ser Leu Trp Ala Ile Asp Asp Ala
1250                1255                1260

Gln Leu Phe Lys Gly Val Thr Val Asp Gly Asp Val Asn Cys Glu Val
1265                1270                1275                1280

Thr Leu Thr Pro Ser Thr Ala Pro Ser Gly Arg Val Asn Val Gln Ala
                1285                1290                1295

Thr Leu Lys Thr Phe Ser Ser Gly Lys Leu Val Pro Ala Tyr Arg Ala
                1300                1305                1310

Val Ile Val Leu Ser Asn Gln Gly Ala Pro Pro Ala Asn Ala Thr Met
                1315                1320                1325

Gln Pro Pro Ser Leu Asp Ala Asp Pro Ala Leu Gln Gly Ser Val Tyr
                1330                1335                1340

Asp Gly Lys Thr Leu Phe His Gly Pro Ala Phe Arg Gly Ile Asp Asp
1345                1350                1355                1360

Val Leu Ser Cys Thr Lys Ser Gln Leu Val Ala Lys Cys Ser Ala Val
                1365                1370                1375

Pro Gly Ser Asp Ala Ala Arg Gly Glu Phe Ala Thr Asp Thr Asp Ala
                1380                1385                1390

His Asp Pro Phe Val Asn Asp Leu Ala Phe Gln Ala Met Leu Val Trp
                1395                1400                1405

Val Arg Arg Thr Leu Gly Gln Ala Ala Leu Pro Asn Ser Ile Gln Arg
                1410                1415                1420

Ile Val Gln His Arg Pro Val Pro Gln Asp Lys Pro Phe Tyr Ile Thr
1425                1430                1435                1440

Leu Arg Ser Asn Gln Ser Gly Gly His Ser Gln His Lys His Ala Leu
                1445                1450                1455

Gln Phe His Asn Glu Gln Gly Asp Leu Phe Ile Asp Val Gln Ala Ser
                1460                1465                1470

Val Ile Ala Thr Asp Ser Leu Ala Phe
                1475                1480

<210> SEQ ID NO 71
<211> LENGTH: 5215
<212> TYPE: DNA
<213> ORGANISM: Schizochytrium aggregatum

<400> SEQUENCE: 71
tgccgtcttt gaggagcatg acccctccaa cgccgcctgc acgggccacg actccatttc        60
tgcgctctcg gcccgctgcg gcggtgaaag caacatgcgc atcgccatca ctggtatgga      120
cgccaccttt ggcgctctca aggactcga gccttcgag cgcgccattt acaccggcgc       180
tcacggtgcc atcccactcc cagaaaagcg ctggcgcttt ctcggcaagg acaaggactt       240
tcttgacctc tgcggcgtca aggccacccc gcacggctgc tacattgaag atgttgaggt       300
cgacttccag cgcctccgca cgcccatgac ccctgaagac atgctcctcc ctcagcagct       360

-continued

```
tctggccgtc accaccattg accgcgccat cctcgactcg ggaatgaaaa agggtggcaa       420
tgtcgccgtc tttgtcggcc tcggcaccga cctcgagctc taccgtcacc gtgctcgcgt       480
cgctctcaag gagcgcgtcc gccctgaagc ctccaagaag ctcaatgaca tgatgcagta       540
cattaacgac tgcggcacat ccacatcgta cacctcgtac attggcaacc tcgtcgccac       600
gcgcgtctcg tcgcagtggg gcttcacggg cccctccttt acgatcaccg agggcaacaa       660
ctccgtctac cgctgcgccg agctcggcaa gtacctcctc gagaccggcg aggtcgatgg       720
cgtcgtcgtt gcgggtgtcg atctctgcgg cagtgccgaa aacctttacg tcaagtctcg       780
ccgcttcaag gtgtccacct ccgatacccc gcgcgccagc tttgacgccg ccgccgatgg       840
ctactttgtc ggcgagggct gcggtgcctt tgtgctcaag cgtgagacta gctgcaccaa       900
ggacgaccgt atctacgctt gcatggatgc catcgtccct ggcaacgtcc ctagcgcctg       960
cttgcgcgag gccctcgacc aggcgcgcgt caagccgggc gatatcgaga tgctcgagct      1020
cagcgccgac tccgcccgcc acctcaagga cccgtccgtc ctgcccaagg agctcactgc      1080
cgaggaggaa atcggcggcc ttcagacgat ccttcgtgac gatgacaagc tcccgcgcaa      1140
cgtcgcaacg ggcagtgtca aggccaccgt cggtgacacc ggttatgcct ctggtgctgc      1200
cagcctcatc aaggctgcgc tttgcatcta caaccgctac ctgcccagca acggcgacga      1260
ctgggatgaa cccgcccctg aggcgccctg ggacagcacc ctctttgcgt gccagacctc      1320
gcgcgcttgg ctcaagaacc ctggcgagcg tcgctatgcg gccgtctcgg gcgtctccga      1380
gacgcgctcg tgctattccg tgctcctctc gaagccgag ggccactacg agcgcgagaa      1440
ccgcatctcg ctcgacgagg aggcgcccaa gctcattgtg cttcgcgccg actcccacga      1500
ggagatcctt ggtcgcctcg acaagatccg cgagcgcttc ttgcagccca cgggcgccgc      1560
cccgcgcgag tccgagctca aggcgcaggc ccgccgcatc ttcctcgagc tcctcggcga      1620
gacccttgcc caggatgccg cttcttcagg ctcgcaaaag cccctcgctc tcagcctcgt      1680
ctccacgccc tccaagctcc agcgcgaggt cgagctcgcg gccaagggta tcccgcgctg      1740
cctcaagatg cgccgcgatt ggagctcccc tgctggcagc cgctacgcgc ctgagccgct      1800
cgccagcgac cgcgtcgcct tcatgtacgg cgaaggtcgc agcccttact acggcatcac      1860
ccaagacatt caccgcattt ggcccgaact ccacgaggtc atcaacgaaa agacgaaccg      1920
tctctgggcc gaaggcgacc gctgggtcat gccgcgcgcc agcttcaagt cggagctcga      1980
gagccagcag caagagtttg atcgcaacat gattgaaatg ttccgtcttg gaatcctcac      2040
ctcaattgcc ttcaccaatc tggcgcgcga cgttctcaac atcacgccca aggccgcctt      2100
tggcctcagt cttggcgaga tttccatgat ttttgccttt tccaagaaga acggtctcat      2160
ctccgaccag ctcaccaagg atcttcgcga gtccgacgtg tggaacaagg ctctggccgt      2220
tgaatttaat gcgctgcgcg aggcctgggg cattccacag agtgtcccca aggacgagtt      2280
ctggcaaggc tacattgtgc gcggcaccaa gcaggatatc gaggcggcca tcgccccgga      2340
cagcaagtac gtgcgcctca ccatcatcaa tgatgccaac accgccctca ttagcggcaa      2400
gcccgacgcc tgcaaggctg cgatcgcgcg tctcggtggc aacattcctg cgcttcccgt      2460
gacccagggc atgtgcggcc actgcccga ggtgggacct tataccaagg atatcgccaa      2520
gatccatgcc aaccttgagt tccccgttgt cgacggcctt gacctctgga ccacaatcaa      2580
ccagaagcgc ctcgtgccac gcgccacggg cgccaaggac gaatgggccc cttcttcctt      2640
tggcgagtac gccggccagc tctacgagaa gcaggctaac ttcccccaaa tcgtcgagac      2700
catttacaag caaaactacg acgtctttgt cgaggttggg cccaacaacc accgtagcac      2760
```

```
cgcagtgcgc accacgcttg gtccccagcg caaccacctt gctggcgcca tcgacaagca    2820
gaacgaggat gcttggacga ccatcgtcaa gcttgtggct tcgctcaagg cccaccttgt    2880
tcctggcgtc acgatctcgc cgctgtacca ctccaagctt gtggcggagg ctcaggcttg    2940
ctacgctgcg ctctgcaagg gtgaaaagcc aagaagaac aagtttgtgc gcaagattca    3000
gctcaacggt cgcttcaaca gcaaggcgga ccccatctcc tcggccgatc ttgccagctt    3060
tccgcctgcg gaccctgcca ttgaagccgc catctcgagc cgcatcatga agcctgtcgc    3120
tcccaagttc tacgcgcgtc tcaacattga cgagcaggac gagacccgag atccgatcct    3180
caacaaggac aacgcgccgt cttcttcttc ttcttcttct tcttcttctt cttcttcttc    3240
ttctccgtcg cctgctcctt cggcccccgt gcaaaagaag gctgctcccg ccgcggagac    3300
caaggctgtt gcttcggctg acgcacttcg cagtgccctg ctcgatctcg acagtatgct    3360
tgcgctgagc tctgccagtg cctccggcaa ccttgttgag actgcgccta gcgacgcctc    3420
ggtcattgtg ccgccctgca acattgcgga tctcggcagc cgcgccttca tgaaaacgta    3480
cggtgtttcg gcgcctctgt acacgggcgc catggccaag gcattgcct ctgcggacct    3540 cgtcattgcc gccggccgcc agggcatcct tgcgtccttt ggcgccggcg gacttcccat    3600
gcaggttgtg cgtgagtcca tcgaaaagat tcaggccgcc ctgcccaatg gcccgtacgc    3660
tgtcaacctt atccattctc cctttgacag caacctcgaa aagggcaatg tcgatctctt    3720
cctcgagaag ggtgtcacct tgtcgaggc ctcggccttt atgacgctca ccccgcaggt    3780
cgtgcggtac cgcgcggctg gcctcacgcg caacgccgac ggctcggtca acatccgcaa    3840
ccgtatcatt ggcaaggtct cgcgcaccga gctcgccgag atgttcatgc gtcctgcgcc    3900
cgagcacctt cttcagaagc tcattgcttc cggcgagatc aaccaggagc aggccgagct    3960
cgcccgccgt gttcccgtcg ctgacgacat cgcggtcgaa gctgactcgg gtggccacac    4020
cgacaaccgc cccatccacg tcattctgcc cctcatcatc aaccttcgcg accgccttca    4080
ccgcgagtgc ggctacccgg ccaaccttcg cgtccgtgtg ggcgccggcg gtggcattgg    4140
gtgcccccag gcggcgctgg ccaccttcaa catgggtgcc tcctttattg tcaccggcac    4200
cgtgaaccag gtcgccaagc agtcgggcac gtgcgacaat gtgcgcaagc agctcgcgaa    4260
ggccacttac tcggacgtat gcatggcccc ggctgccgac atgttcgagg aaggcgtcaa    4320
gcttcaggtc ctcaagaagg gaaccatgtt tccctcgcgc gccaacaagc tctacgagct    4380
cttttgcaag tacgactcgt tcgagtccat gcccccgca gagcttgcgc gcgtcgagaa    4440
gcgcatcttc agccgcgcgc tcgaagaggt ctgggacgag accaaaaact tttacattaa    4500
ccgtcttcac aaccccggaga agatccagcg cgccgagcgc gaccccaagc tcaagatgtc    4560 gctgtgctt cgctggtacc tgagcctggc gagccgctgg gccaacactg gagcttccga    4620
tcgcgtcatg gactaccagg tctggtgcgg tcctgccatt ggttccttca acgatttcat    4680
caagggaact taccttgatc cggccgtcgc aaacgagtac ccgtgcgtcg ttcagattaa    4740
caagcagatc cttcgtggag cgtgcttctt gcgccgtctc gaaattctgc gcaacgcacg    4800
cctttccgat ggcgctgccg ctcttgtggc cagcatcgat gacacatacg tcccggccga    4860
gaagctgtaa gtaagctctc atatatgtta gttgcgtgag accgacacga agataatatc    4920
acatacgctt tgtttgttc tttcaattat ttgtctgtgc ttcatgttgc tcctcagtat    4980
ctagctggcg gctcttatct tctttttaaaa tatctggaca aggacaaaaa caagaataaa    5040
ggcgagaaga tgtgaatttc atttcgactt gagaactcga agagcattga tgcggttagt    5100
```

-continued

```
atatgggtat tttccagaca cttttcatca tcatcatcat catcatcatt atgaagaagt      5160
agtagctgat aaagtagact cactgtttgc agcgagaaaa aaaaaaaaaa aaaaa           5215
```

<210> SEQ ID NO 72
<211> LENGTH: 1622
<212> TYPE: PRT
<213> ORGANISM: Schizochytrium aggregatum

<400> SEQUENCE: 72

| | | | | | | | | | | | | | | |
|---|---|---|---|---|---|---|---|---|---|---|---|---|---|---|
| Ala | Val | Phe | Glu | Glu | His | Asp | Pro | Ser | Asn | Ala | Ala | Cys | Thr | Gly | His |
| 1 | | | | 5 | | | | | 10 | | | | | 15 | |
| Asp | Ser | Ile | Ser | Ala | Leu | Ser | Ala | Arg | Cys | Gly | Gly | Glu | Ser | Asn | Met |
| | | | 20 | | | | | 25 | | | | | 30 | | |
| Arg | Ile | Ala | Ile | Thr | Gly | Met | Asp | Ala | Thr | Phe | Gly | Ala | Leu | Lys | Gly |
| | | | 35 | | | | 40 | | | | | 45 | | | |
| Leu | Asp | Ala | Phe | Glu | Arg | Ala | Ile | Tyr | Thr | Gly | Ala | His | Gly | Ala | Ile |
| | 50 | | | | | 55 | | | | | 60 | | | | |
| Pro | Leu | Pro | Glu | Lys | Arg | Trp | Arg | Phe | Leu | Gly | Lys | Asp | Lys | Asp | Phe |
| 65 | | | | | 70 | | | | | 75 | | | | | 80 |
| Leu | Asp | Leu | Cys | Gly | Val | Lys | Ala | Thr | Pro | His | Gly | Cys | Tyr | Ile | Glu |
| | | | | 85 | | | | | 90 | | | | | 95 | |
| Asp | Val | Glu | Val | Asp | Phe | Gln | Arg | Leu | Arg | Thr | Pro | Met | Thr | Pro | Glu |
| | | | 100 | | | | | 105 | | | | | 110 | | |
| Asp | Met | Leu | Leu | Pro | Gln | Gln | Leu | Leu | Ala | Val | Thr | Thr | Ile | Asp | Arg |
| | | | 115 | | | | | 120 | | | | | 125 | | |
| Ala | Ile | Leu | Asp | Ser | Gly | Met | Lys | Lys | Gly | Gly | Asn | Val | Ala | Val | Phe |
| | 130 | | | | | 135 | | | | | 140 | | | | |
| Val | Gly | Leu | Gly | Thr | Asp | Leu | Glu | Leu | Tyr | Arg | His | Arg | Ala | Arg | Val |
| 145 | | | | | 150 | | | | | 155 | | | | | 160 |
| Ala | Leu | Lys | Glu | Arg | Val | Arg | Pro | Glu | Ala | Ser | Lys | Lys | Leu | Asn | Asp |
| | | | | 165 | | | | | 170 | | | | | 175 | |
| Met | Met | Gln | Tyr | Ile | Asn | Asp | Cys | Gly | Thr | Ser | Thr | Tyr | Thr | Ser |
| | | | 180 | | | | | 185 | | | | | 190 | | |
| Tyr | Ile | Gly | Asn | Leu | Val | Ala | Thr | Arg | Val | Ser | Ser | Gln | Trp | Gly | Phe |
| | | | 195 | | | | | 200 | | | | | 205 | | |
| Thr | Gly | Pro | Ser | Phe | Thr | Ile | Thr | Glu | Gly | Asn | Asn | Ser | Val | Tyr | Arg |
| | | | 210 | | | | | 215 | | | | | 220 | | |
| Cys | Ala | Glu | Leu | Gly | Lys | Tyr | Leu | Leu | Glu | Thr | Gly | Glu | Val | Asp | Gly |
| 225 | | | | | 230 | | | | | 235 | | | | | 240 |
| Val | Val | Val | Ala | Gly | Val | Asp | Leu | Cys | Gly | Ser | Ala | Glu | Asn | Leu | Tyr |
| | | | | 245 | | | | | 250 | | | | | 255 | |
| Val | Lys | Ser | Arg | Arg | Phe | Lys | Val | Ser | Thr | Ser | Asp | Thr | Pro | Arg | Ala |
| | | | | 260 | | | | | 265 | | | | | 270 | |
| Ser | Phe | Asp | Ala | Ala | Ala | Asp | Gly | Tyr | Phe | Val | Gly | Glu | Gly | Cys | Gly |
| | | | 275 | | | | | 280 | | | | | 285 | | |
| Ala | Phe | Val | Leu | Lys | Arg | Glu | Thr | Ser | Cys | Thr | Lys | Asp | Asp | Arg | Ile |
| | | | 290 | | | | | 295 | | | | | 300 | | |
| Tyr | Ala | Cys | Met | Asp | Ala | Ile | Val | Pro | Gly | Asn | Val | Pro | Ser | Ala | Cys |
| 305 | | | | | 310 | | | | | 315 | | | | | 320 |
| Leu | Arg | Glu | Ala | Leu | Asp | Gln | Ala | Arg | Val | Lys | Pro | Gly | Asp | Ile | Glu |
| | | | | 325 | | | | | 330 | | | | | 335 | |
| Met | Leu | Glu | Leu | Ser | Ala | Asp | Ser | Ala | Arg | His | Leu | Lys | Asp | Pro | Ser |
| | | | 340 | | | | | 345 | | | | | 350 | | |
| Val | Leu | Pro | Lys | Glu | Leu | Thr | Ala | Glu | Glu | Ile | Gly | Gly | Leu | Gln |

-continued

```
            355                 360                 365
Thr Ile Leu Arg Asp Asp Lys Leu Pro Arg Asn Val Ala Thr Gly
            370                 375                 380

Ser Val Lys Ala Thr Val Gly Asp Thr Gly Tyr Ala Ser Gly Ala Ala
385                 390                 395                 400

Ser Leu Ile Lys Ala Ala Leu Cys Ile Tyr Asn Arg Tyr Leu Pro Ser
                    405                 410                 415

Asn Gly Asp Asp Trp Asp Glu Pro Ala Pro Glu Ala Pro Trp Asp Ser
            420                 425                 430

Thr Leu Phe Ala Cys Gln Thr Ser Arg Ala Trp Leu Lys Asn Pro Gly
            435                 440                 445

Glu Arg Arg Tyr Ala Ala Val Ser Gly Val Ser Glu Thr Arg Ser Cys
        450                 455                 460

Tyr Ser Val Leu Leu Ser Glu Ala Gly His Tyr Glu Arg Glu Asn
465                 470                 475                 480

Arg Ile Ser Leu Asp Glu Glu Ala Pro Lys Leu Ile Val Leu Arg Ala
                485                 490                 495

Asp Ser His Glu Glu Ile Leu Gly Arg Leu Asp Lys Ile Arg Glu Arg
            500                 505                 510

Phe Leu Gln Pro Thr Gly Ala Ala Pro Arg Glu Ser Glu Leu Lys Ala
            515                 520                 525

Gln Ala Arg Arg Ile Phe Leu Glu Leu Leu Gly Glu Thr Leu Ala Gln
        530                 535                 540

Asp Ala Ala Ser Ser Gly Ser Gln Lys Pro Leu Ala Leu Ser Leu Val
545                 550                 555                 560

Ser Thr Pro Ser Lys Leu Gln Arg Glu Val Glu Leu Ala Ala Lys Gly
                565                 570                 575

Ile Pro Arg Cys Leu Lys Met Arg Arg Asp Trp Ser Ser Pro Ala Gly
            580                 585                 590

Ser Arg Tyr Ala Pro Glu Pro Leu Ala Ser Asp Arg Val Ala Phe Met
        595                 600                 605

Tyr Gly Glu Gly Arg Ser Pro Tyr Tyr Gly Ile Thr Gln Asp Ile His
        610                 615                 620

Arg Ile Trp Pro Glu Leu His Glu Val Ile Asn Glu Lys Thr Asn Arg
625                 630                 635                 640

Leu Trp Ala Glu Gly Asp Arg Trp Val Met Pro Arg Ala Ser Phe Lys
                645                 650                 655

Ser Glu Leu Glu Ser Gln Gln Gln Glu Phe Asp Arg Asn Met Ile Glu
            660                 665                 670

Met Phe Arg Leu Gly Ile Leu Thr Ser Ile Ala Phe Thr Asn Leu Ala
            675                 680                 685

Arg Asp Val Leu Asn Ile Thr Pro Lys Ala Ala Phe Gly Leu Ser Leu
        690                 695                 700

Gly Glu Ile Ser Met Ile Phe Ala Phe Ser Lys Lys Asn Gly Leu Ile
705                 710                 715                 720

Ser Asp Gln Leu Thr Lys Asp Leu Arg Glu Ser Asp Val Trp Asn Lys
                725                 730                 735

Ala Leu Ala Val Glu Phe Asn Ala Leu Arg Glu Ala Trp Gly Ile Pro
            740                 745                 750

Gln Ser Val Pro Lys Asp Glu Phe Trp Gln Gly Tyr Ile Val Arg Gly
            755                 760                 765

Thr Lys Gln Asp Ile Glu Ala Ala Ile Ala Pro Asp Ser Lys Tyr Val
        770                 775                 780
```

-continued

```
Arg Leu Thr Ile Ile Asn Asp Ala Asn Thr Ala Leu Ile Ser Gly Lys
785                 790                 795                 800

Pro Asp Ala Cys Lys Ala Ala Ile Ala Arg Leu Gly Gly Asn Ile Pro
            805                 810                 815

Ala Leu Pro Val Thr Gln Gly Met Cys Gly His Cys Pro Glu Val Gly
            820                 825                 830

Pro Tyr Thr Lys Asp Ile Ala Lys Ile His Ala Asn Leu Glu Phe Pro
            835                 840                 845

Val Val Asp Gly Leu Asp Leu Trp Thr Thr Ile Asn Gln Lys Arg Leu
850                 855                 860

Val Pro Arg Ala Thr Gly Ala Lys Asp Glu Trp Ala Pro Ser Ser Phe
865                 870                 875                 880

Gly Glu Tyr Ala Gly Gln Leu Tyr Glu Lys Gln Ala Asn Phe Pro Gln
            885                 890                 895

Ile Val Glu Thr Ile Tyr Lys Gln Asn Tyr Asp Val Phe Val Glu Val
            900                 905                 910

Gly Pro Asn Asn His Arg Ser Thr Ala Val Arg Thr Thr Leu Gly Pro
            915                 920                 925

Gln Arg Asn His Leu Ala Gly Ala Ile Asp Lys Gln Asn Glu Asp Ala
            930                 935                 940

Trp Thr Thr Ile Val Lys Leu Val Ala Ser Leu Lys Ala His Leu Val
945                 950                 955                 960

Pro Gly Val Thr Ile Ser Pro Leu Tyr His Ser Lys Leu Val Ala Glu
            965                 970                 975

Ala Gln Ala Cys Tyr Ala Ala Leu Cys Lys Gly Glu Lys Pro Lys Lys
            980                 985                 990

Asn Lys Phe Val Arg Lys Ile Gln Leu Asn Gly Arg Phe Asn Ser Lys
            995                 1000                1005

Ala Asp Pro Ile Ser Ser Ala Asp Leu Ala Ser Phe Pro Pro Ala Asp
    1010                1015                1020

Pro Ala Ile Glu Ala Ala Ile Ser Ser Arg Ile Met Lys Pro Val Ala
1025                1030                1035                1040

Pro Lys Phe Tyr Ala Arg Leu Asn Ile Asp Glu Gln Asp Glu Thr Arg
            1045                1050                1055

Asp Pro Ile Leu Asn Lys Asp Asn Ala Pro Ser Ser Ser Ser Ser Ser
            1060                1065                1070

Ser Ser Ser Ser Ser Ser Ser Ser Pro Ser Pro Ala Pro Ser Ala
            1075                1080                1085

Pro Val Gln Lys Lys Ala Ala Pro Ala Ala Glu Thr Lys Ala Val Ala
    1090                1095                1100

Ser Ala Asp Ala Leu Arg Ser Ala Leu Leu Asp Leu Asp Ser Met Leu
1105                1110                1115                1120

Ala Leu Ser Ser Ala Ser Ala Ser Gly Asn Leu Val Glu Thr Ala Pro
            1125                1130                1135

Ser Asp Ala Ser Val Ile Val Pro Pro Cys Asn Ile Ala Asp Leu Gly
        1140                1145                1150

Ser Arg Ala Phe Met Lys Thr Tyr Gly Val Ser Ala Pro Leu Tyr Thr
    1155                1160                1165

Gly Ala Met Ala Lys Gly Ile Ala Ser Ala Asp Leu Val Ile Ala Ala
    1170                1175                1180

Gly Arg Gln Gly Ile Leu Ala Ser Phe Gly Ala Gly Gly Leu Pro Met
1185                1190                1195                1200
```

```
Gln Val Val Arg Glu Ser Ile Glu Lys Ile Gln Ala Ala Leu Pro Asn
                1205                1210                1215

Gly Pro Tyr Ala Val Asn Leu Ile His Ser Pro Phe Asp Ser Asn Leu
            1220                1225                1230

Glu Lys Gly Asn Val Asp Leu Phe Leu Glu Lys Gly Val Thr Phe Val
        1235                1240                1245

Glu Ala Ser Ala Phe Met Thr Leu Thr Pro Gln Val Val Arg Tyr Arg
    1250                1255                1260

Ala Ala Gly Leu Thr Arg Asn Ala Asp Gly Ser Val Asn Ile Arg Asn
1265                1270                1275                1280

Arg Ile Ile Gly Lys Val Ser Arg Thr Glu Leu Ala Glu Met Phe Met
                1285                1290                1295

Arg Pro Ala Pro Glu His Leu Leu Gln Lys Leu Ile Ala Ser Gly Glu
            1300                1305                1310

Ile Asn Gln Glu Gln Ala Glu Leu Ala Arg Arg Val Pro Val Ala Asp
        1315                1320                1325

Asp Ile Ala Val Glu Ala Asp Ser Gly Gly His Thr Asp Asn Arg Pro
    1330                1335                1340

Ile His Val Ile Leu Pro Leu Ile Ile Asn Leu Arg Asp Arg Leu His
1345                1350                1355                1360

Arg Glu Cys Gly Tyr Pro Ala Asn Leu Arg Val Arg Val Gly Ala Gly
                1365                1370                1375

Gly Gly Ile Gly Cys Pro Gln Ala Ala Leu Ala Thr Phe Asn Met Gly
            1380                1385                1390

Ala Ser Phe Ile Val Thr Gly Thr Val Asn Gln Val Ala Lys Gln Ser
        1395                1400                1405

Gly Thr Cys Asp Asn Val Arg Lys Gln Leu Ala Lys Ala Thr Tyr Ser
    1410                1415                1420

Asp Val Cys Met Ala Pro Ala Ala Asp Met Phe Glu Glu Gly Val Lys
1425                1430                1435                1440

Leu Gln Val Leu Lys Lys Gly Thr Met Phe Pro Ser Arg Ala Asn Lys
                1445                1450                1455

Leu Tyr Glu Leu Phe Cys Lys Tyr Asp Ser Phe Glu Ser Met Pro Pro
            1460                1465                1470

Ala Glu Leu Ala Arg Val Glu Lys Arg Ile Phe Ser Arg Ala Leu Glu
        1475                1480                1485

Glu Val Trp Asp Glu Thr Lys Asn Phe Tyr Ile Asn Arg Leu His Asn
    1490                1495                1500

Pro Glu Lys Ile Gln Arg Ala Glu Arg Asp Pro Lys Leu Lys Met Ser
1505                1510                1515                1520

Leu Cys Phe Arg Trp Tyr Leu Ser Leu Ala Ser Arg Trp Ala Asn Thr
                1525                1530                1535

Gly Ala Ser Asp Arg Val Met Asp Tyr Gln Val Trp Cys Gly Pro Ala
            1540                1545                1550

Ile Gly Ser Phe Asn Asp Phe Ile Lys Gly Thr Tyr Leu Asp Pro Ala
        1555                1560                1565

Val Ala Asn Glu Tyr Pro Cys Val Val Gln Ile Asn Lys Gln Ile Leu
    1570                1575                1580

Arg Gly Ala Cys Phe Leu Arg Arg Leu Glu Ile Leu Arg Asn Ala Arg
1585                1590                1595                1600

Leu Ser Asp Gly Ala Ala Ala Leu Val Ala Ser Ile Asp Asp Thr Tyr
                1605                1610                1615

Val Pro Ala Glu Lys Leu
```

-continued

1620

```
<210> SEQ ID NO 73
<211> LENGTH: 1551
<212> TYPE: PRT
<213> ORGANISM: Schizochytrium aggregatum

<400> SEQUENCE: 73
```

| Arg | Ala | Glu | Ala | Gly | Arg | Glu | Pro | Glu | Pro | Ala | Pro | Gln | Ile | Thr | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Thr Ala Ala Glu Ser Gln Gln Gln Gln Gln Gln Gln Gln Gln Gln Gln
                20                  25                  30

Gln Gln Gln Gln Pro Arg Glu Gly Asp Lys Glu Lys Ala Ala Glu Thr
            35                  40                  45

Met Ala Leu Arg Val Lys Thr Asn Lys Lys Pro Cys Trp Glu Met Thr
 50                  55                  60

Lys Glu Glu Leu Thr Ser Gly Lys Thr Glu Val Phe Asn Tyr Glu Glu
 65                  70                  75                  80

Leu Leu Glu Phe Ala Glu Gly Asp Ile Ala Lys Val Phe Gly Pro Glu
                 85                  90                  95

Phe Ala Val Ile Asp Lys Tyr Pro Arg Arg Val Arg Leu Pro Ala Arg
            100                 105                 110

Glu Tyr Leu Leu Val Thr Arg Val Thr Leu Met Asp Ala Glu Val Asn
        115                 120                 125

Asn Tyr Arg Val Gly Ala Arg Met Val Thr Glu Tyr Asp Leu Pro Val
130                 135                 140

Asn Gly Glu Leu Ser Glu Gly Gly Asp Cys Pro Trp Ala Val Leu Val
145                 150                 155                 160

Glu Ser Gly Gln Cys Asp Leu Met Leu Ile Ser Tyr Met Gly Ile Asp
                165                 170                 175

Phe Gln Asn Gln Gly Asp Arg Val Tyr Arg Leu Leu Asn Thr Thr Leu
            180                 185                 190

Thr Phe Tyr Gly Val Ala His Glu Gly Glu Thr Leu Glu Tyr Asp Ile
        195                 200                 205

Arg Val Thr Gly Phe Ala Lys Arg Leu Asp Gly Gly Ile Ser Met Phe
    210                 215                 220

Phe Phe Glu Tyr Asp Cys Tyr Val Asn Gly Arg Leu Leu Ile Glu Met
225                 230                 235                 240

Arg Asp Gly Cys Ala Gly Phe Phe Thr Asn Glu Glu Leu Asp Ala Gly
                245                 250                 255

Lys Gly Val Val Phe Thr Arg Gly Asp Leu Ala Ala Arg Ala Lys Ile
            260                 265                 270

Pro Lys Gln Asp Val Ser Pro Tyr Ala Val Ala Pro Cys Leu His Lys
        275                 280                 285

Thr Lys Leu Asn Glu Lys Glu Met Gln Thr Leu Val Asp Lys Asp Trp
    290                 295                 300

Ala Ser Val Phe Gly Ser Lys Asn Gly Met Pro Glu Ile Asn Tyr Lys
305                 310                 315                 320

Leu Cys Ala Arg Lys Met Leu Met Ile Asp Arg Val Thr Ser Ile Asp
                325                 330                 335

His Lys Gly Gly Val Tyr Gly Leu Gly Gln Leu Val Gly Glu Lys Ile
            340                 345                 350

Leu Glu Arg Asp His Trp Tyr Phe Pro Cys His Phe Val Lys Asp Gln
        355                 360                 365

-continued

```
Val Met Ala Gly Ser Leu Val Ser Asp Gly Cys Ser Gln Met Leu Lys
    370                 375                 380
Met Tyr Met Ile Trp Leu Gly Leu His Leu Thr Thr Gly Pro Phe Asp
385                 390                 395                 400
Phe Arg Pro Val Asn Gly His Pro Asn Lys Val Arg Cys Arg Gly Gln
                405                 410                 415
Ile Ser Pro His Lys Gly Lys Leu Val Tyr Val Met Glu Ile Lys Glu
            420                 425                 430
Met Gly Phe Asp Glu Asp Asn Asp Pro Tyr Ala Ile Ala Asp Val Asn
        435                 440                 445
Ile Ile Asp Val Asp Phe Glu Lys Gly Gln Asp Phe Ser Leu Asp Arg
450                 455                 460
Ile Ser Asp Tyr Gly Lys Gly Asp Leu Asn Lys Lys Ile Val Val Asp
465                 470                 475                 480
Phe Lys Gly Ile Ala Leu Lys Met Gln Lys Arg Ser Thr Asn Lys Asn
                485                 490                 495
Pro Ser Lys Val Gln Pro Val Phe Ala Asn Gly Ala Ala Thr Val Gly
            500                 505                 510
Pro Glu Ala Ser Lys Ala Ser Ser Gly Ala Ser Ala Ser Ala Ser Ala
        515                 520                 525
Ala Pro Ala Lys Pro Ala Phe Ser Ala Asp Val Leu Ala Pro Lys Pro
    530                 535                 540
Val Ala Leu Pro Glu His Ile Leu Lys Gly Asp Ala Leu Ala Pro Lys
545                 550                 555                 560
Glu Met Ser Trp His Pro Met Ala Arg Ile Pro Gly Asn Pro Thr Pro
                565                 570                 575
Ser Phe Ala Pro Ser Ala Tyr Lys Pro Arg Asn Ile Ala Phe Thr Pro
            580                 585                 590
Phe Pro Gly Asn Pro Asn Asp Asn Asp His Thr Pro Gly Lys Met Pro
        595                 600                 605
Leu Thr Trp Phe Asn Met Ala Glu Phe Met Ala Gly Lys Val Ser Met
    610                 615                 620
Cys Leu Gly Pro Glu Phe Ala Lys Phe Asp Asp Ser Asn Thr Ser Arg
625                 630                 635                 640
Ser Pro Ala Trp Asp Leu Ala Leu Val Thr Arg Ala Val Ser Val Ser
                645                 650                 655
Asp Leu Lys His Val Asn Tyr Arg Asn Ile Asp Leu Asp Pro Ser Lys
            660                 665                 670
Gly Thr Met Val Gly Glu Phe Asp Cys Pro Ala Asp Ala Trp Phe Tyr
        675                 680                 685
Lys Gly Ala Cys Asn Asp Ala His Met Pro Tyr Ser Ile Leu Met Glu
    690                 695                 700
Ile Ala Leu Gln Thr Ser Gly Val Leu Thr Ser Val Leu Lys Ala Pro
705                 710                 715                 720
Leu Thr Met Glu Lys Asp Asp Ile Leu Phe Arg Asn Leu Asp Ala Asn
                725                 730                 735
Ala Glu Phe Val Arg Ala Asp Leu Asp Tyr Arg Gly Lys Thr Ile Arg
            740                 745                 750
Asn Val Thr Lys Cys Thr Gly Tyr Ser Met Leu Gly Glu Met Gly Val
        755                 760                 765
His Arg Phe Thr Phe Glu Leu Tyr Val Asp Asp Val Leu Phe Tyr Lys
    770                 775                 780
Gly Ser Thr Ser Phe Gly Trp Phe Val Pro Glu Val Phe Ala Ala Gln
```

-continued

```
            785                 790                 795                 800
Ala Gly Leu Asp Asn Gly Arg Lys Ser Glu Pro Trp Phe Ile Glu Asn
                805                 810                 815

Lys Val Pro Ala Ser Gln Val Ser Ser Phe Asp Val Arg Pro Asn Gly
                820                 825                 830

Ser Gly Arg Thr Ala Ile Phe Ala Asn Ala Pro Ser Gly Ala Gln Leu
                835                 840                 845

Asn Arg Arg Thr Asp Gln Gly Gln Tyr Leu Asp Ala Val Asp Ile Val
            850                 855                 860

Ser Gly Ser Gly Lys Lys Ser Leu Gly Tyr Ala His Gly Ser Lys Thr
865                 870                 875                 880

Val Asn Pro Asn Asp Trp Phe Ser Cys His Phe Trp Phe Asp Ser
                885                 890                 895

Val Met Pro Gly Ser Leu Gly Val Glu Ser Met Phe Gln Leu Val Glu
                900                 905                 910

Ala Ile Ala Ala His Glu Asp Leu Ala Gly Lys Ala Arg His Cys Gln
            915                 920                 925

Pro His Leu Cys Ala Arg Pro Arg Ala Arg Ser Ser Trp Lys Tyr Arg
            930                 935                 940

Gly Gln Leu Thr Pro Lys Ser Lys Lys Met Asp Ser Glu Val His Ile
945                 950                 955                 960

Val Ser Val Asp Ala His Asp Gly Val Asp Leu Val Ala Asp Gly
                965                 970                 975

Phe Leu Trp Ala Asp Ser Leu Arg Val Tyr Ser Val Ser Asn Ile Arg
                980                 985                 990

Val Arg Ile Ala Ser Gly Glu Ala Pro Ala Ala Ser Ser Ala Ala
            995                 1000                1005

Ser Val Gly Ser Ser Ala Ser Ser Val Glu Arg Thr Arg Ser Ser Pro
    1010                1015                1020

Ala Val Ala Ser Gly Pro Ala Gln Thr Ile Asp Leu Lys Gln Leu Lys
1025                1030                1035                1040

Thr Glu Leu Leu Glu Leu Asp Ala Pro Leu Tyr Leu Ser Gln Asp Pro
                1045                1050                1055

Thr Ser Gly Gln Leu Lys Lys His Thr Asp Val Ala Ser Gly Gln Ala
            1060                1065                1070

Thr Ile Val Gln Pro Cys Thr Leu Gly Asp Leu Gly Asp Arg Ser Phe
        1075                1080                1085

Met Glu Thr Tyr Gly Val Val Ala Pro Leu Tyr Thr Gly Ala Met Ala
    1090                1095                1100

Lys Gly Ile Ala Ser Ala Asp Leu Val Ile Ala Ala Gly Lys Arg Lys
1105                1110                1115                1120

Ile Leu Gly Ser Phe Gly Ala Gly Gly Leu Pro Met His Val Arg
            1125                1130                1135

Ala Ala Leu Glu Lys Ile Gln Ala Ala Leu Pro Gln Gly Pro Tyr Ala
                1140                1145                1150

Val Asn Leu Ile His Ser Pro Phe Asp Ser Asn Leu Glu Lys Gly Asn
            1155                1160                1165

Val Asp Leu Phe Leu Glu Lys Gly Val Thr Val Glu Ala Ser Ala
        1170                1175                1180

Phe Met Thr Leu Thr Pro Gln Val Val Arg Tyr Arg Ala Ala Gly Leu
1185                1190                1195                1200

Ser Arg Asn Ala Asp Gly Ser Val Asn Ile Arg Asn Arg Ile Ile Gly
            1205                1210                1215
```

-continued

```
Lys Val Ser Arg Thr Glu Leu Ala Glu Met Phe Ile Arg Pro Ala Pro
            1220                1225                1230

Glu His Leu Leu Glu Lys Leu Ile Ala Ser Gly Glu Ile Thr Gln Glu
        1235                1240                1245

Gln Ala Glu Leu Ala Arg Arg Val Pro Val Ala Asp Asp Ile Ala Val
    1250                1255                1260

Glu Ala Asp Ser Gly Gly His Thr Asp Asn Arg Pro Ile His Val Ile
1265                1270                1275                1280

Leu Pro Leu Ile Ile Asn Leu Arg Asn Arg Leu His Arg Glu Cys Gly
            1285                1290                1295

Tyr Pro Ala His Leu Arg Val Arg Val Gly Ala Gly Gly Val Gly
            1300                1305                1310

Cys Pro Gln Ala Ala Ala Ala Ala Leu Thr Met Gly Ala Ala Phe Ile
            1315                1320                1325

Val Thr Gly Thr Val Asn Gln Val Ala Lys Gln Ser Gly Thr Cys Asp
    1330                1335                1340

Asn Val Arg Lys Gln Leu Ser Gln Ala Thr Tyr Ser Asp Ile Cys Met
1345                1350                1355                1360

Ala Pro Ala Ala Asp Met Phe Glu Glu Gly Val Lys Leu Gln Val Leu
            1365                1370                1375

Lys Lys Gly Thr Met Phe Pro Ser Arg Ala Asn Lys Leu Tyr Glu Leu
            1380                1385                1390

Phe Cys Lys Tyr Asp Ser Phe Asp Ser Met Pro Pro Ala Glu Leu Glu
            1395                1400                1405

Arg Ile Glu Lys Arg Ile Phe Lys Arg Ala Leu Gln Glu Val Trp Glu
    1410                1415                1420

Glu Thr Lys Asp Phe Tyr Ile Asn Gly Leu Lys Asn Pro Glu Lys Ile
1425                1430                1435                1440

Gln Arg Ala Glu His Asp Pro Lys Leu Lys Met Ser Leu Cys Phe Arg
            1445                1450                1455

Trp Tyr Leu Gly Leu Ala Ser Arg Trp Ala Asn Met Gly Ala Pro Asp
            1460                1465                1470

Arg Val Met Asp Tyr Gln Val Trp Cys Gly Pro Ala Ile Gly Ala Phe
            1475                1480                1485

Asn Asp Phe Ile Lys Gly Thr Tyr Leu Asp Pro Ala Val Ser Asn Glu
    1490                1495                1500

Tyr Pro Cys Val Val Gln Ile Asn Leu Gln Ile Leu Arg Gly Ala Cys
1505                1510                1515                1520

Tyr Leu Arg Arg Leu Asn Ala Leu Arg Asn Asp Pro Arg Ile Asp Leu
            1525                1530                1535

Glu Thr Glu Asp Ala Ala Phe Val Tyr Glu Pro Thr Asn Ala Leu
            1540                1545                1550

<210> SEQ ID NO 74
<211> LENGTH: 30
<212> TYPE: DNA
<213> ORGANISM: Schizochytrium aggregatum

<400> SEQUENCE: 74
taccgcggca agactatccg caacgtcacc                                    30

<210> SEQ ID NO 75
<211> LENGTH: 30
<212> TYPE: DNA
<213> ORGANISM: Schizochytrium aggregatum
```

<400> SEQUENCE: 75

```
gccgtcgtgg gcgtccacgg acacgatgtg                                      30
```

<210> SEQ ID NO 76
<211> LENGTH: 4767
<212> TYPE: DNA
<213> ORGANISM: Schizochytrium aggregatum

<400> SEQUENCE: 76

```
cgagcagagg ccggccgcga gcccgagccc gcgccgcaga tcactagtac cgctgcggaa      60
tcacagcagc agcagcagca gcagcagcag cagcagcagc agcagcagcc acgagaggga     120
gataaagaaa aagcggcaga gacgatggcg ctccgtgtca agacgaacaa gaagccatgc     180
tgggagatga ccaaggagga gctgaccagc ggcaagaccg aggtgttcaa ctatgaggaa     240
ctcctcgagt tcgcagaggg cgacatcgcc aaggtcttcg acccgagtt cgccgtcatc      300
gacaagtacc cgcgccgcgt gcgcctgccc gcccgcgagt acctgctcgt gacccgcgtc     360
accctcatgg acgccgaggt caacaactac cgcgtcggcg cccgcatggt caccgagtac     420
gatctccccg tcaacggaga gctctccgag gcggagact gccctgggc cgtcctggtc       480
gagagtggcc agtgcgatct catgctcatc tcctacatgg gcattgactt ccagaaccag     540
ggcgaccgcg tctaccgcct gctcaacacc acgctcacct tttacggcgt ggcccacgag     600
ggcgagaccc tcgagtacga cattcgcgtc accggcttcg ccaagcgtct cgacggcggc     660
atctccatgt tcttcttcga gtacgactgc tacgtcaacg gccgcctcct catcgagatg     720
cgcgatggct gcgccggctt cttcaccaac gaggagctcg acgccggcaa gggcgtcgtc     780
ttcacccgcg gcgacctcgc cgcccgcgcc aagatcccaa agcaggacgt ctcccctac      840
gccgtcgccc cctgcctcca caagaccaag ctcaacgaaa aggagatgca gaccctcgtc     900
gacaaggact gggcatccgt ctttggctcc aagaacggca tgccggaaat caactacaaa     960
ctctgcgcgc gtaagatgct catgattgac gcgtcacca gcattgacca caagggcggt     1020
gtctacggcc tcggtcagct cgtcggtgaa agatcctcg agcgcgacca ctggtacttt     1080
ccctgccact tgtcaagga tcaggtcatg gccggatccc tcgtctccga cggctgcagc     1140
cagatgctca agatgtacat gatctggctc ggcctccacc tcaccaccgg acccttgac      1200
ttccgcccgg tcaacggcca ccccaacaag gtccgctgcc gcggccaaat ctccccgcac    1260
aagggcaagc tcgtctacgt catggagatc aaggagatgg gcttcgacga ggacaacgac   1320
ccgtacgcca ttgccgacgt caacatcatt gatgtcgact cgaaaaggg ccaggacttt     1380
agcctcgacc gcatcagcga ctacggcaag ggcgacctca acaagaagat cgtcgtcgac     1440
tttaagggca tcgctctcaa gatgcagaag cgctccacca caagaaccc ctccaaggtt     1500
cagcccgtct ttgccaacgg cgccgccact gtcggccccg aggcctccaa ggcttcctcc   1560
ggcgccagcg ccagcgccag cgccgccccg gccaagcctg ccttcagcgc cgatgttctt    1620
gcgcccaagc ccgttgccct tcccgagcac atcctcaagg gcgacgccct cgcccccaag     1680
gagatgtcct ggcacccat ggcccgcatc ccgggcaacc cgacgccctc ttttgcgccc     1740
tcggcctaca gccgcgcaa catcgccttt acgcccttcc ccggcaaccc caacgataac     1800
gaccacaccc cgggcaagat gccgctcacc tggttcaaca tggccgagtt catggccggc     1860
aaggtcagca tgtgcctcgg ccccgagttc gccaagttcg acgactgaa caccagccgc    1920
agccccgctt gggacctcgc tctcgtcacc cgcgccgtgt ctgtgtctga cctcaagcac     1980
```

-continued

```
gtcaactacc gcaacatcga cctcgacccc tccaagggta ccatggtcgg cgagttcgac    2040
tgccccgcgg acgcctggtt ctacaagggc gcctgcaacg atgcccacat gccgtactcg    2100
atcctcatgg agatcgccct ccagacctcg ggtgtgctca cctcggtgct caaggcgccc    2160
ctgaccatgg agaaggacga catcctcttc cgcaacctcg acgccaacgc cgagttcgtg    2220
cgcgccgacc tcgactaccg cggcaagact atccgcaacg tcaccaagtg cactggctac    2280
agcatgctcg gcgagatggg cgtccaccgc ttcacctttg agctctacgt cgatgatgtg    2340
ctcttttaca agggctcgac ctcgttcggc tggttcgtgc ccgaggtytt tgccgcccag    2400
gccggcctcg acaacggccg caagtcggag ccctggttca ttgagaacaa ggttccggcc    2460
tcgcaggtct cctcctttga cgtgcgcccc aacggcagcg gccgcaccgc catcttcgcc    2520
aacgccccca gcggcgccca gctcaaccgc cgcacggacc agggccagta cctcgacgcc    2580
gtcgacattg tctccggcag cggcaagaag agcctcggct acgccacgg ttccaagacg    2640 gtcaacccga cgactggtt cttctcgtgc cacttttggt ttgactcggt catgcccgga    2700
agtctcggtg tcgagtccat gttccagctc gtcgaggcca tcgccgccca cgaggatctc    2760
gctggcaaag cacggcattg ccaaccccac ctttgtgcac gcccccgggc aagatcaagc    2820
tggaagtacc gcggscagct cacgcccaag agcaagaaga tggactcgga ggtccacatc    2880
gtgtccgtgg acgcccacga cggcgttgtc gacctcgtcg ccgacggctt cctctgggcc    2940
gacagcctcc gcgtctactc ggtgagcaac attcgcgtgc gcatcgcctc cggtgaggcc    3000 cctgcgccc cctcctccgc cgcctctgtg ggctcctcgg cttcgtccgt cgagcgcacg    3060
cgctcgagcc ccgctgtcgc ctccggcccg gcccagacca tcgacctcaa gcagctcaag    3120
accgagctcc tcgagctcga tgcccgctc tacctctcgc aggacccgac cagcggccag    3180
ctcaagaagc acaccgacgt ggcctccggc caggccacca tcgtgcagcc ctgcacgctc    3240
ggcgacctcg gtgaccgctc cttcatggag acctacggcg tcgtcgcccc gctgtacacg    3300
ggcgccatgg ccaagggcat tgcctcggcg gacctcgtca tcgccgccgg caagcgcaag    3360
atcctcggct cctttggcgc cggcggcctc cccatgcacc acgtgcgcgc cgccctcgag    3420
aagatccagg ccgccctgcc tcagggcccc tacgccgtca acctcatcca ctcgcctttt    3480
gacagcaacc tcgagaaggg caacgtcgat ctcttcctcg agaagggcgt cactgtggtg    3540
gaggcctcgg cattcatgac cctcaccccg caggtcgtgc gctaccgcgc cgccggcctc    3600
tcgcgcaacg ccgacggttc ggtcaacatc cgcaaccgca tcatcggcaa ggtctcgcgc    3660
accgagctcg ccgagatgtt catccgcccg gccccggagc acctcctcga aagctcatc     3720 gcctcgggcg agatcaccca ggagcaggcc gagctcgcgc gccgcgttcc cgtcgccgac    3780
gatatcgctg tcgaggctga ctcgggcggc cacaccgaca accgccccat ccacgtcatc    3840
ctcccgctca tcatcaacct ccgcaaccgc ctgcaccgcg agtgcggcta ccccgcgcac    3900
ctccgcgtcc gcgttggcgc cggcggtggc gtcggctgcc cgcaggccgc cgccgccgcg    3960
ctcaccatgg gcgccgcctt catcgtcacc ggcactgtca accaggtcgc caagcagtcc    4020
ggcacctgcg acaacgtgcg caagcagctc tcgcaggcca cctactcgga tatctgcatg    4080
gccccggccg ccgacatgtt cgaggagggc gtcaagctcc aggtcctcaa gaagggaacc    4140
atgttcccct cgcgcgccaa caagctctac gagctctttt gcaagtacga ctccttcgac    4200
tccatgcctc ctgccgagct cgagcgcatc gagaagcgta tcttcaagcg cgcactccag    4260
gaggtctggg aggagaccaa ggacttttac attaacggtc tcaagaaccc ggagaagatc    4320
cagcgcgccg agcacgaccc caagctcaag atgtcgctct gcttccgctg gtaccttggt    4380
```

-continued

```
cttgccagcc gctgggccaa catgggcgcc ccggaccgcg tcatggacta ccaggtctgg    4440
tgtggcccgg ccattggcgc cttcaacgac ttcatcaagg gcacctacct cgacccccgct   4500 gtctccaacg agtacccctg tgtcgtccag atcaacctgc aaatcctccg tggtgcctgc    4560
tacctgcgcc gtctcaacgc cctgcgcaac gacccgcgca ttgacctcga gaccgaggat    4620
gctgcctttg tctacgagcc caccaacgcg ctctaagaaa gtgaaccttg tcctaacccg    4680
acagcgaatg gcgggagggg gcgggctaaa agatcgtatt acatagtatt tttcccctac    4740
tctttgtgaa aaaaaaaaa aaaaaaa                                         4767
```

<210> SEQ ID NO 77
<211> LENGTH: 7959
<212> TYPE: DNA
<213> ORGANISM: Vibrio marinus

<400> SEQUENCE: 77

```
atggctaaaa agaacaccac atcgattaag cacgccaagg atgtgttaag tagtgatgat     60
caacagttaa attctcgctt gcaagaatgt ccgattgcca tcattggtat ggcatcggtt    120
tttgcagatg ctaaaaactt ggatcaattc tgggataaca tcgttgactc tgtggacgct    180
attattgatg tgcctagcga tcgctggaac attgacgacc attactcggc tgataaaaaa    240
gcagctgaca agacatactg caaacgcggt ggtttcattc cagagcttga ttttgatccg    300
atggagtttg gtttaccgcc aaatatcctc gagttaactg acatcgctca attgttgtca    360
ttaattgttg ctcgtgatgt attaagtgat gctggcattg gtagtgatta tgaccatgat    420
aaaattggta tcacgctggg tgtcggtggt ggtcagaaac aaatttcgcc attaacgtcg    480
cgcctacaag gcccggtatt agaaaaagta ttaaaagcct caggcattga tgaagatgat    540
cgcgctatga tcatcgacaa atttaaaaaa gcctacatcg gctgggaaga gaactcattc    600
ccaggcatgc taggtaacgt tattgctggt cgtatcgcca atcgttttga ttttggtggt    660
actaactgtg tggttgatgc ggcatgcgct ggctcccttg cagctgttaa aatggcgatc    720
tcagacttac ttgaatatcg ttcagaagtc atgatatcgg gtggtgtatg ttgtgataac    780
tcgccattca tgtatatgtc attctcgaaa acaccagcat ttaccaccaa tgatgatatc    840
cgtccgtttg atgacgattc aaaaggcatg ctggttggtg aaggtattgg catgatggcg    900
tttaaacgtc ttgaagatgc tgaacgtgac ggcgacaaaa ttattctcgt actgaaaggt    960
atcggtacat cttcagatgg tcgtttcaaa tctatttacg ctccacgccc agatggccaa   1020
gcaaaagcgc taaacgtgc ttatgaagat gccggttttg ccctgaaaac atgtggtcta   1080
attgaaggcc atggtacggg taccaaagcg ggtgatgcca cagaatttgc tggcttgacc   1140
aaacactttg gcgccgccag tgatgaaaag caatatatcg ccttaggctc agttaaatcg   1200
caaattggtc atactaaatc tgcggctggc tctgcgggta tgattaaggc ggcattagcg   1260
ctgcatcata aaatcttacc tgcaacgatc catatcgata aaccaagtga agccttggat   1320
atcaaaaaca gcccgttata cctaaacagc gaaacgcgtc cttggatgcc acgtgaagat   1380
ggtattccac gtcgtgcagg tatcagctca tttggttttg gcggcaccaa cttccatatt   1440
attttagaag agtatcgccc aggtcacgat agcgcatatc gcttaaactc agtgagccaa   1500
actgtgttga tctcggcaaa cgaccaacaa ggtattgttg ctgagttaaa taactggcgt   1560
actaaactgg ctgtcgatgc tgatcatcaa gggtttgtat ttaatgagtt agtgacaacg   1620
tggccattaa aaacccccatc cgttaaccaa gctcgtttag gttttgttgc gcgtaatgca   1680
```

```
aatgaagcga tcgcgatgat tgatacggca ttgaaacaat tcaatgcgaa cgcagataaa   1740
atgacatggt cagtacctac cggggtttac tatcgtcaag ccggtattga tgcaacaggt   1800
aaagtggttg cgctattctc agggcaaggt tcgcaatacg tgaacatggg tcgtgaatta   1860
acctgtaact tcccaagcat gatgcacagt gctgcggcga tggataaaga gttcagtgcc   1920
gctggtttag gccagttatc tgcagttact ttccctatcc ctgtttatac ggatgccgag   1980
cgtaagctac aagaagagca attacgttta acgcaacatg cgcaaccagc gattggtagt   2040
ttgagtgttg gtctgttcaa aacgtttaag caagcaggtt ttaaagctga ttttgctgcc   2100
ggtcatagtt tcggtgagtt aaccgcatta tgggctgccg atgtattgag cgaaagcgat   2160
tacatgatgt tagcgcgtag tcgtggtcaa gcaatggctg cgccagagca acaagatttt   2220
gatgcaggta agatggccgc tgttgttggt gatccaaagc aagtcgctgt gatcattgat   2280
acccttgatg atgtctctat tgctaacttc aactcgaata accaagttgt tattgctggt   2340
actacggagc aggttgctgt agcggttaca accttaggta atgctggttt caaagttgtg   2400
ccactgccgg tatctgctgc gttccataca cctttagttc gtcacgcgca aaaaccattt   2460
gctaaagcgg ttgatagcgc taaatttaaa gcgccaagca ttccagtgtt tgctaatggc   2520
acaggcttgg tgcattcaag caaaccgaat gacattaaga aaaacctgaa aaaccacatg   2580
ctggaatctg ttcatttcaa tcaagaaatt gacaacatct atgctgatgg tggccgcgta   2640
tttatcgaat ttggtccaaa gaatgtatta actaaattgg ttgaaaacat tctcactgaa   2700
aaatctgatg tgactgctat cgcggttaat gctaatccta acaacctgc ggacgtacaa   2760 atgcgccaag ctgcgctgca aatggcagtg cttggtgtcg cattagacaa tattgacccg   2820
tacgacgccg ttaagcgtcc acttgttgcg ccgaaagcat caccaatgtt gatgaagtta   2880
tctgcagcgt cttatgttag tccgaaaacg aagaaagcgt ttgctgatgc attgactgat   2940
ggctggactg ttaagcaagc gaaagctgta cctgctgttg tgtcacaacc acaagtgatt   3000
gaaaagatcg ttgaagttga aagatagtt gaacgcattg tcgaagtaga gcgtattgtc   3060
gaagtagaaa aaatcgtcta cgttaatgct gacggttcgc ttatatcgca aaataatcaa   3120
gacgttaaca gcgctgttgt tagcaacgtg actaatagct cagtgactca tagcagtgat   3180
gctgaccttg ttgcctctat tgaacgcagt gttggtcaat ttgttgcaca ccaacagcaa   3240
ttattaaatg tacatgaaca gtttatgcaa ggtccacaag actacgcgaa aacagtgcag   3300
aacgtacttg ctgcgcagac gagcaatgaa ttaccggaaa gtttagaccg tacattgtct   3360
atgtataacg agttccaatc agaaacgcta cgtgtacatg aaacgtacct gaacaatcag   3420
acgagcaaca tgaacaccat gcttactggt gctgaagctg atgtgctagc aaccccaata   3480
actcaggtag tgaatacagc cgttgccact agtcacaagg tagttgctcc agttattgct   3540
aatacagtga cgaatgttgt atctagtgtc agtaataacg cggcggttgc agtgcaaact   3600
gtggcattag cgcctacgca agaaatcgct ccaacagtcg ctactacgcc agcacccgca   3660
ttggttgcta tcgtggctga acctgtgatt gttgcgcatg ttgctacaga gttgcacca   3720 attacaccat cagttacacc agttgtcgca actcaagcgg ctatcgatgt agcaactatt   3780
aacaaagtaa tgttagaagt tgttgctgat aaaaccggtt atccaacgga tatgctggaa   3840
ctgagcatgg acatggaagc tgacttaggt atcgactcaa tcaaacgtgt tgagatatta   3900
ggcgcagtac aggaattgat ccctgactta cctgaactta atcctgaaga tcttgctgag   3960
ctacgcacgc ttggtgagat tgtcgattac atgaattcaa aagcccaggc tgtagctcct   4020
acaacagtac ctgtaacaag tgcacctgtt tcgcctgcat ctgctggtat tgatttagcc   4080
```

```
cacatccaaa acgtaatgtt agaagtggtt gcagacaaaa ccggttaccc aacagacatg    4140
ctagaactga gcatggatat ggaagctgac ttaggtattg attcaatcaa gcgtgtggaa    4200
atcttaggtg cagtacagga gatcataact gatttacctg agctaaaccc tgaagatctt    4260
gctgaattac gcaccctagg tgaaatcgtt agttacatgc aaagcaaagc gccagtcgct    4320
gaaagtgcgc cagtggcgac ggctcctgta gcaacaagct cagcaccgtc tatcgatttg    4380
aaccacattc aaacagtgat gatggatgta gttgcagata agactggtta tccaactgac    4440
atgctagaac ttggcatgga catggaagct gatttaggta tcgattcaat caaacgtgtg    4500
gaaatattag gcgcagtgca ggagatcatc actgatttac ctgagctaaa cccagaagac    4560
ctcgctgaat tacgcacgct aggtgaaatc gttagttaca tgcaaagcaa agcgccagtc    4620
gctgagagtg cgccagtagc gacggcttct gtagcaacaa gctctgcacc gtctatcgat    4680
ttaaaccata tccaaacagt gatgatgaa gtggttgcag acaaaaccgg ttatccagta    4740
gacatgttag aacttgctat ggacatggaa gctgacctag gtatcgattc aatcaagcgt    4800
gtagaaattt taggtgcggt acaggaaatc attactgact tacctgagct aaaccctgaa    4860
gatcttgctg aactacgtac attaggtgaa atcgttagtt acatgcaaag caaagcgccc    4920
gtagctgaag cgcctgcagt acctgttgca gtagaaagtg cacctactag tgtaacaagc    4980
tcagcaccgt ctatcgattt agaccacatc caaaatgtaa tgatggatgt tgttgctgat    5040
aagactggtt atcctgccaa tatgcttgaa ttagcaatgg acatggaagc cgaccttggt    5100
attgattcaa tcaagcgtgt tgaaattcta ggcgcggtac aggagatcat tactgattta    5160
cctgaactaa acccagaaga cttagctgaa ctacgtacgt tagaagaaat tgtaacctac    5220
atgcaaagca aggcgagtgg tgttactgta aatgtagtgg ctagccctga aaataatgct    5280
gtatcagatg catttatgca aagcaatgtg gcgactatca cagcggccgc agaacataag    5340
gcggaattta accggcgcc gagcgcaacc gttgctatct ctcgtctaag ctctatcagt    5400
aaaataagcc aagattgtaa aggtgctaac gccttaatcg tagctgatgg cactgataat    5460
gctgtgttac ttgcagacca cctattgcaa actggctgga atgtaactgc attgcaacca    5520
acttgggtag ctgtaacaac gacgaaagca tttaataagt cagtgaacct ggtgacttta    5580
aatggcgttg atgaaactga atcaacaac attattactg ctaacgcaca attggatgca    5640
gttatctatc tgcacgcaag tagcgaaatt aatgctatcg aatacccaca agcatctaag    5700
caaggcctga tgttagcctt cttattagcg aaattgagta agtaactca agccgctaaa    5760 gtgcgtggcg cctttatgat tgttactcag cagggtggtt cattaggttt tgatgatatc    5820
gattctgcta caagtcatga tgtgaaaaca gacctagtac aaagcggctt aaacggttta    5880
gttaagacac tgtctcacga gtgggataac gtattctgtc gtgcggttga tattgcttcg    5940
tcattaacgg ctgaacaagt tgcaagcctt gttagtgatg aactacttga tgctaacact    6000
gtattaacag aagtgggtta tcaacaagct ggtaaaggcc ttgaacgtat cacgttaact    6060
ggtgtggcta ctgacagcta tgcattaaca gctggcaata acatcgatgc taactcggta    6120
tttttagtga gtggtggcgc aaaaggtgta actgcacatt gtgttgctcg tatagctaaa    6180
gaatatcagt ctaagttcat cttattggga cgttcaacgt tctcaagtga cgaaccgagc    6240
tgggcaagtg gtattactga tgaagcggcg ttaaagaaag cagcgatgca gtctttgatt    6300
acagcaggtg ataaaccaac acccgttaag atcgtacagc taatcaaacc aatccaagct    6360
aatcgtgaaa ttgcgcaaac cttgtctgca attaccgctg ctggtggcca agctgaatat    6420
```

```
gtttctgcag atgtaactaa tgcagcaagc gtacaaatgg cagtcgctcc agctatcgct    6480
aagttcggtg caatcactgg catcattcat ggcgcgggtg tgttagctga ccaattcatt    6540
gagcaaaaaa cactgagtga ttttgagtct gtttacagca ctaaaattga cggtttgtta    6600
tcgctactat cagtcactga agcaagcaac atcaagcaat tggtattgtt ctcgtcagcg    6660
gctggtttct acggtaaccc cggccagtct gattactcga ttgccaatga gatcttaaat    6720
aaaaccgcat accgctttaa atcattgcac ccacaagctc aagtattgag ctttaactgg    6780
ggtccttggg acggtggcat ggtaacgcct gagcttaaac gtatgtttga ccaacgtggt    6840
gtttacatta ttccacttga tgcaggtgca cagttattgc tgaatgaact agccgctaat    6900
gataaccgtt gtccacaaat cctcgtgggt aatgacttat ctaaagatgc tagctctgat    6960
caaaagtctg atgaaaagag tactgctgta aaaaagccac aagttagtcg tttatcagat    7020
gctttagtaa ctaaaagtat caaagcgact aacagtagct ctttatcaaa caagactagt    7080
gctttatcag acagtagtgc ttttcaggtt aacgaaaacc acttttttagc tgaccacatg    7140 atcaaaggca atcaggtatt accaacggta tgcgcgattg cttggatgag tgatgcagca    7200
aaagcgactt atagtaaccg agactgtgca ttgaagtatg tcggtttcga agactataaa    7260
ttgtttaaag gtgtggtttt tgatggcaat gaggcggcgg attaccaaat ccaattgtcg    7320
cctgtgacaa gggcgtcaga acaggattct gaagtccgta ttgccgcaaa gatctttagc    7380
ctgaaaagtg acggtaaacc tgtgtttcat tatgcagcga caatattgtt agcaactcag    7440
ccacttaatg ctgtgaaggt agaacttccg acattgacga aaagtgttga tagcaacaat    7500
aaagtaactg atgaagcaca agcgttatac agcaatggca ccttgttcca cggtgaaagt    7560
ctgcagggca ttaagcagat attaagttgt gacgacaagg gcctgctatt ggcttgtcag    7620
ataaccgatg ttgcaacagc taagcaggga tccttcccgt tagctgacaa caatatcttt    7680
gccaatgatt tggtttatca ggctatgttg gtctgggtgc gcaaacaatt tggtttaggt    7740
agcttacctt cggtgacaac ggcttggact gtgtatcgtg aagtggttgt agatgaagta    7800 tttatctgc aacttaatgt tgttgagcat gatctattgg gttcacgcgg cagtaaagcc    7860
cgttgtgata ttcaattgat tgctgctgat atgcaattac ttgccgaagt gaaatcagcg    7920
caagtcagtg tcagtgacat tttgaacgat atgtcatga                          7959
```

<210> SEQ ID NO 78  
<211> LENGTH: 2652  
<212> TYPE: DNA  
<213> ORGANISM: Vibrio marinus

<400> SEQUENCE: 78

```
atgacggaat tagctgttat tggtatggat gctaaattta gcggacaaga caatattgac      60
cgtgtggaac gcgctttcta tgaaggtgct tatgtaggta atgttagccg cgttagtacc     120
gaatctaatg ttattagcaa tggcgaagaa caagttatta ctgccatgac agttcttaac     180
tctgtcagtc tactagcgca aacgaatcag ttaaatatag ctgatatcgc ggtgttgctg     240
attgctgatg taaaaagtgc tgatgatcag cttgtagtcc aaattgcatc agcaattgaa     300
aaacagtgtg cgagttgtgt tgttattgct gatttaggcc aagcattaaa tcaagtagct     360
gatttagtta ataaccaaga ctgtcctgtg ctgtaattg gcatgaataa ctcggttaat     420
ttatctcgtc atgatcttga atctgtaact gcaacaatca gctttgatga aaccttcaat     480
ggttataaca atgtagctgg gttcgcgagt ttacttatcg cttcaactgc gtttgccaat     540
gctaagcaat gttatatata cgccaacatt aagggcttcg ctcaatcggg cgtaaatgct     600
```

```
caatttaacg ttggaaacat tagcgatact gcaaagaccg cattgcagca agctagcata    660
actgcagagc aggttggttt gttagaagtg tcagcagtcg ctgattcggc aatcgcattg    720
tctgaaagcc aaggtttaat gtctgcttat catcatacgc aaactttgca tactgcatta    780
agcagtgccc gtagtgtgac tggtgaaggc gggtgttttt cacaggtcgc aggtttattg    840
aaatgtgtaa ttggtttaca tcaacgttat attccggcga ttaaagattg gcaacaaccg    900
agtgacaatc aaatgtcacg gtggcggaat tcaccattct atatgcctgt agatgctcga    960
ccttggttcc cacatgctga tggctctgca cacattgccg cttatagttg tgtgactgct   1020
gacagctatt gtcatattct tttacaagaa aacgtcttac aagaacttgt tttgaaagaa   1080
acagtcttgc aagataatga cttaactgaa agcaagcttc agactcttga acaaaacaat   1140
ccagtagctg atctgcgcac taatggttac tttgcatcga gcgagttagc attaatcata   1200
gtacaaggta atgacgaagc acaattacgc tgtgaattag aaactattac agggcagtta   1260
agtactactg gcataagtac tatcagtatt aaacagatcg cagcagactg ttatgcccgt   1320
aatgatacta acaaagccta tagcgcagtg cttattgccg agactgctga agagttaagc   1380
aaagaaataa ccttggcgtt tgctggtatc gctagcgtgt ttaatgaaga tgctaaagaa   1440
tggaaaaccc cgaagggcag ttattttacc gcgcagcctg caaataaaca ggctgctaac   1500
agcacacaga atggtgtcac cttcatgtac ccaggtattg gtgctacata tgttggttta   1560
gggcgtgatc tatttcatct attcccacag atttatcagc ctgtagcggc tttagccgat   1620
gacattggcg aaagtctaaa agatacttta cttaatccac gcagtattag tcgtcatagc   1680
tttaaagaac tcaagcagtt ggatctggac ctgcgcggta acttagccaa tatcgctgaa   1740
gccggtgtgg gttttgcttg tgtgtttacc aaggtatttg aagaagtctt tgccgttaaa   1800
gctgactttg ctacaggtta tagcatgggt gaagtaagca tgtatgcagc actaggctgc   1860
tggcagcaac cgggattgat gagtgctcgc cttgcacaat cgaataccct taatcatcaa   1920
ctttgcggcg agttaagaac actacgtcag cattggggca tggatgatgt agctaacggt   1980
acgttcgagc agatctggga aacctatacc attaaggcaa cgattgaaca ggtcgaaatt   2040
gcctctgcag atgaagatcg tgtgtattgc accattatca atacacctga tagcttgttg   2100
ttagccggtt atccagaagc ctgtcagcga gtcattaaga atttaggtgt gcgtgcaatg   2160
gcattgaata tggcgaacgc aattcacagc gcgccagctt atgccgaata cgatcatatg   2220
gttgagctat accatatgga tgttactcca cgtattaata ccaagatgta ttcaagctca   2280
tgttatttac cgattccaca acgcagcaaa gcgatttccc acagtattgc taaatgtttg   2340
tgtgatgtgg tggatttccc acgtttggtt aataccttac atgacaaagg tgcgcgggta   2400
ttcattgaaa tgggtccagg tcgttcgtta tgtagctggg tagataagat cttagttaat   2460
ggcgatggcg ataataaaaa gcaaagccaa catgtatctg ttcctgtgaa tgccaaaggc   2520
accagtgatg aacttactta tattcgtgcg attgctaagt taattagtca tggcgtgaat   2580
ttgaatttag atagccttgt taacgggtca atcctggtta aagcaggcca tatagcaaac   2640
acgaacaaat ag                                                        2652
```

<210> SEQ ID NO 79
<211> LENGTH: 6057
<212> TYPE: DNA
<213> ORGANISM: Vibrio marinus

<400> SEQUENCE: 79

-continued

```
atggatttaa agagagtaat tatggaaaat attgcagtag taggtattgc taatttgttc      60
ccgggctcac aagcaccgga tcaattttgg cagcaattgc ttgaacaaca agattgccgc     120
agtaaggcga ccgctgttca aatgggcgtt gatcctgcta aatataccgc caacaaaggt     180
gacacagata aattttactg tgtgcacggc ggttacatca gtgatttcaa ttttgatgct     240
tcaggttatc aactcgataa tgattattta gccggtttag atgaccttaa tcaatggggg     300
ctttatgtta cgaaacaagc ccttaccgat gcgggttatt ggggcagtac tgcactagaa     360
aactgtggtg tgattttagg taatttgtca ttcccaacta atcatctaa tcagctgttt      420
atgcctttgt atcatcaagt tgttgataat gccttaaagg cggtattaca tcctgatttt     480
caattaacgc attacacagc accgaaaaaa acacatgctg acaatgcatt agtagcaggt     540
tatccagctg cattgatcgc gcaagcggcg ggtcttggtg gttcacattt tgcactggat     600
gcggcttgtg cttcatcttg ttatagcgtt aagttagcgt gtgattacct gcatacgggt     660
aaagccaaca tgatgcttgc tggtgcggta tctgcagcag atcctatgtt cgtaaatatg     720
ggtttctcga tattccaagc ttacccagct aacaatgtac atgccccgtt tgaccaaaat     780
tcacaaggtc tatttgccgg tgaaggcgcg ggcatgatgg tattgaaacg tcaaagtgat     840
gcagtacgtg atggtgatca tatttacgcc attattaaag cggcgcatt atcgaatgac     900
ggtaaaggcg agtttgtatt aagcccgaac accaagggcc aagtattagt atatgaacgt     960
gcttatgccg atgcagatgt tgacccgagt acagttgact atattgaatg tcatgcaacg    1020
ggcacaccta agggtgacaa tgttgaattg cgttcgatgg aaacctttt cagtcgcgta    1080
aataacaaac cattactggg ctcggttaaa tctaaccttg gtcatttgtt aactgccgct    1140
ggtatgcctg gcatgaccaa agctatgtta gcgctaggta aaggtcttat tcctgcaacg    1200
attaacttaa agcaaccact gcaatctaaa aacggttact ttactggcga gcaaatgcca    1260
acgacgactg tgtcttggcc aacaactccg ggtgccaagg cagataaacc gcgtaccgca    1320
ggtgtgagcg tatttggttt tggtggcagc aacgcccatt tggtattaca acagccaacg    1380
caaacactcg agactaattt tagtgttgct aaaccacgtg agcctttggc tattattggt    1440
atggacagcc attttggtag tgccagtaat ttagcgcagt tcaaaacctt attaaataat    1500
aatcaaaata ccttccgtga attaccagaa caacgctgga aaggcatgga agtaacgct    1560
aacgtcatgc agtcgttaca attacgcaaa gcgcctaaag gcagttacgt tgaacagcta    1620
gatattgatt tcttgcgttt taaagtaccg cctaatgaaa aagattgctt gatcccgcaa    1680
cagttaatga tgatgcaagt ggcagacaat gctgcgaaag acggaggtct agttgaaggt    1740
cgtaatgttg cggtattagt agcgatgggc atggaactgg aattacatca gtatcgtggt    1800
cgcgttaatc taaccaccca aattgaagac agcttattac agcaaggtat taacctgact    1860
gttgagcaac gtgaagaact gaccaatatt gctaaagacg tgttgcctc ggctgcacag    1920
ctaaatcagt atacgagttt cattggtaat attatggcgt cacgtatttc ggcgttatgg    1980
gattttctg gtcctgctat taccgtatcg gctgaagaaa actctgttta tcgttgtgtt    2040
gaattagctg aaaatctatt tcaaaccagt gatgttgaag ccgttattat tgctgctgtt    2100
gatttgtctg gttcaattga aaacattact ttacgtcagc actacggtcc agttaatgaa    2160
aagggatctg taagtgaatg tggtccggtt aatgaaagca gttcagtaac caacaatatt    2220
cttgatcagc aacaatggct ggtgggtgaa ggcgcagcgg ctattgtcgt taaaccgtca    2280
tcgcaagtca ctgctgagca gtttatgcg cgtattgatg cggtgagttt tgcccctggt    2340
agcaatgcga aagcaattac gattgcagcg gataaagcat taacacttgc tggtatcagt    2400
```

```
gctgctgatg tagctagtgt tgaagcacat gcaagtggtt ttagtgccga aaataatgct    2460
gaaaaaaccg cgttaccgac tttataccca agcgcaagta tcagttcggt gaaagccaat    2520
attggtcata cgtttaatgc ctcgggtatg gcgagtatta ttaaaacggc gctgctgtta    2580
gatcagaata cgagtcaaga tcagaaaagc aaacatattg ctattaacgg tctaggtcgt    2640
gataacagct gcgcgcatct tatcttatcg agttcagcgc aagcgcatca agttgcacca    2700
gcgcctgtat ctggtatggc caagcaacgc ccacagttag ttaaaaccat caaactcggt    2760
ggtcagttaa ttagcaacgc gattgttaac agtgcgagtt catctttaca cgctattaaa    2820
gcgcagtttg ccggtaagca cttaaacaaa gttaaccagc cagtgatgat ggataacctg    2880
aagccccaag gtattagcgc tcatgcaacc aatgagtatg tggtgactgg agctgctaac    2940
actcaagctt ctaacattca agcatctcat gttcaagcgt caagtcatgc acaagagata    3000
gcaccaaacc aagttcaaaa tatgcaagct acagcagccg ctgtaagttc acccctttct    3060
caacatcaac acacagcgca gcccgtagcg gcaccgagcg ttgttggagt gactgtgaaa    3120
cataaagcaa gtaccaaaat tcatcagcaa gcgtctacgc ataaagcatt tttagaaagt    3180
cgtttagctg cacagaaaaa cctatcgcaa cttgttgaat tgcaaaccaa gctgtcaatc    3240
caaactggta gtgacaatac atctaacaat actgcgtcaa caagcaatac agtgctaaca    3300
aatcctgtat cagcaacgcc attaacactt gtgtctaatg cgcctgtagt agcgacaaac    3360
ctaaccagta cagaagcaaa agcgcaagca gctgctacac aagctggttt tcagataaaa    3420
ggacctgttg gttacaacta tccaccgctg cagttaattg aacgttataa taaaccagaa    3480
aacgtgattt acgatcaagc tgatttggtt gaattcgctg aaggtgatat tggtaaggta    3540
tttggtgctg aatacaatat tattgatggc tattcgcgtc gtgtacgtct gccaacctca    3600
gattacttgt tagtaacacg tgttactgaa cttgatgcca aggtgcatga atacaagaaa    3660
tcatacatgt gtactgaata tgatgtgcct gttgatgcac cgttcttaat tgatggtcag    3720
atcccttggt ctgttgccgt cgaatcaggc cagtgtgatt tgatgttgat ttcatatatc    3780
ggtattgatt tccaagcgaa aggcgaacgt gtttaccgtt tacttgattg tgaattaact    3840
ttccttgaag agatggcttt tggtggcgat actttacgtt acgagatcca cattgattcg    3900
tatgcacgta acggcgagca attattattc ttcttccatt acgattgtta cgtagggggat    3960 aagaaggtac ttatcatgcg taatggttgt gctggtttct ttactgacga agaacttttct   4020 gatggtaaag gcgttattca taacgacaaa gacaaagctg agtttagcaa tgctgttaaa    4080
tcatcattca cgccgttatt acaacataac cgtggtcaat acgattataa cgacatgatg    4140
aagttggtta atggtgatgt tgccagttgt tttggtccgc aatatgatca aggtggccgt    4200
aatccatcat tgaaattctc gtctgagaag ttcttgatga ttgaacgtat taccaagata    4260
gacccaaccg tggtcattg gggactaggc tgttagaaag tcagaaaga tttagaccct    4320 gagcattggt atttcccttg tcactttaaa ggtgatcaag taatggctgg ttcgttgatg    4380
tcggaaggtt gtggccaaat ggcgatgttc ttcatgctgt ctcttggtat gcataccaat    4440
gtgaacaacg ctcgtttcca accactacca ggtgaatcac aaacggtacg ttgtcgtggg    4500
caagtactgc cacagcgcaa taccttaact taccgtatgg aagttactgc gatgggtatg    4560
catccacagc cattcatgaa agctaatatt gatattttgc ttgacggtaa agtggttgtt    4620
gatttcaaaa acttgagcgt gatgatcagc gaacaagatg agcattcaga ttaccctgta    4680
acactgccga gtaatgtggc gcttaaagcg attactgcac ctgttgcgtc agtagcacca    4740
```

-continued

```
gcatcttcac cgctaacag cgcggatcta gacgaacgtg gtgttgaacc gtttaagttt    4800
cctgaacgtc cgttaatgcg tgttgagtca gacttgtctg caccgaaaag caaaggtgtg    4860
acaccgatta agcattttga agcgcctgct gttgctggtc atcatagagt gcctaaccaa    4920
gcaccgttta caccttggca tatgtttgag tttgcgacgg gtaatatttc taactgtttc    4980
ggtcctgatt ttgatgttta tgaaggtcgt attccacctc gtacaccttg tggcgattta    5040
caagttgtta ctcaggttgt agaagtgcag ggcgaacgtc ttgatcttaa aaatccatca    5100
agctgtgtag ctgaatacta tgtaccggaa gacgcttggt actttactaa aaacagccat    5160
gaaaactgga tgccttattc attaatcatg gaaattgcat tgcaaccaaa tggctttatt    5220
tctggttaca tgggcacgac gcttaaatac cctgaaaaag atctgttctt ccgtaacctt    5280
gatggtagcg gcacgttatt aaagcagatt gatttacgcg gcaagaccat tgtgaataaa    5340
tcagtcttgg ttagtacggc tattgctggt ggcgcgatta ttcaaagttt cacgtttgat    5400
atgtctgtag atggcgagct atttatact ggtaaagctg tatttggtta ctttagtggt    5460
gaatcactga ctaaccaact gggcattgat aacggtaaaa cgactaatgc gtggtttgtt    5520
gataacaata ccccgcagc gaatattgat gtgtttgatt taactaatca gtcattggct    5580
ctgtataaag cgcctgtgga taaaccgcat tataaattgg ctggtggtca gatgaacttt    5640
atcgatacag tgtcagtggt tgaaggcggt ggtaaagcgg cgtggctta tgtttatggc    5700 gaacgtacga ttgatgctga tgattggttc ttccgttatc acttccacca agatccggtg    5760
atgccaggtt cattaggtgt tgaagctatt attgagttga tgcagaccta tgcgcttaaa    5820
aatgatttgg gtggcaagtt tgctaaccca cgtttcattg cgccgatgac gcaagttgat    5880
tggaaatacc gtgggcaaat tacgccgctg aataaacaga tgtcactgga cgtgcatatc    5940
actgagatcg tgaatgacgc tggtgaagtg cgaatcgttg gtgatgcgaa tctgtctaaa    6000
gatggtctgc gtatttatga agttaaaaac atcgttttaa gtattgttga agcgtaa      6057
```

<210> SEQ ID NO 80
<211> LENGTH: 1665
<212> TYPE: DNA
<213> ORGANISM: Vibrio marinus

<400> SEQUENCE: 80

```
atgaatatag taagtaatca ttcggcagct acaaaaaagg aattaagaat gtcgagttta      60
ggttttaaca ataacaacgc aattaactgg gcttggaaag tagatccagc gtcagttcat     120
acacaagatg cagaaattaa agcagcttta atggatctaa ctaaacctct ctatgtggcg     180
aataattcag gcgtaactgg tatagctaat catacgtcag tagcaggtgc gatcagcaat     240
aacatcgatg ttgatgtatt ggcgtttgcg caaaagttaa acccagaaga tctgggtgat     300
gatgcttaca agaaacagca cggcgttaaa tatgcttatc atggcggtgc gatggcaaat     360
ggtattgcct cggttgaatt ggttgttgcg ttaggtaaag cagggctgtt atgttcattt     420
ggtgctgcag gtctagtgcc tgatgcggtt gaagatgcaa ttcgtcgtat tcaagctgaa     480
ttaccaaatg gcccttatgc ggttaacttg atccatgcac cagcagaaga agcattagag     540 cgtggcgcg ttgaacgttt cctaaaactt ggcgtcaaga cggtagaggc ttcagcttac     600
cttggtttaa ctgaacacat tgtttggtat cgtgctgctg gtctaactaa aaacgcagat     660
ggcagtgtta atatcggtaa caaggttatc gctaaagtat cgcgtaccga agttggtcgc     720
cgctttatgg aacctgcacc gcaaaaatta ctggataagt tattagaaca aaataagatc     780 accctgaac aagctgcttt agcgttgctt gtacctatgg ctgatgatat tactgggaa      840
```

```
gcggattctg gtggtcatac agataaccgt ccgtttttaa cattattacc gacgattatt    900
ggtctgcgtg atgaagtgca agcgaagtat aacttctctc ctgcattacg tgttggtgct    960
ggtggtggta tcggaacgcc tgaagcagca ctcgctgcat taacatggg cgcggcttat    1020
atcgttctgg gttctgtgaa tcaggcgtgt gttgaagcgg gtgcatctga atatactcgt    1080
aaactgttat cgacagttga atggctgat gtgactatg cacctgctgc agatatgttt    1140
gaaatgggtg tgaagctgca agtattaaaa cgcggttcta tgttcgcgat gcgtgcgaag    1200
aaactgtatg acttgtatgt ggcttatgac tcgattgaag atatcccagc tgctgaacgt    1260
gagaagattg aaaaacaaat cttccgtgca aacctagacg agatttggga tggcactatc    1320
gctttcttta ctgaacgcga tccagaaatg ctagcccgtg caacgagtag tcctaaacgt    1380
aaaatggcac ttatcttccg ttggtatctt ggcctttctt cacgctggtc aaacacaggc    1440
gagaagggac gtgaaatgga ttatcagatt tgggcaggcc aagtttagg tgcattcaac    1500
agctgggtga aggttctta ccttgaagac tatacccgcc gtggcgctgt agatgttgct    1560
ttgcatatgc ttaaaggtgc tgcgtattta caacgtgtaa accagttgaa attgcaaggt    1620
gttagcttaa gtacagaatt ggcaagttat cgtacgagtg attaa                    1665

<210> SEQ ID NO 81
<211> LENGTH: 2910
<212> TYPE: DNA
<213> ORGANISM: Shewanella putrefaciens

<400> SEQUENCE: 81
atgagtatgt ttttaaattc aaaactttcg cgctcagtca aacttgccat atccgcaggc    60
ttaacagcct cgctagctat gcctgttttt gcagaagaaa ctgctgctga agaacaaata    120
gaaagagtcg cagtgaccgg atcgcgaatc gctaaagcag agctaactca accagctcca    180
gtcgtcagcc tttcagccga agaactgaca aaatttggta atcaagattt aggtagcgta    240
ctagcagaat tacctgctat tggtgcaacc aacactatta ttggtaataa caatagcaac    300
tcaagcgcag gtgttagctc agcagacttg cgtcgtctag gtgctaacag aaccttagta    360
ttagtcaacg gtaagcgcta cgttgccggc caacccgggct cagctgaggt agatttgtca    420
actataccaa ctagcatgat ctcgcgagtt gagattgtaa ccggcggtgc ttcagcaatt    480
tatggttcgg acgctgtatc aggtgttatc aacgttatcc ttaaagaaga cttttgaaggc    540
tttgagttta acgcacgtac tagcggttct actgaaagtg taggcactca agagcactct    600
tttgacattt tgggtggtgc aaacgttgca gatggacgtg gtaatgtaac cttctacgca    660
ggttatgaac gtacaaaaga agtcatggct accgacattg ccaattcga tgcttgggga    720
acaattaaaa acgaagccga tggtggtgaa gatgatggta ttccagacag actacgtgta    780
ccacgagttt attctgaaat gattaatgct accggtgtta tcaatgcatt tggtggtgga    840
attggtcgct caacctttga cagtaacggc aatcctattg cacaacaaga acgtgatggg    900
actaacagct ttgcatttgg ttcattccct aatggctgtg acacatgttt caacactgaa    960
gcatacgaaa actatattcc agggtagaa agaataaacg ttggctcatc attcaacttt    1020
gattttaccg ataacattca attttacact gacttcagat atgtaaagtc agatattcag    1080
caacaatttc agccttcatt ccgttttggt aacattaata tcaatgttga agataacgcc    1140
tttttgaatg acgacttgcg tcagcaaatg ctcgatgcgg tcaaaccaa tgctagtttt    1200
gccaagtttt ttgatgaatt aggaaatcgc tcagcagaaa ataaacgcga acttttccgt    1260
```

```
tacgtaggtg gctttaaagg tggctttgat attagcgaaa ccatatttga ttacgacctt      1320
tactatgttt atggcgagac taataaccgt cgtaaaaccc ttaatgacct aattcctgat      1380
aactttgtcg cagctgtcga ctctgttatt gatcctgata ctggcttagc agcgtgtcgc      1440
tcacaagtag caagcgctca aggcgatgac tatacagatc ccgcgtctgt aaatggtagc      1500
gactgtgttg cttataaccc atttggcatg ggtcaagctt cagcagaagc ccgcgactgg      1560
gtttctgctg atgtgactcg tgaagacaaa ataactcaac aagtgattgg tggtactctc      1620
ggtaccgatt ctgaagaact atttgagctt caaggtggtg caatcgctat ggttgttggt      1680
tttgaatacc gtgaagaaac gtctggttca acaaccgatg aatttactaa agcaggtttc      1740
ttgacaagcg ctgcaacgcc agattcttat ggcgaatacg acgtgactga gtattttgtt      1800
gaggtgaaca tcccagtact aaaagaatta ccttttgcac atgagttgag ctttgacggt      1860
gcataccgta atgctgatta ctcacatgcc ggtaagactg aagcatggaa agctggtatg      1920
ttctactcac cattagagca acttgcatta cgtggtacgg taggtgaagc agtacgagca      1980
ccaaacattg cagaagcctt tagtccacgc tctcctggtt ttggccgcgt ttcagatcca      2040
tgtgatgcag ataacattaa tgacgatccg gatcgcgtgt caaactgtgc agcattgggg      2100
atccctccag gattccaagc taatgataac gtcagtgtag ataccttatc tggtggtaac      2160
ccagatctaa aacctgaaac atcaacatcc tttacaggtg gtcttgtttg dacaccaacg      2220
tttgctgaca atctatcatt cactgtcgat tattatgata ttcaaattga ggatgctatt      2280
ttgtcagtag ccacccagac tgtggctgat aactgtgttg actcaactgg cggacctgac      2340
accgacttct gtagtcaagt tgatcgtaat ccaacgacct atgatattga acttgttcgc      2400
tctggttatc taaatgccgc ggcattgaat accaaaggta ttgaatttca agctgcatac      2460
tcattagatc tagagtcttt caacgcgcct ggtgaactac gcttcaacct attggggaac      2520
caattacttg aactagaacg tcttgaattc caaaatcgtc ctgatgagat taatgatgaa      2580
aaaggcgaag taggtgatcc agagctgcag ttccgcctag gcatcgatta ccgtctagat      2640
gatctaagtg ttagctggaa cacgcgttat attgatagcg tagtaactta tgatgtctct      2700
gaaaatggtg gctctcctga agatttatat ccaggccaca taggctcaat gacaactcat      2760
gacttgagcg ctacatacta catcaatgag aacttcatga ttaacggtgg tgtacgtaac      2820
ctatttgacg cacttccacc tggatacact aacgatgcgc tatatgatct agttggtcgc      2880
cgtgcattcc taggtattaa ggtaatgatg                                       2910

<210> SEQ ID NO 82
<211> LENGTH: 864
<212> TYPE: DNA
<213> ORGANISM: Shewanella putrefaciens

<400> SEQUENCE: 82
atggcaaaaa taatagtga acacttggat gaagctacta ttacttcgaa taagtgtacg        60
caaacagaga ctgaggctcg gcatagaaat gccactacaa cacctgagat gcgccgattc      120
atacaagagt cggatctcag tgttagccaa ctgtctaaaa tattaaatat cagtgaagct      180
accgtacgta agtggcgcaa gcgtgactct gtcgaaaact gtcctaatac cccgcaccat      240
ctcaatacca cgctaacccc tttgcaagaa tatgtggttg tgggcctgcg ttatcaattg      300
aaaatgccat tagacagatt gctcaaagca acccaagagt ttatcaatcc aaacgtgtcg      360
cgctcaggtt tagcaagatg tttgaagcgt tatggcgttt cacgggtgag tgatatccaa      420
agcccacacg taccaatgcg ctactttaat caaattccag tcactcaagg cagcgatgtg      480
```

-continued

```
caaacctaca ccctgcacta tgaaacgctg gcaaaaacct tagccttacc tagtaccgat      540
ggtgacaatg tggtgcaagt ggtgtctctc accattccac caaagttaac cgaagaagca      600
cccagttcaa ttttgctcgg cattgatcct catagcgact ggatctatct cgacatatac      660
caagatggca atacacaagc cacgaataga tatatggctt atgtgctaaa acacgggcca      720
ttccatttac gaaagttact cgtgcgtaac tatcacacct ttttacagcg ctttcctgga      780
gcgacgcaaa atcgccgccc ctctaaagat atgcctgaaa caatcaacaa gacgcctgaa      840
acacaggcac ccagtggaga ctca                                             864
```

<210> SEQ ID NO 83
<211> LENGTH: 8268
<212> TYPE: DNA
<213> ORGANISM: Shewanella putrefaciens

<400> SEQUENCE: 83

```
atgagccaga cctctaaacc tacaaactca gcaactgagc aagcacaaga ctcacaagct       60
gactctcgtt taaataaacg actaaaagat atgccaattg ctattgttgg catggcgagt      120 attttttgcaa actctcgcta tttgaataag ttttgggact taatcagcga aaaaattgat      180
gcgattactg aattaccatc aactcactgg cagcctgaag aatattacga cgcagataaa      240
accgcagcag acaaaagcta ctgtaaacgt ggtggctttt tgccagatgt agacttcaac      300
ccaatggagt ttggcctgcc gccaaacatt ttggaactga ccgattcatc gcaactatta      360
tcactcatcg ttgctaaaga agtgttggct gatgctaact tacctgagaa ttacgaccgc      420
gataaaattg gtatcacctt aggtgtcggc ggtggtcaaa aaattagcca cagcctaaca      480
gcgcgtctgc aatacccagt attgaagaaa gtattcgcca atagcggcat tagtgacacc      540
gacagcgaaa tgcttatcaa gaaattccaa gaccaatatg tacactggga agaaaactcg      600
ttcccaggtt cacttggtaa cgttattgcg ggccgtatcg ccaaccgctt cgattttggc      660
ggcatgaact gtgtggttga tgctgcctgt gctggatcac ttgctgctat gcgtatggcg      720
ctaacagagc taactgaagg tcgctctgaa atgatgatca ccggtggtgt gtgtactgat      780 aactcacccct ctatgtatat gagcttttca aaaacgcccg cctttaccac taacgaaacc      840
attcagccat ttgatatcga ctcaaaaggc atgatgattg gtgaaggtat tggcatggtg      900
gcgctaaagc gtcttgaaga tgcagagcgc gatggcgacc gcatttactc tgtaattaaa      960
ggtgtgggtg catcatctga cggtaagttt aaatcaatct atgcccctcg cccatcaggc      1020
caagctaaag cacttaaccg tgcctatgat gacgcaggtt ttgcgccgca taccttaggt     1080
ctaattgaag ctcacggaac aggtactgca gcaggtgacg cggcagagtt tgccggcctt     1140
tgctcagtat ttgctgaagg caacgatacc aagcaacaca ttgcgctagg ttcagttaaa     1200
tcacaaattg gtcatactaa atcaactgca ggtacagcag gtttaattaa agctgctctt     1260
gctttgcatc acaaggtact gccgccgacc attaacgtta gtcagccaag ccctaaactt     1320
gatatcgaaa actcaccgtt ttatctaaac actgagactc gtccatggtt accacgtgtt     1380
gatggtacgc cgcgccgcgc gggtattagc tcatttggtt ttggtggcac taacttccat     1440
tttgtactag aagagtacaa ccaagaacac agccgtacta tagcgaaaaa agctaagtat     1500
cgtcaacgcc aagtggcgca aagcttcctt gttagcgcaa gcgataaagc atcgctaatt     1560
aacgagttaa acgtactagc agcatctgca agccaagctg agtttatcct caaagatgca     1620
gcagcaaact atggcgtacg tgagcttgat aaaaatgcac cacggatcgg tttagttgca     1680
```

-continued

```
aacacagctg aagagttagc aggcctaatt aagcaagcac ttgccaaact agcagctagc    1740
gatgataacg catggcagct acctggtggc actagctacc gcgccgctgc agtagaaggt    1800
aaagttgccg cactgtttgc tggccaaggt tcacaatatc tcaatatggg ccgtgacctt    1860
acttgttatt acccagagat gcgtcagcaa tttgtaactg cagataaagt atttgccgca    1920
aatgataaaa cgccgttatc gcaaactctg tatccaaagc ctgtatttaa taaagatgaa    1980
ttaaaggctc aagaagccat tttgaccaat accgccaatg cccaaagcgc aattggtgcg    2040
atttcaatgg gtcaatacga tttgtttact gcggctggct ttaatgccga catggttgca    2100
ggccatagct ttggtgagct aagtgcactg tgtgctgcag gtgttatttc agctgatgac    2160
tactacaagc tggcttttgc tcgtggtgag gctatggcaa caaaagcacc ggctaaagac    2220
ggcgttgaag cagatgcagg agcaatgttt gcaatcataa ccaagagtgc tgcagacctt    2280
gaaaccgttg aagccaccat cgctaaattt gatggggtga agtcgctaa ctataacgcg    2340 ccaacgcaat cagtaattgc aggcccaaca gcaactaccg ctgatgcggc taaagcgcta    2400
actgagcttg gttacaaagc gattaacctg ccagtatcag gtgcattcca cactgaactt    2460
gttggtcacg ctcaagcgcc atttgctaaa gcgattgacg cagccaaatt tactaaaaca    2520
agccgagcac tttactcaaa tgcaactggc ggactttatg aaagcactgc tgcaaagatt    2580
aaagcctcgt taagaaaaca tatgcttcaa tcagtgcgct ttactagcca gctagaagcc    2640
atgtacaacg acggcgcccg tgtatttgtt gaatttggtc caagaacat cttacaaaaa    2700 ttagttcaag gcacgcttgt caacactgaa atgaagttt gcactatctc tatcaaccct    2760
aatcctaaag ttgatagtga tctgcagctt aagcaagcag caatgcagct agcggttact    2820
ggtgtggtac tcagtgaaat tgacccatac caagccgata ttgccgcacc agcgaaaaag    2880
tcgccaatga gcatttcgct taatgctgct aaccatatca gcaaagcaac tcgcgctaag    2940
atggccaagt ctttagagac aggtatcgtc acctcgcaaa tagaacatgt tattgaagaa    3000
aaaatcgttg aagttgagaa actggttgaa gtcgaaaaga tcgtcgaaaa agtggttgaa    3060
gtagagaaag ttgttgaggt tgaagctcct gttaattcag tgcaagccaa tgcaattcaa    3120
acccgttcag ttgtcgctcc agtaatagag aaccaagtcg tgtctaaaaa cagtaagcca    3180
gcagtccaga gcattagtgg tgatgcactc agcaacttttt ttgctgcaca gcagcaaacc    3240
gcacagttgc atcagcagtt cttagctatt ccgcagcaat atggtgagac gttcactacg    3300
ctgatgaccg agcaagctaa actggcaagt tctggtgttg caattccaga gagtctgcaa    3360
cgctcaatgg agcaattcca ccaactacaa gcgcaaacac tacaaagcca cacccagttc    3420
cttgagatgc aagcgggtag caacattgca gcgttaaacc tactcaatag cagccaagca    3480
acttacgctc cagccattca caatgaagcg attcaaagcc aagtggttca agccaaaact    3540
gcagtccagc cagtaatttc aacacaagtt aaccatgtgt cagagcagcc aactcaagct    3600
ccagctccaa aagcgcagcc agcacctgtg acaactgcag ttcaaactgc tccggcacaa    3660
gttgttcgtc aagccgcacc agttcaagcc gctattgaac cgattaatac aagtgttgcg    3720
actacaacgc cttcagcctt cagcgccgaa acagccctga gcgcaacaaa agtccaagcc    3780
actatgcttg aagtggttgc tgagaaaacc ggttacccaa ctgaaatgct agagcttgaa    3840
atggatatgg aagccgattt aggcatcgat tctatcaagc gtgtagaaat tcttggcaca    3900
gtacaagatg agctaccggg tctacctgag cttagccctg aagatctagc tgagtgtcga    3960
acgctaggcg aaatcgttga ctatatgggc agtaaactgc cggctgaagg ctctatgaat    4020
tctcagctgt ctacaggttc cgcagctgcg actcctgcag cgaatggtct ttctgcggag    4080
```

```
aaagttcaag cgactatgat gtctgtggtt gccgaaaaga ctggctaccc aactgaaatg    4140
ctagagcttg aaatggatat ggaagccgat ttaggcatag attctatcaa gcgcgttgaa    4200
attcttggca cagtacaaga tgagctaccg ggtctacctg agcttagccc tgaagatcta    4260
gctgagtgtc gtactctagg cgaaatcgtt gactatatga actctaaact cgctgacggc    4320
tctaagctgc cggctgaagg ctctatgaat tctcagctgt ctacaagtgc cgcagctgcg    4380
actcctgcag cgaatggtct ctctgcggag aaagttcaag cgactatgat gtctgtggtt    4440
gccgaaaaga ctggctaccc aactgaaatg ctagaacttg aaatggatat ggaagctgac    4500
cttggcatcg attcaatcaa gcgcgttgaa attcttggca cagtacaaga tgagctaccg    4560 gtttacctg agctaaatcc agaagatttg gcagagtgtc gtactcttgg cgaaatcgtg     4620
acttatatga actctaaact cgctgacggc tctaagctgc cagctgaagg ctctatgcac    4680
tatcagctgt ctacaagtac cgctgctgcg actcctgtag cgaatggtct ctctgcagaa    4740
aaagttcaag cgaccatgat gtctgtagtt gcagataaaa ctggctaccc aactgaaatg    4800
cttgaacttg aaatggatat ggaagccgat ttaggtatcg attctatcaa gcgcgttgaa    4860
attcttggca cagtacaaga tgagctaccg gtttacctg agctaaatcc agaagatcta     4920
gcagagtgtc gcaccctagg cgaaatcgtt gactatatgg gcagtaaact gccggctgaa    4980
ggctctgcta atacaagtgc cgctgcgtct cttaatgtta gtgccgttgc ggcgcctcaa    5040
gctgctgcga ctcctgtatc gaacggtctc tctgcagaga aagtgcaaag cactatgatg    5100
tcagtagttg cagaaaagac cggctaccca actgaaatgc tagaacttgg catggatatg    5160
gaagccgatt taggtatcga ctcaattaaa cgcgttgaga ttcttggcac agtacaagat    5220
gagctaccgg gtctaccaga gcttaatcct gaagatttag ctgagtgccg tacgctgggc    5280
gaaatcgttg actatatgaa ctctaagctg gctgacggct ctaagcttcc agctgaaggc    5340
tctgctaata caagtgccac tgctgcgact cctgcagtga atggtctttc tgctgacaag    5400
gtacaggcga ctatgatgtc tgtagttgct gaaaagaccg gctacccaac tgaaatgcta    5460
gaacttggca tggatatgga agcagacctt ggtattgatt ctattaagcg cgttgaaatt    5520
cttggcacag tacaagatga gctcccaggt ttacctgagc ttaatcctga agatctcgct    5580
gagtgccgca cgcttggcga aatcgttagc tatatgaact ctcaactggc tgatggctct    5640
aaactttcta caagtgcggc tgaaggctct gctgatacaa gtgctgcaaa tgctgcaaag    5700
ccggcagcaa tttcggcaga accaagtgtt gagcttcctc ctcatagcga ggtagcgcta    5760
aaaaagctta atgcggcgaa caagctagaa aattgtttcg ccgcagacgc aagtgttgtg    5820
attaacgatg atggtcacaa cgcaggcgtt ttagctgaga aacttattaa acaaggccta    5880
aaagtagccg ttgtgcgttt accgaaaggt cagcctcaat cgccactttc aagcgatgtt    5940
gctagctttg agcttgcctc aagccaagaa tctgagcttg aagccagtat cactgcagtt    6000
atcgcgcaga ttgaaactca ggttggcgct attggtggct ttattcactt gcaaccagaa    6060
gcgaatacag aagagcaaac ggcagtaaac ctagatgcgc aaagttttac tcacgttagc    6120
aatgcgttct tgtgggccaa attattgcaa ccaaagctcg ttgctggagc agatgcgcgt    6180
cgctgttttg taacagtaag ccgtatcgac ggtggctttg gttacctaaa tactgacgcc    6240
ctaaaagatg ctgagctaaa ccaagcagca ttagctggtt taactaaaac cttaagccat    6300
gaatggccac aagtgttctg tcgcgcgcta gatattgcaa cagatgttga tgcaacccat    6360
cttgctgatg caatcaccag tgaactattt gatagccaag ctcagctacc tgaagtgggc    6420
```

```
ttaagcttaa ttgatggcaa agttaaccgc gtaactctag ttgctgctga agctgcagat      6480
aaaacagcaa aagcagagct taacagcaca gataaaatct tagtgactgg tggggcaaaa      6540
ggggtgacat ttgaatgtgc actggcatta gcatctcgca gccagtctca ctttatctta      6600
gctgggcgca gtgaattaca agctttacca agctgggctg agggtaagca aactagcgag      6660
ctaaaatcag ctgcaatcgc acatattatt tctactggtc aaaagccaac gcctaagcaa      6720
gttgaagccg ctgtgtggcc agtgcaaagc agcattgaaa ttaatgccgc cctagccgcc      6780
tttaacaaag ttggcgcctc agctgaatac gtcagcatgg atgttaccga tagcgccgca      6840
atcacagcag cacttaatgg tcgctcaaat gagatcaccg gtcttattca tggcgcaggt      6900
gtactagccg acaagcatat tcaagacaag actcttgctg aacttgctaa agtttatggc      6960
actaaagtca acggcctaaa agcgctgctc gcggcacttg agccaagcaa aattaaatta      7020
cttgctatgt tctcatctgc agcaggtttt tacggtaata tcggccaaag cgattacgcg      7080
atgtcgaacg atattcttaa caaggcagcg ctgcagttca ccgctcgcaa cccacaagct      7140
aaagtcatga gctttaactg gggtccttgg gatggcggca tggttaaccc agcgcttaaa      7200
aagatgttta ccgagcgtgg tgtgtacgtt attccactaa aagcaggtgc agagctattt      7260
gccactcagc tattggctga aactggcgtg cagttgctca ttggtacgtc aatgcaaggt      7320
ggcagcgaca ctaaagcaac tgagactgct tctgtaaaaa agcttaatgc gggtgaggtg      7380
ctaagtgcat cgcatccgcg tgctggtgca caaaaaacac cactacaagc tgtcactgca      7440
acgcgtctgt taaccccaag tgccatggtc ttcattgaag atcaccgcat tggcggtaac      7500
agtgtgttgc caacggtatg cgccatcgac tggatgcgtg aagcggcaag cgacatgctt      7560
ggcgctcaag ttaaggtact tgattacaag ctattaaaag gcattgtatt tgagactgat      7620
gagccgcaag agttaacact tgagctaacg ccagacgatt cagacgaagc tacgctacaa      7680
gcattaatca gctgtaatgg gcgtccgcaa tacaaggcga cgcttatcag tgataatgcc      7740
gatattaagc aacttaacaa gcagtttgat ttaagcgcta aggcgattac cacagcaaaa      7800
gagctttata gcaacggcac cttgttccac ggtccgcgtc tacaagggat ccaatctgta      7860
gtgcagttcg atgatcaagg cttaattgct aaagtcgctc tgcctaaggt tgaacttagc      7920
gattgtggtg agttcttgcc gcaaacccac atgggtggca gtcaaccttt tgctgaggac      7980
ttgctattac aagctatgct ggtttgggct cgccttaaaa ctggctcggc aagtttgcca      8040
tcaagcattg gtgagtttac ctcataccaa ccaatggcct ttggtgaaac tggtaccata      8100
gagcttgaag tgattaagca aacaaacgc tcacttgaag cgaatgttgc gctatatcgt      8160
gacaacggcg agttaagtgc catgtttaag tcagctaaaa tcaccattag caaaagctta      8220
aattcagcat ttttacctgc tgtcttagca aacgacagtg aggcgaat                  8268
```

<210> SEQ ID NO 84
<211> LENGTH: 2313
<212> TYPE: DNA
<213> ORGANISM: Shewanella putrefaciens

<400> SEQUENCE: 84

```
atgccgctgc gcatcgcact tatcttactg ccaacaccgc agtttgaagt taactctgtc        60
gaccagtcag tattagccag ctatcaaaca ctgcagcctg agctaaatgc cctgcttaat       120
agtgcgccga cacctgaaat gctcagcatc actatctcag atgatagcga tgcaaacagc       180
tttgagtcgc agctaaatgc tgcgaccaac gcaattaaca atggctatat cgtcaagctt       240
gctacggcaa ctcacgcttt gttaatgctg cctgcattaa aagcggcgca aatgcggatc       300
```

```
catcctcatg cgcagcttgc cgctatgcag caagctaaat cgacgccaat gagtcaagta    360
tctggtgagc taaagcttgg cgctaatgcg ctaagcctag ctcagactaa tgcgctgtct    420
catgctttaa gccaagccaa gcgtaactta actgatgtca gcgtgaatga gtgttttgag    480
aacctcaaaa gtgaacagca gttcacagag gtttattcgc ttattcagca acttgctagc    540
cgcacccatg tgagaaaaga ggttaatcaa ggtgtggaac ttggccctaa acaagccaaa    600
agccactatt ggtttagcga atttcaccaa aaccgtgttg ctgccatcaa ctttattaat    660
ggccaacaag caaccagcta tgtgcttact caaggttcag gattgttagc tgcgaaatca    720
atgctaaacc agcaaagatt aatgtttatc ttgccgggta acagtcagca acaaataacc    780
gcatcaataa ctcagttaat gcagcaatta gagcgtttgc aggtaactga ggttaatgag    840
ctttctctag aatgccaact agagctgctc agcataatgt atgacaactt agtcaacgca    900
gacaaactca ctactcgcga tagtaagccc gcttatcagg ctgtgattca agcaagctct    960
gttagcgctg caaagcaaga gttaagcgcg cttaacgatg cactcacagc gctgtttgct    1020
gagcaaacaa cgccacatc aacgaataaa ggcttaatcc aatacaaaac accggcgggc    1080
agttacttaa ccctaacacc gcttggcagc aacaatgaca acgcccaagc gggtcttgct    1140
tttgtctatc cgggtgtggg aacggtttac gccgatatgc ttaatgagct gcatcagtac    1200
ttccctgcgc tttacgccaa acttgagcgt gaaggcgatt taaaggcgat gctacaagca    1260
gaagatatct atcatcttga ccctaaacat gctgcccaaa tgagcttagg tgacttagcc    1320
attgctggcg tggggagcag ctacctgtta actcagctgc tcaccgatga gtttaatatt    1380
aagcctaatt ttgcattagg ttactcaatg ggtgaagcat caatgtgggc aagcttaggc    1440
gtatggcaaa acccgcatgc gctgatcagc aaaacccaaa ccgacccgct atttacttct    1500
gctatttccg gcaaattgac cgcggttaga caagcttggc agcttgatga taccgcagcg    1560
gaaatccagt ggaatagctt tgtggttaga agtgaagcag cgccgattga agccttgcta    1620
aaagattacc cacacgctta cctcgcgatt attcaagggg atacctgcgt aatcgctggc    1680
tgtgaaatcc aatgtaaagc gctacttgca gcactgggta aacgcggtat tgcagctaat    1740
cgtgtaacgg cgatgcatac gcagcctgcg atgcaagagc atcaaaatgt gatggatttt    1800
tatctgcaac cgttaaaagc agagcttcct agtgaaataa gctttatcag cgccgctgat    1860
ttaactgcca gcaaacggt gagtgagcaa gcacttagca gccaagtcgt tgctcagtct    1920
attgccgaca ccttctgcca aaccttggac tttaccgcgc tagtacatca cgcccaacat    1980
caaggcgcta agctgtttgt tgaaattggc gcggatagac aaaactgcac cttgatagac    2040
aagattgtta acaagatgg tgccagcagt gtacaacatc aaccttgttg cacagtgcct    2100
atgaacgcaa aagtagcca agatattacc agcgtgatta agcgcttgg ccaattaatt    2160 agccatcagg tgccattatc ggtgcaacca tttattgatg gactcaagcg cgagctaaca    2220 cttttgccaat tgaccagcca acagctggca gcacatgcaa atgttgacag caagtttgag    2280
tctaaccaag accatttact tcaaggggaa gtc                                2313
```

<210> SEQ ID NO 85
<211> LENGTH: 6012
<212> TYPE: DNA
<213> ORGANISM: Shewanella putrefaciens

<400> SEQUENCE: 85

```
atgtcattac cagacaatgc ttctaaccac ctttctgcca accagaaagg cgcatctcag     60
```

-continued

```
gcaagtaaaa ccagtaagca aagcaaaatc gccattgtcg gtttagccac tctgtatcca      120
gacgctaaaa ccccgcaaga attttggcag aatttgctgg ataaacgcga ctctcgcagc      180
accttaacta acgaaaaact cggcgctaac agccaagatt atcaaggtgt gcaaggccaa      240
tctgaccgtt tttattgtaa taaaggcggc tacattgaga acttcagctt taatgctgca      300
ggctacaaat tgccggagca aagcttaaat ggcttggacg acagcttcct ttgggcgctc      360
gatactagcc gtaacgcact aattgatgct ggtattgata tcaacggcgc tgatttaagc      420
cgcgcaggtg tagtcatggg cgcgctgtcg ttcccaacta cccgctcaaa cgatctgttt      480
ttgccaattt atcacagcgc cgttgaaaaa gccctgcaag ataaactagg cgtaaaggca      540
tttaagctaa gcccaactaa tgctcatacc gctcgcgcgg caaatgagag cagcctaaat      600
gcagccaatg gtgccattgc ccataacagc tcaaaagtgg tggccgatgc acttggcctt      660
ggcggcgcac aactaagcct agatgctgcc tgtgctagtt cggtttactc attaaagctt      720
gcctgcgatt acctaagcac tggcaaagcc gatatcatgc tagcaggcgc agtatctggc      780
gcggatcctt tctttattaa tatgggattc tcaatcttcc acgcctaccc agaccatggt      840
atctcagtac cgtttgatgc cagcagtaaa ggtttgtttg ctggcgaagg cgctggcgta      900
ttagtgctta acgtcttga agatgccgag cgcgacaatg acaaaatcta tgcggttgtt      960
agcggcgtag gtctatcaaa cgacggtaaa ggccagtttg tattaagccc taatccaaaa     1020
ggtcaggtga aggcctttga acgtgcttat gctgccagtg acattgagcc aaaagacatt     1080
gaagtgattg agtgccacgc aacaggcaca ccgcttggcg ataaaattga gctcacttca     1140
atggaaacct tctttgaaga caagctgcaa ggcaccgatg caccgttaat tggctcagct     1200
aagtctaact taggccacct attaactgca gcgcatgcgg ggatcatgaa gatgatcttc     1260
gccatgaaag aaggttacct gccgccaagt atcaatatta gtgatgctat cgcttcgccg     1320
aaaaaactct tcggtaaacc aaccctgcct agcatggttc aaggctggcc agataagcca     1380
tcgaataatc attttggtgt aagaacccgt cacgcaggcg tatcggtatt ggctttggt      1440
ggctgtaacg cccatctgtt gcttgagtca tacaacggca aaggaacagt aaaggcagaa     1500
gccactcaag taccgcgtca agctgagccg ctaaaagtgg ttggccttgc ctcgcacttt     1560
gggcctctta gcagcattaa tgcactcaac aatgctgtga cccaagatgg gaatggcttt     1620
atcgaactgc cgaaaaagcg ctggaaaggc cttgaaaagc acagtgaact gttagctgaa     1680
tttggcttag catctgcgcc aaaaggtgct tatgttgata acttcgagct ggacttttta     1740
cgctttaaac tgccgccaaa cgaagatgac cgtttgatct cacagcagct aatgctaatg     1800
cgagtaacag acgaagccat tcgtgatgcc aagcttgagc cggggcaaaa agtagcctgta    1860
ttagtggcaa tggaaactga gcttgaactg catcagttcc gcggccgggt taacttgcat     1920
actcaattag cgcaaagtct tgccgccatg ggcgtgagtt tatcaacgga tgaataccaa     1980
gcgcttgaag ccatcgccat ggacagcgtg cttgatgctg ccaagctcaa tcagtacacc     2040
agctttattg gtaatattat ggcgtcacgc gtggcgtcac tatgggactt taatggccca     2100
gccttcacta tttcagcagc agagcaatct gtgagccgct gtatcgatgt ggcgcaaaac     2160
ctcatcatgg aggataacct agatgcggtg gtgattgcag cggtcgatct ctctggtagc     2220
tttgagcaag tcattcttaa aaatgccatt gcacctgtag ccattgagcc aaacctcgaa     2280
gcaagcctta atccaacatc agcaagctgg aatgtcggtg aaggtgctgg cgcggtcgtg     2340
cttgttaaaa atgaagctac atcgggctgc tcatacggcc aaattgatgc acttggcttt     2400
gctaaaactg ccgaaacagc gttggctacc gacaagctac tgagccaaac tgccacagac     2460
```

-continued

```
tttaataagg ttaaagtgat tgaaactatg gcagcgcctg ctagccaaat tcaattagcg   2520
ccaatagtta gctctcaagt gactcacact gctgcagagc agcgtgttgg tcactgcttt   2580
gctgcagcgg gtatggcaag cctattacac ggcttactta acttaaatac tgtagcccaa   2640
accaataaag ccaattgcgc gcttatcaac aatatcagtg aaaaccaatt atcacagctg   2700
ttgattagcc aaacagcgag cgaacaacaa gcattaaccg cgcgtttaag caatgagctt   2760
aaatccgatg ctaaacacca actggttaag caagtcacct taggtggccg tgatatctac   2820
cagcatattg ttgatacacc gcttgcaagc cttgaaagca ttactcagaa attggcgcaa   2880
gcgacagcat cgacagtggt caaccaagtt aaacctatta aggccgctgg ctcagtcgaa   2940
atggctaact cattcgaaac ggaaagctca gcagagccac aaataacaat tgcagcacaa   3000
cagactgcaa acattggcgt caccgctcag gcaaccaaac gtgaattagg tacccccacca  3060 atgacaacaa ataccattgc taatacagca aataatttag acaagactct tgagactgtt   3120
gctggcaata ctgttgctag caaggttggc tctggcgaca tagtcaattt tcaacagaac   3180
caacaattgg ctcaacaagc tcacctcgcc tttcttgaaa gccgcagtgc gggtatgaag   3240
gtggctgatg ctttattgaa gcaacagcta gctcaagtaa caggccaaac tatcgataat   3300
caggccctcg atactcaagc cgtcgatact caaacaagcg agaatgtagc gattgccgca   3360
gaatcaccag ttcaagttac aacacctgtt caagttacaa cacctgttca aatcagtgtt   3420
gtggagttaa aaccagatca cgctaatgtg ccaccataca cgccgccagt gcctgcatta   3480
aagccgtgta tctggaacta tgccgattta gttgagtacg cagaaggcga tatcgccaag   3540
gtatttggca gtgattatgc cattatcgac agctactcgc gccgcgtacg tctaccgacc   3600
actgactacc tgttggtatc gcgcgtgacc aaacttgatg cgaccatcaa tcaatttaag   3660
ccatgctcaa tgaccactga gtacgacatc cctgttgatg cgccgtactt agtagacgga   3720 caaatcccctt gggcggtagc agtagaatca ggccaatgtg acttgatgct tattagctat   3780
ctcggtatcg actttgagaa caaaggcgag cgggtttatc gactactcga ttgtaccctc   3840
accttcctag gcgacttgcc acgtggcgga gataccctac gttacgacat taagatcaat   3900
aactatgctc gcaacggcga caccctgctg ttcttcttct cgtatgagtg ttttgttggc   3960
gacaagatga tcctcaagat ggatggcggc tgcgctggct tcttcactga tgaagagctt   4020
gccgacggta aaggcgtgat tcgcacagaa gaagagatta agctcgcag cctagtgcaa   4080 aagcaacgct ttaatccgtt actagattgt cctaaaaccc aatttagtta tggtgatatt   4140
cataagctat taactgctga tattgagggt tgttttggcc caagccacag tggcgtccac   4200
cagccgtcac tttgtttcgc atctgaaaaa ttcttgatga ttgaacaagt cagcaaggtt   4260
gatcgcactg gcggtacttg gggacttggc ttaattgagg gtcataagca gcttgaagca   4320
gaccactggt acttcccatg tcatttcaag ggcgaccaag tgatggctgg ctcgctaatg   4380
gctgaaggtt gtggccagtt attgcagttc tatatgctgc accttggtat gcatacccaa   4440 actaaaatg gtcgtttcca acctcttgaa aacgcctcac agcaagtacg ctgtcgcggt   4500
caagtgctgc cacaatcagg cgtgctaact taccgtatgg aagtgactga atcggtttc   4560 agtccacgcc catatgctaa agctaacatc gatatcttgc ttaatggcaa agcggtagtg   4620
gatttccaaa acctagggt gatgataaaa gaggaagatg agtgtactcg ttatccactt   4680
ttgactgaat caacaacggc tagcactgca caagtaaacg ctcaaacaag tgcgaaaaag   4740
gtatacaagc cagcatcagt caatgcgcca ttaatggcac aaaattcctga tctgactaaa   4800
```

-continued

```
gagccaaaca agggcgttat tccgatttcc catgttgaag caccaattac gccagactac      4860
ccgaaccgtg tacctgatac agtgccattc acgccgtatc acatgtttga gtttgctaca      4920
ggcaatatcg aaaactgttt cgggccagag ttctcaatct atcgcggcat gatcccacca      4980
cgtacaccat gcggtgactt acaagtgacc acacgtgtga ttgaagttaa cggtaagcgt      5040
ggcgacttta aaagccatc atcgtgtatc gctgaatatg aagtgcctgc agatgcgtgg       5100
tatttcgata aaaacagcca cggcgcagtg atgccatatt caattttaat ggagatctca     5160
ctgcaaccta acggctttat ctcaggttac atgggcacaa ccctaggctt ccctggcctt     5220
gagctgttct tccgtaactt agacggtagc ggtgagttac tacgtgaagt agatttacgt     5280
ggtaaaacca tccgtaacga ctcacgttta ttatcaacag tgatggccgg cactaacatc     5340
atccaaagct ttagcttcga gctaagcact gacggtgagc ctttctatcg cggcactgcg     5400
gtatttggct atttaaagg tgacgcactt aaagatcagc taggcctaga taacggtaaa      5460
gtcactcagc catggcatgt agctaacggc gttgctgcaa gcactaaggt gaacctgctt     5520
gataagagct gccgtcactt taatgcgcca gctaaccagc cacactatcg tctagccggt     5580
ggtcagctga actttatcga cagtgttgaa attgttgata atggcggcac cgaaggttta     5640
ggttacttgt atgccgagcg caccattgac ccaagtgatt ggttcttcca gttccacttc     5700
caccaagatc cggttatgcc aggctcctta ggtgttgaag caattattga aaccatgcaa     5760
gcttacgcta ttagtaaaga cttgggcgca gatttcaaaa atcctaagtt tggtcagatt     5820
ttatcgaaca tcagtggaa gtatcgcggt caaatcaatc cgctgaacaa gcagatgtct      5880
atggatgtca gcattacttc aatcaaagat gaagacggta agaaagtcat cacaggtaat     5940
gccagcttga gtaaagatgg tctgcgcata tacgaggtct tcgatatagc tatcagcatc     6000
gaagaatctg ta                                                         6012
```

<210> SEQ ID NO 86
<211> LENGTH: 1629
<212> TYPE: DNA
<213> ORGANISM: Shewanella putrefaciens

<400> SEQUENCE: 86

```
atgaatccta cagcaactaa cgaaatgctt tctccgtggc catgggctgt gacagagtca       60
aatatcagtt ttgacgtgca agtgatggaa caacaactta agagatttag ccgggcatgt      120
tacgtggtca atcatgccga ccacggcttt ggtattgcgc aaactgccga tatcgtgact      180
gaacaagcgg caaacagcac agatttacct gttagtgctt ttactcctgc attaggtacc     240
gaaagcctag cgacaataa tttccgccgc gttcacggcg ttaaatacgc ttattacgca       300
ggcgctatgg caaacggtat ttcatctgaa gagctagtga ttgccctagg tcaagctggc     360
attttgtgtg gttcgtttgg agcagccggt cttattccaa gtcgcgttga agcggcaatt     420
aaccgtattc aagcagcgct gccaaatggc ccttatatgt ttaaccttat ccatagtcct     480
agcgagccag cattagagcg tggcagcgta gagctatttt taaagcataa ggtacgcacc     540
gttgaagcat cagctttctt aggtctaaca ccacaaatcg tctattaccg tgcagcagga     600
ttgagccgag acgcacaagg taagttgtg gttggtaaca aggttatcgc taaagtaagt      660
cgcaccgaag tggctgaaaa gtttatgatg ccagcgcccg caaaaatgct acaaaaacta     720
gttgatgacg ttcaattac cgctgagcaa atggagctgg cgcaacttgt acctatggct     780
gacgacatca ctgcagaggc cgattcaggt ggccatactg ataaccgtcc attagtaaca     840
ttgctgccaa ccatttagc gctgaaagaa gaaattcaag ctaaatacca atacgacact      900
```

```
cctattcgtg tcggttgtgg tggcggtgtg ggtacgcctg atgcagcgct ggcaacgttt      960
aacatgggcg cggcgtatat tgttaccggc tctatcaacc aagcttgtgt tgaagcgggc     1020
gcaagtgatc acactcgtaa attacttgcc accactgaaa tggccgatgt gactatggca     1080
ccagctgcag atatgttcga gatgggcgta aaactgcagg tggttaagcg cggcacgcta     1140
ttcccaatgc gcgctaacaa gctatatgag atctacaccc gttacgattc aatcgaagcg     1200
atcccattag acgagcgtga aaagcttgag aaacaagtat tccgctcaag cctagatgaa     1260
atatgggcag gtacagtggc gcactttaac gagcgcgacc ctaagcaaat cgaacgcgca     1320
gagggtaacc ctaagcgtaa aatggcattg attttccgtt ggtacttagg tctttctagt     1380
cgctggtcaa actcaggcga agtgggtcgt gaaatggatt atcaaatttg ggctggccct     1440
gctctcggtg catttaacca atgggcaaaa ggcagttact tagataacta tcaagaccga     1500
aatgccgtcg atttggcaaa gcacttaatg tacggcgcgg cttacttaaa tcgtattaac     1560
tcgctaacgg ctcaaggcgt taaagtgcca gcacagttac ttcgctggaa gccaaaccaa     1620
agaatggcc                                                            1629
```